(12) United States Patent
Rapp et al.

(10) Patent No.: US 7,550,650 B2
(45) Date of Patent: *Jun. 23, 2009

(54) PRODUCTION OF A TRANSGENIC AVIAN BY CYTOPLASMIC INJECTION

(75) Inventors: Jeffrey C. Rapp, Athens, GA (US); Leandro Christmann, Watkinsville, GA (US)

(73) Assignee: Synageva BioPharma Corp., Waltham, MA (US)

( * ) Notice: Subject to any disclaimer, the term of this patent is extended or adjusted under 35 U.S.C. 154(b) by 945 days.

This patent is subject to a terminal disclaimer.

(21) Appl. No.: 10/679,034

(22) Filed: Oct. 2, 2003

(65) Prior Publication Data

US 2007/0180546 A1    Aug. 2, 2007

Related U.S. Application Data

(63) Continuation-in-part of application No. 10/251,364, filed on Sep. 18, 2002, now Pat. No. 7,312,374.

(60) Provisional application No. 60/322,969, filed on Sep. 18, 2001, provisional application No. 60/351,550, filed on Jan. 25, 2002.

(51) Int. Cl.
C12N 15/00 (2006.01)
A01K 67/027 (2006.01)

(52) U.S. Cl. .......................................... 800/21; 800/19

(58) Field of Classification Search ................... 800/21, 800/19

See application file for complete search history.

(56) References Cited

U.S. PATENT DOCUMENTS

| | | | |
|---|---|---|---|
| 4,237,224 | A | 12/1980 | Cohen et al. |
| 4,603,112 | A | 7/1986 | Paoletti et al. |
| 4,722,848 | A | 2/1988 | Paoletti et al. |
| 4,769,330 | A | 9/1988 | Paoletti et al. |
| 4,997,763 | A | 3/1991 | Hughes et al. |
| 5,011,780 | A | 4/1991 | Perry |
| 5,162,215 | A | 11/1992 | Bosselman et al. |
| 5,174,993 | A | 12/1992 | Paoletti et al. |
| 5,175,384 | A | 12/1992 | Krimpenfort et al. |
| 5,338,683 | A | 8/1994 | Paoletti et al. |
| 5,340,740 | A | 8/1994 | Petitte et al. |
| 5,494,807 | A | 2/1996 | Paoletti et al. |
| 5,505,941 | A | 4/1996 | Paoletti et al. |
| 5,580,859 | A | 12/1996 | Felgner et al. |
| 5,589,466 | A | 12/1996 | Felgner et al. |
| 5,591,639 | A | 1/1997 | Bebbington |
| 5,656,479 | A | 8/1997 | Petitte et al. |
| 5,731,178 | A | 3/1998 | Sippel et al. |
| 6,027,722 | A | 2/2000 | Hodgson |
| 6,423,488 | B1 | 7/2002 | Harvey |
| 6,730,822 | B1 * | 5/2004 | Ivarie et al. ............ 800/19 |
| 2002/0108132 | A1 | 8/2002 | Rapp |
| 2002/0116732 | A1 | 8/2002 | Christmann |
| 2002/0199214 | A1 | 12/2002 | Rapp |
| 2003/0126628 | A1 | 7/2003 | Harvey et al. |
| 2003/0140363 | A1 | 7/2003 | Rapp |

FOREIGN PATENT DOCUMENTS

| | | |
|---|---|---|
| WO | WO 87/05325 A1 | 9/1987 |
| WO | WO 90/11355 A1 | 10/1990 |
| WO | WO 92/06180 A1 | 4/1992 |
| WO | WO 92/19749 A1 | 11/1992 |
| WO | WO 92/20316 A2 | 11/1992 |
| WO | WO 92/22635 A1 | 12/1992 |
| WO | WO 93/04701 A1 | 3/1993 |
| WO | WO 93/25234 A1 | 12/1993 |
| WO | WO 94/06920 A1 | 3/1994 |
| WO | WO 94/11524 A1 | 5/1994 |
| WO | WO 97/47739 A1 | 12/1997 |
| WO | WO 99/10505 A2 | 3/1999 |
| WO | WO 99/19472 A1 | 4/1999 |
| WO | WO 99/42569 A1 | 8/1999 |
| WO | WO 00/09674 A1 | 2/2000 |
| WO | WO 00/69257 A2 | 11/2000 |
| WO | WO 0220752 A2 | 3/2002 |
| WO | WO 02/064727 A3 | 8/2002 |
| WO | WO 02/079447 A2 | 10/2002 |

OTHER PUBLICATIONS

Vick, Proc. R. Soc. Lond., 1993, vol. 251, p. 179-182.*
Love, Bio/Technology, 1994, vol. 12, p. 60-63.*
Tanaka (1994, J. Reprod. Fert., vol. 100, p. 447-449).*

(Continued)

*Primary Examiner*—Michael C. Wilson
(74) *Attorney, Agent, or Firm*—Kyle D. Yesland

(57) ABSTRACT

This invention provides methods for the stable introduction of heterologous coding sequences into the genome of a bird and expressing the coding sequences to produce desired proteins or to alter the phenotype of the bird. The present invention provides preferred methods for introducing a transgene into the cytoplasm of avian embryonic cells by cytoplasmic microinjection. The embryo then develops into a transgenic adult capable of expressing a heterologous protein and/or capable of generating a line of transgenic birds through breeding. Synthetic vectors and gene promoters useful in the methods are also provided by the present invention, as are transgenic birds that express heterologous protein and avian eggs containing heterologous protein.

38 Claims, 72 Drawing Sheets

OTHER PUBLICATIONS

Thoraval, Transgenic Research, 1995, vol. 4, p. 369-376.*
Sayegh, Dec. 15, 1999, vol. 72, p. 31-37.*
Mohammed (1998, Immunotechnology, vol. 4, p. 115-125).*
Ishida (2002, Cloning Stem Cells, vol. 4, p. 91-102) s.*
Harvey (Nature Biotech, Apr. 2002, vol. 19, p. 396-399).*
Ivarie (Trends in Biotechnology, Jan. 2003, vol. 21, p. 14-19).*
Naito (Transgenic Animals: Generation and Use, 1997, Ed. By Louis Marie Houdebine, Harwood Academic Publishers, p. 69-73).*
Bachiller et al. Liposome-mediated DNA uptake by sperm cells. *Molecular Reproduction and Development.* 1991, 30:194-200, Wiley-Liss, Inc.
Baldari et al., A novel leader peptide which allows efficient secretion of a fragment of human interleukin 1β in *Saccharomyces cerevisiae E.M.B.O.J.*, 1987, 6:229-234.
Cibelli et al. Cloned transgenic calves produced from nonquiescent fetal fibroblasts. *Science.* May 22, 1998; 280:1256-1258.
Collas et al., Nuclear localization signals enhance germline transmission of a transgene in zebrafish, 1998, *Transgenic Research* 7, 303-309.
Etches et al. Strategies for the production of transgenic chickens. *Methods Mol Biol.* 1997;62:433-50.
Eyestone and Campbell. Nuclear transfer from somatic cells: applications in farm animal species. *J. Reprod Fertil Suppl.* 1999;54:489-97.
Eyal-Giladi H. From Cleavage to Primitive Streak Formation: A Complementary Normal Table and a New Look at the First Stages of the Development of the Chick. 1976; *Dev. Biol.* 49:321-337.
Furuta et al. Proliferation of exogenously injected primordial germ cells (PGCs) into bulsulfan-treated chicken embryos. *Asian J Androl.* Dec. 1999;1(4):187-90.
Gagne et al. Electroporation of Bovine Spermatozoa to carry foreign DNA in oocytes. 1991 *Mol. Reprod. Dev.* 29: 6-15.
Gilbert and Wood-Fush, A technique for the fistulation of the hen's oviduct through the abdominal wall, with recovery of the ovum. *J. Reprod. Fertil.* 1963, 5:451-453.
Godbey, W. et al. Tracking the intracellular path of poly(ethylenimine)/DNA complexes for gene delivery. Apr. 1999, *Proc Natl Acad Sci USA* 96:5177-5181.
Jaenisch R. Retroviruses and Embryogenesis: Microinjection of Moloney Leukemia Virus into Midgestation Mouse Embryos. *Cell.* Jan. 1980;19(1):181-8.
Lechardeur, D. et al. (1999) Metabolic instability of plasmid DNA in the cytosol: a potential barrier to gene transfer *Gene Ther.* 6:482-97.
Li et al. Ballistic transfection of avian primordial germ cell in ovo. *Transgenic Research* 1995, 4:26-9.
Love, et al. Transgenic Birds by DNA Microinjection. *Bio/Technology.* Jan. 1994; 12:60-63.
Mueller et al. Chimeric pigs following blastocyst injection of transgenic porcine primordial germ cells. *Molecular Reproduction and Development.* 1999, 54:244-254.
Muramatsu et al. Gene gun-mediated in vivo analysis of tissue-specific repression of gene transcription driven by the chicken ovalbumin promoter in the liver and oviduct of laying hens. *Mol Cell Biochem.* Aug. 1998; 185(1-2):27-32.
Naito et al. Introduction of exogenous DNA into somatic and germ cells of chickens by microinjection into the germinal disc of fertilized ova. *Molecular Reproduction and Development.* 1994, 37:167-171.
Naito et al. Production of germline chimeric chickens, with high transmission rate of donor-derived gametes, produced by transfer of primordial germ cells. *Mol Reprod Dev.* Oct. 1994;39 (2):153-61.
Nakanishi and Iritani, Gene transfer in the chicken by sperm-mediated methods. *Molecular Reproduction and Development.* 1993, 36:258-261.
Olsen &Neher, The site of fertilization in the domestic fowl. *J. Exp. Zoo* 1948, 109:355-366.
Page et al. "Transgenesis in mice by cytoplasmic injection of polylysine/DNA mixtures"; *Transgenic Research*, 1995;vol. 4, pp. 353-360.
Pancer et al. Recovery of ova and their re-insertion into the hen's oviduct through a fistula. *Br Poult Sci.* Dec. 1989; 30(4):953-7.
Phi-Van and Stratling, The matrix attachment regions of the chicken lysozyme gene co-map with the boundaries of the chromatin domain. 1988; *E.M.B.O.J.* 7(3): 655-664.
Pollard H., et al., Polyethylenimine but Not Cationic Lipids Promotes Transgene Delivery to the Nucleus in Mammalian Cells*. *J. Biol chem.*, 1998, 273: 7507-11.
Sang and Perry. Episomal Replication of Cloned DNA Injected into the Fertilised Ovum of the Hen, *Gallus domesticus. Mol. Reprod and Devlp.*1989, 1:98-106.
Schiest RH, Petes TD. Integration of DNA fragments by illegitimate recombination in *Saccharomyces cerevisiae. Proc Natl Acad Sci U S A.* Sep. 1, 1991;88(17):7585-9.
Tanaka et al. Chick production by in vitro fertilization of the fowl ovum. *J Reprod Fertil.* 1994, 100:447-449.
Molecular Structure and Flanking Nucleotide Sequences of the Natural Chick Ovomucoid Gene,Lai et al; Cell 18:829-842 (Nov. 1979).
DNA methylation: organ specific variations in the methylation pattern within and around ovalbumin and other chicken genes, Mandel et al; Nucleic Acids Research 7:2081-2103(1979).
Ovoinhibitor Introns Specify Functional Domains as in the Related and Linked Ovomucoid Gene*, Scott et al; Journal of Biol. Chemistry, 262:5899-5907(1987).
Deoxyribonuclease 1 Sensitivity of the Ovomucoid-Ovoinhibitor Gene Complex in Oviduct Nuclei and Relative Location of CR1 Repetitive Sequences, Scott et al; Biochemistry 26:6831-6840 (1987).
Isolation and characterization of the chicken ovomucoid gene, Lidenmaier et al; Nucleic Acids Research, 7:1221-1232 (1979).
The chick ovomucoid gene contains at least six intervening sequences, Catterall et al; Nature 278:323-327 (Mar. 1979).
Effect of Estrogen on Gene Expression In the Chick Oviduct. Regulation of the Ovomucoid Gene, Tsai et al; Biochemistry 17:5773-5780 (1978).
Identification of potential ovomucoid mRNA precursors in chick oviduct nuclei, Nordstrom et al; Nature 278:328-331 (Mar. 1979).
mRNA Complexity and Egg White Protein mRNA Content in Mature and Hormone-Withdrawn Oviduct, Hynes et al; Cell 11:923-932 (Aug. 1977).
The Hardwiring of development; organization and function of genomic regulatory systems. Amone et al; Development, 124(10):1851-64 (1997).
Harvey, Validating the hen as a bioreactor for the production of exogenous . . . , Poultry Science, vol. 82, No. 6 p. 927-930 (2003).
Jeong et al., Migration activity of chicken gonadal primordial germ . . . , Asian-Australasian Jounal Animal Sciences vol. 15, No. 9 p. 1227-1231 (2002).
Lampard et al., Secretion of foreign proteins mediated by chicken . . . Biochem. Cell Biol, vol. 80 No. 6 p. 777-788 (2002).
Park et al., Birth of Germline chimeras by transfer of chicken embryonic.. Molecular Reproduction and Development vol. 65, No. 4 p. 389-395 (2003).
Ivarie et al., Avian transgenesis: progress towards the promise, Trends in Biotechnology, vol. 21 No. 1 p. 14-19 (2003).

* cited by examiner

SEQ ID NO: 6

```
TGCCGCCTTC TTTGATATTC ACTCTGTTGT ATTTCATCTC TTCTTGCCGA TGAAAGGATA  60
TAACAGTCTG TATAACAGTC TGTGAGGAAA TACTTGGTAT TTCTTCTGAT CAGTGTTTTT  120
ATAAGTAATG TTGAATATTG GATAAGGCTG TGTGTCCTTT GTCTTGGGAG ACAAAGCCCA  180
CAGCAGGTGG TGGTTGGGGT GGTGGCAGCT CAGTGACAGG AGAGGTTTTT TTGCCTGTTT  240
TTTTTTTTTT TTTTTTTTTT AAGTAAGGTG TTCTTTTTTC TTAGTAAATT TTCTACTGGA  300
CTGTATGTTT TGACAGGTCA GAAACATTTC TTCAAAAGAA GAACCTTTTG GAAACTGTAC  360
AGCCCTTTTC TTTCATTCCC TTTTTGCTTT CTGTGCCAAT GCCTTTGGTT CTGATTGCAT  420
TATGGAAAAC GTTGATCGGA ACTTGAGGTT TTTATTTATA GTGTGGCTTG AAAGCTTGGA  480
TAGCTGTTGT TACACGAGAT ACCTTATTAA GTTTAGGCCA GCTTGATGCT TTATTTTTTC  540
CCTTTGAAGT AGTGAGCGTT CTCTGGTTTT TTTCCTTTGA AACTGGTGAG GCTTAGATTT  600
TTCTAATGGG ATTTTTTACC TGATGATCTA GTTGCATACC CAAATGCTTG TAAATGTTTT  660
CCTAGTTAAC ATGTTGATAA CTTCGGATTT ACATGTTGTA TATACTTGTC ATCTGTGTTT  720
CTAGTAAAAA TATATGGCAT TTATAGAAAT ACGTAATTCC TGATTTCCTT TTTTTTTATC  780
TCTATGCTCT GTGTGTACAG GTCAAACAGA CTTCACTCCT ATTTTTATTT ATAGAATTTT  840
ATATGCAGTC TGTCGTTGGT TCTTGTGTTG TAAGGATACA GCCTTAAATT TCCTAGAGCG  900
ATGCTCAGTA AGGCGGGTTG TCACATGGGT TCAAATGTAA AACGGGCACG TTTGGCTGCT  960
GCCTTCCCGA GATCCAGGAC ACTAAACTGC TTCTGCACTG AGGTATAAAT CGCTTCAGAT  1020
CCCAGGGAAG TGCAGATCCA CGTGCATATT CTTAAAGAAG AATGAATACT TTCTAAAATA  1080
TTTTGGCATA GGAAGCAAGC TGCATGGATT TGTTGGGAC TTAAATTATT TTGGTAACGG  1140
AGTGCATAGG TTTTAAACAC AGTTGCAGCA TGCTAACGAG TCACAGCGTT TATGCAGAAG  1200
TGATGCCTGG ATGCCTGTTG CAGCTGTTTA CGGCACTGCC TTGCAGTGAG CATTGCAGAT  1260
AGGGGTGGGG TGCTTTGTGT CGTGTTCCCA CACGCTGCCA CACAGCCACC TCCCGGAACA  1320
CATCTCACCT GCTGGGTACT TTTCAAACCA TCTTAGCAGT AGTAGATGAG TTACTATGAA  1380
ACAGAGAAGT TCCTCAGTTG GATATTCTCA TGGGATGTCT TTTTTCCCAT GTTGGGCAAA  1440
GTATGATAAA GCATCTCTAT TTGTAAATTA TGCACTTGTT AGTTCCTGAA TCCTTTCTAT  1500
AGCACCACTT ATTGCAGCAG GTGTAGGCTC TGGTGTGGCC TGTGTCTGTG CTTCAATCTT  1560
TTAAAGCTTC TTTGGAAATA CACTGACTTG ATTGAAGTCT CTTGAAGATA GTAAACAGTA  1620
CTTACCTTTG ATCCCAATGA AATCGAGCAT TTCAGTTGTA AAAGAATTCC GCCTATTCAT  1680
ACCATGTAAT GTAATTTTAC ACCCCCAGTG CTGACACTTT GGAATATATT CAAGTAATAG  1740
ACTTTGGCCT CACCCTCTTG TGTACTGTAT TTTGTAATAG AAAATATTTT AAACTGTGCA  1800
TATGATTATT ACATTATGAA AGAGACATTC TGCTGATCTT CAAATGTAAG AAAATGAGGA  1860
GTGCGTGTGC TTTTATAAAT ACAAGTGATT GCAAATTAGT GCAGGTGTCC TTAAAAAAAA  1920
AAAAAAAAAG TAATATAAAA AGGACCAGGT GTTTTACAAG TGAAATACAT TCCTATTTGG  1980
TAAACAGTTA CATTTTTATG AAGATTACCA GCGCTGCTGA CTTTCTAAAC ATAAGGCTGT  2040
ATTGTCTTCC TGTACCATTG CATTTCCTCA TTCCCAATTT GCACAAGGAT GTCTGGGTAA  2100
ACTATTCAAG AAATGGCTTT GAAATACAGC ATGGGAGCTT GTCTGAGTTG GAATGCAGAG  2160
TTGCACTGCA AAATGTCAGG AAATGGATGT CTCTCAGAAT GCCCAACTCC AAAGGATTTT  2220
ATATGTGTAT ATAGTAAGCA GTTTCCTGAT TCCAGCAGGC CAAAGAGTCT GCTGAATGTT  2280
GTGTTGCCGG AGACCTGTAT TTCTCAACAA GGTAAGATGG TATCCTAGCA ACTGCGGATT  2340
TTAATACATT TTCAGCAGAA GTACTTAGTT AATCTCTACC TTAGGGATC GTTTCATCAT  2400
TTTTAGATGT TATACTTGAA ATACTGCATA ACTTTTAGCT TTCATGGGTT CCTTTTTTTC  2460
AGCCTTTAGG AGACTGTTAA GCAATTTGCT GTCCAACTTT TGTGTTGGTC TTAAACTGCA  2520
ATAGTAGTTT ACCTTGTATT GAAGAAATAA AGACCATTTT TATATTAAAA AATACTTTTG  2580
TCTGTCTTCA TTTTGACTTG TCTGATATCC TTGCAGTGCC CATTATGTCA GTTCTGTCAG  2640
ATATTCAGAC ATCAAAACTT AACGTGAGCT CAGTGGAGTT ACAGCTGCGG TTTTGATGCT  2700
```

FIG. 1A

```
GTTATTATTT CTGAAACTAG AAATGATGTT GTCTTCATCT GCTCATCAAA CACTTCATGC 2760
AGAGTGTAAG GCTAGTGAGA AATGCATACA TTTATTGATA CTTTTTTAAA GTCAACTTTT 2820
TATCAGATTT TTTTTTCATT TGGAAATATA TTGTTTTCTA GACTGCATAG CTTCTGAATC 2880
TGAAATGCAG TCTGATTGGC ATGAAGAAGC ACAGCACTCT TCATCTTACT TAAACTTCAT 2940
TTTGGAATGA AGGAAGTTAA GCAAGGGCAC AGGTCCATGA AATAGAGACA GTGCGCTCAG 3000
GAGAAAGTGA ACCTGGATTT CTTTGGCTAG TGTTCTAAAT CTGTAGTGAG GAAAGTAACA 3060
CCCGATTCCT TGAAAGGGCT CCAGCTTTAA TGCTTCCAAA TTGAAGGTGG CAGGCAACTT 3120
GGCCACTGGT TATTTACTGC ATTATGTCTC AGTTTCGCAG CTAACCTGGC TTCTCCACTA 3180
TTGAGCATGG ACTATAGCCT GGCTTCAGAG GCCAGGTGAA GGTTGGGATG GGTGGAAGGA 3240
GTGCTGGGCT GTGGCTGGGG GGACTGTGGG GACTCCAAGC TGAGCTTGGG GTGGGCAGCA 3300
CAGGGAAAAG TGTGGGTAAC TATTTTTAAG TACTGTGTTG CAAACGTCTC ATCTGCAAAT 3360
ACGTAGGGTG TGTACTCTCG AAGATTAACA GTGTGGGTTC AGTAATATAT GGATGAATTC 3420
ACAGTGGAAG CATTCAAGGG TAGATCATCT AACGACACCA GATCATCAAG CTATGATTGG 3480
AAGCGGTATC AGAAGAGCGA GGAAGGTAAG CAGTCTTCAT ATGTTTTCCC TCCACGTAAA 3540
GCAGTCTGGG AAAGTAGCAC CCCTTGAGCA GAGACAAGGA AATAATTCAG GAGCATGTGC 3600
TAGGAGAACT TTCTTGCTGA ATTCTACTTG CAAGAGCTTT GATGCCTGGC TTCTGGTGCC 3660
TTCTGCAGCA CCTGCAAGGC CCAGAGCCTG TGGTGAGCTG GAGGGAAAGA TTCTGCTCAA 3720
GTCCAAGCTT CAGCAGGTCA TTGTCTTTGC TTCTTCCCCC AGCACTGTGC AGCAGAGTGG 3780
AACTGATGTC GAAGCCTCCT GTCCACTACC TGTTGCTGCA GGCAGACTGC TCTCAGAAAA 3840
AGAGAGCTAA CTCTATGCCA TAGTCTGAAG GTAAAATGGG TTTTAAAAAA GAAAACACAA 3900
AGGCAAAACC GGCTGCCCCA TGAGAAGAAA GCAGTGGTAA ACATGGTAGA AAAGGTGCAG 3960
AAGCCCCCAG GCAGTGTGAC AGGCCCCTCC TGCCACCTAG AGGCGGGAAC AAGCTTCCCT 4020
GCCTAGGGCT CTGCCCGCGA AGTGCGTGTT TCTTTGGTGG GTTTTGTTTG GCGTTTGGTT 4080
TTGAGATTTA GACACAAGGG AAGCCTGAAA GGAGGTGTTG GGCACTATTT TGGTTTGTAA 4140
AGCCTGTACT TCAAATATAT ATTTTGTGAG GGAGTGTAGC GAATTGGCCA ATTTAAAATA 4200
AAGTTGCAAG AGATTGAAGG CTGAGTAGTT GAGAGGGTAA CACGTTTAAT GAGATCTTCT 4260
GAAACTACTG CTTCTAAACA CTTGTTTGAG TGGTGAGACC TTGGATAGGT GAGTGCTCTT 4320
GTTACATGTC TGATGCACTT GCTTGTCCTT TTCCATCCAC ATCCATGCAT TCCACATCCA 4380
CGCATTTGTC ACTTATCCCA TATCTGTCAT ATCTGACATA CCTGTCTCTT CGTCACTTGG 4440
TCAGAAGAAA CAGATGTGAT AATCCCCAGC CGCCCCAAGT TTGAGAAGAT GGCAGTTGCT 4500
TCTTTCCCTT TTTCCTGCTA AGTAAGGATT TTCTCCTGGC TTTGACACCT CACGAAATAG 4560
TCTTCCTGCC TTACATTCTG GGCATTATTT CAAATATCTT TGGAGTGCGC TGCTCTCAAG 4620
TTTGTGTCTT CCTACTCTTA GAGTGAATGC TCTTAGAGTG AAAGAGAAGG AAGAGAAGAT 4680
GTTGGCCGCA GTTCTCTGAT GAACACACCT CTGAATAATG GCCAAAGGTG GGTGGGTTTC 4740
TCTGAGGAAC GGGCAGCGTT TGCCTCTGAA AGCAAGGAGC TCTGCGGAGT TGCAGTTATT 4800
TTGCAACTGA TGGTGGAACT GGTGCTTAAA GCAGATTCCC TAGGTTCCCT GCTACTTCTT 4860
TTCCTTCTTG GCAGTCAGTT TATTTCTGAC AGACAAACAG CCACCCCCAC TGCAGGCTTA 4920
GAAAGTATGT GGCTCTGCCT GGGTGTGTTA CAGCTCTGCC CTGGTGAAAG GGGATTAAAA 4980
CGGGCACCAT TCATCCCAAA CAGGATCCTC ATTCATGGAT CAAGCTGTAA GGAACTTGGG 5040
CTCCAACCTC AAAACATTAA TTGGAGTACG AATGTAATTA AACTGCATT CTCGCATTCC 5100
TAAGTCATTT AGTCTGGACT CTGCAGCATG TAGGTCGGCA GCTCCCACTT TCTCAAAGAC 5160
CACTGATGGA GGAGTAGTAA AAATGGAGAC CGATTCAGAA CAACCAACGG AGTGTTGCCG 5220
AAGAAACTGA TGGAAATAAT GCATGAATTG TGTGGTGGAC ATTTTTTTA AATACATAAA 5280
CTACTTCAAA TGAGGTCGGA GAAGGTCAGT GTTTATTAG CAGCCATAAA ACCAGGTGAG 5340
CGAGTACCAT TTTTCTCTAC AAGAAAAACG ATTCTGAGCT CTGCGTAAGT ATAAGTTCTC 5400
```

FIG. 1B

```
CATAGCGGCT GAAGCTCCCC CCTGGCTGCC TGCCATCTCA GCTGGAGTGC AGTGCCATTT 5460
CCTTGGGGTT TCTCTCACAG CAGTAATGGG ACAATACTTC ACAAAAATTC TTTCTTTTCC 5520
TGTCATGTGG GATCCCTACT GTGCCCTCCT GGTTTTACGT TACCCCCTGA CTGTTCCATT 5580
CAGCGGTTTG GAAAGAGAAA AAGAATTTGG AAATAAAACA TGTCTACGTT ATCACCTCCT 5640
CCAGCATTTT GGTTTTTAAT TATGTCAATA ACTGGCTTAG ATTTGGAAAT GAGAGGGGGT 5700
TGGGTGTATT ACCGAGGAAC AAAGGAAGGC TTATATAAAC TCAAGTCTTT TATTTAGAGA 5760
ACTGGCAAGC TGTCAAAAAC AAAAAGGCCT TACCACCAAA TTAAGTGAAT AGCCGCTATA 5820
GCCAGCAGGG CCAGCACGAG GGATGGTGCA CTGCTGGCAC TATGCCACGG CCTGCTTGTG 5880
ACTCTGAGAG CAACTGCTTT GGAAATGACA GCACTTGGTG CAATTTCCTT TGTTTCAGAA 5940
TGCGTAGAGC GTGTGCTTGG CGACAGTTTT TCTAGTTAGG CCACTTCTTT TTTCCTTCTC 6000
TCCTCATTCT CCTAAGCATG TCTCCATGCT GGTAATCCCA GTCAAGTGAA CGTTCAAACA 6060
ATGAATCCAT CACTGTAGGA TTCTCGTGGT GATCAAATCT TTGTGTGAGG TCTATAAAAT 6120
ATGGAAGCTT ATTTATTTTT CGTTCTTCCA TATCAGTCTT CTCTATGACA ATTCACATCC 6180
ACCACAGCAA ATTAAAGGTG AAGGAGGCTG GTGGGATGAA GAGGGTCTTC TAGCTTTACG 6240
TTCTTCCTTG CAAGGCCACA GGAAAATGCT GAGAGCTGTA GAATACAGCC TGGGGTAAGA 6300
AGTTCAGTCT CCTGCTGGGA CAGCTAACCG CATCTTATAA CCCCTTCTGA GACTCATCTT 6360
AGGACCAAAT AGGGTCTATC TGGGGTTTTT GTTCCTGCTG TTCCTCCTGG AAGGCTATCT 6420
CACTATTTCA CTGCTCCCAC GGTTACAAAC CAAAGATACA GCCTGAATTT TTTCTAGGCC 6480
ACATTACATA AATTTGACCT GGTACCAATA TTGTTCTCTA TATAGTTATT CCTTCCCCA 6540
CTGTGTTTAA CCCCTTAAGG CATTCAGAAC AACTAGAATC ATAGAATGGT TTGGATTGGA 6600
AGGGGCCTTA AACATCATCC ATTTCCAACC CTCTGCCATG GGCTGCTTGC CACCCACTGG 6660
CTCAGGCTGC CCAGGGCCCC ATCCAGCCTG GCCTTGAGCA CCTCCAGGGA TGGGGCACCC 6720
ACAGCTTCTC TGGGCAGCCT GTGCCAACAC CTCACCACTC TCTGGGTAAA GAATTCTCTT 6780
TTAACATCTA ATCTAAATCT CTTCTCTTTT AGTTTAAAGC CATTCCTCTT TTTCCCGTTG 6840
CTATCTGTCC AAGAAATGTG TATTGGTCTC CCTCCTGCTT ATAAGCAGGA AGTACTGGAA 6900
GGCTGCAGTG AGGTCTCCCC ACAGCCTTCT CTTCTCCAGG CTGAACAAGC CCAGCTCCTT 6960
CAGCCTGTCT TCGTAGGAGA TCATCTTAGT GGCCCTCCTC TGGACCCATT CCAACAGTTC 7020
CACGGCTTTC TTGTGGAGCC CCAGGTCTGG ATGCAGTACT TCAGATGGGG CCTTACAAAG 7080
GCAGAGCAGA TGGGGACAAT CGCTTACCCC TCCTGCTGG CTGCCCCTGT TTTGATGCAG 7140
CCCAGGGTAC TGTTGGCCTT TCAGGCTCCC AGACCCCTTG CTGATTTGTG TCAAGCTTTT 7200
CATCCACCAG AACCCACGCT TCCTGGTTAA TACTTCTGCC CTCACTTCTG TAAGCTTGTT 7260
TCAGGAGACT TCCATTCTTT AGGACAGACT GTGTTACACC TACCTGCCCT ATTCTTGCAT 7320
ATATACATTT CAGTTCATGT TTCCTGTAAC AGGACAGAAT ATGTATTCCT CTAACAAAAA 7380
TACATGCAGA ATTCCTAGTG CCATCTCAGT AGGGTTTTCA TGGCAGTATT AGCACATAGT 7440
CAATTTGCTG CAAGTACCTT CCAAGCTGCG GCCTCCCATA AATCCTGTAT TTGGGATCAG 7500
TTACCTTTTG GGGTAAGCTT TTGTATCTGC AGAGACCCTG GGGGTTCTGA TGTGCTTCAG 7560
CTCTGCTCTG TTCTGACTGC ACCATTTTCT AGATCACCCA GTTGTTCCTG TACAACTTCC 7620
TTGTCCTCCA TCCTTTCCCA GCTTGTATCT TTGACAAATA CAGGCCTATT TTTGTGTTTG 7680
CTTCAGCAGC CATTTAATTC TTCAGTGTCA TCTTGTTCTG TTGATGCCAC TGGAACAGGA 7740
TTTTCAGCAG TCTTGCAAAG AACATCTAGC TGAAACTTT CTGCCATTCA ATATTCTTAC 7800
CAGTTCTTCT TGTTTGAGGT GAGCCATAAA TTACTAGAAC TTCGTCACTG ACAAGTTTAT 7860
GCATTTTATT ACTTCTATTA TGTACTTACT TTGACATAAC ACAGACACGC ACATATTTTG 7920
CTGGGATTTC CACAGTGTCT CTGTGTCCTT CACATGGTTT TACTGTCATA CTTCCGTTAT 7980
AACCTTGGCA ATCTGCCCAG CTGCCCATCA CAAGAAAGA GATTCCTTTT TTATTACTTC 8040
```

FIG. 1C

```
TCTTCAGCCA ATAAACAAAA TGTGAGAAGC CCAAACAAGA ACTTGTGGGG CAGGCTGCCA 8100
TCAAGGGAGA GACAGCTGAA GGGTTGTGTA GCTCAATAGA ATTAAGAAAT AATAAAGCTG 8160
TGTCAGACAG TTTTGCCTGA TTTATACAGG CACGCCCCAA GCCAGAGAGG CTGTCTGCCA 8220
AGGCCACCTT GCAGTCCTTG GTTTGTAAGA TAAGTCATAG GTAACTTTTC TGGTGAATTG 8280
CGTGGAGAAT CATGATGGCA GTTCTTGCTG TTTACTATGG TAAGATGCTA AAATAGGAGA 8340
CAGCAAAGTA ACACTTGCTG CTGTAGGTGC TCTGCTATCC AGACAGCGAT GGCACTCGCA 8400
CACCAAGATG AGGGATGCTC CCAGCTGACG GATGCTGGGG CAGTAACAGT GGGTCCCATG 8460
CTGCCTGCTC ATTAGCATCA CCTCAGCCCT CACCAGCCCA TCAGAAGGAT CATCCCAAGC 8520
TGAGGAAAGT TGCTCATCTT CTTCACATCA TCAAACCTTT GGCCTGACTG ATGCCTCCCG 8580
GATGCTTAAA TGTGGTCACT GACATCTTTA TTTTTCTATG ATTTCAAGTC AGAACCTCCG 8640
GATCAGGAGG GAACACATAG TGGGAATGTA CCCTCAGCTC CAAGGCCAGA TCTTCCTTCA 8700
ATGATCATGC ATGCTACTTA GGAAGGTGTG TGTGTGTGAA TGTAGAATTG CCTTTGTTAT 8760
TTTTTCTTCC TGCTGTCAGG AACATTTTGA ATACCAGAGA AAAAGAAAAG TGCTCTTCTT 8820
GGCATGGGAG GAGTTGTCAC ACTTGCAAAA TAAAGGATGC AGTCCCAAAT GTTCATAATC 8880
TCAGGGTCTG AAGGAGGATC AGAAACTGTG TATACAATTT CAGGCTTCTC TGAATGCAGC 8940
TTTTGAAAGC TGTTCCTGGC CGAGGCAGTA CTAGTCAGAA CCCTCGGAAA CAGGAACAAA 9000
TGTCTTCAAG GTGCAGCAGG AGGAAACACC TTGCCCATCA TGAAAGTGAA TAACCACTGC 9060
CGCTGAAGGA ATCCAGCTCC TGTTTGAGCA GGTGCTGCAC ACTCCCACAC TGAAACAACA 9120
GTTCATTTTT ATAGGACTTC CAGGAAGGAT CTTCTTCTTA AGCTTCTTAA TTATGGTACA 9180
TCTCCAGTTG GCAGATGACT ATGACTACTG ACAGGAGAAT GAGGAACTAG CTGGGAATAT 9240
TTCTGTTTGA CCACCATGGA GTCACCCATT TCTTTACTGG TATTTGGAAA TAATAATTCT 9300
GAATTGCAAA GCAGGAGTTA GCGAAGATCT TCATTTCTTC CATGTTGGTG ACAGCACAGT 9360
TCTGGCTATG AAAGTCTGCT TACAAGGAAG AGGATAAAAA TCATAGGGAT AATAAATCTA 9420
AGTTTGAAGA CAATGAGGTT TTAGCTGCAT TTGACATGAA GAAATTGAGA CCTCTACTGG 9480
ATAGCTATGG TATTTACGTG TCTTTTTGCT TAGTTACTTA TTGACCCCAG CTGAGGTCAA 9540
GTATGAACTC AGGTCTCTCG GCTACTGGC ATGGATTGAT TACATACAAC TGTAATTTTA 9600
GCAGTGATTT AGGGTTTATG AGTACTTTTG CAGTAAATCA TAGGGTTAGT AATGTTAATC 9660
TCAGGGAAAA AAAAAAAAAG CCAACCCTGA CAGACATCCC AGCTCAGGTG GAAATCAAGG 9720
ATCACAGCTC AGTGCGGTCC CAGAGAACAC AGGGACTCTT CTCTTAGGAC CTTTATGTAC 9780
AGGGCCTCAA GATAACTGAT GTTAGTCAGA AGACTTTCCA TTCTGGCCAC AGTTCAGCTG 9840
AGGCAATCCT GGAATTTTCT CTCCGCTGCA CAGTTCCAGT CATCCCAGTT TGTACAGTTC 9900
TGGCACTTTT TGGGTCAGGC CGTGATCCAA GGAGCAGAAG TTCCAGCTAT GGTCAGGGAG 9960
TGCCTGACCG TCCCAACTCA CTGCACTCAA ACAAGGCGA AACCACAAGA GTGGCTTTTG 10020
TTGAAATTGC AGTGTGGCCC AGAGGGGCTG CACCAGTACT GGATTGACCA CGAGGCAACA 10080
TTAATCCTCA GCAAGTGCAA TTTGCAGCCA TTAAATTGAA CTAACTGATA CTACAATGCA 10140
ATCAGTATCA ACAAGTGGTT TGGCTTGGAA GATGGAGTCT AGGGGCTCTA CAGGAGTAGC 10200
TACTCTCTAA TGGAGTTGCA TTTTGAAGCA GGACACTGTG AAAAGCTGGC CTCCTAAAGA 10260
GGCTGCTAAA CATTAGGGTC AATTTTCCAG TGCACTTTCT GAAGTGTCTG CAGTTCCCCA 10320
TGCAAAGCTG CCCAAACATA GCACTTCCAA TTGAATACAA TTATATGCAG GCGTACTGCT 10380
TCTTGCCAGC ACTGTCCTTC TCAAATGAAC TCAACAAACA ATTTCAAAGT CTAGTAGAAA 10440
GTAACAAGCT TTGAATGTCA TTAAAAAGTA TATCTGCTTT CAGTAGTTCA GCTTATTTAT 10500
GCCCACTAGA AACATCTTGT ACAAGCTGAA CACTGGGGCT CCAGATTAGT GGTAAAACCT 10560
ACTTTATACA ATCATAGAAT CATAGAATGG CCTGGGTTGG AAGGGACCCC AAGGATCATG 10620
AAGATCCAAC ACCCCGCCA CAGGCAGGGC CACCAACCTC CAGATCTGGT ACTAGACCAG 10680
GCAGCCCAGG GCTCCATCCA ACCTGGCCAT GAACACCTCC AGGGATGGAG CATCCACAAC 10740
```

FIG. 1D

```
CTCTCTGGGC AGCCTGTGCC AGCACCTCAC CACCCTCTCT GTGAAGAACT TTTCCCTGAC 10800
ATCCAATCTA AGCCTTCCCT CCTTGAGGTT AGATCCACTC CCCCTTGTGC TATCACTGTC 10860
TACTCTTGTA AAAAGTTGAT TCTCCTCCTT TTTGGAAGGT TGCAATGAGG TCTCCTTGCA 10920
GCCTTCTTCT CTTCTGCAGG ATGAACAAGC CAGCTCCCT  CAGCCTGTCT TTATAGGAGA 10980
GGTGCTCCAG CCCTCTGATC ATCTTTGTGG CCCTCCTCTG GACCCGCTCC AAGAGCTCCA 11040
CATCTTTCCT GTACTGGGGG CCCCAGGCCT GAATGCAGTA CTCCAGATGG GGCCTCAAAA 11100
GAGCAGAGTA AAGAGGGACA ATCACCTTCC TCACCCTGCT GGCCAGCCCT CTTCTGATGG 11160
AGCCCTGGAT ACAACTGGCT TTCTGAGCTG CAACTTCTCC TTATCAGTTC CACTATTAAA 11220
ACAGGAACAA TACAACAGGT GCTGATGGCC AGTGCAGAGT TTTTCACACT TCTTCATTTC 11280
GGTAGATCTT AGATGAGGAA CGTTGAAGTT GTGCTTCTGC GTGTGCTTCT TCCTCCTCAA 11340
ATACTCCTGC CTGATACCTC ACCCCACCTG CCACTGAATG GCTCCATGGC CCCCTGCAGC 11400
CAGGGCCCTG ATGAACCCGG CACTGCTTCA GATGCTGTTT AATAGCACAG TATGACCAAG 11460
TTGCACCTAT GAATACACAA ACAATGTGTT GCATCCTTCA GCACTTGAGA AGAAGAGCCA 11520
AATTTGCATT GTCAGGAAAT GGTTTAGTAA TTCTGCCAAT TAAAACTTGT TTATCTACCA 11580
TGGCTGTTTT TATGGCTGTT AGTAGTGGTA CACTGATGAT GAACAATGGC TATGCAGTAA 11640
AATCAAGACT GTAGATATTG CAACAGACTA TAAAATTCCT CTGTGGCTTA GCCAATGTGG 11700
TACTTCCCAC ATTGTATAAG AAATTTGGCA AGTTTAGAGC AATGTTTGAA GTGTTGGGAA 11760
ATTTCTGTAT ACTCAAGAGG GCGTTTTTGA CAACTGTAGA ACAGAGGAAT CAAAAGGGGG 11820
TGGGAGGAAG TTAAAGAAG  AGGCAGGTGC AAGAGAGCTT GCAGTCCCGC TGTGTGTACG 11880
ACACTGGCAA CATGAGGTCT TTGCTAATCT TGGTGCTTTG CTTCCTGCCC CTGGCTGCCT 11940
TAGGGTGCGA TCTGCCTCAG ACCCACAGCC TGGGCAGCAG GAGGACCCTG ATGCTGCTGG 12000
CTCAGATGAG GAGAATCAGC CTGTTTAGCT GCCTGAAGGA TAGGCACGAT TTTGGCTTTC 12060
CTCAAGAGGA GTTTGGCAAC CAGTTTCAGA AGGCTGAGAC CATCCCTGTG CTGCACGAGA 12120
TGATCCAGCA GATCTTTAAC CTGTTTAGCA CCAAGGATAG CAGCGCTGCT TGGGATGAGA 12180
CCCTGCTGGA TAAGTTTTAC ACCGAGCTGT ACCAGCAGCT GAACGATCTG GAGGCTTGCG 12240
TGATCCAGGG CGTGGGCGTG ACCGAGACCC CTCTGATGAA GGAGGATAGC ATCCTGGCTG 12300
TGAGGAAGTA CTTTCAGAGG ATCACCCTGT ACCTGAAGGA AAGAAGTAC  AGCCCCTGCG 12360
CTTGGGAAGT CGTGAGGGCT GAGATCATGA GGAGCTTTAG CCTGAGCACC AACCTGCAAG 12420
AGAGCTTGAG GTCTAAGGAG TAAAAAGTCT AGAGTCGGGG CGGCCGGCCG CTTCGAGCAG 12480
ACATGATAAG ATACATTGAT GAGTTTGGAC AAACCACAAC TAGAATGCAG TGAAAAAAAT 12540
GCTTTATTTG TGAAATTTGT GATGCTATTG CTTTATTTGT AACCATTATA AGCTGCAATA 12600
AACAAGTTAA CAACAACAAT TGCATTCATT TTATGTTTCA GGTTCAGGGG GAGGTGTGGG 12660
AGGTTTTTTA AAGCAAGTAA AACCTCTACA AATGTGGTAA AATCGATAAG GATCCGTCGA 12720
GCGGCCGC         12728
```

FIG. 1E

SEQ ID NO: 5

```
TGCGATCTGC CTCAGACCCA CAGCCTGGGC AGCAGGAGGA CCCTGATGCT GCTGGCTCAG  60
ATGAGGAGAA TCAGCCTGTT TAGCTGCCTG AAGGATAGGC ACGATTTTGG CTTTCCTCAA 120
GAGGAGTTTG GCAACCAGTT TCAGAAGGCT GAGACCATCC CTGTGCTGCA CGAGATGATC 180
CAGCAGATCT TTAACCTGTT TAGCACCAAG GATAGCAGCG CTGCTTGGGA TGAGACCCTG 240
CTGGATAAGT TTTACACCGA GCTGTACCAG CAGCTGAACG ATCTGGAGGC TTGCGTGATC 300
CAGGGCGTGG GCGTGACCGA GACCCCTCTG ATGAAGGAGG ATAGCATCCT GGCTGTGAGG 360
AAGTACTTTC AGAGGATCAC CCTGTACCTG AAGGAGAAGA AGTACAGCCC CTGCGCTTGG 420
GAAGTCGTGA GGGCTGAGAT CATGAGGAGC TTTAGCCTGA GCACCAACCT GCAAGAGAGC 480
TTGAGGTCTA AGGAGTAA 498
```

FIG. 2

SEQ ID NO: 7

```
TGCCGCCTTC TTTGATATTC ACTCTGTTGT ATTTCATCTC TTCTTGCCGA TGAAAGGATA 60
TAACAGTCTG TATAACAGTC TGTGAGGAAA TACTTGGTAT TTCTTCTGAT CAGTGTTTTT 120
ATAAGTAATG TTGAATATTG GATAAGGCTG TGTGTCCTTT GTCTTGGGAG ACAAAGCCCA 180
CAGCAGGTGG TGGTTGGGGT GGTGGCAGCT CAGTGACAGG AGAGGTTTTT TTGCCTGTTT 240
TTTTTTTTTT TTTTTTTTTT AAGTAAGGTG TTCTTTTTTC TTAGTAAATT TTCTACTGGA 300
CTGTATGTTT TGACAGGTCA GAAACATTTC TTCAAAAGAA GAACCTTTTG GAAACTGTAC 360
AGCCCTTTTC TTTCATTCCC TTTTTGCTTT CTGTGCCAAT GCCTTGGTT CTGATTGCAT 420
TATGGAAAAC GTTGATCGGA ACTTGAGGTT TTTATTTATA GTGTGGCTTG AAAGCTTGGA 480
TAGCTGTTGT TACACGAGAT ACCTTATTAA GTTTAGGCCA GCTTGATGCT TTATTTTTC 540
CCTTTGAAGT AGTGAGCGTT CTCTGGTTTT TTTCCTTTGA AACTGGTGAG GCTTAGATTT 600
TTCTAATGGG ATTTTTACC TGATGATCTA GTTGCATACC CAAATGCTTG TAAATGTTTT 660
CCTAGTTAAC ATGTTGATAA CTTCGGATTT ACATGTTGTA TATACTTGTC ATCTGTGTTT 720
CTAGTAAAAA TATATGGCAT TTATAGAAAT ACGTAATTCC TGATTTCCTT TTTTTTATC 780
TCTATGCTCT GTGTGTACAG GTCAAACAGA CTTCACTCCT ATTTTATTT ATAGAATTTT 840
ATATGCAGTC TGTCGTTGGT TCTTGTGTTG TAAGGATACA GCCTTAAATT TCCTAGAGCG 900
ATGCTCAGTA AGGCGGGTTG TCACATGGGT TCAAATGTAA AACGGGCACG TTTGGCTGCT 960
GCCTTCCCGA GATCCAGGAC ACTAAACTGC TTCTGCACTG AGGTATAAAT CGCTTCAGAT 1020
CCCAGGGAAG TGCAGATCCA CGTGCATATT CTTAAAGAAG AATGAATACT TTCTAAAATA 1080
TTTTGGCATA GGAAGCAAGC TGCATGGATT TGTTTGGGAC TTAAATTATT TTGGTAACGG 1140
AGTGCATAGG TTTTAAACAC AGTTGCAGCA TGCTAACGAG TCACAGCGTT TATGCAGAAG 1200
TGATGCCTGG ATGCCTGTTG CAGCTGTTTA CGGCACTGCC TTGCAGTGAG CATTGCAGAT 1260
AGGGGTGGGG TGCTTTGTGT CGTGTTCCCA CACGCTGCCA CACAGCCACC TCCCGGAACA 1320
CATCTCACCT GCTGGGTACT TTTCAAACCA TCTTAGCAGT AGTAGATGAG TTACTATGAA 1380
ACAGAGAAGT TCCTCAGTTG GATATTCTCA TGGGATGTCT TTTTTCCCAT GTTGGGCAAA 1440
GTATGATAAA GCATCTCTAT TTGTAAATTA TGCACTTGTT AGTTCCTGAA TCCTTTCTAT 1500
AGCACCACTT ATTGCAGCAG GTGTAGGCTC TGGTGTGGCC TGTGTCTGTG CTTCAATCTT 1560
TTAAAGCTTC TTTGGAAATA CACTGACTTG ATTGAAGTCT CTTGAAGATA GTAAACAGTA 1620
CTTACCTTTG ATCCCAATGA AATCGAGCAT TCAGTTGTA AAAGAATTCC GCCTATTCAT 1680
ACCATGTAAT GTAATTTTAC ACCCCAGTG CTGACACTTT GGAATATATT CAAGTAATAG 1740
ACTTTGGCCT CACCCTCTTG TGTACTGTAT TTTGTAATAG AAAATATTTT AAACTGTGCA 1800
TATGATTATT ACATTATGAA AGAGACATTC TGCTGATCTT CAAATGTAAG AAAATGAGGA 1860
GTGCGTGTGC TTTTATAAAT ACAAGTGATT GCAAATTAGT GCAGGTGTCC TTAAAAAAAA 1920
AAAAAAAAG TAATATAAAA AGGACCAGGT GTTTTACAAG TGAAATACAT TCCTATTTGG 1980
TAAACAGTTA CATTTTATG AAGATTACCA GCGCTGCTGA CTTTCTAAAC ATAAGGCTGT 2040
ATTGTCTTCC TGTACCATTG CATTTCCTCA TTCCCAATTT GCACAAGGAT GTCTGGGTAA 2100
ACTATTCAAG AAATGGCTTT GAAATACAGC ATGGGAGCTT GTCTGAGTTG GAATGCAGAG 2160
TTGCACTGCA AAATGTCAGG AAATGGATGT CTCTCAGAAT GCCCAACTCC AAAGGATTTT 2220
ATATGTGTAT ATAGTAAGCA GTTTCCTGAT TCCAGCAGGC CAAAGAGTCT GCTGAATGTT 2280
GTGTTGCCGG AGACCTGTAT TTCTCAACAA GGTAAGATGG TATCCTAGCA ACTGCGGATT 2340
TTAATACATT TCAGCAGAA GTACTTAGTT AATCTCTACC TTTAGGGATC GTTTCATCAT 2400
TTTTAGATGT TATACTTGAA ATACTGCATA ACTTTTAGCT TTCATGGGTT CCTTTTTTC 2460
AGCCTTTAGG AGACTGTTAA GCAATTTGCT GTCCAACTTT TGTGTTGGTC TTAAACTGCA 2520
ATAGTAGTTT ACCTTGTATT GAAGAAATAA AGACCATTTT TATATTAAAA AATACTTTTG 2580
TCTGTCTTCA TTTTGACTTG TCTGATATCC TTGCAGTGCC CATTATGTCA GTTCTGTCAG 2640
ATATTCAGAC ATCAAAACTT AACGTGAGCT CAGTGGAGTT ACAGCTGCGG TTTTGATGCT 2700
```

FIG. 3A

```
GTTATTATTT CTGAAACTAG AAATGATGTT GTCTTCATCT GCTCATCAAA CACTTCATGC 2760
AGAGTGTAAG GCTAGTGAGA AATGCATACA TTTATTGATA CTTTTTTAAA GTCAACTTTT 2820
TATCAGATTT TTTTTTCATT TGGAAATATA TTGTTTTCTA GACTGCATAG CTTCTGAATC 2880
TGAAATGCAG TCTGATTGGC ATGAAGAAGC ACAGCACTCT TCATCTTACT TAAACTTCAT 2940
TTTGGAATGA AGGAAGTTAA GCAAGGGCAC AGGTCCATGA AATAGAGACA GTGCGCTCAG 3000
GAGAAAGTGA ACCTGGATTT CTTTGGCTAG TGTTCTAAAT CTGTAGTGAG GAAAGTAACA 3060
CCCGATTCCT TGAAAGGGCT CCAGCTTTAA TGCTTCCAAA TTGAAGGTGG CAGGCAACTT 3120
GGCCACTGGT TATTTACTGC ATTATGTCTC AGTTTCGCAG CTAACCTGGC TTCTCCACTA 3180
TTGAGCATGG ACTATAGCCT GGCTTCAGAG GCCAGGTGAA GGTTGGGATG GGTGGAAGGA 3240
GTGCTGGGCT GTGGCTGGGG GGACTGTGGG GACTCCAAGC TGAGCTTGGG GTGGGCAGCA 3300
CAGGGAAAAG TGTGGGTAAC TATTTTTAAG TACTGTGTTG CAAACGTCTC ATCTGCAAAT 3360
ACGTAGGGTG TGTACTCTCG AAGATTAACA GTGTGGGTTC AGTAATATAT GGATGAATTC 3420
ACAGTGGAAG CATTCAAGGG TAGATCATCT AACGACACCA GATCATCAAG CTATGATTGG 3480
AAGCGGTATC AGAAGAGCGA GGAAGGTAAG CAGTCTTCAT ATGTTTTCCC TCCACGTAAA 3540
GCAGTCTGGG AAAGTAGCAC CCCTTGAGCA GAGACAAGGA AATAATTCAG GAGCATGTGC 3600
TAGGAGAACT TTCTTGCTGA ATTCTACTTG CAAGAGCTTT GATGCCTGGC TTCTGGTGCC 3660
TTCTGCAGCA CCTGCAAGGC CCAGAGCCTG TGGTGAGCTG GAGGGAAAGA TTCTGCTCAA 3720
GTCCAAGCTT CAGCAGGTCA TTGTCTTTGC TTCTTCCCCC AGCACTGTGC AGCAGAGTGG 3780
AACTGATGTC GAAGCCTCCT GTCCACTACC TGTTGCTGCA GGCAGACTGC TCTCAGAAAA 3840
AGAGAGCTAA CTCTATGCCA TAGTCTGAAG GTAAAATGGG TTTTAAAAAA GAAAACACAA 3900
AGGCAAAACC GGCTGCCCCA TGAGAAGAAA GCAGTGGTAA ACATGGTAGA AAAGGTGCAG 3960
AAGCCCCCAG GCAGTGTGAC AGGCCCCTCC TGCCACCTAG AGGCGGGAAC AAGCTTCCCT 4020
GCCTAGGGCT CTGCCCGCGA AGTGCGTGTT TCTTTGGTGG GTTTTGTTTG GCGTTTGGTT 4080
TTGAGATTTA GACACAAGGG AAGCCTGAAA GGAGGTGTTG GCACTATTT TGGTTTGTAA 4140
AGCCTGTACT TCAAATATAT ATTTGTGAG GGAGTGTAGC GAATTGGCCA ATTTAAAATA 4200
AAGTTGCAAG AGATTGAAGG CTGAGTAGTT GAGAGGGTAA CACGTTTAAT GAGATCTTCT 4260
GAAACTACTG CTTCTAAACA CTTGTTTGAG TGGTGAGACC TTGGATAGGT GAGTGCTCTT 4320
GTTACATGTC TGATGCACTT GCTTGTCCTT TTCCATCCAC ATCCATGCAT TCCACATCCA 4380
CGCATTTGTC ACTTATCCCA TATCTGTCAT ATCTGACATA CCTGTCTCTT CGTCACTTGG 4440
TCAGAAGAAA CAGATGTGAT AATCCCCAGC CGCCCCAAGT TTGAGAAGAT GGCAGTTGCT 4500
TCTTTCCCTT TTTCCTGCTA AGTAAGGATT TTCTCCTGGC TTTGACACCT CACGAAATAG 4560
TCTTCCTGCC TTACATTCTG GGCATTATTT CAAATATCTT TGGAGTGCGC TGCTCTCAAG 4620
TTTGTGTCTT CCTACTCTTA GAGTGAATGC TCTTAGAGTG AAAGAGAAGG AAGAGAAGAT 4680
GTTGGCCGCA GTTCTCTGAT GAACACACCT CTGAATAATG GCCAAAGGTG GGTGGGTTTC 4740
TCTGAGGAAC GGGCAGCGTT TGCCTCTGAA AGCAAGGAGC TCTGCGGAGT TGCAGTTATT 4800
TTGCAACTGA TGGTGGAACT GGTGCTTAAA GCAGATTCCC TAGGTTCCCT GCTACTTCTT 4860
TTCCTTCTTG GCAGTCAGTT TATTCTGAC AGACAAACAG CCACCCCCAC TGCAGGCTTA 4920
GAAAGTATGT GGCTCTGCCT GGGTGTGTTA CAGCTCTGCC CTGGTGAAAG GGGATTAAAA 4980
CGGGCACCAT TCATCCCAAA CAGGATCCTC ATTCATGGAT CAAGCTGTAA GGAACTTGGG 5040
CTCCAACCTC AAAACATTAA TTGGAGTACG AATGTAATTA AAACTGCATT CTCGCATTCC 5100
TAAGTCATTT AGTCTGGACT CTGCAGCATG TAGGTCGGCA GCTCCCACTT TCTCAAAGAC 5160
CACTGATGGA GGAGTAGTAA AAATGGAGAC CGATTCAGAA CAACCAACGG AGTGTTGCCG 5220
AAGAAACTGA TGGAAATAAT GCATGAATTG TGTGGTGGAC ATTTTTTTA AATACATAAA 5280
CTACTTCAAA TGAGGTCGGA GAAGGTCAGT GTTTATTAG CAGCCATAAA ACCAGGTGAG 5340
CGAGTACCAT TTTTCTCTAC AAGAAAAACG ATTCTGAGCT CTGCGTAAGT ATAAGTTCTC 5400
```

FIG. 3B

```
CATAGCGGCT GAAGCTCCCC CCTGGCTGCC TGCCATCTCA GCTGGAGTGC AGTGCCATTT 5460
CCTTGGGGTT TCTCTCACAG CAGTAATGGG ACAATACTTC ACAAAAATTC TTTCTTTTCC 5520
TGTCATGTGG GATCCCTACT GTGCCCTCCT GGTTTTACGT TACCCCCTGA CTGTTCCATT 5580
CAGCGGTTTG GAAAGAGAAA AAGAATTTGG AAATAAAACA TGTCTACGTT ATCACCTCCT 5640
CCAGCATTTT GGTTTTTAAT TATGTCAATA ACTGGCTTAG ATTTGGAAAT GAGAGGGGGT 5700
TGGGTGTATT ACCGAGGAAC AAAGGAAGGC TTATATAAAC TCAAGTCTTT TATTTAGAGA 5760
ACTGGCAAGC TGTCAAAAAC AAAAAGGCCT TACCACCAAA TTAAGTGAAT AGCCGCTATA 5820
GCCAGCAGGG CCAGCACGAG GGATGGTGCA CTGCTGGCAC TATGCCACGG CCTGCTTGTG 5880
ACTCTGAGAG CAACTGCTTT GGAAATGACA GCACTTGGTG CAATTTCCTT TGTTTCAGAA 5940
TGCGTAGAGC GTGTGCTTGG CGACAGTTTT TCTAGTTAGG CCACTTCTTT TTTCCTTCTC 6000
TCCTCATTCT CCTAAGCATG TCTCCATGCT GGTAATCCCA GTCAAGTGAA CGTTCAAACA 6060
ATGAATCCAT CACTGTAGGA TTCTCGTGGT GATCAAATCT TTGTGTGAGG TCTATAAAAT 6120
ATGGAAGCTT ATTTATTTTT CGTTCTTCCA TATCAGTCTT CTCTATGACA ATTCACATCC 6180
ACCACAGCAA ATTAAGGTG AAGGAGGCTG GTGGGATGAA GAGGGTCTTC TAGCTTTACG 6240
TTCTTCCTTG CAAGGCCACA GGAAAATGCT GAGAGCTGTA GAATACAGCC TGGGGTAAGA 6300
AGTTCAGTCT CCTGCTGGGA CAGCTAACCG CATCTTATAA CCCCTTCTGA GACTCATCTT 6360
AGGACCAAAT AGGGTCTATC TGGGGTTTTT GTTCCTGCTG TTCCTCCTGG AAGGCATCT 6420
CACTATTTCA CTGCTCCCAC GGTTACAAAC CAAAGATACA GCCTGAATTT TTTCTAGGCC 6480
ACATTACATA AATTTGACCT GGTACCAATA TTGTTCTCTA TATAGTTATT TCCTTCCCCA 6540
CTGTGTTTAA CCCCTTAAGG CATTCAGAAC AACTAGAATC ATAGAATGGT TTGGATTGGA 6600
AGGGGCCTTA AACATCATCC ATTTCCAACC CTCTGCCATG GCTGCTTGC CACCCACTGG 6660
CTCAGGCTGC CCAGGGCCCC ATCCAGCCTG GCCTTGAGCA CCTCCAGGGA TGGGGCACCC 6720
ACAGCTTCTC TGGGCAGCCT GTGCCAACAC CTCACCACTC TCTGGGTAAA GAATTCTCTT 6780
TTAACATCTA ATCTAAATCT CTTCTCTTTT AGTTTAAAGC CATTCCTCTT TTTCCCGTTG 6840
CTATCTGTCC AAGAAATGTG TATTGGTCTC CCTCCTGCTT ATAAGCAGGA AGTACTGGAA 6900
GGCTGCAGTG AGGTCTCCCC ACAGCCTTCT CTTCTCCAGG CTGAACAAGC CAGCTCCTT 6960
CAGCCTGTCT TCGTAGGAGA TCATCTTAGT GGCCCTCCTC TGGACCCATT CCAACAGTTC 7020
CACGGCTTTC TTGTGGAGCC CCAGGTCTGG ATGCAGTACT TCAGATGGGG CCTTACAAAG 7080
GCAGAGCAGA TGGGGACAAT CGCTTACCCC TCCTGCTGG CTGCCCCTGT TTTGATGCAG 7140
CCCAGGGTAC TGTTGGCCTT TCAGGCTCCC AGACCCCTTG CTGATTGTG TCAAGCTTTT 7200
CATCCACCAG AACCCACGCT TCCTGGTTAA TACTTCTGCC CTCACTTCTG TAAGCTTGTT 7260
TCAGGAGACT TCCATTCTTT AGGACAGACT GTGTTACACC TACCTGCCCT ATTCTTGCAT 7320
ATATACATTT CAGTTCATGT TTCCTGTAAC AGGACAGAAT ATGTATTCCT CTAACAAAAA 7380
TACATGCAGA ATTCCTAGTG CCATCTCAGT AGGGTTTTCA TGGCAGTATT AGCACATAGT 7440
CAATTTGCTG CAAGTACCTT CCAAGCTGCG GCCTCCCATA AATCCTGTAT TGGGATCAG 7500
TTACCTTTTG GGGTAAGCTT TTGTATCTGC AGAGACCCTG GGGGTTCTGA TGTGCTTCAG 7560
CTCTGCTCTG TTCTGACTGC ACCATTTTCT AGATCACCCA GTTGTTCCTG TACAACTTCC 7620
TTGTCCTCCA TCCTTTCCCA GCTTGTATCT TTGACAAATA CAGGCCTATT TTTGTGTTTG 7680
CTTCAGCAGC CATTTAATTC TTCAGTGTCA TCTTGTTCTG TTGATGCCAC TGGAACAGGA 7740
TTTTCAGCAG TCTTGCAAAG AACATCTAGC TGAAAACTTT CTGCCATTCA ATATTCTTAC 7800
CAGTTCTTCT TGTTTGAGGT GAGCCATAAA TTACTAGAAC TTCGTCACTG ACAAGTTTAT 7860
GCATTTTATT ACTTCTATTA TGTACTTACT TTGACATAAC ACAGACACGC ACATATTTTG 7920
CTGGGATTTC CACAGTGTCT CTGTGTCCTT CACATGGTTT TACTGTCATA CTTCCGTTAT 7980
AACCTTGGCA ATCTGCCCAG CTGCCCATCA CAAGAAAAGA GATTCCTTTT TTATTACTTC 8040
TCTTCAGCCA ATAAACAAAA TGTGAGAAGC CCAAACAAGA ACTTGTGGGG CAGGCTGCCA 8100
```

FIG. 3C

```
TCAAGGGAGA GACAGCTGAA GGGTTGTGTA GCTCAATAGA ATTAAGAAAT AATAAAGCTG 8160
TGTCAGACAG TTTTGCCTGA TTTATACAGG CACGCCCAA  GCCAGAGAGG CTGTCTGCCA 8220
AGGCCACCTT GCAGTCCTTG GTTTGTAAGA TAAGTCATAG GTAACTTTTC TGGTGAATTG 8280
CGTGGAGAAT CATGATGGCA GTTCTTGCTG TTTACTATGG TAAGATGCTA AAATAGGAGA 8340
CAGCAAAGTA ACACTTGCTG CTGTAGGTGC TCTGCTATCC AGACAGCGAT GGCACTCGCA 8400
CACCAAGATG AGGGATGCTC CCAGCTGACG GATGCTGGGG CAGTAACAGT GGGTCCCATG 8460
CTGCCTGCTC ATTAGCATCA CCTCAGCCCT CACCAGCCCA TCAGAAGGAT CATCCCAAGC 8520
TGAGGAAAGT TGCTCATCTT CTTCACATCA TCAAACCTTT GGCCTGACTG ATGCCTCCCG 8580
GATGCTTAAA TGTGGTCACT GACATCTTTA TTTTTCTATG ATTTCAAGTC AGAACCTCCG 8640
GATCAGGAGG GAACACATAG TGGGAATGTA CCCTCAGCTC CAAGGCCAGA TCTTCCTTCA 8700
ATGATCATGC ATGCTACTTA GGAAGGTGTG TGTGTGTGAA TGTAGAATTG CCTTTGTTAT 8760
TTTTTCTTCC TGCTGTCAGG AACATTTTGA ATACCAGAGA AAAAGAAAAG TGCTCTTCTT 8820
GGCATGGGAG GAGTTGTCAC ACTTGCAAAA TAAAGGATGC AGTCCCAAAT GTTCATAATC 8880
TCAGGGTCTG AAGGAGGATC AGAAACTGTG TATACAATTT CAGGCTTCTC TGAATGCAGC 8940
TTTTGAAAGC TGTTCCTGGC CGAGGCAGTA CTAGTCAGAA CCCTCGGAAA CAGGAACAAA 9000
TGTCTTCAAG GTGCAGCAGG AGGAAACACC TTGCCCATCA TGAAAGTGAA TAACCACTGC 9060
CGCTGAAGGA ATCCAGCTCC TGTTTGAGCA GGTGCTGCAC ACTCCCACAC TGAAACAACA 9120
GTTCATTTTT ATAGGACTTC CAGGAAGGAT CTTCTTCTTA AGCTTCTTAA TTATGGTACA 9180
TCTCCAGTTG GCAGATGACT ATGACTACTG ACAGGAGAAT GAGGAACTAG CTGGGAATAT 9240
TTCTGTTTGA CCACCATGGA GTCACCCATT TCTTTACTGG TATTTGGAAA TAATAATTCT 9300
GAATTGCAAA GCAGGAGTTA GCGAAGATCT TCATTTCTTC CATGTTGGTG ACAGCACAGT 9360
TCTGGCTATG AAAGTCTGCT TACAAGGAAG AGGATAAAAA TCATAGGGAT AATAAATCTA 9420
AGTTTGAAGA CAATGAGGTT TTAGCTGCAT TTGACATGAA GAAATTGAGA CCTCTACTGG 9480
ATAGCTATGG TATTTACGTG TCTTTTTGCT TAGTTACTTA TTGACCCCAG CTGAGGTCAA 9540
GTATGAACTC AGGTCTCTCG GCTACTGGC  ATGGATTGAT TACATACAAC TGTAATTTTA 9600
GCAGTGATTT AGGGTTTATG AGTACTTTG  CAGTAAATCA TAGGGTTAGT AATGTTAATC 9660
TCAGGGAAAA AAAAAAAAAG CCAACCCTGA CAGACATCCC AGCTCAGGTG GAAATCAAGG 9720
ATCACAGCTC AGTGCGGTCC CAGAGAACAC AGGGACTCTT CTCTTAGGAC CTTTATGTAC 9780
AGGGCCTCAA GATAACTGAT GTTAGTCAGA AGACTTTCCA TTCTGGCCAC AGTTCAGCTG 9840
AGGCAATCCT GGAATTTTCT CTCCGCTGCA CAGTTCCAGT CATCCCAGTT TGTACAGTTC 9900
TGGCACTTTT TGGGTCAGGC CGTGATCCAA GGAGCAGAAG TTCCAGCTAT GGTCAGGGAG 9960
TGCCTGACCG TCCCAACTCA CTGCACTCAA ACAAAGGCGA AACCACAAGA GTGGCTTTTG 10020
TTGAAATTGC AGTGTGGCCC AGAGGGGCTG CACCAGTACT GGATTGACCA CGAGGCAACA 10080
TTAATCCTCA GCAAGTGCAA TTTGCAGCCA TTAAATTGAA CTAACTGATA CTACAATGCA 10140
ATCAGTATCA ACAAGTGGTT TGGCTTGGAA GATGGAGTCT AGGGGCTCTA CAGGAGTAGC 10200
TACTCTCTAA TGGAGTTGCA TTTTGAAGCA GGACACTGTG AAAAGCTGGC CTCCTAAAGA 10260
GGCTGCTAAA CATTAGGGTC AATTTTCCAG TGCACTTTCT GAAGTGTCTG CAGTTCCCCA 10320
TGCAAAGCTG CCCAAACATA GCACTTCCAA TTGAATACAA TTATATGCAG GCGTACTGCT 10380
TCTTGCCAGC ACTGTCCTTC TCAAATGAAC TCAACAAACA ATTTCAAAGT CTAGTAGAAA 10440
GTAACAAGCT TGAATGTCA  TTAAAAGTA  TATCTGCTTT CAGTAGTTCA GCTTATTTAT 10500
GCCCACTAGA AACATCTTGT ACAAGCTGAA CACTGGGGCT CCAGATTAGT GGTAAAACCT 10560
ACTTTATACA ATCATAGAAT CATAGAATGG CCTGGGTTGG AAGGGACCCC AAGGATCATG 10620
AAGATCCAAC ACCCCCGCCA CAGGCAGGGC CACCAACCTC AGATCTGGT  ACTAGACCAG 10680
GCAGCCCAGG GCTCCATCCA ACCTGGCCAT GAACACCTCC AGGGATGGAG CATCCACAAC 10740
CTCTCTGGGC AGCCTGTGCC AGCACCTCAC CACCCTCTCT GTGAAGAACT TTCCCTGAC  10800
ATCCAATCTA AGCCTTCCCT CCTTGAGGTT AGATCCACTC CCCCTTGTGC TATCACTGTC 10860
```

FIG. 3D

```
TACTCTTGTA AAAAGTTGAT TCTCCTCCTT TTTGGAAGGT TGCAATGAGG TCTCCTTGCA 10920
GCCTTCTTCT CTTCTGCAGG ATGAACAAGC CCAGCTCCCT CAGCCTGTCT TTATAGGAGA 10980
GGTGCTCCAG CCCTCTGATC ATCTTTGTGG CCCTCCTCTG ACCCGCTCC AAGAGCTCCA 11040
CATCTTTCCT GTACTGGGGG CCCCAGGCCT GAATGCAGTA CTCCAGATGG GGCCTCAAAA 11100
GAGCAGAGTA AAGAGGGACA ATCACCTTCC TCACCCTGCT GGCCAGCCCT CTTCTGATGG 11160
AGCCCTGGAT ACAACTGGCT TTCTGAGCTG CAACTTCTCC TTATCAGTTC CACTATTAAA 11220
ACAGGAACAA TACAACAGGT GCTGATGGCC AGTGCAGAGT TTTTCACACT TCTTCATTTC 11280
GGTAGATCTT AGATGAGGAA CGTTGAAGTT GTGCTTCTGC GTGTGCTTCT TCCTCCTCAA 11340
ATACTCCTGC CTGATACCTC ACCCCACCTG CCACTGAATG GCTCCATGGC CCCCTGCAGC 11400
CAGGGCCCTG ATGAACCCGG CACTGCTTCA GATGCTGTTT AATAGCACAG TATGACCAAG 11460
TTGCACCTAT GAATACACAA ACAATGTGTT GCATCCTTCA GCACTTGAGA AGAAGAGCCA 11520
AATTTGCATT GTCAGGAAAT GGTTTAGTAA TTCTGCCAAT TAAAACTTGT TTATCTACCA 11580
TGGCTGTTTT TATGGCTGTT AGTAGTGGTA CACTGATGAT GAACAATGGC TATGCAGTAA 11640
AATCAAGACT GTAGATATTG CAACAGACTA TAAAATTCCT CTGTGGCTTA GCCAATGTGG 11700
TACTTCCCAC ATTGTATAAG AAATTTGGCA AGTTTAGAGC AATGTTTGAA GTGTTGGGAA 11760
ATTTCTGTAT ACTCAAGAGG GCGTTTTTGA CAACTGTAGA ACAGAGGAAT CAAAAGGGGG 11820
TGGGAGGAAG TTAAAAGAAG AGGCAGGTGC AAGAGAGCTT GCAGTCCCGC TGTGTGTACG 11880
ACACTGGCAA CATGAGGTCT TTGCTAATCT TGGTGCTTTG CTTCCTGCCC CTGGCTGCCT 11940
TAGGG 11945
```

FIG. 3E

SEQ ID NO: 8

```
AAAGTCTAGAGTCGGGGCGGCCGGCCGCTTCGAGCAGACATGATAAGATACATTGATGAG    60
TTTGGACAAACCACAACTAGAATGCAGTGAAAAAAATGCTTTATTTGTGAAATTTGTGAT   120
GCTATTGCTTTATTTGTAACCATTATAAGCTGCAATAAACAAGTTAACAACAACAATTGC   180
ATTCATTTTATGTTTCAGGTTCAGGGGGAGGTGTGGGAGGTTTTTTAAAGCAAGTAAAAC   240
CTCTACAAATGTGGTAAAATCGATAAGGATCCGTCGAGCGGCCGC   285
```

FIG. 4

SEQ ID NO: 9

```
   1 CGCGTGGTAGGTGGCGGGGGGTTCCCAGGAGAGCCCCCAGCGCGGACGGC
     AGCGCCGTCACTCACCGCTCCGTCTCCCTCCGCCCAGGGTCGCCTGGCGC
     AACCGCTGCAAGGGCACCGACGTCCAGGCGTGGATCAGAGGCTGCCGGCT
     GTGAGGAGCTGCCGCGCCCGGCCCGCCCGCTGCACAGCCGGCCGCTTTGC
 200 GAGCGCGACGCTACCCGCTTGGCAGTTTTAAACGCATCCCTCATTAAAAC
     GACTATACGCAAACGCCTTCCCGTCGGTCCGCGTCTCTTTCCGCCGCCAG
     GGCGACACTCGCGGGGAGGGCGGGAAGGGGCCGGGCGGGAGCCCGCGGC
     CAACCGTCGCCCCGTGACGGCACCGCCCCGCCCCGTGACGCGGTGCGGG
 400 CGCCGGGGCCGTGGGCTGAGCGCTGCGGCGGGGCCGGGCCGGGCCGGGG
     CGGGAGCTGAGCGCGGCGCGGCTGCGGGCGGCGCCCCCTCCGGTGCAATA
     TGTTCAAGAGAATGGCTGAGTTCGGGCCTGACTCCGGGGCAGGGTGAAG
     GTGCGGCGCGGGCGGAGGGACGGGGCGGGCGCGGGGCCGCCCGGCGGGTG
 600 CCGGGGCCTCTGCCGGCCCGCCCGGCTCGGGCTGCTGCGGCGCTTACGGG
     CGCGCTTCTCGCCGCTGCCGCTTCTCTTCTCTCCCGCGCAAGGGCGTCAC
     CATCGTGAAGCCGGTAGTGTACGGGAACGTGGCGCGGTACTTCGGGAAGA
     AGAGGGAGGAGGACGGGCACACGCATCAGTGGACGGTTTACGTGAAGCCC
 800 TACAGGAACGAGGTAGGGCCCGAGCGCGTCGGCCGCCGTTCTCGGAGCGC
     CGGAGCCGTCAGCGCCGCGCCTGGGTGCGCTGTGGGACACAGCGAGCTTC
     TCTCGTAGGACATGTCCGCCTACGTGAAAAAAATCCAGTTCAAGCTGCAC
     GAGAGCTACGGGAATCCTCTCCGAGGTGGGTGTTGCGTCGGGGGTTTGC
1000 TCCGCTCGGTCCCGCTGAGGCTCGTCGCCCTCATCTTTCTTTCGTGCCGC
     AGTCGTTACCAAACGCCGTACGAGATCACCGAAACGGGCTGGGGCGAAT
     TTGAAATCATCATCAAGATATTTTTCATTGATCCAAACGAGCGACCCGTA
     AGTACGCTCAGCTTCTCGTAGTGCTTCCCCCGTCCTGGCGGCCCGGGGCT
1200 GGGCTGCTCGCTGCTGCCGGTCACAGTCCCGCCAGCCGCGGAGCTGACTG
     AGCTCCCTTTCCCGGGACGTGTGCTCTGTGTTCGGTCAGCGAGGCTATCG
     GGAGGGCTTTGGCTGCATTTGGCTTCTCTGGCGCTTAGCGCAGGAGCACG
     TTGTGCTACGCCTGAACTACAGCTGTGAGAAGGCCGTGGAAACCGCTCTC
1400 AAACTGATTTATTGGCGAAATGGCTCTAAACTAAATCGTCTCCTCTCTTT
     GGAAATGCTTTAGAGAAGGTCTCTGTGGTAGTTCTTATGCATCTATCCTA
     AAGCACTTGGCCAGACAATTTAAAGACATCAAGCAGCATTTATAGCAGGC
     ACGTTTAATAACGAATACTGAATTTAAGTAACTCTGCTCACGTTGTATGA
1600 CGTTTATTTTCGTATTCCTGAAAGCCATTAAAATCCTGTGCAGTTGTTTA
     GTAAGAACAGCTGCCACTGTTTTGTATCTAGGAGATAACTGGTGTTTCCC
     TACAGTTCTCAAGCTGATAAAACTCTGTCTTTGTATCTAGGTAACCCTGT
     ATCACTTGCTGAAGCTTTTTCAGTCTGACACCAATGCAATCCTGGGAAAG
1800 AAAACTGTAGTTTCTGAATTCTATGATGAAATGGTATGAAAATTTTAATG
     TCAACCGAGCCTGACTTATTTAAAAAAATTATTGATGGTGCTGTGTAT
     TTTGGTCCTTCCTTAGATATTTCAAGATCCTACTGCCATGATGCAGCAAC
     TGCTAACGACGTCCCGTCAGCTGACACTTGGTGCTTACAAGCATGAAACA
```

FIG. 5A

```
2000  GAGTGTAAGTGCAAAATGAGGATACCTTCGCCGACCGTCATTCACTACTA
      ATGTTTTCTGTGGGATGTGATCGTACAGTGAGTTTGGCTGTGTGAAATTT
      GAATAGCTTGGTATTGGCAGTGATGACGTGATCGATGCCTTGCTTATCAT
      GTTTGAAATGAAGTAGAATAAATGCAGCCTGCTTTATTTGAGATAGTTTG
2200  GTTCATTTTATGGAATGCAAGCAAAGATTATACTTCCTCACTGAATTGCA
      CTGTCCAAAGGTGTGAAATGTGTGGGGATCTGGAGGACCGTGACCGAGGG
      ACATTGGATCGCTATCTCCCATTTCTTTTGCTGTTACCAGTTCAGATTTT
      CTTTTCACCTAGTCTTTAATTCCCAGGGTTTTGTTTTTCCTTGGTCATA
2400  GTTTTGTTTTTCACTCTGGCAAATGATGTTGTGAATTACACTGCTTCAG
      CCACAAAACTGATGGACTGAATGAGGTCATCAAACAAACTTTTCTTCTTC
      CGTATTTCCTTTTTTTTCCCCCACTTATCATTTTTACTGCTGTTGTTGAG
      TCTGTAAGGCTAAAAGTAACTGTTTGTGCTTTTTCAGGACGTGTGCTTT
2600  CCAAATTACTGCCACATATATAAAGAAAGGTTGGAATTTTAAAGATAATT
      CATGTTTCTTCTTCTTTTTGCCACCACAGTTGCAGATCTTGAAGTAAAA
      ACCAGGGAAAAGCTGGAAGCTGCCAAAAAGAAAACCAGTTTTGAAATTGC
      TGAGCTTAAAGAAAGGTTAAAAGCAAGTCGTGAAACCATCAACTGCTTAA
2800  AGAGTGAAATCAGAAAACTCGAAGAGGATGATCAGTCTAAAGATATGTGA
      TGAGTGTTGACTTGGCAGGGAGCCTATAATGAGAATGAAAGGACTTCAGT
      CGTGGAGTTGTATGCGTTCTCCAATTCTGTAACGGAGACTGTATGAAT
      TTCATTTGCAAATCACTGCAGTGTGACAACTGACTTTTATAAATGGC
3000  AGAAAACAAGAATGAATGTATCCTCATTTTATAGTTAAAATCTATGGGTA
      TGTACTGGTTTATTTCAAGGAGAATGGATCGTAGAGACTTGGAGGCCAGA
      TTGCTGCTTGTATTGACTGCATTTGAGTGGTGTAGGAACATTTTGTCTAT
      GGTCCCGTGTTAGTTTACAGAATGCCACTGTTCACTGTTTTGTTTTGTAT
3200  TTTACTTTTTCTACTGCAACGTCAAGGTTTTAAAAGTTGAAAATAAAACA
      TGCAGGTTTTTTTTAAATATTTTTTGTCTCTATCCAGTTTGGGCTTCAA
      GTATTATTGTTAACAGCAAGTCCTGATTTAAGTCAGAGGCTGAAGTGTAA
      TGGTATTCAAGATGCTTAAGTCTGTTGTCAGCAAAACAAAAGAGAAAACT
3400  TCATAAAATCAGGAAGTTGGCATTTCTAATAACTTCTTTATCAACAGATA
      AGAGTTTCTAGCCCTGCATCTACTTTCACTTATGTAGTTGATGCCTTTAT
      ATTTTGTGTGTTTGGATGCAGGAAGTGATTCCTACTCTGTTATGTAGATA
      TTCTATTTAACACTTGTACTCTGCTGTGCTTAGCCTTTCCCCATGAAAAT
3600  TCAGCGGCTGTAAATCCCCTCTTCTTTGTAGCCTCATACAGATGGCAG
      ACCCTCAGGCTTATAAAGGCTTGGGCATCTTCTTTACTGCTTTGAGATTC
      TGTGTTGCAGTAACCTCTGCCAGAGAGGAGAAAAGCCCCACAAACCTCAT
      CCCCTTCTTCTATAGCAATCAGTATTACTAATGCTTTGAGAACAGAGCAC
3800  TGGTTTGAAACGTTTGATAATTAGCATTTAACATGGCTTGGTAAAGATGC
      AGAACTGAAACAGCTGTGACAGTATGAACTCAGTATGGAGACTTCATTAA
      GACAAACAGCTGTTAAAATCAGGCATGTTTCATTGAGGAGGACGGGGCAA
      CTTGCACCAGTGGTGCCCACACAAATCCTTCCTGGCGCTGCAGACCAATT
```

FIG. 5B

```
4000  TTTCTGGCATTCTGACTGCCGTTGCTGCTGGTCACAGAGAGCAACTATTT
      TTATCAGCCACAGGCAATTTGCTTGTAGTATTTTCCAAGTGTTGTAGGTA
      AGTATAAATGCATCGGCTCCAGAGCACTTTGAGTATACTTATTAAAAACA
      TAAATGAAAGACAAATTAGCTTTGCTTGGGTGCACAGAACATTTTTAGTT
4200  CCAGCCTGCTTTTGGTAGAAGCCCTCTTCTGAGGCTAGAACTGACTTTG
      ACAAGTAGAGAAACTGGCAACGGAGCTATTGCTATCGAAGGATCCTTGTT
      AACAAAGTTAATCGTCTTTTAAGGTTTGGTTTATTCATTAAATTTGCTTT
      TAAGCTGTAGCTGAAAAGAACGTGCTGTCTTCCATGCACCAGGTGGCAG
4400  CTCTGTGCAAAGTGCTCTCTGGTCTCACCAGCCTTTTAATTGCCGGGATT
      CTGGCACGTCTGAGAGGGCTCAGACTGGCTTCGTTTGTTTGAACAGCGTG
      TACTGCTTTCTGTAGACATGGCCGGTTTCTCCTGCAGCTTATGAAACT
      GTTCACACTGAACACACTGGAACAGGTTGCCCAAGGAGGCCGTGGATGCC
4600  CCATCCCTGGAGGCATTCAAGGCCAGGCTGGATGTGGCTCTGGGCAGCCT
      GGTCTGGTGGTTGGCGATCCTGCACATAGCAGCGGGGTTGAAACTCGATG
      ATCACTGTGGTCCTTTTCAACCCAGGCTATTCTATGATTCTATGATTCAA
      CAGCAAATCATATGTACTGAGAGAGGAAACAAACACAAGTGCTACTGTTT
4800  GCAAGTTTTGTTCATTTGGTAAAAGAGTCAGGTTTTAAAATTCAAAATCT
      GTCTGGTTTTGGTGTTTTTTTTTTTATTTATTATTTCTTTGGGGTTCT
      TTTTGATGCTTTATCTTTCTGCCAGGACTGTGTGACAATGGGAACGAA
      AAAGAACATGCCAGGCACTGTCCTGGATTGCACACGCTGGTTGCACTCAG
5000  TAGCAGGCTCAGAACTGCCAGTCTTTCCACAGTATTACTTTCTAAACCTA
      ATTTTAATAGCGTTAGTAGACTTCCATCACTGGGCAGTGCTTAGTGAATG
      CTCTGTGTGAACGTTTACTTATAAGCATGTTGGAAGTTTTGATGTTCCT
      GGATGCAGTAGGGAAGGACAGATTAGCTATGTGAAAGTAGATTCTGAGT
5200  ATCGGGGTTACAAAAGTATAGAAACGATGAGAAATTCTTGTTGTAACTA
      ATTGGAATTTCTTTAAGCGTTCACTTATGCTACATTCATAGTATTTCCAT
      TTAAAAGTAGGAAAAGGTAAAACGTGAAATCGTGTGATTTTCGGATGGAA
      CACCGCCTTCCTATGCACCTGACCAACTTCCAGAGGAAAAGCCTATTGAA
5400  AGCCGAGATTAAGCCACCAAAAGAACTCATTTGCATTGGAATATGTAGTA
      TTTGCCCTCTTCCTCCGGGTAATTACTATACTTTATAGGGTGCTTATAT
      GTTAAATGAGTGGCTGGCACTTTTTATTCTCACAGCTGTGGGGAATTCTG
      TCCTCTAGGACAGAAACAATTTTAATCTGTTCCACTGGTGACTGCTTTGT
5600  CAGCACTTCCACCTGAAGAGATCAATACACTCTTCAATGTCTAGTTCTGC
      AACACTTGGCAAACCTACATCTTATTTCATACTCTCTTCATGCCTATGC
      TTATTAAAGCAATAATCTGGGTAATTTTTGTTTTAATCACTGTCCTGACC
      CCAGTGATGACCGTGTCCCACCTAAAGCTCAATTCAGGTCCTGAATCTCT
5800  TCAACTCTCTATAGCTAACATGAAGAATCTTCAAAAGTTAGGTCTGAGGG
      ACTTAAGGCTAACTGTAGATGTTGTTGCCTGGTTTCTGTGCTGAAGGCCG
      TGTAGTAGTTAGAGCATTCAACCTCTAG
```

FIG. 5C

SEQ ID NO: 10

```
   1 TGCCGCCTTCTTTGATATTCACTCTGTTGTATTTCATCTCTTCTTGCCGA
     TGAAAGGATATAACAGTCTGTATAACAGTCTGTGAGGAAATACTTGGTAT
     TTCTTCTGATCAGTGTTTTTATAAGTAATGTTGAATATTGGATAAGGCTG
 151 TGTGTCCTTTGTCTTGGGAGACAAAGCCCACAGCAGGTGGTGGTTGGGGT
     GGTGGCAGCTCAGTGACAGGAGAGGTTTTTTGCCTGTTTTTTTTTTTT
     TTTTTTTTTAAGTAAGGTGTTCTTTTTCTTAGTAAATTTTCTACTGGA
 301 CTGTATGTTTGACAGGTCAGAAACATTTCTTCAAAAGAAGAACCTTTTG
     GAAACTGTACAGCCCTTTTCTTTCATTCCTTTTTGCTTTCTGTGCCAAT
     GCCTTTGGTTCTGATTGCATTATGGAAAACGTTGATCGGAACTTGAGGTT
 451 TTTATTTATAGTGTGGCTTGAAAGCTTGGATAGCTGTTGTTACACGAGAT
     ACCTTATTAAGTTTAGGCCAGCTTGATGCTTTATTTTTTCCCTTTGAAGT
     AGTGAGCGTTCTCTGGTTTTTTTCCTTTGAAACTGGTGAGGCTTAGATTT
 601 TTCTAATGGGATTTTTTACCTGATGATCTAGTTGCATACCCAAATGCTTG
     TAAATGTTTTCCTAGTTAACATGTTGATAACTTCGGATTTACATGTTGTA
     TATACTTGTCATCTGTGTTTCTAGTAAAATATATGGCATTTATAGAAAT
 751 ACGTAATTCCTGATTTCCTTTTTTTTATCTCTATGCTCTGTGTGTACAG
     GTCAAACAGACTTCACTCCTATTTTATTTATAGAATTTATATGCAGTC
     TGTCGTTGGTTCTTGTGTTGTAAGGATACAGCCTTAAATTTCCTAGAGCG
 901 ATGCTCAGTAAGGCGGGTTGTCACATGGGTTCAAATGTAAAACGGGCACG
     TTTGGCTGCTGCCTTCCCGAGATCCAGGACACTAAACTGCTTCTGCACTG
     AGGTATAAATCGCTTCAGATCCCAGGGAAGTGCAGATCCACGTGCATATT
1051 CTTAAAGAAGAATGAATACTTTCTAAAATATTTTGGCATAGGAAGCAAGC
     TGCATGGATTTGTTTGGGACTTAAATTATTTTGGTAACGGAGTGCATAGG
     TTTTAAACACAGTTGCAGCATGCTAACGAGTCACAGCGTTTATGCAGAAG
1201 TGATGCCTGGATGCCTGTTGCAGCTGTTTACGGCACTGCCTTGCAGTGAG
     CATTGCAGATAGGGGTGGGGTGCTTTGTGTCGTGTTCCCACACGCTGCCA
     CACAGCCACCTCCCGGAACACATCTCACCTGCTGGGTACTTTTCAAACCA
1351 TCTTAGCAGTAGTAGATGAGTTACTATGAAACAGAGAAGTTCCTCAGTTG
     GATATTCTCATGGGATGTCTTTTTTCCCATGTTGGGCAAAGTATGATAAA
     GCATCTCTATTTGTAAATTATGCACTTGTTAGTTCCTGAATCCTTTCTAT
1501 AGCACCACTTATTGCAGCAGGTGTAGGCTCTGGTGTGGCCTGTGTCTGTG
     CTTCAATCTTTTAAAGCTTCTTTGGAAATACACTGACTTGATTGAAGTCT
     CTTGAAGATAGTAAACAGTACTTACCTTTGATCCCAATGAAATCGAGCAT
1651 TTCAGTTGTAAAAGAATTCCGCCTATTCATACCATGTAATGTAATTTTAC
     ACCCCAGTGCTGACACTTTGGAATATATTCAAGTAATAGACTTTGGCCT
     CACCCTCTTGTGTACTGTATTTGTAATAGAAAATATTTTAAACTGTGCA
1801 TATGATTATTACATTATGAAAGAGACATTCTGCTGATCTTCAAATGTAAG
     AAAATGAGGAGTGCGTGTGCTTTTATAAATACAAGTGATTGCAAATTAGT
     GCAGGTGTCCTTAAAAAAAAAAAAAAAAGTAATATAAAAGGACCAGGT
1951 GTTTTACAAGTGAAATACATTCCTATTTGGTAAACAGTTACATTTTATG
     AAGATTACCAGCGCTGCTGACTTTCTAAACATAAGGCTGTATTGTCTTCC
     TGTACCATTGCATTTCCTCATTCCCAATTTGCACAAGGATGTCTGGGTAA
2101 ACTATTCAAGAAATGGCTTTGAAATACAGCATGGGAGCTTGTCTGAGTTG
     GAATGCAGAGTTGCACTGCAAAATGTCAGGAAATGGATGTCTCTCAGAAT
     GCCCAACTCCAAAGGATTTTATATGTGTATATAGTAAGCAGTTTCCTGAT
```

FIG. 6A

2251 TCCAGCAGGCCAAAGAGTCTGCTGAATGTTGTGTTGCCGGAGACCTGTAT
TTCTCAACAAGGTAAGATGGTATCCTAGCAACTGCGGATTTTAATACATT
TTCAGCAGAAGTACTTAGTTAATCTCTACCTTTAGGGATCGTTTCATCAT
2401 TTTTAGATGTTATACTTGAAATACTGCATAACTTTTAGCTTTCATGGGTT
CCTTTTTTCAGCCTTTAGGAGACTGTTAAGCAATTTGCTGTCCAACTTT
TGTGTTGGTCTTAAACTGCAATAGTAGTTTACCTTGTATTGAAGAAATAA
2551 AGACCATTTTTATATTAAAAAATACTTTTGTCTGTCTTCATTTTGACTTG
TCTGATATCCTTGCAGTGCCCATTATGTCAGTTCTGTCAGATATTCAGAC
ATCAAAACTTAACGTGAGCTCAGTGGAGTTACAGCTGCGGTTTTGATGCT
2701 GTTATTATTTCTGAAACTAGAAATGATGTTGTCTTCATCTGCTCATCAAA
CACTTCATGCAGAGTGTAAGGCTAGTGAGAAATGCATACATTTATTGATA
CTTTTTTAAAGTCAACTTTTTATCAGATTTTTTTTCATTTGGAAATATA
2851 TTGTTTTCTAGACTGCATAGCTTCTGAATCTGAAATGCAGTCTGATTGGC
ATGAAGAAGCACAGCACTCTTCATCTTACTTAAACTTCATTTGGAATGA
AGGAAGTTAAGCAAGGGCACAGGTCCATGAAATAGAGACAGTGCGCTCAG
3001 GAGAAAGTGAACCTGGATTTCTTTGGCTAGTGTTCTAAATCTGTAGTGAG
GAAAGTAACACCCGATTCCTTGAAAGGGCTCCAGCTTTAATGCTTCCAAA
TTGAAGGTGGCAGGCAACTTGGCCACTGGTTATTTACTGCATTATGTCTC
3151 AGTTTCGCAGCTAACCTGGCTTCTCCACTATTGAGCATGGACTATAGCCT
GGCTTCAGAGGCCAGGTGAAGGTTGGGATGGGTGGAAGGAGTGCTGGGCT
GTGGCTGGGGGACTGTGGGACTCCAAGCTGAGCTTGGGGTGGGCAGCA
3301 CAGGGAAAAGTGTGGGTAACTATTTTAAGTACTGTGTTGCAAACGTCTC
ATCTGCAAATACGTAGGGTGTGTACTCTCGAAGATTAACAGTGTGGGTTC
AGTAATATATGGATGAATTCACAGTGGAAGCATTCAAGGGTAGATCATCT
3451 AACGACACCAGATCATCAAGCTATGATTGGAAGCGGTATCAGAAGAGCGA
GGAAGGTAAGCAGTCTTCATATGTTTTCCCTCCACGTAAAGCAGTCTGGG
AAAGTAGCACCCCTTGAGCAGAGACAAGGAAATAATTCAGGAGCATGTGC
3601 TAGGAGAACTTTCTTGCTGAATTCTACTTGCAAGAGCTTTGATGCCTGGC
TTCTGGTGCCTTCTGCAGCACCTGCAAGGCCCAGAGCCTGTGGTGAGCTG
GAGGGAAAGATTCTGCTCAAGTCCAAGCTTCAGCAGGTCATTGTCTTTGC
3751 TTCTTCCCCCAGCACTGTGCAGCAGAGTGGAACTGATGTCGAAGCCTCCT
GTCCACTACCTGTTGCTGCAGGCAGACTGCTCTCAGAAAAGAGAGCTAA
CTCTATGCCATAGTCTGAAGGTAAAATGGGTTTTAAAAAAGAAAACACAA
3901 AGGCAAAACCGGCTGCCCCATGAGAAGAAAGCAGTGGTAAACATGGTAGA
AAAGGTGCAGAAGCCCCCAGGCAGTGTGACAGGCCCCTCCTGCCACCTAG
AGGCGGGAACAAGCTTCCTGCCTAGGGCTCTGCCCGCGAAGTGCGTGTT
4051 TCTTTGGTGGGTTTTGTTTGGCGTTTGGTTTTGAGATTTAGACACAAGGG
AAGCCTGAAAGGAGGTGTTGGGCACTATTTTGGTTTGTAAAGCCTGTACT
TCAAATATATATTTTGTGAGGGAGTGTAGCGAATTGGCCAATTTAAAATA
4201 AAGTTGCAAGAGATTGAAGGCTGAGTAGTTGAGAGGGTAACACGTTTAAT
GAGATCTTCTGAAACTACTGCTTCTAAACACTTGTTTGAGTGGTGAGACC
TTGGATAGGTGAGTGCTCTTGTTACATGTCTGATGCACTTGCTTGTCCTT
4351 TTCCATCCACATCCATGCATTCCACATCCACGCATTTGTCACTTATCCCA
TATCTGTCATATCTGACATACCTGTCTCTTCGTCACTTGGTCAGAAGAAA
CAGATGTGATAATCCCCAGCCGCCCAAGTTTGAAGAAGATGGCAGTTGCT
4501 TCTTTCCCTTTTTCCTGCTAAGTAAGGATTTTCTCCTGGCTTTGACACCT
CACGAAATAGTCTTCCTGCCTTACATTCTGGGCATTATTTCAAATATCTT

FIG. 6B

```
      TGGAGTGCGCTGCTCTCAAGTTTGTGTCTTCCTACTCTTAGAGTGAATGC
4651  TCTTAGAGTGAAAGAGAAGGAAGAGAAGATGTTGGCCGCAGTTCTCTGAT
      GAACACACCTCTGAATAATGGCCAAAGGTGGGTGGGTTTCTCTGAGGAAC
      GGGCAGCGTTTGCCTCTGAAAGCAAGGAGCTCTGCGGAGTTGCAGTTATT
4801  TTGCAACTGATGGTGGAACTGGTGCTTAAAGCAGATTCCCTAGGTTCCCT
      GCTACTTCTTTTCCTTCTTGGCAGTCAGTTTATTTCTGACAGACAAACAG
      CCACCCCCACTGCAGGCTTAGAAAGTATGTGGCTCTGCCTGGGTGTGTTA
4951  CAGCTCTGCCCTGGTGAAAGGGGATTAAAACGGGCACCATTCATCCCAAA
      CAGGATCCTCATTCATGGATCAAGCTGTAAGGAACTTGGGCTCCAACCTC
      AAAACATTAATTGGAGTACGAATGTAATTAAAACTGCATTCTCGCATTCC
5101  TAAGTCATTTAGTCTGGACTCTGCAGCATGTAGGTCGGCAGCTCCCACTT
      TCTCAAAGACCACTGATGGAGGAGTAGTAAAAATGGAGACCGATTCAGAA
      CAACCAACGGAGTGTTGCCGAAGAAACTGATGGAAATAATGCATGAATTG
5251  TGTGGTGGACATTTTTTTAAATACATAAACTACTTCAAATGAGGTCGGA
      GAAGGTCAGTGTTTTATTAGCAGCCATAAAACCAGGTGAGCGAGTACCAT
      TTTTCTACAAGAAAACGATTCTGAGCTCTGCGTAAGTATAAGTTCTC
5401  CATAGCGGCTGAAGCTCCCCCCTGGCTGCCTGCCATCTCAGCTGGAGTGC
      AGTGCCATTTCCTTGGGGTTTCTCTCACAGCAGTAATGGGACAATACTTC
      ACAAAATTCTTTCTTTTCCTGTCATGTGGGATCCCTACTGTGCCCTCCT
5551  GGTTTTACGTTACCCCCTGACTGTTCCATTCAGCGGTTTGGAAAGAGAAA
      AAGAATTTGGAAATAAAACATGTCTACGTTATCACCTCCTCCAGCATTTT
      GGTTTTTAATTATGTCAATAACTGGCTTAGATTTGGAAATGAGAGGGGGT
5701  TGGGTGTATTACCGAGGAACAAAGGAAGGCTTATATAAACTCAAGTCTTT
      TATTTAGAGAACTGGCAAGCTGTCAAAAACAAAAAGGCCTTACCACCAAA
      TTAAGTGAATAGCCGCTATAGCCAGCAGGGCCAGCACGAGGGATGGTGCA
5851  CTGCTGGCACTATGCCACGGCCTGCTTGTGACTCTGAGAGCAACTGCTTT
      GGAAATGACAGCACTTGGTGCAATTTCCTTTGTTTCAGAATGCGTAGAGC
      GTGTGCTTGGCGACAGTTTTCTAGTTAGGCCACTTCTTTTTTCCTTCTC
6001  TCCTCATTCTCCTAAGCATGTCTCCATGCTGGTAATCCCAGTCAAGTGAA
      CGTTCAAACAATGAATCCATCACTGTAGGATTCTCGTGGTGATCAAATCT
      TTGTGTGAGGTCTATAAAATATGGAAGCTTATTTATTTTTCGTTCTTCCA
6151  TATCAGTCTTCTCTATGACAATTCACATCCACCACAGCAAATTAAAGGTG
      AAGGAGGCTGGTGGGATGAAGAGGGTCTTCTAGCTTTACGTTCTTCCTTG
      CAAGGCCACAGGAAATGCTGAGAGCTGTAGAATACAGCCTGGGGTAAGA
6301  AGTTCAGTCTCCTGCTGGGACAGCTAACCGCATCTTATAACCCCTTCTGA
      GACTCATCTTAGGACCAAATAGGGTCTATCTGGGGTTTTGTTCCTGCTG
      TTCCTCCTGGAAGGCTATCTCACTATTTCACTGCTCCCACGGTTACAAAC
6451  CAAAGATACAGCCTGAATTTTTTCTAGGCCACATTACATAAATTTGACCT
      GGTACCAATATTGTTCTCTATATAGTTATTTCCTTCCCCACTGTGTTTAA
      CCCCTTAAGGCATTCAGAACAACTAGAATCATAGAATGGTTTGGATTGGA
6601  AGGGGCCTTAAACATCATCCATTTCCAACCCTCTGCCATGGGCTGCTTGC
      CACCCACTGGCTCAGGCTGCCCAGGGCCCCATCCAGCCTGGCCTTGAGCA
      CCTCCAGGGATGGGCACCCACAGCTTCTCTGGGCAGCCTGTGCCAACAC
6751  CTCACCACTCTCTGGGTAAAGAATTCTCTTTTAACATCTAATCTAAATCT
      CTTCTCTTTTAGTTTAAAGCCATTCCTCTTTTTCCCGTTGCTATCTGTCC
      AAGAAATGTGTATTGGTCTCCCTCCTGCTTATAAGCAGGAAGTACTGGAA
6901  GGCTGCAGTGAGGTCTCCCCACAGCCTTCTCTTCTCCAGGCTGAACAAGC
```

FIG. 6C

```
            CCAGCTCCTTCAGCCTGTCTTCGTAGGAGATCATCTTAGTGGCCCTCCTC
            TGGACCCATTCCAACAGTTCCACGGCTTTCTTGTGGAGCCCCAGGTCTGG
      7051  ATGCAGTACTTCAGATGGGGCCTTACAAAGGCAGAGCAGATGGGGACAAT
            CGCTTACCCCTCCCTGCTGGCTGCCCCTGTTTTGATGCAGCCCAGGGTAC
            TGTTGGCCTTTCAGGCTCCCAGACCCCTTGCTGATTTGTGTCAAGCTTTT
      7201  CATCCACCAGAACCCACGCTTCCTGGTTAATACTTCTGCCCTCACTTCTG
            TAAGCTTGTTTCAGGAGACTTCCATTCTTTAGGACAGACTGTGTTACACC
            TACCTGCCCTATTCTTGCATATATACATTTCAGTTCATGTTTCCTGTAAC
      7351  AGGACAGAATATGTATTCCTCTAACAAAATACATGCAGAATTCCTAGTG
            CCATCTCAGTAGGGTTTTCATGGCAGTATTAGCACATAGTCAATTGCTG
            CAAGTACCTTCCAAGCTGCGGCCTCCCATAAATCCTGTATTTGGGATCAG
      7501  TTACCTTTTGGGGTAAGCTTTTGTATCTGCAGAGACCCTGGGGGTTCTGA
            TGTGCTTCAGCTCTGCTCTGTTCTGACTGCACCATTTTCTAGATCACCCA
            GTTGTTCCTGTACAACTTCCTTGTCCTCCATCCTTTCCCAGCTTGTATCT
      7651  TTGACAAATACAGGCCTATTTTGTGTTTGCTTCAGCAGCCATTTAATTC
            TTCAGTGTCATCTTGTTCTGTTGATGCCACTGGAACAGGATTTTCAGCAG
            TCTTGCAAAGAACATCTAGCTGAAACTTTCTGCCATTCAATATTCTTAC
      7801  CAGTTCTTCTTGTTTGAGGTGAGCCATAAATTACTAGAACTTCGTCACTG
            ACAAGTTTATGCATTTTATTACTTCTATTATGTACTTACTTTGACATAAC
            ACAGACACGCACATATTTTGCTGGGATTTCCACAGTGTCTCTGTGTCCTT
      7951  CACATGGTTTTACTGTCATACTTCCGTTATAACCTTGGCAATCTGCCCAG
            CTGCCCATCACAAGAAAAGAGATTCCTTTTTATTACTTCTCTTCAGCCA
            ATAAACAAAATGTGAGAAGCCCAAACAAGAACTTGTGGGCAGGCTGCCA
      8101  TCAAGGGAGAGACAGCTGAAGGGTTGTGTAGCTCAATAGAATTAAGAAAT
            AATAAAGCTGTGTCAGACAGTTTTGCCTGATTTATACAGGCACGCCCCAA
            GCCAGAGAGGCTGTCTGCCAAGGCCACCTTGCAGTCCTTGGTTTGTAAGA
      8251  TAAGTCATAGGTAACTTTTCTGGTGAATTGCGTGGAGAATCATGATGGCA
            GTTCTTGCTGTTTACTATGGTAAGATGCTAAAATAGGAGACAGCAAAGTA
            ACACTTGCTGCTGTAGGTGCTCTGCTATCCAGACAGCGATGGCACTCGCA
      8401  CACCAAGATGAGGGATGCTCCCAGCTGACGGATGCTGGGGCAGTAACAGT
            GGGTCCCATGCTGCCTGCTCATTAGCATCACCTCAGCCCTCACCAGCCCA
            TCAGAAGGATCATCCCAAGCTGAGGAAAGTTGCTCATCTTCTTCACATCA
      8551  TCAAACCTTTGGCCTGACTGATGCCTCCCGGATGCTTAAATGTGGTCACT
            GACATCTTTATTTTCTATGATTTCAAGTCAGAACCTCCGGATCAGGAGG
            GAACACATAGTGGGAATGTACCCTCAGCTCCAAGGCCAGATCTTCCTTCA
      8701  ATGATCATGCATGCTACTTAGGAAGGTGTGTGTGTGAATGTAGAATTG
            CCTTTGTTATTTTTTCTTCCTGCTGTCAGGAACATTTTGAATACCAGAGA
            AAAGAAAAGTGCTCTTCTTGGCATGGGAGGAGTTGTCACACTTGCAAAA
      8851  TAAAGGATGCAGTCCCAAATGTTCATAATCTCAGGGTCTGAAGGAGGATC
            AGAAACTGTGTATACAATTTCAGGCTTCTCTGAATGCAGCTTTTGAAAGC
            TGTTCCTGGCCGAGGCAGTACTAGTCAGAACCCTCGGAAACAGGAACAAA
      9001  TGTCTTCAAGGTGCAGCAGGAGGAAACACCTTGCCCATCATGAAAGTGAA
            TAACCACTGCCGCTGAAGGAATCCAGCTCCTGTTTGAGCAGGTGCTGCAC
            ACTCCCACACTGAAACAACAGTTCATTTTATAGGACTTCCAGGAAGGAT
      9151  CTTCTTCTTAAGCTTCTTAATTATGGTACATCTCCAGTTGGCAGATGACT
            ATGACTACTGACAGGAGAATGAGGAACTAGCTGGGAATATTTCTGTTTGA
            CCACCATGGAGTCACCCATTTCTTTACTGGTATTTGGAAATAATAATTCT
```

FIG. 6D

```
 9301 GAATTGCAAAGCAGGAGTTAGCGAAGATCTTCATTTCTTCCATGTTGGTG
      ACAGCACAGTTCTGGCTATGAAAGTCTGCTTACAAGGAAGAGGATAAAAA
 9401 TCATAGGGATAATAAATCTAAGTTGAAGACAATGAGGTTTTAGCTGCAT
      TTGACATGAAGAAATTGAGACCTCTACTGGATAGCTATGGTATTTACGTG
      TCTTTTTGCTTAGTTACTTATTGACCCCAGCTGAGGTCAAGTATGAACTC
 9551 AGGTCTCTCGGCTACTGGCATGGATTGATTACATACAACTGTAATTTTA
      GCAGTGATTTAGGGTTTATGAGTACTTTTGCAGTAAATCATAGGGTTAGT
      AATGTTAATCTCAGGGAAAAAAAAAAAGCCAACCCTGACAGACATCCC
 9701 AGCTCAGGTGGAAATCAAGGATCACAGCTCAGTGCGGTCCCAGAGAACAC
      AGGGACTCTTCTCTTAGGACCTTTATGTACAGGGCCTCAAGATAACTGAT
      GTTAGTCAGAAGACTTTCCATTCTGGCCACAGTTCAGCTGAGGCAATCCT
 9851 GGAATTTTCTCTCCGCTGCACAGTTCCAGTCATCCCAGTTTGTACAGTTC
      TGGCACTTTTGGGTCAGGCCGTGATCCAAGGAGCAGAAGTTCCAGCTAT
      GGTCAGGGAGTGCCTGACCGTCCCAACTCACTGCACTCAAACAAAGGCGA
10001 AACCACAAGAGTGGCTTTTGTTGAAATTGCAGTGTGGCCCAGAGGGGCTG
      CACCAGTACTGGATTGACCACGAGGCAACATTAATCCTCAGCAAGTGCAA
      TTTGCAGCCATTAAATTGAACTAACTGATACTACAATGCAATCAGTATCA
10151 ACAAGTGGTTTGGCTTGGAAGATGGAGTCTAGGGGCTCTACAGGAGTAGC
      TACTCTCTAATGGAGTTGCATTTTGAAGCAGGACACTGTGAAAAGCTGGC
      CTCCTAAAGAGGCTGCTAAACATTAGGGTCAATTTTCCAGTGCACTTTCT
10301 GAAGTGTCTGCAGTTCCCCATGCAAAGCTGCCCAAACATAGCACTTCCAA
      TTGAATACAATTATATGCAGGCGTACTGCTTCTTGCCAGCACTGTCCTTC
      TCAAATGAACTCAACAAACAATTTCAAAGTCTAGTAGAAAGTAACAAGCT
10451 TTGAATGTCATTAAAAAGTATATCTGCTTTCAGTAGTTCAGCTTATTTAT
      GCCCACTAGAAACATCTTGTACAAGCTGAACACTGGGGCTCCAGATTAGT
      GGTAAAACCTACTTTATACAATCATAGAATCATAGAATGGCCTGGGTTGG
10601 AAGGGACCCCAAGGATCATGAAGATCCAACACCCCGCCACAGGCAGGGC
      CACCAACCTCCAGATCTGGTACTAGACCAGGCAGCCCAGGGCTCCATCCA
      ACCTGGCCATGAACACCTCCAGGGATGGAGCATCCACAACCTCTCTGGGC
10751 AGCCTGTGCCAGCACCTCACCACCCTCTCTGTGAAGAACTTTTCCCTGAC
      ATCCAATCTAAGCCTTCCCTCCTTGAGGTTAGATCCACTCCCCCTTGTGC
      TATCACTGTCTACTCTTGTAAAAGTTGATTCTCCTCCTTTTGGAAGGT
10901 TGCAATGAGGTCTCCTTGCAGCCTTCTTCTCTTCTGCAGGATGAACAAGC
      CCAGCTCCCTCAGCCTGTCTTTATAGGAGAGGTGCTCCAGCCCTCTGATC
      ATCTTTGTGGCCCTCCTCTGGACCCGCTCCAAGAGCTCCACATCTTTCCT
11051 GTACTGGGGGCCCCAGGCCTGAATGCAGTACTCCAGATGGGGCCTCAAAA
      GAGCAGAGTAAAGAGGGACAATCACCTTCCTCACCCTGCTGGCCAGCCCT
      CTTCTGATGGAGCCCTGGATACAACTGGCTTTCTGAGCTGCAACTTCTCC
11201 TTATCAGTTCCACTATTAAAACAGGAACAATACAACAGGTGCTGATGGCC
      AGTGCAGAGTTTTCACACTTCTTCATTTCGGTAGATCTTAGATGAGGAA
      CGTTGAAGTTGTGCTTCTGCGTGTGCTTCTTCCTCCTCAAATACTCCTGC
11351 CTGATACCTCACCCCACCTGCCACTGAATGGCTCCATGGCCCCCTGCAGC
      CAGGGCCCTGATGAACCCGGCACTGCTTCAGATGCTGTTTAATAGCACAG
      TATGACCAAGTTGCACCTATGAATACACAAACAATGTGTTGCATCCTTCA
11501 GCACTTGAGAAGAAGAGCCAAATTTGCATTGTCAGGAAATGGTTTAGTAA
      TTCTGCCAATTAAAACTTGTTTATCTACCATGGCTGTTTTTATGGCTGTT
      AGTAGTGGTACACTGATGATGAACAATGGCTATGCAGTAAAATCAAGACT
```

FIG. 6E

11651 GTAGATATTGCAACAGACTATAAAATTCCTCTGTGGCTTAGCCAATGTGG
TACTTCCCACATTGTATAAGAAATTTGGCAAGTTTAGAGCAATGTTTGAA
GTGTTGGGAAATTTCTGTATACTCAAGAGGGCGTTTTGACAACTGTAGA
11801 ACAGAGGAATCAAAAGGGGTGGGAGGAAGTTAAAAGAAGAGGCAGGTGC
AAGAGAGCTTGCAGTCCCGCTGTGTGTACGACACTGGCAACATGAGGTCT
TTGCTAATCTTGGTGCTTTGCTTCCTGCCCCTGGCTGCCTTAGGGTGCGA
11951 TCTGCCTCAGACCCACAGCCTGGGCAGCAGGAGGACCCTGATGCTGCTGG
CTCAGATGAGGAGAATCAGCCTGTTTAGCTGCCTGAAGGATAGGCACGAT
TTTGGCTTTCCTCAAGAGGAGTTTGGCAACCAGTTTCAGAAGGCTGAGAC
12101 CATCCCTGTGCTGCACGAGATGATCCAGCAGATCTTTAACCTGTTTAGCA
CCAAGGATAGCAGCGCTGCTTGGGATGAGACCCTGCTGGATAAGTTTTAC
ACCGAGCTGTACCAGCAGCTGAACGATCTGGAGGCTTGCGTGATCCAGGG
12251 CGTGGGCGTGACCGAGACCCCTCTGATGAAGGAGGATAGCATCCTGGCTG
TGAGGAAGTACTTTCAGAGGATCACCCTGTACCTGAAGGAGAAGAAGTAC
AGCCCCTGCGCTTGGGAAGTCGTGAGGGCTGAGATCATGAGGAGCTTTAG
12401 CCTGAGCACCAACCTGCAAGAGAGCTTGAGGTCTAAGGAGTAAAAAGTCT
AGAGTCGGGGCGGCGCGTGGTAGGTGGCGGGGGGTTCCCAGGAGAGCCCC
CAGCGCGGACGGCAGCGCCGTCACTCACCGCTCCGTCTCCCTCCGCCCAG
12551 GGTCGCCTGGCGCAACCGCTGCAAGGGCACCGACGTCCAGGCGTGGATCA
GAGGCTGCCGGCTGTGAGGAGCTGCCGCGCCCGGCCCGCCCGCTGCACAG
CCGGCCGCTTTGCGAGCGCGACGCTACCCGCTTGGCAGTTTTAAACGCAT
12701 CCCTCATTAAAACGACTATACGCAAACGCCTTCCCGTCGGTCCGCGTCTC
TTTCCGCCGCCAGGGCGACACTCGCGGGGAGGGCGGGAAGGGGCCGGGC
GGGAGCCCGCGGCCAACCGTCGCCCCGTGACGGCACCGCCCCGCCCCCGT
12851 GACGCGGTGCGGGCGCCGGGGCCGTGGGGCTGAGCGCTGCGGCGGGGCCG
GGCCGGGCCGGGGCGGGAGCTGAGCGCGGCGCGGCTGCGGGCGGCGCCCC
CTCCGGTGCAATATGTTCAAGAGAATGGCTGAGTTCGGGCCTGACTCCGG
13001 GGGCAGGGTGAAGGTGCGGCGCGGGCGGAGGGACGGGGCGGGCGCGGGGC
CGCCCGGCGGGTGCCGGGGCCTCTGCCGGCCCGCCCGGCTCGGGCTGCTG
CGGCGCTTACGGGCGCGCTTCTCGCCGCTGCCGCTTCTCTTCTCTCCCGC
13151 GCAAGGGCGTCACCATCGTGAAGCCGGTAGTGTACGGGAACGTGGCGCGG
TACTTCGGGAAGAAGAGGGAGGAGGACGGGCACACGCATCAGTGGACGGT
TTACGTGAAGCCCTACAGGAACGAGGTAGGGCCCGAGCGCGTCGGCCGCC
13301 GTTCTCGGAGCGCCGGAGCCGTCAGCGCCGCGCCTGGGTGCGCTGTGGA
CACAGCGAGCTTCTCTCGTAGGACATGTCCGCCTACGTGAAAAAAATCCA
GTTCAAGCTGCACGAGAGCTACGGGAATCCTCTCCGAGGTGGGTGTTGCG
13451 TCGGGGGGTTTGCTCCGCTCGGTCCCGCTGAGGCTCGTCGCCCTCATCTT
TCTTTCGTGCCGCAGTCGTTACCAAACCGCCGTACGAGATCACCGAAACG
13551 GGCTGGGGCGAATTTGAAATCATCATCAAGATATTTTTCATTGATCCAAA
CGAGCGACCCGTAAGTACGCTCAGCTTCTCGTAGTGCTTCCCCGTCCTG
GCGGCCCGGGGCTGGCTGCTCGCTGCTGCCGGTCACAGTCCCGCCAGCC
13701 GCGGAGCTGACTGAGCTCCCTTTCCCGGGACGTGTGCTCTGTGTTCGGTC
AGCGAGGCTATCGGGAGGGCTTTGGCTGCATTTGGCTTCTCTGGCGCTTA
GCGCAGGAGCACGTTGTGCTACGCCTGAACTACAGCTGTGAGAAGGCCGT
13851 GGAAACCGCTCTCAAACTGATTTATTGGCGAAATGGCTCTAAACTAAATC
GTCTCCTCTCTTTGGAAATGCTTTAGAGAAGGTCTCTGTGGTAGTTCTTA
TGCATCTATCCTAAAGCACTTGGCCAGACAATTTAAAGACATCAAGCAGC

FIG. 6F

```
14001 ATTTATAGCAGGCACGTTTAATAACGAATACTGAATTTAAGTAACTCTGC
      TCACGTTGTATGACGTTTATTTTCGTATTCCTGAAAGCCATTAAAATCCT
      GTGCAGTTGTTTAGTAAGAACAGCTGCCACTGTTTTGTATCTAGGAGATA
14151 ACTGGTGTTTCCCTACAGTTCTCAAGCTGATAAAACTCTGTCTTTGTATC
      TAGGTAACCCTGTATCACTTGCTGAAGCTTTTTCAGTCTGACACCAATGC
      AATCCTGGGAAAGAAAACTGTAGTTTCTGAATTCTATGATGAAATGGTAT
14301 GAAAATTTTAATGTCAACCGAGCCTGACTTTATTTAAAAAAAATTATTGA
      TGGTGCTGTGTATTTTGGTCCTTCCTTAGATATTTCAAGATCCTACTGCC
      ATGATGCAGCAACTGCTAACGACGTCCCGTCAGCTGACACTTGGTGCTTA
14451 CAAGCATGAAACAGAGTGTAAGTGCAAAATGAGGATACCTTCGCCGACCG
      TCATTCACTACTAATGTTTCTGTGGGATGTGATCGTACAGTGAGTTTGG
      CTGTGTGAAATTTGAATAGCTTGGTATTGGCAGTGATGACGTGATCGATG
14601 CCTTGCTTATCATGTTTGAAATGAAGTAGAATAAATGCAGCCTGCTTTAT
      TTGAGATAGTTTGGTTCATTTTATGGAATGCAAGCAAAGATTATACTTCC
      TCACTGAATTGCACTGTCCAAAGGTGTGAAATGTGTGGGGATCTGGAGGA
14751 CCGTGACCGAGGGACATTGGATCGCTATCTCCCATTTCTTTTGCTGTTAC
      CAGTTCAGATTTTCTTTTCACCTAGTCTTTAATTCCCAGGGTTTTGTTTT
      TTCCTTGGTCATAGTTTTTGTTTTTCACTCTGGCAAATGATGTTGTGAAT
14901 TACACTGCTTCAGCCACAAAACTGATGGACTGAATGAGGTCATCAAACAA
      ACTTTTCTTCTTCCGTATTTCCTTTTTTTCCCCCACTTATCATTTTTAC
      TGCTGTTGTTGAGTCTGTAAGGCTAAAAGTAACTGTTTTGTGCTTTTTCA
15051 GGACGTGTGCTTTCCAAATTACTGCCACATATATAAAGAAAGGTTGGAAT
      TTTAAAGATAATTCATGTTTCTTCTTCTTTTTGCCACCACAGTTGCAGA
      TCTTGAAGTAAAAACCAGGGAAAAGCTGGAAGCTGCCAAAAAGAAAACCA
15201 GTTTTGAAATTGCTGAGCTTAAAGAAAGGTTAAAAGCAAGTCGTGAAACC
      ATCAACTGCTTAAAGAGTGAAATCAGAAAACTCGAAGAGGATGATCAGTC
      TAAAGATATGTGATGAGTGTTGACTTGGCAGGGAGCCTATAATGAGAATG
15351 AAAGGACTTCAGTCGTGGAGTTGTATGCGTTCTCTCCAATTCTGTAACGG
      AGACTGTATGAATTTCATTTGCAAATCACTGCAGTGTGTGACAACTGACT
      TTTTATAAATGGCAGAAAACAAGAATGAATGTATCCTCATTTTATAGTTA
15501 AAATCTATGGGTATGTACTGGTTTATTTCAAGGAGAATGGATCGTAGAGA
      CTTGGAGGCCAGATTGCTGCTTGTATTGACTGCATTTGAGTGGTGTAGGA
      ACATTTGTCTATGGTCCCGTGTTAGTTTACAGAATGCCACTGTTCACTG
15651 TTTTGTTTTGTATTTTACTTTTTCTACTGCAACGTCAAGGTTTTAAAAGT
      TGAAAATAAAACATGCAGGTTTTTTTTAAATATTTTTTGTCTCTATCCA
      GTTTGGGCTTCAAGTATTATTGTTAACAGCAAGTCCTGATTTAAGTCAGA
15801 GGCTGAAGTGTAATGGTATTCAAGATGCTTAAGTCTGTTGTCAGCAAAAC
      AAAAGAGAAAACTTCATAAAATCAGGAAGTTGGCATTTCTAATAACTTCT
      TTATCAACAGATAAGAGTTTCTAGCCCTGCATCTACTTTCACTTATGTAG
15951 TTGATGCCTTTATATTTGTGTGTTTGGATGCAGGAAGTGATTCCTACTC
      TGTTATGTAGATATTCTATTTAACACTTGTACTCTGCTGTGCTTAGCCTT
16051 TCCCCATGAAAATTCAGCGGCTGTAAATCCCCCTCTTCTTTTGTAGCCTC
      ATACAGATGGCAGACCCTCAGGCTTATAAAGGCTTGGGCATCTTCTTTAC
      TGCTTTGAGATTCTGTGTTGCAGTAACCTCTGCCAGAGAGGAGAAAAGCC
16201 CCACAAACCTCATCCCCTTCTTCTATAGCAATCAGTATTACTAATGCTTT
      GAGAACAGAGCACTGGTTTGAAACGTTTGATAATTAGCATTTAACATGGC
      TTGGTAAAGATGCAGAACTGAAACAGCTGTGACAGTATGAACTCAGTATG
```

FIG. 6G

16351 GAGACTTCATTAAGACAAACAGCTGTTAAAATCAGGCATGTTTCATTGAG
      GAGGACGGGGCAACTTGCACCAGTGGTGCCCACACAAATCCTTCCTGGCG
      CTGCAGACCAATTTTTCTGGCATTCTGACTGCCGTTGCTGCTGGTCACAG
16501 AGAGCAACTATTTTATCAGCCACAGGCAATTTGCTTGTAGTATTTTCCA
      AGTGTTGTAGGTAAGTATAAATGCATCGGCTCCAGAGCACTTTGAGTATA
      CTTATTAAAAACATAAATGAAAGACAAATTAGCTTTGCTTGGGTGCACAG
16651 AACATTTTTAGTTCCAGCCTGCTTTTTGGTAGAAGCCCTCTTCTGAGGCT
      AGAACTGACTTTGACAAGTAGAGAAACTGGCAACGGAGCTATTGCTATCG
16751 AAGGATCCTTGTTAACAAAGTTAATCGTCTTTTAAGGTTTGGTTTATTCA
      TTAAATTTGCTTTTAAGCTGTAGCTGAAAAAGAACGTGCTGTCTTCCATG
16851 CACCAGGTGGCAGCTCTGTGCAAAGTGCTCTCTGGTCTCACCAGCCTTTT
      AATTGCCGGGATTCTGGCACGTCTGAGAGGGCTCAGACTGGCTTCGTTTG
      TTTGAACAGCGTGTACTGCTTTCTGTAGACATGGCCGGTTTCTCTCCTGC
17001 AGCTTATGAAACTGTTCACACTGAACACACTGGAACAGGTTGCCCAAGGA
      GGCCGTGGATGCCCCATCCCTGGAGGCATTCAAGGCCAGGCTGGATGTGG
      CTCTGGGCAGCCTGGTCTGGTGGTTGGCGATCCTGCACATAGCAGCGGGG
17151 TTGAAACTCGATGATCACTGTGGTCCTTTTCAACCCAGGCTATTCTATGA
      TTCTATGATTCAACAGCAAATCATATGTACTGAGAGAGGAAACAAACACA
      AGTGCTACTGTTTGCAAGTTTTGTTCATTTGGTAAAAGAGTCAGGTTTTA
17301 AAATTCAAAATCTGTCTGGTTTTGGTGTTTTTTTTTTTATTTATTATT
      TCTTTGGGGTTCTTTTTGATGCTTTATCTTTCTCTGCCAGGACTGTGTGA
      CAATGGGAACGAAAAGAACATGCCAGGCACTGTCCTGGATTGCACACGC
17451 TGGTTGCACTCAGTAGCAGGCTCAGAACTGCCAGTCTTTCCACAGTATTA
      CTTTCTAAACCTAATTTTAATAGCGTTAGTAGACTTCCATCACTGGGCAG
      TGCTTAGTGAATGCTCTGTGTAACGTTTTACTTATAAGCATGTTGGAAG
17601 TTTTGATGTTCCTGGATGCAGTAGGGAAGGACAGATTAGCTATGTGAAAA
      GTAGATTCTGAGTATCGGGGTTACAAAAAGTATAGAAACGATGAGAAATT
      CTTGTTGTAACTAATTGGAATTTCTTTAAGCGTTCACTTATGCTACATTC
17751 ATAGTATTTCCATTTAAAAGTAGGAAAAGGTAAAACGTGAAATCGTGTGA
      TTTTCGGATGGAACACCGCCTTCCTATGCACCTGACCAACTTCCAGAGGA
      AAAGCCTATTGAAAGCCGAGATTAAGCCACCAAAAGAACTCATTTGCATT
17901 GGAATATGTAGTATTTGCCCTCTTCCTCCCGGGTAATTACTATACTTTAT
      AGGGTGCTTATATGTTAAATGAGTGGCTGGCACTTTTTATTCTCACAGCT
      GTGGGGAATTCTGTCCTCTAGGACAGAAACAATTTTAATCTGTTCCACTG
18051 GTGACTGCTTTGTCAGCACTTCCACCTGAAGAGATCAATACACTCTTCAA
      TGTCTAGTTCTGCAACACTTGGCAAACCTCACATCTTATTTCATACTCTC
      TTCATGCCTATGCTTATTAAAGCAATAATCTGGGTAATTTTGTTTAAT
18201 CACTGTCCTGACCCCAGTGATGACCGTGTCCCACCTAAAGCTCAATTCAG
      GTCCTGAATCTCTTCAACTCTCTATAGCTAACATGAAGAATCTTCAAAAG
      TTAGGTCTGAGGGACTTAAGGCTAACTGTAGATGTTGTTGCCTGGTTTCT
18351 GTGCTGAAGGCCGTGTAGTAGTTAGAGCATTCAACCTCTAGAAGAAGCTT
      GGCCAGCTGGTCGACCTGCAGATCCGGCCCTCGAGGGGGGCCCGGTACC
      CAGCTTTTGTTCCCTTTAGTGAGGGTTAATTTCGAGCTTGGCGTAATCAT
18501 GGTCATAGCTGTTTCCTGTGTGAATTGTTATCCGCTCACAATTCCACAC
      AACATACGAGCCGGAAGCATAAAGTGTAAAGCCTGGGGTGCCTAATGAGT
      GAGCTAACTCACATTAATTGCGTTGCGCTCACTGCCCGCTTTCCAGTCGG
18651 GAAACCTGTCGTGCCAGCTGCATTAATGAATCGGCCAACGCGCGGGGAGA

FIG. 6H

```
        GGCGGTTTGCGTATTGGGCGCTCTTCCGCTTCCTCGCTCACTGACTCGCT
        GCGCTCGGTCGTTCGGCTGCGGCGAGCGGTATCAGCTCACTCAAAGGCGG
 18801  TAATACGGTTATCCACAGAATCAGGGGATAACGCAGGAAAGAACATGTGA
        GCAAAAGGCCAGCAAAAGGCCAGGAACCGTAAAAAGGCCGCGTTGCTGGC
        GTTTTTCCATAGGCTCCGCCCCCTGACGAGCATCACAAAAATCGACGCT
 18951  CAAGTCAGAGGTGGCGAAACCCGACAGGACTATAAAGATACCAGGCGTTT
        CCCCCTGGAAGCTCCCTCGTGCGCTCTCCTGTTCCGACCCTGCCGCTTAC
        CGGATACCTGTCCGCCTTTCTCCCTTCGGGAAGCGTGGCGCTTTCTCATA
 19101  GCTCACGCTGTAGGTATCTCAGTTCGGTGTAGGTCGTTCGCTCCAAGCTG
        GGCTGTGTGCACGAACCCCCCGTTCAGCCCGACCGCTGCGCCTTATCCGG
        TAACTATCGTCTTGAGTCCAACCCGGTAAGACACGACTTATCGCCACTGG
 19251  CAGCAGCCACTGGTAACAGGATTAGCAGAGCGAGGTATGTAGGCGGTGCT
        ACAGAGTTCTTGAAGTGGTGGCCTAACTACGGCTACACTAGAAGGACAGT
        ATTTGGTATCTGCGCTCTGCTGAAGCCAGTTACCTTCGGAAAAAGAGTTG
 19401  GTAGCTCTTGATCCGGCAAACAAACCACCGCTGGTAGCGGTGGTTTTTTT
        GTTTGCAAGCAGCAGATTACGCGCAGAAAAAAAGGATCTCAAGAAGATCC
        TTTGATCTTTTCTACGGGGTCTGACGCTCAGTGGAACGAAAACTCACGTT
 19551  AAGGGATTTTGGTCATGAGATTATCAAAAAGGATCTTCACCTAGATCCTT
        TTAAATTAAAAATGAAGTTTTAAATCAATCTAAAGTATATATGAGTAAAC
        TTGGTCTGACAGTTACCAATGCTTAATCAGTGAGGCACCTATCTCAGCGA
 19701  TCTGTCTATTTCGTTCATCCATAGTTGCCTGACTCCCCGTCGTGTAGATA
        ACTACGATACGGGAGGGCTTACCATCTGGCCCCAGTGCTGCAATGATACC
        GCGAGACCCACGCTCACCGGCTCCAGATTTATCAGCAATAAACCAGCCAG
 19851  CCGGAAGGGCCGAGCGCAGAAGTGGTCCTGCAACTTTATCCGCCTCCATC
        CAGTCTATTAATTGTTGCCGGGAAGCTAGAGTAAGTAGTTCGCCAGTTAA
        TAGTTTGCGCAACGTTGTTGCCATTGCTACAGGCATCGTGGTGTCACGCT
 20001  CGTCGTTTGGTATGGCTTCATTCAGCTCCGGTTCCCAACGATCAAGGCGA
        GTTACATGATCCCCCATGTTGTGCAAAAAGCGGTTAGCTCCTTCGGTCC
        TCCGATCGTTGTCAGAAGTAAGTTGGCCGCAGTGTTATCACTCATGGTTA
 20151  TGGCAGCACTGCATAATTCTCTTACTGTCATGCCATCCGTAAGATGCTTT
        TCTGTGACTGGTGAGTACTCAACCAAGTCATTCTGAGAATAGTGTATGCG
        GCGACCGAGTTGCTCTTGCCCGGCGTCAATACGGGATAATACCGCGCCAC
 20301  ATAGCAGAACTTTAAAAGTGCTCATCATTGGAAAACGTTCTTCGGGGCGA
        AAACTCTCAAGGATCTTACCGCTGTTGAGATCCAGTTCGATGTAACCCAC
        TCGTGCACCCAACTGATCTTCAGCATCTTTTACTTTCACCAGCGTTTCTG
 20451  GGTGAGCAAAAACAGGAAGGCAAAATGCCGCAAAAAAGGGAATAAGGGCG
        ACACGGAAATGTTGAATACTCATACTCTTCCTTTTTCAATATTATTGAAG
        CATTTATCAGGGTTATTGTCTCATGAGCGGATACATATTTGAATGTATTT
 20601  AGAAAAATAAACAAATAGGGGTTCCGCGCACATTTCCCCGAAAAGTGCCA
        CCTAAATTGTAAGCGTTAATATTTTGTTAAAATTCGCGTTAAATTTTTGT
        TAAATCAGCTCATTTTTTAACCAATAGGCCGAAATCGGCAAAATCCCTTA
 20751  TAAATCAAAAGAATAGACCGAGATAGGGTTGAGTGTTGTTCCAGTTTGGA
        ACAAGAGTCCACTATTAAAGAACGTGGACTCCAACGTCAAAGGGCGAAAA
        ACCGTCTATCAGGGCGATGGCCCACTACGTGAACCATCACCCTAATCAAG
 20901  TTTTTTGGGGTCGAGGTGCCGTAAAGCACTAAATCGGAACCCTAAAGGGA
        GCCCCCGATTTAGAGCTTGACGGGGAAAGCCGGCGAACGTGGCGAGAAAG
        GAAGGGAAGAAAGCGAAAGGAGCGGGCGCTAGGGCGCTGGCAAGTGTAGC
```

FIG. 6I

```
21051 GGTCACGCTGCGCGTAACCACCACACCCGCCGCGCTTAATGCGCCGCTAC
      AGGGCGCGTCCCATTCGCCATTCAGGCTGCGCAACTGTTGGGAAGGGCGA
      TCGGTGCGGGCCTCTTCGCTATTACGCCAGCTGGCGAAAGGGGGATGTGC
21201 TGCAAGGCGATTAAGTTGGGTAACGCCAGGGTTTTCCCAGTCACGACGTT
      GTAAAACGACGGCCAGTGAATTGTAATACGACTCACTATAGGGCGAATTG
21301 GAGCTCCACCGCGGTGGCGGCCGCTCTAG
```

FIG. 6J

SEQ ID NO: 11

GTACCGGGCCCCCCCTCGAGGTGAATATCCAAGAATGCAGAACTGCATGGAAAGCAGAGCTG
CAGGCACGATGGTGCTGAGCCTTAGCTGCTTCCTGCTGGGAGATGTGGATGCAGAGACGAAT
GAAGGACCTGTCCCTTACTCCCCTCAGCATTCTGTGCTATTTAGGGTTCTACCAGAGTCCTT
AAGAGGTTTTTTTTTTTTGGTCCAAAAGTCTGTTTGTTTGGTTTTGACCACTGAGAGCAT
GTGACACTTGTCTCAAGCTATTAACCAAGTGTCCAGCCAAAATCGATGTCACAACTTGGGAA
TTTTCCATTTGAAGCCCCTTGCAAAAACAAGAGCACCTTGCCTGCTCCAGCTCCTGGCTGT
GAAGGGTTTTGGTGCCAAAGAGTGAAAGGCTTCCTAAAAATGGGCTGAGCCGGGGAAGGGGG
GCAACTTGGGGGCTATTGAGAAACAAGGAAGGACAAACAGCGTTAGGTCATTGCTTCTGCAA
ACACAGCCAGGGCTGCTCCTCTATAAAGGGGAAGAAAGAGGCTCCGCAGCCATCACAGACC
CAGAGGGGACGGTCTGTGAATCAAGCTT

FIG. 14

SEQ ID NO: 17
IFN-A
ATGGCTTTGACCTTTGCCTTACTGGTGGCTCTCCTGGTGCTGAGCTGCAAGAGCAGCTGCTCTGT
GGGCTGCGATCTGCCTCA

SEQ ID NO: 18
IFN-B
GACCCACAGCCTGGGCAGCAGGAGGACCCTGATGCTGCTGGCTCAGATGAGGAGAATCAGCCTGT
TTAGCTGCCTGAAGGATAGGCACGATTTTGGCTTT

SEQ ID NO: 19
IFN-C
CTCAAGAGGAGTTTGGCAACCAGTTTCAGAAGGCTGAGACCATCCCTGTGCTGCACGAGATG

SEQ ID NO: 20
IFN-D
TCCAGCAGATCTTTAACCTGTTTAGCACCAAGGATAGCAGCGCTGCTTGGGATGAGACCCTGCTG
GATAAGTTTTACACCGAGCTGTACCAGCA

SEQ ID NO: 21
IFN-E
CTGAACGATCTGGAGGCTTGCGTGATCCAGGGCGTGGGCGTGACCGAGACCCCTCTGATGAAGGA
GGATAGCATCCT

SEQ ID NO: 22
IFN-F
GCTGTGAGGAAGTACTTTCAGAGGATCACCCTGTACCTGAAGGAGAAGAAGTACAGCCCTTGCGC
TTGGGAAGTCGTGAGGG

SEQ ID NO: 23
IFN-G
CTGAGATCATGAGGAGCTTTAGCCTGAGCACCAACCTGCAAGAGAGCTTGAGGTCTAAGGAGTAA

SEQ ID NO: 24
IFN-1
CCCAAGCTTTCACCATGGCTTTGACCTTTGCCTT

SEQ ID NO: 25
IFN-2b
ATCTGCCTCAGACCCACAG

FIG. 15A

SEQ ID NO: 26
IFN-3c
GATTTTGGCTTTCCTCAAGAGGAGTT

SEQ ID NO: 27
IFN-4b
GCACGAGATGATCCAGCAGAT

SEQ ID NO: 28
IFN-5
ATCGTTCAGCTGCTGGTACA

SEQ ID NO: 29
IFN-6
CCTCACAGCCAGGATGCTAT

SEQ ID NO: 30
IFN-7
ATGATCTCAGCCCTCACGAC

SEQ ID NO: 31
IFN-2
CTGTGGGTCTGAGGCAGAT

SEQ ID NO: 32
IFN-3b
AACTCCTCTTGAGGAAAGCCAAAATC

SEQ ID NO: 33
IFN-4
ATCTGCTGGATCATCTCGTGC

SEQ ID NO: 34
IFN-8
TGCTCTAGACTTTTACTCCTTAGACCTCAAGCTCT

FIG. 15B

SEQ ID NO: 22
Oligo 1. TCACTCGAGGTGAATATCCAAGAAT

SEQ ID NO: 23
Oligo 2. GAGATCGATTTTGGCTGGACACTTG

SEQ ID NO: 24
Oligo 3. CACATCGATGTCACAACTTGGGAAT

SEQ ID NO: 25
Oligo 4. TCTAAGCTTCGTCACAGACCGTCCC

FIG. 22

```
   1 agcttgcatg cctgcaggtc gactctagag gatccccggg taccgagctc gaattcgccc
  61 tatagtgagt cgtattacaa ttcactggcc gtcgttttac aacgtcgtga ctgggaaaac
 121 cctggcgtta cccaacttaa tcgccttgca gcacatcccc ctttcgccag ctggcgtaat
 181 agcgaagagg cccgcaccga tcgcccttcc caacagttgc gcagcctgaa tggcgaatgg
 241 cgcctgatgc ggtattttct ccttacgcat ctgtgcggta tttcacaccg catatggtgc
 301 actctcagta caatctgctc tgatgccgca tagttaagcc agccccgaca cccgccaaca
 361 cccgctgacg cgaacccctt gcggccgcat cgaatataac ttcgtataat gtatgctata
 421 cgaagttatt agcgatgagc tcggacttcc attgttcatt ccacggacaa aaacagagaa
 481 aggaaacgac agaggccaaa aagctcgctt tcagcacctg tcgtttcctt tcttttcaga
 541 gggtatttta ataaaaaca ttaagttatg acgaagaaga acggaaacgc cttaaaccgg
 601 aaaattttca taaatagcga aaaccgcga ggtcgccgcc cgtaacctg tcggatcacc
 661 ggaaaggacc cgtaaagtga atgattat catctacata tcacaacgtg cgtggaggcc
 721 atcaaaccac gtcaaataat caattatgac gcaggtatcg tattaattga tctgcatcaa
 781 cttaacgtaa aaacaacttc agacaataca atcagcgac actgaatacg ggcaacctc
 841 atgtccgagc tcgcgagctc gtcgacagcg acacacttgc atcggatgca gcccggttaa
 901 cgtgccggca cggcctgggt aaccaggtat tttgtccaca taaccgtgcg caaaatgttg
 961 tggataagca ggacacagca gcaatccaca gcaggcatac aaccgcacac cgaggttact
1021 ccgttctaca ggttacgacg acatgtcaat acttgccctt gacaggcatt gatggaatcg
1081 tagtctcacg ctgatagtct gatcgacaat acaagtggga ccgtggtccc agaccgataa
1141 tcagaccgac aacacgagtg ggatcgtggt cccagactaa taatcagacc gacgatacga
1201 gtgggaccgt ggtcccagac taataatcag accgacgata cgagtgggac cgtggttcca
1261 gactaataat cagaccgacg atacgagtgg gaccgtggtc cagactaat aatcagaccg
1321 acgatacgag tgggaccatg gtcccagact aataatcaga ccgacgatac gagtgggacc
1381 gtggtcccag tctgattatc agaccgacga tacgagtggg accgtggtcc cagactaata
1441 atcagaccga cgatacgagt gggaccgtgg tcccagacta ataatcagac cgacgatacg
1501 agtgggaccg tggtcccagt ctgattatca gaccgacgat acaagtggaa cagtgggccc
1561 agagagaata ttcaggccag ttatgctttc tggcctgtaa caaaggacat taagtaaaga
1621 cagataaacg tagactaaaa cgtggtcgca tcagggtgct ggcttttcaa gttccttaag
1681 aatggcctca attttctcta tacactcagt tggaacacga gacctgtcca ggttaagcac
1741 cattttatcg cccttataca atactgtcgc tccaggagca aactgatgtc gtgagcttaa
1801 actagttctt gatgcagatg acgtttaag cacagaagtt aaaagagtga taacttcttc
1861 agcttcaaat atcaccccag ctttttctg ctcatgaagg ttagatgcct gctgcttaag
1921 taattcctct ttatctgtaa aggcttttg aagtgcatca cctgaccggg cagatagttc
1981 accggggtga gaaaaagag caacaactga tttaggcaat tggcggtgt tgatacagcg
2041 ggtaataatc ttcgtgaaaa tattttccgc atcagccagc gcagaaatat tccagcaaa
2101 ttcattctgc aatcggcttg cataacgctg accacgttca taagcacttg ttgggcgata
2161 atcgttaccc aatctggata atgcagccat ctgctcatca tccagctcgc caaccagaac
2221 acgataatca ctttcggtaa gtgcagcagc tttacgacgg cgactcccat cggcaatttc
2281 tatgacacca gatactcttc gaccgaacgc cggtgtctgt tgaccagtca gtagaaaaga
2341 agggatgaga tcatccagtg cgtcctcagt aagcagctcc tggtcacgtt cattacctga
2401 ccatacccga gaggtcttct caacactatc accccggagc acttcaagag taaacttcac
2461 atcccgacca catacaggca agtaatggc attaccgcga gccattactc ctacgcgcgc
2521 aattaacgaa tccaccatcg gggcagctgg tgtcgataac gaagtatctt caaccggttg
2581 agtattgagc gtatgttttg gaataacagg cgcacgcttc attatctaat ctcccagcgt
2641 ggtttaatca gacgatcgaa aatttcattg cagacaggtt cccaaataga aagagcattt
2701 ctccaggcac cagttgaaga gcgttgatca atggcctgtt caaaaacagt tctcatccgg
2761 atctgacctt taccaacttc atccgtttca cgtacaacat ttttagaac catgcttccc
2821 caggcatccc gaatttgctc ctccatccac ggggactgag agccattact attgctgtat
2881 ttggtaagca aaatacgtac atcaggctcg aacccttta gatcaacgtt cttgagcaga
2941 tcacgaagca tatcgaaaaa ctgcagtgcg gaggtgtagt caaacaactc agcaggcgtg
3001 ggaacaatca gcacatcagc agcacatacg acattaatcg tgccgatacc caggttaggc
3061 gcgctgtcaa taactatgac atcatagtca tgagcaacag tttcaatggc cagtcggagc
3121 atcaggtgtg gatcggtggg cagtttacct tcatcaaatt tgcccattaa ctcagtttca
3181 atacggtgca gagccagaca ggaaggaata atgtcaagcc ccggccagca gtgggctttt
3241 attgcataag tgacatcgtc cttttcccca agatagaaag gcaggagagt gtcttctgca
3301 tgaatatgaa gatctggtac ccatccgtga tacattgagg ctgttccctg gggtcgtta
3361 ccttccacga gcaaaacacg tagccccttc agagccagat cctgagcaag atgaacagaa
3421 actgaggttt tgtaaacgcc accttatgg gcagcaaccc cgatcaccgg tggaaatacg
```

Figure 24A

```
3481 tcttcagcac gtcgcaatcg cgtaccaaac acatcacgca tatgattaat ttgttcaatt
3541 gtataaccaa cacgttgctc aacccgtcct cgaatttcca tatccgggtg cggtagtcgc
3601 cctgctttct cggcatctct gatagcctga gaagaaaccc caactaaatc cgctgcttca
3661 cctattctcc agcgccgggt tattttcctc gcttccgggc tgtcatcatt aaactgtgca
3721 atggcgatag ccttcgtcat ttcatgacca gcgtttatgc actggttaag tgtttccatg
3781 agtttcattc tgaacatcct ttaatcattg ctttgcgttt ttttattaaa tcttgcaatt
3841 tactgcaaag caacaacaaa atcgcaaagt catcaaaaaa ccgcaaagtt gtttaaaata
3901 agagcaacac tacaaaagga gataagaaga gcacatacct cagtcactta ttatcactag
3961 cgctcgccgc agccgtgtaa ccgagcatag cgagcgaact ggcgaggaag caaagaagaa
4021 ctgttctgtc agatagctct tacgctcagc gcaagaagaa atatccaccg tgggaaaaac
4081 tccaggtaga ggtacacacg cggatagcca attcagagta ataaactgtg ataatcaacc
4141 ctcatcaatg atgacgaact aaccccccgat atcaggtcac atgacgaagg gaaagagaag
4201 gaaatcaact gtgacaaact gccctcaaat ttggcttcct taaaaattac agttcaaaaa
4261 gtatgagaaa atccatgcag gctgaaggaa acagcaaaac tgtgacaaat taccctcagt
4321 aggtcagaac aaatgtgacg aaccaccctc aaatctgtga cagataaccc tcagactatc
4381 ctgtcgtcat ggaagtgata tcgcggaagg aaaatacgat atgagtcgtc tggcggcctt
4441 tcttttctc aatgtatgag aggcgcattg gagttctgct gttgatctca ttaacacaga
4501 cctgcaggaa gcggcggcgg aagtcaggca tacgctggta actttgaggc agctggtaac
4561 gctctatgat ccagtcgatt ttcagagaga cgatgcctga gccatccggc ttacgatact
4621 gacacaggga ttcgtataaa cgcatggcat acggattggt gatttctttt gtttcactaa
4681 gccgaaactg cgtaaaccgg ttctgtaacc cgataaagaa gggaatgaga tatgggttga
4741 tatgtacact gtaaagccct ctggatggac tgtgcgcacg tttgataaac caaggaaaag
4801 attcatagcc tttttcatcg ccggcatcct cttcagggcg ataaaaaacc acttccttcc
4861 ccgcgaaact cttcaatgcc tgccgtatat ccttactggc ttccgcagag gtcaatccga
4921 atatttcagc atatttagca acatggatct cgcagatacc gtcatgttcc tgtagggtgc
4981 catcagattt tctgatctgg tcaacgaaca gatacagcat acgttttga tcccgggaga
5041 gactatatgc cgcctcagtg aggtcgtttg actggacgat tcgcgggcta ttttacgtt
5101 tcttgtgatt gataaccgct gtttccgcca tgacagatcc atgtgaagtg tgacaagttt
5161 ttagattgtc acactaaata aaaagagtc aataagcagg gataactttg tgaaaaaaca
5221 gcttcttctg agggcaattt gtcacagggt taagggcaat ttgtcacaga caggactgtc
5281 atttgagggt gatttgtcac actgaaaggg caatttgtca caacaccttc tctagaacca
5341 gcatggataa aggcctacaa ggcgctctaa aaagaagat ctaaaaacta taaaaaaaat
5401 aattataaaa atatcccgt ggataagtgg ataaccccaa gggaagtttt ttcaggcatc
5461 gtgtgtaagc agaatatata agtgctgttc cctggtgctt cctcgctcac tcgagggctt
5521 cgccctgtcg ctcgactgcg gcgagcacta ctggctgtaa aaggacagac cacatcatgg
5581 ttctgtgttc attaggttgt tctgtccatt gctgacataa tccgctccac ttcaacgtaa
5641 caccgcacga agatttctat tgttcctgaa ggcatattca aatcgtttc gttaccgctt
5701 gcaggcatca tgacagaaca ctacttccta taaacgctac acaggctcct gagattaata
5761 atgcggatct ctacgataat gggagatttt cccgactgtt tcgttcgctt ctcagtggat
5821 aacagccagc ttctctgttt aacagacaaa aacagcatat ccactcagtt ccacatttcc
5881 atataaaggc caaggcattt attctcagga taattgtttc agcatcgcaa ccgcatcaga
5941 ctccggcatc gcaaactgca cccggtccg gcagccaca tccagcgcaa aaaccttcgt
6001 gtagacttcc gttgaactga tggacttatg tccatcagg ctttgcagaa ctttcagcgg
6061 tataccggca tacagcatgt gcatcgcata ggaatggcgg aacgtatgtg tgtgaccgg
6121 aacagagaac gtcacaccgt cagcagcagc ggcggcaacc gcctcccaa tccaggtcct
6181 gaccgttctg tccgtcactt cccagatccg cgctttctct gtccttcctg tgcgacggtt
6241 acgccgctcc atgagcttat cgcgaataaa tacctgtgac ggaagatcac ttcgcagaat
6301 aaataaatcc tggtgtccct gttgataccg ggaagccctg ggccaacttt tggcgaaaat
6361 gagacgttga tcggcacgta agaggttcca actttcacca taatgaaata agatcactac
6421 cgggcgtatt ttttgagtta tcgagatttt caggagctaa ggaagctaaa atggagaaaa
6481 aaatcactgg atataccacc gttgatatat cccaatggca tcgtaaagaa catttgaggg
6541 catttcagtc agttgctcaa tgtacctata accagaccgt tcagctggat attacggcct
6601 ttttaaagac cgtaaagaaa aataagcaca gttttatcc ggcctttatt cacattcttg
6661 cccgcctgat gaatgctcat ccggaattta catctggaat tacgtatggc aatgaaagac
6721 ggtgagctgg tgatatggga tagtgttcac ccttgttaca ccgttttcca tgagcaaact
6781 gaaacgtttt catcgctctg gagtgaatac cacgacgatt tccggcagtt ctacacata
6841 tattcgcaag atgtggcgtg ttacggtgaa aacctggcct atttccctaa agggtttatt
6901 gagaatatgt ttttcgtctc agccaatccc tgggtgagtt tcaccagttt tgatttaaac
```

Figure 24B

```
 6961 gtggccaata tggacaactt cttcgccccc gttttcacca tgggcaaata ttatacgcaa
 7021 ggcgacaagg tgctgatgcc gctggcgatt caggttcatc atgccgtttg tgatggcttc
 7081 catgtcggca gaatgcttaa tgaattacaa cagtactgcg atgagtggca gggcggggcg
 7141 taattttttt aaggcagtta ttggtgccct taaacgcctg gttgctacgc ctgaataagt
 7201 gataataagc ggatgaatgg cagaaattcg atgataagct gtcaaacatg agaattggtc
 7261 gacggcccgg gcggccgcaa ggggttcgcg ttggccgatt cattaatgca gctggcacga
 7321 caggtttccc gactggaaag cgggcagtga gcgcaacgca attaatgtga gttagctcac
 7381 tcattaggca ccccaggctt tacactttat gcttccggct cgtatgttgt gtggaattgt
 7441 gagcggataa caatttcaca caggaaacag ctatgaccat gattacgcca agctatttag
 7501 gtgacactat agaatactca agctttgtgc tttctgcctg aataaaagaa acctgaactc
 7561 tgttcaccca gtccctgtca ggcaattact gacagagcac ctatggtctg tgtttggcca
 7621 gaacataggc taaggaagat acctcctgtt tataaagcac gcctttggca tctggcaagt
 7681 aattagtgat ggcgcatgag agctctgact agggcagggt gtgggacagg ctggctctaa
 7741 ttgtgccctg tttatcttgt tgatgcacac ggctggtttc tttcacccac agctgtctct
 7801 ctagacaaca tacctttatg gagaggaacg tgtcttttcc aatcttgggt tttcattcag
 7861 aattggagtg aactggtctc catcagatag cattggctgc ggtgatttat tcttttacac
 7921 ttcctagtta agcaggataa ctctctggct ctgctgtgtc taggcaattt aaatgattta
 7981 taaagcatag ctgttttaag gaaatctttt tttaaacatt tgacttgcca atgtgtggtc
 8041 ctaaaggcag aaggactgtt ccagagtgtc aggcagagac ctaccctgga tttcgttgtt
 8101 cagctaccca ttcagtgtgg cttttggcaa ggaattctct ggacctgact tccctacctg
 8161 cagagctggg ataagctatc aaaccatctc ctccacacac tgtgagggtg ggaaaaaaac
 8221 ccaaaccctt aaaagtgctg tataaaggcg ccttaaggct cagtatagca tgtgtgctgc
 8281 tgatgcccca gacctgtttg cgggtcctga aggtcatagg agaactgctc agaagagaca
 8341 gaaatgctta agaaggtttt actacaaaag tcttgtgatg ttaacacata atatcacatt
 8401 gtgcagaagg tacaaatgcc ccctcctatc cctgcacacc tggaagctca aggtatggaa
 8461 gggtttgttg tctgcagcct cttcgctgcc ctctgctttt taagatcctg ggtagtgtgc
 8521 tcagtgtgtg ccctcagcag tttgggaaac ggacatcttc atgcaaaatt aagcaaggaa
 8581 gtgttgcttt tatactcaga gtagaatcta agttcttcag gcaggctctt gtgtgccgcc
 8641 tctattagaa ataaaactcc cccggatcag aagatgaatg tgctcagcta agaacacaga
 8701 tttatttgct ttacaatgcg tgctatggtt taagaaaaac acatcaggca aacaatttat
 8761 ggtttgccac tgagttgtgc ctgaaggaaa cacaactgtt agagatgtaa ttgattgggc
 8821 ggtgacgctg tgtggattca tgggagatgc atcttggtca gcatgtctgt gtgaaaccac
 8881 atttctggtg ctgctgcagg acgagtgccg ggagttccgg gatctgttca agaatgggaa
 8941 gctttcctgc acgagggaga atgatcccgt ccgggattcc tcggggaagc agcacagcaa
 9001 taagtgcatc atgtgtgcgg agaagttgtg agtagaggaa gccaatgttt gttatcgaga
 9061 gtggcaatgg ggccggggtg ggctcctaca gcaatgttct cctcactttc tcatccttct
 9121 ctttcagcaa aagggagaat gagcagaagg cgacctcaac cagagggaaa caaaaggtga
 9181 ggttaaagta ttgggttcat atacaagtct ataggattct tacccaatat taccacactt
 9241 gatttctttg tcactctggg gatccatgtg gcttttcctg cttgtatctc gttgatgctc
 9301 tttcatgccc tgagagaata gtttgtctga acgctgcagt ctatcccact gaccgcagtg
 9361 acatgggagc aaacccatc gcaataagaa gctgagcaga actgccctga catctggcac
 9421 aagggcaaga aggcactgct gctgagagcg ctaatgaggt tgaaaagaaa atctgggtga
 9481 gaagctttaa atgtgagctc tgagatgctc aaaagttcat tatgtcgtgg gaggagagtt
 9541 cagccctgtg ctgtccctgg ggtggctcgg tttcagcttt ccctgattgg aaacctcact
 9601 ctcatgatgc agctgctgtg cccttgtgca ccgatacttc tctggtgaga gcaattcagc
 9661 aaggggaagg aaaaagaagc actaagtaaa tcttgccatt tctgtcttgc gaggaactgg
 9721 tacggtcccc ttaagcctca ttcttgggga taatcctgtt tcagtgcttt tcctaatgac
 9781 agtggcacaa aaaaaatgga agcgttaatg aaacttgctg atggcaaagc tgggagggag
 9841 gatcagcaga tcactcagga ctaattggat agcactgagg cctggagtaa tagaaacaag
 9901 ataaaatgta ataacagaga gtgcaagatc acacaggcag tgattaacga gaattcctgc
 9961 tcatcaatta gaaatgacaa aggataagaa agctctgcat ttattagtgg gtcacggatg
10021 cggcaggcct gagaaggagg caaatgcaca tctcagcaag gtctgtgcag cagaggtcgg
10081 gctggcagca aatctccaga aatactgctt gaagagaga gggtttgaga gacgctgtta
10141 gggagaagca gctctgccac agcaggtctg gggttcacct ggggtttggc tcattgcctc
10201 cctgtgtccc tcctccacgc tgccagtgct gcactgggaa ggtgtgggta agaagcaatg
10261 gctaagggat ctggttatac acctcctgta tctgctattt gggattggct actgcagggc
10321 ctcaggtccc tgacttaaaa gtggggactt cgaagcatgt tgcattgtg ctgtcgtgcc
10381 ttagatgttg ctgctgggtc ctcaaagtcc tgttggttgt ggggtggggg ggacttcttg
```

Figure 24C

```
10441 cttcctatgt gaagttttct gagctgcaac ttcagcaaca gctgtaagag tgcattaagg
10501 gcagtgggag aagtgggagg gaccccatta cctcatcggg tatcgctggc atgctttgga
10561 tagccccacg tggagcgtga caattagagc acggcagaga gctcccaaca cgtgccatgc
10621 aggcagaggc acccgccgct cttctgactc actctgtttg tagccatgag gctgtgccac
10681 gtgccctctt ctctctctca cacctgggct ctcctggggc gcgtttggga agcctctgga
10741 ggatcggagg gatgtggcag ggtgccctga ctgctgctcc ttccgcagga tgactgcagt
10801 gagtaccgct cccagtttga ggctggcgga cgcctgtcct gcacgcggga gaacgacccc
10861 gtcagggatt cctctggcaa gcagcacacc aacaagtgcc tcatgtgtgc cgagaagctg
10921 tgagtacagt tcctggcaac agcaaagagg gaaacctcac attgcgaaac tgcagcttct
10981 gcctgtgtgg ctgcgcctgg gggagtcccg agtcccagcg gccccccagg agctgctcct
11041 gctgtagggc tgtggctact gcccctcttc ccacctcccc cctaacccct cagggagcag
11101 aggagaagca gggttgatag agagcagccc tttccttggg gcagctccca aggaaagttt
11161 cccacgcgtg tactttgcct tccagatgct ctctctactc catagagca tatgcagaag
11221 cagccctgat atgaaagcag ccacctggag ccgggatgta gcatacagtg ggaatggtga
11281 ggagaaggga gaaggcttag gggtgggaat taggtgcagg gccaccaggg atggggaggc
11341 tggtgcctaa tgacatgatg ctggcttgca gggcagcccc aggtcctggc agcgttcgca
11401 ctgccatagt gctcctttct ttctcctctc ccttttttcc agcaaaaaag aagctcaaag
11461 aggaggtcag tctggtggaa ctgcccagcg caacaagcag tccactgcag agtgtgcaaa
11521 ccaggtgaga ctgagctcag agcctcacca ggcttgggaa aaggggttgg tggatctggg
11581 gaccccgatg gtcaagggct gcctgtggtc ctggtgtttg gggtgcagga gcctgctggt
11641 gatggcagag aggcaggttg cattgcaagc cctgctagtt catgggatgg gtttgtgtat
11701 gagcgtgcat agtgggcagt tctggactcc tctatggggc acgcatcaga gctatttctt
11761 cagaaagagc cccatggttc ctagggtcca gggggatgag agggaaggac aggagctgct
11821 ttaatctcac tgctttactg cttggttgtc aaacacgatc ctgccccttt tccagaagag
11881 ctgcagtggc tcagggttac agcggggtgt aaatgagaga cggccgttct ccacaaacag
11941 agggtgagta cagcagcact gggatcccag cctggcccca caagtcctgg ggtcttgaca
12001 ctgagaagaa acacataaaa tagggcatat acaacccttt ctccttttcca aagacattct
12061 tgcttcccct gcacacgaag cactggtgac tgctacactc aaaatccctc cccagccttg
12121 ccccctgaat cctgcctcct ggcaggcaca cacttgtcct gctgcctggt ccagcgcatc
12181 ctcatctgct gacctgaggc agtgctgtgt gtgcaccatg tgctgtctgg gcactgagcg
12241 actcctctgg gtttttaggg ctgccaggct ctggcagggt gcagatgctg tgttatctaa
12301 gccttgagga actctcttag tcttcctgtt tttgttggtg aggcccattc atctgccccc
12361 agtcagcact gccagcagac aaacagtgca cagctctcca tggcagcaat ggctgtagca
12421 tatgtagggg ccaggtttct gggatcatct ctgtgacgga catctcttgc tgaccgccca
12481 taaggactca aaagtcccgt tgcagggagt gcctccatcc catggcaagc caagtgccct
12541 gttgaaaaaa caaggtgcag aataatggca atggacctta gtgcagttta attccaccct
12601 gggggtgatga tgtggctgag tgggtctgca tacccttggc tgtgccatga gctctgtgct
12661 ttctctccct gccagcccac aaggagactt ggctcaggac tgcagcccgg cacctggccg
12721 ccagggacag agcggaggca ccaacaccta ccagccggta tgcccagctc atgtgggtca
12781 ggcacagcct ttcccagcag ctgccccagt ttccattgtc aacctaaagc ctcacaatgg
12841 gacctgtatc cttggagggg tttaaatggg tggtagagtc cgtaccctga tgctgtcccc
12901 tggcctcaaa gaggagtgag gctgcacacg tccaaacggg agtcactgaa gccagtgctg
12961 ctgctggtgt tggctcactg tagaagtatg tcaggtatga gagagcatcc tccaggaggt
13021 gatggtggtg tcccttcctg catgctgaga tgttgggttg aagactgtgg ccagagcagg
13081 gtgctggggc tgagcggggg ataaggacaa ggctgataag aggaggggag agggagtagt
13141 gggggaggac acggtgagca atagataacg actgtttgtg gaatcatgtg ggagggagaa
13201 gagggtgtat gctctctcca tctccacaaa aagaaatttt gttattttca accaagctaa
13261 agcagaaatt atgaaactaa taggagaaaa taagttacta taaaaggat gactaacctg
13321 tggatcttgc tgtcacgggg tgttgccaag agctacagtg attaaaaaaa atgacttgcc
13381 acttatagtc catacagcaa tttaggtaac attttggaag ggataggaaa tgcctttctg
13441 tggggctgga gggacctgag tgcagactgc cttaactctc tctgaagtct ctgtcactga
13501 ctgcccttag aaaaatgata ttagaataga aaaccaggg aggcggttca ggtatggcag
13561 ttttaatgca ttccagagga agcattaggc ataataatgc cagtctgctt cagggcttag
13621 tggtatttcc tggtagctcc ggtgaaggag tggatgctga tcagcctgac tgacgagggg
13681 tgattcagag agcagatctg tgtctctcct cgctgcaggg ccacccgtgg gctctgtccc
13741 agggagatgc tgtcctgaag gagaggtggc agtcactgtg aggactgtgg ggactgttg
13801 gtgtggcggc ggttgcacac gcgtgggtca caccgtgggc agtggtgtct ggtgtgtggg
13861 aaggcatctg gcagggaact gcaaaggtca gcgctgtctg tctttgtgtc atcgttaatt
```

Figure 24D

```
13921 acccaggtga gggaggaagc agcacattaa tgaaattagc aagtgatgtt taaacagagg
13981 gtgttactgc agcaacctgt gccactgaac ccctgcatt gcccagctgg gaaacctttc
14041 ttctccatgg tgctttcaac cccatagtgc tgctgacccc agcaaagcaa tgagccattg
14101 cttagtgctg aatggggttt ttttctcca agtgggacag gaggtgagat gtccttcctg
14161 cagctcttct ccaattgcac catttgcagt cattgcaaca tttttatag gacctggaga
14221 agggatggg aacagagaat tcactccttt tgtctctgca tcttttttt tttggccttt
14281 ggtgcagagg tgggcagtga ggctgaggaa gagaggggc tgtaggatct ctgacctctg
14341 ctgtctgaaa cttgccatga ttctgcaggc acctgtgcca gaatgctcat gggctgataa
14401 tctaatcatg aggagtcttg ttcctcctgc tccgagctct ttctagctgt gccacgtctg
14461 ctttgtagga aattcgatgc ctagatgctc ctgctgttat gctggagaat aaaacgagag
14521 ggcacgctta attagtcaga gcttttcata catgtttgca tctcttcatt ccgtgggtgt
14581 caagttgtgc tgtgtgtcgg gctgcccttg gcagctgga ctcaattgtc aaggttttcc
14641 ctttgtttct gccaagtggc ttgcagaagc aacaggtgtg aaagctctga taaggacaa
14701 aggacaggta gcagaagttt attgtattct cgtggatttg cagggagaag taaaagtgcc
14761 ctggactgag atgtcagggt ggatcagatg agtgtatcca tgcctggcaa tggggtcagg
14821 gcagctttgt ccccacatcg tggctggttg gcccaatagg aggcgttacc tctttgctga
14881 aggtgtgatg gagctcaggg caacgcctgg tttgtgagtg ctttgagcgg tgcgcaggag
14941 ggtcttgcaa gagaaccagc accaaatgtg atttctttct ctcttcagct ggactgtgat
15001 cgaattctgc acggggtaaa gggtggaagg attttctgca gcgaatcctc acaacccgtc
15061 tgtggcactg atgggaaaac atacagaaat gaatgtgact tgtgttcagc tgccatgtga
15121 gtaggcggag agatttcagt aatacagggc catccaccat tcccgagtgt cttttgcagc
15181 acagtgtttg ttttgatata ccatgactca ctatcaagtg tgtccttggt gcctcgctgt
15241 taagcaaaca tagatcaaat gtctgagatt aatatgatga cagctaatta agatacacaa
15301 cttttccagag tcccttattc cctttctgct caatcatagg attgtttggg gagtaataaa
15361 tgccatcaaa ttggaagtag catcaaaggt ttaaggagcc cacagaggac caccgtgacg
15421 atgtcaggga gctgtggcac tggaagtgaa taagcaatgt cttgttctcc ctttgcagga
15481 gagcatcagt ttacatcacg gtaaactacc gaggtgaatg ccgaaagact gtccctgaaa
15541 tggtaagtgc ctccctgctg tggcatccca ttcttgttc tgggtgtgtg ctggagaccc
15601 agcctggatc ccgtatctgt ggtgggatca tcagagccct gttagcaggg tgcttgtggt
15661 tcacatgcgt aaatacactt caggcttgga tttaaggcat tttgaggcat aatctccacg
15721 ttttttccag gctgtgtggt aggggagtga catgtctggg aaaacatgtg gctttcctcc
15781 tgggattttg gtgaggccaa gaaaagattg caatcgcaca accataagg gcctaatttc
15841 ccaaatgata tccaggcagt tggttgggaa ggaaatatat ccctaagtg gtatccttt
15901 gggaaaggtc ttgaatcttg tgtgattgcc ttgtagtaga tgagtcaaag atttgttagt
15961 ggtgctttgt cttcccgctc gtggcagctc agcggcattc agagctttgg tttggagcca
16021 gggtgtccca gtttgtgtgt cttgagtgta tgggactgac cttagtgttg gcatggactg
16081 ttggaaagct gagtattcat ttccccaggg aaacaccgac atctatcccc attccaaact
16141 tggaatgaat caaaatatca aatcagccaa atggagaagt tgtgcaagtt ttttttgcaa
16201 tgagagagat ggcttctgaa tatgaatttg ctgacagttt gtaggtaaaa cagtattgcc
16261 cgttgaaaag ctttagagca aaattaccat catagggctt ttactctcct ctgcttattg
16321 acaggatgcc cacccatccc cacaacatta gaatgaggc atccccattc ctcttcctct
16381 cttctgtgaa gtaccagagt gctctcaacg ctgtttaaag ctgaagaaaa aatgcagaga
16441 aagagttttg cttgtgatcg tgctggaggt ctttgtgtct cgccctttgg tgcgatggag
16501 ccattgctgg tttgtgtatg ctgggagtgg aggcactatg catacctgct ggtggctgtg
16561 ctaatgatgc tggagacaga caaggttggg tgtaccacgg caactgaaaa ccagagagga
16621 ctccctcaga gttgtgcctg gctgggattc ctcaccattt tgtgttttac caagacgttt
16681 taccagctct ccagtctttg cagttagagg aatatgccat acactaaaag tcagacaatt
16741 tgtagctatt ccaaggagag ctggaagcaa ttaagggaa agtgataagg ttttccact
16801 ggggaaaatc ccccacaaaa aacacccctc caaacaaaga cttattattt cgttctttat
16861 gtatattgtg tcacctgaag aatcagattg gaaatttatg gaagcccatt ccttagcaa
16921 accccttgtg tccatcaaag acttcccttt tttttctcag ttggaagctt atgaacaatg
16981 tactgaccag tgttatttta tgcctctgaa attcatgcta acattcagct taatgcatcc
17041 ttctgaaggc ccaggcactc gctgtgtgaa ggagatcaca gtgcctttgg cgtcagaaat
17101 gatttcaggc tgttgcaata cgcagcacga agatgcaaag gcccaaagac ttgagccttg
17161 gaaaagata ggagattgct gcccgaaaat gtagtttgtc cttgagttgt gttttgaaat
17221 tagccacggt aatgctgtgt tgcctgccaa aatgtgtgtc caagctcaga gcctgcagcc
17281 attcctgcta gcaaagcccc tcctggattt ccagcagttt gtggcagtcc ttccctagca
17341 gtggctggat tgccatcagg gagggatggc tgtaggaagg gacaggagaa atgtggttgg
```

Figure 24E

```
17401 agagagatct gacattaaag ggtgcatccg gacagcctgc actgatgtgg tggaaaacct
17461 tcctgcagag agagccctgg ggctggctgg cagctgggcc cctgctgcct gtgtgagctc
17521 tgtgccacaa ccagcctcct ctgatcctgt tctgctttac tgcagatgaa tgtagctgag
17581 tctagggttt agatttctat gtttattttt aacaaggcag ctggcctctg cgtcctccat
17641 gctgtgacat acagctgtat taatggtggg tctttccaga atgtttcact ttcaatgctg
17701 tattttttt tattttgcag tttctctttt tgttcagatg cttttcaca catctcccat
17761 gtgacagata ccagtctgtc catgttagtt gacaggtcag gcaaaaaaa aaaagggata
17821 tccagtttct cctttttaat ctgttttcta aagaacaaag aactcccagc tttctaatgg
17881 gcaaggccat tttcttacag tgctcttttt gtcataccct tcttaagaat gtagtagaag
17941 ggaaaagaaa caaacaaaaa acccaggacc ttttccagct tgatattggt tttggaaagc
18001 acacagatcc aggctgaaat ctgtttgttt tctgagtctg gcagtgaccc atccactgcc
18061 ccatcccacc tggttcctgt ggccactgag ctgcccaaag gggctgtcat gtagcccta
18121 atgctctgcc agcgtaacag cagtggatgt acttgtggat ccacttatat tttgctcttt
18181 ctttccagaa ataatggagt tcagactgcc agcaaatacc agggatcagc tgtgaccaaa
18241 ggtacagtgg tgcggtgatt tgctccctct tggacaactt gtccgcattt cacaagggtt
18301 tgggtgtcag accttgcctg ggcaggctgc tgggtatgtc tggggcaaag ggctctgcaa
18361 cacacccttc cctattgcca cagcacaaga atgaggcgtg tgtcttttgc agaagtagca
18421 aggtgatggg aagcccctgc caaggggct gagccctttg gggtgtgcaa acttcatgag
18481 gacctcctca tctctcaggg gtgggccttg cccgttcctt ttccctcaga tatccctgca
18541 gaggggggaag gatgctggca gagcagagta ctgcagtccc tcctcacaag gaggtggagg
18601 tgcccaaag caacctggct ttgagctttc cttgtggttc ttctgtgtcc cttgccttt
18661 ggagccatag taataaaccc gtctgccccc tgtttctcta ggacaagtaa aggaagatct
18721 gatgtcaggc accagggaag ctgctgagtt ccccagtgct gttggatcca ccttcatctc
18781 cttctgcagc caacgggcct gtccttgctc aggtggaggg tgaagggctg tggggaccca
18841 gtggtggctt cccacgttgg ccccacgcat gttgttgtag tcgctgctcg gctcgggctc
18901 tgccgcctcg ctgtgtctta gcatgtttct acaataaaga taactccaca gcgtcctgtc
18961 gcttttcttc actgagcctc acgggaggga cgtgtgagtc cccgctccgg ctgctcgcca
19021 cgcgtccctt gagctctaaa gcaccaaacc caagcggaga tgtcagacgc agagaagaag
19081 aacgtggtct gggttctgtt agcagggacc agcagttggg ttctctgact cgctgtgtag
19141 ggctttgggt gtatctcttt gtctcccttc agccctttc tcttgcctgt aaaaacggac
19201 attaaaggat gcttacctac ctcagagggt tgtttggaga ttttaattgg tttacgttag
19261 agagcccacg ggtggaattc tgttcctatg tgccaatgct ggtgtgcagg aggtttaact
19321 gttgcagtca tggcctcttc cagccaacac ccgatgggcc gtatgtattt cctgttcttt
19381 cgtttatggc tgttacttaa agcaaatatg ttcttatttg tataaacttt attgcaggac
19441 atttccagaa gaccttgagt gaacgtacag tgtttgagtc cactttagct gtgacctgat
19501 ctgcaaatac actctgctgt agataaggct ggagtaactt tcagattttg gcagggtttc
19561 gctcaatgcc aattaatttg gctccctcca cagatattga tttttttttt tcttttcaat
19621 taagttatcg agatcttttt ttcttaatgc agctaatgaa aatcgatttt tactctcata
19681 aagtacttcc gcatgtgtca cattgatctg tctatggctt gattatcggc aggctttgac
19741 atgaggttaa tatttgtgt gctggttttt tttcaccgtg tgcaaacact tggtttaga
19801 aatatgttac cgctgcttat ttctacgtgg aaaatcccac ggcgtggtta tgcatggcag
19861 aagtcaccag tttgatccaa tttagctgtt tctagggatg caagattcct ctgcctttga
19921 gcgggtgaat cctcgggtgt tatttataca ttctgagaag gatgaacaga agacggtaaa
19981 aacgtttgct aatgatgtct gctggctgat tccggctaaa atcgtgtgca gggacctcga
20041 cgtgatttt ataaaggcag ctcacaattt gaggcttaaa gtaagttctt gcaaatgaaa
20101 atgggcgcac ttgagcgcgc tattataact tgtagtgatt tcaagcactt agatttgaa
20161 ataatcgccc ataaaaacct gcattaattg tgctccaaaa ccaatgagct gatgaggagg
20221 gtgccctggt agcctctttt gctggatttg agcaccttct gaatttctcc tgccaccagc
20281 agaaattagc cacagaaatc atagctgcta taagggttta ttaatcagat tacgaaactg
20341 ctaagaaggc acacaacagt gacttgctga agctgcctgt gctgctgtta gcgagcctcc
20401 cgtaggtagc aatgctaact ccttcctttt agcagtttac ccactgcttc cttccatcac
20461 tccttccttt tgtagggcct acttttgcag tttgatccag tggcttgcag gcaatatctg
20521 tccccagcgg tgctctatgc agctgacctc caggtagggc tccatgtgag cgatgcaatg
20581 tgttatttcc atggggttcc taagaaggag gaagcaaaaa gctcaggagg tgctccaaat
20641 atattatcct gtcctctgtt ttgctctttg tggtgccctt taacactgta aagagaccat
20701 aggagtcctc tatgaacctg gaaggtacc agcactatgg gaggtcttca gtttgctgta
20761 aattatgctt tattagaggt atttcttctg ccaagaccca ctgaccccat gcggctcaca
20821 gtgttttcta aggctttgca ggactggtgt tacgaattgg caccctccag gcctctcaca
```

Figure 24F

```
20881 aatctcctgc ttctcacagc gtttcttcaa gttctcccaa gcacagctga gttttgagct
20941 caactgctcc ctgcaggggc cttgagcctc ctgccttttt gcataaaagg tgtcaggtac
21001 ttatgcaatc cttagaggca tgcaaatgct gctctggtta tatactgagg actgttgatt
21061 ctggcagaac cctttgcaga ccttgtactc ccttgctatt tcccaatccc tgcagcctag
21121 cagctctgcc taacaactgc catagccaac acagcagcag gctgtgcatg tgcaaggtg
21181 atgtggaaag ggatgattgt atgaaagcgt gatgctgtgg tactgcctct gcaggagact
21241 cgcactattt gtgtaagagg accttatttg tctgctgcag agctgtttca aggctgtcca
21301 tacaccctg tgatgctgag cccctccaag caatgcactg ggaaaggag gctgggggga
21361 gaccttattg ctctcctcca atatttgaaa ggtgcttaca gcgagagcag ggttggtctc
21421 ttctcactgg tgacaggatg aggggaaatg gcctcaagtt gcaccagggt atgtttagat
21481 tggatatcag gaaacactta tttactaaaa ggttgttaag cactggaatc agctccccag
21541 ggaggtggtt gagtcaccat ccctggatgt gtttaaaaac tgtttggata tggtgctcag
21601 ggacatgatt tagcggaggg ttgttagtta gggtagtgtg gttaggttgt ggttcactcg
21661 atggtcttta aggtctttc caacctgagc aattctatga tatggatccc tggggctttc
21721 agtcttatct ccctggatta tcacaggttc agctctatgg cccattgat ttataccggg
21781 gtctgatgaa caggttttc tcttggctct tcagggatcc tatttagcac ttttggtac
21841 attccctgc cctacaagtc tccctgatac acagagctct tatccaagac ttgggaccct
21901 ccctactcca gccctctgca ggaggtttct tgctaaccag tcctccaacc aggactgcag
21961 tacacgacaa agagctggaa gaggtctgca atacttcccc agcatgaagg tatgagcact
22021 ccttttgagt aggttactga aagtagtaag atgtcaatac aaccaactgc aagatacaaa
22081 accgcatgaa aattcagttt actttgatgc tgaagggctg aaaagaaatg ctgtggtgtt
22141 agcacagatg cactgctggc aaagtgaaaa tgagcaaaga ggatgagatg gatggacagc
22201 tgatggaaaa actcttccta attgctccac agagcagctt gctcgcctgc agggctgcag
22261 catggagctg cttgtgcata atgcagacac cccaagacca gtgctgtttg tcttagccaa
22321 gacacagttg cagctgcagc aatttttct agatgtcagt tccttccta tgttgctgac
22381 aggtgtttgc tgttctgtcc ctttaatctg tatcctacag caaacattcc ttgaatttaa
22441 taacttagct ggaagacaat tgctgtgatc ttgatagaac atgctgagcc aatctatttt
22501 aactgcagat ttagtttgca aatactgtct ccttgccgat aagattcagg tgtcatcttt
22561 gtggacattg gcaggaattt tcttgaccgt gacaggtttt acagagtctg gcaattaagc
22621 tgtcaagaca catttttcctc tgccaggaag cattaattga tgatagtctt ggctgcaata
22681 ggcacagaga gatggatatt gtaatcagaa tgaatagagg tccttgtagt tgagagctac
22741 gttggtccaa agttttgtag tcgttgacgt ttggtgatac tgagataagg aacaaggcac
22801 gagatattag agctaaatat caggcacagc atgagaataa agacctctct agctggaact
22861 gttggtatct ggggagattt taactttctg gatgcatact gcaaagtact aatattagta
22921 gagctactgg atgcgagagc aaatagtttt ccattaagta atcccaaaaa tcatgttgtt
22981 gttggtttgc ttttcaagtg cgaggggtgt tggagatgta tttccctcag aaaataaacc
23041 tgatatgatt caacctgagc tctctctgtt taaatcacac tgaaaataga tctgcaaatg
23101 gggattttga ttaccgagta cagaatatga aagattaaaa cttgggaaag ttagggttct
23161 gattgagaaa acttttgttt ttgtggccga cccttgcagc ttacaaaaat ctgcctaaat
23221 aaaggagaac accacattta gaacccatcc aagctatgct acttcagtac tgggcaaaac
23281 ttcaggagac gtttgaagaa aactgaagac gtgaagtata aaggaatgat tgatgtgcac
23341 agtaaactt cttgaaggt aatcacgcat gggctaatat caatctttac aaagttggct
23401 gacttcctag ataaaggaag tacagtagat ctagtctacc caggcagcaa aaatgtttga
23461 cctgttgccc tgtggggtgg tgtcacctgg gcttggggag ggggtcagg atgaggttac
23521 aggggatgtg gaagcatact gtggaggagc aggtggggca cccacaggag ttagcagtga
23581 gcagacagaa aggtggatct gaggaccgaa cttcgtattt tgttccttg cattaataca
23641 caaaaagcag acacacacac agagcagatt gctgctggtt tttgtttct tttttaaaca
23701 gcagaagagc aggattttc ccacagagaa tggggtgacc ttctaggctg tgattgcctg
23761 ggctcaagct gagatgaaac gcagtgatga ggagcacaaa accgtgctct gaggttaaat
23821 aatgagggct tcggctatca gttcagagct cagtaaaaac tgcagaggag gaggaagacc
23881 taattgcatg tagccagcca caggcaaat gagagctgca gcgtgctggg gcagatccgg
23941 gagcagaggg gccgtggcac gctcctgtt cactggctcc cctggagcca cacaaaaggc
24001 ccttcctgg caattgtgcc cacatcaatc attagctaga aaccagagc tgggtaaata
24061 cgttttggct tcccgtcttg atgacagatt gggtgttaca tcacaaggtg ggaccacttg
24121 atatgacaac acgctatata ttcccgctgc tacctctgcc cttcctcccc cactctgaga
24181 gcaagcgggc tgtgtgtgca ccgaggtgct ctgccatgag gactgccagg cagtttgtac
24241 aggtggctct ggccctctgc tgctttgcag gtgagtgttt cctgctatac cccgtaggtg
24301 actatagcta gaccagagac taggctatct gtgagagtat ctgggtattg taatgtgtta
```

Figure 24G

```
24361 gagagccttg ttccatgaag gaatgctctt tctgacagtg tagcaaaaca ccagactgca
24421 agatccaggt ttcagcaaac ctcatacaga cgactgtttt cgtcgtggtt tataggagca
24481 aattgctgag ggagcagtgc tagtgcaggg caggagcttg cacgtgcaag cactgagtat
24541 aacggcaaag caaagctatg tgaaatggct cctgtgtcca tgtaagcaat acaaacactg
24601 catcttgtat catctataaa ttttctgtgc tgttcctggc agctgagaag tttgttgtgg
24661 gaagaacagt gctagtggtc aacagccacc tgaaacgtgc atgtctgagc tcctgcaagt
24721 caaatacaga gtcttgcaga agagtttaaa ctcagtgcag gcttgaaaat acctacattt
24781 cttccctggg gcatcttagg aactggctaa cacatgtggc ctcctactga aagtgcagtg
24841 aaacttcatt taataacctc tgattcattt tatggacgta catcactggc ataatgtaaa
24901 attgcatttt cctaaaccca ataagccaat caacaacggt atctaaatgt aactgtttca
24961 tcgaaagatt tgcatatgtc atctctgcat attaataata tgtatttatt ttctgtctct
25021 acttttcttt tagatattgc ctttggaatt gaggtgagtt acagatttt tttcccatt
25081 attcttttct attccaggct tctggtcaaa taagagcagt atataattac ctgatgagca
25141 agtggattaa tctaatgaaa gcctggttgc tcaaataata cttgccagtg catgattgaa
25201 tgatattgcc aagtcacgaa aaagtaaaac acccccgtt tatactattt tccattcatg
25261 caataaaatg aagaaggaa gaattgtacg atcctattat gttaactttt ggatataact
25321 gcgttagtcc aagtcaaggg gtggtagtta cctcctcgag aggaaagctg tcttaagatg
25381 ataagctcca aagcatcaaa gacagtgatt ctggtatctt tttctataca gtaagacaca
25441 cactacagtg ttcctgccta tacccatatc aaagcgagga aagcagcagg gtctgtgcag
25501 tgcatttgtc tgcaggttct tcccacgcag ttatgagatt cctgcaaatc accagagact
25561 gcagcgtgat tggaaacgat cagattttga gttgagcggc tgtggagcat ggccaggctc
25621 ccaattacca gctgccttcg ttaggcgctg tctcacccac agctctcctt cctccatgtc
25681 atgcttcccc cagtccccg caggaaagcg tgatcagaag aagattccca cctcctgact
25741 gcctgagcag attccaaatg atacctcagg tgtttgtccc ggctggagct gtgggtggca
25801 ggaggttttcc atactgtctt ttgttgtgga aactgacccc agggctgatg ttgtgctgct
25861 tccataggtt aattgcagcc tgtatgccag cggcatcggc aaggatggga cgagttgggt
25921 agcctgcccg aggaacttga agcctgtctg tggcacagat ggctccacat acagcaatga
25981 gtgcgggatc tgcctctaca acaggtgagc ttatgtggaa gcccagggga gctgcagggc
26041 aggagactcg aggtgagggc ggcagctctg tccccaaaat atggtctgtg tggaggagta
26101 tgtgagttag taccaggatg ctgacctcca gcctgggggt ggtggctgct ctctgccatc
26161 tctgacacag atctgcgttc ttccagggag cacggggcaa acgtggagaa ggaatatgat
26221 ggagagtgca ggccaaagca cgttacggta agtccaacag taagatgaag tcttgctctg
26281 ttggtgccca taagactta ttttatttc atagaatcat tgaacagctt aggttggaag
26341 ggaccttaaa gatcattggg ctctaacccc cctggcctgg ccgggctgcc ttcaaccaaa
26401 tcagtttgcc cagtcaaatg ggccttgggc acctccaggg atggggcacc tgctctgctc
26461 agcctgttac ttatttactt gttttttcc cattcctgct atccttacag attgattgct
26521 ctccgtacct ccaagttgta agagatggta acaccatggt agcctgccca aggattctga
26581 aaccagtctg tggctcagat agcttcactt atgacaacga atgtgggatt gcgcctaca
26641 acgcgtaagt cttttctgtg gagcatcctt ctgggtaatt agagatggct aagtcccttg
26701 gaaacgctta cataaaacac tttctaagcc tttcttaggg tagatgtttc tgtgggactc
26761 tttgaagctg gctacttgtg attctccagc cagctgcaga tttcttcccc atcctctgtc
26821 tgtgctcatg aagggaatca caaaaagac agaggacaac ccacagcaga ggcatgaata
26881 gatcaaagtg ttgctcagtg ctgtgtgata tggaaatacc atgcattttc tgctcacaag
26941 tggttgctac cacctgtggg ctgcatccag accactcagc agttccttac gtgaagggtg
27001 ggaccttgct ttcttgcccc agtatctaag gcttttcacg aggctctcta actaaacag
27061 ctctttcttt cagagaacat cacaccaaca tttccaaact gcacgatgga gaatgcaagc
27121 tggagatcgg ctcggtaagt gtaacagaaa taaaaatcca tctcctaggg ctgttaacgg
27181 agagaatccc attgattttc ctaagaaaat gtatgaccgg gctgatcggg ggtcccggtc
27241 cacgctctgc ttcctgcctg gtgagggtgg cttctgaaac aaagcggtaa aggaagaggc
27301 cccagatttt ccttgcattg tgctgtgcag attggcaggt ttctctctgg aggcgacaag
27361 catttccacc ctttgtaaca agcattcaaa attctagtgc tggtagcttg ttagatata
27421 gtgagattca taagagcacc aagcatacat atttataggg tatagcttat tgtatattta
27481 tactggggta agagtccagt gcctcaggaa gaaaagctta tatttcag cacaaaaatt
27541 ctgggatgca gggagtccgt tctccaacag acggattcct cctttatcac ttcaactccc
27601 gtgcttaact gcagggaatc tgaattatta agcaatcaca gcactgggga aggaaggaga
27661 aaaccaaca caaccaaaa caatgttaat cagatttcca gctgttggaa atatttccc
27721 acttaattca aggctgttgt gtcgatgaga agagggctga aaaggctgtt ttcagttcct
27781 ctgcctgaag gttccattct ctaagagagg tccctttct tgtctcctag agaatgaggg
```

Figure 24H

```
27841 tagtgttctg aaagcctatt tctgatagac agtttagtta agtgtagcag ggctttgtcc
27901 tgtcacaaaa actaggaagc cgggaataca ggatgaaaag gtgttacatt gacttctccc
27961 gtgtagcaca ggctccggga gggcttattc tccttatttt ggcaggttga ctgcagtaag
28021 tacccatcca cagtctctaa ggatggcagg actttggtag cctgcccaag gatcctgagc
28081 ccggtttgcg gcaccgatgg tttcacctat gacaacgaat gcgggatctg cgcccacaat
28141 gcgtaagtgc tgctcatctc ccactcctcc aaagtagcca gcaatgcttt gccgtgctgg
28201 gagccttcct tctacgttgc tgcttatgcc tgtttcttca agcctcttag aaactgcatt
28261 ttttttgttg ttgttcttac tgagttttct tctgatgcct tctttgtgat cacgagggga
28321 aatctgcaag actcagaaca cagctccttg gattagtctg tgggctgggc agtgactgag
28381 cagagaaagg aatagttcag aatcttgctt taaataacac gagaagacgt gatgagcttg
28441 ttaacgagca gagtaatgta gctatatcaa tacaatcgtg cagagaggct gaagccctac
28501 tttgttaggt acctgcttta ggctacgtct ggttcattct gcatgcaagt gtttaaacca
28561 agagttaaag catctcctta ctcactttgt ctccctcttt cagagagcag aggacccatg
28621 tcagcaagaa gcatgatgga aaatgcaggc aggagattcc tgaagtgagt atacaacgta
28681 aggtgtattt ctccccttgc ctctgcccac tgagctattt gctgaggcca cgtctactct
28741 gaaagtgagc tggcttgaag cctggctctc tgcacgtgtc ctttgggatg tgccaacgtg
28801 tatccaacac acaaacagtg tggaagttgg gcaggggaa cttaggtctt taaggatga
28861 tcactaaatg cattgccagc aaagtccttt tgtgccagtg aagtcctatt atgtttgcct
28921 tcttttgttt cattctatag tgcagagaga aaggagatg atatatcttt gttggttttt
28981 ttttttgtttg tttgttttgc ttttctgcca tatctagcaa actgtttcag taggttgtga
29041 cccctttgga tcacaagtga agctcagtgg catttgggat tgactgagct gtctgccctg
29101 gtgatttggc atctcacaga ttacacagcg ccatgtagct cctcctgggc atgagagagt
29161 ttctgcagag ctgactcagg ctggctttga gagaactgaa gtgtagcacc agcgttgttt
29221 cagcatccca gcgtaaaaga catggattgc agcaggaggc aatgctaggg tttgtctttg
29281 agagcaaggg cttttcagg gctgacgctc ctactttttg cagattgact gtgatcaata
29341 cccaacaaga aaaccactg gtggcaaact cctggtgcgc tgcccaagga ttctgctccc
29401 agtctgtggc acagacggat ttacttatga caacgagtgt ggcatttgtg cccataatgc
29461 gtaagtactg caaacaggac ttccttttgt agcgactagc cacgttagta ctgcagatgg
29521 cttcccctcc acccttcatc ttcttctttc tttcttttt tttgatagca gtatgtctat
29581 atgtctcctg ttcttccttc aacctcctga agctctgtcg cctcggtttc ctttcctgat
29641 gtgctcctca gggagctgtg ggagagccag ctaacagctg agtgtcctat gagggctgtg
29701 gcatttgtgc agaggaaaaa gagaatgggt ctgctacaag tagacctgag aagcctgtaa
29761 cttcttagga tcatgatccc taatggcagc cttccctttt cagacaacat gggactgagg
29821 ttaagaagag ccacgatgga agatgcaagg agcggagcac cccggtaagt ggggatggat
29881 gtcagatgag cgccagctcc tgtacgtgcc ttgtggctgc agaggttgct aaccagggtc
29941 tgtccattca ggcagcagag aaggggaatg ggccaggatt taggtaacaa aatgtcccaa
30001 tactgcaggt ctctggaggg aaacatcaga ggcagcccag aacagcacag cctgttttag
30061 cacagtagga gaggaagagc agaagctgtg ttagatgcct gtgtagtcat tcagtgctag
30121 gatttccatt gcagcagaca ggttaaaaaa tctctgtacc gtggtcagcc aagaaaaggc
30181 tgcttgcagg aatgcacgca gaatagctc tataaacatg cacggtaaca atatgtgctg
30241 ataatatctc agcacattta ttctgcttat gcagagcagc tctaaacac tgaaaataac
30301 tttgtgcatc tcaagggatt gctgtatctt ttctgtagta aagacacact gttatggtgc
30361 tgtctttgct ataatttgct cttggactgt gtggggaaat atgggtaata agagctacta
30421 cacaggggaa ggtatgcaaa acgattgtga agtgtcagaa gcttagccag tgtagactga
30481 cttccagtgc catcagtaga tacttgctta tttatcctca aatattggaa ctgtttttaa
30541 gtactgtgag gatttctgca gcagcagctg atgagctgat ggaacagttt cttcttgccg
30601 ttttgaaaac gtggaaacaa aatctaaggc ttagctaagt caggcatgac ctaatgtcaa
30661 actggacata acatcaaact ccttatatca aattcctttg aataatgctt gttttgaaac
30721 ttggacatac gctgcataag gaagatgatc tttctggtct gctattcctt tgcgttccct
30781 ttgttagtga gcaatatcaa acccaaccac aattagttca tttataatgg gagactaaac
30841 tgaaatcaac cctgatttt cctatggctc gaggcagtct gtccccagc tcccagcacc
30901 tgactcagca tccttactgt tttctcccca gcttgactgc acccaatacc tgagcaatac
30961 ccaaaacggt gaagccatta ccgcctgccc cttcatcctg caggaggtct gtggcactga
31021 cggcgtcacc tacagcaacg actgttctct gtgtgcccac aacatgtaag ccctgcaggt
31081 cacccactcg tgtgtcaccg cagctgcttg ttgagctttg tcaactctgt tttctctctc
31141 ttccagtgaa ttgggaacca gcgttgccaa aaagcacgat gggaggtgca gagaggaggt
31201 tcctgaggta agcgataaag aaaacaagag cttgaggtgg tgcttattgc ctaacaagta
31261 caacgctggc tggttttggt gatgctgggt catgccctcc tgctgccatc cttcctgcag
```

Figure 24I

```
31321 gtaaacatca accctggcag cagggatgct gtgcattttc tgcatgtagt cagggaaaga
31381 aagagaagag gacgggtgag gaatgagtta tgatgcaggt agcataaatg atttaaggcg
31441 ttacgaagaa atctctttcc cacagcagtc tatcatacct gccgtgggag tgtagctgtc
31501 tgttctggca atatgggaaa gggacacaga gcacccgcag gtacctggtg ccttctggat
31561 acctgtgctg tgcaaaagga tgttgtgcaa agatcagaaa actacctgca ttttgaatgc
31621 ttttacctaa tgtaccagag gattcaaaca cctctctctt cctattgtaa atgcgatata
31681 atgtaatgta taccaacaat gaatcttgta aaataccag ataaactata tttggccagc
31741 tctaaactat ttacgctcac tggggaatag aaaaacaaag ccatctcatt atcttgtgtt
31801 tgaaagagtc aacgtcgtga gtcagatatt tcatttctat gcaaacagac tatgaaatgt
31861 cattgctttg tttcctgcgt atgctctgtg ctcagaccaa gtcagatgca taaatcagtg
31921 aggaagagct cacactggag aaactgggat agctgaaact caaggccagt tcttcaaatg
31981 gcataaatca ttttgaactg ctgttggtcc ttctgtccga ttgcaacaca cagaaccagc
32041 ccctcgcaac aaaaggcatg tcagcacatc tcctcagttc ttgtgggccg tgacacactc
32101 cttggccaca ctgagcttct cttgcaggaa ttgcataaat cacgccagtt tgatttgcag
32161 attatttatg agctgcgttt tgcagcgtcc cagcaagtgg ttcagcaagc tctaagggca
32221 tcgtgataaa tgcagggctg aatgagtgat acgcgcttc aagctttgat tcagtcttct
32281 ccagtataag gctgtgacag aaaattgata gttttcaatg aagaatgagt caatgcataa
32341 ccataatcca tcctgtggca gatcttgaaa ggcagaggcg taaggaaggg ggttgtgtct
32401 gagcacccct acacagagca tttgctgcct ttgtttccta gcttgactgc agcaagtaca
32461 aaacctccac gctgaaggat ggcagacagg tggtggcctg caccatgatc tacgatcccg
32521 tctgtgctac caatggtgtc acctatgcca gcgaatgcac gctgtgcgct cacaacctgt
32581 aagtactcat tcatctccag ggggacccac cgtggctgtg actggacaca tctttgagtg
32641 ctgaataaca tgcaagggct ctgtctaaaa tctcgtgctg catgggtcct gtctgcctat
32701 ccccgtttcc ctggttgcca tggttggtgt ttgagatggg catttagcaa ggcccactgc
32761 ccccagtgac ccagaaaaag ggttcactgc ctgggaaagc attattccaa aagacacatc
32821 cctagtcctt aagggcatgt tcttgctaat gcttctcagg caatgcttag ctaatttatc
32881 tgaaattgtc ctgtgtacca catgggaacg aggttgtgct cttgtactac ggttgtaaat
32941 gggaagggtt tctgctaata tccatctctc cttcctccag ggagcagcgg accaatcttg
33001 gcaagagaaa gaatggaaga tgtgaagagg atataacaaa ggtgagtgtg aaaggatggg
33061 cacaaagagt tacagtcgta ggggaccgtc ctctgctcca catcaaaaac tgggggagcg
33121 gtgtgcagcc ctggcgaggt cgcttgggaa tgtcatactg gttatagaat agctgccatc
33181 catcccatgg gaatggacat ggcagtgaac aggaacagtg tgaggtcaca tccctcacca
33241 ggaggaactg agctgattac tgccgtaatt ttccagtttc actctttgtg ctggggaat
33301 actgtttgct cccaggcaga gactcacatc ttccttgtgt gtgcaggaac attgccgtga
33361 gttccagaaa gtctctccca tctgcaccat ggaatacgta ccccactgtg gctctgatgg
33421 cgtaacatac agcaacagat gtttcttctg caacgcatat gtgtaagtat aggagtgaaa
33481 cccttcctgt aactgctaca aacgcagagt tgattttata aggagttctt tactaacact
33541 ttatgggtgt gtgctagaca tttcggatgc accgtgacgt gcaaggaggt gctttttttgc
33601 tttttaagaa aaaatgcaaa gcacccacat ctgccatgt gtatgtggct tcctgtttta
33661 tttagtttca aagacatttt gctaattttc accagcatag tttgtcccac aagctcatca
33721 gggtatgggg aaagtacttc accaaactac ctggagcgtt tcaagtgtgt gaaacctgtc
33781 atctttcctt taattttcat aatgaaagga agtggttggc cttctgagac tgttctttat
33841 cttctgccaa cattatcaac atttgggctg gtaaggagag gaacaaggct gcagcacaaa
33901 ttctattgtg tttaatcctt tcttctcttt tcattaggca gagcaatagg actctcaacc
33961 tcgtgagtat ggcagcgtgt taactctgca ctggagtcca tcgtgggaaa caatctgcct
34021 tgcacatgag tcttcgtggg ccaatattcc ccaacggttt tccttcagct tgtcttgtct
34081 cccaagctct caaaacacct ttttggtgaa taaactcact tggcaacgtt tatctgtctt
34141 accttagtgt cacgtttcat ccctattccc ctttctcctc ctccgtgtgg tacacagtgg
34201 tgcacactgg ttcttctgtt gatgttctgc tctgacagcc aatgtgggta aagttcttcc
34261 tgccatgtgt ctgtgttgtt ttcacttcaa aaagggccct gggctccct tggagctctc
34321 aggcatttcc ttaatcatca cagtcacgct ggcaggatta gtctctccta aaccttagaa
34381 tgacctgaac gtgtgctccc tctttgtagt cagtgcaggg agacgtttgc ctcaagatca
34441 gggtccatct cacccacagg gcaattccca agatgaggtg gatggtttac tctcacaaaa
34501 agttttctta cgttttgcta gaaggagag ctcactgcct acctgtgaat tcccctagtc
34561 ctggttctgc tgccaccgct gcctgtgcag cctgtcccat ggaggggca gcaactgctg
34621 tcacaaaggt gatcccaccc tgtctccact gaaatgacct cagtgccacg tgttgtatag
34681 gatataaagt acgggagggg aatgcccggc tcccttcagg gttgcagggc agaagtgtct
34741 gtgtatagag tgtgtgtctt aatctattaa tgcaacagaa caacttcagt cctggtgttt
```

Figure 24J

```
34801 tgtgggctgg aattgcccat gtggtaggga caggcctgct aaatcactgc aatcgcctat
34861 gttctgaagg tatttgggaa agaaagggat ttgggggatt gcctgtgatt ggctttaatt
34921 gaatggcaaa tcacaggaaa gcagttctgc tcaacagttg gttgtttcag ccaattcttg
34981 cagccaaaga gccgggtgcc cagcgatata atagttgtca cttgtgtctg tatggatgac
35041 agggaggtag ggtgacctga ggaccaccct ccagcttctg ccagcgtagg tacagtcacc
35101 acctccagct ccacacgagt cccatcgtgg tttaccaaag aaacacaatt atttggacca
35161 gtttggaaag tcacccggtg tattgtgagg ctagattaat aggctgaagg caaatgttcc
35221 caacttggag atactgttgg tattgtatca gggaacaggg ccatagcacc tccatgctat
35281 tagattccgg ctggcatgta cttttcaaga tgatttgtaa ctaacaatgg cttattgtgc
35341 ttgtcttaag tctgtgtcct aatgtaaatg ttcctttggt ttatataacc ttcttgccgt
35401 ttgctcttca ggtgttcttg cagaacactg gctgcttttaa tctagtttaa ctgttgcttg
35461 attattctta gggataagat ctgaataaac tttttgtggc tttggcagac tttagcttgg
35521 gcttagctcc cacattagct tttcagcct tttctgtgaa gctatcaaga tcctactcag
35581 tgacattagc tgggtgcagg tgtaccaaat cctgctctgt ggaacacatt gtctgatgat
35641 accgaaggca aacgtgaact caaagaggca cagagttaag aagaagtctg tgcaattcag
35701 aggaaaagcc aaagtggcca ttagacacac tttccatgca gtatttgcca gtaggtttca
35761 tataaaacta caaaatggaa taaaccacta caaatgggaa aaacctgata ctggaattta
35821 aatattcacc caggctcaag gggtgtttca tggagtaaca tcactctata aaagtagggc
35881 agccaattat tcacagacaa agcttttttt tttttctgtg ctgcagtgct gttttcggc
35941 tgatccaggg ttacttattg tgggtctgag agctgaatga tttctccttg tgtcatgttg
36001 gtgaaggaga tatggccagg gggagatgag catgttcgag aggaaacgtt gcatttggt
36061 ggcttgggag aaaggtagaa cgatatcagg tctacagtgt cactaaggga tctgaaggat
36121 ggttttacag aacagttgac ttggctgggt gcaggcttgg ctgtaaatgg atgaaggat
36181 ggacagatgg gtggacagag atttctgtgc aggagatcat ctcctgagct cggtgcttga
36241 cagactgcag atccatccca taaccttctc cagcatgaga gcgcggggag ctttggtact
36301 gttcagtctg ctgcttgttg cttcctgggt gcacagtggt gatttctta ctcacacagg
36361 gcaaaaacct gagcagcttc aaagtgaaca ggttgctctc ataggccatt cagttgtcaa
36421 gatgaggttt ttggtttctt gttttgtaag gtgggaagaa gcactgaagg atcggttgcg
36481 agggcagggg tttagcactg ttcagagaag tcttatttta actcctctca tgaacaaaaa
36541 gagatgcagg tgcagattct ggcaaggatg cagtgaagga gaaagccctg aatttctgat
36601 atatgtgcaa tgttgggcac ctaacattcc ctgctgaagc acagcagctc cagctccatg
36661 cagtactcac agctggtgca gccctcggct ccagggtctg agcagtgctg ggactcatga
36721 ggttccatgt cttttcacact gataatggtc caatttctgg aatgggtgcc catccttgga
36781 ggtccccaag gccaggctgg ctgcgtctcc gagcagcccg atctggtggt gagtagccag
36841 cccatggcag gagttagagc ctgatggtct ttaaggtccc ttccaaccta agccatccta
36901 cgattctagg aatcatgact tgtgagtgtg tattgcagag gcaatatttt aaagttataa
36961 atgttttctc ccccttcctg tttgtcaaag ttatcttgat cgccttatca atgcttttgg
37021 agtctccagt cattttttctt acaacaaaaa gaggaggaag aatgaagaga atcatttaat
37081 ttcttgattg aatagtagga ttcagaaagc tgtacgtaat gccgtctctt tgtatcgagc
37141 tgtaaggttt ctcatcattt atcagcgtgg tacatatcag cacttttcca tctgatgtgg
37201 aaaaaaaat ccttatcatc tacagtctct gtacctaaac atcgctcaga ctctttacca
37261 aaaaagctat aggttttaaa actacatctg ctgataattt gccttgtttt agctcttctt
37321 ccatatgctg cgtttgtgag aggtgcgtgg atgggcctaa actctcagtt gctgagcttg
37381 atgggtgctt aagaatgaag cactcactgc tgaaactgtt ttcatttcac aggaatgttt
37441 tagtggcatt gttttataa ctacatattc ctcagataaa tgaaatccag aaataattat
37501 gcaaactcac tgcatccgtt gcacaggtct ttatctgcta gcaaaggaaa taatttgggg
37561 atggcaaaaa cattccttca gacatctata tttaaggaa tataatcctg gtacccaccc
37621 acttcatccc tcattatgtt cacactcaga gatactcatt ctcttgttgt tatcatttga
37681 tagcgttttc tttggttctt tgccacgctc tgggctatgg ctgcacgctc tgcactgatc
37741 agcaagtaga tgcgagggaa cagcagtga gaggggctgc cctcagctgg cacccagccg
37801 ctcagcctag gaggggacct tgcctttcca ccagctgagg tgcagcccta caagcttaca
37861 cgtgctgcga gcaggtgagc aaagggagtc tcatggtgt gtttcttgct gcccggaagc
37921 aaaactttac tttcattcat tccccttgaa gaatgaggaa tgtttggaaa cggactgctt
37981 tacgttcaat ttctctcttc cctttaaggc tcagccaggg gccattgctg aggacggcat
38041 cggggccccc tggaccaaat ctgtggcaca gatggtttca cttacatcag tggatgtggg
38101 atctgcgcct gtaatgtgtc cttctgaagg aaggaacgtg ccttccaagt gccagcccca
38161 cagccccag cccctccctg tgctgctcca attcatctcc tcttcctcct tctcccttg
38221 ctgtttgtgc tcgggtagaa atcatgaaga tttagaagag aaaacaaaat aactggagtg
```

Figure 24K

```
38281 gaaacccagg tgatgcagtt cattcagctg tcataggttt gtcattgcta taggtctgta
38341 tcagagatgc taacaccact ttgctgtcgg tgcttaactc gggtgaactc tccttcactc
38401 gcatcatttg cgggccttat ttacatcccc agcatccatc accctctggg aaaatgggca
38461 cactggatct ctaatggaag actttccctc tttcagagcc tgtgggatgt gcagtgacaa
38521 gaaacgtgga ggggctgagc agcagcactg ccccaggga gcaggagcgg atgccatcgg
38581 tggcagcatc ccaaatgatg tcagcggatg ctgagcaggc agcggacgaa cagacagaag
38641 cgatgcgtac accttctgtt gacatggcat ttggcagcga tttaacactc gcttcctagt
38701 cctgctattc tccacaggct gcattcaaat gaacgaaggg aagggaggca aaaagatgca
38761 aaatccgaga caagcagcag aaatatttct tcgctacgga agcgtgcgca acaaccttc
38821 tccaacagca ccagaagagc acagcgtaac cttttcaag accagaaaag gaattcaca
38881 aagcctctgt ggataccagc gcgttcagct ctcctgatag cagatttctt gtcaggttgc
38941 aaatggggta tggtgccagg aggtgcaggg accatatgat catatacagc acagcagtca
39001 ttgtgcatgt attaatatat attgagtagc agtgttactt tgccaaagca atagttcaga
39061 gatgagtcct gctgcatacc tctatcttaa aactaactta taaatagtaa aaccttctca
39121 gttcagccac gtgctcctct ctgtcagcac caatggtgct tcgcctgcac ccagctgcaa
39181 ggaatcagcc cgtgatctca ttaacactca gctctgcagg ataaattaga ttgttccact
39241 ctcttttgtt gttaattacg acggaacaat tgttcagtgc tgatggtcct aattgtcagc
39301 tacagaaaac gtctccatgc agttccttct gctccagcaa actgtccagg ctatagcacc
39361 gtgatgcatg ctacctctca ctccatcctt cttctctttc ccaccaggga gagctgtgtg
39421 ttttcactct cagccgctct gaacaatacc aaactgctac gcactgcctc cctcggaaag
39481 agaatcccct tgttgctttt ttatttacag gatccttctt aaaaagcaga ccatcattca
39541 ctgcaaaccc agagcttcct gcctctcctt ccacaaccga aaacagccgg cttcatttgt
39601 cttttttaaa tgctgttttc caggtgaatt ttggccagcg tgttggctga gatccaggag
39661 cacgtgtcag ctttctgctc tcattgctcc tgttctgcat tgcctctttc tggggcttcc
39721 aagagggggg gagactttgc acggggatga gataatgccc ctttcttag ggtggctgct
39781 gggcagcaga gtggctctgg gtcactgtgg caccaatggg aggcaccagt ggggtgtgt
39841 tttgtgcagg gaggaagcat tcacagaatg gggctgatcc tgaagcttgc agtccaaggc
39901 tttgtctgtg tacccagtga aatccttcct ctgttacata aagcccagat aggactcaga
39961 aatgtagtca ttccagcccc cctcttcctc agatctggag cagcacttgt ttgcagccag
40021 tcctccccaa aatgcacaga cctcgccgag tggagggaga tgtaaacagc gaaggttaat
40081 tacctccttg tcaaaaacac tttgtggtcc atagatgttt ctgtcaatct tacaaaacag
40141 aaccgagggc agcgagcact gaaggcgtgt tcccatgctg agttaatgag acttggcagc
40201 tcgctgtgca gagatgatcc ctgtgcttca tgggaggctg taacctgtct ccccatcgcc
40261 ttcacaccgc agtgctgtcc tggacacctc accctccata agctgtagga tgcagctgcc
40321 cagggatcaa gagacttttc ctaaggctct taggactcat cttttgccgct cagtagcgtg
40381 cagcaattac tcatcccaac tatactgaat gggtttctgc cagctctgct tgtttgtcaa
40441 taagcatttt ttcattttgc ctctaagttt ctctcagcag caccgctttg ggtgacttca
40501 gtggccgcct ggaacccgag gggcacagcc accacctccc tgttgctgct gctccgggga
40561 ctcacgtgct gctggatggg gggaagcatg aagttcctca cccagacacc tgggttgcaa
40621 tggttgcagt gtgctcttct tggtatgcag attgtttcta gccattactt gtagaaatgt
40681 gctgtggaag ccctttgtat ctctttctgt ggcccttcag caaaagctgt gggaaagctc
40741 tgaggctgct ttcttgggtc gtggaggaat tgtatgttcc ttctttaaca aaaattatcc
40801 ttaggagaga gcactgtgca agcattgtgc acataaaaca attcaggttg aaagggctct
40861 ctggaggttt ccagcctgac tactgctcga agcaaggcca ggttcaaaga tggctcagga
40921 tgctgtgtgc cttcctgatt atctgtgcca ccaatggagg agattcacag ccactctgct
40981 tcccgtgcca ctcatggaga ggaatattcc cttatattca gatagaatgt catcctttag
41041 ctcagccttc cctataaccc catgagggag ctgcagatcc ccatactctc ctcttctctg
41101 gggtgaaggc cgtgtcctcc agcccccctt cccaccctgt gccctgagca gcccgctggc
41161 ctctgctgga tgtgtgccca tatgtcaatg cctgtccttg cagtccagcc tggaacattt
41221 aattcatcac cagggtaatg tggaactgtg tcatcttccc ctgcagggta caaagttctg
41281 cacggggtcc tttcggttca ggaaaacctt cgctggtgct acctgaatca agctctattt
41341 aataagttca taagcacatg gatgtgtttt cctagagata cgttttaatg gtatcagtga
41401 ttttatttg ctttgttgct tacttcaaac agtgcctttg gcaggaggt gagggacggg
41461 tctgccgttg gctctgcagt gatttctcca ggcgtgtggc tcaggtcaga tagtggtcac
41521 tctgtggcca aagaaggac aaagatggaa attgcagatt gagtcatgtt aagcaggcat
41581 cttggagtga tttgaggcag tttcatgaaa gagctacgac cacttattgt tgttttcccc
41641 ttttacaaca gaagttttca tcaaaataac gtggcaaagc ccaggaatgt ttgggaaaag
41701 tgtagttaaa tgttttgtaa ttcatttgtc ggagtgttac cagctaagaa aaagtccta
```

Figure 24L

```
41761 cctttggtat ggtagtcctg cagagaatac gacatcaata ttagtttgga aaaaaacacc
41821 accaccacca gaaactgtaa tggaaaatgt aaaccaagaa attccttggg taagagagaa
41881 aggatgtcgt atactggcca agtcctgccc agctgtcagc ctgctgaccc tctgcagctc
41941 aggaccatga aacgtggcac tgtaagacgt gtccctgcct tgcttgctc acagatctct
42001 gccctcgtgc tgactcctgc acacaagagc atttccctgt agccaaacag cgattagcca
42061 taagctgcac ctgactttga ggattaagag tttgcaatta agtggattgc agcaggagat
42121 cagtggcagg gttgcagatg aaatcctttc taggggtagc taagggctga gcaacctgtc
42181 ctacagcaca agccaaacca gccaagggtt ttcctgtgct gttcacagag gcagggccag
42241 ctggagctgg aggaggttgt gctgggactc ttctccctgt gctgagaatg gagtgatttc
42301 tgggtgctgt tcctgtggct tgcactgagc agctcaaggg agatcggtgc tcctcatgca
42361 gtgccaaaac tcgtgtttga tgcagaaaga tggatgtgca cctccctcct gctaatgcag
42421 ccgtgagctt atgaaggcaa tgagccctca gtgcagcagg agctgtagtg cactcctgta
42481 ggtgctaggg aaaatctctg gttcccaggg atgcattcat aaggacaata tatcttgagg
42541 ctgtgccaaa tctttctgaa atattcatgc atgttccctt aatttataga aacaaacaca
42601 gcagaataat tattccaatg cctcccctcg aaggaaaccc atatttccat gtagaaatgt
42661 aacctatata cacacagcca tgctgcatcc ttcagaacat gccagtgctc atctcccatg
42721 gcaaaatact acaggtattc tcactatgtt ggacctgtga aaggaaccat ggtaagaaac
42781 tcaggttaaa ggtatggctg caaaactact cataccaaaa cagcagagct ccagacctcc
42841 tcttaggaaa gagccacttg gagagggatg gtgtgaaggc tggaggtgag agacagagcc
42901 tgtcccagtt ttcctgtctc tattttctga aatgtctgca ggaggaaagg acaactgtac
42961 tttcaggcat agctggtgcc ctcacgtaaa taagttcccc gaacttctgt gtcatttgtt
43021 cttaagatgc tttggcagaa cactttgagt caattcgctt aactgtgact aggtctgtaa
43081 ataagtgctc cctgctgata aggttcaagt gacatttta gtggtatttg acagcattta
43141 ccttgctttc aagtcttcta ccaagctctt ctatacttaa gcagtgaaac cgccaagaaa
43201 cccttccttt tatcaagcta gtgctaaata ccattaactt cataggttag atacggtgct
43261 gccagcttca cctggcagtg gttggtcagt tctgctggtg acaaagcctc cctggcctgt
43321 gcttttacct agaggtgaat atccaagaat gcagaactgc atggaaagca gagctgcagg
43381 cacgatggtg ctgagcctta gctgcttcct gctgggagat gtggatgcag agacgaatga
43441 aggacctgtc ccttactccc ctcagcgttc tgtgctattt agggttctac cagagtcctt
43501 aagaggtttt tttttttttt tggtccaaaa gtctgtttgt ttggttttga ccactgagag
43561 catgtgacac ttgtctcaag ctattaacca agtgtccagc caaaatcaat tgcctgggag
43621 acgcagacca ttacctggag gtcaggacct caataaatat taccagcctc attgtgccgc
43681 tgacagattc agctggctgc tctgtgttcc agtccaacag ttcggacgcc acgtttgtat
43741 atatttgcag gcagcctcgg ggggaccatc tcaggagcag agcaccggca gccgcctgca
43801 gagccgggca gtacctcacc atggccatgg caggcgtctt cgtgctgttc tctttcgtgc
43861 tttgtggctt cctcccaggt gagtaactcc cagagtgctg cagaagcttt gtgcctgcca
43921 gtcctggctc tccttagcag aacatggtgg tgaccatcag agagagactc ccctacaaag
43981 tgcctgcaaa ggctgcctca gtacatcagt attaaacgga ttactgttgt gctgggtgtc
44041 tgttgggttc tgtgctccca acacatttct tacgctctca gctctgttac actgcttgca
44101 tttgctgcac agttgcatag aatggataaa tgcttgaaac aaggccataa cgaggtggtc
44161 agacctccag gaactagtta gggaaatatt gtcatggccc aagcaagctc tgtgcaggaa
44221 cctggcagct ttcctgcaat gcttttgctg ctaatggaga aacaagagat gcaaacaagc
44281 caggatctga tgttctcctt ctgtatttac atctcatgaa attacaaagt caaagacaag
44341 cgtggtttat ttcttacact cagcttcttt aaaatgtata tccctgacaa cagatgctgt
44401 gtatgtttgc ttatcctgta tgtgactatt tgcatttgca tttatctcta ttgactcagg
44461 tttcttttca gatatgtgat agatgttttc tagggacaaa acggatgtgt aatagataa
44521 ggaaggaaaa gatattcatt tttcaattaa taaatctacc tatctcttaa ctttttttt
44581 tttttaagaa cagagctatt caagaactcg tttcatcagc cagcaataag aagctaaatt
44641 atgtttatca gcattaaaca aaaatcatat atagtttgct tagttcaaga atcgaatcgg
44701 tggaaatcac tcagtttggt tctctgtgct ggagttttgc acacacattt cagctagctg
44761 tggtctcact gatcagactg cctttgtttc ccatttttgt ccccttttt tccccagatg
44821 ctgcctttgg ggctgaggtg agtaagagag ttcttcttgt ccacttttct cttttctctt
44881 ttctctctct ctcttttttt cccccgtct taattagtat cactataatc agatcccaga
44941 gtgtaaaatg ttaaattatg cagttcgag ctctacatct atgctgcatg taagtaatgt
45001 agcagtgata taaaactgtt agatgaatta atttctgacc aactctgaac tggtctaagc
45061 tttaagttga tcatatgttc tactaaataa tacagtggtt tgggttggaa gggtccttta
45121 agatcatcta cttccaaccc ctctgctata ggcagggaca actcccacta gacaagattg
45181 ctcaaagctc catccatatg atcagctgta gactgatggc tgtagactat agcattaaaa
```

Figure 24M

```
45241 actacccaa agcagcctac tgaaagaaga aagtactgtg aggtgctaca gcttccaaat
45301 cccatgttgt tagacctgtt cttttgaata aacgtgtttg tacgttgaga atgaatgagt
45361 aacaatggca gaacactgga ggggccaact ctcaggcttt gcaaaatggt gcctgggggg
45421 catgatagat ccctgctggt ttatcacatg gggagctgca tggctataac cccattgccc
45481 agttctctcc cactgcatgg agagaaggct ggatctggtc gctgccctgc tgaaaatggc
45541 agatgtaact acaaaatgtc actttgtcct gttactgtgt gtttctttgt caggtggact
45601 gcagtaggtt tcccaacgct acagacaagg aaggcaaaga tgtattggtt tgcaacaagg
45661 acctccgccc catctgtggt accgatggag tcacttacac caacgattgc ttgctgtgtg
45721 cctacagcat gtgtgtactg cagagagagc tcatactgca agcaagcagc tgtgcttagg
45781 gctcctgaca gcacccctt ccaacaaaca gtgatctgtc acatgtcact tatgtcaact
45841 ctttcaggga aagcttgagt atcactgcgt gacactcggt tgcctagaca tcactttggt
45901 tactgtgtct tttttgttga tgtaatttat tcaggttttt ctcctccatc tcggggatga
45961 ggcagatgac agccctagg gcatatttca tcccagcaaa aaaggagcaa aaggatggag
46021 aggtgctcca gtctgaatgg tccaaaacag tcctaaagat ttcagagtct ttagatccct
46081 gccagccact cagtatggca ctaccctctc caatacaaat atatatatat acaaagatga
46141 cttagccaga ctcagcctca ttgcattagg tacatattcc caataacgag aagctgagct
46201 tcctaatacc tgttttccct cttcagagaa tttggaacca atatcagcaa agagcacgat
46261 ggagaatgca aggaaactgt tcctgtaagt gaaaccaagt tcatcctttg tgcagccaaa
46321 actgcttatt gacttgccca ataaataatg taaatgctga ctaagaggcc atgtgagatg
46381 tcagaatctt gtattgatca tcttcaggtg aagtttcatc acaataacac aaaaaaagac
46441 tttatttcct gctgaggtgg catttttagga gacccaacgc acgcgctccg ctggtctacg
46501 tggtccctgt aagccctcac cagcgctttg ctgtgtgctc cttccacaga tgaactgcag
46561 tagttatgcc aacacgacaa gcgaggacgg aaaagtgatg gtcctctgca caggccctt
46621 caaccccgtc tgtggtactg atggagtcac ctacgacaat gagtgtctgc tgtgtgccca
46681 caaagtgtaa gtaccgagct gtgctccctt ggcaggaatg ggtcctgcgc tcctggcagc
46741 cactctttga gcactgggat ttccaatgag gctttttctg tatggctctt ggactccgtc
46801 cctcctctcc ctgataacct catgctgttt cctttgtga ttagaaagag aactgtggct
46861 tgatcttga gagagaagca gagagctggg tggggactta agagaagcac tctgttctgt
46921 gttaactaag ttaaaagggt ctgtgtggca cacactgcct tgcagaggac agcagtgaac
46981 ctctgctgca cctatattgt aaaacaacct agctcctagg ccatgacagc ctgtccactc
47041 tcctcctttg catcatgcaa tactgcaaca ctgtggcaca tagtaccacc tcccataagg
47101 actgatatgt tgaaccagtg tgtcagagac cagtagcatc tctgtcttca ggatcatcag
47161 gtagcattct atatacaggg tgttgcccag gactccgagt cccatgaagt atggcagggg
47221 ttttggaact ggatgacctt cgaggtcact tccacccaa gccattctat tattctgtga
47281 aagccaggga ggtgggggtg cttgcaggggc tggtatcttg agcagtgtgg gcacaaacta
47341 ggctgggcat ctgcagccca tcagcactgc ggggatgtgg agttcagcac agcaggatgc
47401 aggcacagct ccctaacatg gatttttttc ctttcagaga gcaggggcc agcgttgaca
47461 agaggcatga tggtggatgt aggaaggaac ttgctgctgt gagtgtgagt agcacaatga
47521 aggagcaggt tctggtccca ctgatgtcaa gggaaacatg gccagcatct ttagtagcct
47581 caggagcatc agttgtgctt cagcacagag aagatttttac tttctacaca cgtaatacac
47641 attatccaca gtaatgtcag gaaggggaaga ggatgactgc acaggcaggg atcagtaaaa
47701 gaccataagc agaaataacc catgagggca gaactgagaa taagaactga gactagatcc
47761 aggggtcag accaatgggc catcaaaccc atgatggttt gatgcagagt ccactctttc
47821 agcattcata agaattgagt aggggggagt aagggtgggg tgagtacgta cggatcttcc
47881 caaacaccct tccaacctac agctatgcac ctcagccagg tgtgatttct gtgtagttca
47941 caagcctcag tggatttctc tcccatggga ttctccagcc tctttctgga cctgtataca
48001 cggtagttgg gttggttttt ttttctgtc tctctttttt tcccccact acaatgtccc
48061 tcagcaaaca tagtcctcat ctctcaaaca aacaaatctc attctctaag tacccagata
48121 agagctgatt tttgctttaa gcctgtgggg gagatgctgg actattataa aggtatcagt
48181 gctgcctctt ctccagacac caatgttttt tccatttaat ttcctgaaca ggtcaggaac
48241 acggtgcaac atgattgtaa gcacagcacg ttcatggagc gagctgctgc tgcagctcag
48301 aaatgcagca gtcagattgt gatatgcatc tcttacacag gaattatgc tctattttta
48361 tattattaaa tctagcatac gagaaaggac atccagttta tatcagatcg tgcaaggaag
48421 ttaattattt ttagtttgat cattatcatc ggcactgcag ctgtagctag ggagggggttg
48481 aagctcttca gctatcgact ccttcatatc ctccacgtta caattgtgtt tttgcaggtt
48541 gactgcagcg agtaccctaa gcctgactgc acggcagaag acagacctct ctgtggctcc
48601 gacaacaaaa catatggcaa caagtgcaac ttctgcaatg cagtcgtgta cgtacagccc
48661 tgattgcatt cacgttgtcg gctgcctcct acaggcacca gcttgcacag ttcctgcttt
```

Figure 24N

```
48721 cgttgctgat tgctgaccag gatctggggg cagaaaagaa caccgggcat cacgccagcc
48781 attcatttga ttttcacca gagcttgtct ggtttgttag gatggatgtt ttgaacgcca
48841 ttaaccttaa gggaagtttt ccttgctgcg aagaaaatca gatttggtgt tcattatag
48901 ttttcagaag gggttaaacg atttcactca tctcctaata atcaggtagc tgaggagatg
48961 ctgagtctgc cagttcttgg gctctgggca ggatcccatc tcctgccttc tctaggacag
49021 agctcagcag gcagggctct gtggctctgt gtctaaccca cttcttcctc tcctcgcttt
49081 cagggaaagc aacgggactc tcactttaag ccattttgga aaatgctgaa tatcagagct
49141 gagagaattc accacaggat ccccactggc gaatcccagc gagaggtctc acctcggttc
49201 atctcgcact ctggggagct cagctcactc ccgatttcct ttctcaataa actaaatcag
49261 caacactcct ttgtcttgtt taatgctctg cctcatgcaa tgttttcttc tgatttgttg
49321 gacggtgata ccagactcaa tatgttccat gctcgtggct ctggggtata acaagaacaa
49381 catcttgctc ccatccctgt cataaaaggc agaaaattaa atacagatgc ataaacctcg
49441 gctgtgtgac tttgcgcata aatgacagtc agcctccatt agtgttcaga ccctttaga
49501 cagctgaaat actgctacga actgctgatg ctggctgagc tcccatggt acgtgtggtg
49561 cactttccct gcgcagcatt agcagtgaaa gcagctcagg gtgcggtggt ggccaaaccc
49621 agggccgatc ccacggcctc ctgtacctgg tcatacccac gggcacagct gctagtgagg
49681 tgcgtgcttt tcagacacgt catataagtg tgccctgcct acatgtctgg gtcctccaaa
49741 tgacgttgca aggtttatct catcttggaa ttgtcctta ctgaccacca agtgttttga
49801 gatgaatgcc ctcctaggtc tggttctgct cttgctgct ggtcttttct catagtagtc
49861 cttgccagcc caagtatctg agcagtgttt tgcaatccaa ggacaaagta ccctctgcc
49921 tttgagagtg tgacctctgt cattggcaca ttgtccgtga aatatatttt gcttttgtcc
49981 tttgttggtg tattgaactg atgttttctt gatccacatg agagaaactt taataaaaat
50041 tataaaaaat aatgcctccc ttaagcattt cttttccctg atggaatgag gccattcaaa
50101 agaaggatgc tttggcggta aaacagagga tttatgttga gatgggcaga tgaatcaagc
50161 agtgatttcc agtttggatt gaactttct gggatccagg ctgtgggcct catgtcattc
50221 tgtcatcatc aggctatcag tctgctgctg caaatcctcc ccacaacgct aatggctttt
50281 agggaaaatc gcaattgtta gttctttgct aatgcccata aaacttcttc catcacttgt
50341 ccagctccag gactcccttc agccccaggt ttccctcttg ctctctctcc cagttcagtt
50401 tttctggatt tgctatgatt tgatgatgca ttattgacag gacaagggga aatggtttca
50461 aaccagagga gaggagattt agactggaca taagcaagac atttttaca atggtggtga
50521 ggcactgaca gaggttgccc agagaggtgg tggtgcccca tccatggaga cagccaaggt
50581 caggaggggc tctgagcact gatggagctg tgggtgcccc tgttcattgc aggggttgg
50641 accagatggc ctttaaagat cccttccaac tcaaatgctt caatgattct gtgattctat
50701 tgggttgaag catgccaact aagactttcc actctggaaa acattcaatt cagttcaaca
50761 acattttcca gcaacagtga gaaagcactg catataggta agcactgata acatgcacat
50821 ggaggaaatc ctgcagcatt ctctcttcag gtttgtacag ttgcccttt gcccacagga
50881 attttccatg gtccttcagc aggcacctgt cacacacttc actggaaata atgaagccga
50941 gggcgtactt cacatattta aacctgcaat tgctgttgat aaagaagcat tctttgtggc
51001 tcacttgtgt aagtgccatc aagatttaca accctgacac cagagctgga acgctggtta
51061 tttcaaagta ggggtggct aaaccaaacg tgaatgcaca cagccacgca cacacagatc
51121 aggtggccat ccaagggcag aagggccgca ttccatgagc acgatgcact tctgcccttt
51181 gctgctgccc aggtgagtgg ctgtgctcct gctccgtgct tcgtcgagtg ctggctgtaa
51241 aaacacaaca aacatcctca gactggaaag agctgtgttc tacaaggact tatttactcc
51301 tagagggatg tgttgaaaa gacttgacat caaagactat cacttatggg gtaatatttt
51361 agcaacagaa ctgagtgggt aagaacaact gtgggaacag ctccgcgctc ggtgctagtt
51421 tatgcataat gaaagcagtg acacgtacgt ggtaccacga catccaccat tgaacctccg
51481 aaacgctgca gaatcacaaa ttcttttact gaatggaagc gagcgtttcc cgcagtcatc
51541 ctgaactgag atgcaattgg aggggctgag cggctgcagc agcgttaggg gagtttcacc
51601 tcgctgagcc ctcccgttat ttcagtgctg ttgtggagct gcacgcagga gctgccgcca
51661 gtccgtgcca gctctgcggc cctgcttccc ggcaccttg cttatctctg agcacctgtc
51721 cttgctcatc ctgtgaatca cggagaattg ctttctcttc ctcccttttca tttcgcgcgt
51781 ccttctccac ccgggctgta accctcctga gaaaaaacgt agtacggaat cgatgttgta
51841 aacactcagc gtggcacaac gttttgcctg aaatcccttt tgtctgagag tcacacactg
51901 aattgcaagt tgtttattca ggacatgcac tcacggattt taacactaac gaaggagatg
51961 aattgcattt gtgtcacact tcctattccc ttctttactc cagaccccac tgcactgaag
52021 gtaagggaca gatctttcag gtttttttt tttttctcc atcatttctt tcctcaaagc
52081 agtttccgta taaatcatta ctaatcgcat tgtgatcgag cgtttgaaag ccctgagtca
52141 tcccacagcc tgagcaatat ttgctacaga tattaccgag tgaaatggcc atttttcatct
```

Figure 240

```
52201 gatggtttca aaaaaaaaaa aaagataata ataataataa taataataaa taaatagcgc
52261 agcattcagt tggtgtccaa gttattgtca cggttactgc agcagcactg aggatgttta
52321 catgggattt acatcactgg aggctgaaag ggcactgcag gcgtgtaccg cgctattcgc
52381 tgccccatcc ttaagctctt ctttgacatc tgctgatggt cggtgctggg ggaagcccgg
52441 ggctgtgggg gtctcctggc atctgccctg ctgatagctg tgctgctgag ggtatttctg
52501 tgagcacaag gctgcatcga tccacagggc gactgcagtg cctgcgccgt accccgcaat
52561 ttctgctctc gggagcgcat cccacactgc gggtctgatg gcgtaacata tgccagcgag
52621 tgtttattcc gcaatgcatt tctgggtgta tgaaaataaa tctcttcgct cactgagtgg
52681 tgaacttcaa ctgtcttatc aacctcaggg actgcctgga gatggaaggt ggttgtgttt
52741 ggcgctctcc tcttctcttg ctagcaaggg cagcactttt ttttttaaac tgggaggatt
52801 taccagggac tcctttcttt caggtaaaaa gaagtcacat ttagcagaga tcttcatctc
52861 cacgttgggt aatttgctga agagctcgct tccagcaaat acagtctatt tcctacagcc
52921 tatttgttct tcttttaaat taagtcttta tcgtgccttt gaatgttagt aataagagga
52981 agtagctgga atagctttcc gaatgttctg ttttggttaa gttcctctgt gatgtatcct
53041 taagcagagg gagggatgca cagcagaagc gcagaggttc aatctctgag gccctgagct
53101 ctttctctcc agaactcatt gagttctcac cttgctgtgc cctgcgcagc gctcacatca
53161 cagcccaccg ggctccagct cagacaggag gaccctctct ggctgtgttc cttacagggg
53221 atgctgccca agcctcgtc ctgaactttg agtgctcctg ataaagcctg aagctatgct
53281 caataaaaaa aaaaaacctt cagcattttg gtcttgcttt catactacgt atcatgctgt
53341 tgttttttt tcttaagatg ctgtgtgatt gcatcactgc aacagtcctg gggtgtgggt
53401 cttaatggga aaattacagg gagaaagaac gggttgtctg atttatgaag aaatcaaccc
53461 ctccaaaagg ccatgagctt ctgctttctt ccagatttcc aaaagaaagc cactgctggg
53521 gatgagatcc agtgcagtgt tcagggcatc ctgtgcagac attgactcct taggagctga
53581 aaataaagta gtggtgggta cccgtaggtg tgggaagcct ttctgcagcc acctggtctg
53641 cctcccaaag cagaggatgg gatgttttcc cctccgggca gcaccaacag aggggtggca
53701 gcagggtgag gaagatgatt ggcccctctg ctctgctctt gtggggacca catgcagtat
53761 tgcatccagg cctggggccc cagcatgaga aagacgtgga actgttggag tgggtccata
53821 ggaggccatg aagacaatca cagggctgga gcacctctct tatgaagaaa ggctgaggga
53881 gctgggcttg ttcagcatca agaagggaaa gctgagagga caccctcattg gagtcttcca
53941 gtacttgaag ggagcttgca agcaggaagg ggaacaaact tctacatggt ctgacagaga
54001 tagaacaagg gggagtggct ttaagctaaa agagggaaga tttgggtgag atgttgggaa
54061 gaaatacttt actcagaggt tggtgtgaca ctggcactgc tgcccagagc tgtgggtgcc
54121 ccatccctgt acatgagctg aaggccagat tggatggggc tctgtgcagc ctgatctggt
54181 gggggcagc cagcccatgg caggggttgg ggtagatggg ttgtatggcc ttttcaacc
54241 caaaccattc aatgattcta tgattctcag ataagcctgc ctgcccacat ctgagctcac
54301 ggtgctcgct gggggtgggg tatggtacac taaatgatgc tcagaggact gcacgcagga
54361 cctgccgcag acgtttatca cctcacccac cacttagctg ctgcttgtag ttaattacgt
54421 cagctgtcac ttgtagagaa tcctttgaga tccttgggcc tccggaaatc ttggctgatg
54481 aaaggaaggg ctcagagtca tagcgttaat ttattattca ttaacaccaa agtgtcggct
54541 gtacgggcag tgggctcaca gtcaaatagt taatgatctt aagtgacaat gtgtcacttt
54601 gcagacagca gagagaacag ctctcctaag ggagacagca tctttccaat tctgcagcca
54661 ttcagtgcca agctcctctt tgggacgaaa gtgaagatga ggaaggcaat gaggatgagg
54721 aggggcctca aggaactgg ctggcttgga gacaagtgat gatcccagct gctctcaggg
54781 tcccagcggt cttcaaaggg catcttgcag gggctgtgtc ctctgaacag caaacccag
54841 gtcatagagg ggaaagtgtg agcagagatg gacaaatct cccatcctgc cacggagctg
54901 cactgctaag ggggtgatgg ggagcagcat gggaccccag cgttcccccc atccctgcac
54961 caggcccagc tctgcgggat ggcgaggagg acaaggctct gtcacaagca tcgctggcaa
55021 ttattatttt gttgttgctg ctcaataaaa tcctgacaca gtacaacaca atatcctctc
55081 atcattacta atctaactct ccctccagga aatttcaggc aggaaacgtt gtctgcctgc
55141 cgaggtgctt tatggcactg ttctttagtg gtacctcagc acttcgtgtc attatctggt
55201 gtcagtgaat ttaggaaatg ccattcaatt accccgcaaa ctgattaacg cattgcgtgc
55261 agttattttg ttctgctcta ttttatatca gttcctctgt tttatgtatt tctctacttg
55321 ttgctggcca gaacacacct cgggccagtc tagaccttgc tgttgatgca gcttttcccc
55381 agggcttcat cagcacaaat ggtttgtcaa cgtgggaaa aataaaatta tgctttaaaa
55441 taaaccacc tggagatgct gttctggggt ctggctgtgt cacagctatt gcagcgatgg
55501 agctgaggga tgggatgtg ctgggccgga tcctcagcgc tttgctataa gccaaataat
55561 tccagacacc cttcttccct cagatatcat ctgtgcttaa gcagcaggag atatgcaggc
55621 agcgatcaga tagctgagct gcaaggagaa atatcacaag agcgcggctt agagcagggg
```

Figure 24P

```
55681 ctttgctcgc tctaaattga attcccatcc tcataggaga tccagtcctg ccccgtgtg
55741 catcgctccg gtaacagcaa tgtgttttgc tccatcttgc agagggtcca gaagctgggg
55801 aaaggaaatg tgtcgtgcgt tcgtccctgc agcagctcgg cccataaaat taatgaaaat
55861 ctttttttagg tcatggtaga ttacagattt ctttgagata gagaatctca agagcagagg
55921 agaagattct cagaaaatag cagtgatatg agatggcata acgctgagtt ggaaactggg
55981 gaggatttcc agggttactg gaaatttact taagcacgag agaatgcatc gtgtgactgc
56041 cagtgcttcc ccactcacat ggctataacc ttcttgcata caattaccat cttgaactt
56101 gaaatagctg aaagagtttt atttgatctt ttcaatggat cttacatctg cagaaaaaaa
56161 aaaaaaggc tagaaataat cctgcactca aactcacttt actgaaccac catcatgaaa
56221 ctccagcaac acacagggat tgggcaggc gtgttcatct tcctcttccc atttgcaaca
56281 tgtgtatggc atttcctgaa gctcactcct ccaaatgcat tgagacagtt gttttcatt
56341 cttcctaatg cctgcatcca cccatctgct gatcggcaat tatttctatc ccattccctt
56401 ctgtttctta ttaatcaagc tctttatgca atcccacgta acactttgcc cagctgccct
56461 gccctaacca ctaccaatta tctcatcctg ttttatagac cctgtagcaa gactctggcc
56521 ttgctcctct tcctctccct gatagagctt tggtgcagg gctggctggc tcctcaggtg
56581 ttcagaggat cagaggtctc ccagaaggat cttgttaatc aaggacaggt gctggctata
56641 tgggaggatg gcaccgtatc ctaaagctct acaagaagga gacggagctc agcctgggag
56701 gacagagaga agcagcagca caggtttcag gatccaggga tggcagacct gggtgtgggc
56761 tcataggatt gaagaaggga taggctgtgc tcctgtagcc tcactgcaga agcagcactg
56821 ctatctcccc agcgaagctg tgtgtgcccc atccctggag gtgctcagga ccaggtggga
56881 tggggccctg ggcagtctga gccggaggga gcagccggcc cacagcaggg gttggaatgg
56941 ggtgggtttt aagttcccct ccaaccaaag ccatttcttg atctctgttg gtggctggtg
57001 caagttctga ggaaacctca ttttcagctc aggcgttctt gtccctgggg aaaaatcaat
57061 attaatgctt cagtgattac tgctcgcctt ccaaatgtgc ttctgatcag ttcaagaaat
57121 ctgacagtca cgtcgctcag gatgctaaga atacaacaga aacagctttg aaaggaaccc
57181 ttcaactctt gatatttgtg aatgagctcc aaagaacatt actcatttat ttttcaggaa
57241 aatgatttca ttgacatgaa caggccaaag cctacaagct ctgttttgtg actgcagctc
57301 cttacacttt cagctgcatt ttcatgattt atgtgcccat gatgagactt gaacacctcc
57361 caggataatg ggaaaagcag ttctgatttc ccatttaaaa cgtaggctgc ctttaagcca
57421 tgtgtgtggc tcaggctcct tctgaagcac aaaggtgttc caccctcgc tccttttca
57481 ttacaacttt caatcaaaaa tgtgttttat gagatatttg ttttgccatg tatctgtgac
57541 ggagttgaac cccttagtga aacctctgtt cttcacttag ctgagaggta tttcttaggg
57601 aatgtgatgc cctaaattta ttgtggtgta atagaagggg ggatgtgtgg actcaccttc
57661 tgtttgttgt ggctgcagtg gttttatgca ctacctgagt attaagcaag ccctttcat
57721 ctgcacggaa caccctcctgc ttgccagtgg gatgaaacaa caacaacaaa gatttaaggt
57781 ttgctattct caatgtttct taatcgggtt cacattgatt gccaacagat gaataattcc
57841 tccttctcca tggatgtacc tcttaaactt gtgaagtctt aggtaacgct tttctgctgt
57901 gatgactgtt tcagtcccct cagtgagaaa tcaggcgcac cagtaagaca caaaggagac
57961 cgtggagatg ttcattgtgc cctcagcatc tccaaaaggc actgctgcct gccgagcccc
58021 agacttcgct cctgtaaaag caaagcatgt ccaattctgc tgtgccataa gagtcctgtg
58081 gagcccagac acggcgtagc gtgtgtaaca tagcgtgcac gagctcaaac gctttcaaca
58141 aatcagcttt tttgctttgc caacttccat atgtaatttc acaacatcta gtattgagac
58201 agtgctgttg tttgggcagc ataaatcact cattgtacag cagggcgcct ctcttaacaa
58261 gttgggtgta gttcatgttt ttgtctaatt cctctgcgca tctctctaac aaacaactat
58321 tcttttagggc tcgactcaat aatcaataca ttttttttcag tttacagagc aaataattac
58381 ttgacctgat gacttcacaa ggttagggag atgggtgtat aaagtctgca gtgtgaaggc
58441 agagcaacat ctctgcagac cttgagagca acaggtctgc aagtaacagg ctgcacagcc
58501 acctctgcca tggaggcaat gagagctgct gccctccttg gattggtgct tctcagctcc
58561 tttcctggta agttgttttt gttacattct ctgcttatat ctctactcct actgaactaa
58621 atgtggttca ggatgccttt agaatcctaa aagagagctc agcctgccgg agaagtgatg
58681 gtttggtaaa acatgagctc tcttctaatg atctttatcc ttgtgcaaat atttacgtaa
58741 ctctagcagg atgcctctgt ctgacataaa ctcattatcc tcagtaagtc tcatagcact
58801 cgagagagaa aatgtatacc ctatttcttc cttagtgagt caaagtttat attttcaccc
58861 aaaatggcta ttttttttaa tcataggata tagcttgctt ataggaactg gataaaatat
58921 ttaggaaaca agtaattctc agtgataaaa aagaagtatg tgatgactct gtagggaaat
58981 tgataattcc agaggaattg taaccaagga cgccgtaaca ttctgtattt tataacctct
59041 gttttttcca gatattgttt ctggtcatca acgggtgagt agcagatctg catcatttag
59101 ttgtggtttc tatgaataga tgaataattc atactcacac catatcctac gggagcctag
```

Figure 24Q

```
59161 agggagaaaa aaaaaaaaga aaagaaaata acaagggaag gagaaaaagg gcccccagga
59221 attatgtgac attttttcccc cagcaaataa gaaaacatct ttgtcagaga aagataacgt
59281 accacgttgg tgataagagt tggcaattaa taatgcagag tgggagccgg cgtggcacag
59341 cgtgccagca gaaaatctgc acagcttttc cctaactgcc tccatatctc ccctgcctga
59401 ttccctgagg acccatcagt cagtcgtgtg tctgccatgc caaaagcctc agtagtgaca
59461 ctgtgctcag gcatactgta aggaacgctg taatttgctc ccacttcttc accgtggagg
59521 agtgacagag aataaaatga ccgcctgcag cacggctatg cgtggaaaac acaagcagac
59581 ccttccgtgc cctgcagagc tgtcccactt gtgctcttcc caggcctcct gcggtgagta
59641 ccggctgtta ggcagcagga acctcgcctg ttccaggatc ttccagcccg tctgtggcac
59701 caataacatc acctaccccca atgagtgctc gctctgcaga gaaatcctgt gagtagcgat
59761 cgcccgatta cccatcgtga tggctcaggt ggcagacaga agccttttga attgtgacta
59821 atcacgggtg gattcgattt ttttttcccc tgtttctgtc ttcccagagt gcaggctgtg
59881 tttcttcctt gtcaaaactc ctgagtctaa ttaattagtg gggctgggcg tggagaggct
59941 tgatgagtga ggtgactgca tggcaccacc aggttaaccc ttccccctcct tctctcctag
60001 ccggagtggg acggttgaca agaagcacga tgggaggtgt gtgaaggtat ggttccagct
60061 cagccactgt gtggagcgat ggcagaatcc cttcccagca ctgattgtac atttagaatg
60121 gacagctcca aacccattgg aaatgtaaca gaaggaaga atttcaggtc ttttatatat
60181 atatatatat atatatatat gtatgtatta atttcatttt gaacagtgca aatctgtttc
60241 aacggtgagt tttgagatgt tatcttgtgt agcacagctg acttaaaaac agaatcctct
60301 catttcaata atcctttggt gttgttgaaa tagttcccctt tagacttaga cagaagtctg
60361 ttgaaattaa gaagttcccc aaggaagtct ggattttgac taaatcataa ttttgtaaca
60421 gggaaaaaga aaaaaaaaaa ggattccatc agaacatcta ccctgaggtt tgtttatcaa
60481 tacacggagc tgccacgaag tggagaagtg tctctatttt tagattagag agataatgta
60541 aagaaacact ccggctgtgc aattgaacat aatgctacaa ttttcacttc agtacactca
60601 gagtaatggc aggaacaccg aggtgagcat cagctccatt ttcaagtgga gcagacattt
60661 cacagcagca gttgctgcca tgtagggcat gttaggcaca gatcctatgt ggtggcattt
60721 ggggtggaaa gccctaagat gacaccaaca aaacccattc tgtgaaccca ttttcctccag
60781 gattctgctg ggctcatgtc ctcaaaggca ggacttcacc tgcctgtgct cccttgcccg
60841 cactgtgctg ggttggaagc tcacatctcc atacagcccc actcaccgtg agtctggggg
60901 tgggagacac ctctcacacc atgcaccatt acacagggct gacggaagtg ttgttctgtg
60961 gctgtttcag gttgattgca ctggctacat gagaacaact gatgggcttg gaacagcctg
61021 catccagcag tacagcccgc tctatgccac caacgggctc gtctacagca acaagtgcac
61081 cttctgctcg gcagtggcgt gagtggtggg tcacaccctg ggtgctgggg tctgggtggt
61141 ggtgtttgca gcatattgag gcttctggag tggctgtgct gtgctcattc attctcaact
61201 tgctttcttc cccaaggaat ggagaggaca tagatctgct cgctgttgga aaagagcccg
61261 aggtaaagct cgaaagtctg cgctatgaac tgttgttata atatattata cagcacaaat
61321 tcagtgagtc agaactacgc aatagcaatg tcttcactgt gctggtgtat ttgtcctgga
61381 aaaagggttt gaggaaaatg actcaagtat gccagggtca gaggacgatg aacaaaactc
61441 ctggctcctg tgtcagtatc acctgcacag cccctgacag gggttgatgc tcagagcatt
61501 gttcagatgg tggctgtgcc agaggtgctc accgctcctg gtgagcgtgg ggctcatgca
61561 gcaccagctg tcattacttg ggtgggtgga cttcatagtg tgctgttgga gacacactgc
61621 ttcctggcag cccctctctg ctggctgctg aaccagagca gagcaggtag cgggccgcca
61681 gccggggagc actgctttgg ctgtgtcgct gcttctgagg gtatttagta gattttttccc
61741 tctgacttct ccttttgtgc tctgctgggc aagagcatta gaatttgcag agttgctaga
61801 acaacaggag cctgcatctg aaaaaatgtt ttttttgctt tgccatgaca taaatgtaaa
61861 gcgcccatgt aggaaaatac accaaacaaa ggcttctcaa tacgttcttg ctccattacc
61921 tacagattga ctgcagtgaa ttcaagagca ctgatgccta ctgcactgaa gagtacatgc
61981 cccttttgcgg ctctgacggc gtaacgtatg gaacaaatg ccacttctgc attgcagttt
62041 tgtaagtaca gtgctcccca tgcagccatg aaaccactgc tgtgccggag tatgaaggca
62101 gaagctgcca ggaagccttt tgctcccgt tatccccttg gtaaatccgt ccccatcccc
62161 aacctgatcc cagctctacc tctgctgtgc cttcccaag cactgcagat cttgaacaca
62221 ggtgagtctt ctccctccct caccattaaa ttcagattct catttgcggg tcatagcgc
62281 tcctgatcca tccctgcgag agtaatttga gtggtaactg tagaaggagt atccaaaatt
62341 acagggtttg tcccagatct ctctaacatg acaaaacgtg taacctgggg aatcaggaga
62401 cgggtgaagg tgcaactggg acagcatgga gcattggctt gcccatgcaa agtcagcagt
62461 ggcaccatca gggctataaa accaccttcc atgtcagtga ttttggcctc ctcctttctc
62521 tgcaggaaga gtcatggatc tctgtctctg cagcaccgtg gagaatgctg aatgctggat
62581 cgtaaccttt accctcatcc atctttcact tccaaagcct gcaattccaa cacgctcttc
```

Figure 24R

```
62641 cccgctccct gctgtacatt gctttctgcc ttgacccgcc agtaaatcac agacagcaac
62701 tctcttcgcc atgggctggt gtgttattta tttatttatt tatttattgt tgttattatt
62761 ttttccaggg cagaggtaaa agtcttcagg ctttcaggca cttatctgtc aggcaggaga
62821 agttttgaaa taaaccacaa taaaggccaa agtgcaacac ccatcacaca aaagccataa
62881 gccctcacga aagtgcgtca ccccattcca aaccatcaga agaggaaatg ttgctataaa
62941 acacatgctg ctctccccag ttctgtgtct tacagcacat aaatggattt gctttaagag
63001 tcaggatgtg gctttgtaga agcacggagc cctggaggaa gcagtccttt tgggagcctt
63061 ggtatggagg aaagatggct ttgatacacc tgagcaaggg gcaagtctgg cggcacgtta
63121 caaggaggct tatggcaaag ggaggagact atctcacagg gaagaaaatt aggaactgtt
63181 gcttccttga agggtgtgtc ccttgagagt gtggtgatca gcagaaaatt gcagccagct
63241 gggcaaggct gtaatgagcc taatgaggac cagaggagaa accagattgg gctcaggctt
63301 cttggaaaag agatctgaaa agctgcactg ggagcgtttg aggcagagga aagagaaagg
63361 actcttcagg aaaaggtttg ggagtcttca tgcctagaaa agaaaggaca gaaggagtgc
63421 ttggtagctc caaggtcgtt tctgtctgca gtgaaaggtg atgtgtggat gatgcgtgtg
63481 agcgttcaca gtgatgtgcc atctctttgg gcgagtcaag gaatgagtat gcaaacaaca
63541 ggtgaaaagt cccaagtgcc tccactcatg ccaccttccc cttcctttct ccacctccca
63601 tcctctcatt acgtaggaag acattcagct gttcaggctg atattgagga caaaatctgt
63661 gacttccaag cttttctctg gctttatttc ctgaaatagg ctgtatcttg acctagaaat
63721 cttatgggtg cttcctgcca gaagatggga agctgtcctt taatagcgtg tcagggcagt
63781 gctccgtcct aggaagacag atggaacttt gaaatgttta ttctattagc acaggcagta
63841 taaagcacag tgtgcctctg tgcctgctgg tgagaaaagg caagctgcag agccgtgagg
63901 gtgctccctg ctaatctgcc tagaagggaa aagagtagac aagaaatagc atatgctact
63961 actgaatgtg agcagaagac ctttagtgaa ggacacagct cagctgtaat gtcctgttgg
64021 ccaggaggtt tgttgagtta tcgcagagcg gtagagttct ggtcagagca ggaaggtgcc
64081 ttcaacagca agatcccatg gtaggcctct tctgcagtgt gctggcacaa gcctggtacc
64141 tgctcaggag caaaaaaagg ctttggaaaa gctcaaagaa gggctgatgt cttacaggga
64201 aagggagggc aaaaggcaag tgcagagcat atggctgtac agacaaaaac ccttcagaaa
64261 atggaaaagg ttttttatcaa gtaagcccag aagttggccc agtgcaggta aacacttggc
64321 taggtaacag tgaggctctg cccagccata cccattcctc tgtaaggcaa atcccaggtg
64381 cctttgtctt gtctggtcct gttctgttcc tatttttctg agaaatcaga cagaacttcc
64441 ccacctacag catcaagcag ctactttata ggtgaagaag tgcaaagaga agcaataagg
64501 ataatcacca cttggctaat ttagtctctt cctctcagcc cacaaaggac tggtccctgt
64561 ggtacatttt ctaaggcttt tcccagtcag ctgtgctgta gcaaatgaaa tgtttggcta
64621 gataaagagc tgaggtatta gtgctggggc ggcgagcagt gtctggagca agaaaaggca
64681 aacgagggat tctgcgagtg gcagaactaa gcctgatttt gaatggcgtt gtggctggcg
64741 gacttgtaaa ttatatgaga ggctgtgctg tgagctcacc ctaatagaca tctgagaact
64801 cacctgtcaa tcgcggttcc tctgctgtgt gggttttatg gtgtctagtg agctgcaagc
64861 tctaatgctt tccaggtgc agggcagttg tggcattgct ctcctacaga aactctcact
64921 tgctggctga ggatgtttag gaagtccttg gttgctagaa aaaatatatt gaagtgcttt
64981 ttttgtttgt tgtttttcca ttcttgtgtg aaattttgtt ggaatcacag aatcatagag
65041 gttgaaagag aaactctgga aattatcaag ttcaaccct tgctaaagca ggcttcatac
65101 agtaggttgc agttacaaca tttgctgggg aaatgaatat gaagatctgt ctataaagag
65161 tgttcccata gcacttgttt ctttaggaaa gcatgctgaa attctaaagg ctgtgcctat
65221 ctgaagagat actttgcaag tggtgcaact aaatgctgct cttggtggag agatggctgg
65281 agatggatcg atggttgggt gatcttcgtg gtcttttcca actttaatga ttctatgatt
65341 ctatactctt tacacagaat cagctgggaa tagagtgaga gtcctgat tccccaccaa
65401 attcctttga ttgatgcttg gtgtggaagc agagctctgg gacacgttgg tgagtgtgaa
65461 aactggaaaa cattgacagc tatagtttaa atagttcagg gaggagaggc agccatccta
65521 tgtgggactc tgcacacggc tatgagagca tcagtgcgct tctccacccc aacccaacaa
65581 atttagagcc atcctccaaa atagccaggg acaacgcat aattggtttc acagacaaca
65641 cattctcatg ctgtgattta tttcgtaatg tctggtgagt gtcatcacgc cgtgctcaaa
65701 gcctggagct ggcattcagc gaggacccag agaatgaaaa ttaccagctt ccccgatgaa
65761 tcaccacttt gaaaattcac ccttgtgaga atcctgtgac tattcagaaa aaaaaaaaa
65821 aaagaagaag aagaagaaga agatattca ggcccaagtc tatcagtcat gtaattagcc
65881 cttctaggt ttgatgtgga cagggcggca ttcctaaagc accataaaca cggccgggac
65941 caataatggc tctagaatcg aagcggagaa gttctcacaa ttaaggtgag aatgaggcc
66001 agcagcggat aggtacataa atacacggag gcagggccgt gagcacgctg tgggcttgtg
66061 gctgagacaa caacctcccaa accggtcgct tgccggggac taaaagagca gcatgaaggc
```

Figure 24S

```
66121  aacaggcacc tcggtgctcc tcagcctgct gctgctgctg tcgttcttct cgggtaagtt
66181  atatttctgt agcctagaaa gaaactttat gacgagagca acttcagaga gccttgatca
66241  acggatgaca ggcttgaaga gaaagctgag caagtagaaa atatctgcgg gactcgcttg
66301  cttgtgtcac atctttccat tcctcgtgtg cctccgcagt gaataacact gtggaggtgt
66361  cactgggaga cagaatgagc aaattgtaag cagctcgttc agcagaggca ccaaagcaga
66421  gcgtaattat gagttttggt ggaaatgttt gctggagagc tttgctgaac cagttagaga
66481  agaaactcat acctcagggt catcagctcc tgttctgatg ctaagcactt gggggttggt
66541  gttctcctca gagatgtggc agcgtaatta gatgaaagtt tcagcttcca aatacgttgc
66601  agaggagggc tcgaaaatta aattcagatg tcctcgagga acccgaacaa agagggcaaa
66661  ttgaaagggt ccagcgttta tttatcttga ggtttacacg tctctctgtt ggtctgggga
66721  ggctggctga tggtttgggg gtgtgtaggg cacaccgggg tgctcaaatg ctcgcgtgcg
66781  gccgatgcga atgtggaagc gttgcggtgg ccattactga agactgcaga ccaaggatta
66841  tttatacttg tttttctgtg aataatttga ataaagaatt cgcttgagaa aatcgcaggc
66901  tgtgcatgga gagaagaggt gaattacttt gtacacatca ttaattatga aatattcatc
66961  tgtctttaat tgagtcttaa ttggggctgg gttccgtcag agtgctaaag cttcttttcca
67021  aggccaggca gaatagcagc aaactctgtg atctcaaata agataaacag atgccaagag
67081  acgttctcac aaagtcttgt gtagctgcat gtaatattta aaaaattat ctaatgagct
67141  gttttgtaaa taatatgcag atagccctaa cggcggcttc cctgtccagc ctagctgagg
67201  atgtgacaga tacagcagtg gcaaggatca aacactgaaa ggcatcgcag caggcagaag
67261  ctgggtgggg tgatggatgg tcccgctgag cgtgatgctg caatgctccc agcctgcacc
67321  ctaaccaaag ggatgcccca ttgcaatgcg ccccagcccc tgcagcgctg tgtgcagccc
67381  actccctgtc cccgacacca caggatccat cccgtggctg tgacctggcc ccatgcaaag
67441  tttgcaggca ggaaatagca aagaggatgg actgattgtc tccaggccca gagcctgtgc
67501  ctgcagcagg tattttgct ctgctgctgt ctggcactgc ctgttctgcc ccagatcacg
67561  ccaggctatc cctttgtatc tcatccggat gaggctgttc tgggagcctc ggctgtgctg
67621  tactgcagac ggctctgatg ctgactgcgg ggtctcctcc atctcccctg tgtgcttttg
67681  ttaccgtact ggccagtttt gtaattcaga ggtgcaagag cctaaaagcc ataagactca
67741  atgaagcttt aaaatctctg ctgagagagg ctcagctctt acatagctcc ccgcttcccc
67801  ggcggtggct gcctgccagg gagatgggtt tatgtgtctg tggtgcagtt agcagctgaa
67861  tgactgatta catggtattt tagtaacatt tttcaaatag caaaatactg aaaagcaatt
67921  ccgataatgt atttcctacc cctcctccac cacacagaac ggcagaggag ggaaaacctg
67981  gtgtgtgctg tgctgcagtt tgcaaaggga tttgtgactt cggttcagtc ctctcagaaa
68041  ataatgctaa tgtggataaa atctttttt ttgttgcaat tctaggtgta gcagctcaag
68101  acattgaaga ggttagtgca gctctttctg ctttctgaat ctgcattttc tcctggctct
68161  ggaagaatgc ttttctaaca gatcttggtg cattggtgca tgctgaactg ctttgggttt
68221  tgctgggatc aggtgggtcc tgccaaggtg ccccaatgct tcggagtgct cacacagtac
68281  aggggtgtta gctatggcca cagtagcaaa caagttgggg atgatttagc tggtttagca
68341  catgctcccc atggtctgat ccagcacagg gctgtctgca gtatcgcttc tgtctgcttt
68401  gctcctccac gaaacaaatg tgatatcagg agtgatatac tcctttaaac catatccata
68461  actgggcttt gtccaaaagc ctgttcactt catagaatca ttaaggttgg aaagaccact
68521  atggtcatcg agtgcaacca ctccatgccc agatccctgt gtatggcagc cccaggccac
68581  gtggtggtgt gagctgcatg gtaccgggca ctgatatggg gctgcatcag tgctgatgct
68641  ctcctgttga acccactcat gttcttggaa caccagagct gctccctggt ggtgacagct
68701  tccctcctct gccacagggc agaaattccc ccatttcagc cagttctgac aggcctttgt
68761  ttttcaagta gcaggccgt gcctcgttgc tgcttttggc ctctgggtgg gaagaagatc
68821  acattagaga tcttctttcc tgtttggaaa gcgaaacccg acggtttatt gctgttatta
68881  tttttgattt cttttgcaga tctgcaaaga gttcttaaac aggagcgtgt tctgcaccag
68941  ggagtccaac cctcactgcg gcacggatgg cgtgacgtac ggcaacaagt gtgccttctg
69001  caaggccgtg ctgtaagtgg gggcggtggg atacggaccc acacagggat ggtccacttc
69061  caaccccgcg ctgctgctcc cctcacacag agcaatccct ggccatagaa tcatagaact
69121  agagaatggt taaggttgga aaagaccaat aagtgcatct agttcaaatg gcagctcctc
69181  accgccacgc tgggaatat tcagcttaa tgttgattca tttctaggct tagtgtgatg
69241  ctcatagccg tacagagatg gcacagagcc tgggaggcca ttgtacctgc ctgtaccttc
69301  tgcgtgggct aaattgatgc acatttcct ctgtgtgcca caggctgaag ctctccctgt
69361  ccacacctct ggatgctgaa gtgtgtggag gaacgcaggc ttatgcatgc caaattatta
69421  gaggaaagtc atagactcgt agaatcatag attcgtttga gtcgaatggg acctttgaag
69481  gtcatctggt ccagcatccc tgcaacgagc agggaaagtg ctgaaatgaa agtctgaatg
69541  gacttagtgg aaaagtacac aaaatctcag aggaagggct gcagtttctc ctctcctgtc
```

Figure 24T

```
69601  tcctctaaag gagctgtaat aggagccaac acctctggac tgaaggcctg caaaaattga
69661  tttatcctta tcaatcctgc actctggagg ctgccttatc ctaagggaaa ttagagaaga
69721  gggaaagatg gcttgatgct ccctgtgagg caccagagtg aggcaaatga tcgtgctcgg
69781  agggacaagc tccctgtccc agccgctgtg tctgtgctgg atgccataca ctgctttgtt
69841  tccataccgc tccttttaca ggaggagtgg agggaagata cgattgaagc acatggggaa
69901  gtgctgagcc tgagcaccaa gcactgatct tcgtcggtca caggtgcagg agcctgggca
69961  cggcagcagc tgtcctcatc tctgccatat ctgctcaata aagtaaagct cagcacacct
70021  ccttgactgg attcctttt ccataacacc cggataagcc ttccatgcag ccgtgctagc
70081  agctaaaatg tttgccgcac tgtgctgtta catcttagaa tcacagaatc aggcaccatg
70141  ctgcctgagc aggagcaatg attcccacag ctcttccatg ccatgccatg ccatgccatg
70201  ccatgccatg ccatgccatg ccatgccatg ccatgccatg ccatgccatg ccatgccatc
70261  ccatcccatc ccatcccatc ccatcccact gacaaatgga cacatggcca cccagcttga
70321  ctgtcccatg ggtgggtgac agcatgcaac gttgcctctc agcagcctcc ccatatgtgt
70381  ccctctcgct gaggtgtgag catgaaggtg gcagagagct atgagtggtg tggctgtgga
70441  tgcctcatct gcttgggaag ccagaagcaa acaggctgag gctgaggagt gttgctgcat
70501  gtaagcctgc accgggaagg tggcagggga agctggcttt aggcagaaac acaaaggctt
70561  tgctttcctt gtgtgtccta agagaggact ttgcctcaaa gactgtcaac tcgccagcat
70621  caggttgcag ttgcacacaa acttgatttc tttctttagt tttcacactg ctgctctctc
70681  tctccttgat gctggctgga aaatccttct ttgcgccagc gagggaaaat aaagcctata
70741  gtctctcccc attcgctgta caaaatatac acagggaaat gcttgtggca tccctcgtt
70801  aaaacgttgg cagcacatca atgggactct actcacttaa tgttgaacac ttaagtttca
70861  aagggagctt tagatttat cgtgaggtca gccaactcat tttgcaaaca cctctatgct
70921  gagcatctca gctcctggat ggtgtttgga cagagctgag tgtttgcctg tggtgccacg
70981  ctgcaggctt tgaagtgaat tgggacatta tattttgtag ccaaggagag ttgcagtttg
71041  ctttgttcca attcagatgt ttctttagta aacacaacag ctagacctcc agaacatgga
71101  taagcttgag gggaggaaaa agcacctcct gcacgaggac agctgatcac aaaggacccc
71161  agtgggcagt gggagaacct tcatcatcct ctctaccgcc tggatcagga tgagccctgc
71221  atacccttt caactggagt taccctgtga gccaacttgt ggctctggag tagtgctgta
71281  tctcaataca gtttctcaga tgggaagagg catttcaatg agaggggga tatgggacat
71341  ttctatgcct gagatggctc tcggagactc caaaagcctc acggcgtatc cccatgccta
71401  atccttttta atctggaggc tgaaataaca aggacagatc acaagagaac agaagcggcg
71461  agacttctct gctttataat cagcctgcat tttgctcttt cagtgcaaac agcaaataga
71521  accgcctctg tacccctcca gacccaacca ccatcccag caacactgtg gcaggctgga
71581  gaagggtggc tctgcccctc cttgcctcaa ctggttgtgt cagcacgacc ataaccagag
71641  ctctccttgg ccccagctgg gcttatccat gtaaacctct cagtgcccca ggagctggct
71701  ggtggtcctg tccatttcac tttcctccag caggtgttcc ctttaacaag catccaagtg
71761  cctggagcag gagcaggcac tgcagaagat gagctcaggc aaggacatgg catgtgggga
71821  tccatgctgt tgtgcaatgc agatgacgtt agatacgtgc aaagcagatc tcagcaatca
71881  cccaacgact cataactgca atcatggaac gcaattgcat ctggaagtat aaaagcacag
71941  tgataccagg aagctcttgt taatggcaca gccattttgg agcaatttgc ccaggtgggg
72001  agagccctca cagcgccttc agtcacaggg agtggtgtga gtgccccat ggctgctccc
72061  agccccagc cctgggtgat ggggtcact tggctgtaac cctctgaaca caggacagt
72121  gagacagccc tctggcctgg ctgagctctt ggctacgtcc agctgcagtc ctgggcacat
72181  actgaaccag aaagcaagca ttcagctggt attttttcctt taatttcctt cctccacatt
72241  ttaagtgtg ggattttttt tttttttttt tgacagcttt gagagatgag tgagtcacga
72301  agcactcgag atctctatta gataacagag catctctgca gctcttcctg gggaggggagt
72361  tccttggacc aagggcaag gctgggtgag aattgtccca gcatcacagt ggctgctcca
72421  tcacctgaca cagcccctct gcagtgaaac aagggaagca ttacatcttt gcacggctgc
72481  tttcactgaa caaaagcgc tgcttcacag ctgagcacca tgatgaaggg gaaggagcat
72541  ctccatgatg aaggggaagg agcatctcca catctccatc acgagctctg tctgctggt
72601  gatcggctg acaccatggt gtgccctgac tcctggccca tttaactgct gtgcaccagt
72661  gcctcctccc cagcatagcc ctgtgtccct gccacaactc attgcaatcc tttgtcctac
72721  ttcttccctt gacattcaca gctcttgata aggcttttg agccactcct ggctgatgtg
72781  ggctggtggt tcctgctgca gggttcccac cacccagctg gcagcattc ggttgttgtt
72841  ccagttccca ggggattggg acagattgga agggtctttg ggactgtgga agagtatctc
72901  ctgaagtcag ggcagactgc tcagcgcttt gtcccatcca gacttgaaaa catccaaggg
72961  tggagaacac acagactccc tgggctgcca gtcccagagt ttgactgtca tcacgttgaa
73021  gacttttgc cttgtctcca tttgcaacct ctttccttc agctgcccca tctctcagcc
```

Figure 24U

```
73081 atgcaccact ggggagccca gctctgtctg gtcaggaaca gagcccttac agagccacag
73141 catcctcctg aagtgtccat ctcaccactc agcctcagca agtgctccag ccctcaactc
73201 ccatttccca ttatctttct atcactggat atgggaggga aggcagagct gtggggccaa
73261 gagaaacgat tgctcaggag gcagttggga aactttatt gcaaagcact gaagagatat
73321 aaagtgacat tgcaggaaa aagtagaagg gtatctgtgt gtgttggttc ctttaaggat
73381 tagagagcag ctgagctttg ggatgagagg gctcccagat gctgtgaatc agctaacaga
73441 tccctccacc ccgtcattgg tggtgaagtt aaatagggc ccaggggaaa catcagggtt
73501 gttttctttt ttacggactc cagagcaagg agaaggtgag ggggttgtgc tttggaatgg
73561 gagtgaaaga gtttgttggt gttttcctct ccccagaata agtagtgtgg tgtaggagcg
73621 tctcatagga gtagctgcgt taattgtggc tggtgttagc atcctataat gttgctccag
73681 aaatgctgga gcaggcttat aatgatgtgt atgtattacc ataatacatg aagggagaat
73741 ggggggggg ggggtagatt taagatgtat gcccttagaa aggcgggtgt cacttaaaga
73801 agtacttgct ttatagctcc agtgatagaa ttcattgaga tactctgaac ctatggggca
73861 tgaagtgacc agatcttcag tttggtcagc tctggggtt tctgggggga gcgggatag
73921 agcctcaatc caggtctgaa agacaaggct gagatgtgct gggcctgggg tgctgccctg
73981 agcaacgtgg ggctggccct agagagcagc attagtgcct gcagcagggc tggcccttgt
74041 gcccagtgtg tggggtaagg tggggaacgt aggtgctgca taatgtggtg cttctgatct
74101 aaaactgctc tgttaattgg gagtgaccag agatggccct atggctttct tcccaaagag
74161 ctctgtgtcc ttctctgcag ggtaatctgt gataaaaaca tcgcctatgc tctgccctgc
74221 agatgcaggg gttttttgtca tcctccttct cgagacatac tctaatcctt acgcaagcag
74281 ggagctccaa gcttttggtg ataacctctc aaggaggagc tggaagggca gctctgccga
74341 gcagtgactg cgctgcacgg ggcgcatcct gcaggaggcg gtggtgtaag cgggactccg
74401 ctcgttcccg gctatggggc tccccctgct gaccgccggg cggtggccag gagacctcgg
74461 ggccgctgct gcccctcggt ggtgcttttc gggacagctt tcaggatggg gcagcccagc
74521 tgctctcgcg gggaattaag cggctcggtg cagggcggca cggcgctgag ctgccccagc
74581 aaagcgccgc tcgtcccgcg gcaccttcgg tagatgctct ctgcttggca gtccttggt
74641 cgttctcttg gccggtggcc accccagcat cgctcggggc tcggtgccat ccccccaggg
74701 gcctgcggag gtgccggtgc ccgtcccggg ggtggcggac gggcggtgca gtaccgatgc
74761 tgggcgctgg gtgctgccgc agaccgagcg gcgctgcgcg gctccggggc gctcctggag
74821 tgcgagctga gcaacctggt agaaaataa gtgttgtccc gtgataaacg tcatcgtgct
74881 gagctctcag actctgccag aggcctgaat gaagctgcgt caggggagaa tcaggttggg
74941 gctaaggaaa ggtcctgccc cagagggcgg tgggtataga aggggtgccc agggcagtgg
75001 gtgcagtgct gggctcccag agctggagga gcgtctggac agtgctcagg tttggatgtt
75061 gggtggtttt ctgaagggac ggattctggg ctcgtttatc ctgagggtcc cttccaactt
75121 gggttgttct attcaatgaa tattgtttat gttcattcta ttctatgatc ttgttcaggc
75181 tctcactgct gcctccaagg gttcagctcc cccagagctg cagggcttc agccacttgc
75241 ttacagtgct catttcatgc ctggcccatg gcttctgcct gagccttgtg ggagatcagc
75301 tgctgccaga aacccagccc tcagcactcc acttgcccag cttgctgcct tagtagtcta
75361 acttggcagt ggtctgacat gacttgaggt tgttttttat ttccaaggtg ccactgactt
75421 ttttccttcc atagtttctg gaagcatttc cttcctactt gactgagtcg tgctctgtgg
75481 atctgtaatt atccaccttg gctatgtgtc ctttacggga ttttatatgt taacctccca
75541 agatcatttt gctgctctca tcttagtggc tgctgtgagc tccaccagca ccacactgga
75601 tgagctgcag gctgaggccg ggcacctctc ctgactctgc tcttctctga ccccagagct
75661 gtgcagttgg gatcctaaca ccatgcagat gctccaggac ctgcaccgag ccccagcact
75721 ggcactcatc tcttctttcc acccctctga gagcaacaag tggctctgca atggcaatgt
75781 aagtgaaacc gggcgggtat cttagagcac ctgga
```

Figure 24V

```
   1 gaattccgcc cctctccctc ccccccccct aacgttactg gccgaagccg cttggaataa
  61 ggccggtgtg cgtttgtcta tatgttattt tccaccatat tgccgtcttt tggcaatgtg
 121 agggcccgga aacctggccc tgtcttcttg acgagcattc ctaggggtct ttcccctctc
 181 gccaaaggaa tgcaaggtct gttgaatgtc gtgaaggaag cagttcctct ggaagcttct
 241 tgaagacaaa caacgtctgt agcgacccttt tgcaggcagc ggaaccccccc acctggcgac
 301 aggtgcctct gcggccaaaa gccacgtgta taagatacac ctgcaaaggc ggcacaaccc
 361 cagtgccacg ttgtgagttg atagttgtg gaaagagtca aatggctctc ctcaagcgta
 421 ttcaacaagg ggctgaagga tgcccagaag gtacccatt gtatgggatc tgatctgggg
 481 cctcggtgca catgctttac gtgtgtttag tcgaggttaa aaaacgtcta ggccccccga
 541 accacgggga cgtggttttc ctttgaaaaa cacgatgata agcttgccac aaccatggga
 601 tggagctgta tcatcctctt cttggtggcc acagctaccg gtgtgcactc cnnnnnnnnn
 661 nnnnnnnnnn nnnnnnnnnn nnnnnnnnnn nnnnnnnnnn nnnnnnnnnn nnnnnnnnnn
 721 nnnnnnnnnn nnnnnnnnnn nnnnnnnnnn nnnnnnnnnn nnnnnnnnnn nnnnnnnnnn
 781 nnnnnnnnnn nnnnnnnnnn nnnnnnnnnn nnnnnnnnnn nnnnnnnnnn nnnnnnnnnn
 841 nnnnnnnnnn nnnnnnnnnn nnnnnnnnnn nnnnnnnnnn nnnnnnnnnn nnnnnnnnnn
 901 nnnnnnnnnn nnnnnnnnnn nnnnnnnnnn nnnnnnnnnn nnnnnnnnnn nnnnnnnnnn
 961 nnnnnnnnnn nnnnnnnnnn nnnnnnnnnn nnnnnnnnnn nnnnnnnnnn nnnnnnnnnn
1021 nnnnnnnnnn nnnnnnnnnn nnnnnnnnnn nnnnnnnnnn nnnnnnnnnn nnnnnnnnnn
1081 nnnnnnnnnn nnnnnnnnnn nnnnnnnnnn nnnnnntagg gatccactag tccagtgtgg
1141 tggaattc
```

Figure 25A

```
   1 gaattccgcc cctctccctc cccccccct aacgttactg gccgaagccg cttggaataa
  61 ggccggtgtg cgtttgtcta tatgttattt tccaccatat tgccgtcttt tggcaatgtg
 121 agggcccgga aacctggccc tgtcttcttg acgagcattc ctaggggtct ttcccctctc
 181 gccaaaggaa tgcaaggtct gttgaatgtc gtgaaggaag cagttcctct ggaagcttct
 241 tgaagacaaa caacgtctgt agcgacectt tgcaggcagc ggaaccccc acctggcgac
 301 aggtgcctct gcggccaaaa gccacgtgta taagatacac ctgcaaaggc ggcacaaccc
 361 cagtgccacg ttgtgagttg gatagttgtg gaaagagtca atggctctc ctcaagcgta
 421 ttcaacaagg ggctgaagga tgcccagaag gtacccatt gtatgggatc tgatctgggg
 481 cctcggtgca catgctttac gtgtgtttag tcgaggttaa aaaacgtcta ggcccccga
 541 accacgggga cgtggttttc ctttgaaaaa cacgatgata agcttgccac aaccatggga
 601 tggagctgta tcatcctctt cttggtggcc acagcaaccg gtgtccatag tnnnnnnnnn
 661 nnnnnnnnnn nnnnnnnnnn nnnnnnnnnn nnnnnnnnnn nnnnnnnnnn nnnnnnnnnn
 721 nnnnnnnnnn nnnnnnnnnn nnnnnnnnnn nnnnnnnnnn nnnnnnnnnn nnnnnnnnnn
 781 nnnnnnnnnn nnnnnnnnnn nnnnnnnnnn nnnnnnnnnn nnnnnnnnnn nnnnnnnnnn
 841 nnnnnnnnnn nnnnnnnnnn nnnnnnnnnn nnnnnnnnnn nnnnnnnnnn nnnnnnnnnn
 901 nnnnnnnnnn nnnnnnnnnn nnnnnnnnnn nnnnnnnnnn nnnnnnnnnn nnnnnnnnnn
 961 nnnnnnnnnn nnnnnnnnnn nnnnnnnnnn nnnnnnnnnn nnnnnnnnnn nnnnnnnnnn
1021 nnnnnnnnnn nnnnnnnnnn nnnnnnnnnn nnnnnnnnnn nnnnnnnnnn nnnnnnnnnn
1081 nnnnnnnnnn nnnnnnnnnn nnnnnnnnnn nnnnnnnnnn nnnnnnnnnn nnnnnnnnnn
1141 nnnnnnnnnn nnnnnnnnnn nnnnnnnnnn nnnnnnnnnn nnnnnnnnnn nnnnnnnnnn
1201 nnnnnnnnnn nnnnnnnnnn nnnnnnnnnn nnnnnnnnnn nnnnnnnnnn nnnnnnnnnn
1261 nnnnnnnnnn nnnnnnnnnn nnnnnnnnnn nnnnnnnnnn nnnnnnnnnn nnnnnnnnnn
1321 nnnnnnnnnn nnnnnnnnnn nnnnnnnnnn nnnnnnnnnn nnnnnnnnnn nnnnnnnnnn
1381 nnnnnnnnnn nnnnnnnnnn nnnnnnnnnn nnnnnnnnnn nnnnnnnnnn nnnnnnnnnn
1441 nnnnnnnnnn nnnnnnnnnn nnnnnnnnnn nnnnnnnnnn nnnnnnnnnn nnnnnnnnnn
1501 nnnnnnnnnn nnnnnnnnnn nnnnnnnnnn nnnnnnnnnn nnnnnnnnnn nnnnnnnnnn
1561 nnnnnnnnnn nnnnnnnnnn nnnnnnnnnn nnnnnnnnnn nnnnnnnnnn nnnnnnnnnn
1621 nnnnnnnnnn nnnnnnnnnn nnnnnnnnnn nnnnnnnnnn nnnnnnnnnn nnnnnnnnnn
1681 nnnnnnnnnn nnnnnnnnnn nnnnnnnnnn nnnnnnnnnn nnnnnnnnnn nnnnnnnnnn
1741 nnnnnnnnnn nnnnnnnnnn nnnnnnnnnn nnnnnnnnnn nnnnnnnnnn nnnnnnnnnn
1801 nnnnnnnnnn nnnnnnnnnn nnnnnnnnnn nnnnnnnnnn nnnnnnnnnn nnnnnnnnnn
1861 nnnnnnnnnn nnnnnnnnnn nnnnnnnnnn nnnnnnnnnn nnnnnnnnnn nnnnnnnnnn
1921 nnnnnnnnnn nnnnnnnnnn nnnnnnnnnn nnnnnnnnnn nnnnnnnnnn nnnnnnnnnn
1981 nnnnnnnnnn nnnnntgagt gcgacggccg gcaagggatc ccccgggctg caggaattc
```

Figure 25B

PRODUCTION OF A TRANSGENIC AVIAN BY CYTOPLASMIC INJECTION

CROSS REFERENCE TO RELATED APPLICATIONS

The application is a continuation-in-part and claims the benefit of U.S. application Ser. No. 10/251,364, filed Sep. 18, 2002, now issued U.S. Pat. No. 7,312,374, issued Dec. 25, 2007, which claims the benefit of U.S. Provisional Application No. 60/322,969, filed Sep. 18, 2001, and U.S. Provisional Application No. 60/351,550, filed Jan. 25, 2002, all of which are incorporated by reference herein in their entireties.

1. FIELD OF THE INVENTION

The present invention relates to methods of producing a transgenic avian by introducing a nucleic acid encoding a heterologous protein into an avian embryo preferably by cytoplasmic injection, but also by other methods of introducing nucleic acids into embryonic cells, including but not limited to, nuclear transfer, retroviral vector infection, and fertilization with sperm containing the nucleic acid. The present invention further relates to a transgenic avian expressing a heterologous polypeptide, which, preferably, is deposited into the white of the avian egg. The invention further provides vectors containing coding sequences for heterologous proteins, the expression of which is under the control of a promoter and other regulatory elements that cause expression of the heterologous protein and preferably, lead to deposition of the protein in the avian egg. Also included in the invention are avian eggs derived from the transgenic avians and the heterologous proteins isolated therefrom.

2. BACKGROUND

The field of transgenics was initially developed to understand the action of a single gene in the context of the whole animal and the phenomena of gene activation, expression, and interaction. This technology has also been used to produce models for various diseases in humans and other animals and is amongst the most powerful tools available for the study of genetics, and the understanding of genetic mechanisms and function. From an economic perspective, the use of transgenic technology for the production of specific proteins or other substances of pharmaceutical interest (Gordon et al., 1987, *Biotechnology* 5: 1183-1187; Wilmut et al., 1990, *Theriogenology* 33: 113-123) offers significant advantages over more conventional methods of protein production by gene expression.

Heterologous nucleic acids have been engineered so that an expressed protein may be joined to a protein or peptide that will allow secretion of the transgenic expression product into milk or urine, from which the protein may then be recovered. These procedures have had limited success and may require lactating animals, with the attendant costs of maintaining individual animals or herds of large species, including cows, sheep, or goats.

The hen oviduct offers outstanding potential as a protein bioreactor because of the high levels of protein production, the promise of proper folding and post-translation modification of the target protein, the ease of product recovery, and the shorter developmental period of chickens compared to other potential animal species. The production of an avian egg begins with formation of a large yolk in the ovary of the hen. The unfertilized oocyte or ovum is positioned on top of the yolk sac. After ovulation, the ovum passes into the infundibulum of the oviduct where it is fertilized, if sperm are present, and then moves into the magnum of the oviduct, lined with tubular gland cells. These cells secrete the egg-white proteins, including ovalbumin, lysozyme, ovomucoid, conalbumin and ovomucin, into the lumen of the magnum where they are deposited onto the avian embryo and yolk.

2.1 Microinjection

Historically, transgenic animals have been produced almost exclusively by microinjection of the fertilized egg. Mammalian pronuclei from fertilized eggs are microinjected in vitro with foreign, i.e., xenogeneic or allogeneic, heterologous DNA or hybrid DNA molecules. The microinjected fertilized eggs are then transferred to the genital tract of a pseudopregnant female (e.g., Krimpenfort et al., in U.S. Pat. No. 5,175,384). However, the production of a transgenic avian using microinjection techniques is more difficult than the production of a transgenic mammal. In avians, the opaque yolk is positioned such that visualization of the pronucleus, or nucleus of a single-cell embryo, is impaired thus preventing efficient injection of the these structures with heterologous DNA. What is therefore needed is an efficient method of introducing a heterologous nucleic acid into a recipient avian embryonic cell.

Cytoplasmic DNA injection has previously been described for introduction of DNA directly into the germinal disk of a chick embryo by Sang and Perry, 1989, *Mol. Reprod. Dev.* 1: 98-106, Love et al., 1994, Biotechnology 12: 60-3, and Naito et al., 1994, *Mol. Reprod. Dev.* 37:167-171; incorporated herein by reference in their entireties. Sang and Perry described only episomal replication of the injected cloned DNA, while Love et al. suggested that the injected DNA becomes integrated into the cell's genome and Naito et al. showed no direct evidence of integration. In all these cases, the germinal disk was not visualized during microinjection, i.e., the DNA was injected "blind" into the germinal disk. Such prior efforts resulted in poor and unstable transgene integration. None of these methods were reported to result in expression of the transgene in eggs and the level of mosaicism in the one transgenic chicken reported to be obtained was one copy per 10 genome equivalents.

2.2 Retroviral Vectors

Other techniques have been used in efforts to create transgenic chickens expressing heterologous proteins in the oviduct. Previously, this has been attempted by microinjection of replication defective retroviral vectors near the blastoderm (PCT Publication WO 97/47739, entitled Vectors and Methods for Tissue Specific Synthesis of Protein in Eggs of Transgenic Hens, by MacArthur). Bosselman et al. in U.S. Pat. No. 5,162,215 also describes a method for introducing a replication-defective retroviral vector into a pluripotent stem cell of an unincubated chick embryo, and further describes chimeric chickens whose cells express a heterologous vector nucleic acid sequence. However, the percentage of $G_1$ transgenic offspring (progeny from vector-positive male $G_0$ birds) was low and varied between 1% and approximately 8%. Such retroviral vectors have other significant limitations, for example, only relatively small fragments of nucleic acid can be inserted into the vectors precluding, in most instances, the use of large portions of the regulatory regions and/or introns of a genomic locus which, as described herein, can be useful in obtaining significant levels of heterologous protein expression. Additionally, retroviral vectors are generally not appropriate for generating transgenics for the production of pharmaceuticals due to safety and regulatory issues.

2.3 Transfection of Male Germ Cells, Followed by Transfer to Recipient Testis Other methods include in vitro stable transfection of male germ cells, followed by transfer to a recipient testis. PCT Publication WO 87/05325 discloses a method of transferring organic and/or inorganic material into sperm or egg cells by using liposomes. Bachiller et al. (1991, *Mol. Reprod. Develop.* 30: 194-200) used Lipofectin-based liposomes to transfer DNA into mice sperm, and provided evidence that the liposome transfected DNA was overwhelmingly contained within the sperm's nucleus although no transgenic mice could be produced by this technique. Nakanishi & Iritani (1993, *Mol. Reprod. Develop.* 36: 258-261) used Lipofectin-based liposomes to associate heterologous DNA with chicken sperm, which were in turn used to artificially inseminate hens. There was no evidence of genomic integration of the heterologous DNA either in the DNA-liposome treated sperm or in the resultant chicks.

Several methods exist for transferring DNA into sperm cells. For example, heterologous DNA may also be transferred into sperm cells by electroporation that creates temporary, short-lived pores in the cell membrane of living cells by exposing them to a sequence of brief electrical pulses of high field strength. The pores allow cells to take up heterologous material such as DNA, while only slightly compromising cell viability. Gagne et al. (1991, *Mol. Reprod. Dev.* 29: 6-15) disclosed the use of electroporation to introduce heterologous DNA into bovine sperm subsequently used to fertilize ova. However, there was no evidence of integration of the electroporated DNA either in the sperm nucleus or in the nucleus of the egg subsequent to fertilization by the sperm.

Another method for transferring DNA into sperm cells was initially developed for integrating heterologous DNA into yeasts and slime molds, and later adapted to sperm, is restriction enzyme mediated integration (REMI) (Shemesh et al., PCT International Publication WO 99/42569). REMI utilizes a linear DNA derived from a plasmid DNA by cutting that plasmid with a restriction enzyme that generates single-stranded cohesive ends. The linear, cohesive-ended DNA together with the restriction enzyme used to produce the cohesive ends is then introduced into the target cells by electroporation or liposome transfection. The restriction enzyme is then thought to cut the genomic DNA at sites that enable the heterologous DNA to integrate via its matching cohesive ends (Schiestl and Petes, 1991, *Proc. Natl. Acad. Sci. USA* 88: 7585-7589).

It is advantageous, before the implantation of the transgenic germ cells into a testis of a recipient male, to depopulate the testis of untransfected male germ cells. Depopulation of the testis has commonly been by exposing the whole animal to gamma irradiation by localized irradiation of the testis. Gamma radiation-induced spermatogonial degeneration is probably related to the process of apoptosis. (Hasegawa et al., 1998, *Radiat. Res.* 149:263-70). Alternatively, a composition containing an alkylating agent such as busulfan (MYLERAN™) can be used, as disclosed in Jiang F. X., 1998, *Anat. Embryol.* 198(1):53-61; Russell and Brinster, 1996, *J. Androl.* 17(6):615-27; Boujrad et al., *Andrologia* 27(4), 223-28 (1995); Linder et al., 1992, *Reprod. Toxicol.* 6(6):491-505; Kasuga and Takahashi, 1986, *Endocrinol. Jpn* 33(1):105-15. These methods likewise have not resulted in efficient transgenesis or heterologous protein production in avian eggs.

2.4 Nuclear Transfer

Nuclear transfer from cultured cell populations provides an alternative method of genetic modification, whereby donor cells may be sexed, optionally genetically modified, and then selected in culture before their use. The resultant transgenic animal originates from a single transgenic nucleus and mosaics are avoided. The genetic modification is easily transmitted to the offspring. Nuclear transfer from cultured somatic cells also provides a route for directed genetic manipulation of animal species, including the addition or "knock-in" of genes, and the removal or inactivation or "knock-out" of genes or their associated control sequences (Polejaeva et al., 2000, *Theriogenology*, 53: 117-26). Gene targeting techniques also promise the generation of transgenic animals in which specific genes coding for endogenous proteins have been replaced by exogenous genes such as those coding for human proteins.

The nuclei of donor cells are transferred to oocytes or zygotes and, once activated, result in a reconstructed embryo. After enucleation and introduction of donor genetic material, the reconstructed embryo is cultured to the morula or blastocyte stage, and transferred to a recipient animal, either in vitro or in vivo (Eyestone and Campbell, 1999, *J Reprod Fertil Suppl.* 54:489-97). Double nuclear transfer has also been reported in which an activated, previously transferred nucleus is removed from the host unfertilized egg and transferred again into an enucleated fertilized embryo.

The embryos are then transplanted into surrogate mothers and develop to term. In some mammalian species (mice, cattle and sheep) the reconstructed embryos can be grown in culture to the blastocyst stage before transfer to a recipient female. The total number of offspring produced from a single embryo, however, is limited by the number of available blastomeres (embryos at the 32-64 cell stage are the most widely used) and the efficiency of the nuclear transfer procedure. Cultured cells can also be frozen and stored indefinitely for future use.

Two types of recipient cells are commonly used in nuclear transfer procedures: oocytes arrested at the metaphase of the second meiotic division (MII) and which have a metaphase plate with the chromosomes arranged on the meiotic spindle, and pronuclear zygotes. Enucleated two-cell stage blastomeres of mice have also been used as recipients. In agricultural mammals, however, development does not always occur when pronuclear zygotes are used, and, therefore, MII-arrested oocytes are the preferred recipient cells.

Although gene targeting techniques combined with nuclear transfer hold tremendous promise for nutritional and medical applications, current approaches suffer from several limitations, including long generation times between the founder animal and production transgenic herds, and extensive husbandry and veterinary costs. It is therefore desirable to use a system where cultured somatic cells for nuclear transfer are more efficiently employed.

What is needed, therefore, is an efficient method of generating transgenic avians that express a heterologous protein encoded by a transgene, particularly in the oviduct for deposition into egg whites.

3. SUMMARY OF THE INVENTION

This invention provides methods for the stable introduction of heterologous coding sequences into the genome of a bird and expressing those heterologous coding sequences to produce desired proteins. Synthetic vectors and gene promoters useful in the methods are also provided by the present invention, as are transgenic birds that express a heterologous protein and avian eggs containing a heterologous protein. In a preferred embodiment, the vectors useful in methods of the invention are not eukaryotic viral, more preferably not retroviral, vectors (although the vectors may contain transcriptional regulatory elements, such as promoters, from eukaryotic viruses). In other embodiments, however, the vectors are eukaryotic viral vectors or are retroviral vectors. In certain embodiments, a bacterial artificial chromosome (BAC) vector is preferred.

One aspect of the present invention is a method of producing a transgenic avian capable of expressing a heterologous protein. The method comprises isolating an early stage embryo from a fertilized hen, and microinjecting into the isolated embryo a selected nucleic acid that encodes the desired heterologous protein. The microinjected avian embryo is transferred to the oviduct of a recipient hen for in vivo development and to be laid as a shelled egg (or, alternatively, cultured ex vivo). The shelled egg is incubated to hatch a transgenic chick that has incorporated, preferably, integrated into its genome, the selected nucleic acid.

The present invention provides methods for introducing a transgene into the cytoplasm of avian embryonic cells by cytoplasmic microinjection. The cells may be embryonic cells as, for example, from a single cell embryo visualized through overlying yolk or tissue by using, for example, light microscopy, or a camera system such as a CCD camera with a microscopic lens (e.g., as disclosed in PCT International Publication WO 02/064727 by Christmann, which is incorporated by reference herein in its entirety). Microelectroporation can optionally be used to enhance the uptake of exogenous DNA into the cell nucleus and improving the efficiency of DNA integration. The cytoplasmically microinjected embryo is then, preferably, returned to a female bird to be laid as a hard-shell egg or, as an alternative, cultured ex vivo. After hatching from the hard-shelled egg, a transgenic chick is produced that expresses a heterologous protein and/or that can be bred to generate a line of transgenic birds expressing a heterologous protein.

In alternative embodiments, the nucleic acid is introduced by infection or injection of the nucleic acid contained within a retroviral vector, sperm-mediated transgenesis, or nuclear transfer.

In one embodiment, the present invention provides methods for producing heterologous proteins in avians. Transgenes are introduced by, most preferably, cytoplasmic microinjection into one embryonic cell, preferably the germinal disk of an early stage embryo, that then develop into a transgenic bird. The protein of interest may be expressed in the tubular gland cells of the magnum of the oviduct, secreted into the lumen, or deposited within the egg white onto the egg yolk or expressed, for example, in the serum of the bird. Such transgenic birds can also be bred to identify birds that carry the transgene in their germ line. The exogenous genes can therefore be transmitted to birds by both cytoplasmic microinjection of the exogenous gene into bird embryonic cells, and by subsequent stable transmission of the exogenous gene to the bird's offspring in a Mendelian fashion.

The present invention provides for a method of producing a heterologous protein in an avian oviduct. The method comprises, as a first step, providing a vector containing a coding sequence and a promoter that functions in avians, preferably in the avian magnum, operably linked to the coding sequence, so that the promoter can effect expression of the nucleic acid in the tubular gland cells of the magnum of an avian oviduct and/or in any other desired tissue of the avian. In a preferred embodiment, the vector containing the transgene is not a eukaryotic viral vector (preferably, not a retroviral vector, such as but not limited to reticuloendotheliosis virus (REV), ALV or MuLV) or derived from a eukaryotic virus (but, in certain embodiments, may contain promoter and/or other gene expression regulatory sequences from a eukaryotic virus, such as, but not limited to, a Rous sarcoma virus viral promoter or a cytomegalovirus promoter). Next, the vector is introduced into avian embryonic cells by cytoplasmic microinjection so that the vector sequence may be randomly inserted into the avian genome. Finally, a mature transgenic avian that expresses the exogenous protein in its oviduct is derived from the transgenic embryonic cells or by breeding a transgenic avian derived from the transgenic embryonic cells.

In particular embodiments, the level of mosaicism of the transgene (percentage of cells containing the transgene) in avians hatched from microinjected embryos (i.e., the $G_0$s) is greater than 5%, 10%, 25%, 50%, 75% or 90%, or is the equivalent of one copy per one genome, two genomes, five genomes, seven genomes or eight genomes, as determined by any number of techniques known in the art and described infra. In additional particular embodiments, the percentage of $G_0$s that transmit the transgene to progeny ($G_1$s) is greater than 5%, preferably, greater than 10%, 20%, 30%, 40%, and, most preferably, greater than 50%. In other embodiments, the efficiency of transgenesis (i.e., number of $G_0$s containing the transgene) is greater than 2%, 5%, 10%, 20%, 30%, 40%, 50%, 60%, 70%, 80% or 99%.

This method can also be used to produce an avian egg containing an exogenous protein when the exogenous protein, that is expressed for example, in the tubular gland cells or fibroblast cells, is also secreted into the oviduct lumen and deposited, e.g., into the white of an egg. In other embodiments of the invention, the exogenous protein is expressed in the liver, or secreted into the blood, and deposited into the yolk. In preferred embodiments, the level of expression of the heterologous protein in the egg white of eggs laid by $G_0$ and/or $G_1$ chicks and/or their progeny is greater than 5 ng, 10 ng, 50 ng, 100 ng, 250 ng, 500 ng, 750 ng, 1 µg, 5 µg, 10 µg, 50 µg, 100 µg, 250 µg, 500 µg, or 750 µg, more preferably greater than 1 mg, 2 mg, 5 mg, 10 mg, 20 mg, 50 mg, 100 mg, 200 mg, 500 mg, 700 mg, 1 gram, 2 grams, 3 grams, 4 grams or 5 grams.

The present invention further provides promoters useful for expression of the heterologous protein in the egg. For example, the promoter comprises regions of at least two promoters derived from an avian including, but not limited to, an ovomucoid, ovalbumin, conalbumin, lysozyme, or ovotransferrin, or any other promoter that directs expression of a gene in an avian, particularly in a specific tissue of interest, such as the magnum. Alternatively, the promoter used in the expression vector may be derived from that of the lysozyme gene that is expressed in both the oviduct and macrophages. In other embodiments the promoter is a viral or non-avian promoter, e.g., cytomegalovirus or Rous sarcoma virus promoter. In certain embodiments, the promoter is constitutive in avian cells. In other embodiments, the promoter is inducible. In particular embodiments, the gene regulatory sequences are flanked by matrix attachment regions (MARs), preferably, but not limited to those associated with the lysozyme gene in chickens or other avians. The nucleic acid encoding the polypeptide may be operably linked to a transcription promoter and/or a transcription terminator. In other embodiments, prior to microinjection, the vector is mixed with a nuclear localization signal peptide to facilitate targeting of the injected vector to the nucleus.

Other embodiments of the invention provide for transgenic avians, such as chickens or quail, carrying a transgene in the genetic material of their germ-line tissue, preferably where the transgene was not introduced into the avian genome using a eukaryotic viral promoter. The transgene incorporated into the genomic DNA of a recipient bird can encode at least one polypeptide that may be, for example, but is not limited to, a cytokine, a growth factor, enzyme, structural protein, immunoglobulin, or any other polypeptide of interest that is capable of being expressed by an avian cell or tissue. Preferably, the heterologous protein is a mammalian, or preferably a human, protein or derived from a mammalian, or preferably a human, protein (e.g., a derivative or variant thereof). In particular embodiments, the invention provides heterologous proteins isolated or purified from an avian tissue, preferably serum, more preferably eggs, most preferably egg whites, and pharmaceutical compositions comprising such heterologous proteins. In a more preferred embodiment, the heterologous protein is an antibody that is human (including antibodies produced from human immunoglobulin sequences in mice or in antibody libraries or synthetically produced but having variable domain framework regions that are the same as or homologous to human framework regions) or humanized.

The present invention further relates to nucleic acid vectors (preferably, not derived from eukaryotic viruses, except, in certain embodiments, for eukaryotic viral promoters and/or enhancers) and transgenes inserted therein that incorporate multiple polypeptide-encoding regions, wherein a first polypeptide-encoding region is operatively linked to a transcription promoter and a second polypeptide-encoding region is operatively linked to an Internal Ribosome Entry Sequence (IRES). For example, the vector may contain coding sequences for two different heterologous proteins (e.g., the heavy and light chains of an immunoglobulin) or the coding sequences for all or a significant part of the genomic sequence for the gene from which the promoter driving expression of the transgene is derived, and the heterologous protein desired to be expressed (e.g., a construct containing the genomic coding sequences, including introns, of the avian lysozyme gene when the avian lysozyme promoter is used to drive expression of the transgene, an IRES, and the coding sequence for the heterologous protein desired to be expressed downstream (i.e., 3' on the RNA transcript of the IRES)). Thus, in certain embodiments, the nucleic acid encoding the heterologous protein is introduced into the 5' untranslated or 3' untranslated regions of an endogenous gene, such as but not limited to, lysozyme, ovalbumin, ovotransferrin, and ovomucoid, with an IRES sequence directing translation of the heterologous sequence. In a specific embodiment, an IRES-cDNA cassette encoding a heterologous polypeptide is inserted into the 3' UTR region of the ovomucoid region of OMC24, a BAC clone containing full-length ovoinhibitor and ovomucoid genes (e.g. at residue an EcoRI site at position 49,146 of SEQ ID NO:42).

Such nucleic acid constructs, when inserted into the genome of a bird and expressed therein, will generate individual polypeptides that may be post-translationally modified, for example, glycosylated or, in certain embodiments, be present as complexes, such as heterodimers with each other in the white of the avian egg. Alternatively, the expressed polypeptides may be isolated from an avian egg and combined in vitro, or expressed in a non-reproductive tissue such as serum. In other embodiments, for example, but not limited to, when expression of both heavy and light chains of an antibody is desired, two separate constructs, each containing a coding sequence for one of the heterologous proteins operably linked to a promoter (either the same or different promoters), are introduced by microinjection into cytoplasm of one or more embryonic cells and transgenic avians harboring both transgenes in their genomes and expressing both heterologous proteins are identified. Alternatively, two transgenic avians each containing one of the two heterologous proteins (e.g., one transgenic avian having a transgene encoding the light chain of an antibody and a second transgenic avian having a transgene encoding the heavy chain of the antibody) can be bred to obtain an avian containing both transgenes in its germline and expressing both transgene encoded proteins, preferably in eggs.

In other embodiments, the present invention further provides methods for the introduction to an avian genome of at least one transgene encoding at least one heterologous polypeptide including sperm-mediated transfer where nucleic acids are incorporated into avian sperm by liposomes, electroporation, restriction enzyme mediated integration (REMI), or similar methods. The modified sperm may then be returned to the testis of a male bird which then may be mated with a female to generate transgenic offspring, or the modified sperm may be used directly to fertilize the female bird by artificial insemination to generate transgenic offspring.

The present invention further provides methods for incorporating a transgene into the nucleus of an avian cell cultured in vitro including by transfection, cytoplasmic microinjection or pronuclear microinjection. The transgenic cell nucleus may then be transferred to a fertilized enucleated cell. The enucleated cell may be an embryonic cell of a bird egg visualized through overlying yolk or tissue by using two photon laser scanning microscopy.

For convenience, certain terms employed in the specification, examples, and appended claims are collected here.

3.1 Definitions

The term "avian" as used herein is intended to refer to any species, subspecies or race of organism of the taxonomic class ava, such as, but not limited to, such organisms as chicken, turkey, duck, goose, quail, pheasants, parrots, finches, hawks, crows and ratites including ostrich, emu and cassowary. The term includes the various known strains of *Gallus gallus*, or chickens, (for example, White Leghorn, Brown Leghorn, Barred-Rock, Sussex, New Hampshire, Rhode Island, Ausstralorp, Minorca, Amrox, California Gray, Italian Partidge-colored), as well as strains of turkeys, pheasants, quails, duck, ostriches and other poultry commonly bred.

The term "embryonic cells" as used herein refers to cells that are typically single cell embryos, or the equivalent thereof, and is meant to encompass dividing embryos, such as two-cell, four-cell, or even later stages as described by Eyal-Giladi and Kochav (1976, *Dev. Biol.* 49:321-337) and ova 1, 2, 3, 4, 5, 6, 7, 8, 9, 10, 12, 14, 16, 18, or 20 hours after the preceding lay. The embryonic cells may be isolated freshly, maintained in culture, or reside within an embryo. Although the present invention is generally described in terms of microinjection of a single-cell embryo, it should be recognized that other cells from an early stage embryo are suitable for cytoplasmic injection in the methods of the present injection. For example, cells obtained from a stage later than a stage I embryo, up to and including a stage X embryo, i.e., stages II-X, may be useful in the present invention. Chick developmental stages are described in the following reference, Eyal-Giladi and Kochav, 1976, *Dev. Biol.* 49(2):321-37, which is hereby incorporated by reference in its entirety.

The term "nucleic acid" as used herein refers to any natural and synthetic linear and sequential arrays of nucleotides and nucleosides, for example cDNA, genomic DNA, mRNA, tRNA, oligonucleotides, oligonucleosides and derivatives thereof. Representative examples of the nucleic acids of the present invention include bacterial plasmid vectors including expression, cloning, cosmid and transformation vectors such as, but not limited to, pBR322, animal viral vectors such as, but not limited to, modified adenovirus, influenza virus, polio virus, pox virus, retrovirus, and the like, vectors derived from bacteriophage nucleic acid, e.g., plasmids and cosmids, artificial chromosomes, such as but not limited to, Yeast Artificial Chromosomes (YACs) and Bacterial Artificial Chromosomes (BACs), and synthetic oligonucleotides like chemically synthesized DNA or RNA. The term "nucleic acid" further includes modified or derivatised nucleotides and nucleosides such as, but not limited to, halogenated nucleotides such as, but not only, 5-bromouracil, and derivatised nucleotides such as biotin-labeled nucleotides.

As used herein the terms "polypeptide" and "protein" refer to a polymer of amino acids of three or more amino acids in a serial array, linked through peptide bonds. The term "polypeptide" includes proteins, protein fragments, protein analogues, oligopeptides and the like. The term "polypeptides" contemplates polypeptides as defined above that are encoded by nucleic acids, produced through recombinant technology, isolated from an appropriate source such as a bird, or are synthesized. The term "polypeptides" further contemplates polypeptides as defined above that include chemically modified amino acids or amino acids covalently or noncovalently linked to labeling ligands.

The term "fragment" as used herein to refers to an at least 10, 20, 50, 75, 100, 150, 200, 250, 300, 500, 1000, 2000 or 5000 nucleotide long portion of a nucleic acid (e.g., cDNA) that has been constructed artificially (e.g., by chemical synthesis) or by cleaving a natural product into multiple pieces, using restriction endonucleases or mechanical shearing, or enzymatically, for example, by PCR or any other polymerizing technique known in the art, or expressed in a host cell by recombinant nucleic acid technology known to one of skill in the art. The term "fragment" as used herein may also refer to an at least 5, 10, 20, 30, 40, 50, 75, 100, 150, 200, 250, 300, 400, 500, 1000, 2000, or 5000 amino acid portion of a polypeptide, which portion is cleaved from a naturally occurring polypeptide by proteolytic cleavage by at least one protease, or is a portion of the naturally occurring polypeptide synthesized by chemical methods or using recombinant DNA technology (e.g., expressed from a portion of the nucleotide sequence encoding the naturally occurring polypeptide) known to one of skill in the art.

The term "isolated nucleic acid" as used herein refers to a nucleic acid that has been removed from other components of the cell containing the nucleic acid or from other components of chemical/synthetic reaction used to generate the nucleic acid. In specific embodiments, the nucleic acid is 50%, 60%, 70%, 80%, 90%, 95%, 99% or 100% pure. The techniques used to isolate and characterize the nucleic acids and proteins of the present invention are well known to those of skill in the art and standard molecular biology and biochemical manuals may be consulted to select suitable protocols without undue experimentation. See, for example, Sambrook et al, 2001, Molecular Cloning: A Laboratory Manual, 3rd ed., Cold Spring Harbor Press; the content of which is herein incorporated by reference in its entirety.

By the use of the term "enriched" in reference to nucleic acid it is meant that the specific DNA or RNA sequence constitutes a significantly higher fraction of the total DNA or RNA present in the cells or solution of interest than in normal or diseased cells or in the cells from which the sequence was taken. Enriched does not imply that there are no other DNA or RNA sequences present, just that the relative amount of the sequence of interest has been significantly increased, for example, by 1 fold, 2 fold, 5 fold, 10 fold, 50 fold, 100 fold, 500 fold, 1000 fold, 10,000 fold, 100,000 fold, or 1,000,000 fold. The other DNA may, for example, be derived from a yeast or bacterial genome, or a cloning vector, such as a plasmid or a viral vector.

The terms "transcription regulatory sequences" and "gene expression control regions" as used herein refer to nucleotide sequences that are associated with a gene nucleic acid sequence and which regulate the transcriptional expression of the gene. Exemplary transcription regulatory sequences include enhancer elements, hormone response elements, steroid response elements, negative regulatory elements, and the like. The "transcription regulatory sequences" may be isolated and incorporated into a vector nucleic acid to enable regulated transcription in appropriate cells of portions of the vector DNA. The "transcription regulatory sequence" may precede, but is not limited to, the region of a nucleic acid sequence that is in the region 5' of the end of a protein coding sequence that may be transcribed into mRNA. Transcriptional regulatory sequences may also be located within a protein coding region, in regions of a gene that are identified as "intron" regions, or may be in regions of nucleic acid sequence that are in the region of nucleic acid.

The term "promoter' as used herein refers to the DNA sequence that determines the site of transcription initiation by an RNA polymerase. A "promoter-proximal element" may be a regulatory sequence within about 200 base pairs of the transcription start site. A "magnum-specific" promoter, as used herein, is a promoter that is primarily or exclusively active in the tubular gland cells of the avian magnum. Useful promoters also include exogenously inducible promoters. These are promoters that can be "turned on" in response to an exogenously supplied agent or stimulus, which is generally not an endogenous metabolite or cytokine. Examples include an antibiotic-inducible promoter, such as a tetracycline-inducible promoter, a heat-inducible promoter, a light-inducible promoter, or a laser inducible promoter. (e.g., Halloran et al., 2000, *Development* 127: 1953-1960; Gemer et al., 2000, *Int. J. Hyperthermia* 16: 171-81; Rang and Will, 2000, *Nucleic Acids Res.* 28: 1120-5; Hagihara et al., 1999, *Cell Transplant* 8: 4314; Huang et al., 1999, *Mol. Med.* 5: 129-37; Forster et al., 1999, *Nucleic Acids Res.* 27: 708-10; Liu et al., 1998, *Biotechniques* 24: 624-8, 630-2; the contents of which have been incorporated herein by reference in their entireties).

To facilitate manipulation and handling of the nucleic acid to be administered, the nucleic acid is preferably inserted into a cassette where it is operably linked to a promoter. The promoter should be capable of driving expression in the desired cells. The selection of appropriate promoters can be readily accomplished. For some applications, a high expression promoter is preferred such as the cytomegalovirus (CMV) promoter. Other promoters useful in the present invention include the Rous Sarcoma Virus (RSV) promoter (Davis et al., 1993, *Hum. Gene Therap.* 4:151). In other embodiments, all or a portion of the, for example, lysozyme, ovomucoid, ovalbumin, albumin, conalbumin or ovotransferrin promoters, which direct expression of proteins present in egg white, are used, as detailed infra, or synthetic promoters such as the MDOT promoter described infra.

The terms "operably" or "operatively linked" refer to the configuration of the coding and control sequences so as to perform the desired function. Thus, control sequences operably linked to a coding sequence are capable of effecting the expression of the coding sequence and regulating in which tissues, at what developmental timepoints, or in response to which signals, etc., a gene is expressed. A coding sequence is operably linked to or under the control of transcriptional regulatory regions in a cell when DNA polymerase will bind the promoter sequence and transcribe the coding sequence into mRNA that can be translated into the encoded protein. The control sequences need not be contiguous with the coding sequence, so long as they function to direct the expression thereof. Thus, for example, intervening untranslated yet transcribed sequences, can be present between a promoter sequence and the coding sequence and the promoter sequence can still be considered "operably linked" to the coding sequence. Such intervening sequences include but are not limited to enhancer sequences which are not transcribed or are not bound by polymerase.

The term "expressed" or "expression" as used herein refers to the transcription from a gene to give an RNA nucleic acid molecule complementary at least in part to a region of one of the two nucleic acid strands of the gene. The term "expressed" or "expression" as used herein also refers to the translation from said RNA nucleic acid molecule to give a protein or polypeptide or a portion thereof.

The term "matrix attachment region" or "MAR" as used herein refers to a DNA sequence having an affinity or intrinsic binding ability for the nuclear scaffold or matrix. The MAR elements of the chicken lysozyme locus are described by Phi-Van et al., 1996, *E.M.B.O. J.* 76:665-664 and Phi-Van, L. and Stratling, W. H., 1996, *Biochem.* 35:10735-10742; incorporated herein by reference in their entireties.

The term "probe" as used herein, when referring to a nucleic acid, refers to a nucleotide sequence that can be used to hybridize with and thereby identify the presence of a complementary sequence, or a complementary sequence differing from the probe sequence but not to a degree that prevents hybridization under the hybridization stringency conditions used. The probe may be modified with labels such as, but not only, radioactive groups, biotin, and the like.

The term "nucleic acid vector" as used herein refers to a natural or synthetic single or double stranded plasmid or viral nucleic acid molecule, or any other nucleic acid molecule, such as but not limited to YACs, BACs, bacteriophage-derived artificial chromosome (BBPAC), cosmid or P1 derived artificial chromosome (PAC), that can be transfected or transformed into cells and replicate independently of, or within, the host cell genome. A circular double stranded vector can be linearized by treatment with an appropriate restriction enzyme based on the nucleotide sequence of the vector. A nucleic acid can be inserted into a vector by cutting the vector with restriction enzymes and ligating the pieces together. The nucleic acid molecule can be RNA or DNA.

The term "expression vector" as used herein refers to a nucleic acid vector that comprises regulatory sequences operably linked to a nucleotide sequence coding at least one polypeptide. As used herein, the term "regulatory sequences" includes promoters, enhancers, and other elements that may control gene expression.

The term "recombinant cell" refers to a cell that has a new combination of nucleic acid segments that are not covalently linked to each other in nature in that particular configuration. A new configuration of nucleic acid segments can be introduced into an organism using a wide array of nucleic acid manipulation techniques available to those skilled in the art. A recombinant cell can be a single eukaryotic cell, such as a mammalian cell, or a single prokaryotic cell. The recombinant cell may harbor a vector that is extragenomic. An extragenomic nucleic acid vector does not insert into the cell's genome. A recombinant cell may further harbor a vector or a portion thereof (e.g., the portion containing the regulatory sequences and the coding sequence) that is intragenomic. The term intragenomic defines a nucleic acid construct incorporated within the recombinant cell's genome.

The terms "recombinant nucleic acid" and "recombinant DNA" as used herein refer a combination of at least two nucleic acids that is not naturally found in a eukaryotic or prokaryotic cell in that particular configuration. The nucleic acids may include, but are not limited to, nucleic acid vectors, gene expression regulatory elements, origins of replication, suitable gene sequences that when expressed confer antibiotic resistance, protein-encoding sequences and the like. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

As used herein, the term "transgene" means a nucleic acid sequence (encoding, for example, a human interferon polypeptide) that is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location that differs from that of the natural gene or its insertion results in a knockout). A trangene also includes a regulatory sequence designed to be inserted into the genome such that it regulates the expression of an endogenous coding sequence, e.g., to increase expression and or to change the timing and or tissue specificity of expression, etc. (e.g., to effect "gene activation").

As used herein, a "transgenic avian" is any avian species, including the chicken, in which one or more of the cells of the avian may contain heterologous nucleic acid introduced by way of human intervention, such as by transgenic techniques known in the art, and particularly, as described herein. The nucleic acid is introduced into a cell, directly or indirectly by introduction into a precursor of the cell, by way of deliberate genetic manipulation, such as by microinjection or by infection with a recombinant virus. The term genetic manipulation does not include classical cross-breeding, or in vitro fertilization (although it does include fertilization with sperm into which a transgene has been introduced), but rather is directed to the introduction of a recombinant DNA molecule. This molecule may be integrated within a chromosome, or it may be extrachromosomally replicating DNA. In the typical transgenic avian, the transgene causes cells to express a recombinant form of the subject polypeptide, e.g. either agonistic or antagonistic forms, or a form in which the gene has been disrupted. The terms "chimeric avian" or "mosaic avian" are used herein to refer to avians in which the recombinant gene is found, or in which the recombinant is expressed in some but not all cells of the avian. The term "tissue-specific chimeric avian" indicates that the recombinant gene is present and/or expressed in some tissues but not others.

The term "chromosomal positional effect (CPE)" as used herein refers to the variation in the degree of gene transcription as a function of the location of the transcribed locus within the cell genome. Random transgenesis may result in a transgene being inserted at different locations in the genome so that individual cells of a population of transgenic cells may each have at least one transgene, each at a different location and therefore each in a different genetic environment. Each cell, therefore, may express the transgene at a level specific for that particular cell and dependant upon the immediate genetic environment of the transgene. In a transgenic avian, as a consequence, different tissues may exhibit different levels of transgene expression.

The term "cytokine" as used herein refers to any secreted polypeptide that affects the functions of cells and is a molecule that modulates interactions between cells in the immune, inflammatory or hematopoietic response. A cytokine includes, but is not limited to, monokines and lymphokines regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lympnokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-alpha) and Tumor Necrosis Factor beta (TNF-beta).

The term "antibody" as used herein refers to polyclonal and monoclonal antibodies and fragments thereof, and immunologic binding equivalents thereof. The term "antibody" refers to a homogeneous molecular entity, or a mixture such as a polyclonal serum product made up of a plurality of different molecular entities, and may further comprise any modified or derivatised variant thereof that retains the ability to specifically bind an epitope. A monoclonal antibody is capable of selectively binding to a target antigen or epitope. Antibodies may include, but are not limited to polyclonal antibodies, monoclonal antibodies (mAbs), humanized or chimeric antibodies, camelized single chain antibodies (scFvs), Fab fragments, F(ab')$_2$ fragments, disulfide-linked Fvs (sdFv) fragments produced by a Fab expression library, anti-idiotypic (anti-Id) antibodies, intrabodies, synthetic antibodies, and epitope-binding fragments of any of the above.

The term "immunoglobulin polypeptide" as used herein refers to a polypeptide derived from a constituent polypeptide of an immunoglobulin. An "immunoglobulin polypeptide" may be, but is not limited to, an immunoglobulin (preferably an antibody) heavy or light chain and may include a variable region, a diversity region, joining region and a constant region or any combination, variant or truncated form thereof. The term "immunoglobulin polypeptides" further includes single-chain antibodies comprised of, but not limited to, an immunoglobulin heavy chain variable region, an immunoglobulin light chain variable region and optionally a peptide linker.

The term "male germ cells" as used herein refers to spermatozoa (i.e., male gametes) and developmental precursors thereof. In fetal development, primordial germ cells are thought to arise from the embryonic ectoderm, and are first seen in the epithelium of the endodermal yolk sac at the E8 stage. From there they migrate through the hindgut endoderm to the genital ridges. In the sexually mature male vertebrate animal, there are several types of cells that are precursors of spermatozoa, and which can be genetically modified, including the primitive spermatogonial stem cells, known as A0/As, which differentiate into type B spermatogonia. The latter further differentiate to form primary spermatocytes, and enter a prolonged meiotic prophase during which homologous chromosomes pair and recombine. Useful precursor cells at several morphological/developmental stages are also distinguishable: preleptotene spermatocytes, leptotene spermatocytes, zygotene spermatocytes, pachytene spermatocytes, secondary, spermatocytes, and the haploid spermatids. The latter undergo further morphological changes during spermatogenesis, including the reshaping of their nucleus, the formation of aerosome, and assembly of the tail. The final changes in the spermatozoon (i.e., male gamete) take place in the genital tract of the female, prior to fertilization.

The terms "ovum" and "oocyte" are used interchangeably herein. Although only one ovum matures at a time, an animal is born with a finite number of ova. In avian species, such as a chicken, ovulation, which is the shedding of an egg from the ovarian follicle, occurs when the brain's pituitary gland releases a luteinizing hormone. Mature follicles form a stalk or pedicle of connective tissue and smooth muscle. Immediately after ovulation the follicle becomes a thin-walled sac, the post-ovulatory follicle. The mature ovum erupts from its sac and starts its journey through the oviduct. Eventually, the ovum enters the infundibulum where fertilization occurs. Fertilization must take place within 15 minutes of ovulation, before the ovum becomes covered by albumen. During fertilization, sperm (avians have polyspermic fertilization) penetrate the blastodisc. When the sperm lodges within this germinal disk, an embryo begins to form as a "blastoderm" or "zygote."

The term "donor cell" is used herein to describe the source of the nuclear structure that is transplanted to the recipient enucleated cytoplast. All cells of normal karyotype, including embryonic, fetal, and adult somatic cells, preferably in a quiescent state, may be nuclear donors. The use of non-quiescent cells as nuclear donors has been described by Cibelli, et al., 1998, *Science* 280: 1256-8.

This application uses gene nomenclature accepted by the Cucurbit Genetics Cooperative as it appears in the *Cucurbit Genetics Cooperative Report*, 1995, 18:85; herein incorporated by reference in its entirety. Using this gene nomenclature, genes are symbolized by italicized Roman letters. If a mutant gene is recessive to the normal type, then the symbol and name of the mutant gene appear in italicized lower case letters.

3.2 Abbreviations

Abbreviations used in the present specification include the following: aa, amino acid(s); bp, base pair(s); CDNA, DNA complementary to RNA; nt, nucleotide(s); SSC, sodium chloride-sodium citrate; MAR, matrix attachment region; DMSO, dimethyl sulfoxide; TPLSM, two photon laser scanning microscopy; REMI, restriction enzyme mediated integration; mAb, monoclonal antibody, WEFs, whole embryo fibroblasts.

4. BRIEF DESCRIPTION OF THE FIGURES

FIGS. 1A-E illustrate the nucleotide sequence (SEQ ID NO: 6) comprising the chicken lysozyme gene expression control region (SEQ ID NO: 7), the nucleotide sequence encoding the chicken expression optimized human interferon α2b (IFNMAGMAX; SEQ ID NO: 5) and a SV40 polyadenylation signal sequence (SEQ ID NO: 8).

FIG. 2 illustrates the nucleotide sequence SEQ ID NO: 5 encoding the chicken expression optimized human interferon α2b (IFNMAGMAX).

FIGS. 3A-E illustrate the nucleotide sequence SEQ ID NO: 7 encoding the chicken lysozyme gene expression control region.

FIG. 4 illustrates the nucleotide sequence SEQ ID NO: 8 encoding the SV40 polyadenylation signal sequence.

FIGS. 5A-C illustrate the nucleotide sequence SEQ ID NO: 9 encoding the chicken lysozyme 3' domain.

FIGS. 6A-J illustrate the nucleotide sequence SEQ ID NO: 10 encoding the lysozyme gene expression control region (SEQ ID NO: 7) linked to the nucleic acid insert SEQ ID NO: 5 encoding the chicken expression-optimized human interferon α2b (IFNMAGMAX) and the chicken lysozyme 3' domain SEQ ID NO: 9.

FIG. 7 illustrates the results of the PCR analysis of chick blood DNA. Lanes 4 and 5 and lanes 11 and 12 contain PCR products from blood DNA collected from bird #8305.

Figure 11:
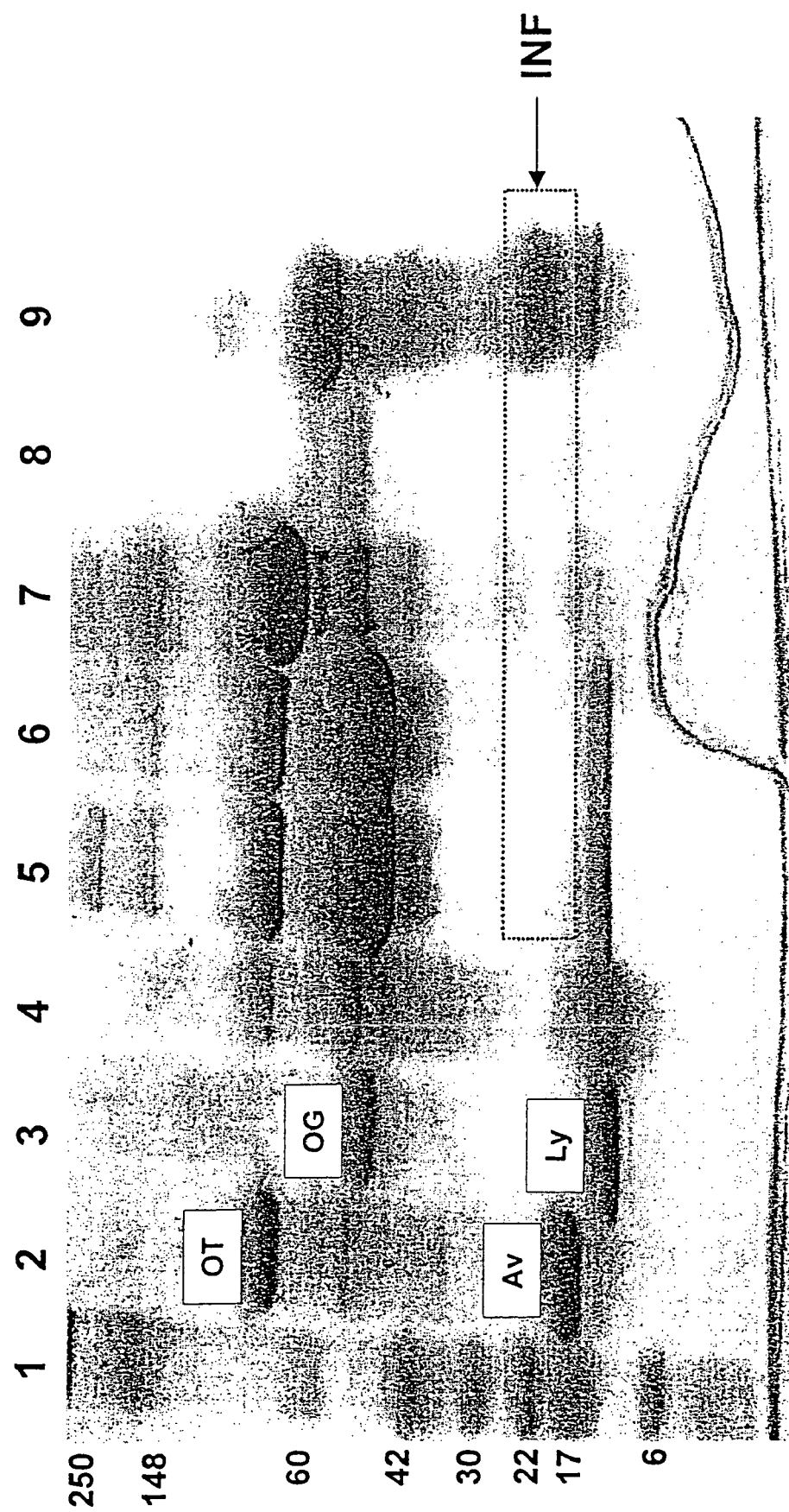

FIG. 11 illustrates the results of a Western blot analysis of the protein contents of fractions from the purification of human IFN-α2b purified from the pooled egg whites obtained from transgenic chicken AVI-029. 1, HIC pool (artifact); 2, HIC pool; 3, cation exchange Pool #2; 4, cation exchange Pool #1; 5, solubilized egg white; 6, pooled egg white; 7, ovoglobulins; 8, ovalbumin/lysozyme markers; 9, transferrin/avidin markers: 10, molecular weight markers.

Figure 12:
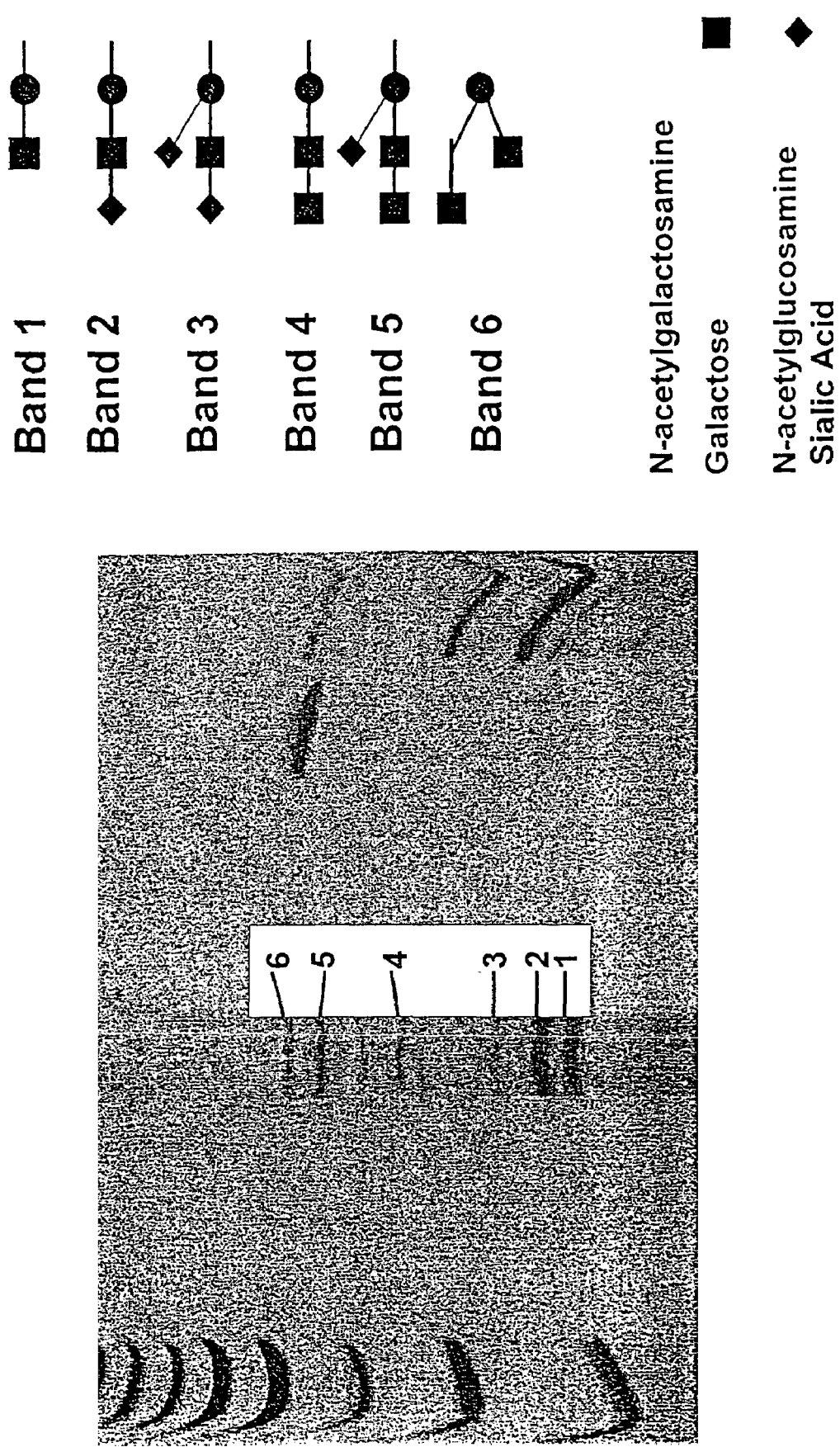

FIG. 12 illustrates the glycosylation analysis of IFN-α2b purified from the pooled egg whites obtained from transgenic chicken AVI-029.

Figure 13:
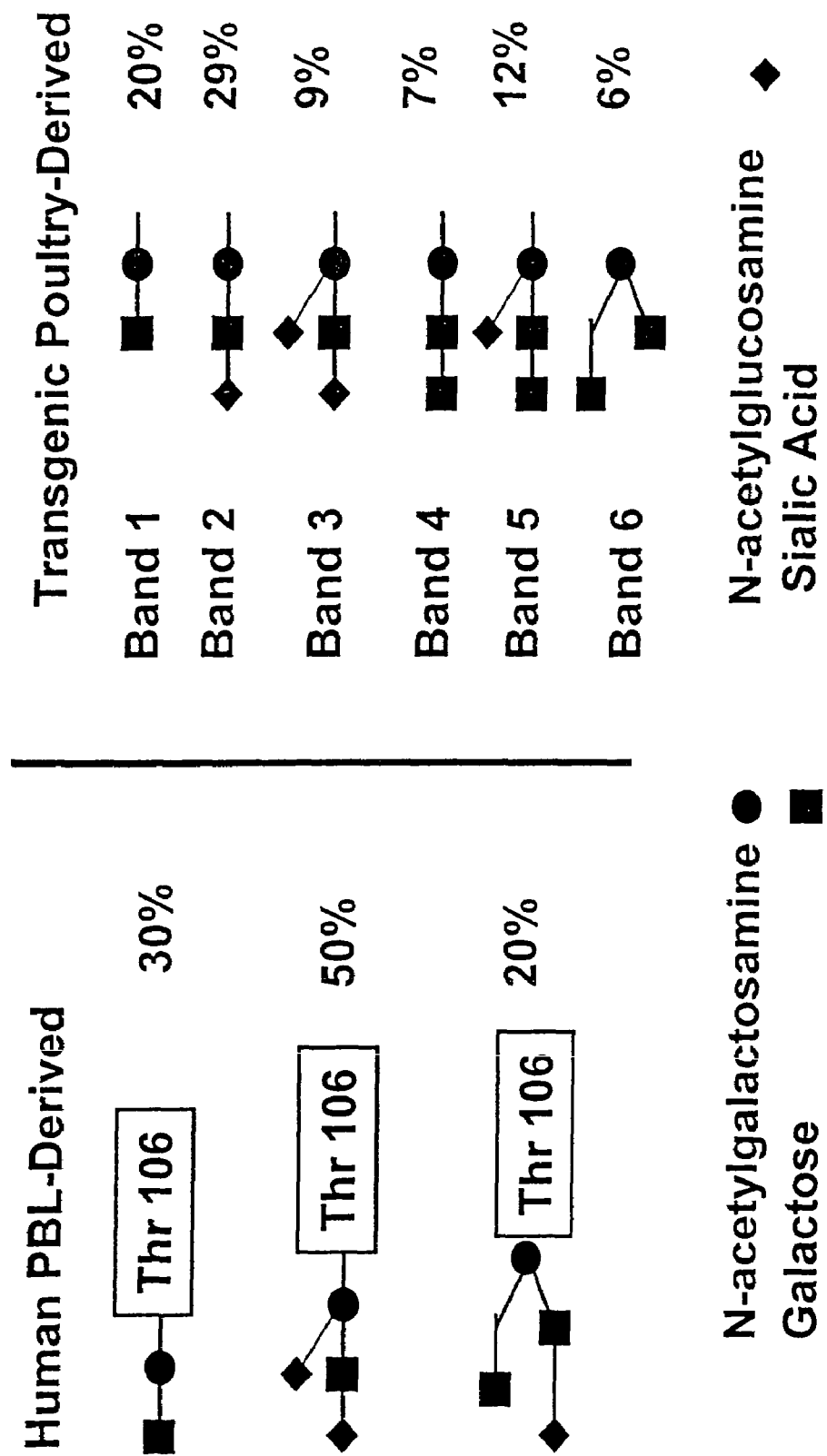

FIG. 13 compares the identities and relative proportions of glycosylated side-chains of human and transgenic chicken human IFN-α2b.

FIG. 14 illustrates the nucleic acid sequence SEQ ID NO: 11 of the combinatorial promoter MDOT.

FIGS. 15A-B illustrate the oligonucleotides and primers (SEQ ID NOS: 17-34) used in the formation of the chicken codon optimized human interferon α2b-encoding nucleic acid.

Figure 16:
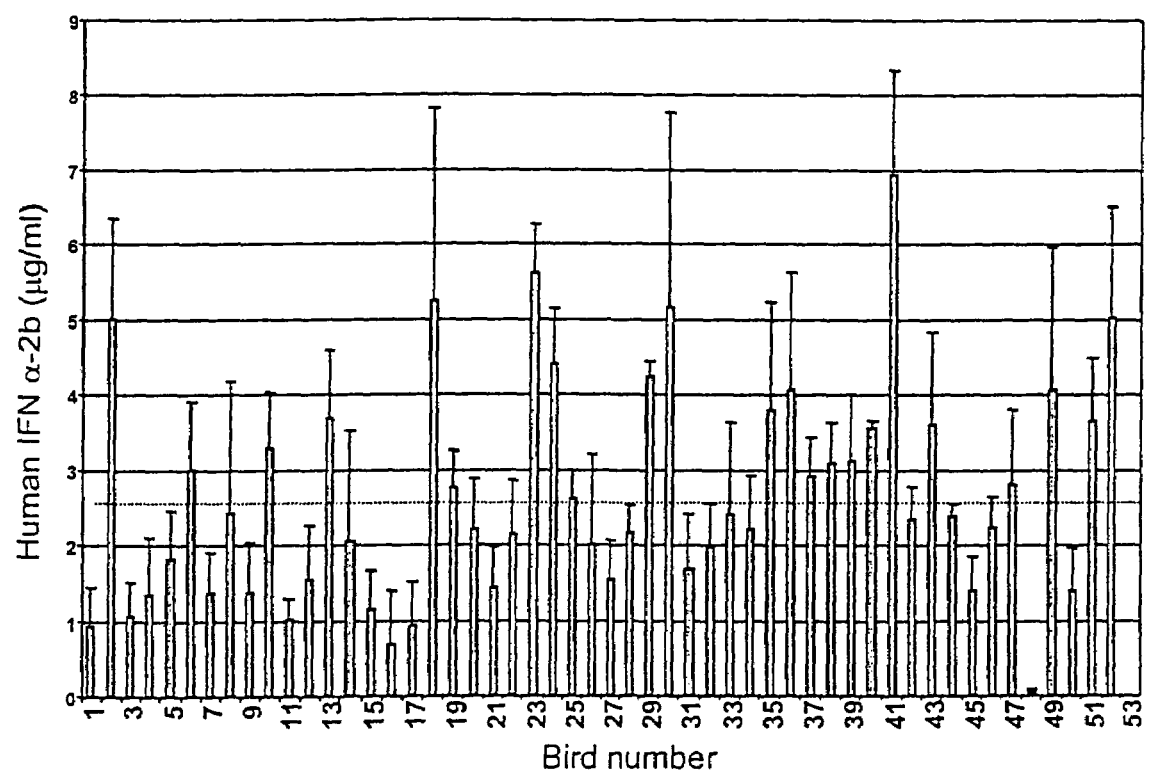

FIG. 16 illustrates the levels of expression of human α2b in eggs as determined by ELISA.

Figure 17:
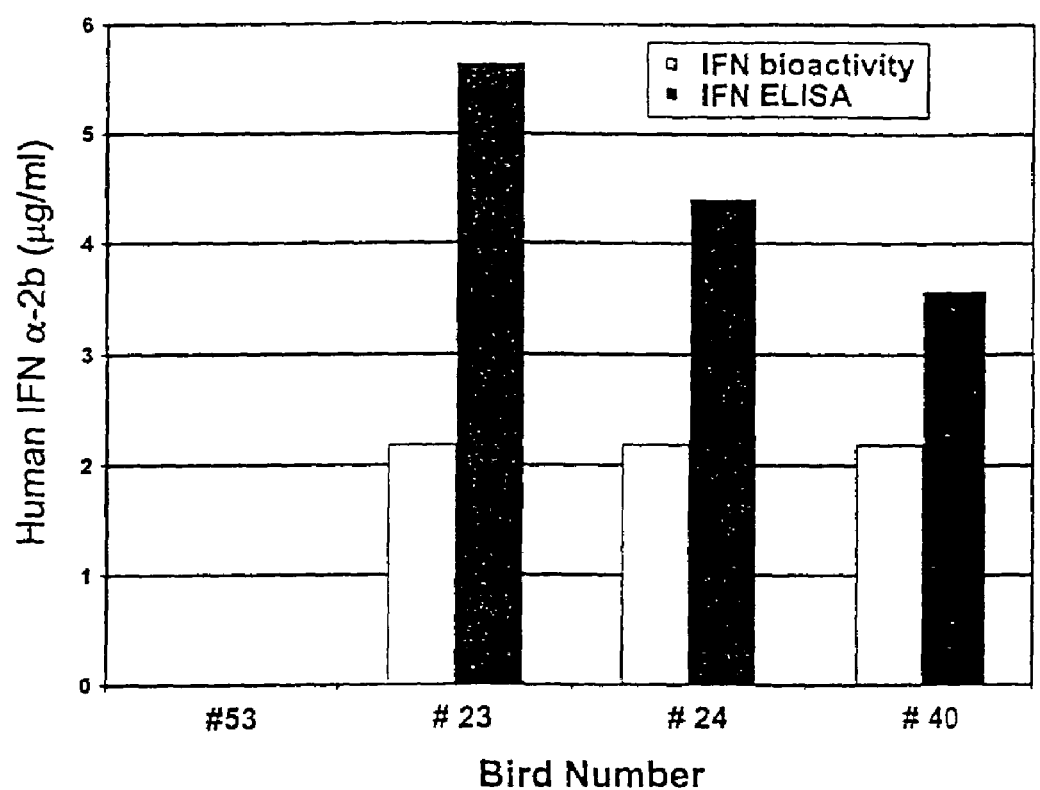

FIG. 17 illustrates the bioactivity versus the mass of human interferon α2b in $G_2$ hen egg whites.

Figure 18:
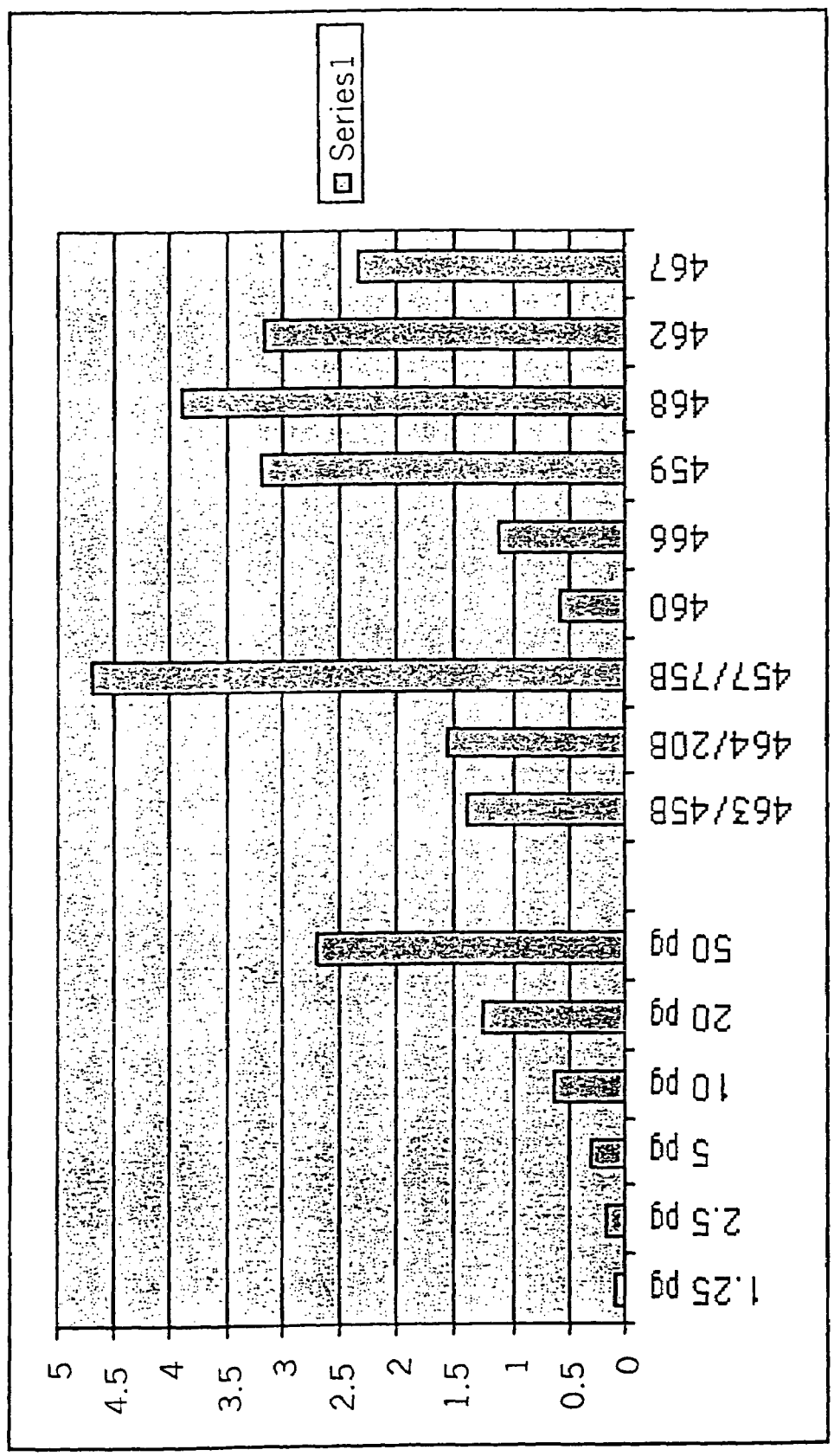

FIG. 18 illustrates interferon serum levels in chicks producing human interferon α2b.

Figure 19:
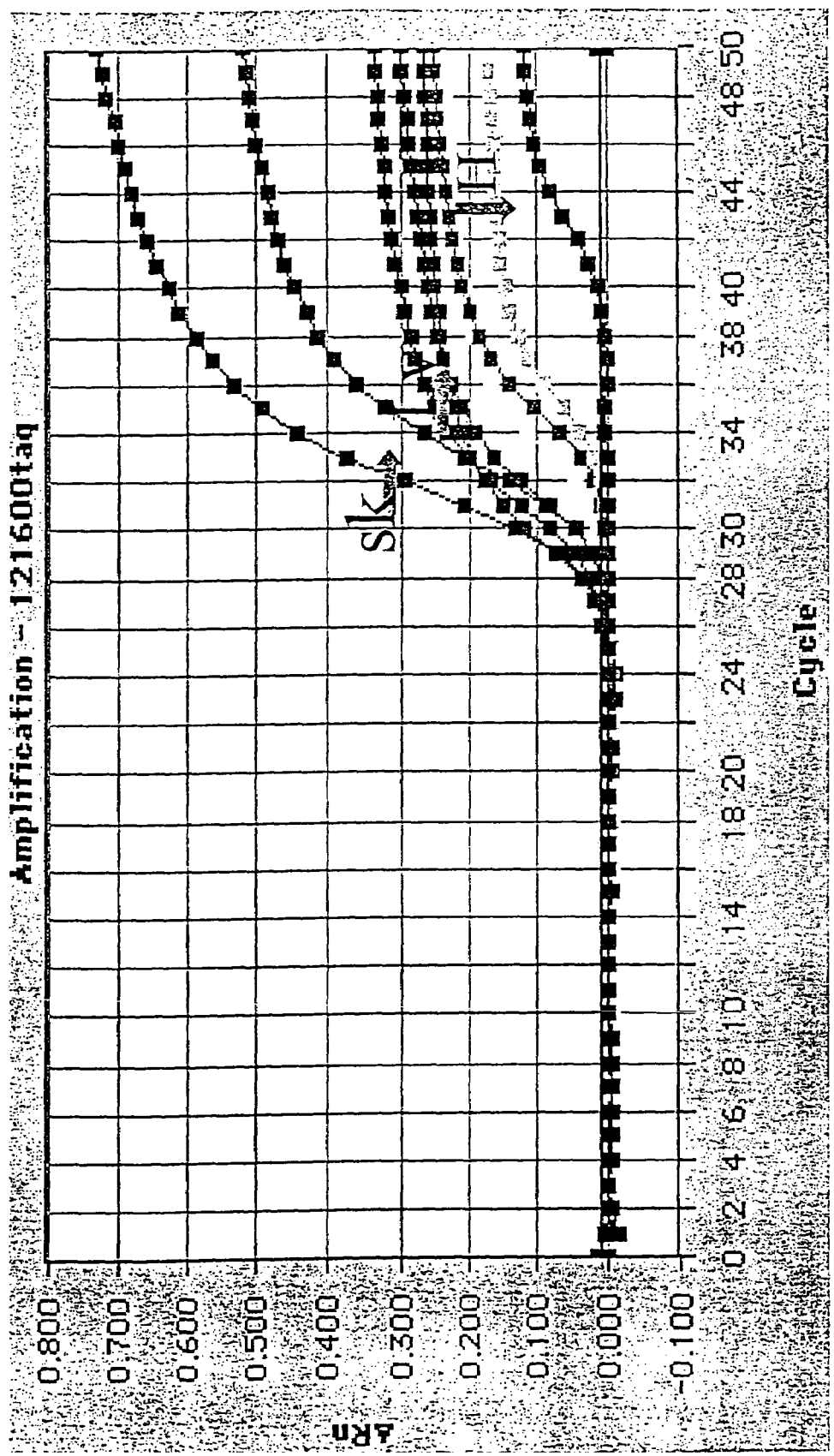

FIG. 19 illustrates the presence of a pLNHX-MDOT-IFN transgene in chicks.

Figure 20:
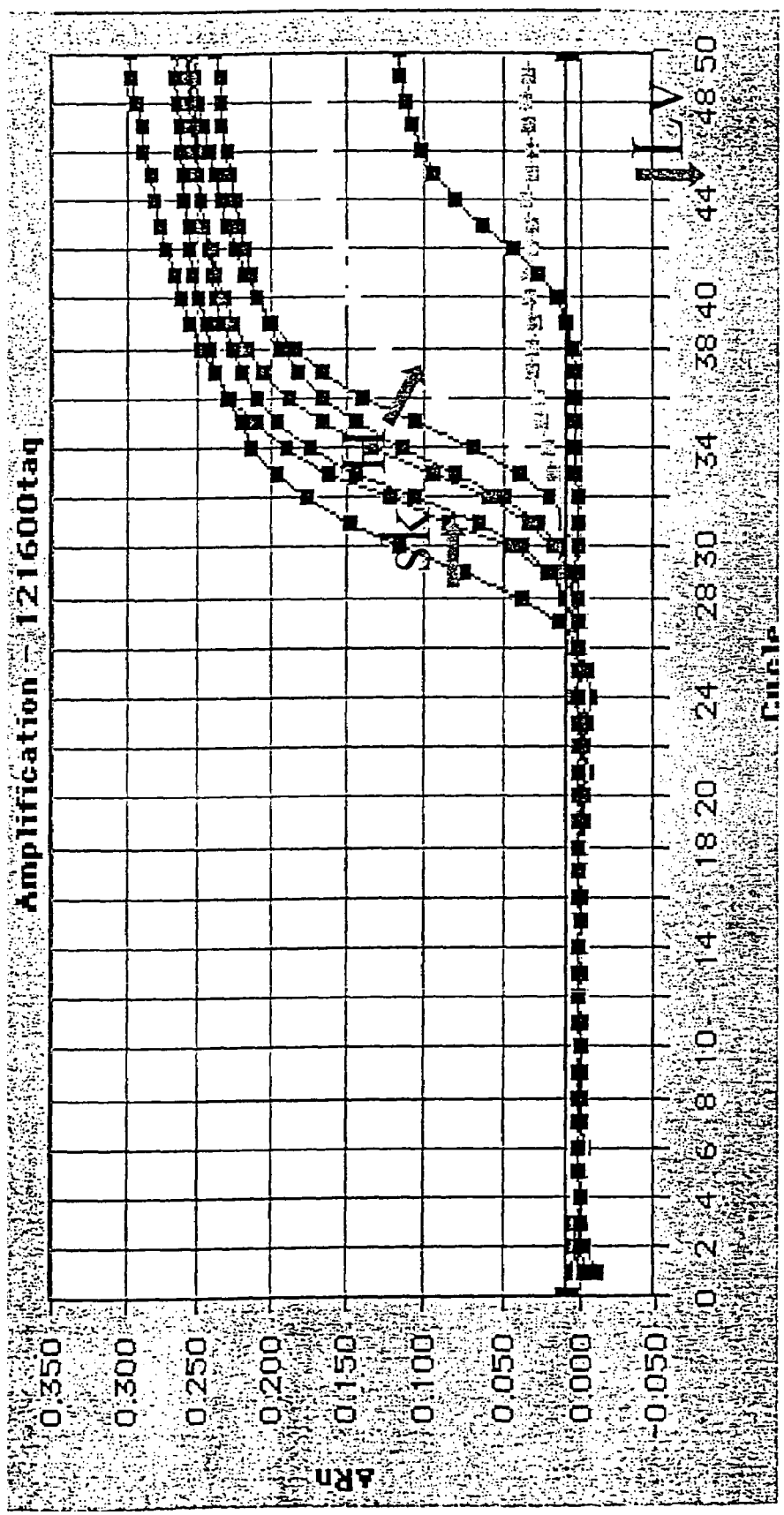

FIG. 20 illustrates the presence of a pLNHX-MDOT-IFN transgene in chicks.

Figure 21:
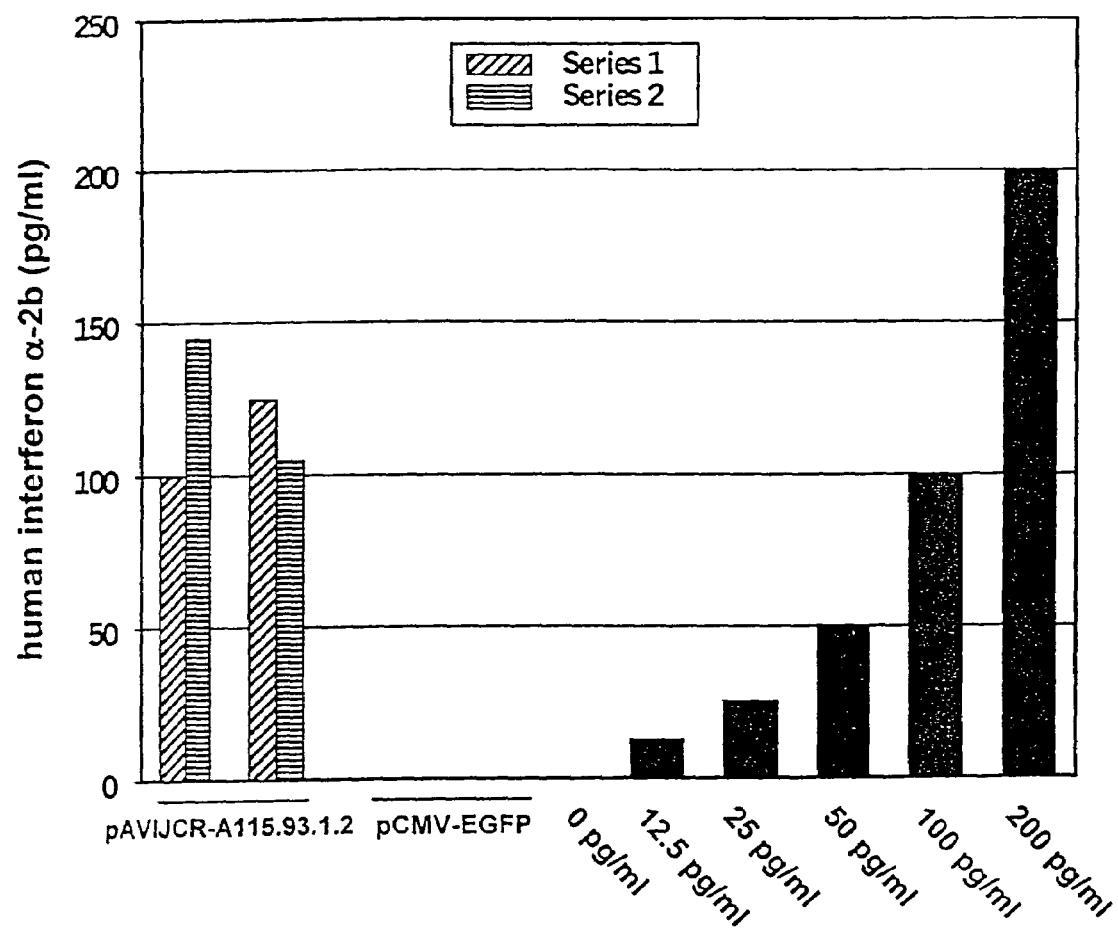

FIG. 21 illustrates the production of human interferon by quail oviduct cells transfected with pAVIJCR-A115.93.1.2.

FIG. 22 illustrates the primers (SEQ ID NOS: 38-41) used in the synthesis of the MDOT promoter.

Figure 23:
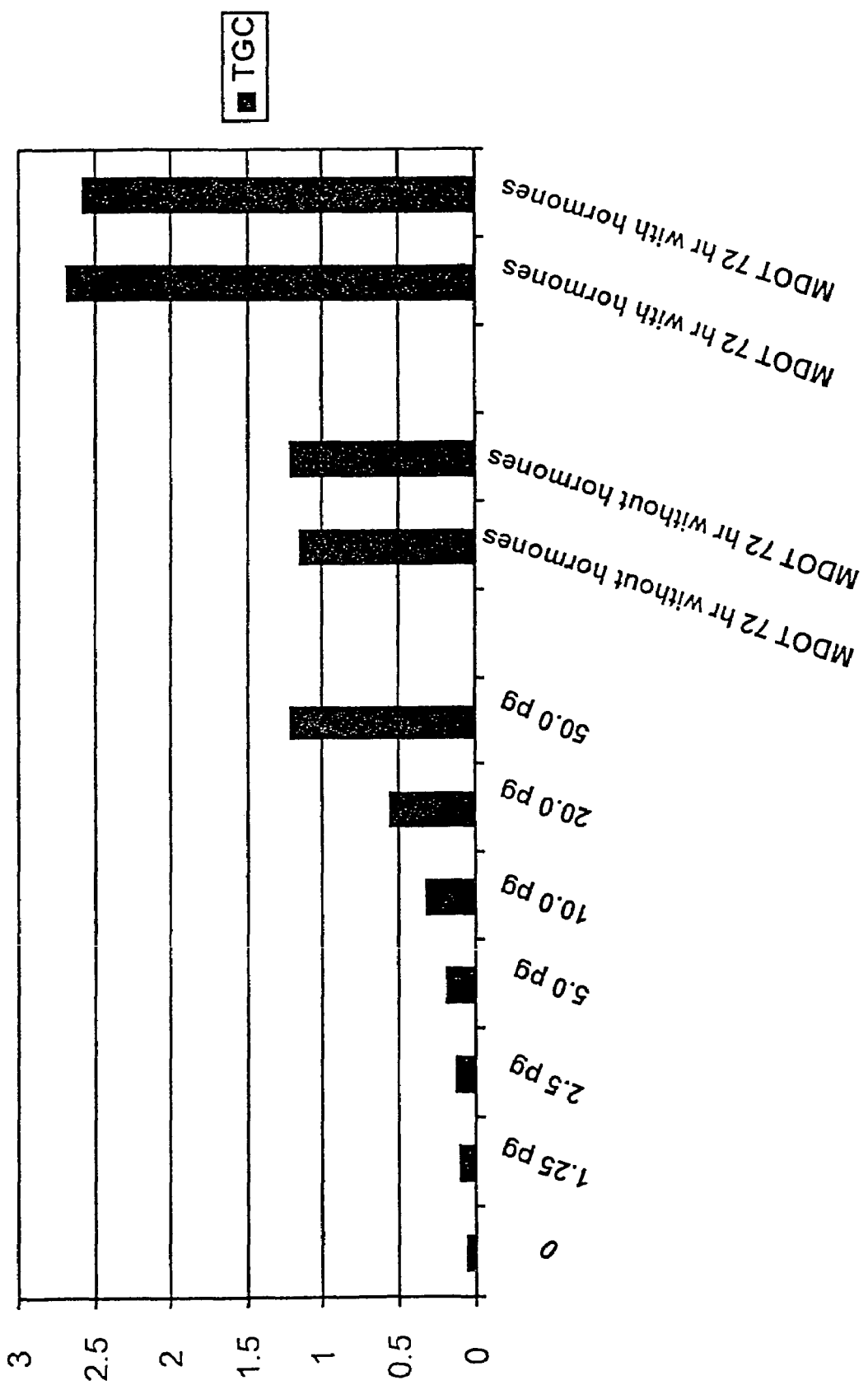

FIG. 23 illustrates the induction of human interferon α2b by hormonally treated transfected cells.

FIGS. 24A-V illustrate the nucleotide sequence (SEQ ID NO:42) of OMC24, a chicken BAC clone containing the entire ovoinhibitor and ovomucoid genes.

FIGS. 25A-B illustrate the nucleotide sequences of A) IRES-light chain cassette (SEQ ID NO:47) and B) IRES-heavy chain cassette (SEQ ID NO:48). The string of n's represents the location of the DNA encoding the light or heavy chain of the monoclonal antibody.

Figure 26:
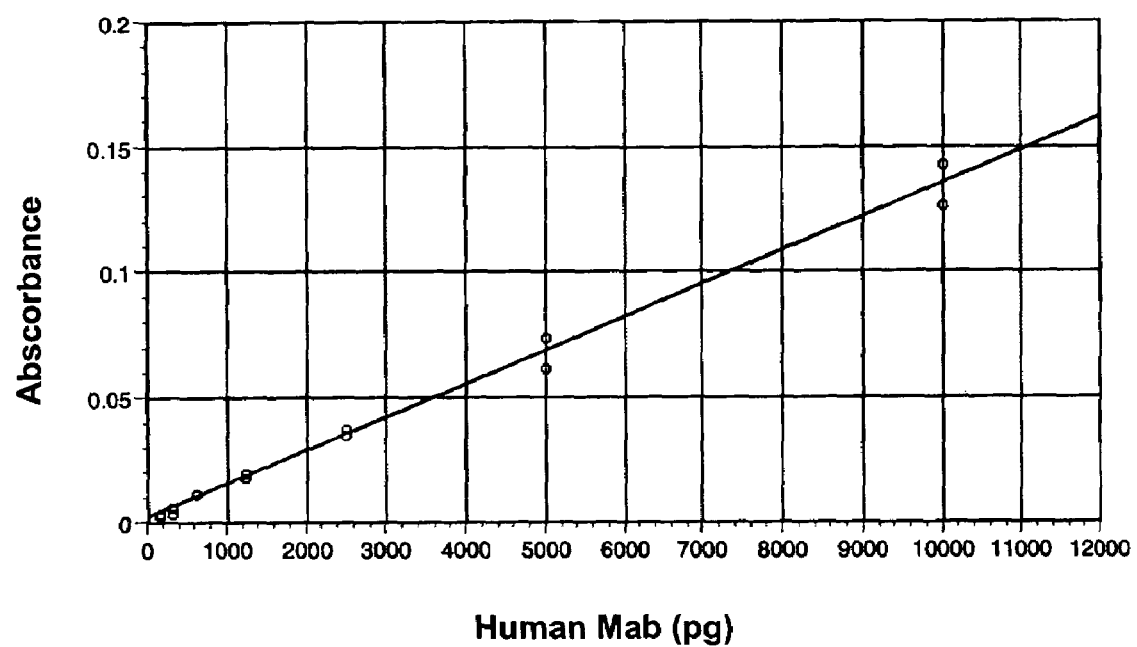

FIG. 26 illustrates the detection of transgenic avian derived hMab via sandwich ELISA.

Figure 27:
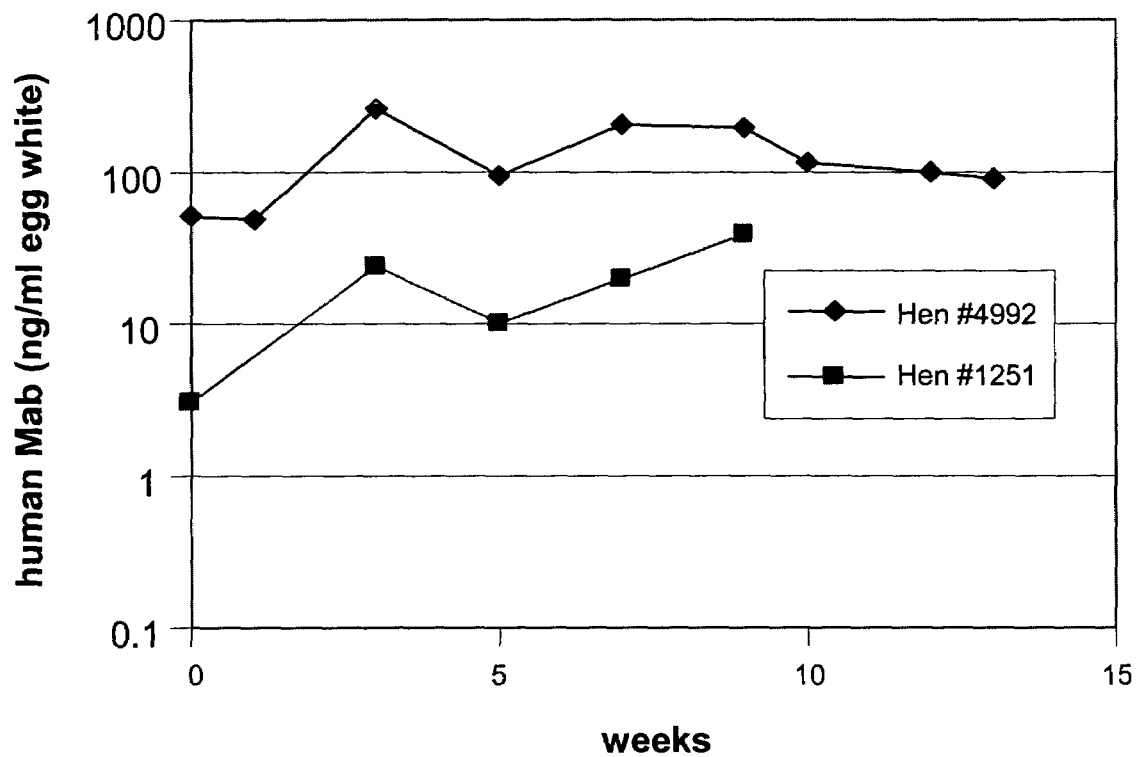

FIG. 27 illustrates the stability of hMab expression in transgenic hen. The amount of hMab in egg white material was quantitated via sandwich ELISA for the specific human Ig (H+L).

Figure 28:
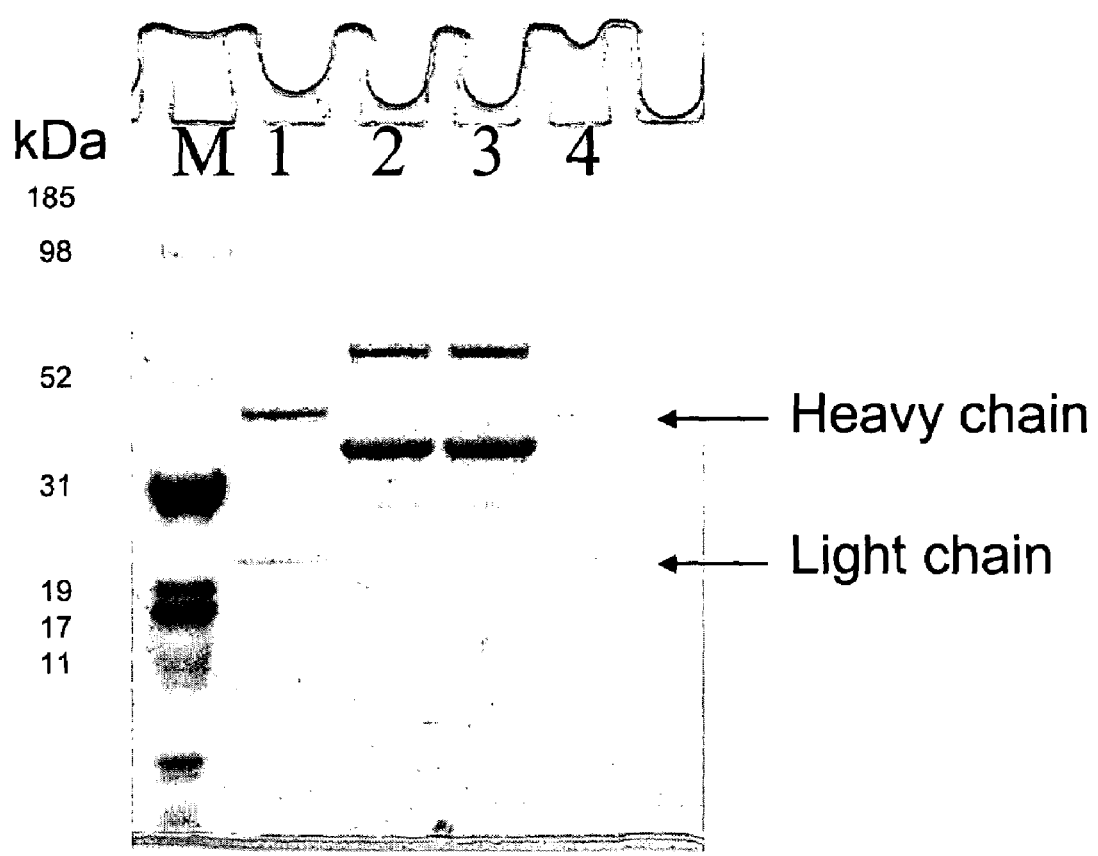

FIG. 28 illustrates SDS-PAGE analysis of partially purified hMab derived from a single transgenic hen. (M) Multi-mark standard, lane 1) 1 µg purified hMab (produced by mammalian cells), lane 2) 5 µg pre-column (transgenic avian egg white), lane 3) 5 µg column flow thru (transgenic avian egg white), lane 4) partially purified hMab (transgenic avian egg white).

Figure 29:
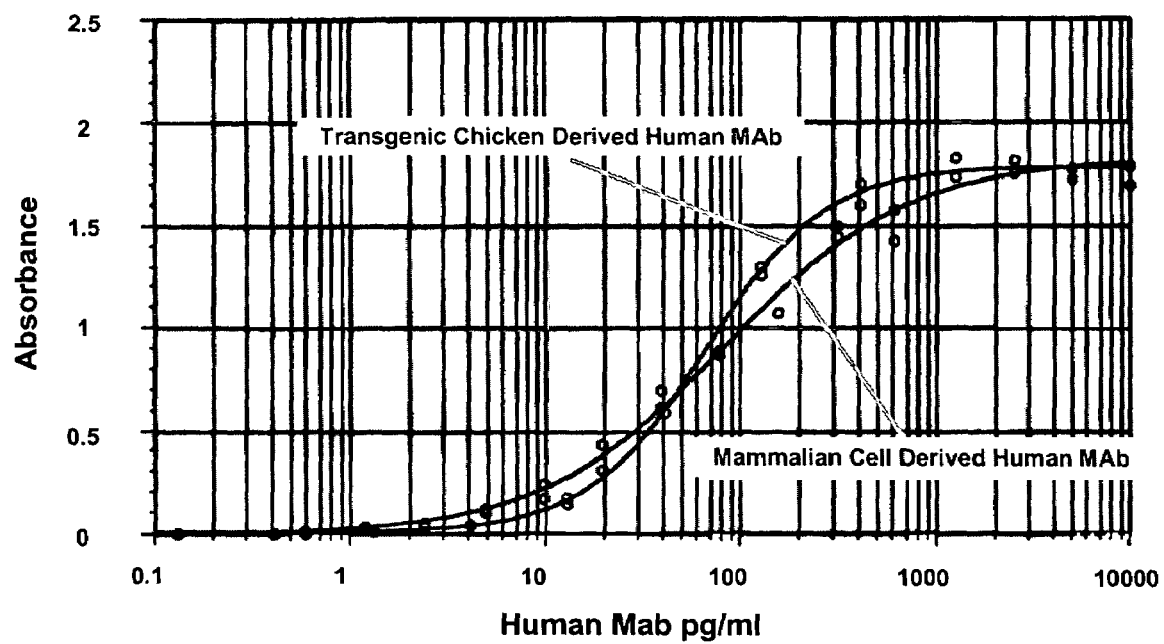

FIG. 29 illustrates the antigen binding ability of hMab derived from transgenic avian. The level of antigen binding per picogram of transgenic avian derived and mammalian cell derived hMab is graphed. Curves were generated by plotting absorbance vs. amount of hMab.

FIGS. 30A-F illustrate the ability of transgenic avian derived hMab to bind target antigen expressed on cell surface. Mammalian cells were transfected with either a Luciferase expression plasmid (A, C, and E) or an expression plasmid carrying cDNA of the hMab's target antigen (B, D, and F). Collected cells were treated with one of three primary antibodies: the antigen specific hMab produced by mammalian cells (A and B), transgenic hen (hen #4992) (C and D), or human antibody of the same isotype but with different antigen specificity (E and F). Cells that exhibited APC-associated fluorescence are delineated with a box within each graph.

5. DETAILED DESCRIPTION OF THE INVENTION

The present invention relates to methods of introducing nucleic acids into avian embryonic cells to produce a transgenic chicken, or other avian species, carrying the transgene in the genetic material in all or most of its tissue, including germ-line tissue. The methods and vectors of the present invention further generate transgenic avians that express heterologous genes in the serum of the avian and/or are deposited into an avian egg, preferably in the egg white. Vectors containing promoters that direct high level of expression of the heterologous protein in the avian, particularly in the magnum for deposition into the avian egg are provided. Additional regulatory elements, such as MAR's, IRES's, enhancers, polyadenlyation signals, etc., may be included in the vectors of the invention to improve expression and efficiency.

Using the methods of the invention, transgenic avians that express significant quantities of useful heterologous proteins, e.g., therapeutic and diagnostic proteins, including immunoglobulins, industrially useful proteins and other biologics etc. in the avian egg white are produced. The heterologous protein can then be readily purified from the avian egg. The methods of the invention provide improved efficiencies of transgenesis, transmission of the transgene and/or level of heterologous protein expression.

The transgenic avians of the invention are most preferably generated using cytoplasmic microinjection of nucleic acid into avian embryonic cells. Other methods contemplated by the invention include sperm-mediated transgenesis, nuclear transfer and injection or infection with a retroviral vector. Once the nucleic acid has been introduced into the embryo (or ovum which is then fertilized in vitro), the embryo is preferably returned to the avian using ovum transfer or, alternatively, is cultured ex vivo.

5.1 Methods of Transgenesis

5.1.1 Cytoplasmic Injection

The present invention provides methods of introducing nucleic acids containing a transgene, preferably, nucleic acid vectors of the invention as described in Section 5.2, infra, into an embryonic avian cell or an avian ovum by microinjection into the cell. In preferred embodiments, the nucleic acid is introduced by microinjection into the cytoplasm of the cell;

however, in other embodiments of the invention, the nucleic acid is introduced into a nucleus or pronucleus, or is deposited in the perinuclear space.

In the method of the present invention, fertilized ova, and preferably stage I embryos, are isolated from euthanized hens between forty-five minutes and four hours after oviposition of the previous egg. It is, however, contemplated that the methods of the present invention may be applied to recipient cells of other stages of embryonic development such as stage I-X, as described by Eyal-Giladi and Kochav (1976, *Dev. Biol.* 49:321-337). Alternatively, eggs may be isolated from hens whose oviducts have been fistulated as described by Gilbert and Woodgush, 1963, *J. of Reprod. and Fertility* 5: 451-453 and Pander et al., 1989, *Br. Poult. Sci.* 30: 953-7; incorporated herein in their entireties. Also, unfertilized eggs can be injected by in-vitro fertilization performed by any method known in the art, for example, but not limited to, the method of Tanaka et al., 1994, *J. Reprod. Fertility* 100:447-449 (the content of which is incorporated herein in its entirety).

In particular, microinjection into the germinal disk can be accomplished as described in Example 1, infra. Briefly, once the fertilized ovum or embryo has been obtained, the albumen capsule is optionally removed and the ovum placed in a dish with the germinal disk facing upwards. Remnants of the albumen capsule may be removed from over the germinal disk if necessary and/or desired. Phosphate buffered saline (PBS) or any other appropriate physiological solution may be added to the dish to prevent drying of the ovum.

Preferably, prior to microinjection, the surface of the embryo is visualized using a lateral imaging system described previously (International Patent Publication WO 02/064,727), this system allows precise imaging of the injection site and facilitates accurate needle placement and injection within the germinal disk of the recipient embryo.

In one embodiment, allowing the visualization of the embryo's pronuclear or nuclear structures, a dye such as MITO TRACKER® (300 nM, Molecular Probes catalog number M-7510), can be added to the cylinder. Other dyes, such as DAPI (4",6"-diamidino-2-phenylindole hydrochloride), HOECHST® 33342 (bis-benzimide), or Syto 59, can also be used in methods of the invention. Visualization generally is performed after approximately 20 minutes of incubation. Imaging using the MITOTRACKER® dye shows intense labeling of the region around the nucleus while the nucleus itself does not take up the dye. This allows localization of the embryo's nuclear structures for injection while not causing excessive damage to its structure since the content of the pronuclei are not labeled and therefore are not bleached during imaging. The nucleic acid solution (generally 1-100 nanoliters) is then injected into the cytoplasm or, alternatively, into the pronucleus or perinuclear space.

Any suitable microinjection assembly and methods for microinjecting and reimplanting avian eggs are contemplated as useful in the method of cytoplasmic injection of the present invention. A particularly suitable apparatus and method for use in the present invention is fully described in U.S. patent application Ser. No. 09/919,143 by Christmann, now abandoned, and PCT Publication WO 02/064727, incorporated herein by reference in their entireties. The microscope/micromanipulation unit may be an IM-16 microinjector and a MM-188NE micromanipulator, both from NIKON®/NAR-ISHIGE, adapted to an upright Nikon Eclipse E800 microscope adapted to operate under both transmitted and reflected light conditions. This unique configuration allows the loading of a DNA solution into a micropipette while observing the pipette with a dry or water immersion lenses under diascopic illumination or transmitted light. Pipette loading is followed by the prompt localization and positioning of the germinal disk under the microscope and subsequent guided injection of DNA solution into the germinal disk using dry or water-immersion lenses under fiber optic, as well as episcopic, illumination (through the objectives and onto the embryo surface).

In certain embodiments, the microinjected cell will also be subjected to microelectroporation. The application of electrical current, e.g., microelectroporation, enhances the uptake of exogenous DNA fragments by cultured cells and the uptake of nucleic acids in the cytoplasm of a cell into the nucleus. Enhancement of nuclear uptake of the heterologous DNA will promote earlier chromosomal integration of the exogenous DNA molecules, thus reducing the degree of genetic mosaicism observed in transgenic avian founders.

Accordingly, in specific embodiments, a sample of nucleic acid will be microinjected using the methods described immediately above, and then, delivered to a recipient cell nucleus by microelectroporation. In a system suitable for use in microelectroporating early stage avian cells, a cathode will be located within the lumen of the DNA delivery micropipette. Alternatively, the cathode electrode may be located on the exterior surface of the micropipette. For either option, the electrode is situated close or adjacent to the exit orifice of the pipette so that the electrode and the micropipette may be introduced into the recipient cell together. Alternatively, the micropipette will be introduced into the cytoplasm and used to guide a cathode to make electrical contact with the cytoplasm of the targeted cell.

In one arrangement of the electrodes of the microelectroporation system, the anode is located on the micropipette and, therefore, will enter the cell or cells with the micropipette and the cathode. In another arrangement, an anode is in electrical contact with the solution that surrounds the targeted recipient early stage avian cell. In yet another version, the anode is individually positioned within the cytoplasm, or the nucleus, of the recipient cell. The anode and cathode are electrically connected to an electrical pulse generator capable of delivering a timed electrical pulse to the electrodes. One suitable apparatus for generating a timed electrical pulse according to the present invention is a Kation Scientific Iontaphorsis pump BAB-500 or ECM 830 manufactured by BTX®. After microinjection of the nucleic acid, the recipient cell will be pulsed at least once with about 0.1 to about 20.0 microamps for about 0.1 to about 60 secs.

After injection and, optionally, microelectroporation, the embryo is allowed to proceed through the natural in vivo cycle of albumen deposition and hard-shell formation. In preferred embodiments, the embryo is surgically transferred into the infundibulum of a recipient hen, where it is allowed to move into the infundibulum and into the anterior magnum by gravity feed, such that the recipient hen produces a hard shell egg that is incubated to produce a transgenic chick. See, e.g., Olsen and Neher, 1948, *J. Exp. Zoo* 109:355-366, which is incorporated by reference in its entirety. The transgenic embryo is then laid as a hard-shell egg and may be incubated to hatch a trans-genic chick. In an alternate embodiment of the present invention, the injected embryo is transferred into the oviduct of a recipient hen, a soft-shell egg is collected between 12 and 24 hours after ovum transfer by injecting the hen with sufficient oxytocin to induce ovipositioning. The soft shell egg can subsequently be incubated, and a chick hatched, using an in-vitro culture system as, for example, that described by Perry in U.S. Pat. No. 5,011,780 (the contents of which is incorporated herein in its entirety). In either case, the hatched chick may be allowed to attain sexual maturity whereupon it can be used, for example, to breed new generations of heterozygous or homozygous transgenic progeny. Sexually mature female transgenic avians are particularly useful for the expression of a heterologous nucleic acid to yield a heterologous polypeptide in the white of an egg.

The hatched chick can then be tested for presence of the transgene and/or expression of the heterologous protein encoded by the transgene using methods well known in the art. In a particular embodiment, blood cells of the hatched chick are screened using methods disclosed in U.S. Pat. No. 6,423,488, issued Jul. 3, 2002, which is hereby incorporated by reference in its entirety.

5.1.2 Transgenesis of Blastodermal Cells

In alternative embodiments, a transgene can be introduced into avian embryonic blastodermal cells, to produce a transgenic chicken, or other avian species, that carries the transgene in the genetic material of its germ-line tissue. The methods and vectors of the present invention further generate transgenic avians capable of expressing heterologous genes in the serum of the avian and /or deposited in an avian egg. The blastodermal cells are typically stage VII-XII cells, or the equivalent thereof, and preferably are near stage X. The cells useful in the present invention include embryonic germ (EG) cells, embryonic stem (ES) cells & primordial germ cells (PGCs). The embryonic blastodermal cells may be isolated freshly, maintained in culture, or reside within an embryo.

A variety of vectors useful in carrying out the methods of the present invention are described herein, in Section 5.2 infra. These vectors may be used for stable introduction of an exogenous coding sequence into the genome of a bird. In alternative embodiments, the vectors may be used to produce exogenous proteins in specific tissues of an avian, and in the oviduct in particular. In still further embodiments, the vectors are used in methods to produce avian eggs which contain exogenous protein.

In some cases, introduction of a vector of the present invention into the embryonic blastodermal cells is performed with embryonic blastodermal cells that are either freshly isolated or in culture. The transgenic cells are then typically injected into the subgerminal cavity beneath a recipient blastoderm in an egg. In some cases, however, the vector is delivered directly to the cells of a blastodermal embryo.

In one embodiment of the invention, vectors used for transfecting blastodermal cells and generating random, stable integration into the avian genome contain a coding sequence and a magnum-specific promoter in operational and positional relationship to express the coding sequence in the tubular gland cell of the magnum of the avian oviduct. The magnum-specific promoter may optionally be a segment of the ovalbumin promoter region which is sufficiently large to direct expression of the coding sequence in the tubular gland cells. Other exemplary promoters include the promoter regions of the ovalbumin, lysozyme, conalbumin, ovomucoid, or ovomucin genes. Alternatively, the promoter may be a promoter that is largely, but not entirely, specific to the magnum, such as the lysozyme promoter. Other suitable promoters may be artificial constructs such as a combination of nucleic acid regions derived from at least two avian gene promoters. One such embodiment of the present invention is the MDOT construct comprising regions derived from the chicken ovomucin and ovotransferrin promoters In an alternative embodiment of the invention, transgenes containing constitutive promoters are used, but the transgenes are engineered so that expression of the transgene effectively becomes magnum-specific. Thus, a method for producing an exogenous protein in an avian oviduct provided by the present invention involves generating a transgenic avian that bears two transgenes in its tubular gland cells. One transgene comprises a first coding sequence operably linked to a constitutive promoter. The second transgene comprises a second coding sequence that is operably linked to a magnum-specific promoter, where expression of the first coding sequence is either directly or indirectly dependent upon the cellular presence of the protein expressed by the second coding sequence.

Optionally, site-specific recombination systems, such as the Cre-loxP or FLP-FRT systems, are utilized to implement the magnum-specific activation of an engineered constitutive promoter. In one embodiment, the first transgene contains an FRT-bounded blocking sequence which blocks expression of the first coding sequence in the absence of FTP, and the second coding sequence encodes FTP. In another embodiment, the first transgene contains a loxP-bounded blocking sequence which blocks expression of the first coding sequence in the absence of the Cre enzyme, and the second coding sequence encodes Cre. The loxP-bounded blocking sequence may be positioned in the 5' untranslated region of the first coding sequence and the loxP-bounded sequence may optionally contain an open reading frame.

For instance, in one embodiment of the invention, magnum-specific expression is conferred on a constitutive transgene, by linking a cytomegalovirus (CMV) promoter to the coding sequence of the protein to be secreted (CDS). The 5' untranslated region (UTR) of the coding sequence contains a loxP-bounded blocking sequence. The loxP-bounded blocking sequence contains two loxP sites, between which is a start codon (ATG) followed by a stop codon, creating a short, nonsense open reading frame (ORF). Note that the loxP sequence contains two start codons in the same orientation. Therefore, to prevent them from interfering with translation of the coding sequence after loxP excision, the loxP sites must be orientated such that the ATGs are in the opposite strand.

In the absence of Cre enzyme, the cytomegalovirus promoter drives expression of a small open reading frame (ORF). Ribosomes will initiate at the first ATG, the start codon of the ORF, then terminate without being able to reinitiate translation at the start codon of the coding sequence. To be certain that the coding sequence is not translated, the first ATG is out of frame with the coding sequence's ATG. If the Cre enzyme is expressed in cells containing the CMV-cDNA transgene, the Cre enzyme will recombine the loxP sites, excising the intervening ORF. Translation will begin at the start codon of the coding sequence, resulting in synthesis of the desired protein.

To make this system tissue specific, the Cre enzyme is expressed under the control of a tissue-specific promoter, such as the magnum-specific ovalbumin promoter, in the same cell as the CMV-loxP-coding sequence transgene. Although a truncated ovalbumin promoter may be fairly weak, it is still tissue-specific and will express sufficient amounts of the Cre enzyme to induce efficient excision of the interfering ORF. In fact, low levels of recombinase should allow higher expression of the recombinant protein since it does not compete against coding sequence transcripts for translation machinery.

Alternate methods of blocking translation of the coding sequence include inserting a transcription termination signal and/or a splicing signal between the loxP sites. These can be inserted along with the blocking ORF or alone. In another embodiment of the invention, a stop codon can be inserted between the loxP sites in the signal peptide of the coding sequence. Before recombinase is expressed, the peptide terminates before the coding sequence. After recombinase is expressed (under the direction of a tissue specific promoter), the stop codon is excised, allowing translation of the coding sequence. The loxP site and coding sequence are juxtaposed such that they are in frame and the loxP stop codons are out of frame. Since signal peptides are able to accept additional sequence (Brown et al., *Mol. Gen. Genet.* 197:351-7 (1984)), insertion of loxP or other recombinase target sequences (i.e. FRT) is unlikely to interfere with secretion of the desired coding sequence. In one expression vector, the loxP site is present in the signal peptide such that the amino acids encoded by loxP are not present in the mature, secreted protein. Before Cre enzyme is expressed, translation terminates at the stop codon, preventing expression of β-lactamase. After recombinase is expressed (only in magnum cells), the loxP sites recombine and excise the first stop codon. Therefore, β-lactamase is expressed selectively only in magnum cells.

In the aforementioned embodiments, the blocking ORF can be any peptide that is not harmful to chickens. The blocking ORF can also be a gene that is useful for production of the ALV-transduction particles and/or transgenic birds. In one embodiment, the blocking ORF is a marker gene.

For instance, the blocking ORF could be the neomycin resistance gene, which is required for production of transduction particles. Once the transgene is integrated into the chicken genome, the neomycin resistance gene is not required and can be excised.

Alternatively, β-lactamase can be used as the blocking ORF as it is an useful marker for production of transgenic birds. (For specific examples of the use of β-lactamase as a marker in transgenic birds, see Example 13, below.) As an example, the blocking ORF is replaced by β-lactamase and the downstream coding sequence now encodes a secreted biopharmaceutical. β-Lactamase will be expressed in blood and other tissues; it will not be expressed in the magnum after magnum-specific expression of Cre and recombination-mediated excision of β-lactamase, allowing expression of the desired protein.

The Cre and loxP transgenes could be inserted into the chicken genome via mediated transgenesis either simultaneously or separately. Any method of transgenesis that results in stable integration into the chicken genome is suitable including, but not limited to, viral integration and sperm-mediated integration. Both the ovalbumin promoter-recombinase and CMV-loxP-CDS transgenes could be placed simultaneously into chickens. However, the efficiencies of transgenesis are low and therefore the efficiency of getting both transgenes into the chicken genome simultaneously is low. In an alternative and preferred method, one flock is produced that carries the magnum-specific promoter/recombinase transgene and a second is produced that carries the CMV-loxP-CDS transgene. The flocks would then be crossed to each other. Hens resulting from this outbreeding will express the coding sequence and only in their magnum.

As mentioned above, the vectors produced according to the methods of the invention may optionally be provided with a 3' UTR containing a polyadenylation site to confer stability to the RNA produced. In a preferred embodiment, the 3' UTR may be that of the exogenous gene, or selected from the group consisting of the ovalbumin, lysozyme, or SV40 late region. However, the ovalbumin 3' UTR is not suitable in a PMGI vector that is to be inserted into the endogenous ovalbumin gene because the addition of ovalbumin sequences to the PMGI vector will interfere with proper targeting.

5.1.3 Viral Host Cell Transformation

In another embodiment, a method of introducing a nucleic acid comprising a nucleic acid sequence encoding one of the subject polypeptides and the associated gene expression control regions in a cell is using of a viral vector containing nucleic acid, e.g. a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors are generally understood to be the recombinant gene delivery system of choice for the transfer of heterologous genes in vivo. These vectors provide efficient delivery of genes into cells, and the transferred nucleic acids are stably integrated into the chromosomal DNA of the host. Recombinant retrovirus can be constructed wherein the retroviral coding sequences (gag, pol, env) have been replaced by nucleic acid encoding a polypeptide, thereby rendering the retrovirus replication defective. Protocols for producing recombinant retroviruses and for infecting cells in vitro or in vivo with such viruses can be found in Current Protocols in Molecular Biology, Ausubel et al., (1989) (eds.) Greene Publishing Associates, Sections 9.10-9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include psiCrip, psiCre, psi2 and psiAm.

Furthermore, it is possible to limit the infection spectrum of retroviruses and consequently of retroviral-based vectors, by modifying the viral packaging proteins on the surface of the viral particle (see, for example PCT publications WO 93/25234, WO 94/06920, and WO 94/11524). For instance, strategies for the modification of the infection spectrum of retroviral vectors include coupling antibodies specific for cell surface antigens to the viral env protein (Roux et al., 1989, *Proc. Natl. Acad. Sci.* 86: 9079-9083; Julan et al., *J. Gen. Virol.* 73: 3251-3255 (1992); and Goud et al., 1993, *Virology* 163: 251-254); or coupling cell surface ligands to the viral env proteins (Neda et al., 1991, *J. Biol. Chem.* 266, 14143-14146), and which are incorporated herein by reference in their entireties. Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector into an amphotropic vector. Moreover, use of retroviral gene delivery can be further enhanced by the use of tissue- or cell-specific transcriptional regulatory sequences that control expression of the nucleic acid encoding an immunoglobulin polypeptide of the retroviral vector.

One retrovirus for randomly introducing a transgene into the avian genome is the replication-deficient ALV retrovirus. To produce an appropriate ALV retroviral vector, a pNLB vector is modified by inserting a region of the ovalbumin promoter and one or more exogenous genes between the 5' and 3' long terminal repeats (LTRs) of the retrovirus genome. Any coding sequence placed downstream of the ovalbumin promoter will be expressed at high levels and only in the tubular gland cells of the oviduct magnum because the ovalbumin promoter drives the high level of expression of the ovalbumin protein and is only active in the oviduct tubular gland cells. While a 7.4 kb ovalbumin promoter has been found to produce the most active construct when assayed in cultured oviduct tubular gland cells, the ovalbumin promoter must be shortened for use in the retroviral vector. In a preferred embodiment, the retroviral vector comprises a 1.4 kb segment of the ovalbumin promoter; a 0.88 kb segment would also suffice.

Any of the vectors of the present invention may also optionally include a coding sequence encoding a signal peptide that will direct secretion of the protein expressed by the vector's coding sequence from the tubular gland cells of the oviduct. This aspect of the invention effectively broadens the spectrum of exogenous proteins that may be deposited in avian eggs using the methods of the invention. Where an exogenous protein would not otherwise be secreted, the vector bearing the coding sequence is modified to comprise a DNA sequence comprising about 60 bp encoding a signal peptide from the lysozyme gene. The DNA sequence encoding the signal peptide is inserted in the vector such that it is located at the N-terminus of the protein encoded by the cDNA.

Construction of one vector is reported in Example 10, below. β-lactamase may be expressed from the CMV promoter and utilizes a poly adenylation signal (pA) in the 3' long terminal repeat (LTR). β-Lactamase has a natural signal peptide; thus, it is found in blood and in egg white.

Avian embryos have been successfully transduced with pNLB-CMV-BL transduction particles (see Examples 11 and 12, below). The egg whites of eggs from the resulting stably transduced hens were found to contain up to 20 mg of secreted, active β-lactamase per egg (see Example 13, below).

Another viral gene delivery system useful in the present invention utilizes adenovirus-derived vectors. The genome of an adenovirus can be manipulated such that it encodes a gene product of interest, but is inactivated in terms of its ability to replicate in a normal lytic viral life cycle (see, for example, Berkner et al., 1988, BioTechniques 6:616; Rosenfeld et al., 1991, Science 252:431-434; and Rosenfeld et al., 1992, Cell 68:143-155; incorporated herein by reference in their entireties). Suitable adenoviral vectors derived from the adenovirus strain Ad type 5 dl324 or other strains of adenovirus (e.g., Ad2, Ad3, Ad7 etc.) are well known to those skilled in the art. The virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Most replication-defective adenoviral vectors currently in use and therefore favored by the present invention are deleted for all or parts of the viral E1 and E3 genes but retain as much as 80% of the adenoviral genetic material (see, for example, Jones et al., 1979, Cell 16: 683; Berkner et al., supra; and Graham et al., in Methods in Molecular Biology, E. J. Murray, (1991) Ed. (Humana, Clifton, N.J.) vol. 7. pp. 109-127; all of which are incorporated herein by reference in their entireties). Expression of an inserted nucleic acid encoding a polypeptide such as IFNMAGMAX, an immuno globulin, EPO, GM-CSF, can be under control of, for example, the lysozyme promoter, the ovalbumin promoter, artificial promoter construct sequences and the like.

Yet another viral vector system useful for delivery of, for example, the subject nucleic acid encoding an immunoglobulin polypeptide, is the adeno-associated virus (AAV). Vectors containing as little as 300 base pairs of AAV can be packaged and can integrate. Space for heterologous DNA is limited to about 4.5 kb. An AAV vector such as that described in Tratschin et al., 1985, Mol. Cell. Biol. 5, 3251-3260, can be used to introduce DNA into cells. A variety of nucleic acids have been introduced into different cell types using AAV vectors (see, for example, Hermonat et al., 1984, Proc. Natl. Acad. Sci. 81: 6466-6470; Tratschin et al., 1985, Mol. Cell. Biol. 4:2072-2081; Wondisford et al., 1988, Mol. Endocrinol. 2: 32-39; Tratschin et al., 1984, J. Virol. 51: 611-619; and Flotte et al., 1993, J. Biol. Chem. 268: 3781-3790, incorporated herein by reference in their entireties).

Other viral vector systems that may have application in the methods according to the present invention have been derived from, but are not limited to, herpes virus, vaccinia virus, avian leucosis virus and several RNA viruses.

5.1.4 Generation of Transgenic Avian Zygotes by Nuclear Transfer and TPLSM

In another embodiment, transgenes may be introduced into the ovum of an animal, according to the present invention, by nuclear transfer via two-photon visualization and ablation, wherein the nuclear donor contains a desired heterologous DNA sequence in its genome. One of ordinary skill in the art will be able to readily adapt conventional methods to insert the desired transgene into the genome of the nuclear donor prior to injection of the nuclear donor into the recipient cytoplast, or prior to fusion of the nuclear donor cell with the recipient cell. For example, a vector that contains one or more transgene(s) encoding at least one polypeptide chain of an antibody, may be delivered into the nuclear donor cell through the use of a delivery vehicle. The transgene is then transferred along with the nuclear donor into the recipient ovum. Following zygote reconstruction, the ovum is transferred into the reproductive tract of a recipient hen. In one embodiment of the present invention, the ovum is transferred into the infundibulum of the recipient hen. After reconstruction, the embryo containing the transgene develops inside the recipient hen and travels through the oviduct thereof where it is encapsulated by natural egg white proteins and a natural egg shell. The egg is laid and can be incubated and hatched to produce a transgenic chick. The resulting transgenic chick will carry one or more desired transgene(s) in its germ line. Following maturation, the transgenic avian may lay eggs that contain one or more desired heterologous protein(s) that can be easily harvested.

In another embodiment of the present invention, a nuclear donor cell is transfected with a vector construct that contains a transgene encoding at least one polypeptide chain. Methods for transfection of somatic cell nuclei are well known in the art and include, by way of example, the use of retroviral vectors, retrotransposons, adenoviruses, adeno-associated viruses, naked DNA, lipid-mediated transfection, electroporation and direct injection into the nucleus. Such techniques, particularly as applied to avians, are disclosed in Bosselman (U.S. Pat. No. 5,162,215), Etches (PCT Publication No. WO 99/10505), Hodgson (U.S. Pat. No. 6,027,722), Hughes (U.S. Pat. No. 4,997,763), Ivarie (PCT Publication No. WO 99/19472), MacArthur (PCT Publication No. WO 97/47739), Perry (U.S. Pat. No. 5,011,780), Petitte (U.S. Pat. Nos. 5,340, 740 and 5,656,749), and Simkiss (PCT Publication No. WO 90/11355), the disclosures of which are incorporated by reference herein in their entireties.

Nuclear transfer allows the cloning of animal species, wherein individual steps are common to the procedures of embryonic, fetal and adult cell cloning. These steps include, but are not limited to, preparation of a cytoplast, donor cell nucleus (nuclear donor) isolation and transfer to the cytoplast to produce a reconstructed embryo, optional reconstructed embryo culture, and embryo transfer to a synchronized host animal.

The present invention may use this approach to nuclear transfer in animals by employing two-photon visualization. In embodiments of the invention, the recipient animal is an avian including, but not limited to, chickens, ducks, turkeys, quails, pheasants and ratites. In this method, a fertilized or unfertilized egg is removed from an animal and manipulated in vitro, wherein the genetic material of the egg is visualized and removed and the ablated nucleus replaced with a donor nucleus. Optionally, the donor nucleus may be genetically modified with, for example, a transgene encoding an immunoglobulin polypeptide. Two-photon laser scanning microscopy (TPLSM) may be used to visualize the nuclear structures. Following visualization, the nucleus in the recipient cell, such as a fertilized or unfertilized egg, is removed or ablated, optionally using TPLSM.

TPLSM is based on two-photon excited fluorescence in which two photons collide simultaneously with a fluorescent molecule. Their combined energy is absorbed by the fluorophore, inducing fluorescent emission that is detected by a photomultiplier tube and converted into a digital image. See Squirrell et al., 1999, Nature Biotechnol. 17:763-7 and Piston et al., 1999, Trends Cell Biol. 9:66-9, incorporated herein by reference in their entireties. TPLSM generates images of living, optically dense structures for prolonged periods of time, while not affecting their viability. TPLSM utilizes biologically innocuous pulsed near-infrared light, usually at a wavelength of about 700 nm to about 1000 nm, which is able to penetrate deep into light-scattering specimens. TPLSM may employ different lasers, such as a mode-locked laser, where the wavelength is fixed, or a tunable laser that can be tuned to wavelengths between about 700 nm and about 1000 nm, depending upon the range of emission of the dye used. For DAPI and Hoescht 33342 dyes, 720-770 nm is preferred. New fluorophores are being produced with different ranges of emission and the invention is not limited to the presently available dyes and their respective emission ranges.

Furthermore, lasers used in TPLSM can be grouped into femtosecond and picosecond lasers. These lasers are distinguished by their pulse duration. A femtosecond laser is preferred since it is particularly suitable for visualization without harming the specimen.

TPLSM produces noninvasive, three-dimensional, real-time images of the optically dense avian egg. Visualization of the metaphase plate or pronucleus in avian eggs during nuclear transfer has been prevented by the yolk. Two-photon imaging with femtosecond lasers operating in the near infra-red, however, allows visualization of nuclear structures without damaging cellular constituents. Prior to visualization, specimens may be incubated or injected with DNA-specific dyes such as DAPI (4',6'-diamidino-2-phenylindole hydrochloride) or Hoescht 33342 (bis-benzimide), the albumen capsule is removed and the ovum placed in a dish with the germinal disk facing the top. Remnants of the albumen capsule are removed from the top of the germinal disk.

An aqueous solution, for example phosphate-buffered saline (PBS), is added to prevent drying of the ovum. A cloning cylinder is placed around the germinal disk and DAPI in PBS is added to the cylinder. Alternatively, a DAPI-PBS solution may be injected into the germinal disk with a glass pipette, whereupon the dye enters the nuclear structures. For dye injection, removal of the albumen capsule is not necessary, whereas injection of nuclei into the disk is facilitated in the absence of the capsule.

Images of the inside of the early avian embryo can be generated through the use of TPLSM. Visualization may be performed after about 10 to 15 minutes of incubation or about 10 minutes after dye injection. During visualization, the germinal disk is placed under the microscope objective and the pronuclear structures are searched within the central area of the disk using relatively low laser powers of about 3-6 milliwatts. Once the structures are found they may be ablated by using higher laser power or mechanically removed, guided by TPLSM.

Nuclear transfer also requires the destruction or enucleation of the pronucleus before a nuclear donor can be introduced into the oocyte cytoplast. Two-photon laser-mediated ablation of nuclear structures provides an alternative to microsurgery to visualize the pronucleus lying about 25 µm beneath the ovum's vitelline membrane within the germinal disk. Higher laser powers than those used for imaging are used for enucleation, with minimal collateral damage to the cell. The wavelength for ablation generally ranges from about 700 nm to 1000 nm, at about 30 to about 70 milliwatts. TPLSM and two-photon laser-mediated ablation are more efficient than alternative methods because they are less operator dependent and less invasive, which results in improved viability of the recipient cell.

A nucleus from a cultured somatic cell (nuclear donor) may then be injected into the enucleated recipient cytoplast by a micromanipulation unit comprising a microinjector and a micromanipulator. The donor nucleus is introduced into the germinal disk though guided injection using episcopic illumination (i.e., light coming through the objective onto the sample). Alternatively, a donor cell may be fused to the recipient cell using methods well known in the art, e.g. by means of fusion-promoting chemicals, such as polyethylene glycol, inactivated viruses, such as Sendai virus, or electrical stimulation. The reconstructed zygote may then be surgically transferred to the oviduct of a recipient hen to produce a hard shell egg. Alternatively, the reconstructed embryo may be cultured for 24 hours and screened for development prior to surgical transfer.

The egg can be harvested after laying and before hatching of a chick, or further incubated to generate a cloned chick, optionally genetically modified. The cloned chick may carry a transgene in all or most of its cells. After maturation, the transgenic avian may lay eggs that contain one or more desired, heterologous protein(s). The cloned chick may also be a knock-in chick expressing an alternative phenotype or capable of laying eggs having an heterologous protein therein. The reconstructed egg may also be cultured to term using the ex ovo method described by Perry et al. (supra).

5.1.5 Zygote Reconstruction by Ovum Transfer

Another embodiment of the invention provides for a method of producing a cloned animal comprising nuclear transfer in combination with ovum transfer. Two-photon visualization and ablation may be used to perform nuclear transfer, as described above. Accordingly, the replacement of the recipient cell's nucleus with the donor cell's nucleus results in a reconstructed zygote. Preferably, pronuclear stage eggs are used as recipient cytopiasts already activated by fertilization. Alternatively, unactivated metaphase II eggs may serve as recipient cytoplast and activation induced after renucleation. The ovum may be cultured via ovum transfer, wherein the ovum containing the reconstructed zygote is transferred to a recipient hen. The ovum is surgically transferred into the oviduct of the recipient hen shortly after oviposition. This is accomplished according to normal husbandry procedures (oviposition, incubation, and hatching; see Tanaka et al., supra).

Alternatively, the ovum may be cultured to stage X prior to transfer into a recipient hen. More specifically, reconstructed stage I embryos are cultured for 24-48 hours to stage X. This allows for developmental screening of the reconstructed embryo prior to surgical transfer. Stage I embryos are enclosed within a thick albumen capsule. In this novel procedure, the albumen capsule is removed, after which the nuclear donor is injected into the germinal disk. Subsequently, the capsule and germinal disk are recombined by placing the thick capsule in contact with the germinal disk on top of the yolk. Embryos develop to stage X at similar rates as those cultured with their capsules intact. At stage X, the embryo is transferred to the oviduct of a recipient hen.

Once transferred, the embryo develops inside the recipient hen and travels through the oviduct of the hen where it is encapsulated by natural egg white proteins and a natural egg shell. The egg which contains endogenous yolk and an embryo from another hen, is laid and can then be incubated and hatched like a normal chick. The resulting chick may carry a transgene in all or most of its cells. Preferably, the transgene is at least in the oviduct cells of the recipient chick. Following maturation, the cloned avian may express a desired phenotype or may be able to lay eggs that contain one or more desired, heterologous protein(s).

5.1.6 Sperm-Mediated Integration of Heterologous Transgenes

Detailed descriptions of methods of sperm-mediated transfer of nucleic acid suitable for use in the present invention are described in the PCT Publication WO 00/697257, incorporated herein by reference in its entirety. The first method of incorporating heterologous genetic material into the genome of an avian delivers a nucleic acid using known gene delivery systems to male germ cells in situ in the testis of the male avian (e.g., by in vivo transfection or transduction). The second, in vitro, method of incorporating heterologous genetic material into the genome of an avian involves isolating male germ cells ex corpora, delivering a polynucleotide thereto and then returning the transfected cells to the testes of a recipient male bird.

In Vivo Method

The in vivo method employs injection of the gene delivery mixture, preferably into the seminiferous tubules, or into the pete testis, and most preferably into the vas efferens or vasa efferentia, using, for example, a micropipette and a picopump delivering a precise measured volume under controlled amounts of pressure. A small amount of a suitable, non-toxic dye can be added to the gene delivery mixture (fluid) to confirm delivery and dissemination to the seminiferous tubules of the testis. The genetically modified germ cells differentiate in their own milieu. Progeny animals exhibiting the nucleic acid's integration into its germ cells (transgenic animals) are selected. The selected progeny can then be mated, or their sperm utilized for insemination or in vitro fertilization to produce further generations of transgenic progeny.

In Vitro Method

Male germ cells are obtained or collected from the donor male bird by any means known in the art such as, for example, transection of the testes. The germ cells are then exposed to a gene delivery mixture, preferably within several hours, or cryopreserved for later use. When the male germ cells are obtained from the donor vertebrate by transection of the testes, the cells can be incubated in an enzyme mixture known for gently breaking up the tissue matrix and releasing undamaged cells such as, for example, pancreatic trypsin, collagenase type I, pancreatic DNAse type I, as well as bovine serum albumin and a modified DMEM medium. After washing the cells, they can be placed in an incubation medium such as DMEM, and the like, and plated on a culture dish for genetic modification by exposure to a gene delivery mixture.

Whether employed in the in vivo method or in vitro method, the gene delivery mixture, once in contact with the male germ cells, facilitates the uptake and transport of heterologous genetic material into the appropriate cell location for integration into the genome and expression. A number of known gene delivery methods can be used for the uptake of nucleic acid sequences into the cell. Such methods include, but are not limited to viral vectors, liposomes, electroporation and Restriction Enzyme Mediated Integration (REMI) (discussed below). In both the in vivo or in vitro method, a gene delivery mixture typically comprises a polynucleotide encoding the desired trait or product (for example, immunoglobulin polypeptides) and a suitable promoter sequence such as, for example, a tissue-specific promoter, an IRES or the like and optionally agents that increase the uptake of or comprise the polynucleotide sequence, such as liposomes, retroviral vectors, adenoviral vectors, adenovirus enhanced gene delivery systems and the like, or combinations thereof. A reporter construct, including a genetic selection marker, such as the gene encoding for Green Fluorescent Protein, can further be added to the gene delivery mixture. Targeting molecules, such as the c-kit ligand, can be added to the gene delivery mixture to enhance the transfer of genetic material into the male germ cell. An immunosuppressing agent, such as cyclosporin or a corticosteroid may also be added to the gene delivery mixture as known in the art.

Any of a number of commercially available gene delivery mixtures can be used, to which the polynucleotide encoding a desired trait or product is further admixed. The final gene delivery mixture comprising the polynucleotide can then be admixed with the cells and allowed to interact for a period of between about 2 hours to about 16 hours, at a temperature of between about 33° C. to about 37° C. After this period, the cells are preferably placed at a lower temperature of about 33° C. to about 34° C., for about 4 hours to about 20 hours, preferably about 16 to 18 hrs.

Isolating and/or selecting genetically transgenic germ cells (and transgenic somatic cells, and of transgenic vertebrates) is by any suitable means, such as, but not limited to, physiological and/or morphological phenotypes of interest using any suitable means, such as biochemical, enzymatic, immunochemical, histologic, electrophysiologic, biometric or like methods, and analysis of cellular nucleic acids, for example the presence or absence of specific DNAs or RNAs of interest using conventional molecular biological techniques, including hybridization analysis, nucleic acid amplification including, but not limited to, polymerase chain reaction, transcription-mediated amplification, reverse transcriptase-mediated ligase chain reaction, and/or electrophoretic technologies.

A preferred method of isolating or selecting male germ cell populations comprises obtaining specific male germ cell populations, such as spermatogonia, from a mixed population of testicular cells by extrusion of the cells from the seminiferous tubules and enzyme digestion. The spermatogonia, or other male germ cell populations, can be isolated from a mixed cell population by methods such as the utilization of a promoter sequence that is specifically or selectively active in cycling male germ line stem cell populations. Suitable promoters include B-Myb or a specific promoter, such as the c-kit promoter region, c-raf-1 promoter, ATM (ataxia-telangiectasia) promoter, vasa promoter, RBM (ribosome binding motif) promoter, DAZ (deleted in azoospermia) promoter, XRCC-1 promoter, HSP 90 (heat shock gene) promoter, cyclin A1 promoter, or FRMI (from Fragile X site) promoter and the like. A selected promoter may be linked to a reporter construct, for example, a construct comprising a gene encoding Green Fluorescent Protein (or enhanced Green Fluorescent Proteini, EGFP), Yellow Fluorescent Protein, Blue Fluorescent Protein, a phycobiliprotein, such as phycoerythrin or phycocyanin, or any other protein which fluoresces under suitable wave-lengths of light, or encoding a light-emitting protein, such as luciferase or apoaequorin. The unique promoter sequences drive the expression of the reporter construct only during specific stages of male germ cell development (e.g., Mailer et al., 1999, J. Biol. Chem. 276(16):11220-28; Schrans-Stassen et al., 1999, Endocrinology 140: 5894-5900, incorporated herein by reference in their entireties). In the case of a fluorescent reporter construct, the cells can be sorted with the aid of, for example, a FACS set at the appropriate wavelength(s), or they can be selected by chemical methods.

Male germ cells that have the DNA modified in the desired manner are isolated or selected, and transferred to the testis of a suitable recipient animal. Further selection can be attempted after biopsy of one or both of the recipient male's testes, or after examination of the animal's ejaculate amplified by the polymerase chain reaction to confirm that the desired nucleic acid sequence had been incorporated.

The genetically modified germ cells isolated or selected as described above are preferably transferred to a testis of a recipient male avian, preferably a chicken, that can be, but need not be, the same donor animal. Before transferring the genetically modified male germ cells to the recipient animal, the testes of the recipient can be depopulated of endogenous germ cells, thereby facilitating the colonization of the recipient testis by the genetically modified germ cells, by any suitable means, including by gamma irradiation, by chemical treatment, by means of infectious agents such as viruses, or by autoimmune depletion or by combinations thereof, preferably by a combined treatment of the vertebrate with an alkylating agent and gamma irradiation.

The basic rigid architecture of the gonad should not be destroyed, nor significantly damaged. Disruption of tubules may lead to impaired transport of testicular sperm and result in infertility. Sertoli cells should not be irreversibly damaged, as they provide a base for development of the germ cells during maturation, and for preventing the host immune defense system from destroying grafted foreign spermatogonia.

In a preferred method, a cytotoxic alkylating agent, such as, but not limited to, bisulfan (1,4-butanediol dimethanesulphonate), chlorambucil, cyclophosphamide, melphalan, or ethyl ethanesulfonic acid, is combined with gamma irradiation, to be administered in either sequence. The dose of the alkylating agent and the dose of gamma radiation are in an amount sufficient to substantially depopulate the testis. The alkylating agent can be administered by any pharmaceutically acceptable delivery system, including but not limited to, intraperitoneal, intravenous, or intramuscular injection, intravenous drip, implant, transdermal or transmucosal delivery systems.

The isolated or selected genetically modified germ cells are transferred into the recipient testis by direct injection using a suitable micropipette. Support cells, such as Leydig or Sertoli cells, that can be unmodified or genetically modified, can be transferred to a recipient testis along with the modified germ cells.

A union of male and female gametes to form a transgenic zygote is brought about by copulation of the male and female vertebrates of the same species, or by in vitro or in vivo artificial means. If artificial means are chosen, then incorporating into the genome a genetic selection marker that is expressed in male germ cells is particularly useful.

Suitable artificial means include, but are not limited to, artificial insemination, in vitro fertilization (IVF) and/or other artificial reproductive technologies, such as intracytoplasmic sperm injection (ICSI), subzonal insemination (SUZI), or partial zona dissection (PZD). Also others, such as cloning and embryo transfer, cloning and embryo splitting, and the like, can be employed.

The transgenic vertebrate progeny can, in turn, be bred by natural mating, artificial insemination, or by in vitro fertilization (IVF) and/or other artificial reproductive technologies, such as intracytoplasmic sperm injection (ICSI) and chicken intracytoplasmic sperm injection (CHICSI™), subzonal insemination (SUZI), or partial zona dissection (PZD), to obtain further generations of transgenic progeny. Although the genetic material is originally inserted solely into the germ cells of a parent animal, it will ultimately be present in the germ cells of future progeny and subsequent generations thereof. In addition, the genetic material will also be present in cells of the progeny other than germ cells, i.e., somatic cells.

5.1.7 Generation of Transgenic Avian Zygotes by Restriction Enzyme-Mediated Integration (REMI)

The REMI method for stably integrating heterologous DNA into the genomic DNA of a recipient cell is described by Shemesh et al. in PCT Publication No. WO 99/42569 and incorporated herein by reference in its entirety. This REMI method comprises in part an adaptation of the REMI technique disclosed by Schiest and Petes (1991, Proc. Nat. Acad. Sci. U.S.A. 88: 7585-7589) and Kuspa and Loomis (1992, Proc. Nat. Acad. Sci. U.S.A., 89: 8803-8807), both incorporated herein by reference in their entireties.

The REMI method is suitable for introducing heterologous DNA into the genome nucleic acid of sperm and sperm precursor cells, or ovum, embryonic cell, or somatic cell of an animal, preferably an avian, more preferably a chicken.

The heterologous nucleic acid to be integrated into, for example, the sperm nuclear DNA is converted to a linear double stranded DNA possessing single-stranded cohesive ends by contacting the heterologous DNA with a type II restriction enzyme that upon scission, generates such ends. The nucleic acid to be cut can be a circular nucleic acid such as in a plasmid or a viral vector or a linear nucleic acid that possesses at least one recognition and cutting site outside of the genes or regulatory regions critical to the desired post-integration function of the nucleic acid, and no recognition and cutting sites within the critical regions.

Alternatively, the heterologous DNA to be integrated into the sperm nuclear DNA can be prepared by chemically and/or enzymatically adding cohesive ends to a linear DNA (see, for example Sambrook et al., *Molecular Cloning: A Laboratory Manual*. 3rd ed., Cold Spring Harbor Laboratory, Cold Spring Harbor, N.Y. (2001) incorporated herein by reference in its entirety). The added cohesive ends must be able to hybridize to the cohesive ends characteristic of a nucleic acid cleaved by a type II restriction endonuclease. Alternatively, the cohesive ends can be added by combining the methods based on type II restriction enzyme cutting and chemical and/or enzymatic addition.

According to the present invention, a heterologous nucleic acid encoding at least one polypeptide, and the appropriate restriction enzyme can be introduced into sperm cells together or sequentially by way of, for example, electroporation, or lipofection. Preferably electroporation may be used, and most preferably lipofection is used. However, the present invention contemplates that any technique capable of transferring heterologous material into sperm could be used so long as the technique preserves enough of the sperm's motility and fertilization functions, such that the resultant sperm will be able to fertilize the appropriate oocytes. It is understood that the heterologous nucleic acid may be integrated into the genome of a recipient cell such as a spermatogonial cell or a spermatogonial precursor cell for subsequent transfer to an embryo or the testicular material of the recipient male animal, preferably a chicken. It is further understood that the heterologous nucleic acid may not be integrated into the genome of the recipient cell.

The combination of REMI as described in the present application, plus a relatively benign method of transferring heterologous material into a cell may result in heterologous nucleic acid being stably integrated into genomic DNA of a high fraction of the treated sperm, while not diminishing to any great extent, the viability of the sperm or their ability to fertilize oocytes. Examples of suitable methods for the introduction of the genetically modified sperm, spermatogonial cells or precuror spermatogonial cells into a recipient avian, preferably a chicken, are as described above.

5.1.8 Breeding and Maintenance of Transgenic Avians

A union of male and female gametes from transgenic birds generated by the cytoplasmically microinjected embryos, thereby forming a transgenic zygote, is brought about by copulation of the male and female vertebrates of the same species, or by in vitro or in vivo artificial means. Suitable artificial means include, but are not limited to, artificial insemination, in vitro fertilization (IVF) and/or other artificial reproductive technologies, such as intracytoplasmic sperm injection (ICSI), subzonal insemination (SUZI), or partial zona dissection (PZD). Also others, such as cloning and embryo transfer, cloning and embryo splitting, and the like, can be employed.

The transgenic avian progeny can, in turn, be bred by natural mating, artificial insemination, or by in vitro fertilization (IVF) and/or other artificial reproductive technologies, such as intracytoplasmic sperm injection (ICSI) and chicken intracytoplasmic sperm injection (CHICSI™), subzonal insemination (SUZI), or partial zona dissection (PZD), to obtain further generations of transgenic progeny.

Using the methods of the invention for producing transgenic avians, particularly methods using vectors that are not derived from eukaryotic viruses, and, preferably, the methods of cytoplasmic micro-injection described herein, the level of mosaicism of the transgene (percentage of cells containing the transgene) in avians hatched from microinjected embryos (i.e., the $G_0$s) is greater than 5%, 10%, 25%, 50%, 75% or 90%, or is the equivalent of one copy per one genome, two genomes, five genomes, seven genomes or eight genomes, as determined by any number of techniques known in the art and described infra. In additional particular embodiments, the percentage of $G_0$s that transmit the transgene to progeny ($G_1$s) is greater than 5%, preferably, greater than 10%, 20%, 30%, 40%, and, most preferably, greater than 50%, 60%, 70%, 80%, 90%. In other embodiments, the transgene is detected in 10%, 20%, 30%, 40%, and most preferably, greater than 50%, 60%, 70%, 80%, 90% of chicks hatching from embryos into which nucleic acids have been introduced using methods of the invention.

5.2 Vectors

A variety of vectors useful in carrying out the methods of the present invention are described herein. These vectors may be used for stable introduction of a selected heterologous polypeptide-coding sequence (and/or regulatory sequences) into the genome of an avian, in particular, to generate transgenic avians that produce exogenous proteins in specific tissues of an avian, and in the oviduct in particular, or in the serum of an avian. In still further embodiments, the vectors are used in methods to produce avian eggs containing exogenous protein.

In particular embodiments, preferably for use in the microinjection, sperm-mediated transgenesis, and nuclear transfer methods described herein, the vectors of the invention are not derived from eukaryotic viral vectors or retroviral vectors (except in certain embodiments for containing eukaryotic viral regulatory elements such as promoters, origins of replication, etc). In particular embodiments, the vector is not an REV, ALV or MuLV vector. In particular, useful vectors include, bacteriophages such as lambda derivatives, such as λgt11, λgt WES.tB, Charon 4, and plasmid vectors such as pBR322, pBR325, pACYC177, pACYC184, pUC8, pUC9, pUC18, pUC19, pLG339, pR290, pKC37, pKC101, SV40, pBLUESCRIPT® II SK +/− or KS +/− (see "Stratagene Cloning Systems" Catalog (1993) from STRATAGENE®, La Jolla, Calif., which is hereby incorporated by reference), pQE, pIH821, pGEX, pET series (see Studier, F. W. et. al., 1990, "Use of T7 RNA Polymerase to Direct Expression of Cloned Genes" *Gene Expression Technology* 185, which is hereby incorporated by reference) and any derivatives thereof, cosmid vectors and, in preferred embodiments, artificial chromosomes, such as, but not limited to, YACs, BACs, BBPACs or PACs. Such artificial chromosomes are useful in that a large nucleic acid insert can be propagated and introduced into the avian cell.

In other particular embodiments, as detailed above in section 5.2, infra, the vectors of the invention are derived from eukaryotic viruses, preferably avian viruses, and can be replication competent or, preferably, replication deficient. In particular embodiments, the vectors are derived from REV, ALV or MuLV. Nucleic acid sequences or derivatives or truncated variants thereof, may be introduced into viruses such as vaccinia virus. Methods for making a viral recombinant vector useful for expressing a protein under the control of the lysozyrne promoter are analogous to the methods disclosed in U.S. Pat. Nos. 4,603,112; 4,769,330; 5,174,993; 5,505,941; 5,338,683; 5,494,807; 4,722,848; Paoletti, E., 1996, *Proc. Natl. Acad. Sci.* 93: 11349-11353; Moss, 1996, *Proc. Natl. Acad. Sci.* 93: 11341-11348; Roizman, 1996, *Proc. Natl. Acad. Sci.* 93: 11307-11302; Frolov et al., 1996, *Proc. Natl. Acad. Sci.* 93: 11371-11377; Gruhaus et al., 1993, *Seminars in Virology* 3: 237-252 and U.S. Pat. Nos. 5,591,639; 5,589, 466; and 5,580,859 relating to DNA expression vectors, inter alia; the contents of which are incorporated herein by reference in their entireties.

Recombinant viruses can also be generated by transfection of plasmids into cells infected with virus.

Preferably, vectors can replicate (i.e., have a bacterial origin of replication) and be manipulated in bacteria (or yeast) and can then be introduced into avian cells. Preferably, the vector comprises a marker that is selectable and/or detectable in bacteria or yeast cells and, preferably, also in avian cells, such markers include, but are not limited to, Amp$^r$, tet$^r$, LacZ, etc. Preferably, such vectors can accommodate (i.e., can be used to introduce into cells and replicate) large pieces of DNA such as genomic sequences, for example, large pieces of DNA consisting of at least 25 kb, 50 kb, 75 kb, 100 kb, 150 kb, 200 kb or 250 kb, such as BACs, YACs, cosmids, etc.

The insertion of a DNA fragment into a vector can, for example, be accomplished by ligating the DNA fragment into a vector that has complementary cohesive termini. However, if the complementary restriction sites used to fragment the DNA are not present in the vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and the transgene may be modified by homopolymeric tailing.

The vector can be cloned using methods known in the art, e.g., by the methods disclosed in Sambrook et al., 2001, Molecular Cloning, A Laboratory Manual, Third Edition, Cold Spring Harbor Laboratory Press, N.Y.; Ausubel et al., 1989, Current Protocols in Molecular Biology, Green Publishing Associates and Wiley Interscience, N.Y., both of which are hereby incorporated by reference in their entireties. Preferably, the vectors contain cloning sites, for example, restriction enzyme sites that are unique in the sequence of the vector and insertion of a sequence at that site would not disrupt an essential vector function, such as replication.

As discussed above, vectors used in certain methods of the invention preferably can accommodate, and in certain embodiments comprise, large pieces of heterologous DNA such as genomic sequences, particularly avian genomic sequences. Such vectors can contain an entire genomic locus, or at least sufficient sequence to confer endogenous regulatory expression pattern, e.g., high level of expression in the magnum characteristic of lysozyme, ovalbumin, ovomucoid, ovotransferrin, etc, and to insulate the expression of the transgene sequences from the effect of regulatory sequences surrounding the site of integration of the transgene in the genome. Accordingly, as detailed below, in preferred embodiments, the transgene is inserted in an entire genomic loci or significant portion thereof.

To manipulate large genomic sequences contained in, for example, a BAC, nucleotide sequences coding for the heterologous protein to be expressed and/or other regulatory elements may be inserted into the BAC by directed homologous recombination in bacteria, e.g., the methods of Heintz WO 98/59060; Heintz et al., WO 01/05962; Yang et al., 1997, *Nature Biotechnol.* 15: 859-865; Yang et al., 1999, *Nature Genetics* 22: 327-35; which are incorporated herein by reference in their entireties. Alternatively, large genomic sequences can be inserted into a vector using RecA-Assisted Restriction Endonuclease (RARE cleavage) as described by Ferrin (2001, Mol Biotechnology 18:233-241), herein incorporated by reference in its entirety.

In a preferred embodiment, an avian BAC library is screened for the presence of a complete genomic locus for ovomucoid, ovalbumin, conalbumin, lysozyme, or ovotransferrin, or any other gene that may be expressed in a specific tissue of interest, such as the magnum. Chicken BAC libraries with redundant coverage of the chicken genome have been described by Crooijmans et al. (2000, Mamm Genome 11:360-363) and Kato et al. (2002, Poult Sci 81:1501-1508), and Zimmer et al. (1997, Genomics 42:217-226), the disclosure of which are incorporate herein by reference in their entireties. Once the desired BAC clone is obtained, it can be further manipulated using standard cloning techniques to create an expression vector with desired attributes. An example of a BAC clone containing the entire ovoinhibitor and ovomucoid genes is OMC24 (SEQ ID NO:42) is described in Example 36. OMC24 contains full-length ovoinhibitor and ovomucoid genes. An IRES-cDNA cassette comprising nucleic acids which encode a heterologous polypeptide is inserted downstream of the ovomucoid coding sequence, preferably in the sequence coding for the 3'-UTR of the ovomucoid mRNA.

Alternatively, the BAC can also be engineered or modified by "E-T cloning," as described by Muyrers et al. (1999, *Nucleic Acids Res.* 27(6): 1555-57, incorporated herein by reference in its entirety). Using these methods, specific DNA may be engineered into a BAC independently of the presence of suitable restriction sites. This method is based on homologous recombination mediated by the recE and recT proteins ("ET-cloning") (Zhang et al., 1998, Nat. Genet. 20(2): 123-28; incorporated herein by reference in its entirety). Homologous recombination can be performed between a PCR fragment flanked by short homology arms and an endogenous intact recipient such as a BAC. Using this method, homologous recombination is not limited by the disposition of restriction endonuclease cleavage sites or the size of the target DNA. A BAC can be modified in its host strain using a plasmid, e.g., pBAD-αβγ, in which recE and recT have been replaced by their respective functional counterparts of phage lambda (Muyrers et al., 1999, *Nucleic Acids Res.* 27(6): 1555-57). Preferably, a BAC is modified by recombination with a PCR product containing homology arms ranging from 27-60 bp. In a specific embodiment, homology arms are 50 bp in length.

In another embodiment, a transgene is inserted into a yeast artificial chromosome (YAC) (Burke et al., 1987, *Science* 236: 806-12; and Peterson et al., 1997, *Trends Genet.* 13:61, both of which are incorporated by reference herein in their entireties).

In other embodiments, the transgene is inserted into another vector developed for the cloning of large segments of genomic DNA, such as a cosmid or bacteriophage P1 (Sternberg et al., 1990, *Proc. Natl. Acad. Sci. USA* 87: 103-07). The approximate maximum insert size is 30-35 kb for cosmids and 100 kb for bacteriophage P1. In another embodiment, the transgene is inserted into a P-1 derived artificial chromosome (PAC) (Mejia et al., 1997, *Genome Res* 7:179-186). The maximum insert size is 300 kb.

Vectors containing the appropriate heterologous sequences may be identified by any method well known in the art, for example, by sequencing, restriction mapping, hybridization, PCR amplification, etc. In a preferred method with avian BAC libraries, multi-dimensional PCR screening is performed (see Crooijmans et al., 2000, Mamm Genome 11:360-363; Kato et al., 2002, Poult Sci 81:1501-1508).

The vectors of the invention comprise one or more nucleotide sequences encoding a heterologous protein desired to be expressed in the transgenic avian, as well as regulatory elements such as promoters, enhancers, MARs, IRES's and other translation control elements, transcriptional termination elements, polyadenylation sequences, etc, as discussed infra. In particular embodiments, the vector of the invention contains at least two nucleotide sequences coding for heterologous proteins, for example, but not limited to, the heavy and light chains of an immunoglobulin.

In a preferred embodiment, the nucleotide sequence encoding the heterologous protein is inserted into all or a significant portion of a nucleic acid containing the genomic sequence of an endogenous avian gene, preferably an avian gene that is expressed in the magnum, e.g., lysozyme, ovalbumin, ovomucoid, conalbumin, ovotransferrin, etc. For example, the heterologous gene sequence may be inserted into or replace a portion of the 3' untranslated region (UTR) or 5' untranslated region (UTR) or an intron sequence of the endogenous gene genomic sequence. Preferably, the heterologous gene coding sequence has its own IRES. For descriptions of IRESes, see, e.g., Jackson et al., 1990, *Trends Biochem Sci.* 15(12):477-83; Jang et al., 1988, *J. Virol.* 62(8): 2636-43; Jang et al., 1990, *Enzyme* 44(1-4):292-309; and Martinez-Salas, 1999, *Curr. Opin. Biotechnol.* 10(5):458-64; Palmenberg et al., U.S. Pat. No. 4,937,190, which are incorporated by reference herein in their entireties. In another embodiment, the heterologous protein coding sequence is inserted at the 3' end of the endogenous gene coding sequence. In another preferred embodiment, the heterologous gene coding sequences are inserted using 5' direct fusion wherein the heterologous gene coding sequences are inserted in-frame adjacent to the initial ATG sequence (or adjacent the nucleotide sequence encoding the first two, three, four, five, six, seven or eight amino acids) of the endogenous gene or replacing some or all of the sequence of the endogenous gene coding sequence. In yet another specific embodiment, the heterologous gene coding sequence is inserted into a separate cistron in the 5' region of the endogenous gene genomic sequence and has an independent IRES sequence. A preferred IRES sequence is the IRES from encephalomyocarditis virus (EMCV) IRES (Mountford et al., 1994, Proc Natl Acad Sci USA 91:4303-4307). Representative IRES-cDNA cassettes utilizing the EMCV IRES are provided in SEQ ID NOs. 47 and 48.

The present invention further relates to nucleic acid vectors (preferably, not derived from eukaryotic viruses, except, in certain embodiments, for eukaryotic viral promoters and/or enhancers) and transgenes inserted therein that incorporate multiple polypeptide-encoding regions, wherein a first polypeptide-encoding region is operatively linked to a transcription promoter and a second polypeptide-encoding region is operatively linked to an IRES. For example, the vector may contain coding sequences for two different heterologous proteins (e.g., the heavy and light chains of an immunoglobulin) or the coding sequences for all or a significant part of the genomic sequence for the gene from which the promoter driving expression of the transgene is derived, and the heterologous protein desired to be expressed (e.g., a construct containing the genomic coding sequences, including introns, of the avian lysozyme gene when the avian lysozyme promoter is used to drive expression of the transgene, an IRES, and the coding sequence for the heterologous protein desired to be expressed downstream (i.e., 3' on the RNA transcript of the IRES)). Thus, in certain embodiments, the nucleic acid encoding the heterologous protein is introduced into the 5' untranslated or 3' untranslated regions of an endogenous gene, such as but not limited to, lysozyme, ovalbumin, ovotransferrin, and ovomucoid, with an IRES sequence directing translation of the heterologous sequence.

Such nucleic acid constructs, when inserted into the genome of a bird and expressed therein, will generate individual polypeptides that may be post-translationally modified, for example, glycosylated or, in certain embodiments, form complexes, such as heterodimers with each other in the white of the avian egg. Alternatively, the expressed polypeptides may be isolated from an avian egg and combined in vitro, or expressed in a non-reproductive tissue such as serum. In other embodiments, for example, but not limited to, when expression of both heavy and light chains of an antibody is desired, two separate constructs, each containing a coding sequence for one of the heterologous proteins operably linked to a promoter (either the same or different promoters), are introduced by microinjection into cytoplasm of one or more embryonic cells and transgenic avians harboring both transgenes in their genomes and expressing both heterologous proteins are identified. Alternatively, two transgenic avians each containing one of the two heterologous proteins (e.g., one transgenic avian having a transgene encoding the light chain of an antibody and a second transgenic avian having a transgene encoding the heavy chain of the antibody) can be bred to obtain an avian containing both transgenes in its germline and expressing both transgene encoded proteins, preferably in eggs.

Recombinant expression vectors can be designed for the expression of the encoded proteins in eukaryotic cells. Useful vectors may comprise constitutive or inducible promoters to direct expression of either fusion or non-fusion proteins. With fusion vectors, a number of amino acids are usually added to the expressed target gene sequence such as, but not limited to, a protein sequence for thioredoxin, a polyhistidine, or any other amino acid sequence that facilitates purification of the expressed protein. A proteolytic cleavage site may further be introduced at a site between the target recombinant protein and the fusion sequence. Additionally, a region of amino acids such as a polymeric histidine region may be introduced to allow binding of the fusion protein to metallic ions such as nickel bonded to a solid support, and thereby allow purification of the fusion protein. Once the fusion protein has been purified, the cleavage site allows the target recombinant protein to be separated from the fusion sequence. Enzymes suitable for use in cleaving the proteolytic cleavage site include, but are not limited to, Factor Xa and thrombin. Fusion expression vectors that may be useful in the present invention include pGex (AMRAD® Corp., Melbourne, Australia), pRIT5 (PHARMACIA®, Piscataway, N.J.) and pMAL (NEW ENGLAND BIOLABS®, Beverly, Mass.), fusing glutathione S-transferase, protein A, or maltose E binding protein, respectively, to the target recombinant protein.

Once a promoter and a nucleic acid encoding a heterologous protein of the present invention have been cloned into a vector system, it is ready to be incorporated into a host cell. Such incorporation can be carried out by the various forms of transformation noted above, depending upon the vector/host cell system. It is contemplated that the incorporation of the DNA of the present invention into a recipient cell may be by any suitable method such as, but not limited to, viral transfer, electroporation, gene gun insertion, sperm-mediated transfer to an ovum, microinjection and the like. Suitable host cells include, but are not limited to, bacteria, virus, yeast, mammalian cells, and the like. In particular, the present invention contemplates the use of recipient avian cells, such as chicken cells or quail cells.

Another aspect of the present invention, therefore, is a method of expressing a heterologous polypeptide in a eukaryotic cell by transfecting an avian cell with a recombinant DNA comprising an avian tissue-specific promoter operably linked to a nucleic acid insert encoding a polypeptide and, optionally, a polyadenylation signal sequence, and culturing the transfected cell in a medium suitable for expression of the heterologous polypeptide under the control of the avian lysozyme gene expression control region.

Yet another aspect of the present invention is a eukaryotic cell transformed with an expression vector according to the present invention and described above. In one embodiment of the present invention, the transformed cell is a chicken oviduct cell and the nucleic acid insert comprises the chicken lysozyme gene expression control region, a nucleic acid insert encoding a human interferon α2b and codon optimized for expression in an avian cell, and an SV40 polyadenylation sequence.

In another embodiment, the transformed cell is a quail oviduct cell and the nucleic acid insert comprises the artificial avian promoter construct MDOT (SEQ ID NO.:11) operably linked to an interferon-encoding sequence, as described in Example 34 below.

In yet another embodiment of the present invention, a quail oviduct cell is transfected with the nucleic acid insert comprising the MDOT artificial promoter construct operably linked to an erythropoietin (EPO)-encoding nucleic acid, wherein the transfected quail produces heterologous erythropoietin.

5.2.1 Promoters

The vectors of the invention contain promoters that function in avian cells, preferably, that are tissue-specific and, in preferred embodiments, direct expression in the magnum or serum or other tissue such that expressed proteins are deposited in eggs, more preferably, that are specific for expression in the magnum. Alternatively, the promoter directs expression of the protein in the serum of the transgenic avian. Introduction of the vectors of the invention, preferably, generate transgenics that express the heterologous protein in tubular gland cells where it is secreted into the oviduct lumen and deposited, e.g., into the white of an egg. In preferred embodiments, the promoter directs a level of expression of the heterologous protein in the egg white of eggs laid by $G_0$ and/or $G_1$ chicks and/or their progeny that is greater than 5 ng, 10 ng, 50 ng, 100 ng, 250 ng, 500 ng, 750 ng, 1 μg, 5 μg, 10 μg, 50 μg, 100 μg, 250 μg, 500 μg, or 750 μg, more preferably greater than 1 mg, 2 mg, 5 mg, 10 mg, 20 mg, 50 mg, 100 mg, 200 mg, 500 mg, 700 mg, 1 gram, 2 grams, 3 grams, 4 grams or 5 grams. Such levels of expression can be obtained using the promoters of the invention.

In preferred embodiments, the promoters of the invention are derived from genes that express proteins present in significant levels in the egg white and/or the serum. For example, the promoter comprises regions of an ovomucoid, ovalbumin, conalbumin, lysozyme or ovotransferrin promoter or any other promoter that directs expression of a gene in an avian, particularly in a specific tissue of interest, such as the magnum or in the serum. Alternatively, the promoter used in the expression vector may be derived from that of the lysozyme gene that is expressed in both the oviduct and macrophages. Portions of two or more of these, and other promoters that function in avians, may be combined to produce effective synthetic promoter.

The promoter may optionally be a segment of the ovalbumin promoter region that is sufficiently large to direct expression of the coding sequence in the tubular gland cells. Other exemplary promoters include the promoter regions of the ovalbumin, lysozyme, ovomucoid, ovotransferrin or ovomucin genes (for example, but not limited to, as disclosed in co-pending U.S. patent application Ser. No. 09/922,549, filed Aug. 3, 2001, now issued U.S. Pat. No. 7,176,300, issued Feb. 13, 2007, and Ser. No. 10/114,739, filed Apr. 1, 2002, now issued U.S. Pat. No. 7,199,279, issued Apr. 3, 2007, by Rapp, and U.S. patent application Ser. No. 09/998,716, filed Nov. 30, 2001, now issued U.S. Pat. No. 6,875,588, issued Apr. 5, 2005, and PCT Publication No. WO 03/048364, both entitled "Ovomucoid Promoter and Methods of Use," by Harvey et al., all of which are incorporated by reference herein in their entireties). Alternatively, the promoter may be a promoter that is largely, but not entirely, specific to the magnum, such as the lysozyme promoter. Other suitable promoters may be artificial constructs such as a combination of nucleic acid regions derived from at least two avian gene promoters. One such embodiment of the present invention is the MDOT construct (SEQ ID NO: 11) comprising regions derived from the chicken ovomucin and ovotransferrin promoters, including but not limited to promoters altered, e.g., to increase expression, and inducible promoters, e.g., the tet$^r$ system.

The ovalbumin gene encodes a 45 kD protein that is also specifically expressed in the tubular gland cells of the magnum of the oviduct (Beato, 1989, *Cell* 56:335-344). Ovalbumin is the most abundant egg white protein, comprising over 50 percent of the total protein produced by the tubular gland cells, or about 4 grams of protein per large Grade A egg (Gilbert, "Egg albumen and its formation" in *Physiology and Biochemistry of the Domestic Fowl*, Bell and Freeman, eds., Academic Press, London, New York, pp. 1291-1329). The ovalbumin gene and over 20 kb of each flanking region have been cloned and analyzed (Lai et al., 1978, *Proc. Natl. Acad. Sci. USA* 75:2205-2209; Gannon et al., 1979, *Nature* 278:428-424; Roop et al., 1980, *Cell* 19:63-68; and Royal et al., 1975, *Nature* 279:125-132).

The ovalbumin gene responds to steroid hormones such as estrogen, glucocorticoids, and progesterone, which induce the accumulation of about 70,000 ovalbumin mRNA transcripts per tubular gland cell in immature chicks and 100,000 ovalbumin mRNA transcripts per tubular gland cell in the mature laying hen (Palmiter, 1973, *J Biol. Chem.* 248:8260-8270; Palmiter, 1975, *Cell* 4:189-197). The 5' flanking region contains four DNAse I-hypersensitive sites centered at −0.25, −0.8, −3.2, and −6.0 kb from the transcription start site. These sites are called HS-I, -II, -III, and -IV, respectively. Promoters of the invention may contain one, all, or a combination of HS-I, HS-II, HS-III and HS-IV. Hypersensitivity of HS-II and -III are estrogen-induced, supporting a role for these regions in hormone-induction of ovalbumin gene expression.

HS-I and HS-II are both required for steroid induction of ovalbumin gene transcription, and a 1.4 kb portion of the 5' region that includes these elements is sufficient to drive steroid-dependent ovalbumin expression in explanted tubular gland cells (Sanders and McKnight, 1988, *Biochemistry* 27: 6550-6557). HS-I is termed the negative-response element ("NRE") because it contains several negative regulatory elements which repress ovalbumin expression in the absence of hormone (Haekers et al., 1995, *Mol. Endo.* 9:1113-1126). Protein factors bind these elements, including some factors only found in oviduct nuclei suggesting a role in tissue-specific expression. HS-II is termed the steroid-dependent response element ("SDRE") because it is required to promote steroid induction of transcription. It binds a protein or protein complex known as Chirp-I. Chirp-I is induced by estrogen and turns over rapidly in the presence of cyclohexamide (Dean et al., 1996, *Mol. Cell. Biol.* 16:2015-2024). Experiments using an explanted tubular gland cell culture system defined an additional set of factors that bind SDRE in a steroid-dependent manner, including a NFκB-like factor (Nordstrom et al., 1993, *J. Biol. Chem.* 268:13193-13202; Schweers and Sanders, 1991, *J. Biol. Chem.* 266: 10490-10497).

Less is known about the function of HS-III and HS-IV. HS-III contains a functional estrogen response element, and confers estrogen inducibility to either the ovalbumin proximal promoter or a heterologous promoter when co-transfected into HeLa cells with an estrogen receptor cDNA. These data imply that HS-III may play a functional role in the overall regulation of the ovalbumin gene. Little is known about the function of HS-IV, except that it does not contain a functional estrogen-response element (Kato et al., 1992, *Cell* 68: 731-742).

In an alternative embodiment of the invention, transgenes containing constitutive promoters are used, but the transgenes are engineered so that expression of the transgene effectively becomes magnum-specific. Thus, a method for producing an exogenous protein in an avian oviduct provided by the present invention involves generating a transgenic avian having two transgenes in its tubular gland cells. One transgene comprises a first coding sequence operably linked to a constitutive promoter. The second transgene comprises a second coding sequence that is operably linked to a magnum-specific promoter, where expression of the first coding sequence is either directly or indirectly dependent upon the cellular presence of the protein expressed by the second coding sequence.

Additional promoters useful in the present invention include inducible promoters, such as the tet operator and the metallothionein promoter which can be induced by treatment with tetracycline and zinc ions, respectively (Gossen et al., 1992, *Proc. Natl. Acad. Sci.* 89: 5547-5551 and Walden et al., 1987, *Gene* 61: 317-327; incorporated herein by reference in their entireties).

Chicken lysozyme gene expression control region nucleic acid sequences:

The chicken lysozyme gene is highly expressed in the myeloid lineage of hematopoietic cells, and in the tubular glands of the mature hen oviduct (Hauser et al., 1981, *Hematol. and Blood Transfusion* 26: 175-178; Schutz et al., 1978, Cold Spring Harbor Symp. Quart. Biol. 42: 617-624) and is therefore a suitable candidate for an efficient promoter for heterologous protein production in transgenic animals. The regulatory region of the lysozyme locus extends over at least 12 kb of DNA 5' upstream of the transcription start site, and comprises a number of elements that have been individually isolated and characterized. The known elements include three enhancer sequences at about −6.1 kb, −3.9 kb, and −2.7 kb (Grewal et al., 1992, *Mol. Cell Biol.* 12: 2339-2350; Bonifer et al., 1996, *J. Mol. Med.* 74: 663-671), a hormone responsive element (Hecht et al, 1988, *E.M.B.O. J.* 7: 2063-2073), a silencer element and a complex proximal promoter. The constituent elements of the lysozyme gene expression control region are identifiable as DNAase 1 hypersensitive chromatin sites (DHS). They may be differentially exposed to nuclease digestion depending upon the differentiation stage of the cell. For example, in the multipotent progenitor stage of myelomoncytic cell development, or in erythroblasts, the silencer element is a DHS. At the myeloblast stage, a transcription enchancer located −6.1 kb upstream from the gene transcription start site is a DHS, while at the later monocytic stage another enhancer, at −2.7 kb becomes DNAase sensitive (Huber et al., 1995, *DNA and Cell Biol.* 14: 397-402).

This invention also envisions the use of promoters other than the lysozyme promoter, including but not limited to, a cytomegalovirus promoter, an ovomucoid, conalbumin or ovotransferrin promoter or any other promoter that directs expression of a gene in an avian, particularly in a specific tissue of interest, such as the magnum.

One example of an ovomucoid promoter region is described in U.S. Patent Application Publication No. 2003/0126628, published Jul. 3, 2003, now issued U.S. Pat. No. 6,875,588, issued Apr. 5, 2005, by Harvey et al., which is incorporated herein by reference in its entirety. An approximately 10 kb region of the chicken genome lying between the 3' end of the ovoinhibitor gene and the 5' transcription start site of the ovomucoid gene was obtained by PCR amplification. The obtained sequence includes the ovoinhibitor gene 3' untranslated region (Scott et al., 1987, J. Biol. Chem. 262: 5899 -5909), a CR1-like element (Scott et al., 1987, Biochemistry 26: 6831-6840; Genbank Accession No: M17966), and a portion of the 5' untranslated region of the ovomucoid gene (Genbank Accession No: J00897; Lai et al., 1979, Cell 18:829-842.

Another aspect of the methods of the present invention is the use of combinational promoters comprising an artificial nucleic acid construct having at least two regions wherein the regions are derived from at least two gene promoters, including but not limited to a lysozyme, ovomucoid, conalbumin or ovotransferrin promoter. In one embodiment of the present invention, the promoter may comprise a region of an avian ovomucoid promoter and a region of an avian oxotransferrin promoter, thereby generating a MDOT avian artificial promoter construct. The avian MDOT promoter construct of the present invention has the nucleic acid sequence SEQ ID NO: 11 and is illustrated in FIG. 14. This promoter is useful for allowing expression of a heterologous protein in chicken oviduct cells and may be operably linked to any nucleic acid encoding a heterologous polypeptide of interest including, for example, a cytokine, growth hormone, growth factor, enzyme, structural protein or the like.

5.2.2 Matrix Attachment Regions

In preferred embodiments of the invention, the vectors contain matrix attachment regions (MARs) that preferably flank the transgene sequences to reduce position effects on expression when integrated into the avian genome. In fact, 5' MARs and 3' MARs (also referred to as "scaffold attachment regions" or SARs) have been identified in the outer boundaries of the chicken lysozyme locus (Phi-Van et al., 1988, *E.M.B.O.J.* 7: 655-664; Phi-Van, L. and Stratling, W. H., 1996, *Biochem.* 35: 10735-10742). Deletion of a 1.32 kb or a 1.45 kb halves region, each comprising half of a 5' MAR, reduces positional variation in the level of transgene expression (Phi-Van and Stratling, supra).

The 5' matrix-associated region (5' MAR), located about −11.7 kb upstream of the chicken lysozyme transcription start site, can increase the level of gene expression by limiting the positional effects exerted against a transgene (Phi-Van et al., 1988, supra). At least one other MAR is located 3' downstream of the protein encoding region. Although MAR nucleic acid sequences are conserved, little cross-hybridization is seen, indicating significant overall sequence variation. However, MARs of different species can interact with the nucleomatrices of heterologous species, to the extent that the chicken lysozyme MAR can associate with the plant tobacco nucleomatrix as well as that of the chicken oviduct cells (Mlynarona et al., 1994, *Cell* 6: 417-426; von Kries et al., 1990, *Nucleic Acids Res.* 18: 3881-3885).

Gene expression must be considered not only from the perspective of cis-regulatory elements associated with a gene, and their interactions with trans-acting elements, but also with regard to the genetic environment in which they are located. Chromosomal positioning effects (CPEs), therefore, are the variations in levels of transgene expression associated with different locations of the transgene within the recipient genome. An important factor governing CPE upon the level of transgene expression is the chromatin structure around a transgene, and how it cooperates with the cis-regulatory elements. The cis-elements of the lysozyme locus are confined within a single chromatin domain (Bonifer et al., 1996, supra; Sippel et al., pgs. 133-147 in Eckstein F. & Lilley D. M. J. (eds), "Nucleic Acids and Molecular Biology", Vol. 3, 1989, Springer).

The lysozyme promoter region of chicken is active when transfected into mouse fibroblast cells and linked to a reporter gene such as the bacterial chloramphenicol acetyltransferase (CAT) gene. The promoter element is also effective when transiently transfected into chicken promacrophage cells. In each case, however, the presence of a 5' MAR element increased positional independency of the level of transcription (Stief et al., 1989, *Nature* 341: 343-345; Sippel et al., pgs. 257-265 in Houdebine L. M. (ed), "Transgenic Animals: Generation and Use").

The ability to direct the insertion of a transgene into a site in the genome of an animal where the positional effect is limited offers predictability of results during the development of a desired transgenic animal, and increased yields of the expressed product. Sippel and Steif disclose, in U.S. Pat. No. 5,731,178, which is incorporated by reference herein in its entirety, methods to increase the expression of genes introduced into eukaryotic cells by flanking a transcription unit with scaffold attachment elements, in particular the 5' MAR isolated from the chicken lysozyme gene. The transcription unit disclosed by Sippel and Steif was an artificial construct that combined only the −6.1 kb enhancer element and the proximal promoter element (base position −579 to +15) from the lysozyme gene. Other promoter associated elements were not included. However, although individual cis-regulatory elements have been isolated and sequenced, together with short regions flanking DNA, the entire nucleic acid sequence comprising the functional 5' upstream region of the lysozyme gene has not been determined in its entirety and therefore not employed as a functional promoter to allow expression of a heterologous transgene.

Accordingly, vectors of the invention comprise MARs, preferably both 5' and 3' MARs that flank the transgene, including the heterologous protein coding sequences and the regulatory sequences.

5.2.3 Nuclear Localization Signal Peptides

Targeting of the nucleic acids introduced into embryonic cells using methods of the invention may be enhanced by mixing the nucleic acid to be introduced with a nuclear localization signal (NLS) peptide prior to introduction, e.g., microinjection, of the nucleic acid. Nuclear localization signal (NLS) sequences are a class of short amino acid sequences which may be exploited for cellular import of linked cargo into a nucleus. The present invention envisions the use of any NLS peptide, including but not limited to, the NLS peptide of SV40 virus T-antigen.

An NLS sequence of the invention is an amino acid sequence which mediates nuclear transport into the nucleus, wherein deletion of the NLS prevents nuclear transport. In particular embodiments, a NLS is a highly cationic peptide. The present invention envisions the use of any NLS sequence, including but not limited to, SV40 virus T-antigen. NLSs known in the art include, but are not limited to those discussed in Cokol et al., 2000, *EMBO Reports*, 1(5):411-415, Boulikas, T., 1993, *Crit. Rev. Eukaryot. Gene Expr.*, 3:193-227, Collas, P. et al., 1996, *Transgenic Research*, 5: 451-458, Collas and Alestrom, 1997, *Biochem. Cell Biol.* 75: 633-640, Collas and Alestrom, 1998, *Transgenic Resarch*, 7: 303-309, Collas and Alestrom, 1996, *Mol. Reprod. Devel.*, 45:431-438, all of which are incorporated by reference in their entireties.

5.2.4 Codon-Optomized Gene Expression

Another aspect of the present invention provides nucleic acid sequences encoding heterologous polypeptides that are codon-optimized for expression in avian cells, and derivatives and fragments thereof. When a heterologous nucleic acid is to be delivered to a recipient cell for expression therein, the sequence of the nucleic acid sequence may be modified so that the codons are optimized for the codon usage of the recipient species. For example, if the heterologous nucleic acid is transfected into a recipient chicken cell, the sequence of the expressed nucleic acid insert is optimized for chicken codon usage. This may be determined from the codon usage of at least one, and preferably more than one, protein expressed in a chicken cell. For example, the codon usage may be determined from the nucleic acid sequences encoding the proteins ovalbumin, lysozyme, ovomucin and ovotransferrin of chicken. Briefly, the DNA sequence for the target protein may be optimized using the BACKTRANSLATE® program of the Wisconsin Package, version 9.1 (Genetics Computer Group, Inc., Madison, Wis.) with a codon usage table compiled from the chicken (*Gallus gallus*) ovalbumin, lysozyme, ovomucoid, and ovotransferrin proteins. The template and primer oligonucleotides are then amplified, by any means known in the art, including but not limited to PCR with Pfu polymerase (STRATAGENE®, La Jolla Calif.).

In one exemplary embodiment of a heterologous nucleic acid for use by the methods of the present invention, a nucleic acid insert encoding the human interferon α2b polypeptide optimized for codon-usage by the chicken is microinjected into the cytoplasm of a stage 1 embryo. Optimization of the sequence for codon usage is useful in elevating the level of translation in avian eggs.

It is contemplated to be within the scope of the present invention for any nucleic acid encoding a polypeptide to be optimized for expression in avian cells. It is further contemplated that the codon usage may be optimized for a particular avian species used as a source of the host cells. In one embodiment of the present invention, the heterologous polypeptide is encoded using the codon-usage of a chicken.

5.2.5 Specific Vectors of the Invention

In a preferred embodiment, a transgene of the invention comprises a chicken, or other avian, lysozyme control region sequence which directs expression of the coding sequence within the transgene. A series of PCR amplifications of template chicken genomic DNA are used to isolate the gene expression control region of the chicken lysozyme locus. Two amplification reactions used the PCR primer sets 5pLMAR2 (5'-TGCCGCCTTCTTTGATATTC-3') (SEQ ID NO: 1) and LE-6.1kbrev1 (5'-TTGGTGGTAAGGCCTTTTTG-3') (SEQ ID NO: 2) (Set 1) and lys-6.1 (5'-CTGGCAAGCTGT-CAAAAACA-3') (SEQ ID NO: 3) and LysE1Rev (5'-CAGCTCACATCGTCCAAAGA-3') (SEQ ID NO: 4) (Set 2). The amplified PCR products were united as a contiguous isolated nucleic acid by a third PCR amplification step with the primers SEQ ID NOS: 1 and 4, as described in Example 6 below.

The isolated PCR-amplified product, comprising about 12 kb of the nucleic acid region 5' upstream of the native chicken lysozyme gene locus, was cloned into the plasmid pCMV-LysSPIFNMM. pCMV-LysSPIFNMM comprises a modified nucleic acid insert encoding a human interferon α2b sequence and an SV40 polyadenylation signal sequence (SEQ ID NO: 8) 3' downstream of the interferon encoding nucleic acid. The sequence SEQ ID NO: 5 of the nucleic acid insert encoding human interferon α2b was in accordance with avian cell codon usage, as determined from the nucleotide sequences encoding chicken ovomucin, ovalbumin, ovotransferrin and lysozyme.

The nucleic acid sequence (SEQ ID NO: 6) (GenBank Accession No. AF405538) of the insert in pAVIJCR-A115.93.1.2 is shown in FIG. 1A-E. The modified human interferon α2b encoding nucleotide sequence SEQ ID NO: 5 (GenBank Accession No. AF405539) and the novel chicken lysozyme gene expression control region SEQ ID NO: 7 (GenBank Accession No. AF405540), shown in FIGS. 2 and 3A-E respectively. A polyadenylation signal sequence that is suitable for operably linking to the polypeptide-encoding nucleic acid insert is the SV40 signal sequence SEQ ID NO: 8, as shown in FIG. 4.

The plasmid pAVIJR-A115.93.1.2 was restriction digested with enzyme FseI to isolate a 15.4 kb DNA containing the lysozyme 5' matrix attachment region (MAR) and the −12.0 kb lysozyme promoter during the expression of the interferon-encoding insert, as described in Example 7, below. Plasmid pIIIilys was restriction digested with MluI and XhoI to isolate an approximately 6 kb nucleic acids, comprising the 3' lysozyme domain, the sequence of which (SEQ ID NO: 9) is shown in FIG. 5A-C. The 15.4 kb and 6 kb nucleic acids were ligated and the 21.4 kb nucleic acid comprising the nucleic acid sequence SEQ ID NO: 10 as shown in FIG. 6A-J was transformed into recipient STBL4 cells as described in Example 7, below.

The inclusion of the novel isolated avian lysozyme gene expression control region of the present invention upstream of a codon-optimized interferon-encoding sequence in pAVIJCR-A115.93.1.2 allowed expression of the interferon polypeptide in avian cells transfected by cytoplasmic microinjection, as described in Examples 3 and 4, below. The 3' lysozyme domain SEQ ID NO: 9, when operably linked downstream of a heterologous nucleic acid insert, also allows expression of the nucleic acid insert. For example, the nucleic acid insert may encode a heterologous polypeptide such as the α2b interferon encoded by the sequence SEQ ID NO: 5.

It is further contemplated that any nucleic acid sequence encoding a polypeptide may be operably linked to the novel isolated avian lysozyme gene expression control region (SEQ ID NO: 7) and optionally operably linked to the 3' lysozyme domain SEQ ID NO. 9 so as to be expressed in a transfected avian cell. The plasmid construct pAVIJCR-A115.93.1.2 when transfected into cultured quail oviduct cells, which were then incubated for about 72 hours. ELISA assays of the cultured media showed that the transfected cells synthesized a polypeptide detectable with anti-human interferon α2b antibodies. Plasmid construct pAVIJCR-A212.89.2.1 and pAVIJCR-A212.89.2.3 transfected into chicken myelomonocytic HD11 cells yield detectable human α2b interferon, as described in Example 8 below, and shown in FIGS. 8-12.

The isolated chicken lysozyme gene expression control region (SEQ ID NO: 7) for use in the methods of the present invention comprises the nucleotide elements that are positioned 5' upstream of the lysozyme-encoding region of the native chicken lysozyme locus and which are necessary for the regulated expression of a downstream polypeptide-encoding nucleic acid. While not wishing to be bound by any one theory, the inclusion of at least one 5' MAR sequence of or reference element in the isolated control region may confer positional independence to a transfected gene operably linked to the novel lysozyme gene expression control region.

The isolated lysozyme gene expression control region (SEQ ID NO: 7) of the present invention is useful for reducing the positional effect of a transgene operably linked to the lysozyme gene expression control region and transfected into a recipient avian cell. By isolating a region of the avian genome extending from a point 5' upstream of a 5' MAR of the lysozyme locus to the junction between the signal peptide sequence and a polypeptide-encoding region, cis-regulatory elements are also included that may allow gene expression in a tissue-specific manner. The lysozyme promoter region of the present invention, therefore, will allow expression of an operably linked heterologous nucleic acid insert in a transfected avian cell such as, for example, an oviduct cell.

It is further contemplated that a recombinant DNA of the present invention may further comprise the chicken lysozyme 3' domain (SEQ. ID NO: 9) linked downstream of the nucleic acid insert encoding a heterologous polypeptide. The lysozyme 3' domain (SEQ ID NO: 9) includes a nucleic acid sequence encoding a 3' MAR domain that may cooperate with a 5' MAR to direct the insertion of the construct of the present invention into the chromosome of a transgenic avian, or may act independently of the 5' MAR.

Fragments of a nucleic acid encoding a portion of the subject lysozyme gene expression control region may also be useful as an autonomous gene regulatory element that may itself be operably linked to a polypeptide-encoding nucleic acid. Alternatively, the fragment may be combined with fragments derived from other gene promoters, such as an avian ovalbumin or ovomucoid promoter, thereby generating novel promoters having new properties or a combination of properties. As used herein, a fragment of the nucleic acid encoding an active portion of a lysozyme gene expression control region refers to a nucleotide sequence having fewer nucleotides than the nucleotide sequence encoding the entire nucleic acid sequence of the lysozyme gene expression control region, but at least 200 nucleotides.

The present invention also contemplates the use of antisense nucleic acid molecules that are designed to be complementary to a coding strand of a nucleic acid (i.e., complementary to an endogenous DNA or an MRNA sequence) or, alternatively, complimentary to a 5' or 3' untranslated region of the MRNA and therefore useful for regulating the expression of a gene by an avian promoter, including lysozyme or ovomucoid promoters.

Synthesized oligonucleotides can be produced in variable lengths when for example, non-naturally occurring polypeptide sequences are desired. The number of bases synthesized will depend upon a variety of factors, including the desired use for the probes or primers. Additionally, sense or anti-sense nucleic acids or oligonucleotides can be chemically synthesized using modified nucleotides to increase the biological stability of the molecule or of the binding complex formed between the anti-sense and sense nucleic acids. For example, acridine substituted nucleotides can be synthesized. Protocols for designing isolated nucleotides, nucleotide probes, and/or nucleotide primers are well-known to those of ordinary skill, and can be purchased commercially from a variety of sources (e.g., SIGMA GENOSYS®, The Woodlands, Tex. or The Great American Gene Co., Ramona, Calif.).

5.2.6 Recombinant Expression Vectors

A useful application of the novel promoters of the present invention, such as the avian lysozyme gene expression control region (SEQ ID NO: 7) or the MDOT promoter construct (SEQ ID NO: 11, Example 34, below) is the possibility of increasing the amount of a heterologous protein present in a bird, especially a chicken, by gene transfer. In most instances, a heterologous polypeptide-encoding nucleic acid insert transferred into the recipient animal host will be operably linked with a gene expression control region to allow the cell to initiate and continue production of the genetic product protein. A recombinant DNA molecule of the present invention can be transferred into the extra-chromosomal or genomic DNA of the host.

Figure 10:
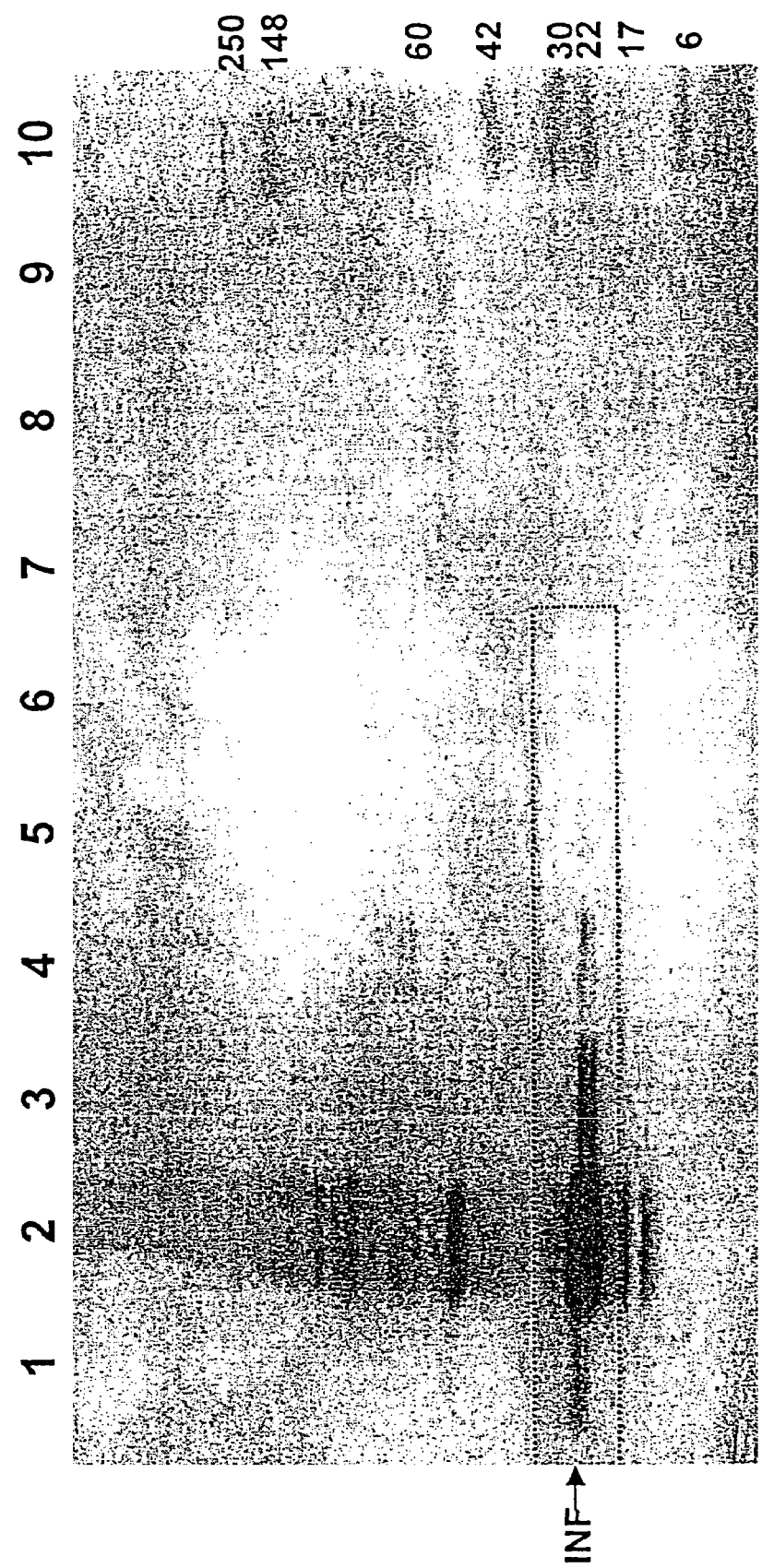
FIG. 10 illustrates the results of SDS-PAGE analysis of human IFN-α2b purified from the pooled egg whites obtained from transgenic chicken AVI-029. 1, molecular weight markers; 2, transferrin/avidin markers; 3, ovalbumin/lysozyme markers; 4, ovoglobulins; 5, pooled egg white; 6, solubilized egg white; 7, cation exchange Pool #1; 8, cation exchange Pool #2; 9, HIC pool.

Expression of a foreign gene in an avian cell permits partial or complete post-translational modification such as, but not only, glycosylation, as shown, for example, in FIGS. 10-12, and/or the formation of the relevant inter- or intra-chain disulfide bonds. Examples of vectors useful for expression in the chicken *Gallus gallus* include pYepSecl (Baldari et al., 1987, *E.M.B.O.J.*, 6: 229-234; incorporated herein by reference in its entirety) and pYES2 (INVITROGEN® Corp., San Diego, Calif.).

The present invention contemplates that the injected cell may transiently contain the injected DNA, whereby the recombinant DNA or expression vector may not be integrated into the genomic nucleic acid. It is further contemplated that the injected recombinant DNA or expression vector may be stably integrated into the genomic DNA of the recipient cell, thereby replicating with the cell so that each daughter cell receives a copy of the injected nucleic acid. It is still further contemplated for the scope of the present invention to include a transgenic animal producing a heterologous protein expressed from an injected nucleic acid according to the present invention.

Heterologous nucleic acid molecules can be delivered to cells using the cytoplasmic microinjection method or any other method of the present invention. The nucleic acid molecule may be inserted into a cell to which the nucleic acid molecule (or promoter coding region) is heterologous (i.e., not normally present). Alternatively, the recombinant DNA molecule may be introduced into cells which normally contain the recombinant DNA molecule or the particular coding region, as, for example, to correct a deficiency in the expression of a polypeptide, or where over-expression of the polypeptide is desired.

Another aspect of the present invention, therefore, is a method of expressing a heterologous polypeptide in an avian cell by transfecting the avian cell with a selected heterologous nucleic acid comprising an avian promoter operably linked to a nucleic acid insert encoding a polypeptide and, optionally, a polyadenylation signal sequence. The transfected cell, which may be an avian embryonic cell microinjected with a heterologous nucleic acid, will generate a transgenic embryo that after introduction into a recipient hen will be laid as a hardshell egg and develop into a transgenic chick.

In another embodiment of the present invention, the nucleic acid insert comprises the chicken lysozyme gene expression control region, a nucleic acid insert encoding a human interferon α2b and codon optimized for expression in an avian cell, and a chicken 3' domain, i.e., downstream enhancer elements.

In one embodiment of the present invention, the transgenic animal is an avian selected from a turkey, duck, goose, quail, pheasant, ratite, and ornamental bird or a feral bird. In another embodiment, the avian is a chicken and the heterologous polypeptide produced under the transcriptional control of the avian promoter is produced in the white of an egg. In yet another embodiment of the present invention, the heterologous polypeptide is produced in the serum of a bird.

5.3 Heterologous Proteins Produced by Transgenic Avians

Methods of the present invention, providing for the production of heterologous protein in the avian oviduct (or other tissue leading to deposition of the protein into the egg) and the production of eggs containing heterologous protein, involve providing a suitable vector coding for the heterologous protein and introducing the vector into embryonic cells such as a single cell embryo such that the vector is integrated into the avian genome. A subsequent step involves deriving a mature transgenic avian from the transgenic embryonic cells produced in the previous steps by transferring the injected cell or cells into the infundibulum of a recipient hen; producing a hard shell egg from that hen; and allowing the egg to develop and hatch to produce a transgenic bird.

A transgenic avian so produced from transgenic embryonic cells is known as a founder. Such founders may be mosaic for the transgene (in certain embodiments, the founder has 5%, 10%, 20%, 30%, 40%, 50%, 60%, 70%, 90%, 100% of the cells containing the transgene. The invention further provides production of heterologous proteins in other tissues of the transgenic avians. Some founders will carry the transgene in the tubular gland cells in the magnum of their oviducts. These birds will express the exogenous protein encoded by the transgene in their oviducts. If the exogenous protein contains the appropriate signal sequences, it will be secreted into the lumen of the oviduct and into the white of an egg.

Some founders are germ-line founders. A germ-line founder is a founder that carries the transgene in genetic material of its germ-line tissue, and may also carry the transgene in oviduct magnum tubular gland cells that express the exogenous protein. Therefore, in accordance with the invention, the transgenic bird may have tubular gland cells expressing the exogenous protein and the offspring of the transgenic bird will also have oviduct magnum tubular gland cells that express the exogenous protein. Alternatively, the offspring express a phenotype determined by expression of the exogenous gene in a specific tissue of the avian. In preferred embodiments, the heterologous proteins are produced from transgenic avians that were not (or the founder ancestors were not) using a eukaryotic viral vector, or a retroviral vector.

The present invention can be used to express, in large yields and at low cost, a wide range of desired proteins including those used as human and animal pharmaceuticals, diagnostics, and livestock feed additives. Proteins such as growth hormones, cytokines, structural proteins and enzymes, including human growth hormone, interferon, lysozyme, and β-casein, are examples of proteins that are desirably expressed in the oviduct and deposited in eggs according to the invention. Other possible proteins to be produced include, but are not limited to, albumin, α-1 antitrypsin, antithrombin III, collagen, factors VIII, IX, X (and the like), fibrinogen, hyaluronic acid, insulin, lactoferrin, protein C, erythropoietin (EPO), granulocyte colony-stimulating factor (G-CSF), granulocyte macrophage colony-stimulating factor (GM-CSF), tissue-type plasminogen activator (tPA), feed additive enzymes, somatotropin, and chymotrypsin. Immunoglobulins and genetically engineered antibodies, including immunotoxins that bind to surface antigens on human tumor cells and destroy them, can also be expressed for use as pharmaceuticals or diagnostics. It is contemplated that immunoglobulin polypeptides expressed in avian cells following transfection by the methods of the present invention may include monomeric heavy and light chains, single-chain antibodies or multimeric immunoglobulins comprising variable heavy and light chain regions, i.e., antigen-binding domains, or intact heavy and light immunoglobulin chains.

5.3.1 Protein Recovery

The protein of the present invention may be produced in purified form by any known conventional technique. For example, chicken cells may be homogenized and centrifuged. The supernatant can then be subjected to sequential ammonium sulfate precipitation and heat treatment. The fraction containing the protein of the present invention is subjected to gel filtration in an appropriately sized dextran or polyacrylamide column to separate the proteins. If necessary, the protein fraction may be further purified by HPLC. In another embodiment, an affinity column is used, wherein the protein is expressed with a tag.

Accordingly, the invention provides proteins that are produced by transgenic avians of the invention. In a preferred embodiment, the protein is produced and isolated from an avian egg. In another embodiment, the protein is produced and isolated from avian serum.

5.3.2 Multimeric Proteins

The invention, in preferred embodiments, provides methods for producing multimeric proteins, preferably immunoglobulins, such as antibodies, and antigen binding fragments thereof.

In one embodiment of the present invention, the multimeric protein is an immunoglobulin, wherein the first and second heterologous polypeptides are an immunoglobulin heavy and light chains respectively. Illustrative examples of this and other aspects and embodiments of the present invention for the production of heterologous multimeric polypeptides in avian cells are fully disclosed in U.S. patent application Ser. No. 09/877,374, filed Jun. 8, 2001, by Rapp, which is incorporated herein by reference in its entirety. In one embodiment of the present invention, therefore, the multimeric protein is an immunoglobulin wherein the first and second heterologous polypeptides are an immunoglobulin heavy and light chain respectively. Accordingly, the invention provides immunoglobulin and other multimeric proteins that have been produced by transgenic avians of the invention.

In the various embodiments of this aspect of the present invention, an immunoglobulin polypeptide encoded by the transcriptional unit of at least one expression vector may be an immunoglobulin heavy chain polypeptide comprising a variable region or a variant thereof, and may further comprise a D region, a J region, a C region, or a combination thereof. An immunoglobulin polypeptide encoded by the transcriptional unit of an expression vector may also be an immunoglobulin light chain polypeptide comprising a variable region or a variant thereof, and may further comprise a J region and a C region. It is also contemplated to be within the scope of the present invention for the immunoglobulin regions to be derived from the same animal species, or a mixture of species including, but not only, human, mouse, rat, rabbit and chicken. In preferred embodiments, the antibodies are human or humanized.

In other embodiments of the present invention, the immunoglobulin polypeptide encoded by the transcriptional unit of at least one expression vector comprises an immunoglobulin heavy chain variable region, an immunoglobulin light chain variable region, and a linker peptide thereby forming a single-chain antibody capable of selectively binding an antigen.

Another aspect of the present invention provides a method for the production in an avian of an heterologous protein capable of forming an antibody suitable for selectively binding an antigen comprising the step of producing a transgenic avian incorporating at least one transgene, wherein the transgene encodes at least one heterologous polypeptide selected from an immunoglobulin heavy chain variable region, an immunoglobulin heavy chain comprising a variable region and a constant region, an immunoglobulin light chain variable region, an immunoglobulin light chain comprising a variable region and a constant region, and a single-chain antibody comprising two peptide-linked immunoglobulin variable regions. Preferably, the antibody is expressed such that it is deposited in the white of the developing eggs of the avian. The hard shell avian eggs thus produced can be harvested and the heterologous polypeptide capable of forming or which formed an antibody can be isolated from the harvested egg. It is also understood that the heterologous polypeptides may also be expressed under the transcriptional control of promoters that allow for release of the polypeptides into the serum of the transgenic animal. Exemplary promoters for non-tissue specific production of a heterologous protein are the CMV promoter and the RSV promoter.

In one embodiment of this method of the present invention, the transgene comprises a transcription unit encoding a first and a second immunoglobulin polypeptide operatively linked to a transcription promoter, a transcription terminator and, optionally, an internal ribosome entry site (IRES)(see, for example, U.S. Pat. No. 4,937,190 to Palmenberg et al., the contents of which is incorporated herein by reference in its entirety).

In an embodiment of this method of the present invention, the isolated heterologous protein is an antibody capable of selectively binding to an antigen. In this embodiment, the antibody may be generated within the serum of an avian or within the white of the avian egg by combining at least one immunoglobulin heavy chain variable region and at least one immunoglobulin light chain variable region, preferably cross-linked by at least one di-sulfide bridge. The combination of the two variable regions will generate a binding site capable of binding an antigen using methods for antibody reconstitution that are well known in the art.

It is, however, contemplated to be within the scope of the present invention for immunoglobulin heavy and light chains, or variants or derivatives thereof, to be expressed in separate transgenic avians, and therefore isolated from separate media including serum or eggs, each isolate comprising a single species of immunoglobulin. polypeptide. The method may further comprise the step of combining a plurality of isolated heterologous immunoglobulin polypeptides, thereby producing an antibody capable of selectively binding to an antigen. In this embodiment, two individual transgenic avians may be generated wherein one transgenic produces serum or eggs having an immunoglobulin heavy chain variable region, or a polypeptide comprising such, expressed therein. A second transgenic animal, having a second transgene, produces serum or eggs having an immunoglobulin light chain variable region, or a polypeptide comprising such, expressed therein. The polypeptides may be isolated from their respective sera and eggs and combined in vitro to generate a binding site capable of binding an antigen.

Examples of therapeutic antibodies that can be used in methods of the invention include but are not limited to HERCEPTIN® (Trastuzumab) (Genentech, Calif.) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); ICM3 is a humanized anti-ICAM3 antibody (ICOS Pharm); IDEC-114 is a primatied anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-β2 antibody (Cambridge Ab Tech).

5.4 Pharmaceutical Compositions

The present invention further provides pharmaceutical compositions, formulations, dosage units and methods of administration comprising the heterologous proteins produced by the transgenic avians using methods of the invention. Preferably, compositions of the invention comprise a prophylactically or therapeutically effective amount of the heterologous protein, and a pharmaceutically acceptable carrier.

The term "carrier" refers to a diluent, adjuvant, excipient, or vehicle with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propyleneglycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in "Remington's Pharmaceutical Sciences" by E. W. Martin.

In a preferred embodiment, the heterologous proteins are formulated in accordance with routine procedures as a pharmaceutical composition adapted for intravenous administration to human beings. Typically, compounds of the invention for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the heterologous protein of the invention is to be administered by infusion, it can be dispensed, for example, with an infusion bottle containing sterile pharmaceutical grade water or saline. Where the composition of the invention is administered by injection, an ampoule of sterile water for injection or saline can be provided so that the ingredients may be mixed prior to administration.

Compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharin, cellulose, magnesium carbonate, etc. Such vehicles are preferably of pharmaceutical grade.

Further, the effect of the heterologous proteins may be delayed or prolonged by proper formulation. For example, a slowly soluble pellet of the compound may be prepared and incorporated in a tablet or capsule. The technique may be improved by making pellets of several different dissolution rates and filling capsules with a mixture of the pellets. Tablets or capsules may be coated with a film which resists dissolution for a predictable period of time. Even the parenteral preparations may be made long-acting, by dissolving or suspending the compound in oily or emulsified vehicles which allow it to disperse only slowly in the serum.

5.5 Transgenic Avians

Another aspect of the present invention concerns transgenic avians, preferably chicken or quail, produced by methods of the invention described in section 5.1 infra, preferably by microinjecting a nucleic acid comprising a transgene into an avian embryo by the cytoplasmic microinjection methods of the present invention. Following introduction of the selected nucleic acid into an early stage avian embryo by the methods of the present invention, the embryo is transferred into the reproductive tract of a recipient hen. The embryo containing the transgene then develops inside the recipient hen and travels through the oviduct thereof, where it is encapsulated by natural egg white proteins and a natural egg shell. The egg is laid and can be incubated and hatched to produce a transgenic chick. The resulting transgenic avian chick (i.e., the G0) will carry one or more desired transgene(s) some or all of its cells, preferably in its germ line. These G0 transgenic avians can be bred using methods well known in the art to generate second generation (i.e., G1s) transgenic avians that carry the transgene, i.e., achieve germline transmission of the transgene. In preferred embodiments, the methods of the invention result in germline transmission, i.e., percentage of G0s that transmit the transgene to progeny (G1s), that is greater than 5%, preferably, greater than 10%, 20%, 30%, 40%, and, most preferably, greater than 50%, 60%, 70%, 80%, 90% or even 100%. In other embodiments, the efficiency of transgenesis (i.e., number of G0s containing the transgene) is greater than 2%. 5%, 10%, 20%, 30%, 40%, 50%, 60%, 70%, 80% or 99%.

Following maturation, the transgenic avian and/or transgenic progeny thereof, may lay eggs containing one or more desired heterologous protein(s) expressed therein and that can be easily harvested therefrom. The G1 chicks, when sexually mature, can then be bred to produce progeny that are homozygous or heterozygous for the transgene.

A transgenic avian of the invention may contain at least one transgene, at least two transgenes, at least 3 transgenes, at least 4 transgenes, at least 5 transgenes, and preferably, though optionally, may express the subject nucleic acid encoding a polypeptide in one or more cells in the animal, such as the oviduct cells of the chicken. In embodiments of the present invention, the expression of the transgene may be restricted to specific subsets of cells, tissues, or developmental stages utilizing, for example, cis-acting sequences that control expression in the desired pattern. Toward this end, it is contemplated that tissue-specific regulatory sequences, or tissue-specific promoters, and conditional regulatory sequences may be used to control expression of the transgene in certain spatial patterns. Moreover, temporal patterns of expression can be provided by, for example, conditional recombination systems or prokaryotic transcriptional regulatory sequences. The inclusion of a 5' MAR region, and optionally the 3' MAR on either end of the sequence, in the expression cassettes suitable for use in the methods of the present invention may allow the heterologous expression unit to escape the chromosomal positional effect (CPE) and therefore be expressed at a more uniform level in transgenic tissues that received the transgene by a route other than through germ line cells.

The transgenes may, in certain embodiments, be expressed conditionally, e.g., the heterologous protein coding sequence is under the control of an inducible promoter, such as a prokaryotic promoter or operator that requires a prokaryotic inducer protein to be activated. Operators present in prokaryotic cells have been extensively characterized in vivo and in vitro and can be readily manipulated to place them in any position upstream from or within a gene by standard techniques. Such operators comprise promoter regions and regions that specifically bind proteins such as activators and repressors. One example is the operator region of the lexA gene of E. coli to which the LexA polypeptide binds. Other exemplary prokaryotic regulatory sequences and the corresponding trans-activating prokaryotic proteins are disclosed by Brent and Ptashne in U.S. Pat. No. 4,833,080 (the contents of which is herein incorporated by reference in its entirety). Transgenic animals can be-created which harbor the subject transgene under transcriptional control of a prokaryotic sequence or other activator sequence that is not appreciably activated by avian proteins. Breeding of this transgenic animal with another animal that is transgenic for the corresponding trans-activator can be used to activate of the expression of the transgene. Moreover, expression of the conditional transgenes can also be induced by gene therapy-like methods wherein a gene encoding the trans-activating protein, e.g., a recombinase or a prokaryotic protein, is delivered to the tissue and caused to be expressed, such as in a cell-type specific manner.

Transactivators in these inducible or repressible transcriptional regulation systems are designed to interact specifically with sequences engineered into the transgene. Such systems include those regulated by tetracycline ("tet systems"), interferon, estrogen, ecdysone, Lac operator, progesterone antagonist RU486, and rapamycin (FK506) with tet systems being particularly preferred (see, e.g., Gingrich and Roder, 1998, Annu. Rev. Neurosci. 21: 377-405; incorporated herein by reference in its entirety). These drugs or hormones (or their analogs) act on modular transactivators composed of natural or mutant ligand-binding domains and intrinsic or extrinsic DNA binding and transcriptional activation domains. In certain embodiments, expression of the heterologous peptidecan be regulated by varying the concentration of the drug or hormone in medium in vitro or in the diet of the transgenic animal in vivo.

In a preferred embodiment, the control elements of the tetracycline-resistance operon of E. coli is used as an inducible or repressible transactivator or transcriptional regulation system ("tet system") for conditional expression of the transgene. A tetracycline-controlled transactivator can require either the presence or absence of the antibiotic tetracycline, or one of its derivatives, e.g., doxycycline (dox), for binding to the tet operator of the tet system, and thus for the activation of the tet system promoter (Ptet).

In a specific embodiment, a tetracycline-repressed regulatable system (TrRS) is used (Agha-Mohammadi and Lotze, 2000, J. Clin. Invest. 105(9): 1177-83; Shockett et al., 1995, Proc. Natl. Acad. Sci. USA 92: 6522-26 and Gossen and Bujard, 1992, Proc. Natl. Acad. Sci. USA 89: 5547-51; incorporated herein by reference in their entireties).

In another embodiment, a reverse tetracycline-controlled transactivator, e.g., rtTA2 S-M2, is used. rtTA2 S-M2 transactivator has reduced basal activity in the absence doxycycline, increased stability in eukaryotic cells, and increased doxycycline sensitivity (Urlinger et al., 2000, Proc. Natl. Acad. Sci. USA 97(14): 7963-68; incorporated herein by reference in its entirety). In another embodiment, the tet-repressible system described by Wells et al. (1999, Transgenic Res. 8(5): 371-81; incorporated herein by reference in its entirety) is used. In one aspect of the embodiment, a single plasmid Tet-repressible system is used. In another embodiment, the GAL4-UAS system (Ornitz et al., 1991, Proc. Natl. Acad. Sci. USA 88:698-702; Rowitch et al., 1999, J. Neuroscience 19(20):8954-8965; Wang et al., 1999, Proc. Natl. Acad. Sci. USA 96:8483-8488; Lewandoski, 2001, Nature Reviews (Genetics) 2:743-755) or a GAL4-VP16 fusion protein system (Wang et al., 1999, Proc. Natl. Acad. Sci. USA 96:8483-8488) is used.

In other embodiments, conditional expression of a transgene is regulated by using a recombinase system that is used to turn on or off the gene's expression by recombination in the appropriate region of the genome in which the potential drug target gene is inserted. The transgene is flanked by recombinase sites, e.g., FRT sites. Such a recombinase system can be used to turn on or off expression a transgene (for review of temporal genetic switches and "tissue scissors" using recombinases, see Hennighausen & Furth, 1999, Nature Biotechnol. 17: 1062-63). Exclusive recombination in a selected cell type may be mediated by use of a site-specific recombinase such as Cre, FLP-wild type (wt), FLP-L or FLPe. Recombination may be effected by any art-known method, e.g., the method of Doetschman et al. (1987, Nature 330: 576-78; incorporated herein by reference in its entirety); the method of Thomas et al., (1986, Cell 44: 419-28; incorporated herein by reference in its entirety); the Cre-loxP recombination system (Sternberg and Hamilton, 1981, J. Mol. Biol. 150: 467-86; Lakso et al., 1992, Proc. Natl. Acad. Sci. USA 89: 6232-36; which are both incorporated herein by reference in their entireties); the FLP recombinase system of Saccharomyces cerevisiae (O'Gorman et al., 1991, Science 251: 1351-55); the Cre-loxP-tetracycline control switch (Gossen and Bujard, 1992, Proc. Natl. Acad. Sci. USA 89: 5547-51, incorporated herein by reference in its entirety); and ligand-regulated recombinase system (Kellendonk et al., 1999, J. Mol. Biol. 285: 175-82; incorporated herein by reference in its entirety). Preferably, the recombinase is highly active, e.g., the Cre-loxP or the FLPe system, and has enhanced thermostability (Rodriguez et al., 2000, Nature Genetics 25: 139-40; incorporated herein by reference in its entirety).

In a specific embodiment, the ligand-regulated recombinase system of Kellendonk et al. (1999, J. Mol. Biol. 285: 175-82; incorporated herein by reference in its entirety) can be used. In this system, the ligand-binding domain (LBD) of a receptor, e.g., the progesterone or estrogen receptor, is fused to the Cre recombinase to increase specificity of the recombinase.

In the case of an avian, a heterologous polypeptide or polypeptides encoded by the transgenic nucleic acid may be secreted into the oviduct lumen of the mature animal and deposited as a constituent component of the egg white into eggs laid by the animal. It is also contemplated to be within the scope of the present invention for the heterologous polypeptides to be produced in the serum of a transgenic avian.

A leaky promoter such as the CMV promoter may be operably linked to a transgene, resulting in expression of the transgene in all tissues of the transgenic avian, resulting in production of, for example, immunoglobulin polypeptides in the serum. Alternatively, the transgene may be operably linked to an avian promoter that may express the transgene in a restricted range of tissues such as, for example, oviduct cells and macrophages so that the heterologous protein may be identified in the egg white or the serum of a transgenic avian. Transgenic avians produced by the cytoplasmic microinjection method of the present invention will have the ability to lay eggs that contain one or more desired heterologous protein(s) or variant thereof.

One embodiment of the present invention, therefore, is a transgenic avian produced by the cytoplasmic microinjection methods of the present invention and having a heterologous polynucleotide sequence comprising a nucleic acid insert encoding a heterologous polypeptide and operably linked to an avian lysozyme gene expression control region, the gene expression control region comprising at least one 5' matrix attachment region, an intrinsically curved DNA region, at least one transcription enhancer, a negative regulatory element, at least one hormone responsive element, at least one avian CR1 repeat element, and a proximal lysozyme promoter and signal peptide-encoding region.

Another embodiment of the present invention provides a transgenic avian further comprising a transgene with a lysozyme 3' domain.

Accordingly, the invention provides transgenic avians produced by methods of the invention, preferably by cytoplasmic microinjection as described infra. In preferred embodiments, the transgenic avian contains a transgene comprising a heterologous peptide coding sequence operably linked to a promoter and, in certain embodiments, other regulatory elements. In more preferred embodiments, the transgenic avians of the invention produce heterologous proteins, preferably in a tissue specific manner, more preferably such that they are deposited in the serum and, most preferably, such that the heterologous protein is deposited into the egg, particularly in the egg white. In preferred embodiments, the transgenic avians produce eggs containing greater than 5 ng, 10 ng, 50 ng, 100 ng, 250 ng, 500 ng, 750 ng, 1 µg, 5 µg, 10 µg, 50 µg, 100 µg, 250 µg, 500 µg, or 750 µg, more preferably greater than 1 mg, 2 mg, 5 mg, 10 mg, 20 mg, 50 mg, 100 mg, 200 mg, 500 mg, 700 mg, 1 gram, 2 grams, 3 grams, 4 grams or 5 grams of the heterologous protein. In preferred embodiments, the transgenic avians produce an immunoglobulin molecule and deposit the immunoglobulin in the egg or serum of the avian, and preferably, the immunoglobulin isolated from the egg or serum specifically binds its cognate antigen. The antibody so produced may bind the antigen with the same, greater or lesser affinity than the antibody produced in a mammalian cell, such as a myeloma or CHO cell.

In specific embodiments, the transgenic avians of the invention were not produced or are not progeny of a transgenic ancestor produced using a eukaryotic viral vector, more particularly, not a retroviral vector (although, in certain embodiments, the vector may contain sequences derived from a eukaryotic viral vector, such as promoters, origins of replication, etc.). The transgenic avians of the invention include G0 avians, founder transgenic avians, G1 transgenic avians, avians containing the transgene in the sperm or ova, avians mosaic for the transgene and avians containing copies of the transgene in most or all of the cells. Contemplated by the invention are transgenic avians in which the transgene is episomal. In more preferred embodiments, the transgenic avians have the transgene integrated into one or more chromosomes. Chromosomal integration can be detected using a variety of methods well known in the art, such as, but not limited to, Southern blotting, PCR, etc.

6. EXAMPLES

The present invention is further illustrated by the following examples. Each example is provided by way of explanation of the invention, and is not intended to be a limitation of the invention. In fact, it will be apparent to those skilled in the art that various modifications, combination, additions, deletions and variations can be made in the present invention without departing from the scope or spirit of the invention. For instance, features illustrated or described as part of one embodiment can be used in another embodiment to yield a still further embodiment. It is intended that the present invention covers such modifications, combinations, additions, deletions and variations as come within the scope of the appended claims and their equivalents.

The contents of all references, published patent applications, and patents cited throughout the present application are hereby incorporated by reference in their entirety.

6.1 Example 1

Cytoplasmic Microinjections (a) Preparation of DNA for microinjection: The plasmid pAVIJCR-A115.93.1.2 (containing the −12.0 kb lysozyme promoter controlling expression of human interferon α2b) was purified with a QIAGEN® Plasmid Maxi Kit (QIAGEN®, Valencia, Calif.), and 100 µg of the plasmid were restriction digested with NotI restriction enzyme. The digested DNA was phenol/CHCl$_3$ extracted and ethanol precipitated. Recovered DNA was resuspended in 1 mM Tris-HCl (pH 8.0) and 0.1 mM EDTA, then placed overnight at 4° C. DNA was quantified by spectrophotometry and diluted to the appropriate concentration. DNA samples which were bound with the SV40 T antigen nuclear localization signal peptide (NLS peptide, amino acid sequence CGGP-KKKRKVG (SEQ ID NO: 12)) were first resuspended in 0.25 M KCl, and NLS peptide was added to achieve a peptide DNA molar ratio of 100:1 (Collas and Alestrom, 1996, *Mol. Reprod. Develop.* 45: 431-438, the contents of which are incorporated by reference in its entirety). The DNA samples were bound to the SV40 T antigen NLS peptide by incubation for 15 minutes.

(b) Cytoplasmic microinjections: The germinal disc of the avian egg was positioned in, and illuminated by the incident light beam, then the micropipette was moved to a position whereby the tip of the micropipette was over the area of the germinal disc and therefore optimally placed for the insertion of the micropipette into the germinal disc. The tip of the micropipette was then pressed onto the vitelline membrane of the avian egg, to a depth of about 20 microns below the general plane of the membrane. The vitelline membrane resisted penetration by the micropipette and therefore the tip indented the vitelline membrane without piercing the membrane. The depth of the indentation formed by the pressure of the tip of the micropipette on the vitelline membrane can be determined by two methods. The micropipette may be premarked about 20 microns from the tip. When the mark is about level with the general plane of the membrane, the tip will enter the germinal disc once the vitelline membrane is penetrated. The distance for the micropipette to be depressed may also be controlled by using the micropipette bevel as reference. In this method, the injection needle penetrates the vitelline membrane up to a point where only the apical end of the opening of the bevel is visible above the vitelline membrane, while the remaining of the opening is located inside the germinal disk. The movement of the micropipette relative to an avian germinal disc is monitored by the obliquely angled macro monitoring unit, comprising a focusable macro lens capable of delivering a focused magnified image of the avian germinal disc to an electronic camera for display by a monitor. The oblique angle of the macro lens shows the depth of movement of the micropipette relative to the vitelline membrane and the degree of indentation thereof, more distinctly than if a vertical microscope objective is used to monitor the microinjection. Pulses of piezo-electric induced oscillations were applied to the micropipette once it was in contact with the indented vitelline membrane. The vibrating tip of the micropipette drills through the vitelline membrane. The fluid contents of the micropipette are then injected into the germinal disc by positive hydraulic pressure exerted on the lumen and the contents therein, by the pressure-regulating system.

Approximately 100 nanoliters of DNA were injected into a germinal disc of stage 1 White Leghorn embryos obtained two hours after oviposition of the previous egg. DNA amounts per injection ranged from 1 nanoliter to 100 nanoliters.

Injected embryos were surgically transferred to recipient hens via ovum transfer according to the method of Christmann et al. (PCT Publication WO 02/20752, the contents of which are incorporated by reference in its entirety), and hard shell eggs were incubated and hatched (Olsen and Neher, 1948, *J. Exp. Zoo.* 109: 355-366).

6.2 Example 2

PCR Analysis of Chick Blood DNA (a) DNA extraction. Whole blood from one-week old chicks was collected with heparinized capillary tubes. Red blood cell (RBC) nuclei were released and washed with lysis buffer solution. DNA's from RBC nuclei were extracted by digestion with proteinase K (1 mg/ml) and precipitated with ethanol. Purified DNA was resuspended in 1 mM Tris-HCl (pH 8.0) and 0.1 mM EDTA and quantitated.

Figure 7:
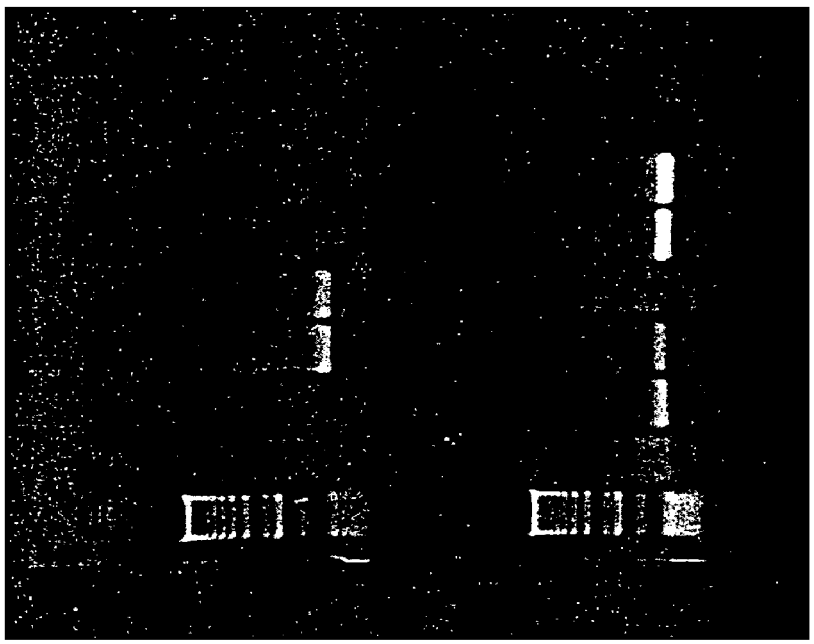

(b) PCR analysis of chick blood DNA. Genomic DNA samples from one-week old chicks were analyzed by PCR using primers LYS051 for (5'-TGCATCCTTCAGCACTTGAG-3')(SEQ ID NO: 13) and IFN-3 (5'-AACTCCTCTTGAGGAAAGCC-3')(SEQ ID NO: 14)). This primer set amplifies a 584 bp region of the transgene carried by the pAVIJCR-A115.93.1.2 plasmid. Three hundred nanograms of genomic DNA were added to a 50 µl reaction mixture (1 ×Promega PCR Buffer with 1.5 mM $MgCl_2$, 200 µM of each dNTP, 5 µM primers) and 1.25 units of Taq DNA polymerase (Promega). The reaction mixtures were heated for 4 minutes at 94° C., and then amplified for 34 cycles at 94° C. for 1 min, 60° C. for 1 min and 72° C. for 1 min. The samples were heated in a final cycle for 4 minutes at 72° C. PCR products were detected on a 0.8% agarose gel with ethidium bromide staining, as shown in FIG. 7.

6.3 Example 3

Human Interferon α2b Expression in Chick Serum

Figure 8:
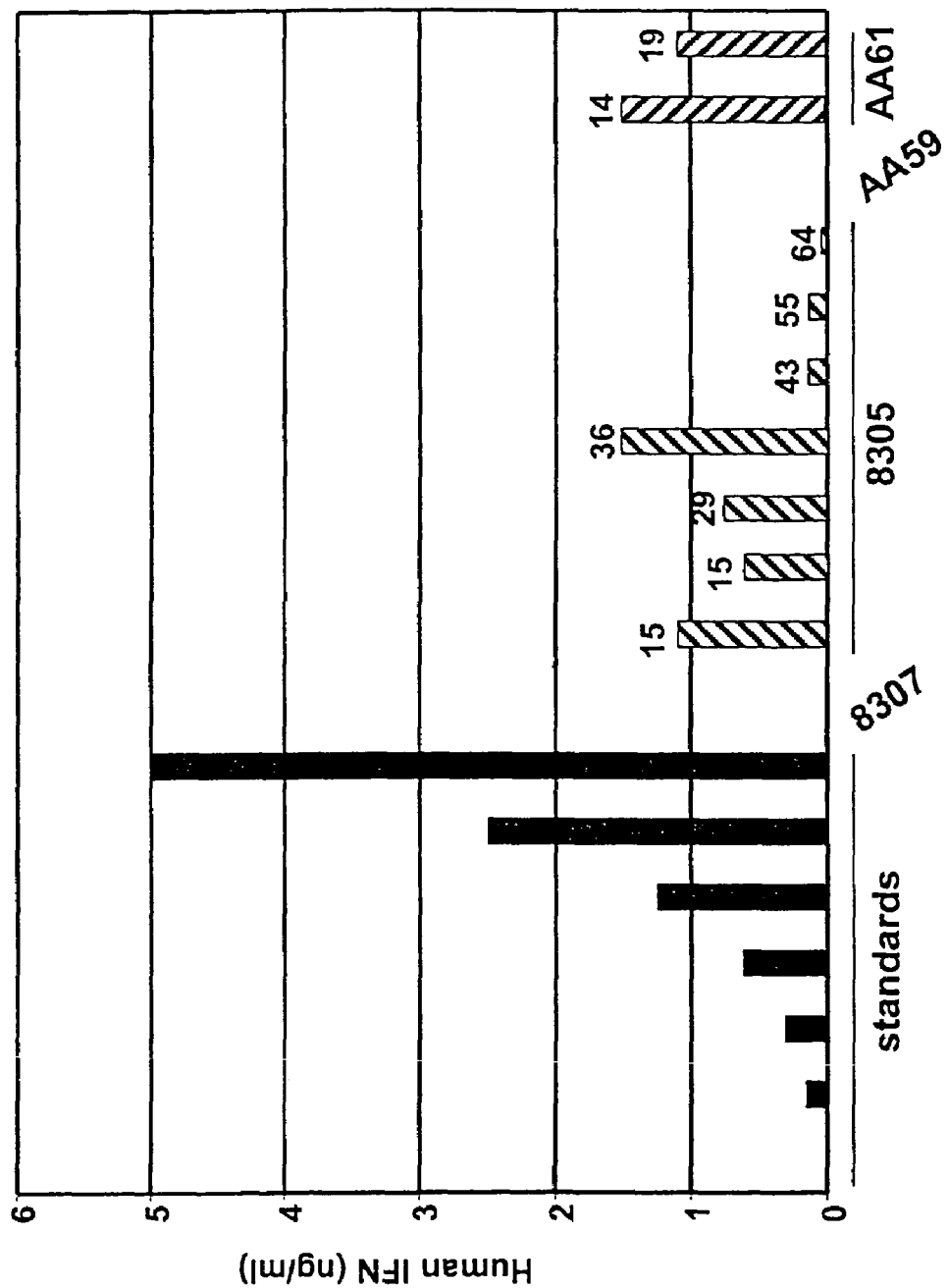
FIG. 8 illustrates the results of ELISA for human IFN α2b in transgenic hen serum. 8307 and AA59 are serum samples collected from negative control birds. Numbers on top of the bars represent the number of days after hatching that the serum was collected.
Figure 9:
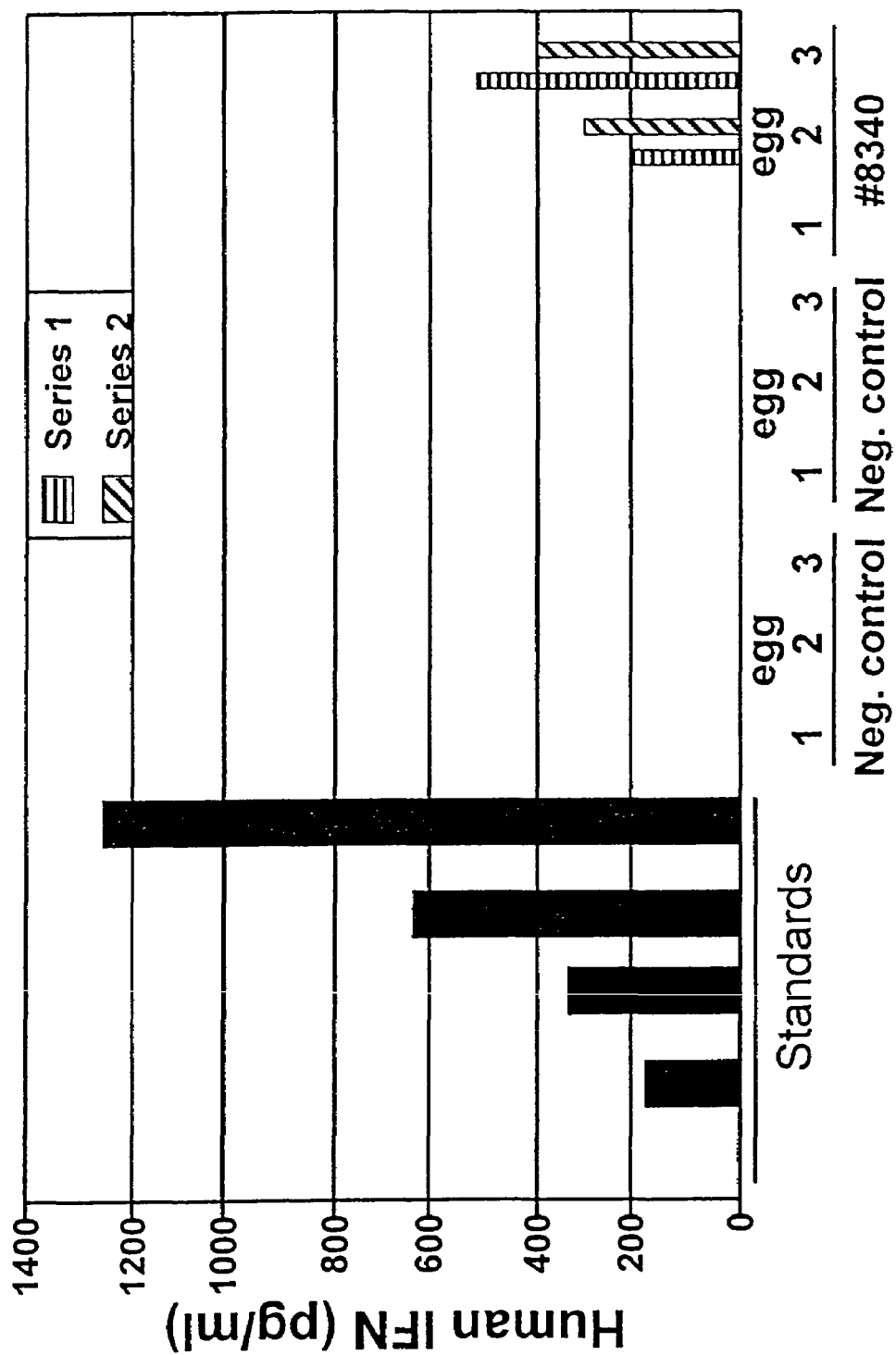
FIG. 9 illustrates the results of ELISA for human IFN α2b in transgenic hen egg white. Three eggs from each hen were assayed.

One week after hatching, blood was collected from chicks using heparinized capillary tubes. Blood was then added to an equal volume of phosphate buffered saline, centrifuged at 200×g, and 100 microliters of the supernatant were assayed by human IFN ELISA (PBL Biomedical Laboratories, New Brunswick, N.J.), as shown in FIGS. 8 and 9.

6.4 Example 4

Human Intereron α2b Expression in Egg White of Transgenic Hens

Once hens have reached sexual maturity and began to lay (approximately 22-24 weeks of age), eggs were collected and the egg whites were assayed by ELISA using human IFN ELISA (PBL Biomedical Laboratories, New Brunswick, N.J.) according to the manufacturer's instructions. The results of PCR and ELISA analysis of blood and egg white are given in Table 1 below that summarizes results of PCR and ELISA analysis.

TABLE 1

Analysis of Transgene Presence and Interferon Expression

| Bird # | Nuclear Signal | Localization | Sex | PCR (Blood) | ELISA (Blood) | ELISA (egg white) |
|---|---|---|---|---|---|---|
| 8305 | −NLS | | M | + | + | NA |
| 8331 | | | F | − | − | + |
| 8340 | −NLS | | F | − | − | + |
| AA123 | +NLS | | F | + | + | NA |
| AA61 | +NLS | | M | + | + | |
| AA105 | +NLS | | F | − | + | |
| AA115 | +NLS | | M | + | − | NA |

−NLS: DNA injected without NLS peptide; +NLS: DNA injected with NLS peptide; NA: not applicable.

As shown in Table 1, one bird (#8305) of 69 produced using microinjection of DNA without the NLS peptide was positive for both the presence of the transgene and the expression of interferon in the blood. Because this bird is a male, he can be bred to a non-transgenic hen to establish germline transmission of the transgene.

FIGS. 8 and 9 demonstrate the expression of human interferon in the blood of #8305, as compared to standards. FIG. 7 illustrates the PCR results from the serum of for several birds, including bird 8305, obtained at different intervals after hatching. As can be seen in lanes 4, 5, 11, and 12 of FIG. 7, positive signal indicated the presence of the transgene at two different collection periods. Other PCR positive bands were seen in birds produced by microinjection of DNA covalently linked to the NLS peptide as described above. Table 1 shows that 4 birds, AA123, AA61, AA105 and AA115, of 43 tested were PCR positive, ELISA positive or both. Expression levels of human IFN in bird AA61, as compared to standards, are also illustrated in FIGS. 8 and 9. PCR-positive male birds can be bred to determine germline transmission, and eggs collected from transgenic females to assay for IFN expression, as described above, as chicks reach sexual maturity

6.5 Example 5

Purification and Identification of Human Interferon-α2b from Transgenic Eggs One hundred eggs were cracked and the egg whites separated from the yolks by manual manipulation and pooled. The pooled egg white was solubilized by adding 3 volumes of deionized water per volume of egg white, followed by adjusting the pH to 5.0 with the drop-wise addition of 1N HCl. The solubilized egg white was clarified by centrifugation at 3750 g for 20 minutes at 4° C.

The solubilized egg white was fractionated by cation exchange chromatography using SP-Sepharose HP. Two chromatographic runs were performed, the first in 50 mM sodium acetate at pH 5.0, the second in 50 mM sodium acetate at pH 4.0. A commercially available ELISA kit specific for human interferon-α was used to identify interferon-containing fractions.

The cation-exchange purified material was further purified by hydrophobic interaction chromatography on Phenyl-Sepharose, with the interferon fraction eluting after the addition of 1M acetic acid, pH 4.5, containing 0.5% triton X-100.

The results of SDS-PAGE and Western Blot analyses of the products at each step of the purification procedure are shown in FIGS. 10 and 11 respectively. A peak of interferon with a molecular weight of approximately 22,000 daltons was seen following the hydrophobic interaction chromatography step. The purity of the interferon at this stage was estimated to be approximately 50%, based on the intensity of staining.

An analysis of the carbohydrate content of the human IFN-α2b purified from the transgenic chicken AVI-029 is shown in FIG. 12. Bands 1, 2 and 3 are the unsialyated, mono- and disialylated saccharides. Sialic acid linkage is alpha 2-3 to galactose and alpha 2-6 to N-acetylgalactosamine. The glycosylation of the human IFN-α2b produced by human cells is compared to that produced in chicken cells, as shown in FIG. 13.

6.6 Example 6

Construction of Lysozyme Promoter Plasmids

The chicken lysozyme gene expression control region was isolated by PCR amplification. Ligation and reamplification of the fragments thereby obtained yielded a contiguous nucleic acid construct comprising the chicken lysozyme gene expression control region operably linked to a nucleic acid sequence optimized for codon usage in the chicken (SEQ ID NO: 5) and encoding a human interferon α2b polypeptide optimized for expression in an avian cell.

White Leghorn Chicken (*Gallus gallus*) genomic DNA was PCR amplified using the primers 5pLMAR2 (SEQ ID NO: 1) and LE-6.1kbrev1 (SEQ ID NO: 2) in a first reaction, and Lys-6.1 (SEQ ID NO: 3) and LysE1rev (SEQ ID NO: 4) as primers in a second reaction. PCR cycling steps were: denaturation at 94° C. for 1 minute; annealing at 60° C. for 1 minute; extension at 72° C. for 6 minutes, for 30 cycles using TAQ PLUS PRECISION DNA polymerase (STRATAGENE®, LaJolla, Calif.). The PCR products from these two reactions were gel purified, and then united in a third PCR reaction using only 5pLMAR2 (SEQ ID NO: 1) and LysE1rev (SEQ ID NO: 4) as primers and a 10-minute extension period. The resulting DNA product was phosphorylated, gel-purified, and cloned into the EcoR V restriction site of the vector pBLUESCRIPT® KS, resulting in the plasmid p12.0-lys.

p12.0-lys was used as a template in a PCR reaction with primers 5pLMAR2 (SEQ ID NO: 1) and LYSBSU (5'-CCCCCCCCTAAGGCAGCCAGGGGCAGGAAGCAAA-3') (SEQ ID NO: 5) and a 10 minute extension time. The resulting DNA was phosphorylated, gel-purified, and cloned into the EcoRV restriction site of pBLUESCRIPT® KS, forming plasmid p12.0lys-B.

p12.0lys-B was restriction digested with Not I and Bsu36 I, gel-purified, and cloned into Not I and Bsu36 I digested pCMV-LysSPIFNMM, resulting in p12.0-lys-LSPIFNMM. p12.0-lys-LSPIFNMM was digested with Sal I and the SalI-toNotI primer (5'-TCGAGCGGCCGC-3') (SEQ ID NO: 16) was annealed to the digested plasmid, followed by Not I digestion. The resulting 12.5 kb Not I fragment, comprising the lysozyme promoter region linked to IFNAGMAX-encoding region and an SV40 polyadenylation signal sequence, was gel-purified and ligated to Not I cleaved and dephosphorylated pBLUESCRIPT® KS, thereby forming the plasmid pAVIJCR-A115.93.1.2, which was then sequenced.

6.7 Example 7

Construction of Plasmids which Contain the 3' Lysozyme Domain

The plasmid pAVIJCR-A115.93.1.2 was restriction digested with FseI and blunt-ended with T4 DNA polymerase. The linearized, blunt-ended pAVIJCR-A115.93.1.2 plasmid was then digested with XhoI restriction enzyme, followed by treatment with alkaline phosphatase. The resulting 15.4 kb DNA band containing the lysozyme 5' matrix attachment region (MAR) and –12.0 kb lysozyme promoter driving expression of a human interferon was gel purified by electroelution.

The plasmid pIIIilys was restriction digested with MluI, then blunt-ended with the Klenow fragment of DNA polymerase. The linearized, blunt-ended pIIIilys plasmid was digested with XhoI restriction enzyme and the resulting 6 kb band containing the 3' lysozyme domain from exon 3 to the 3' end of the 3' MAR was gel purified by electroelution. The 15.4 kb band from pAVIJCR-A115.93.1.2 and the 6 kb band from pIIIilys were ligated with T4 DNA ligase and transformed into STBL4 cells (Invitrogen Life Technologies, Carlsbad, Calif.) by electroporation. The resulting 21.3 kb plasmids from two different bacterial colonies were named pAVIJCR-A212.89.2.1 and pAVIJCR-A212.89.2.3 respectively.

6.8 Example 8

Transfection of Chicken HD11 Cells with pAVIJCR-A212.89.2.1 and pAVIJCR-A212.89.2.3

Chicken cells transfected with plasmids having the 3' lysozyme domain linked to a nucleic acid expressing human α2b interferon express the heterologous polypeptide. Chicken myelomonocytic HD11 cells were transfected with plasmid pAVIJCR-A212.89.2.1 and pAVIJCR-A212.89.2.3 to test the functionality of the plasmids. One million HD11 cells were plated per each well of a 24-well dish. The next day, HD11 cells were transfected with 1 μg of plasmid DNA per 4 μl of LIPOFECTAMINE 2000 (Invitrogen Life Technologies). For comparison, independent wells were also transfected with the parent vector pAVIJCR-A115.93.1.2. After 5 hours of transfection, the cell medium was changed with fresh medium. 48 hours later, cell medium was harvested by centrifugation at 110×g for 5 min and assayed for human interferon by ELISA (PBL Biomedicals, Flanders, N.J.).

The transfected cells expressed the heterologous human α2b interferon at least to the level seen with a plasmid not having the 3' lysozyme domain operably linked to the human α2b interferon encoding nucleic acid.

6.9 Example 9

Cytoplasmic Microelectroporation

The application of electrical current has been shown to enhance the uptake of exogenous DNA fragments by cultured cells. The DNA fragments will be injected into the germinal disk according to the above-described methods. Enhancement of nuclear uptake of the heterologous DNA will promote earlier chromosomal integration of the exogenous DNA molecules, thus reducing the degree of genetic mosaicism observed in transgenic avian founders.

A sample of nucleic acid will be microinjected into the cytoplasm of a recipient stage 1 avian cell, and delivered to a recipient cell nucleus by microelectroporation. In a system suitable for use in microelectroporating early stage avian cells, a cathode will be located within the lumen of the DNA delivery micropipette. Another possible location for the electrode is on the exterior surface of the micropipette. For either option, the electrode is situated close or adjacent to the exit orifice of the pipette so that the electrode and the micropipette may be introduced into the recipient cell together. Alternatively, the micropipette will be introduced into the cytoplasm and used to guide a cathode to make electrical contact with the cytoplasm of the targeted cell.

The placement of the anode is optional. In one arrangement of the electrodes of the microelectroporation system, the anode is located on the micropipette and, therefore, will enter the cell or cells with the micropipette and the cathode. In another arrangement, an anode is in electrical contact with the Ringers solution that will surround the targeted recipient early stage avian cell. In yet another version, the anode is individually positioned within the cytoplasm, or the nucleus, of the recipient stage 1 cell. The anode and cathode are electrically connected to an electrical impulse generator capable of delivering a timed electrical pulse to the electrodes. One suitable apparatus for generating a timed electrical pulse according to the present invention is a Kation Scientific Iontaphorsis pump BAB-500.

A solution of a selected nucleic acid will be microinjected through the inserted micropipette into the recipient cell according to the protocols described in the examples above. The recipient cell will be pulsed at least once with about 0.1 to about 20.0 microamps for about 0.1 to about 60 secs.

This novel intracellular DNA microelectroporation method will enhance the efficiency of transgenesis, increase the efficiency of chromosomal integration of heterologous transgenic DNA, and reduce mosaicism of the transgenic founder animal by ensuring that more recipient cells receive and incorporate the nucleic acid at each delivery to a cell than is the case with non-electroporated microinjection.

6.10 Example 10

Construction of an ALV-Based Vector Having β-Lactamase Encoding Sequences

The lacZ gene of pNLB, a replication-deficient avian leukosis virus (ALV)-based vector (Cosset et al., 1991, *J. Virol.* 65: 3388-94), was replaced with an expression cassette consisting of a cytomegalovirus (CMV) promoter and the reporter gene β-lactamase (β-La or BL).

To efficiently replace the lacZ gene of pNLB with a transgene, an intermediate adaptor plasmid was first created, pNLB-Adapter. pNLB-Adapter was created by inserting the chewed back ApaI/ApaI fragment of pNLB (Cosset et al., 1991, *J. Virol.* 65:3388-94) (in pNLB, the 5' ApaI sites reside 289 bp upstream of lacZ and the 3' ApaI sites reside 3' of the 3' LTR and Gag segments) into the chewed-back KpnI/SacI sites of pBLUESCRIPT®KS(−). The filled-in MluI/XbaI fragment of pCMV-BL (Moore et al., 1997, *Anal. Biochem.* 247: 203-9) was inserted into the chewed-back KpnI/NdeI sites of pNLB-Adapter, replacing lacZ with the CMV promoter and the BL gene (in pNLB, KpnI resides 67 bp upstream of lacZ and NdeI resides 100 bp upstream of the lacZ stop codon), thereby creating pNLB-Adapter-CMV-BL. To create pNLB-CMV-BL, the HindIII/BlpI insert of pNLB (containing lacZ) was replaced with the HindIII/BlpI insert of pNLB-Adapter-CMV-BL. This two step cloning was necessary because direct ligation of blunt-ended fragments into the HindIII/BlpI sites of pNLB yielded mostly rearranged subclones, for unknown reasons.

6.11 Example 11

Production of Transduction Particles Having an ALV-Based Vector Having β-Lactamase Encoding Sequences Sentas and Isoldes were cultured in F10 (GIBCO®), 5% newborn calf serum (GIBCO®), 1% chicken serum (GIBCO®), 50 µg/ml phleomycin (Cayla Laboratories) and 50 µg/ml hygromycin (SIGMA®). Transduction particles were produced as described in Cosset et al., 1991, herein incorporated by reference, with the following exceptions. Two days after transfection of the retroviral vector pNLB-CMV-BL (from Example 10, above) into $9 \times 10^5$ Sentas, virus was harvested in fresh media for 6-16 hours and filtered. All of the media was used to transduce $3 \times 10^6$ Isoldes in three 100 mm plates with polybrene added to a final concentration of 4 µg/ml. The following day the media was replaced with media containing 50 µg/ml phleomycin, 50 µg/ml hygromycin and 200 µg/ml G418 (SIGMA®). After 10-12 days, single G418$^r$ colonies were isolated and transferred to 24-well plates. After 7-10 days, titers from each colony was determined by transduction of Sentas followed by G418 selection. Typically 2 out of 60 colonies gave titers at $1-3 \times 10^5$. Those colonies were expanded and the virus concentrated to $2-7 \times 10^7$ as described in Allioli et al., 1994, *Dev. Biol.* 165:30-7, herein incorporated by reference. The integrity of the CMV-BL expression cassette was confirmed by assaying for β-lactamase in the media of cells transduced with NLB-CMV-BL transduction particles.

6.12 Example 12

Production of Chickens Transgenic for β-Lactamase

Stage X embryos in freshly laid eggs were transduced with NLB-CMV-BL transduction particles (from Example 11, above) as described in Thoraval et al., 1995, *Transgenic Res.* 4:369-377, herein incorporated by reference, except that the eggshell hole was covered with 1-2 layers of eggshell membrane and, once dry, DUCO® model cement.

Approximately 120 White Leghorns were produced by transduction of the stage X embryos with NLB-CMV-BL transduction particles. These birds constitute chimeric founders, not fully transgenic birds. Extensive analysis of DNA in the blood and sperm from the transduced chickens indicates that 10-20% of the birds had detectable levels of the transgene in any given tissue. Of those birds carrying the transgene, approximately 2-15% of the cells in any given tissue were actually transgenic.

6.13 Example 13

β-Lactamase Activity Assay in Blood and Egg White

When hens produced in Example 12, above, began to lay eggs, the egg whites of those eggs were assayed for the presence of β-lactamase. The β-lactamase assay was carried out as described in Moore et al., 1997, *Anal. Biochem.* 247: 203-9, herein incorporated by reference, with the following modifications.

To assay blood from two to ten day old chicks, the leg vein was pricked with a scalpel. 50 µl of blood was collected in a heparinized capillary tube (Fisher), of which 25 µl was transferred to 100 µl phosphate-buffered saline (PBS) in a 96-well plate. Various dilutions of purified 0-lactamase (CALBIOCHEM®) was added to some wells prior to addition of blood from control (non-transduced) chicks to establish a β-lactamase standard curve. After one day at 4° C., the plate was centrifuged for 10 minutes at 730×g. 25 µl of the supernatant was added to 75 µl of PBS. 100 µl of 20 µM 7-(thienyl-2-acetamido)-3-[2-(4-N,N-dimethylaminophenylazo)pyridinium-methyl]-3-cephem-4-carboxylic acid (PADAC, from CALBIOCHEM®) in PBS was added, and the wells were read immediately on a plate reader in a 10 minute kinetic read at 560 nm or left overnight in the dark at room temperature. Wells were scored positive if the well had turned from purple to yellow. To assay blood from older birds, the same procedure was followed except that 200-300 µl blood was drawn from the wing vein using a syringe primed with 50 µl of heparin (SIGMA®).

Analysis of the NLB-CMV-BL transduced flock revealed nine chickens that had significant levels of β-lactamase in their blood. Three of these chickens were males and these were the only three males that had significant levels of the NLB-CMV-BL transgene in their sperm as determined by PCR analysis. Thus, these are the males to be out bred to obtain fully transgenic $G_1$ offspring. The other six chickens were the hens that expressed β-lactamase in their magnum tissue (see below). Other birds had low levels of β-lactamase (just above the level of detection) in their blood but did not have transgenic sperm or eggs containing β-lactamase. Thus β-lactamase expression in blood is a strong indicator of whether a chicken was successfully transduced.

To assay β-iactamase in egg white, fleshly laid eggs were transferred that day to a 4° C. cooler, at which point the β-lactamase is stable for at least one month. (Bacterially-expressed, purified β-lactamase added to egg white was determined to lose minimal activity over several weeks at 4° C., confirming the stability of β-lactamase in egg white.) To collect egg white samples, eggs were cracked onto plastic wrap. The egg white was pipetted up and down several times to mix the thick and thin egg whites. A sample of the egg white was transferred to a 96-well plate. 10 µl of the egg white sample was transferred to a 96-well plate containing 100 µl of PBS supplemented with 1.5 µl of 1 M $NaH_2PO_4$, pH 5.5 per well. After addition of 100 µl of 20 µM PADAC, the wells were read immediately on a plate reader in a 10 minute or 12 hour kinetic read at 560 nm. Various dilutions of purified β-lactamase was added to some wells along with 10 µl of egg white from control (non-transduced) hens to establish a β-lactamase standard curve. Egg white from both untreated and NLB-CMV-BL transduced hens were assayed for the presence of β-lactamase.

Significant levels of β-lactamase were detected in the egg white of six hens, as shown in Table 2, below. Eggs laid by Hen 1522, the first hen to demonstrate expression in eggs, have 0.3 mg or higher of active β-lactamase per egg. Also shown is β-lactamase production from three other NLB-CMV-BL transduced hens (Hen 1549, Hen 1790 and Hen 1593). Every hen that laid eggs containing β-lactamase also had significant levels of β-lactamase in its blood.

TABLE 2

Expression of β-lactamase in eggs of NLB-CMV-BL treated hens.

| Hen # | Average mg of β-lactamase per egg | # of eggs assayed |
|---|---|---|
| Control | 0.1± 0.07 | 29 |
| 1522 | 0.31 ± 0.07 | 20 |
| 1549 | 0.96 ± 0.15 | 22 |
| 1581 | 1.26 ± 0.19 | 12 |
| 1587 | 1.13 ± 0.13 | 15 |
| 1790 | 0.68 ± 0.15 | 13 |
| 1793 | 1.26 ± 0.18 | 12 |

Controls were eggs from untreated hens. The low level of BL in these eggs was due to spontaneous breakdown of PADAC during the course of the kinetic assay. The other hens were transduced with NLB-CMV-BL as described in Example 12. Egg white from each egg was assayed in triplicate.

Based on the β-lactamase activity assay, the expression levels of β-lactamase appeared to range from 0.1 to 1.3 mg per egg (assuming 40 milliliters of egg white per egg). However, these assay quantities were significantly less than the quantities obtained by western blot assay and were determined to be deceptively lower than the true values. The difference in results between the enzymatic activity assay and a western blot analysis was due to a β-lactamase inhibitor in egg white. The activity of purified β-lactamase was inhibited by egg white such that 50 µl of egg white in a 200 µl reaction resulted in nearly 100% inhibition, whereas 10 µl of egg white in a 200 µl reaction resulted in only moderate inhibition. Furthermore, spontaneous breakdown of the enzymatic substrate, PADAC, during the course of the assay also contributed to the erroneously low calculation of β-lactamase concentration.

6.14 Example 14

Isolation and Ex Vivo Transfection of Blastodermal Cells

Donor blastodermal cells are isolated from fertilized eggs of Barred Plymouth Rock hens using a sterile annular ring of Whatman filter paper which is placed over a blastoderm and lifted after cutting through the yolk membrane of the ring. The ring bearing the attached blastoderm is transferred to phosphate-buffered saline (PBS) in a petri dish ventral side up, and adhering yolk is removed by gentle pipetting. The area opaca is dissected away with a hair loop and the translucent stage X blastoderm is transferred via a large-bore pipette tip to a microfuge tube. About 30,000-40,000 cells are isolated per blastoderm and for a typical experiment 10 blastoderms are collected.

Cells are dispersed by brief trypsin (0.2%) digestion, washed once by low speed centrifugation in Dulbecco's modified Eagle's medium (DMEM) and then transfected with linearized plasmids via lipofectin (16 mg/200 ml, BRL) for 3 hours at room temperature. Cells are washed free of lipofectin with medium and then 400-600 cells are injected into γ-irradiated (650 rads) recipient stage X embryos from the Athens-Canadian randombred line (AC line). Injection is through a small window (~0.5 cm) into the subgerminal cavity beneath the recipient blastoderms. Windows are sealed with fresh egg shell membrane and DUCO® plastic cement. Eggs are then incubated at 39.1° C. in a humidified incubator with 90° rotation every 2 hr.

6.15 Example 15

Identification of Transgenic Mosaics by PCR Assay

Among the chicks which hatch from embryos containing transfected or transduced blastodermal cells, only those exhibiting Barred Plymouth Rock feather mosaicism are retained. Even if no reporter gene is present in the transgene, transgenic mosaics can be identified by PCR assay.

To identify transgenic mosaics, DNA blood and black feather pulp of individual chicks are assayed by PCR for the presence of the transgene using a primer pair specific to the transgene as described by Love et al., 1994, *Bio/Technology* 12:60-63. Transgene chimeras are induced, withdrawn and re-induced with diethylstilbestrol (DES) pellets and excised magnums analyzed for expression of reporter activity. Blood and liver are assayed to monitor tissue specificity.

Male and female blood DNA was collected at 10 to 20 days post-hatch. Blood is drawn from a wing vein into a heparinized syringe and one drop is immediately dispensed into one well of a flat-bottom 96-well dish containing a buffer which lyses cytoplasmic membranes exclusively. The plate is then briefly centrifuged, which pellets the nuclei. The supernatant is removed and a second lysis buffer is added which releases genomic DNA from nuclei and degrades nucleases. The DNA is ethanol precipitated in the plate, washed with 70% ethanol, dried and resuspended in 100 μl of water per well. As much as 80 μg of DNA suitable for PCR and TAQMAN™ (Perkin Elmer/Applied Biosystems) analysis can be obtained from one drop (8 μl) of chick blood.

The isolated DNA is tested for the presence of the transgenes using the TAQMAN® sequence detection assay to evaluate the efficiency of the embryo transduction process. The TAQMAN® sequence detection system allows the direct detection of a specific sequence. A fluorescently-labeled oligonucleotide probe complementary to an internal region of a desired PCR product only fluoresces when annealed to the desired PCR product, which in this case is complementary to the transgene. Because all of the detection occurs in the PCR tube during the cycling process, the TAQMAN® system allows high-throughput PCR (no gel electrophoresis is need) as well as sequence detection analogous to and as sensitive as Southern analysis. 1 μl of the isolated DNA, which contains 600-800 ng of DNA, is used for the TAQMAN® reaction. Each reaction contains two sets of primer pairs and TAQMAN® probes. The first set detects the chicken glyceraldehyde 3-phosphate dehydrogenase gene (GAPDH) and is used as an internal control for the quality of the genomic DNA and also serves as a standard for quantitation of the transgene dosage. The second set is specific for the desired transgene. Fluorescence is detected in a dissecting stereomicroscope equipped with epifluorescence detection. The two TAQMAN® probes are attached to different dyes that fluoresce at unique wavelengths: thus both PCR products are detected simultaneously in an ABI/PE 7700 Sequence Detector. It is estimated that up to 180 birds will hatch, and 20% (36 birds) will contain the transgene in their blood.

6.16 Example 16

Production of Fully Transgenic $G_1$ Chickens Expressing β-Lactamase

Males are selected for breeding as a single male can give rise to 20 to 30 $G_1$ offspring per week as opposed to 6 $G_1$ offspring per female per week, thereby speeding the expansion of $G_1$ transgenics. The feed of $G_0$ males is supplemented with sulfamethazine, which accelerates the sexual maturation of males such that they can start producing sperm at 10-12 weeks of age instead of 20-22 weeks without influencing their health or fertility.

Sperm DNA of all males are screened for the presence of the transgene. Sperm are collected and the DNA extracted using Chelex-100. Briefly, 3 μl of sperm and 200 μl of 5% Chelex-100 are mixed, followed by addition of 2 μl of 10 mg/ml proteinase K and 7 μl of 2 M DTT. Samples are incubated at 56° C. for 30-60 minutes. Samples are boiled for 8 minutes and vortexed vigorously for 10 seconds. After centrifugation at 10 to 15 kG for 2-3 minutes, the supernatant is ready for PCR or TAQMAN® analysis. The DNAs are analyzed by the TAQMAN® assay using a TAQMAN® probe and primers complementary to the transgene. Of the 90 $G_0$ males, it is estimated that 5%, or 4 to 5, will have the transgene in their sperm DNA.

As noted above in Example 13, the NLB-CMV-BL transduced flock included three males that had significant levels of the NLB-CMV-BL transgene in their sperm as determined by PCR analysis. Thus, these males are chosen for further breeding to obtain fully transgenic $G_1$ offspring.

By breeding germline transgenic males to 90 non-transgenic White Leghorn females per week, about 16 $G_1$ offspring per week will be obtained. Hatched chicks are vent-sexed and screened for the presence of the transgene in their blood DNA by the TAQMAN® assay. Twenty male and female $G_1$ transgenics will be obtained or 40 total, which will take up to 3 weeks.

Males will be kept for farther breeding and females tested for expression of transgenes in the egg.

6.17 Example 17 pNLB-CMV-IFN Vector Having an IFN Encoding Sequence

The DNA sequence for human interferon α2b based on hen oviduct optimized codon usage was created using the BACK-TRANSLATE program of the Wisconsin Package, version 9.1 (Genetics Computer Group. Inc., Madison, Wis.) with a codon usage table compiled from the chicken (*Gallus gallus*) ovalbumin, lysozyme, ovomucoid, and ovotransferrin proteins. The template and primer oligonucleotides (SEQ ID NOS: 17-34) shown in FIG. 15A-B were amplified by PCR with Pfu polymerase (STRATAGENE®, La Jolla, Calif.) using 20 cycles of 94° C. for 1 min., 50° C. for 30 sec., and 72° C. for 1 min. and 10 sec.

PCR products were purified from a 12% polyacrylamide-TBE gel by the "crush and soak" method (Maniatis et al. 1982), then combined as templates in an amplification reaction using only IFN-1 (SEQ ID NO: 24) and IFN-8 (SEQ ID NO: 34) as primers. The resulting PCR product was digested with Hind III and Xba I and gel purified from a 2% agarose-TAE gel, then ligated into Hind III and Xba I digested, alkaline phosphatase-treated, pBLUESCRIPT® KS (STRATAGENE®), resulting in the plasmid pBluKSP-IFNMagMax. Both strands were sequenced by cycle sequencing on an ABI PRISM 377 DNA Sequencer (Perkin-Elmer, Foster City, Calif.) using universal T7 or T3 primers. Mutations in pBluKSP-IFN derived from the original oligonucleotide templates were corrected by site-directed mutagenesis with the Transformer Site-Directed Mutagenesis Kit (Clontech, Palo Alto, Calif.). The interferon coding sequence was then removed from the corrected pBluKSP-IFN with Hind III and Xba 1, purified from a 0.8% agarose-TAE Gel, and ligated to Hind III and Xba I digested, alkaline phosphatase-treated pCMV-BetaLa-3B-dH. The resulting plasmid was pCMV-IFN which contained IFN coding sequence controlled by the cytomegalovirus immediate early promoter/enhancer and SV40 polyA site.

To clone the IFN coding sequence controlled by the CMV promoter/enhancer into the NLB retroviral plasmid, pCMV-IFN was first digested with ClaI and XbaI, then both ends were filled in with Klenow fragment of DNA polymerase (New England BioLabs, Beverly, Mass.). pNLB-adapter was digested with Nde I and Kpn I, and both ends were made blunt by T4 DNA polymerase (New England BioLabs). Appropriate DNA fragments were purified on a 0.8% agarose-TAE gel, then ligated and transformed into DH5α cells. The resulting plasmid was pNLB-adapter-CMV-IFN.

This plasmid was then digested with Mlu I and partially digested with Blp I and the appropriate fragment was gel purified. pNLB-CMV-EGFP was digested with Mlu I and Blp I, then alkaline-phosphatase treated and gel purified. The Mlu I/Blp I partial fragment of pNLB-adapter-CMV-IFN was ligated to the large fragment derived from the Mlu I/Blp I digest of pNLB-CMV-EGFP, creating pNLB-CMV-IFN.

6.18 Example 18

Production of pNLB-CMV-IFN Transduction Particles

Senta packaging cells (Cosset et al., 1991) were plated at a density of $3 \times 10^5$ cells/35 mm tissue culture dish in F-10 medium (Life Technologies) supplemented with 50% calf serum (Atlanta Biologicals), 1% chicken serum (Life Technologies), 50 µg/ml hygromycin (SIGMA®), and 50 µg/ml phleomycin (CAYLA, Toulouse, France). These cells were transfected 24 h after plating with 2 µg of CsCl-purified pNLB-CMV-IFN DNA and 6 µl of Lipofectin liposomes (Life Technologies) in a final volume of 500 µl Optimem (Life Technologies). The plates were gently rocked for four hours at 37° C. in a 5% $CO_2$ incubator. For each well, the media was removed, washed once with 1 ml of Optimem and re-fed with 2 mls of F-10 medium supplemented with 50% calf serum, 1% chicken serum, 50 µg/ml hygromycin, and 50 µg/ml phleomycin. The next day, medium from transfected Sentas was recovered and filtered through a 0.45 micron filter.

This medium was then used to transduce Isolde cells. 0.3 ml of the filtered medium recovered from Senta cells was added to 9.6 ml of F-10 (Life Technologies) supplemented as described above, in addition to polybrene (SIGMA®) at a final concentration of 4 µg/ml. This mixture was added to $10^6$ Isolde packaging cells (Cosset et al., 1991) plated on a 100 mm dish the previous day, then replaced with fresh F-10 medium (as described for Senta growth) 4 hours later.

The next day, the medium was replaced with fresh medium which also contained 200 µg/ml neomycin (G418, SIGMA®). Every other day, the medium was replaced with fresh F-10 medium supplemented with 50% calf serum, 1% chicken serum, 50 µg/ml hygromycin, 50 µg/ml phleomycin, and 200 µg/ml neomycin. Eleven to twelve days later, single colonies were visible by eye, and these were picked and placed into 24 well dishes. When some of the 24 well dishes became confluent, medium was harvested and titered to determine the cell lines with the highest production of retrovirus.

Titering was performed by plating $7.5 \times 10^4$ Senta cells per well in 24 well plates on the day prior to viral harvest and transduction. The next day 1 ml of fresh F-10 medium supplemented with 50% calf serum, 1% chicken serum, 50 µg/ml hygromycin, and 50 µg/ml phleomycin was added to each well of the isolated Isolde colonies. Virus was harvested for 8-10 hours. The relative density of each well of Isoldes was noted. After 8-10 hours, 2 and 20 µl of media from each well of Isoldes was added directly to the media of duplicate wills of the Sentas. Harvested medium was also tested for the presence of interferon by IFN ELISA and for interferon bioreactivity. The next day the media was replaced with F-10 medium supplemented with 50% calf serum, 1% chicken serum, 50 µg/ml hygromycin, 50 µg/ml phleomycin, and 200 µg/ml neomycin. When obvious neomycin-resistant colonies were evident in the wells of transduced Sentas, the number of colonies was counted for each well.

The Isolde colony producing the highest titer was determined by taking into account the number of colonies and correcting for the density of the Isolde cells when the viral particles were harvested (i.e., if two Isolde colonies gave rise to media with the same titer, but one was at a 5% density and the other was at a 50% density at the time of viral harvest, the one at the 5% density was chosen for further work, as was the case in the present example).

The Isolde cell line producing the highest titer of IFN-encoding transducing particles was scaled up to six T-75 tissue culture flasks. When flasks were confluent, cells were washed with F-10 medium (unsupplemented) and transducing particles were then harvested for 16 hours in 14 ml/flask of F-10 containing 1% calf serum (Atlanta Biologicals) and 0.2% chicken serum (Life Technologies). Medium was harvested, filtered through a 0.45 micron syringe filter, then centrifuged at 195,000×g in a Beckman 60Ti rotor for 35 min. Liquid was removed except for 1 ml, and this was incubated with the pellet at 37° C. with gentle shaking for one hour. Aliquots were frozen at −70° C. Transducing particles were then titered on Senta cells to determine concentrations used to inject embryos.

6.19 Example 19

Production of Chimeric Transgenic Chickens

Approximately 300 White Leghorn (strain Line 0) eggs were windowed according to the Speksnijder procedure described in U.S. Pat. No. 5,897,998, incorporated herein by reference in its entirety, then injected with about $7 \times 10^4$ transducing particles per egg. Eggs hatched 21 days after injection and human interferon levels were measured by IFN ELISA from serum samples collected from chicks one week after hatch.

6.20 Example 20

Production of Fully Transgenic $G_1$ Chickens for Selective Breeding from Males Expressing Human Interferon To screen for $G_0$ roosters which contained the interferon transgene in their sperm, DNA was extracted from rooster sperm samples by Chelex-100 extraction (Walsh et al., 1991). DNA samples were then subjected to TAQMAN® analysis on a 7700 Sequence Detector (Perkin Elmer) using the "neo for-1" (5'-TGGATTGCACGCAGGTTCT-3') (SEQ ID NO: 35) and "neo rev-1" (5'-GTGCCCAGTCATAGCCGAAT-3') (SEQ ID NO: 36) primers and FAM labeled NEO-PROBE1 (5'-CCTCTCCACCCAAGCGGCCG-3') (SEQ ID NO: 37) to detect the transgene. Three $G_0$ roosters with the highest levels of the transgene in their sperm samples were bred to nontransgenic SPAFAS (White Leghorn) hens by artificial insemination.

Blood DNA samples were screened for the presence of the transgene by TAQMAN® analysis as described in Example 15, above. Out of 1,597 offspring, one rooster was found to be transgenic (a.k.a. "Alphie"). Alphie's serum was tested for the presence of human interferon by hIFN ELISA. hIFN was present at 200 nanograms/ml.

Alphie's sperm was used for artificial insemination of nontransgenic SPAFAS (White Leghorn) hens. To date, 106 out of 202 (about 52%) offspring contain the transgene as detected by TAQMAN® analysis. These breeding results follow a Mendelian inheritance pattern and indicate that Alphie is transgenic.

6.21 Example 21

Production of Human Interferon α2b in the Egg White of $G_2$ Transgenic Hens

Human lung carcinoma cells were incubated with diluted egg white samples, then washed and challenged with mengovirus. After incubation, cells were stained with crystal violet to assess viral interference.

Expression levels of human IFN α2b in egg white produced by $G_2$ hens as determined by ELISA are shown in FIG. 16. The bioactivity versus the mass of human IFN α2b produced in $G_2$ hen egg white is shown in FIG. 17. Bioactivity was determined by a viral inhibition assay, and mass was determined by IFN ELISA. Bird number 53 was a control bird and represented egg white from a non-transgenic hen.

6.22 Example 22

Transfection of Cultured Quail Oviduct Cells

The oviduct was removed from a Japanese quail (*Coturnix coturnix japonica*) and the magnum portion was minced and enzymatically dissociated with 0.8 mg/ml collagenase (SIGMA® Chemical Co., St. Louis, Mo.) and 1.0 mg/ml dispase (ROCHE® Molecular Biochemicals, Indianapolis, Ind.) by shaking and titurating for 30 min at 37° C. The cell suspension was then filtered through sterile surgical gauze, washed three times with F-12 medium (Life Technologies, Grand Island, N.Y.) by centrifugation at 200×g, and resuspended in OPTIMEM™ (Life Technologies) such that the $OD_{600}$ was approximately 2. 300 µl of cell suspension was plated per well of a 24-well dish. For each transfection, 2.5 µl of DMRE-C liposomes (Life Technologies) and 1 µg of DNA were preincubated 15 minutes at room temperature in 100 µl of OPTIMEM™, then added to the oviduct cells. Cells with DNA/liposomes were incubated for 5 hours at 37° C. in 5% $CO_2$. Next, 0.75 ml of DMEM (Life Technologies) supplemented with 15% fetal bovine serum (FBS) (Atlanta Biologicals, Atlanta, Ga.), 2× penicillin/streptomycin (Life Technologies), $10^{-6}$ M insulin (SIGMA®), $10^{-8}$ M β-estradiol (SIGMA®), and $10^{-7}$ M corticosterone (SIGMA®) was added to each well, and incubation continued for 72 hours. Medium was then harvested and centrifuged at 110×g for 5 minutes.

6.23 Example 23

Transfection of Cultured Chicken Whole Embryo Fibroblasts

To obtain whole embryo fibroblasts (WEFs), fertile chicken eggs were incubated for approximately 65 hours. Embryos were collected using filter paper rings, then washed three times in phosphate buffered saline with glucose (PBS-G) followed by a wash in calcium- and magnesium-free EDTA (CMF-EDTA). Embryos were then incubated in fresh CMF-EDTA at 4° C. with gentle shaking for 30 minutes. CMF-EDTA was removed, and replaced with 0.5% trypsin solution (no EDTA) at 37° C. for 3 minutes. Cells were titurated 10 times, then 5% chicken serum was added to inhibit the trypsin reaction. The cell suspension was then added to α-MEM (Life Technologies) supplemented with 2.2 g/l $NaHCO_3$, 2.52 g/L EPPS, 0.18 g/l D-glucose, 5% FBS, 5% chick serum (heat inactivated at 55° C. for 1 hour), $5 \times 10^{-5}$ M (β-mercaptoethanol, 0.2 mM L-glutamine, 2× penicillin/streptomycin and centrifuged. Cells were resuspended in α-MEM supplemented as described above, and plated on 6-well dishes at a density of $2 \times 10^5$ cells per well.

For each transfection, 6 µl of FuGene 6 liposomes (ROCHE® Molecular Biochemicals) and 2 µg of DNA were preincubated 15 min at room temperature in 100 µl of OPTI-MEM™, then added to the WEFs. WEFs with DNA/liposomes were incubated 5 hours at 37° C. in 5% $CO_2$. The transfection medium was then removed and replaced with 2 ml of α-MEM supplemented as described above. Medium was removed 72 hours after transfection and centrifuged at 110×g for 5 minutes.

WEFs were transfected either with the heavy and light immunoglobulin polypeptides encoded by separate plasmids (p1083 and p1086 respectively) each under the control of the CMV promoter or encoded on the same reactor under the transcriptional control of a CMV promoter and including an IRES translational element as described in U.S. patent application Ser. No. 09/877,374, filed 8 Jun. 2002 and incorporated herein by reference in its entirety. The supernatants were analyzed for antibody content by ELISA and FACs.

6.24 Example 24

Generation of Transgenic Chickens Expressing Antibodies

A retroviral vector, based on either avian leukosis virus (ALV) or Moloney murine leukemia virus (MoMLV), will be constructed such that the light (L) and heavy (H) chains of a monoclonal antibody (MAb) will be linked by an internal ribosome entry site (IRES) element. Both genes will then be transcriptionally regulated by a promoter such as the cytomegalovirus (CMV) immediate early promoter/enhancer or a promoter that demonstrates tissue specificity for the hen oviduct (for example, the lysozyme promoter, ovalbumin promoter, an artificial promoter construct such as MDOT, and the like). The promoter-L chain-IRES-H chain DNA expression cassette will be flanked by the long terminal repeats (LTRs) of the retrovirus. Stage X chicken embryos will be injected with transducing particles containing the above construct to generate transgenic chickens.

Alternatively, the heavy and light chains will be included in separate retroviral vectors and separate lines of transgenic chickens will be generated. Each line will either express the heavy or light chain of the MAb. Once germline transmission of the transgene is established in the two lines, they will be bred to each other to express heavy and light chains together to make functional MAbs in the offspring.

The above DNA constructs can also be integrated into a chicken genome by sperm-mediated transgenesis (SMT). SMT may involve transfection, electroporation, or incubation of sperm with the desired DNA construct (for example, the lysozyme promoter controlling expression of heavy and light chains of the MAb) and fertilization of ovum with the treated sperm by artificial insemination or by chicken intracytoplasmic sperm injection (ChICS™).

6.25 Example 25

Preparation of Recipient Avian Cytoplasts by TPLSM

Incubation

Ova were isolated from euthanized hens between 2-4 hours after oviposition of the previous egg. Alternatively, eggs were isolated from hens whose oviducts have been fistulated (Gilbert & Woodgush, 1963, *J. Reprod. & Fertility* 5: 451-453) and (Pander et al., 1989, *Br. Poult. Sci.* 30: 953-7). Before generating images of the avian early embryo, DNA was incubated with a specific dye according to the following protocol.

The albumen capsule was removed and the ovum placed in a dish with the germinal disk facing the top. Remnants of the albumen capsule were removed from the top of the germinal disk. Phosphate buffered saline was added to the dish to prevent drying of the ovum. A cloning cylinder was placed around the germinal disk and 1.0 µg/ml of DAPI in PBS was added to the cylinder. Visualization was performed after approximately 15 minutes of incubation.

Injection

Preparation of the egg was done as described for incubation. Following removal of the capsule, 10-50 nanoliters of a 0.1 µg/ml solution of DAPI in PBS was injected into the germinal disk using a glass pipette. Visualization was performed approximately 15 minutes after injection.

Visualization

Following incubation, images of the inside of the avian early embryo were generated through the use of TPLSM. The germinal disk was placed under the microscope objective, and the pronuclear structures were searched within the central area of the disk, to a depth of 60 µm using low laser power of 3-6 milliwatts at a wavelength of 750 nm. Once the structures were found they were subsequently ablated.

Nuclear Ablation and Enucleation

Pronuclear structures were subjected to laser-mediated ablation. In these experiments, an Olympus 20×/0.5 NA (Numerical Aperture) water immersion lens was used. The x and y planes to be ablated were defined with the two photon software, while the z plane (depth) was just under 10 µm for this type of objective. Since the pronuclear structure was about 20 µm in diameter, the ablation comprised two steps (2 times 10 µm). The focal point was lowered to visualize the remaining of the pronucleus, which was subsequently ablated. The laser power used to ablate the pronuclei was between 30 to 70 milliwatts at a wavelength of 750 nm. For the ablation experiments, the image was zoomed by a factor of 4 to 5, giving an area compression of 16-25 fold. Then the power was increased 10-12 fold for a total intensity increase of 160-300 fold compared to the visualization intensity of 3-6 milliwatts. The ablation intensity (power density) is the functional parameter, i.e. the power increase of 10-12 fold results in ablation power of 30-70 milliwatts, but the zoom factor compressed this power into an area 16-25× smaller giving a power density increase of 160-300 fold.

6.26 Example 26

Preparation of the Nuclear Donor Cell and Isolation of the Donor Nucleus

Avian fibroblast cells in culture were trypsinized (0.25% Trypsin and 1 µM EDTA), centrifuged twice in PBS containing 5% of fetal calf serum (FCS) and placed in a 60 mm plastic dish in PBS containing 5% of FCS. Using the microscope/micromanipulation unit described in Example 27 below, under transmission light, the nuclear donors were then isolated by repeated pipetting of the cells, which disrupted the cytoplasmic membrane and released the nucleus from inside the cell.

6.27 Example 27

Preparation of the Reconstructed Zygote

A micromanipulation unit, comprising an IM-16 microinjector and a MM-188NE micromanipulator, both from NIKON®/MARISHIGE, were adapted to an upright NIKON® Eclipse E800. This microscope was adapted to operate under both transmission and reflective light conditions. This unique configuration has allowed us to morphologically examine and prepare (isolate the nuclei, as described above) somatic cells in suspension and to load the injection pipette using dry or water immersion lenses under diascopic illumination or transmitted light. This was followed by prompt localization and positioning of the germinal disk under the microscope and subsequent guided injection of the somatic cells, using dry and long distance lenses under fiber optic as well as episcopic illumination (light coming from the side and through the objectives onto the sample respectively).

6.28 Example 28

Production of Transgenic Chickens by Direct Pronuclear DNA Injection

Production of transgenic chickens by direct DNA injection can be by two methods: (a) injection of a DNA directly into the germinal disk, commonly described as cytoplasmic injection, as described for avian species by Sang & Perry, 1989, *Mol. Reprod. Dev.* 1: 98-106, and Love et al., 1994, *Biotechnology* (N.Y.) 12: 60-3, incorporated herein by reference in their entireties. Sang & Perry described only episomal replication of the injected cloned DNA. Love et al. suggested that the injected DNA becomes integrated into the cell's genome. In both cases, injection was into pronuclear stage eggs. This procedure, therefore, is cytoplasmic injection of pronuclear stage eggs, not pronuclear injection; and (b) imaging of the egg using multiphoton microscopy to allow localization of the pronuclear structures. The DNA solution is then injected directly into the pronucleus.

DNA Preparation

The plasmid pAVIJCR-A115.93.1.2 containing the chicken lysozyme promoter region, and controlling expression of human interferon α2b, was purified with a QIAGEN® Plasmid Maxi Kit (QIAGEN®, Valencia, Calif.), and 5 µg of the plasmid DNA were restriction digested with the restriction enzyme Not I. A 12.7 kb fragment was purified by gel electrophoresis and electroelution, phenol/chloroform extraction, and ethanol precipitation. The DNA was resuspended in 1 mM Tris-HCl, pH8.0 and 0.1 mM EDTA (0.1× TE) to a final concentration of 5 pg/nl and then used for microinjections.

Pronuclear Injection (i) Preparation of ova. Ova were isolated from euthanized hens between two and four hours after oviposition of the previous egg. Alternatively, eggs were isolated from hens whose oviducts have been fistulated as described by Gilbert & Woodgush, 1963, *J. of Reprod. and Fertility* 5: 451-453 and Pander et al., 1989, *Br. Poult. Sci.* 30: 953-7 and incorporated herein in their entireties.

The albumen capsule was removed and the ovum placed in a dish with the germinal disk facing upwards. Remnants of the albumen capsule were removed from over the germinal disk. Phosphate buffered saline (PBS) was added to the dish to prevent drying of the ovum. A cloning cylinder could be placed around the germinal disk to reduce the depression of the ooplasmic membrane formed during subsequent pipette penetration, thereby facilitating the injection.

(ii) Injection. Between about 1-100 nanoliters of DNA solution was injected into a germinal disk using a glass pipette after removal of the capsule. The microinjection assembly and methods for microinjecting and reimplanting avian eggs are fully described in U.S. patent application Ser. No. 09/919,143, filed 31 Jul. 2001, now abandoned.

Briefly, the microscope/micromanipulation unit is an IM-16 microinjector and a MM-188NE micromanipulator, both from NIKON®/MARISHIGE, adapted to an upright NIKON® Eclipse E800 microscope adapted to operate under both transmitted and reflected light conditions. This unique configuration allows the loading of a DNA solution into a micropipette while observed with a pipette dry or water immersion lenses under diascopic illumination or transmitted light. Pipette loading is followed by the prompt localization and positioning of the germinal disk under the microscope and subsequent guided injection of DNA solution into the germinal disk using dry and long working distance lenses under fiber optic as well as episcopic illumination (side illumination and directly through the objectives and onto the sample, respectively).

(iii) Localization of the Avian Embryo. A cloning cylinder is placed around the germinal disk and MITOTRACKER® (300 nM) in PBS was added to the cylinder. Visualization is performed after approximately 20 minutes of incubation. Imaging using this dye shows intense labeling of the region around the nucleus while the nucleus itself does not take up the dye. This will allow localization of the pronucleus for injection while not causing excessive damage to its structure, since the content of the pronuclei are not labeled and therefore are bleached during imaging. Once the pronucleus is localized, the DNA solution can be delivered into it using a microinjector. Cytoplasmic or pronuclear injected eggs can then be surgically transferred to a recipient hen.

(iv) Ovum transfer. At the time of laying, recipient hens are gas anesthetized using Isofluorine. At this time, the infludibulum is receptive to receiving a donor ovum but has not yet ovulated. Feathers are removed from the abdominal area, and the area is scrubbed with betadine, and rinsed with 70% ethanol. The bird is placed in a supine position and a surgical drape is placed over the bird with the surgical area exposed. An incision approximately 2 inches long is made beginning at the junction of the sternal rib to the breastbone and running parallel to the breastbone and through the smooth muscle layers and the peritoneum, to locate the infundibulum. The infundibulum is externalized and opened using gloved hands and the donor ovum is gently applied to the open infundibulum. The ovum is allowed to move into the infundibulum and into the anterior magnum by gravity feed. The infundibulum is returned to the body cavity and the incision closed using interlocking stitches both for the smooth muscle layer and the skin. The recipient hen is returned to her cage and allowed to recover with free access to both feed and water. Recovery time for the bird to be up, moving and feeding is usually within 45 minutes. Eggs laid by the recipient hens are collected the next day, set, and incubated. They will hatch 21 days later.

The procedure described by Love et al., 1994, in *Biotechnology* (N.Y.) 12: 60-63, resulted in 5.5% survival to sexual maturity using the Perry ex ovo procedure. Following injection and surgical transfer by the methods described herein, however, a survival rate between about 50% and about 70% is expected, i.e., hatching, and most of the hatched birds should reach maturity.

6.29 Example 29

MuLV and VSV Viral Transfection of Avian Eggs

Preparation of MuLV/VSVg viral stocks. GP-293 cells at 70-80% confluence were transfected with 10 μg of the plasmid pVSVg or pLNHX-CMVE-MDOT-IFN. Sixty hours after transfection, the supernatant was collected and centrifuged at 1000 rpm for 5 minutes to remove cells. The supernatant was filtered through a 0.45 micron filter and the filtrate was centrifuged at 20,000 rpm to pellet the virus. The viral pellet was resuspended in 400 ml of STE buffer. To determine the viral titer, a 100-fold dilution of the viral stock was made and 5 μl of the serially diluted stock was used to infect Sentas cells. Forty-eight hours after infection, the cells were grown in medium containing 100 μg/ml G418. Colonies that were formed after two weeks in the selection medium were counted to determine the viral titer.

Isolation of blastodermal cells from stage XBarred Plymouth Rock (BPR) embryos. Freshly laid eggs were collected. The embryo at this stage consists of about 50,000-60,000 cells in a small circular area called the blastodermal disc. The discs from about 30 embryos were dissected from the eggs and the cells dissociated using 1×PBS (phosphate buffer saline) containing 0.05% trypsin. The cells were centrifuged at 500 rpm for 5 minutes. The pellet was gently washed with 1×PBS and pelleted again and counted using a hemocytometer.

Interferon (IFN) assay. Blood samples were collected from 6 wk old chicks and the interferon levels in the serum were measured using the hu-IFN-α ELISA Kit (PBL Biomedical Lab., New Brunswick, N.J.).

119 WL stage X eggs were injected with 5 μl of pLNHX-MDOT-IFN/VSVg virus with a titer $6\times10^4$/ml). 53 injected eggs survived, of which 20 hatched. Sperm samples were tested from the males at sexual maturity. Two males, # A 24 and A 34, showed the presence of the transgene and therefore were used for further breeding for testing the germ-line transmission.

Freshly isolated $2\times10^5$ BRD cells from stage X embryos were infected with $1.5\times10^4$ pLNHX-MDOT-IFNNVSVg virus at 37° C. for 1 hour. The cells were gently stirred every 10-15 minutes. While the blastodermal cells were being thus processed, 150 freshly laid WL (stage X) eggs were irradiated at 600 rads and set aside for the injections. A 5 μl cell suspension containing about 4000-5000 blastodermal cells were injected into each of 85 irradiated stage X WL eggs through a hole drilled in the shell. The eggs were sealed and incubated to hatch. Out of 85 stage X WL eggs that were injected with the BRD cells infected with pLNHX-MDOT-IFNNVSVg virus, 47 survived and 15 of these hatched. The feather chimerism in these birds was between 5-85%.

In an alternative experiment, freshly isolated $6\times10^5$ BRD cells from stage X embryos were mixed with $4\times10^5$ pLNHX-CMVE-MDOT-IFN viral particle and incubated at 37° C. for 1 hour. The cells were gently stirred every 10-15 minutes. While the blastodermal cells were being processed, 150 freshly laid WL (stage X) eggs were collected and irradiated at 600 rads and set aside for the injections. A 5 μl cell suspension containing about 4000-5000 cells was injected into each of 107 irradiated stage X WL eggs through a small hole drilled in the shell. The eggs were sealed and incubated to hatch.

Out of 107 stage X WL eggs injected with the BPR cells infected with the pLNHX-CMVE-CMVE-MDOT-IFN virus, 53 of these survived, of which 17 hatched. These birds showed varying degree of feather chimerism that ranged from 2-85%, as shown in Table 3 below.

TABLE 3

Chimera distribution of chicks transgenic for pLNHX-CMVE-MDOT-IFN virus

| Bird # | Chimerism % Black | Status | Sex |
|---|---|---|---|
| 457 | 75% | | Male |
| 458 | 15% | DEAD | |
| 459 | | | Female |
| 460 | | | |
| 461 | 85% | DEAD | |
| 462 | | | Female |
| 463 | 45% | | Male |
| 464 | 20% | | Male |
| 465 | 30% | DEAD | |
| 466 | | | Male |
| 467 | | | Female |
| 468 | | | |
| 469 | 30% | DEAD | |
| 470 | 2% | DEAD | |
| 471 | | DEAD | |
| 472 | | DEAD | |
| 473 | | DEAD | |

Blood samples were collected from these chicks when they were 6 wk old. Interferon levels in 100 μl serum sample was analyzed using the h-IFN-ELISA Kit. Results of the assay are shown in FIG. 18. The successful detection of the transgene-encoded product (i.e. interferon) indicates that the BPR-injected cells were stably integrated into different tissues and thereby demonstrating that Moloney leukemia viruses pseudotyped with VSVg can be used for generating transgenic birds.

In a parallel experiment with a different MuLV/VSVg pseudotyped virus (pLNHX-MDOT-IFN), feather chimeric chicks that did not hatch (i.e. died during the incubation period) were collected. Three tissues, skin heart and lung, from these birds were analyzed for the presence of the transgene by TAQMAN® analysis. In three chicks, all three tissues showed the presence of the transgene. In the fourth chick, as shown in FIGS. 19 and 20, the transgene was detected in two of the tissues. These results show that the injected BPR cells infected with Moloney viruses pseudotyped with VSVg are stably integrated into different tissues of the chick.

6.30 Example 30

Construction of Lysozyme Promoter Plasmids

The chicken lysozyme gene expression control region isolated by PCR amplification is fully disclosed in U.S. patent application Ser. No. 09/922,549, filed 3 Aug. 2001, now issued U.S. Pat. No. 7,176,300, issued Feb. 13, 2007, and incorporated herein by reference in its entirety. Ligation and reamplification of the fragments thereby obtained yielded a functionally contiguous nucleic acid construct comprising the chicken lysozyme gene expression control region operably linked to a nucleic acid sequence encoding a human interferon α2b polypeptide and optimized for codon usage in the chicken. Briefly, chicken (*Gallus gallus* (White Leghorn)) genomic DNA was PCR amplified using the primers 5pLMAR2 and LE-6.1kbrev1 in a first reaction, and Lys-6.1 and LysE1rev as primers in a second reaction. PCR cycling steps were: denaturation at 94° C. for 1 minute; annealing at 60° C. for 1 minute; extension at 72° C. for 6 minutes, for 30 cycles using TAQ PLUS PRECISION™ DNA polymerase (STRATAGENE®, LaJolla, Calif.). The PCR products from these two reactions were gel purified, and then united in a third PCR reaction using only 5pLMAR2 and LysE1rev as primers and a 10 minute extension period. The resulting DNA product was phosphorylated, gel-purified, and cloned into the EcoR V restriction site of the vector pBLUESCRIPT® KS, resulting in the plasmid p12.0-lys.

p12.0-lys was used as a template in a PCR reaction with primers 5pLMAR2 and LYSBSU and a 10 minute extension time. The resulting DNA was phosphorylated, gel-purified, and cloned into the EcoR V restriction site of pBLUESCRIPT® KS, forming plasmid p12.0lys-B.

p12.0lys-B was restriction digested with Not I and Bsu36 I, gel-purified, and cloned into Not I and Bsu36 I digested pCMV-LysSPIFNMM, resulting in p12.0-lys-LSPIFNMM. p12.0-lys-LSPIFM was digested with Sal I and the SalItoNotI primer was annealed to the digested plasmid, followed by Not I digestion. The resulting 12.5 kb Not I fragment, comprising the lysozyme promoter region linked to IFNMAGMAX-encoding region and an SV40 polyadenylation signal sequence, was gel-purified and ligated to Not I cleaved and dephosphorylated pBLUESCRIPT® KS, thereby forming the plasmid pAVIJCR-A115.93.1.2.

6.31 Example 31

Complete Lysozyme Promoter and IFNMAGMAX Sequences

The complete sequences of the lysozyme gene promoter and the codon-optimized human interferon α2b nucleic acid are fully disclosed in U.S. patent application Ser. No. 09/922,549, filed 3 Aug. 2001, now issued U.S. Pat. No. 7,176,300, issued Feb. 13, 2007, and incorporated herein by reference in its entirety. The complete nucleotide sequence of the approximately 12.5 kb chicken lysozyme promoter region/IFNMAGMAX construct spans the 5' matrix attachment region (5' MAR), through the lysozyme signal peptide, to the sequence encoding the gene IFNMAGMAX and the subsequent polyadenylation signal sequence. The IFNMAGMAX nucleic acid sequence had been synthesized as described in Example 17 above. The expressed IFN α2b sequence within plasmid pAVIJCR-A115.93.1.2 functioned as a reporter gene

6.32 Example 32

Expression in Transfected Cultured Avian Oviduct Cells of Human Interferon α2b Regulated by the 12 kb Lysozyme Promoter for lysozyme promoter activity. This plasmid construct may also be used for production of interferon α2b in the egg white of transgenic chickens.

The oviduct was removed from a Japanese quail (*Coturnix coturnix japonica*) and the oviduct cells transfected with the lysozyme promoter-IFNMAGMAX as described in Example 22, above. The supernatant was analyzed by ELISA for human interferon α2b content.

The human interferon α2b contents of medium derived from cultured oviduct cells transfected with either pAVIJCR-A115.93.1.2 or the negative control plasmid pCMV-EGFP, as shown in FIG. 16. Bars to the right of the figure represent the standards for the IFN ELISA.

6.33 Example 33

Production of Heterologous GM-CSF in Serum of Transgenic Chickens

Seventy-three birds were injected with CMV-GMCSF (ALV) wherein a nucleic acid encoding GM-CSF was functionally linked to the cytomegalovirus promoter. All were subsequently tested. Three control birds that had nothing injected were also included. For each bird tested, approximately 100 μl of blood was collected with heparinized tubes then diluted into 100 μl of PBS solution and spun to remove red blood cells. 100 μl of the plasma was then assayed.

As shown in Table 4 (below), three of the experimental birds had GM-CSF plasma levels that were higher than the highest available standard of 500 pg/ml used in the ELISAs.

TABLE 4 production of heterologous GM-CSF by heterologous chickens

| Band # | Diluted sample 100 μl diluent/ 100 μl blood ng/ml | Corrected results ng/ml | M/F | Transgene in sperm | Sperm Transgene +/− evaluation | Con- formation | Egg Weight sample 1 (g) | Protein in egg sample 1 (pg/ml) | Egg Weight sample 2 (g) | Protein in egg sample 2 (pg/ml) |
|---|---|---|---|---|---|---|---|---|---|---|
| 1210 | 0.002 | 0.004 | F | | | | | | | |
| 1212 | 0 | 0 | M | 0 | | | | | | |
| 4545 | 0 | 0 | M | NT | | | | | | |
| 5488 | 0.031 | 0.062 | M | NT | | | | | | |
| 8371 | 0 | 0 | M | 0 | | | | | | |
| 8374 | 0.03 | 0.06 | M | 0 | | | | | | |
| 8375 | 0 | 0 | M | 0 | | | | | | |
| 8376 | 0.003 | 0.006 | F | | | | 53.40 | 0.00 | 53.90 | 0.00 |
| 8380 | 0 | 0 | M | 0 | | | | | | |
| 8387 | 0 | 0 | M | NT | − | | | | | |
| 8389 | 0 | 0 | F | | | | 45.70 | 0.00 | 41.90 | 0.00 |
| 8391 | 0 | 0 | F | | | | 47.20 | 0.00 | 48.90 | 0.00 |
| 8392 | 0.007 | 0.014 | M | 0 | | | | | | |
| 8397 | 0 | 0 | M | NT | − | | | | | |
| 8400 | 0 | 0 | M | 0 | | | | | | |
| 8401 | 0 | 0 | M | NT | − | | | | | |
| 8402 | 0.674 | 1.348 | M | 50 copies | | | | | | |
| 8403 | 0 | 0 | M | 50 copies | | | | | | |
| 8406 | 0 | 0 | F | | | | | | | |
| 8410 | 0 | 0 | F | | | | 45.90 | 0.00 | 47.40 | 0.00 |
| 8413 | 0.003 | 0.006 | F | | | | 41.50 | 0.00 | 43.70 | 0.00 |
| 8415 | 0 | 0 | M | 0 | | | | | | |
| 8416 | 0.039 | 0.078 | M | 50 copies | | | | | | |
| 8417 | 0 | 0 | M | NT | − | | | | | |
| 8424 | 0 | 0 | M | NT | + | + | | | | |
| 8425 | 0 | 0 | F | | | | 44.80 | 0.00 | 44.10 | 0.00 |
| 8426 | 0 | 0 | M | 50 copies | | | | | | |
| 8429 | 0 | 0 | M | 500 copies | − | | | | | |
| 8430 | 0.091 | 0.182 | M | NT | | | | | | |
| 8432 | 0 | 0 | M | 0 | + | | | | | |
| 8433 | 0 | 0 | M | >500 copies | − | − | | | | |
| 8440 | 0 | 0 | M | NT | − | | | | | |
| 8444 | 0 | 0 | M | 0 | − | | | | | |
| 8447 | 0 | 0 | F | | | | 35.60 | 0.00 | 58.90 | 0.00 |
| 8448 | 0 | 0 | M | NT | − | | | | | |
| 8449 | 0 | 0 | F | | | | 49.60 | 0.00 | 46.80 | 0.00 |
| 8452 | 0.706 | 1.412 | F | | | | 41.70 | 4117.25 | 39.80 | 4051.31 |
| 8454 | 0 | 0 | M | 0 | − | | | | | |
| 8455 | 0 | 0 | M | NT | | | | | | |
| 8456 | 0 | 0 | F | | | | | | | |
| 8460 | 0.027 | 0.054 | M | 500 copies | − | − | | | | |
| 8461 | 0 | 0 | M | 500 copies | − | − | | | | |
| 8462 | 0.063 | 0.126 | F | | | | 45.80 | 0.00 | 54.40 | 0.00 |
| 8463 | 0 | 0 | M | 0 | − | | | | | |
| 8464 | 0.057 | 0.114 | M | 0 | | | | | | |
| 8467 | 0 | 0 | F | | | | 53.90 | 0.00 | 51.50 | 0.00 |
| 8468 | 0 | 0 | M | 0 | − | | | | | |

TABLE 4-continued production of heterologous GM-CSF by heterologous chickens

| Band # | Diluted sample 100 μl diluent/ 100 μl blood ng/ml | Corrected results ng/ml | M/F | Transgene in sperm | Sperm Transgene +/− evaluation | Con- formation | Egg Weight sample 1 (g) | Protein in egg sample 1 (pg/ml) | Egg Weight sample 2 (g) | Protein in egg sample 2 (pg/ml) |
|---|---|---|---|---|---|---|---|---|---|---|
| 8470 | 0 | 0 | M | 0 | − | | | | | |
| 8473 | 0 | 0 | F | | | | 40.70 | 0.02 | 56.80 | 0.00 |
| 8475 | 0 | 0 | F | | | | 41.50 | 0.00 | 41.00 | 0.00 |
| 8478 | 0 | 0 | M | 500 copies | − | − | | | | |
| 8482 | 0 | 0 | F | | | | 38.10 | 0.00 | | |
| 8483 | 0 | 0 | M | 50 copies | | | | | | |
| 8485 | 0 | 0 | M | NT | | | | | | |
| 8489 | 0 | 0 | M | 500 copies | + | + | | | | |
| 8490 | 0 | 0 | M | 0 | − | | | | | |
| 8497 | 0 | 0 | M | NT | − | | | | | |
| 8499 | 0 | 0 | M | 500 copies | − | − | | | | |
| 8500 | 0 | 0 | M | 0 | − | | | | | |
| 8501 | 0 | 0 | F | | | | 38.10 | 0.00 | 37.60 | 0.00 |
| 8502 | 0 | 0 | F | | | | 44.10 | 0.01 | 47.10 | 0.00 |
| 8508 | 0.086 | 0.172 | M | NT | + | + | | | | |
| 8509 | 1.068 | 2.136 | F | | | | 72.30 | 0.00 | 48.50 | 0.00 |
| 8514 | 0 | 0 | F | | | | 45.30 | 0.00 | 44.70 | 0.00 |
| 8518 | 0 | 0 | F | | | | 48.70 | 0.00 | 47.30 | 0.00 |
| 8521 | 0 | 0 | F | | | | 49.00 | 0.00 | 47.70 | 0.00 |
| 8525 | 0.016 | 0.032 | F | | | | 54.10 | 0.00 | 49.10 | 0.01 |
| 8526 | 0 | 0 | M | 500 copies | + | ++ | | | | |
| 8528 | 0.013 | 0.026 | M | 500 copies | + | ++ | | | | |
| 8531 | 0 | 0 | M | 0 | − | | | | | |
| 8650 | 0.001 | 0.002 | F | | | | 45.60 | 16.55 | 46.50 | 0.04 |
| 8653 | 0.045 | 0.09 | F | | | | 44.60 | 0.00 | 44.30 | 0.00 |
| 8720 | 0 | 0 | M | NT | | | | | | |
| S8484 (c) | 0 | 0 | F | | | | | | | |
| S8507 (c) | 0 | 0 | F | | | | | | | |
| S8508 (c) | 0 | 0 | F | | | | | | | |

When the dilution is factored in, three birds had greater than approximately 1 ng/ml. Eleven additional birds had GM-CSF levels within the range detectable by ELISA, from 26 pg/ml to 182 pg/ml (with the dilution factored in). Control birds S8484, S8507 and S8508 were negative.

6.34 Example 34

Synthesis of the MDOT Promoter Construct

Amplification of the Ovomucoid and Ovotransferrin Promoter Sequences

Oligonucleotide primers 1 (SEQ ID NO: 38) and 2 (SEQ ID NO: 39), as shown in FIG. 22 were used to amplify the ovomucoid sequences. Oligonucleotide primers 3 (SEQ ID NO: 40) and 4 (SEQ ID NO: 41) were used to amplify the ovotransferrin sequence by PCR. The primers were designed such that the PCR-amplified ovomucoid sequences contained an Xho I restriction cleavage site at the 5' end and a Cla I site at the 3' end. Similarly, the PCR-amplified ovotransferrin product had a Cla I restriction site at the 5' end and a Hind III site at the 3' end. The overlapping Cla I site was used to splice the two-PCR products to create the MDOT promoter construct. The nucleic acid sequence SEQ ID NO: 11 of the MDOT promoter construct is shown in FIG. 14. The final product was cloned in a bluescript vector between the Xho I and Hind III sites. From the bluescript vector the promoter region was released by Kpn I/Hind III restriction digestion and cloned into the prc-CMV-IFN vector to replace the CMV promoter to create MDOT-IFN (clone #10). This plasmid was tested in vitro.

Interferon Synthesis Directed by the MDOT Promoter in Transfected Oviduct Cells.

The promoter activity was tested in vitro by transfecting the plasmid construct into tubular gland cells isolated from the quail oviduct. The transfected cells were treated with hormones (progesterone, estrogen and insulin). At 72 hrs after transfection, the supernatant media of the transfected cells were collected and the interferon levels analyzed using an ELISA assay. The results, as shown in FIG. 23 show a significant induction of interferon α2b expression in hormonally treated cells.

6.35 Example 35

Production of Erythropoietin the Serum of Transgenic Chickens

Sixty birds were injected with a nucleic acid construct comprising a nucleic acid region encoding erythropoietin (EPO) 3' of, and operably linked to, the MDOT artificial promoter in the ALV vector (MDOT-EPO (ALV)) described in Example 34, above. All birds were subsequently tested. Two control birds that had nothing injected were also tested. Approximately 100 μl of blood from each bird was diluted into 100 μl of PBS/EDTA solution and spun to remove red blood cells. 100 μl of the plasma was then assayed.

As shown in Table 5 below, twenty-three of the experimental birds had EPO levels in their plasma higher than the highest available ELISA standard of 1540 pg/ml.

TABLE 5

Production of erythropietin under the control of promoter MDOT

| | ELISA | | | Taqman ® | | EGG ELISA | | | | | |
|---|---|---|---|---|---|---|---|---|---|---|---|
| | Diluted sample | | | Sperm | | | | | | | |
| Band # | (100 ul diluent/ 100 ul blood) ng/ml | corrected results ng/ml | M/F | Transgene +/− evaluation | Con- firmation | Protein in egg (pg/ml) | | Protein in egg (pg/ml) | | Protein in egg (pg/ml) | |
| 300 | 6.067 | 12.134 | F | | | 1011.403 | 697.186 | 2792.153 | 1848.942 | 2529.037 | 1711.554 |
| 301 | 0.45 | 0.9 | M | + | | | | | | | |
| 302 | 6.187 | 12.374 | M | ++ | ++ | | | | | | |
| 303 | 0.771 | 1.542 | M | +++ | +++ | | | | | | |
| 304 | 0.56 | 1.12 | M | − | | | | | | | |
| 305 | 0.545 | 1.09 | F | | | 1562.893 | | 1859.896 | 2405.046 | 1702.548 | 1926.763 | 2108.639 |
| 306 | 0.682 | 1.364 | M | + | | | | | | | |
| 307 | 6.245 | 12.49 | M | + | | | | | | | |
| 308 | 6.24 | 12.48 | F | | | NT | | 17918.84 | 24599.5 | 17378.85 | 25764.39 |
| 309 | 6.211 | 12.422M | − | | | | | | | | |
| 310 | 6.25 | 12.5 | M | − | − | | | | | | |
| 311 | 6.245 | 12.49 | M | ++ | ++ | | | | | | |
| 312 | 2.239 | 4.478 | M | + | | | | | | | |
| 314 | 4.545 | 9.09 | F | | | 691.466 | | 1979.496 | 2203.295 | 2128.271 | 1869.904 |
| 316 | 4.738 | 9.476 | M | − | | | | | | | |
| 317 | 1.841 | 3.682 | F | | | 0 | | 149.161 | 0 | | |
| 320 | 1.028 | 2.056 | M | ++ | | | | | | | |
| 321 | 0.029 | 0.058 | M | − | | | | | | | |
| 322 | 0 | 0 | M | − | | | | | | | |
| 323 | 6.148 | 12.296 | M | ++ | ++ | | | | | | |
| 324 | 0 | 0 | F | | | NT | | 0 | 0 | | |
| 325 | 1.683 | 3.366 | F | | | NT | | | | | |
| 327 | 0 | 0 | M | NT | | | | | | | |
| 328 | 0 | 0 | M | − | | | | | | | |
| 329 | 0.975 | 1.95 | M | NT | | | | | | | |
| 330 | 6.263 | 12.526 | F | | | 4118.945 | 2592.051 | 7515.93 | 5638.896 | | |
| 331 | 0.533 | 1.066 | M | + | | | | | | | |
| 332 | 0.319 | 0.638 | M | + | | | | | | | |
| 333 | 1.969 | 3.938 | M | redo | − | | | | | | |
| 334 | 0 | 0 | F | | | | | 0 | 0 | | |
| 335 | 0 | 0 | F | | | NT | | 0 | 0 | | |
| 336 | 0.356 | 0.712 | F | | | NT | | 1800.975 | 2360.708 | 1536.928 | 2551.83 |
| 337 | 0.437 | 0.874 | M | − | | | | | | | |
| 338 | 0.306 | 0.612 | F | | | NT | | 0 | 0 | 0 | |
| 339 | 6.255 | 12.51 | M | ++ | ++ | | | | | | |
| 340 | 0.009 | 0.018 | M | − | | | | | | | |
| 341 | 0.436 | 0.872 | M | ++ | ++ | | | | | | |
| 342 | 2.314 | 4.628 | M | ++ | ++ | | | | | | |
| 343 | 0.083 | 0.166 | M | − | | | | | | | |
| 344 | 0.219 | 0.438 | M | ++ | + | | | | | | |
| 345 | 0.195 | 0.39 | F | | | 0 | | 375.962 | 1465.575 | 349.881 | 1936.851 |
| 346 | 0.429 | 0.858 | F | | | NT | | | | | |
| 348 | 0.422 | 0.844 | M | + | | | | | | | |
| 349 | 1.199 | 2.398 | M | − | | | | | | | |
| 350 | 0.1 | 0.2 | M | +++ | +++ | | | | | | |
| 352 | 0.29 | 0.58 | F | | | NT | | 141.163 | 296.148 | | |
| 353 | 0.572 | 1.144 | F | | | NT | | 802.981 | 747.527 | | |
| 354 | 6.243 | 12.486 | F | | | NT | | 0 | | | |
| 356 | 1.225 | 2.45 | M | + | | | | | | | |
| 357 | 0.038 | 0.076 | F | | | NT | | 118.717 | 0 | | |
| 359 | 0.002 | 0.004 | F | | | NT | | 52.913 | 38.691 | | |
| 360 | 2.318 | 4.636 | M | + | | | | | | | |
| 362 | 1.055 | 2.11 | F | | | NT | | 0 | 0 | | |
| 363 | 6.242 | 12.484 | F | | | 517.406 | | 1005.69 | 2033.381 | 747.537 | 1980.494 |
| 365 | 0.446 | 0.892 | M | ++ | ++ | | | | | | |
| 367 | | | | | | | | 0 | 92.454 | | |
| 368 | | | | | | | | 0 | 69.274 | | |
| 369 | | | M | − | | | | | | | |
| 608 | 6.191 | 12.382 | M | NT | ++ | | | | | | |
| 609 | 0 | 0 | M | NT | | | | 0 | 0 | | |
| 1173 | 0 | 0 | M | NT | − | | | | | | |
| 1174 | 1.614 | 3.228 | M | NT | ++ | | | | | | |
| 1175 | 6.252 | 12.504 | M | NT | − | | | | | | |
| 1204 | 0 | 0 | F | | | NT | | | | | |
| 367 | 0 | 0 | F | | | NT | | | | | |

When the dilution is factored in, 23 birds have greater than approximately 3080 pg/ml. An additional 27 birds had EPO levels within the range detectable by ELISA, from 58 pg/ml to 2450 pg/ml (with the dilution factored in). Control birds were negative.

6.36 Example 36

Isolation of Ovomucoid BAC Clone

Two sets of PCR primers were used to screen a chicken BAC library constructed by Martien Groenen and Richard Crooijmans using two-dimensional screening (Crooijmans et al., 2000, Mamm Genome 11:360-363) for a clone containing the entire ovoinhibitor and ovomucoid gene. The first set of PCR primers, OM5 (5'-CGGGCAGTACCTCACCATGGA-CATGT-3'; SEQ ID NO: 43) and OM6 (5'-ATTCGCT-TAACTGTGACTAGG-3'; SEQ ID NO:44) overlaps the 5' untranslated region on the ovomucoid gene. The second set, Ovoinhibitor 1 (5'-CGAGGAACTTGAAGCCTGTC-3'; SEQ ID NO:45) and Ovoinhibitor 2 (5'-GGCCTG-CACTCTCCATCATA-3'; SEQ ID NO:46), overlap exon 3 and exon 4 of the ovoinhibitor gene. One clone, designated OMC24 (SEQ ID NO:42), was sequenced using standard shotgun-sequencing strategy (Green, 2001, Nat Rev Genet 2:573-583), and found to contain a 68,295 basepair (bp) insert and encompasses the entire ovoinhibitor and ovomucoid genes (FIG. 24A-V).

6.37 Example 37

Construction of Ovomucoid BAC Expression Vectors Encoding a Monoclonal Antibody OMC24 was used to construct two expression vectors, one carrying the light (kappa) chain cDNA of a human IgG1 kappa monoclonal antibody (hMab) and the other carrying the corresponding heavy chain cDNA of the monoclonal antibody. DNA fragments composed of an internal ribosome entry site (IRES) sequence followed by a cDNA encoding the heavy or light chain of the monoclonal antibody were constructed (SEQ ID NOs 47 and 48, respectively, and depicted in FIG. 25). The IRES used was an encephalomyocarditis virus (EMCV) IRES (Mountford et al., 1994, Proc Natl Acad Sci USA 91:4303-4307). Each expression vector was generated by RARE digestion of OMC24 at an EcoRI site at position 49,146, in the 3' UTR of the ovomucoid transcript, followed by ligation of the appropriate IRES-cDNA cassette. RARE cleavage utilizes RecA protein combined with sequence-specific oligonucleotides to block DNA from the action of DNA modifying enzymes, including restriction endonucleases (Ferrin, 2001, Flexible Genetic Engineering Using RecA Protein, Molecular Biotechnology, 18: 233-241).

6.38 Example 38

Production of Chickens Transgenic with Monoclonal Antibody Sequences

Transgenic hens were generated using cytoplasmic microinjection as described in Example 1 except as provided below. Single avian embryos were injected with NotI linearized forms of the two OMC24-derived expression vectors carrying the light and heavy chain cDNAs of the IgG1 kappa monoclonal antibody suspended in BAC buffer (10 mM tris, pH 7.5, 0.1 mM EDTA, 30 µM spermine, 70 µM spermidine, 100 mM NaCl) (Schedl et al., 1993, Nucleic Acids Res 21:4783-4787 and Montoliu et al., 1995, J Mol Biol 246:486-492). Transgenic hens obtained were subsequently grown to sexual maturity. Eggs were collected from transgenic hens and egg white material was assayed for the expressed hMab using sandwich ELISA as described by Harlow et al., Antibodies: a laboratory manual. 1988, Cold Spring Harbor, N.Y.: Cold Spring Harbor Laboratory. xiii (FIG. 26). The hMab molecule was captured by a kappa light chain specific monoclonal antibody in the assay and quantitated with an alkaline phosphatase-linked detection antibody specific for the Fc portion of the captured hMab. Hens # 4992 and #1251 express an average of 150 ng and 19 ng of hMab per milliliter of egg white, respectively (FIG. 27). Eggs from transgenic hens #4992 and #1251 were collected over several weeks. These levels of hMab protein are significantly higher than the levels of hMab detected in serum from the transgenic hens. The preferential expression of the hMab into the egg white of transgenic hens is likely due to tissue specificity imparted by regulatory elements of the ovomucoid locus.

Eggs of hen #4992 were collected and hMab was partially purified by passage over a protein A column and subsequent elution with the appropriate buffer. The partially purified antibody was run on denaturing SDS-PAGE gel under reducing conditions and compared with the same hMab produced by recombinant expression in cultured mammalian cells (See Harlow et al., Antibodies: a laboratory manual. 1988, Cold Spring Harbor, N.Y.: Cold Spring Harbor Laboratory. xiii.). Both the heavy and light chain of the hMab obtained from the transgenic avian migrated with the respective chains of the hMab obtained from mammalian cell culture (FIG. 28).

The hMab purified from egg white of hen #4992 was assayed for target antigen binding by ELISA (FIG. 29). The hMab was captured in microplate wells coated with the monoclonal antibody's target antigen. Antibody-antigen complexes were quantitated using isotype-specific secondary antibody conjugated with alkaline phosphatase. The ability of hMab obtained from the transgenic avian to bind the target antigen was compared with that of the same hMab produced by mammalian cells. Plots of the two preparations of hMab suggest that equal amounts of avian and mammalian derived hMab had similar antigen binding abilities (FIG. 29). Human serum IgGI kappa (Sigma-Aldrich I 5154), as a negative control, did not bind to antigen in this assay.

Figure 30:
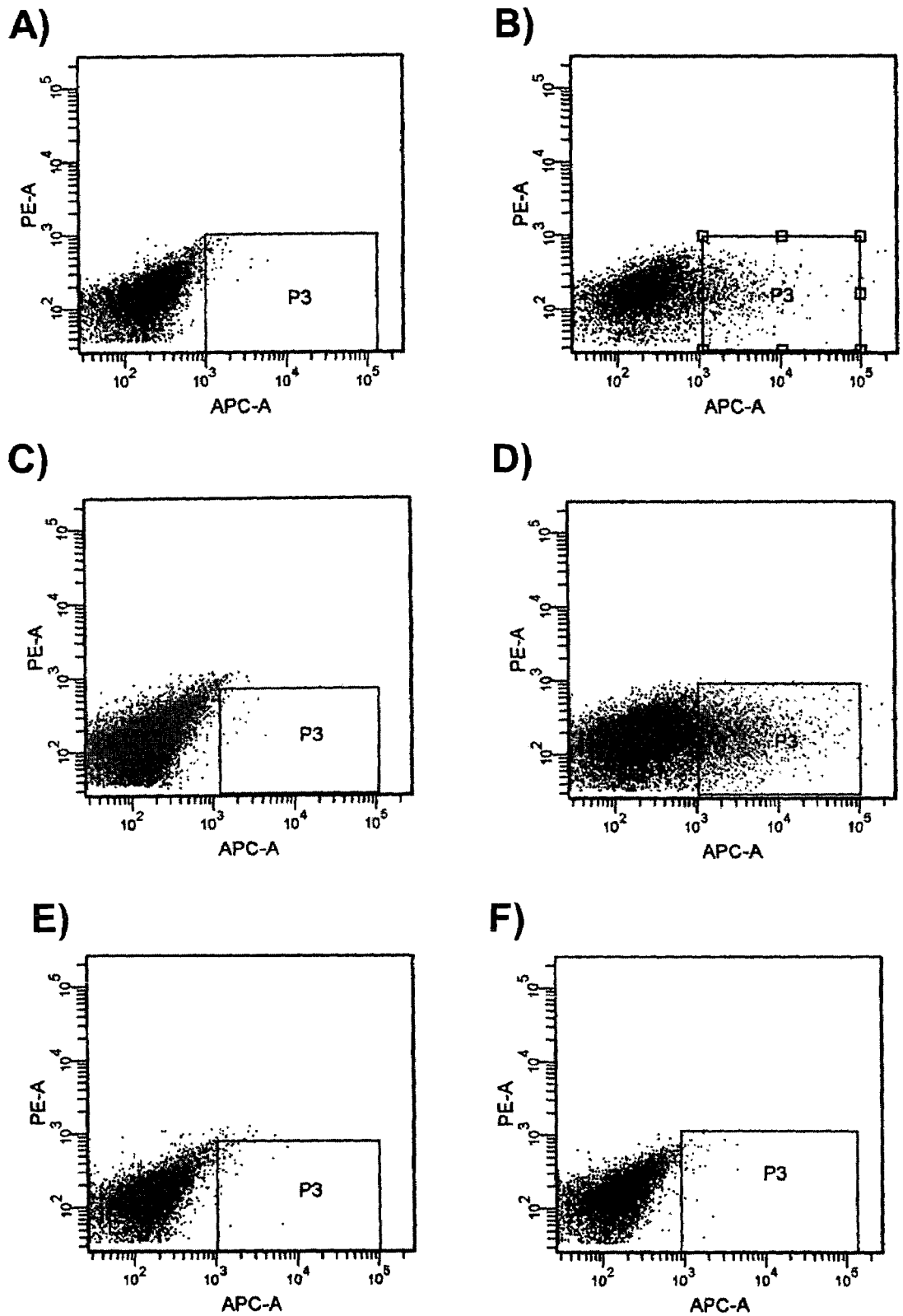

The target antigen of the hMab is typically expressed on the surface of various cells. The ability of the avian derived hMab to bind its target antigen expressed on a cell surface is demonstrated in FIG. 30. A mammalian cell line was transfected with an expression vector encoding the target antigen or a plasmid carrying a luciferase expression cassette. Transfected cells were collected and used for FACS analysis (FIG. 30, all panels). FACS was performed on a FACSAria Cell Sorter according to the manufacturer's instructions (Becton, Dickinson and Company, Franklin Lakes, N.J.). Cells were incubated with one of three primary antibodies: (1) the antigen-specific hMab produced by mammalian cells, (2) the antigen-specific hMab produced by the transgenic hen (hen #4992), or (3) human serum IgG1 kappa (Sigma-Aldrich I 5154). An anti-IgG1 kappa antibody conjugated with allophycocyanin (APC) was used to detect primary antibodies bound to the cells. Cells were sorted, counted and signal generated by the APC of the secondary antibody was quantitated. Both the mammalian and avian derived antigen-specific hMabs bound to cells transfected with the target antigen expression vector (FIGS. 30b and 30d, respectively). Neither mammalian nor avian derived hMab bound to cells transfected with the luciferase expression vector (FIGS. 30a and 30c, respectively). The negative control human antibody did not bind to cells transfected with either expression vector (FIGS. 30e and 30f, respectively).

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method of producing a transgenic avian, the method comprising:
   microinjecting into a cell of an avian embryo a DNA molecule comprising a transgene containing a nucleotide sequence encoding a heterologous polypeptide;
   introducing the microinjected avian embryo into an oviduct of a recipient hen, such that the recipient hen lays a shelled egg containing the microinjected avian embryo; and
   incubating the shelled egg containing the microinjected avian embryo until the shelled egg hatches;
   testing a hatched chick for the presence of the transgene; and
   developing a chick that tests positive for the transgene to sexual maturity, thereby producing a transgenic avian containing the transgene.

2. The method of claim 1, wherein the avian embryo is a stage I embryo

3. The method of claim 1, wherein the heterologous polypeptide is delivered to egg white of an avian egg produced by the transgenic avian.

4. The method of claim 1, wherein the avian is a chicken.

5. The method of claim 1, wherein the nucleotide sequence encoding the heterologous polypeptide is operably linked to a transcriptional regulatory element that can direct gene expression in one or more cells of the transgenic avian.

6. The method of claim 5, wherein the transcriptional regulatory element is a promoter region of an avian gene which encodes a protein selected from the group consisting of ovalbumin, lysozyme, ovomucoid, ovomucin, conalbumin and ovotransferrin.

7. The method of claim 1, wherein the DNA molecule is mixed with a nuclear localization signal (NLS) peptide prior to the microinjection.

8. The method of claim 1, wherein the transgenic comprises an internal ribosome entry site (IRES).

9. The method of claim 8, wherein at least two nucleotide sequences each encoding a heterologous polypeptide are introduced into the avian embryo.

10. The method of claim 9, wherein the heterologous polypeptides comprise heavy and light chains of an antibody.

11. The method of claim 1, wherein the DNA molecule is a bacterial artificial chromosome (BAG).

12. The method of claim 1, wherein the heterologous polypeptide-encoding sequence is operably linked to an IRES.

13. The method of claim 1, wherein the DNA molecule is not a eukaryotic viral vector.

14. The method of claim 1 further comprising isolating the heterologous peptide from the transgenic avian or an egg laid by the transgenic avian.

15. A method comprising:
   microinjecting into a cell of an avian embryo a nucleic acid comprising a transgene containing a nucleotide sequence encoding a non-avian protein;
   introducing the microinjected avian embryo into an oviduct of a recipient hen, such that the recipient hen lays a shelled egg containing the microinjected avian embryo;
   incubating the shelled egg containing the microinjected avian embryo until the shelled egg hatches;
   testing a hatched chick for the presence of the transgene; and
   isolating the non-avian protein from an egg of a chick that tests positive for the transgene and is developed to sexual maturity.

16. The method of claim 15, wherein the avian is a chicken.

17. The method of claim 15, wherein the nucleotide sequence encoding the non-avian protein is operably linked to a transcriptional regulatory element that can direct gene expression in one or more cells of the transgenic avian.

18. The method of claim 17, wherein the transcriptional regulatory element is a promoter region of an avian gene which encodes a protein selected from the group consisting of ovalbumin, lysozyme, ovomucoid, ovomucin, conalbumin and ovotransferrin.

19. The method of claim 15, wherein the transgene comprises an internal ribosome entry site (IRES).

20. The method of claim 15, wherein at least two nucleotide sequences each encoding a non-avian protein are introduced into the avian embryo.

21. The method of claim 20, wherein the non-avian proteins comprise heavy and light chains of an antibody.

22. The method of claim 15, wherein the nucleic acid is a bacterial artificial chromosome (BAC).

23. The method of claim 15, wherein the avian embryo is a stage I embryo.

24. The method of claim 15 wherein the nucleic acid is DNA.

25. The method of claim 15 wherein the non-avian protein is selected from the group consisting of growth hormones, cytokines, structural proteins, enzymes, human growth hormone, interferon, lysozyme, β-casein, albumin, α-1 antitrypsin, antithrombin III, collagen, factors VIII, IX, X, fibrinogen, insulin, lactoferrin, protein C, erythropoietin (EPO), granulocyte colony-stimulating factor (G-CSF), granulocyte macrophage colony-stimulating factor (GM-CSF), tissue-type plasminogen activator (tPA), somatotropin, chymotrypsin, immunoglobulins, antibodies and immunotoxins.

26. The method of claim 15 wherein, the non-avian protein is selected from the group consisting of growth hormones, cytokines, structural proteins, enzymes, human growth hormone, interferon, lysozyme, β-casein, albumin, α-1 antitrypsin, antithrombin III, collagen, factors VIII, IX, X, fibrinogen, insulin, lactoferrin, protein C, erythropoietin (EPO), granulocyte colony-stimulating factor (G-CSF), granulocyte macrophage colony-stimulating factor (GM-CSF), tissue-type plasminogen activator (tPA), somatotropin, ehymotrypsin, immunoglobulins, antibodies and immunotoxins.

27. A method comprising:
microinjecting into a cell of an avian embryo a nucleic acid comprising a transgene containing a nucleotide sequence encoding a pharmaceutical protein;
introducing the microinjected avian embryo into an oviduct of a recipient hen, such that the recipient hen lays a shelled egg containing the microinjected avian embryo;
incubating the shelled egg containing the microinjected avian embryo until the shelled egg hatches;
testing a hatched chick for the presence of the transgene; and
isolating the pharmaceutical protein from an egg of a chick that tests positive for the transgene developed to sexual maturity.

28. The method of claim 27, wherein the avian embryo is a stage I embryo.

29. The method of claim 27, wherein the pharmaceutical protein is delivered to egg white of an avian egg produced by the transgenic avian.

30. The method of claim 27, wherein the nucleotide sequence encoding the pharmaceutical protein is operably linked to a transcriptional regulatory element that can direct gene expression in one or more cells of the transgenic avian.

31. The method of claim 30, wherein the transcriptional regulatory element is a promoter region of an avian gene which encodes a protein selected from the group consisting of ovalbumin, lysozyme, ovomucoid, ovomucin, conalbumin and ovotransferrin.

32. The method of claim 27, wherein the nucleic acid is mixed with a nuclear localization signal (NLS) peptide prior to the microinjection.

33. The method of claim 27, wherein the nucleotide sequence encoding a pharmaceutical protein is optimized for codon usage by an avian.

34. The method of claim 27, wherein the transgene comprises an internal ribosome entry site (IRES).

35. A method comprising:
microinjecting into a cell of a chicken embryo a DNA molecule comprising a transgene containing a nucleotide sequence encoding a pharmaceutical protein;
introducing the microinjected avian embryo into an oviduct of a recipient hen, such that the recipient hen lays a shelled egg containing the microinjected avian embryo;
incubating the shelled egg containing the microinjected avian embryo until the shelled egg batches;
testing a hatched chick for the presence of the transgene; and
isolating the pharmaceutical protein from an egg of a chick that tests positive for the transgene developed to sexual maturity.

36. The method of claim 35 wherein, the pharmaceutical protein is selected from the group consisting of growth hormones, cytokines, structural proteins, enzymes, human growth hormone, interferon, lysozyme, β-casein, albumin, α-1 antitrypsin, antithrombin III, collagen, factors VIII, IX, X, fibrinogen, insulin, lactoferrin, protein C, erythrapoietin (EPO), granulocyte colony-stimulating factor (G-CSF), granulocyte macrophage colony-stimulating factor (GM-CSF), tissue-type plasminogen activator (tPA), somatotropin, chymotrvpsin, immunoglobulins. antibodies and immunotoxins.

37. The method of claim 35 wherein, the transgene comprises a promoter region of an avian gene which encodes a protein selected from the group consisting of ovalbumin, lysozyme, ovomucoid, ovomucin, conalbumin and ovotransferrin.

38. The method of claim 35 wherein, the avian embryo is a stage I embryo.

* * * * *

SEQUENCE LISTING

```
<160> NUMBER OF SEQ ID NOS: 48

<210> SEQ ID NO 1
<211> LENGTH: 20
<212> TYPE: DNA
<213> ORGANISM: Artificial sequence
<220> FEATURE:
<223> OTHER INFORMATION: Primer 5pLMAR2

<400> SEQUENCE: 1
tgccgccttc tttgatattc                                              20

<210> SEQ ID NO 2
<211> LENGTH: 20
<212> TYPE: DNA
<213> ORGANISM: Artificial sequence
<220> FEATURE:
<223> OTHER INFORMATION: Primer LE-6.1kbrev1

<400> SEQUENCE: 2
ttggtggtaa ggcctttttg                                              20

<210> SEQ ID NO 3
<211> LENGTH: 20
<212> TYPE: DNA
<213> ORGANISM: Artificial sequence
<220> FEATURE:
<223> OTHER INFORMATION: Primer lys-6.1

<400> SEQUENCE: 3
ctggcaagct gtcaaaaaca                                              20

<210> SEQ ID NO 4
<211> LENGTH: 20
<212> TYPE: DNA
<213> ORGANISM: Artificial sequence
<220> FEATURE:
<223> OTHER INFORMATION: Primer LysE1rev

<400> SEQUENCE: 4
cagctcacat cgtccaaaga                                              20

<210> SEQ ID NO 5
<211> LENGTH: 498
<212> TYPE: DNA
<213> ORGANISM: Artificial sequence
<220> FEATURE:
<223> OTHER INFORMATION: IFNMAGMAX
```

```
<220> FEATURE:
<221> NAME/KEY: misc_feature
<222> LOCATION: (1)..(498)
<223> OTHER INFORMATION:

<400> SEQUENCE: 5
tgcgatctgc ctcagaccca cagcctgggc agcaggagga ccctgatgct gctggctcag      60
atgaggagaa tcagcctgtt tagctgcctg aaggataggc acgattttgg ctttcctcaa     120
gaggagtttg caaccagtt tcagaaggct gagaccatcc ctgtgctgca cgagatgatc      180
cagcagatct ttaacctgtt tagcaccaag gatagcagcg ctgcttggga tgagaccctg     240
ctggataagt tttacaccga gctgtaccag cagctgaacg atctggaggc ttgcgtgatc     300
cagggcgtgg gcgtgaccga gacccctctg atgaaggagg atagcatcct ggctgtgagg     360
aagtactttc agaggatcac cctgtacctg aaggagaaga agtacagccc ctgcgcttgg     420
gaagtcgtga gggctgagat catgaggagc tttagcctga gcaccaacct gcaagagagc     480
ttgaggtcta aggagtaa                                                    498

<210> SEQ ID NO 6
<211> LENGTH: 12728
<212> TYPE: DNA
<213> ORGANISM: Gallus gallus
<220> FEATURE:
<221> NAME/KEY: misc_feature
<222> LOCATION: (1)..(237)
<223> OTHER INFORMATION: 5prime matrix (scaffold) attachment region
      (MAR)
<220> FEATURE:
<221> NAME/KEY: misc_feature
<222> LOCATION: (261)..(1564)
<223> OTHER INFORMATION: 5prime matrix (scaffold) attachment region
      (MAR)
<220> FEATURE:
<221> NAME/KEY: misc_feature
<222> LOCATION: (1565)..(1912)
<223> OTHER INFORMATION: 5prime matrix (scaffold) attachment region
      (MAR)
<220> FEATURE:
<221> NAME/KEY: misc_feature
<222> LOCATION: (1930)..(2012)
<223> OTHER INFORMATION: 5prime matrix (scaffold) attachment region
      (MAR)
<220> FEATURE:
<221> NAME/KEY: misc_feature
<222> LOCATION: (2013)..(2671)
<223> OTHER INFORMATION: Intrinsically curved DNA
<220> FEATURE:
<221> NAME/KEY: misc_feature
<222> LOCATION: (5848)..(5934)
<223> OTHER INFORMATION: Transcription Enhancer
<220> FEATURE:
<221> NAME/KEY: misc_feature
<222> LOCATION: (9160)..(9325)
<223> OTHER INFORMATION: Transcription Enhancer
<220> FEATURE:
<221> NAME/KEY: misc_feature
<222> LOCATION: (9326)..(9626)
<223> OTHER INFORMATION: Negative Regulatory Element
<220> FEATURE:
<221> NAME/KEY: misc_feature
<222> LOCATION: (9621)..(9660)
<223> OTHER INFORMATION: Hormone Response Element
<220> FEATURE:
<221> NAME/KEY: misc_feature
<222> LOCATION: (9680)..(10060)
<223> OTHER INFORMATION: Hormone Response Element
<220> FEATURE:
<221> NAME/KEY: misc_feature
<222> LOCATION: (10576)..(10821)
<223> OTHER INFORMATION: Chicken CR1 Repeat Sequence
<220> FEATURE:
```

```
<221> NAME/KEY: misc_feature
<222> LOCATION: (10926)..(11193)
<223> OTHER INFORMATION: Chicken CR1 Repeat Sequence
<220> FEATURE:
<221> NAME/KEY: misc_feature
<222> LOCATION: (11424)..(11938)
<223> OTHER INFORMATION: Lysozyme Proximal Promoter and Lysozyme Signal
      Peptide
<220> FEATURE:
<221> NAME/KEY: misc_feature
<222> LOCATION: (11946)..(12443)
<223> OTHER INFORMATION: Human Interferon alpha 2d encoding region
      codon optimized for expression in chicken cells (IFNMAGMAX)
<220> FEATURE:
<221> NAME/KEY: polyA_signal
<222> LOCATION: (12444)..(12728)
<223> OTHER INFORMATION:

<400> SEQUENCE: 6
tgccgccttc tttgatattc actctgttgt atttcatctc ttcttgccga tgaaaggata        60
taacagtctg tataacagtc tgtgaggaaa tacttggtat ttcttctgat cagtgttttt       120
ataagtaatg ttgaatattg gataaggctg tgtgtccttt gtcttgggag acaaagccca       180
cagcaggtgg tggttggggt ggtggcagct cagtgacagg agaggttttt ttgcctgttt       240
tttttttttt tttttttttt aagtaaggtg ttctttttc ttagtaaatt ttctactgga        300
ctgtatgttt tgacaggtca gaaacatttc ttcaaaagaa gaccttttg gaaactgtac        360 agcccttttc tttcattccc ttttgctttt ctgtgccaat gcctttggtt ctgattgcat       420
tatggaaaac gttgatcgga acttgaggtt tttatttata gtgtggcttg aaagcttgga       480
tagctgttgt tacacgagat accttattaa gtttaggcca gcttgatgct ttattttttc       540
cctttgaagt agtgagcgtt ctctggtttt tttcctttga aactggtgag cttagatttt      600
ttctaatggg attttttacc tgatgatcta gttgcatacc caaatgcttg taaatgtttt       660
cctagttaac atgttgataa cttcggattt acatgttgta tacttgtc atctgtgttt        720 ctagtaaaaa tatatggcat ttatagaaat acgtaattcc tgatttcctt ttttttttatc     780 tctatgctct gtgtgtacag gtcaaacaga cttcactcct attttttttt atagaatttt     840
atatgcagtc tgtcgttggt tcttgtgttg taaggataca gccttaaatt tcctagagcg       900
atgctcagta aggcgggttg tcacatgggt tcaaatgtaa aacgggcacg tttggctgct      960
gccttcccga gatccaggac actaaactgc ttctgcactg aggtataaat cgcttcagat      1020
cccagggaag tgcagatcca cgtgcatatt cttaaagaag aatgaatact ttctaaaata     1080
ttttggcata ggaagcaagc tgcatggatt tgtttgggac ttaaattatt ttggtaacgg     1140
agtgcatagg ttttaaacac agttgcagca tgctaacgag tcacagcgtt tatgcagaag     1200
tgatgcctgg atgcctgttg cagctgttta cggcactgcc ttgcagtgag cattgcagat     1260
aggggtgggg tgctttgtgt cgtgttccca cacgctgcca cacagccacc tcccggaaca     1320
catctcacct gctgggtact tttcaaacca tcttagcagt agtagatgag ttactatgaa     1380
acagagaagt tcctcagttg gatattctca tgggatgtct ttttttccat gttgggcaaa     1440
gtatgataaa gcatctctat ttgtaaatta tgcacttgtt agttcctgaa tcctttctat     1500
agcaccactt attgcagcag gtgtaggctc tggtgtggcc tgtgtctgtg cttcaatctt     1560
ttaaagcttc tttggaaata cactgacttg attgaagtct cttgaagata gtaaacagta     1620
cttacctttg atcccaatga aatcgagcat ttcagttgta aaagaattcc gcctattcat     1680
accatgtaat gtaattttac accccagtg ctgacacttt ggaatatatt caagtaatag      1740
actttggcct caccctcttg tgtactgtat tttgtaatag aaaatatttt aaactgtgca     1800
```

```
tatgattatt acattatgaa agagacattc tgctgatctt caaatgtaag aaaatgagga   1860
gtgcgtgtgc ttttataaat acaagtgatt gcaaattagt gcaggtgtcc ttaaaaaaaa   1920
aaaaaaaaag taatataaaa aggaccaggt gttttacaag tgaaatacat tcctatttgg   1980
taaacagtta cattttatg aagattacca gcgctgctga ctttctaaac ataaggctgt    2040
attgtcttcc tgtaccattg catttcctca ttcccaattt gcacaaggat gtctgggtaa   2100
actattcaag aaatggcttt gaaatacagc atgggagctt gtctgagttg aatgcagag    2160
ttgcactgca aaatgtcagg aaatggatgt ctctcagaat gcccaactcc aaaggatttt   2220
atatgtgtat atagtaagca gtttcctgat tccagcaggc caaagagtct gctgaatgtt   2280
gtgttgccgg agacctgtat ttctcaacaa ggtaagatgg tatcctagca actgcggatt   2340
ttaatacatt tcagcagaa gtacttagtt aatctctacc tttagggatc gtttcatcat    2400
ttttagatgt tatacttgaa atactgcata acttttagct ttcatgggtt cctttttttc   2460
agcctttagg agactgttaa gcaatttgct gtccaacttt tgtgttggtc ttaaactgca   2520
atagtagttt accttgtatt gaagaaataa agaccatttt tatattaaaa aatacttttg   2580
tctgtcttca ttttgacttg tctgatatcc ttgcagtgcc cattatgtca gttctgtcag   2640
atattcagac atcaaaactt aacgtgagct cagtggagtt acagctgcgg ttttgatgct   2700
gttattattt ctgaaactag aaatgatgtt gtcttcatct gctcatcaaa cacttcatgc   2760
agagtgtaag gctagtgaga aatgcataca tttattgata ctttttttaaa gtcaacttt   2820
tatcagattt ttttttcatt tggaaatata ttgttttcta gactgcatag cttctgaatc   2880
tgaaatgcag tctgattggc atgaagaagc acagcactct tcatcttact taaacttcat   2940
tttgaatga aggaagttaa gcaagggcac aggtccatga aatagagaca gtgcgctcag    3000
gagaaagtga acctggattt ctttggctag tgttctaaat ctgtagtgag gaaagtaaca   3060
cccgattcct tgaaagggct ccagctttaa tgcttccaaa ttgaaggtgg caggcaactt   3120
ggccactggt tatttactgc attatgtctc agtttcgcag ctaacctggc ttctccacta   3180
ttgagcatgg actatagcct ggcttcagag gccaggtgaa ggttgggatg ggtggaagga   3240
gtgctgggct gtggctgggg ggactgtggg gactccaagc tgagcttggg gtgggcagca   3300
cagggaaaag tgtgggtaac tattttaag tactgtgttg caaacgtctc atctgcaaat    3360
acgtagggtg tgtactctcg aagattaaca gtgtgggttc agtaatatat ggatgaattc   3420
acagtggaag cattcaaggg tagatcatct aacgacacca gatcatcaag ctatgattgg   3480
aagcggtatc agaagagcga ggaaggtaag cagtcttcat atgttttccc tccacgtaaa   3540
gcagtctggg aaagtagcac cccttgagca gagacaagga aataattcag gagcatgtgc   3600
taggagaact ttcttgctga attctacttg caagagcttt gatgcctggc ttctggtgcc   3660
ttctgcagca cctgcaaggc ccagagcctg tggtgagctg gagggaaaga ttctgctcaa   3720
gtccaagctt cagcaggtca ttgtctttgc ttcttccccc agcactgtgc agcagagtgg   3780
aactgatgtc gaagcctcct gtccactacc tgttgctgca ggcagactgc tctcagaaaa   3840
agagagctaa ctctatgcca tagtctgaag gtaaaatggg ttttaaaaaa gaaaacacaa   3900
aggcaaaacc ggctgcccca tgagaagaaa gcagtggtaa acatggtaga aaaggtgcag   3960
aagcccccag gcagtgtgac aggcccctcc tgccacctag aggcgggaac aagcttccct   4020
gcctagggct ctgcccgcga agtgcgtgtt tctttggtgg gttttgtttg gcgtttggtt   4080
ttgagattta gacacaaggg aagcctgaaa ggaggtgttg ggcactattt tggtttgtaa   4140
```

```
agcctgtact tcaaatatat attttgtgag ggagtgtagc gaattggcca atttaaaata   4200
aagttgcaag agattgaagg ctgagtagtt gagagggtaa cacgtttaat gagatcttct   4260
gaaactactg cttctaaaca cttgtttgag tggtgagacc ttggataggt gagtgctctt   4320
gttacatgtc tgatgcactt gcttgtcctt ttccatccac atccatgcat tccacatcca   4380
cgcatttgtc acttatccca tatctgtcat atctgacata cctgtctctt cgtcacttgg   4440
tcagaagaaa cagatgtgat aatccccagc cgccccaagt tgagaagat ggcagttgct    4500
tctttccctt tttcctgcta agtaaggatt ttctcctggc tttgacacct cacgaaatag   4560
tcttcctgcc ttacattctg ggcattattt caaatatctt tggagtgcgc tgctctcaag   4620
tttgtgtctt cctactctta gagtgaatgc tcttagagtg aaagagaagg aagagaagat   4680
gttggccgca gttctctgat gaacacacct ctgaataatg ccaaaggtg ggtgggtttc    4740
tctgaggaac gggcagcgtt tgcctctgaa agcaaggagc tctgcggagt tgcagttatt   4800
ttgcaactga tggtggaact ggtgcttaaa gcagattccc taggttccct gctacttctt   4860
ttccttcttg gcagtcagtt tatttctgac agacaaacag ccaccccac tgcaggctta    4920
gaaagtatgt ggctctgcct gggtgtgtta cagctctgcc ctggtgaaag gggattaaaa   4980
cgggcaccat tcatcccaaa caggatcctc attcatggat caagctgtaa ggaacttggg   5040
ctccaacctc aaaacattaa ttggagtacg aatgtaatta aaactgcatt ctcgcattcc   5100
taagtcattt agtctggact ctgcagcatg taggtcggca gctcccactt tctcaaagac   5160
cactgatgga ggagtagtaa aaatggagac cgattcagaa caaccaacgg agtgttgccg   5220
aagaaactga tggaaataat gcatgaattg tgtggtggac atttttttta aatacataaa   5280
ctacttcaaa tgaggtcgga gaaggtcagt gttttattag cagccataaa accaggtgag   5340
cgagtaccat ttttctctac aagaaaaacg attctgagct ctgcgtaagt ataagttctc   5400
catagcggct gaagctcccc cctggctgcc tgccatctca gctggagtgc agtgccattt   5460
ccttggggtt tctctcacag cagtaatggg acaatacttc acaaaaattc tttcttttcc   5520
tgtcatgtgg gatccctact gtgccctcct ggttttacgt tacccctga ctgttccatt    5580
cagcggtttg gaaagagaaa agaatttgg aaataaaaca tgtctacgtt atcacctcct    5640
ccagcatttt ggttttaat tatgtcaata actggcttag atttggaaat gagagggggt    5700
tgggtgtatt accgaggaac aaaggaaggc ttatataaac tcaagtcttt tatttagaga   5760
actggcaagc tgtcaaaaac aaaaaggcct taccaccaaa ttaagtgaat agccgctata   5820
gccagcaggg ccagcacgag ggatggtgca ctgctggcac tatgccacgg cctgcttgtg   5880
actctgagag caactgcttt ggaaatgaca gcacttggtg caatttcctt tgtttcagaa   5940
tgcgtagagc gtgtgcttgg cgacagtttt tctagttagg ccacttcttt tttccttctc   6000
tcctcattct cctaagcatg tctccatgct ggtaatccca gtcaagtgaa cgttcaaaca   6060
atgaatccat cactgtagga ttctcgtggt gatcaaatct ttgtgtgagg tctataaaat   6120
atggaagctt atttatttt cgttcttcca tatcagtctt ctctatgaca attcacatcc    6180
accacagcaa attaaaggtg aaggaggctg gtgggatgaa gagggtcttc tagctttacg   6240
ttcttccttg caaggccaca ggaaaatgct gagagctgta gaatacagcc tggggtaaga   6300
agttcagtct cctgctggga cagctaaccg catcttataa ccccttctga gactcatctt   6360
aggaccaaat agggtctatc tgggttttt gttcctgctg ttcctcctgg aaggctatct    6420
cactatttca ctgctcccac ggttacaaac caaagataca gcctgaattt tttctaggcc   6480
acattacata aatttgacct ggtaccaata ttgttctcta tatagttatt tccttcccca   6540
```

```
ctgtgtttaa cccottaagg cattcagaac aactagaatc atagaatggt ttggattgga    6600
agggggcctta aacatcatcc atttccaacc ctctgccatg ggctgcttgc cacccactgg   6660
ctcaggctgc ccagggcccc atccagcctg gccttgagca cctccaggga tggggcaccc   6720
acagcttctc tgggcagcct gtgccaacac ctcaccactc tctgggtaaa gaattctctt   6780
ttaacatcta atctaaatct cttctctttt agtttaaagc cattcctctt tttcccgttg   6840
ctatctgtcc aagaaatgtg tattggtctc cctcctgctt ataagcagga agtactggaa   6900
ggctgcagtg aggtctcccc acagccttct cttctccagg ctgaacaagc ccagctcctt   6960
cagcctgtct tcgtaggaga tcatcttagt ggccctcctc tggacccatt ccaacagttc   7020
cacggctttc ttgtggagcc ccaggtctgg atgcagtact tcagatgggg ccttacaaag   7080
gcagagcaga tggggacaat cgcttacccc tccctgctgg ctgcccctgt tttgatgcag   7140
cccagggtac tgttggcctt tcaggctccc agacccttg ctgatttgtg tcaagctttt    7200
catccaccag aacccacgct tcctggttaa tacttctgcc ctcacttctg taagcttgtt   7260
tcaggagact tccattcttt aggacagact gtgttacacc tacctgccct attcttgcat   7320
atatacattt cagttcatgt ttcctgtaac aggacagaat atgtattcct ctaacaaaaa   7380
tacatgcaga attcctagtg ccatctcagt agggttttca tggcagtatt agcacatagt   7440
caatttgctg caagtacctt ccaagctgcg gcctcccata aatcctgtat ttgggatcag   7500
ttacctttg gggtaagctt ttgtatctgc agagaccctg ggggttctga tgtgcttcag    7560
ctctgctctg ttctgactgc accattttct agatcaccca gttgttcctg tacaacttcc   7620
ttgtcctcca tcctttccca gcttgtatct ttgacaaata caggcctatt tttgtgtttg   7680
cttcagcagc catttaattc ttcagtgtca tcttgttctg ttgatgccac tggaacagga   7740
ttttcagcag tcttgcaaag aacatctagc tgaaaacttt ctgccattca atattcttac   7800
cagttcttct tgtttgaggt gagccataaa ttactagaac ttcgtcactg acaagtttat   7860
gcatttatt acttctatta tgtacttact ttgacataac acagacacgc acatattttg    7920
ctgggatttc cacagtgtct ctgtgtcctt cacatggttt tactgtcata cttccgttat   7980
aaccttggca atctgcccag ctgcccatca aagaaaaga gattccttt ttattacttc     8040
tcttcagcca ataaacaaaa tgtgagaagc ccaaacaaga acttgtgggg caggctgcca   8100
tcaagggaga gacagctgaa gggttgtgta gctcaataga attaagaaat aataaagctg   8160
tgtcagacag ttttgcctga tttatacagg cacgccccaa gccagagagg ctgtctgcca   8220
aggccacctt gcagtccttg gtttgtaaga taagtcatag gtaacttttc tggtgaattg   8280
cgtggagaat catgatggca gttcttgctg tttactatgg taagatgcta aaataggaga   8340
cagcaaagta acacttgctg ctgtaggtgc tctgctatcc agacagcgat ggcactcgca   8400
caccaagatg agggatgctc ccagctgacg gatgctgggg cagtaacagt gggtcccatg   8460
ctgcctgctc attagcatca cctcagccct caccagccca tcagaaggat catcccaagc   8520
tgaggaaagt tgctcatctt cttcacatca tcaaaccttt ggcctgactg atgcctcccg   8580
gatgcttaaa tgtggtcact gacatcttta ttttctatg atttcaagtc agaacctccg    8640
gatcaggagg gaacacatag tgggaatgta ccctcagctc caaggccaga tcttccttca   8700
atgatcatgc atgctactta ggaaggtgtg tgtgtgtgaa tgtagaattg cctttgttat   8760
tttttcttcc tgctgtcagg aacattttga ataccagaga aaaagaaaag tgctcttctt   8820
ggcatgggag gagttgtcac acttgcaaaa taaaggatgc agtcccaaat gttcataatc   8880
```

```
tcagggtctg aaggaggatc agaaactgtg tatacaattt caggcttctc tgaatgcagc      8940
ttttgaaagc tgttcctggc cgaggcagta ctagtcagaa ccctcggaaa caggaacaaa      9000
tgtcttcaag gtgcagcagg aggaaacacc ttgcccatca tgaaagtgaa taaccactgc      9060
cgctgaagga atccagctcc tgtttgagca ggtgctgcac actcccacac tgaaacaaca      9120
gttcattttt ataggacttc caggaaggat cttcttctta agcttcttaa ttatggtaca      9180
tctccagttg gcagatgact atgactactg acaggagaat gaggaactag ctgggaatat      9240
ttctgtttga ccaccatgga gtcacccatt tctttactgg tatttggaaa taataattct      9300
gaattgcaaa gcaggagtta gcgaagatct tcatttcttc catgttggtg acagcacagt      9360
tctggctatg aaagtctgct tacaaggaag aggataaaaa tcatagggat aataaatcta      9420
agtttgaaga caatgaggtt ttagctgcat ttgacatgaa gaaattgaga cctctactgg      9480
atagctatgg tatttacgtg tcttttttgct tagttactta ttgaccccag ctgaggtcaa      9540
gtatgaactc aggtctctcg ggctactggc atggattgat tacatacaac tgtaattta       9600
gcagtgattt agggtttatg agtacttttg cagtaaatca tagggttagt aatgttaatc      9660
tcagggaaaa aaaaaaaaag ccaaccctga cagacatccc agctcaggtg gaaatcaagg      9720
atcacagctc agtgcggtcc cagagaacac agggactctt ctcttaggac ctttatgtac      9780
agggcctcaa gataactgat gttagtcaga agactttcca ttctggccac agttcagctg      9840
aggcaatcct ggaattttct ctccgctgca cagttccagt catcccagtt tgtacagttc      9900
tggcactttt tgggtcaggc cgtgatccaa ggagcagaag ttccagctat ggtcagggag      9960
tgcctgaccg tcccaactca ctgcactcaa acaaaggcga aaccacaaga gtggcttttg     10020
ttgaaattgc agtgtggccc agaggggctg caccagtact ggattgacca cgaggcaaca     10080
ttaatcctca gcaagtgcaa tttgcagcca ttaaattgaa ctaactgata ctacaatgca     10140
atcagtatca acaagtggtt tggcttggaa gatggagtct aggggctcta caggagtagc     10200
tactctctaa tggagttgca ttttgaagca ggacactgtg aaaagctggc ctcctaaaga     10260
ggctgctaaa cattagggtc aattttccag tgcactttct gaagtgtctg cagttcccca     10320
tgcaaagctg cccaaacata gcacttccaa ttgaatacaa ttatatgcag gcgtactgct     10380
tcttgccagc actgtccttc tcaaatgaac tcaacaaaca atttcaaagt ctagtagaaa     10440
gtaacaagct ttgaatgtca ttaaaaagta tatctgcttt cagtagttca gcttatttat     10500
gcccactaga aacatcttgt acaagctgaa cactggggct ccagattagt ggtaaaacct     10560
actttataca atcatagaat catagaatgg cctgggttgg aagggacccc aaggatcatg     10620
aagatccaac accccgcca caggcagggc caccaacctc cagatctggt actagaccag     10680
gcagcccagg gctccatcca acctggccat gaacacctcc agggatggag catccacaac     10740
ctctctgggc agcctgtgcc agcacctcac caccctctct gtgaagaact tttccctgac     10800
atccaatcta agccttccct ccttgaggtt agatccactc cccttgtgc tatcactgtc      10860
tactcttgta aaaagttgat tctcctcctt tttggaaggt tgcaatgagg tctccttgca     10920
gccttcttct cttctgcagg atgaacaagc ccagctccct cagcctgtct ttataggaga     10980
ggtgctccag ccctctgatc atctttgtgg ccctcctctg acccgctcc aagagctcca      11040
catctttcct gtactggggg ccccaggcct gaatgcagta ctccagatgg ggcctcaaaa     11100
gagcagagta aagagggaca atcaccttcc tcaccctgct ggccagccct cttctgatgg     11160
agccctggat acaactggct ttctgagctg caacttctcc ttatcagttc cactattaaa     11220
acaggaacaa tacaacaggt gctgatggcc agtgcagagt ttttcacact tcttcatttc     11280
```

```
ggtagatctt agatgaggaa cgttgaagtt gtgcttctgc gtgtgcttct tcctcctcaa    11340
atactcctgc ctgataccct accccacctg ccactgaatg gctccatggc cccctgcagc    11400
cagggccctg atgaacccgg cactgcttca gatgctgttt aatagcacag tatgaccaag    11460
ttgcacctat gaatacacaa acaatgtgtt gcatccttca gcacttgaga agaagagcca    11520
aatttgcatt gtcaggaaat ggtttagtaa ttctgccaat taaaacttgt ttatctacca    11580
tggctgtttt tatggctgtt agtagtggta cactgatgat gaacaatggc tatgcagtaa    11640
aatcaagact gtagatattg caacagacta taaaattcct ctgtggctta gccaatgtgg    11700
tacttcccac attgtataag aaatttggca agtttagagc aatgtttgaa gtgttgggaa    11760
atttctgtat actcaagagg gcgttttga caactgtaga acagaggaat caaaagggg     11820 tgggaggaag ttaaaagaag aggcaggtgc aagagagctt gcagtcccgc tgtgtgtacg    11880
acactggcaa catgaggtct ttgctaatct tggtgctttg cttcctgccc ctggctgcct    11940
tagggtgcga tctgcctcag acccacagcc tgggcagcag gaggaccctg atgctgctgg    12000
ctcagatgag gagaatcagc ctgtttagct gcctgaagga taggcacgat tttggctttc    12060
ctcaagagga gtttggcaac cagtttcaga aggctgagac catccctgtg ctgcacgaga    12120
tgatccagca gatctttaac ctgtttagca ccaaggatag cagcgctgct tgggatgaga    12180
ccctgctgga taagttttac accgagctgt accagcagct gaacgatctg gaggcttgcg    12240
tgatccaggg cgtgggcgtg accgagaccc ctctgatgaa ggaggatagc atcctggctg    12300
tgaggaagta ctttcagagg atcaccctgt acctgaagga gaagaagtac agcccctgcg    12360
cttgggaagt cgtgagggct gagatcatga ggagctttag cctgagcacc aacctgcaag    12420
agagcttgag gtctaaggag taaaaagtct agagtcgggg cggccggccg cttcgagcag    12480
acatgataag atacattgat gagtttggac aaaccacaac tagaatgcag tgaaaaaaat    12540
gctttatttg tgaaatttgt gatgctattg ctttatttgt aaccattata agctgcaata    12600
aacaagttaa caacaacaat tgcattcatt ttatgtttca ggttcagggg gaggtgtggg    12660 aggttttta aagcaagtaa aacctctaca aatgtggtaa aatcgataag gatccgtcga    12720
gcggccgc                                                             12728
```

<210> SEQ ID NO 7
<211> LENGTH: 11945
<212> TYPE: DNA
<213> ORGANISM: Gallus gallus
<220> FEATURE:
<221> NAME/KEY: misc_feature
<222> LOCATION: (1)..(237)
<223> OTHER INFORMATION: 5prime matrix attachment region (MAR)
<220> FEATURE:
<221> NAME/KEY: misc_feature
<222> LOCATION: (261)..(1564)
<223> OTHER INFORMATION: 5prime matrix attachment region (MAR)
<220> FEATURE:
<221> NAME/KEY: misc_feature
<222> LOCATION: (1565)..(1912)
<223> OTHER INFORMATION: 5prime matrix attachment region (MAR)
<220> FEATURE:
<221> NAME/KEY: misc_feature
<222> LOCATION: (1930)..(2012)
<223> OTHER INFORMATION: 5prime matrix attachment region (MAR)
<220> FEATURE:
<221> NAME/KEY: misc_feature
<222> LOCATION: (2013)..(2671)
<223> OTHER INFORMATION: Intrinsically Curved DNA
<220> FEATURE:
<221> NAME/KEY: misc_feature
<222> LOCATION: (5848)..(5934)

```
<223> OTHER INFORMATION: Transcription Enhancer
<220> FEATURE:
<221> NAME/KEY: misc_feature
<222> LOCATION: (9160)..(9325)
<223> OTHER INFORMATION: Transcription Enhancer
<220> FEATURE:
<221> NAME/KEY: misc_feature
<222> LOCATION: (9326)..(9626)
<223> OTHER INFORMATION: Negative Regulatory Element
<220> FEATURE:
<221> NAME/KEY: misc_feature
<222> LOCATION: (9621)..(9660)
<223> OTHER INFORMATION: Hormone Response Element
<220> FEATURE:
<221> NAME/KEY: misc_feature
<222> LOCATION: (9680)..(10060)
<223> OTHER INFORMATION: Hormone Response Element
<220> FEATURE:
<221> NAME/KEY: misc_feature
<222> LOCATION: (10576)..(10821)
<223> OTHER INFORMATION: Chicken CR1 Repeat
<220> FEATURE:
<221> NAME/KEY: misc_feature
<222> LOCATION: (10926)..(11193)
<223> OTHER INFORMATION: Chicken CR1 Repeat
<220> FEATURE:
<221> NAME/KEY: misc_feature
<222> LOCATION: (11424)..(11938)
<223> OTHER INFORMATION: Proximal promoter and lysozyme signal peptide

<400> SEQUENCE: 7
tgccgccttc tttgatattc actctgttgt atttcatctc ttcttgccga tgaaaggata      60
taacagtctg tataacagtc tgtgaggaaa tacttggtat ttcttctgat cagtgttttt     120
ataagtaatg ttgaatattg gataaggctg tgtgtccttt gtcttgggag acaaagccca     180
cagcaggtgg tggttggggt ggtggcagct cagtgacagg agaggttttt ttgcctgttt     240
tttttttttt tttttttttt aagtaaggtg ttcttttttc ttagtaaatt ttctactgga     300
ctgtatgttt tgacaggtca gaaacatttc ttcaaaagaa gaaccttttg gaaactgtac     360 agccctttc tttcattccc tttttgcttt ctgtgccaat gcctttggtt ctgattgcat      420
tatggaaaac gttgatcgga acttgaggtt tttatttata gtgtggcttg aaagcttgga     480
tagctgttgt tacacgagat accttattaa gtttaggcca gcttgatgct ttattttttc     540
cctttgaagt agtgagcgtt ctctggtttt tttcctttga aactggtgag cttagatttt     600
ttctaatggg attttttacc tgatgatcta gttgcatacc caaatgcttg taaatgtttt     660
cctagttaac atgttgataa cttcggattt acatgttgta tatacttgtc atctgtgttt     720
ctagtaaaaa tatatggcat ttatagaaat acgtaattcc tgatttcctt ttttttttatc     780 tctatgctct gtgtgtacag gtcaaacaga cttcactcct attttttattt atagaattttt    840 atatgcagtc tgtcgttggt tcttgtgttg taaggataca gccttaaatt tcctagagcg     900
atgctcagta aggcgggttg tcacatgggt tcaaatgtaa aacgggcacg tttggctgct     960
gccttcccga gatccaggac actaaactgc ttctgcactg aggtataaat cgcttcagat    1020
cccagggaag tgcagatcca cgtgcatatt cttaaagaag aatgaatact ttctaaaata    1080
ttttggcata ggaagcaagc tgcatggatt tgtttgggac ttaaattatt ttggtaacgg    1140
agtgcatagg ttttaaacac agttgcagca tgctaacgag tcacagcgtt tatgcagaag    1200
tgatgcctgg atgcctgttg cagctgttta cggcactgcc ttgcagtgag cattgcagat    1260
aggggtgggg tgctttgtgt cgtgttccca cacgctgcca cacagccacc tcccggaaca    1320
catctcacct gctgggtact tttcaaacca tcttagcagt agtagatgag ttactatgaa    1380
acagagaagt tcctcagttg gatattctca tgggatgtct ttttttcccat gttgggcaaa    1440
```

```
gtatgataaa gcatctctat ttgtaaatta tgcacttgtt agttcctgaa tcctttctat    1500
agcaccactt attgcagcag gtgtaggctc tggtgtggcc tgtgtctgtg cttcaatctt    1560
ttaaagcttc tttggaaata cactgacttg attgaagtct cttgaagata gtaaacagta    1620
cttacctttg atcccaatga aatcgagcat tcagttgta aaagaattcc gcctattcat     1680
accatgtaat gtaattttac accccagtg ctgacactttggaatatatt caagtaatag     1740 actttggcct caccctcttg tgtactgtat tttgtaatag aaaatatttt aaactgtgca    1800
tatgattatt acattatgaa agagacattc tgctgatctt caaatgtaag aaaatgagga    1860
gtgcgtgtgc ttttataaat acaagtgatt gcaaattagt gcaggtgtcc ttaaaaaaaa    1920 aaaaaaaag taatataaaa aggaccaggt gttttacaag tgaaatacat tcctatttgg     1980
taaacagtta cattttatg aagattacca gcgctgctga ctttctaaac ataaggctgt     2040
attgtcttcc tgtaccattg catttcctca ttcccaattt gcacaaggat gtctgggtaa    2100
actattcaag aaatggcttt gaaatacagc atgggagctt gtctgagttg aatgcagag    2160 ttgcactgca aaatgtcagg aaatggatgt ctctcagaat gcccaactcc aaaggatttt    2220
atatgtgtat atagtaagca gtttcctgat tccagcaggc caaagagtct gctgaatgtt    2280
gtgttgccgg agacctgtat ttctcaacaa ggtaagatgg tatcctagca actgcggatt    2340
ttaatacatt tcagcagaa gtacttagtt aatctctacc tttagggatc gtttcatcat    2400
ttttagatgt tatacttgaa atactgcata acttttagct ttcatgggtt cctttttttc    2460
agcctttagg agactgttaa gcaatttgct gtccaacttt tgtgttggtc ttaaactgca    2520
atagtagttt accttgtatt gaagaaataa agaccatttt tatattaaaa aatacttttg    2580
tctgtcttca ttttgacttg tctgatatcc ttgcagtgcc cattatgtca gttctgtcag    2640
atattcagac atcaaaactt aacgtgagct cagtggagtt acagctgcgg ttttgatgct    2700
gttattattt ctgaaactag aaatgatgtt gtcttcatct gctcatcaaa cacttcatgc    2760
agagtgtaag gctagtgaga aatgcataca tttattgata cttttttaaa gtcaacttt    2820 tatcagattt ttttttcatt tggaaatata ttgttttcta gactgcatag cttctgaatc    2880
tgaaatgcag tctgattggc atgaagaagc acagcactct tcatcttact taaacttcat    2940
tttggaatga aggaagttaa gcaagggcac aggtccatga aatagagaca gtgcgctcag    3000
gagaaagtga acctggatttctttggctag tgttctaaat ctgtagtgag gaaagtaaca     3060
cccgattcct tgaaagggct ccagctttaa tgcttccaaa ttgaaggtgg caggcaactt    3120
ggccactggt tatttactgc attatgtctc agtttcgcag ctaacctggc ttctccacta    3180
ttgagcatgg actatagcct ggcttcagag gccaggtgaa ggttgggatg ggtgaagga    3240 gtgctgggct gtggctgggg ggactgtggg gactccaagc tgagcttggg gtgggcagca    3300
cagggaaaag tgtgggtaac tatttttaag tactgtgttg caaacgtctc atctgcaaat    3360
acgtagggtg tgtactctcg aagattaaca gtgtgggttc agtaatatat ggatgaattc    3420
acagtggaag cattcaaggg tagatcatct aacgacacca gatcatcaag ctatgattgg    3480
aagcggtatc agaagagcga ggaaggtaag cagtcttcat atgttttccc tccacgtaaa    3540
gcagtctggg aaagtagcac cccttgagca gagacaagga aataattcag gagcatgtgc    3600
taggagaact ttcttgctga attctacttg caagagcttt gatgcctggc ttctggtgcc    3660
ttctgcagca cctgcaaggc ccagagcctg tggtgagctg gagggaaaga ttctgctcaa    3720
gtccaagctt cagcaggtca ttgtctttgc ttcttccccc agcactgtgc agcagagtgg    3780
```

```
aactgatgtc gaagcctcct gtccactacc tgttgctgca ggcagactgc tctcagaaaa    3840
agagagctaa ctctatgcca tagtctgaag gtaaaatggg ttttaaaaaa gaaaacacaa    3900
aggcaaaacc ggctgcccca tgagaagaaa gcagtggtaa acatggtaga aaaggtgcag    3960
aagcccccag gcagtgtgac aggcccctcc tgccacctag aggcgggaac aagcttccct    4020
gcctagggct ctgcccgcga agtgcgtgtt tctttggtgg gttttgtttg gcgtttggtt    4080
ttgagattta gacacaaggg aagcctgaaa ggaggtgttg ggcactattt tggtttgtaa    4140
agcctgtact tcaaatatat attttgtgag ggagtgtagc gaattggcca atttaaaata    4200
aagttgcaag agattgaagg ctgagtagtt gagagggtaa cacgtttaat gagatcttct    4260
gaaactactg cttctaaaca cttgtttgag tggtgagacc ttggataggt gagtgctctt    4320
gttacatgtc tgatgcactt gcttgtcctt ttccatccac atccatgcat tccacatcca    4380
cgcatttgtc acttatccca tatctgtcat atctgacata cctgtctctt cgtcacttgg    4440
tcagaagaaa cagatgtgat aatccccagc cgccccaagt tgagaagat ggcagttgct    4500
tctttccctt tttcctgcta agtaaggatt ttctcctggc tttgacacct cacgaaatag    4560
tcttcctgcc ttacattctg ggcattattt caaatatctt tggagtgcgc tgctctcaag    4620
tttgtgtctt cctactctta gagtgaatgc tcttagagtg aaagagaagg aagagaagat    4680
gttggccgca gttctctgat gaacacacct ctgaataatg ccaaaggtg ggtgggtttc    4740
tctgaggaac gggcagcgtt tgcctctgaa agcaaggagc tctgcggagt tgcagttatt    4800
ttgcaactga tggtggaact ggtgcttaaa gcagattccc taggttccct gctacttctt    4860
ttccttcttg gcagtcagtt tatttctgac agacaaacag ccacccccac tgcaggctta    4920
gaaagtatgt ggctctgcct gggtgtgtta cagctctgcc ctggtgaaag gggattaaaa    4980
cgggcaccat tcatcccaaa caggatcctc attcatggat caagctgtaa ggaacttggg    5040
ctccaacctc aaaacattaa ttggagtacg aatgtaatta aaactgcatt ctcgcattcc    5100
taagtcattt agtctggact ctgcagcatg taggtcggca gctcccactt tctcaaagac    5160
cactgatgga ggagtagtaa aaatggagac cgattcagaa caaccaacgg agtgttgccg    5220
aagaaactga tggaaataat gcatgaattg tgtggtggac attttttta aatacataaa    5280
ctacttcaaa tgaggtcgga gaaggtcagt gtttattag cagccataaa accaggtgag    5340
cgagtaccat ttttctctac aagaaaaacg attctgagct ctgcgtaagt ataagttctc    5400
catgcggct gaagctcccc cctggctgcc tgccatctca gctggagtgc agtgccattt    5460
ccttggggtt tctctcacag cagtaatggg acaaatacttc acaaaaattc tttcttttcc    5520
tgtcatgtgg gatccctact gtgccctcct ggttttacgt tacccccctga ctgttccatt    5580
cagcggtttg gaaagagaaa aagaaatttgg aaataaaaca tgtctacgtt atcacctcct    5640
ccagcatttt ggttttaat tatgtcaata actggcttag atttggaaat gagaggggggt    5700
tgggtgtatt accgaggaac aaaggaaggc ttatataaac tcaagtcttt tatttagaga    5760
actggcaagc tgtcaaaaac aaaaaggcct taccaccaaa ttaagtgaat agccgctata    5820
gccagcaggg ccagcacgag ggatggtgca ctgctggcac tatgccacgg cctgcttgtg    5880
actctgagag caactgcttt ggaaatgaca gcacttggtg caatttcctt tgtttcagaa    5940
tgcgtagagc gtgtgcttgg cgacagtttt tctagttagg ccacttcttt ttccttctc    6000
tcctcattct cctaagcatg tctccatgct ggtaatccca gtcaagtgaa cgttcaaaca    6060
atgaatccat cactgtagga ttctcgtggt gatcaaatct ttgtgtgagg tctataaaat    6120
atggaagctt atttatttt cgttcttcca tatcagtctt ctctatgaca attcacatcc    6180
```

```
accacagcaa attaaaggtg aaggaggctg gtgggatgaa gagggtcttc tagctttacg    6240
ttcttccttg caaggccaca ggaaaatgct gagagctgta gaatacagcc tggggtaaga    6300
agttcagtct cctgctggga cagctaaccg catcttataa ccccttctga gactcatctt    6360
aggaccaaat agggtctatc tggggttttt gttcctgctg ttcctcctgg aaggctatct    6420
cactatttca ctgctcccac ggttacaaac caaagataca gcctgaattt tttctaggcc    6480
acattacata aatttgacct ggtaccaata ttgttctcta tatagttatt ccttcccca    6540
ctgtgtttaa ccccttaagg cattcagaac aactagaatc atagaatggt ttggattgga    6600
aggggcctta aacatcatcc atttccaacc ctctgccatg ggctgcttgc cacccactgg    6660
ctcaggctgc ccagggcccc atccagcctg gccttgagca cctccaggga tggggcaccc    6720
acagcttctc tgggcagcct gtgccaacac ctcaccactc tctgggtaaa gaattctctt    6780
ttaacatcta atctaaatct cttctctttt agtttaaagc cattcctctt tttcccgttg    6840
ctatctgtcc aagaaatgtg tattggtctc cctcctgctt ataagcagga agtactggaa    6900
ggctgcagtg aggtctcccc acagccttct cttctccagg ctgaacaagc ccagctcctt    6960
cagcctgtct tcgtaggaga tcatcttagt ggccctcctc tggacccatt ccaacagttc    7020
cacggctttc ttgtggagcc ccaggtctgg atgcagtact tcagatgggg ccttacaaag    7080
gcagagcaga tggggacaat cgcttacccc tccctgctgg ctgcccctgt tttgatgcag    7140
cccagggtac tgttggcctt tcaggctccc agacccttg ctgatttgtg tcaagctttt    7200
catccaccag aacccacgct tcctggttaa tacttctgcc ctcacttctg taagcttgtt    7260
tcaggagact tccattcttt aggacagact gtgttacacc tacctgccct attcttgcat    7320
atatacattt cagttcatgt ttcctgtaac aggacagaat atgtattcct ctaacaaaaa    7380
tacatgcaga attcctagtg ccatctcagt agggttttca tggcagtatt agcacatagt    7440
caatttgctg caagtacctt ccaagctgcg gcctcccata aatcctgtat ttgggatcag    7500
ttacctttg gggtaagctt ttgtatctgc agagaccctg ggggttctga tgtgcttcag    7560
ctctgctctg ttctgactgc accatttct agatcaccca gttgttcctg tacaacttcc    7620
ttgtcctcca tcctttccca gcttgtatct ttgacaaata caggcctatt tttgtgtttg    7680
cttcagcagc catttaattc ttcagtgtca tcttgttctg ttgatgccac tggaacagga    7740
ttttcagcag tcttgcaaag aacatctagc tgaaaacttt ctgccattca atattcttac    7800
cagttcttct tgtttgaggt gagccataaa ttactagaac ttcgtcactg acaagtttat    7860
gcattttatt acttctatta tgtacttact ttgacataac acagacacgc acatattttg    7920
ctgggatttc cacagtgtct ctgtgtcctt cacatggttt tactgtcata cttccgttat    7980
aaccttggca atctgcccag ctgcccatca aagaaaaga gattccttt ttattacttc    8040
tcttcagcca ataaacaaaa tgtgagaagc ccaaacaaga acttgtgggg caggctgcca    8100
tcaagggaga gacagctgaa gggttgtgta gctcaataga attaagaaat aataaagctg    8160
tgtcagacag ttttgcctga tttatacagg cacgcccaa gccagagagg ctgtctgcca    8220
aggccaccttt gcagtccttg gtttgtaaga taagtcatag gtaactttc tggtgaattg    8280
cgtggagaat catgatggca gttccttgctg tttactatgg taagatgcta aaataggaga    8340
cagcaaagta acacttgctg ctgtaggtgc tctgctatcc agacagcgat ggcactcgca    8400
caccaagatg agggatgctc ccagctgacg gatgctgggg cagtaacagt gggtcccatg    8460
ctgcctgctc attagcatca cctcagccct caccagccca tcagaaggat catcccaagc    8520
```

```
tgaggaaagt tgctcatctt cttcacatca tcaaacctttt ggcctgactg atgcctcccg   8580
gatgcttaaa tgtggtcact gacatcttta tttttctatg atttcaagtc agaacctccg   8640
gatcaggagg gaacacatag tgggaatgta ccctcagctc caaggccaga tcttccttca   8700
atgatcatgc atgctactta ggaaggtgtg tgtgtgtgaa tgtagaattg cctttgttat   8760
ttttcttcc tgctgtcagg aacattttga ataccagaga aaagaaaag tgctcttctt     8820
ggcatgggag gagttgtcac acttgcaaaa taaaggatgc agtcccaaat gttcataatc   8880
tcagggtctg aaggaggatc agaaactgtg tatacaattt caggcttctc tgaatgcagc   8940
ttttgaaagc tgttcctggc cgaggcagta ctagtcagaa ccctcggaaa caggaacaaa   9000
tgtcttcaag gtgcagcagg aggaaacacc ttgcccatca tgaaagtgaa taaccactgc   9060
cgctgaagga atccagctcc tgtttgagca ggtgctgcac actcccacac tgaaacaaca   9120
gttcattttt ataggacttc caggaaggat cttcttctta agcttcttaa ttatggtaca   9180
tctccagttg gcagatgact atgactactg acaggagaat gaggaactag ctgggaatat   9240
ttctgtttga ccaccatgga gtcacccatt tctttactgg tatttggaaa taataattct   9300
gaattgcaaa gcaggagtta gcgaagatct tcatttcttc catgttggtg acagcacagt   9360
tctggctatg aaagtctgct tacaaggaag aggataaaaa tcatagggat aataaatcta   9420
agtttgaaga caatgaggtt ttagctgcat ttgacatgaa gaaattgaga cctctactgg   9480
atagctatgg tatttacgtg tctttttgct tagttactta ttgaccccag ctgaggtcaa   9540
gtatgaactc aggtctctcg ggctactggc atggattgat tacatacaac tgtaatttta   9600
gcagtgattt agggtttatg agtacttttg cagtaaatca tagggttagt aatgttaatc   9660
tcagggaaaa aaaaaaaaag ccaaccctga cagacatccc agctcaggtg gaaatcaagg   9720
atcacagctc agtgcggtcc cagagaacac agggactctt ctcttaggac ctttatgtac   9780
agggcctcaa gataactgat gttagtcaga agactttcca ttctggccac agttcagctg   9840
aggcaatcct ggaattttct ctccgctgca cagttccagt catcccagtt tgtacagttc   9900
tggcactttt tgggtcaggc cgtgatccaa ggagcagaag ttccagctat ggtcagggag   9960
tgcctgaccg tcccaactca ctgcactcaa acaaaggcga aaccacaaga gtggcttttg  10020
ttgaaattgc agtgtggccc agaggggctg caccagtact ggattgacca cgaggcaaca  10080
ttaatcctca gcaagtgcaa tttgcagcca ttaaattgaa ctaactgata ctacaatgca  10140
atcagtatca acaagtggtt tggcttggaa gatggagtct aggggctcta caggagtagc  10200
tactctctaa tggagttgca ttttgaagca ggacactgtg aaaagctggc ctcctaaaga  10260
ggctgctaaa cattagggtc aattttccag tgcactttct gaagtgtctg cagttcccca  10320
tgcaaagctg cccaaacata gcacttccaa ttgaatacaa ttatatgcag gcgtactgct  10380
tcttgccagc actgtccttc tcaaatgaac tcaacaaaca atttcaaagt ctagtagaaa  10440
gtaacaagct ttgaatgtca ttaaaaagta tatctgcttt cagtagttca gcttatttat  10500
gcccactaga aacatcttgt acaagctgaa cactggggct ccagattagt ggtaaaacct  10560
actttataca atcatagaat catagaatgg cctgggttgg aagggacccc aaggatcatg  10620
aagatccaac accccgcca caggcagggc caccaacctc cagatctggt actagaccag    10680
gcagcccagg gctccatcca acctggccat gaacacctcc agggatggag catccacaac  10740
ctctctgggc agcctgtgcc agcacctcac caccctctct gtgaagaact tttccctgac  10800
atccaatcta agccttccct ccttgaggtt agatccactc ccccttgtgc tatcactgtc  10860
tactcttgta aaaagttgat tctcctcctt tttggaaggt tgcaatgagg tctccttgca  10920
```

-continued

```
gccttcttct cttctgcagg atgaacaagc ccagctccct cagcctgtct ttataggaga    10980
ggtgctccag ccctctgatc atctttgtgg ccctcctctg gacccgctcc aagagctcca    11040
catctttcct gtactggggg ccccaggcct gaatgcagta ctccagatgg ggcctcaaaa    11100
gagcagagta aagagggaca atcaccttcc tcaccctgct ggccagccct cttctgatgg    11160
agccctggat acaactggct ttctgagctg caacttctcc ttatcagttc cactattaaa    11220
acaggaacaa tacaacaggt gctgatggcc agtgcagagt ttttcacact tcttcatttc    11280
ggtagatctt agatgaggaa cgttgaagtt gtgcttctgc gtgtgcttct tcctcctcaa    11340
atactcctgc ctgataccct cccccacctg ccactgaatg gctccatggc cccctgcagc    11400
cagggccctg atgaacccgg cactgcttca gatgctgttt aatagcacag tatgaccaag    11460
ttgcacctat gaatacacaa acaatgtgtt gcatccttca gcacttgaga agaagagcca    11520
aatttgcatt gtcaggaaat ggtttagtaa ttctgccaat taaaacttgt ttatctacca    11580
tggctgtttt tatggctgtt agtagtggta cactgatgat gaacaatggc tatgcagtaa    11640
aatcaagact gtagatattg caacagacta taaaattcct ctgtggctta gccaatgtgg    11700
tacttcccac attgtataag aaatttggca agtttagagc aatgtttgaa gtgttgggaa    11760
atttctgtat actcaagagg gcgttttttga caactgtaga acagaggaat caaaagggg    11820 tgggaggaag ttaaaagaag aggcaggtgc aagagagctt gcagtcccgc tgtgtgtacg    11880
acactggcaa catgaggtct ttgctaatct tggtgctttg cttcctgccc ctggctgcct    11940
taggg                                                                11945
```

<210> SEQ ID NO 8
<211> LENGTH: 285
<212> TYPE: DNA
<213> ORGANISM: SV40
<220> FEATURE:
<221> NAME/KEY: misc_feature
<222> LOCATION: (1)..(285)
<223> OTHER INFORMATION: SV40 Polyadenylation Sequence

<400> SEQUENCE: 8

```
aaagtctaga gtcggggcgg ccggccgctt cgagcagaca tgataagata cattgatgag      60
tttggacaaa ccacaactag aatgcagtga aaaaaatgct ttatttgtga aatttgtgat     120
gctattgctt tatttgtaac cattataagc tgcaataaac aagttaacaa caacaattgc     180
attcatttta tgtttcaggt tcaggggag gtgtgggagg ttttttaaag caagtaaaac     240
ctctacaaat gtggtaaaat cgataaggat ccgtcgagcg ccgc                      285
```

<210> SEQ ID NO 9
<211> LENGTH: 5972
<212> TYPE: DNA
<213> ORGANISM: Gallus gallus
<220> FEATURE:
<221> NAME/KEY: misc_feature
<222> LOCATION: (1)..(5972)
<223> OTHER INFORMATION: Lysozyme 3prime domain

<400> SEQUENCE: 9

```
cgcgtggtag gtggcggggg gttcccagga gagcccccag gcggacggc agcgccgtca       60 ctcaccgctc cgtctccctc cgcccagggt cgcctggcgc aaccgctgca agggcaccga     120
cgtccaggcg tggatcagag gctgccggct gtgaggagct gccgcgcccg gcccgcccgc     180
tgcacagccg gccgctttgc gagcgcgacg ctacccgctt ggcagtttta aacgcatccc     240
```

-continued

```
tcattaaaac gactatacgc aaacgccttc ccgtcggtcc gcgtctcttt ccgccgccag        300
ggcgacactc gcggggaggg cgggaagggg gccgggcggg agcccgcggc caaccgtcgc        360
cccgtgacgg caccgccccg cccccgtgac gcggtgcggg cgccggggcc gtggggctga        420
gcgctgcggc ggggccgggc cgggccgggg cgggagctga gcgcggcgcg gctgcgggcg        480 gcgcccctc cggtgcaata tgttcaagag aatggctgag ttcgggcctg actccggggg         540
cagggtgaag gtgcggcgcg ggcggaggga cgggcgggc gcggggccgc ccggcgggtg         600
ccggggcctc tgccgcccg cccggctcgg gctgctgcgg cgcttacggg cgcgcttctc         660
gccgctgccg cttctcttct ctcccgcgca agggcgtcac catcgtgaag ccggtagtgt        720
acgggaacgt ggcgcggtac ttcgggaaga agagggagga ggacgggcac acgcatcagt       780
ggacggttta cgtgaagccc tacaggaacg aggtagggcc cgagcgcgtc ggccgccgtt       840
ctcggagcgc cggagccgtc agcgccgcgc ctgggtgcgc tgtgggacac agcgagcttc       900
tctcgtagga catgtccgcc tacgtgaaaa aaatccagtt caagctgcac gagagctacg       960
ggaatcctct ccgaggtggg tgttgcgtcg ggggtttgc tccgctcggt cccgctgagg       1020
ctcgtcgccc tcatctttct ttcgtgccgc agtcgttacc aaaccgccgt acgagatcac      1080
cgaaacgggc tggggcgaat ttgaaatcat catcaagata ttttttcattg atccaaacga      1140 gcgacccgta agtacgctca gcttctcgta gtgcttcccc cgtcctggcg gcccggggct      1200
gggctgctcg ctgctgccgg tcacagtccc gccagccgcg gagctgactg agctccctt      1260 cccgggacgt gtgctctgtg ttcggtcagc gaggctatcg ggagggcttt ggctgcattt      1320
ggcttctctg gcgcttagcg caggagcacg ttgtgctacg cctgaactac agctgtgaga      1380
aggccgtgga aaccgctctc aaactgattt attggcgaaa tggctctaaa ctaaatcgtc      1440
tcctctcttt ggaaatgctt tagagaaggt ctctgtggta gttcttatgc atctatccta      1500
aagcacttgg ccagacaatt taaagacatc aagcagcatt tatagcaggc acgtttaata      1560
acgaatactg aatttaagta actctgctca cgttgtatga cgtttatttt cgtattcctg      1620
aaagccatta aaatcctgtg cagttgttta gtaagaacag ctgccactgt tttgtatcta      1680
ggagataact ggtgtttccc tacagttctc aagctgataa aactctgtct ttgtatctag      1740
gtaaccctgt atcacttgct gaagcttttt cagtctgaca ccaatgcaat cctgggaaag      1800
aaaactgtag tttctgaatt ctatgatgaa atggtatgaa aattttaatg tcaaccgagc      1860
ctgactttat ttaaaaaaaa ttattgatgg tgctgtgtat tttggtcctt ccttagatat      1920
ttcaagatcc tactgccatg atgcagcaac tgctaacgac gtcccgtcag ctgacacttg      1980
gtgcttacaa gcatgaaaca gagtgtaagt gcaaaatgag gataccttcg ccgaccgtca      2040
ttcactacta atgttttctg tgggatgtga tcgtacagtg agtttggctg tgtgaaattt      2100
gaatagcttg gtattggcag tgatgacgtg atcgatgcct tgcttatcat gtttgaaatg      2160
aagtagaata aatgcagcct gctttatttg agatagtttg gttcatttta tggaatgcaa      2220
gcaaagatta tacttcctca ctgaattgca ctgtccaaag gtgtgaaatg tgtgggatc      2280 tggaggaccg tgaccgaggg acattggatc gctatctccc atttcttttg ctgttaccag     2340
ttcagatttt cttttcacct agtctttaat tcccagggtt ttgttttttc cttggtcata     2400 gttttgttt tcactctgg caatgatgt tgtgaattac actgcttcag ccacaaaact      2460
gatggactga atgaggtcat caaacaaact tttcttcttc cgtatttcct ttttttttccc    2520 ccacttatca ttttttactgc tgttgttgag tctgtaaggc taaaagtaac tgttttgtgc    2580
tttttcagga cgtgtgcttt ccaaattact gccacatata taaagaaagg ttggaatttt    2640
```

```
aaagataatt catgtttctt cttcttttt gccaccacag ttgcagatct tgaagtaaaa      2700
accagggaaa agctggaagc tgccaaaaag aaaaccagtt ttgaaattgc tgagcttaaa      2760
gaaaggttaa aagcaagtcg tgaaaccatc aactgcttaa agagtgaaat cagaaaactc      2820
gaagaggatg atcagtctaa agatatgtga tgagtgttga cttggcaggg agcctataat      2880
gagaatgaaa ggacttcagt cgtggagttg tatgcgttct ctccaattct gtaacggaga      2940
ctgtatgaat tcatttgca aatcactgca gtgtgtgaca actgactttt tataaatggc      3000
agaaaacaag aatgaatgta tcctcatttt atagttaaaa tctatgggta tgtactggtt      3060
tatttcaagg agaatggatc gtagagactt ggaggccaga ttgctgcttg tattgactgc      3120
atttgagtgg tgtaggaaca ttttgtctat ggtcccgtgt tagtttacag aatgccactg      3180
ttcactgttt tgttttgtat tttacttttt ctactgcaac gtcaaggttt taaaagttga      3240
aaataaaaca tgcaggtttt ttttaaatat ttttttgtct ctatccagtt tgggcttcaa      3300
gtattattgt taacagcaag tcctgattta agtcagaggc tgaagtgtaa tggtattcaa      3360
gatgcttaag tctgttgtca gcaaaacaaa agagaaaact tcataaaatc aggaagttgg      3420
catttctaat aacttcttta tcaacagata agagtttcta gccctgcatc tactttcact      3480
tatgtagttg atgcctttat attttgtgtg tttggatgca ggaagtgatt cctactctgt      3540
tatgtagata ttctatttaa cacttgtact ctgctgtgct tagcctttcc ccatgaaaat      3600
tcagcggctg taaatccccc tcttctttg tagcctcata cagatggcag accctcaggc      3660
ttataaaggc ttgggcatct tctttactgc tttgagattc tgtgttgcag taacctctgc      3720
cagagaggag aaaagcccca caaacctcat ccccttcttc tatagcaatc agtattacta      3780
atgctttgag aacagagcac tggtttgaaa cgtttgataa ttagcattta acatggcttg      3840
gtaaagatgc agaactgaaa cagctgtgac agtatgaact cagtatggag acttcattaa      3900
gacaaacagc tgttaaaatc aggcatgttt cattgaggag gacggggcaa cttgcaccag      3960
tggtgcccac acaaatcctt cctggcgctg cagaccaatt tttctggcat tctgactgcc      4020
gttgctgctg tcacagaga gcaactattt ttatcagcca caggcaattt gcttgtagta      4080
ttttccaagt gttgtaggta agtataaatg catcggctcc agagcacttt gagtatactt      4140
attaaaaaca taaatgaaag acaaattagc tttgcttggg tgcacagaac attttagtt      4200 ccagcctgct ttttggtaga agccctcttc tgaggctaga actgactttg acaagtagag      4260
aaactggcaa cggagctatt gctatcgaag gatccttgtt aacaaagtta atcgtctttt      4320
aaggtttggt ttattcatta aatttgcttt taagctgtag ctgaaaaaga acgtgctgtc      4380
ttccatgcac caggtggcag ctctgtgcaa agtgctctct ggtctcacca gccttttaat      4440
tgccgggatt ctggcacgtc tgagagggct cagactggct tcgtttgttt gaacagcgtg      4500
tactgctttc tgtagacatg gccggttctc tcctgcagc ttatgaaact gttcacactg       4560
aacacactgg aacaggttgc ccaaggaggc cgtggatgcc ccatccctgg aggcattcaa      4620
ggccaggctg gatgtggctc tgggcagcct ggtctggtgg ttggcgatcc tgcacatagc      4680
agcggggttg aaactcgatg atcactgtgg tccttttcaa cccaggctat tctatgattc      4740
tatgattcaa cagcaaatca tatgtactga gagaggaaac aaaacaagt gctactgttt       4800 gcaagttttg ttcatttggt aaaagagtca ggttttaaaa ttcaaaatct gtctggtttt      4860 ggtgttttt ttttttttatt tattatttct ttggggttct ttttgatgct ttatcttct       4920 ctgccaggac tgtgtgacaa tgggaacgaa aaagaacatg ccaggcactg tcctggattg      4980
```

-continued

```
cacacgctgg ttgcactcag tagcaggctc agaactgcca gtctttccac agtattactt      5040
tctaaaccta attttaatag cgttagtaga cttccatcac tgggcagtgc ttagtgaatg      5100
ctctgtgtga acgttttact tataagcatg ttggaagttt tgatgttcct ggatgcagta      5160
gggaaggaca gattagctat gtgaaaagta gattctgagt atcggggtta caaaaagtat      5220
agaaacgatg agaaattctt gttgtaacta attggaattt ctttaagcgt tcacttatgc      5280
tacattcata gtatttccat ttaaaagtag gaaaaggtaa aacgtgaaat cgtgtgattt      5340
tcggatggaa caccgccttc ctatgcacct gaccaacttc cagaggaaaa gcctattgaa      5400
agccgagatt aagccaccaa agaactcat ttgcattgga atatgtagta tttgccctct       5460
tcctcccggg taattactat actttatagg gtgcttatat gttaaatgag tggctggcac      5520 ttttattct cacagctgtg gggaattctg tcctctagga cagaaacaat tttaatctgt       5580
tccactggtg actgctttgt cagcacttcc acctgaagag atcaatacac tcttcaatgt      5640
ctagttctgc aacacttggc aaacctcaca tcttatttca tactctcttc atgcctatgc      5700
ttattaaagc aataatctgg gtaattttg ttttaatcac tgtcctgacc ccagtgatga       5760
ccgtgtccca cctaaagctc aattcaggtc ctgaatctct tcaactctct atagctaaca      5820
tgaagaatct tcaaaagtta ggtctgaggg acttaaggct aactgtagat gttgttgcct      5880
ggtttctgtg ctgaaggccg tgtagtagtt agagcattca acctctagaa gaagcttggc      5940
cagctggtcg acctgcagat ccggccctcg ag                                    5972

<210> SEQ ID NO 10
<211> LENGTH: 18391
<212> TYPE: DNA
<213> ORGANISM: Gallus gallus
<220> FEATURE:
<221> NAME/KEY: misc_feature
<222> LOCATION: (1)..(237)
<223> OTHER INFORMATION: 5prime matrix (scaffold) attachment region
      (MAR)
<220> FEATURE:
<221> NAME/KEY: misc_feature
<222> LOCATION: (261)..(1564)
<223> OTHER INFORMATION: 5prime matrix (scaffold) attachment region
      (MAR)
<220> FEATURE:
<221> NAME/KEY: misc_feature
<222> LOCATION: (1565)..(1912)
<223> OTHER INFORMATION: 5prime matrix (scaffold) attachment region
      (MAR)
<220> FEATURE:
<221> NAME/KEY: misc_feature
<222> LOCATION: (1930)..(2012)
<223> OTHER INFORMATION: 5prime matrix (scaffold) attachment region
      (MAR)
<220> FEATURE:
<221> NAME/KEY: misc_feature
<222> LOCATION: (2013)..(2671)
<223> OTHER INFORMATION: Intrinsically curved DNA
<220> FEATURE:
<221> NAME/KEY: misc_feature
<222> LOCATION: (5848)..(5934)
<223> OTHER INFORMATION: Transcription enhancer
<220> FEATURE:
<221> NAME/KEY: misc_feature
<222> LOCATION: (9160)..(9325)
<223> OTHER INFORMATION: Transcription enhancer
<220> FEATURE:
<221> NAME/KEY: misc_feature
<222> LOCATION: (9326)..(9626)
<223> OTHER INFORMATION: Negative regulatory element
<220> FEATURE:
<221> NAME/KEY: misc_feature
<222> LOCATION: (9621)..(9660)
<223> OTHER INFORMATION: Hormone response element
```

```
<220> FEATURE:
<221> NAME/KEY: misc_feature
<222> LOCATION: (9680)..(10060)
<223> OTHER INFORMATION: Hormone response element
<220> FEATURE:
<221> NAME/KEY: misc_feature
<222> LOCATION: (10576)..(10821)
<223> OTHER INFORMATION: Chicken CR1 Repeat Sequence
<220> FEATURE:
<221> NAME/KEY: misc_feature
<222> LOCATION: (10926)..(11193)
<223> OTHER INFORMATION: Chicken CR1 Repeat Sequence
<220> FEATURE:
<221> NAME/KEY: misc_feature
<222> LOCATION: (11424)..(11938)
<223> OTHER INFORMATION: Lysozyme Proximal Promoter and Lysozyme Signal
      Peptide
<220> FEATURE:
<221> NAME/KEY: misc_feature
<222> LOCATION: (11946)..(12443)
<223> OTHER INFORMATION: human interferon alpha 2b codon-optimized for
      expression in chickens
<220> FEATURE:
<221> NAME/KEY: misc_feature
<222> LOCATION: (12464)..(18391)
<223> OTHER INFORMATION: Chicken Lysozyme 3prime domain

<400> SEQUENCE: 10
tgccgccttc tttgatattc actctgttgt atttcatctc ttcttgccga tgaaaggata      60
taacagtctg tataacagtc tgtgaggaaa tacttggtat ttcttctgat cagtgttttt     120
ataagtaatg ttgaatattg gataaggctg tgtgtccttt gtcttgggag acaaagccca     180
cagcaggtgg tggttggggt ggtggcagct cagtgacagg agaggttttt ttgcctgttt     240
tttttttttt tttttttttt aagtaaggtg ttcttttttc ttagtaaatt ttctactgga     300
ctgtatgttt tgacaggtca gaaacatttc ttcaaaagaa gaacctttg gaaactgtac      360 agccctttc tttcattccc tttttgcttt ctgtgccaat gcctttggtt ctgattgcat      420
tatgaaaaac gttgatcgga acttgaggtt tttatttata gtgtggcttg aaagcttgga     480
tagctgttgt tacacgagat accttattaa gtttaggcca gcttgatgct ttattttttc     540
cctttgaagt agtgagcgtt ctctggtttt tttcctttga aactggtgag cttagattt      600 ttctaatggg attttttacc tgatgatcta gttgcatacc caaatgcttg taaatgtttt     660
cctagttaac atgttgataa cttcggattt acatgttgta tatacttgtc atctgtgttt     720
ctagtaaaaa tatatggcat ttatagaaat acgtaattcc tgatttcctt ttttttttatc     780 tctatgctct gtgtgtacag gtcaaacaga cttcactcct attttatttt atagaattt      840 atatgcagtc tgtcgttggt tcttgtgttg taaggataca gccttaaatt tcctagagcg     900
atgctcagta aggcgggttg tcacatgggt tcaaatgtaa aacgggcacg tttggctgct     960
gccttcccga gatccaggac actaaactgc ttctgcactg aggtataaat cgcttcagat    1020
cccagggaag tgcagatcca cgtgcatatt cttaaagaag aatgaatact ttctaaaata    1080
ttttggcata ggaagcaagc tgcatggatt tgtttgggac ttaaattatt ttggtaacgg    1140
agtgcatagg ttttaaacac agttgcagca tgctaacgag tcacgcgtt tatgcagaag     1200 tgatgcctgg atgcctgttg cagctgttta cggcactgcc ttgcagtgag cattgcagat    1260
aggggtgggg tgctttgtgt cgtgttccca cacgctgcca cacagccacc tcccggaaca    1320
catctcacct gctgggtact tttcaaacca tcttagcagt agtagatgag ttactatgaa    1380
acagagaagt tcctcagttg gatattctca tgggatgtct ttttccat gttgggcaaa     1440 gtatgataaa gcatctctat ttgtaaatta tgcacttgtt agttcctgaa tcctttctat    1500
```

```
agcaccactt attgcagcag gtgtaggctc tggtgtggcc tgtgtctgtg cttcaatctt    1560
ttaaagcttc tttggaaata cactgacttg attgaagtct cttgaagata gtaaacagta    1620
cttacctttg atcccaatga aatcgagcat ttcagttgta aaagaattcc gcctattcat    1680
accatgtaat gtaattttac acccccagtg ctgacacttt ggaatatatt caagtaatag    1740
actttggcct caccctcttg tgtactgtat tttgtaatag aaaatatttt aaactgtgca    1800
tatgattatt acattatgaa agagacattc tgctgatctt caaatgtaag aaaatgagga    1860
gtgcgtgtgc ttttataaat acaagtgatt gcaaattagt gcaggtgtcc ttaaaaaaaa    1920
aaaaaaaaag taatataaaa aggaccaggt gttttacaag tgaaatacat tcctatttgg    1980
taaacagtta cattttatg aagattacca gcgctgctga ctttctaaac ataaggctgt     2040
attgtcttcc tgtaccattg catttcctca ttcccaattt gcacaaggat gtctgggtaa    2100
actattcaag aaatggcttt gaaatacagc atgggagctt gtctgagttg aatgcagag    2160
ttgcactgca aaatgtcagg aaatggatgt ctctcagaat gcccaactcc aaaggatttt    2220
atatgtgtat atagtaagca gtttcctgat tccagcaggc caaagagtct gctgaatgtt    2280
gtgttgccgg agacctgtat ttctcaacaa ggtaagatgg tatcctagca actgcggatt    2340
ttaatacatt ttcagcagaa gtacttagtt aatctctacc tttagggatc gtttcatcat    2400
ttttagatgt tatacttgaa atactgcata acttttagct ttcatgggtt ccttttttc     2460
agcctttagg agactgttaa gcaatttgct gtccaacttt tgtgttggtc ttaaactgca    2520
atagtagtta accttgtatt gaagaaataa agaccatttt tatattaaaa aatacttttg    2580
tctgtcttca ttttgacttg tctgatatcc ttgcagtgcc cattatgtca gttctgtcag    2640
atattcagac atcaaaactt aacgtgagct cagtggagtt acagctgcgg ttttgatgct    2700
gttattattt ctgaaactag aaatgatgtt gtcttcatct gctcatcaaa cacttcatgc    2760
agagtgtaag gctagtgaga aatgcataca tttattgata ctttttttaaa gtcaactttt    2820
tatcagattt tttttttcatt tggaaatata ttgttttcta gactgcatag cttctgaatc    2880
tgaaatgcag tctgattggc atgaagaagc acagcactct tcatcttact taaacttcat    2940
tttggaatga aggaagttaa gcaagggcac aggtccatga aatagagaca gtgcgctcag    3000
gagaaagtga acctggattt ctttggctag tgttctaaat ctgtagtgag gaaagtaaca    3060
cccgattcct tgaaagggct ccagcttta tgcttccaaa ttgaaggtgg caggcaactt     3120
ggccactggt tatttactgc attatgtctc agtttcgcag ctaacctggc ttctccacta    3180
ttgagcatgg actatagcct ggcttcagag gccaggtgaa ggttgggatg ggtggaagga    3240
gtgctgggct gtggctgggg ggactgtggg gactccaagc tgagcttggg gtgggcagca    3300
cagggaaaag tgtgggtaac tattttaag tactgtgttg caaacgtctc atctgcaaat     3360
acgtagggtg tgtactctcg aagattaaca gtgtgggttc agtaatatat ggatgaattc    3420
acagtggaag cattcaaggg tagatcatct aacgacacca gatcatcaag ctatgattgg    3480
aagcggtatc agaagagcga ggaaggtaag cagtcttcat atgtttccc tccacgtaaa     3540
gcagtctggg aaagtagcac cccttgagca gagacaagga ataattcag gagcatgtgc     3600
taggagaact ttcttgctga attctacttg caagagcttt gatgcctggc ttctggtgcc    3660
ttctgcagca cctgcaaggc ccagagcctg tggtgagctg gagggaaaga ttctgctcaa    3720
gtccaagctt cagcaggtca ttgtctttgc ttcttccccc agcactgtgc agcagagtgg    3780
aactgatgtc gaagcctcct gtccactacc tgttgctgca ggcagactgc tctcagaaaa    3840
agagagctaa ctctatgcca tagtctgaag gtaaaatggg ttttaaaaaa gaaaacacaa    3900
```

```
aggcaaaacc ggctgcccca tgagaagaaa gcagtggtaa acatggtaga aaaggtgcag    3960
aagcccccag gcagtgtgac aggcccctcc tgccacctag aggcgggaac aagcttccct    4020
gcctagggct ctgcccgcga agtgcgtgtt tctttggtgg gttttgtttg gcgtttggtt    4080
ttgagattta gacacaaggg aagcctgaaa ggaggtgttg ggcactattt tggtttgtaa    4140
agcctgtact tcaaatatat attttgtgag ggagtgtagc gaattggcca atttaaaata    4200
aagttgcaag agattgaagg ctgagtagtt gagagggtaa cacgtttaat gagatcttct    4260
gaaactactg cttctaaaca cttgtttgag tggtgagacc ttggataggt gagtgctctt    4320
gttacatgtc tgatgcactt gcttgtcctt ttccatccac atccatgcat tccacatcca    4380
cgcatttgtc acttatccca tatctgtcat atctgacata cctgtctctt cgtcacttgg    4440
tcagaagaaa cagatgtgat aatccccagc cgccccaagt ttgagaagat ggcagttgct    4500
tctttccctt tttcctgcta agtaaggatt ttctcctggc tttgacacct cacgaaatag    4560
tcttcctgcc ttacattctg ggcattattt caaatatctt tggagtgcgc tgctctcaag    4620
tttgtgtctt cctactctta gagtgaatgc tcttagagtg aaagagaagg aagagaagat    4680
gttggccgca gttctctgat gaacacacct ctgaataatg gccaaggtg ggtgggtttc    4740 tctgaggaac gggcagcgtt tgcctctgaa agcaaggagc tctgcggagt tgcagttatt    4800
ttgcaactga tggtggaact ggtgcttaaa gcagattccc taggttccct gctacttctt    4860
ttccttcttg gcagtcagtt tatttctgac agacaaacag ccaccccac tgcaggctta    4920 gaaagtatgt ggctctgcct gggtgtgtta cagctctgcc ctggtgaaag gggattaaaa    4980
cgggcaccat tcatcccaaa caggatcctc attcatggat caagctgtaa ggaacttggg    5040
ctccaacctc aaaacattaa ttggagtacg aatgtaatta aaactgcatt ctcgcattcc    5100
taagtcattt agtctggact ctgcagcatg taggtcggca gctcccactt tctcaaagac    5160
cactgatgga ggagtagtaa aaatggagac cgattcagaa caaccaacgg agtgttgccg    5220
aagaaactga tggaaataat gcatgaattg tgtggtggac attttttta aatacataaa    5280 ctacttcaaa tgaggtcgga gaaggtcagt gtttttattag cagccataaa accaggtgag    5340
cgagtaccat ttttctctac aagaaaaacg attctgagct ctgcgtaagt ataagttctc    5400
catagcggct gaagctcccc cctggctgcc tgccatctca gctggagtgc agtgccattt    5460
ccttggggtt tctctcacag cagtaatggg acaatacttc acaaaaattc tttcttttcc    5520
tgtcatgtgg gatccctact gtgccctcct ggttttacgt taccccctga ctgttccatt    5580
cagcggtttg gaaagagaaa aagaatttgg aaataaaaca tgtctacgtt atcacctcct    5640
ccagcatttt ggttttaat tatgtcaata actggcttag atttggaaat gagaggggt    5700 tgggtgtatt accgaggaac aaaggaaggc ttatataaac tcaagtcttt tatttagaga    5760
actggcaagc tgtcaaaaac aaaaaggcct taccaccaaa ttaagtgaat agccgctata    5820
gccagcaggg ccagcacgag ggatggtgca ctgctggcac tatgccacgg cctgcttgtg    5880
actctgagag caactgcttt ggaaatgaca gcacttggtg caatttcctt tgtttcagaa    5940
tgcgtagagc gtgtgcttgg cgacagtttt tctagttagg ccacttcttt tttccttctc    6000
tcctcattct cctaagcatg tctccatgct ggtaatccca gtcaagtgaa cgttcaaaca    6060
atgaatccat cactgtagga ttctcgtggt gatcaaatct ttgtgtgagg tctataaaat    6120
atggaagctt atttatttt cgttcttcca tatcagtctt ctctatgaca attcacatcc    6180
accacagcaa attaaaggtg aaggaggctg gtgggatgaa gagggtcttc tagctttacg    6240
```

```
ttcttccttg caaggccaca ggaaaatgct gagagctgta gaatacagcc tggggtaaga    6300
agttcagtct cctgctggga cagctaaccg catcttataa cccttctga gactcatctt    6360 aggaccaaat agggtctatc tggggttttt gttcctgctg ttcctcctgg aaggctatct    6420
cactatttca ctgctcccac ggttacaaac caaagataca gcctgaattt tttctaggcc    6480
acattacata aatttgacct ggtaccaata ttgttctcta tatagttatt tccttcccca    6540
ctgtgtttaa cccttaagg cattcagaac aactagaatc atagaatggt ttggattgga    6600
aggggcctta aacatcatcc atttccaacc ctctgccatg gctgcttgc cacccactgg    6660 ctcaggctgc ccagggcccc atccagcctg gccttgagca cctccaggga tggggcaccc    6720
acagcttctc tgggcagcct gtgccaacac ctcaccactc tctgggtaaa gaattctctt    6780
ttaacatcta atctaaatct cttctctttt agtttaaagc cattcctctt tttcccgttg    6840
ctatctgtcc aagaaatgtg tattggtctc cctcctgctt ataagcagga agtactggaa    6900
ggctgcagtg aggtctcccc acagccttct cttctccagg ctgaacaagc ccagctcctt    6960
cagcctgtct tcgtaggaga tcatcttagt ggccctcctc tggacccatt ccaacagttc    7020
cacggctttc ttgtggagcc ccaggtctgg atgcagtact tcagatgggg ccttacaaag    7080
gcagagcaga tggggacaat cgcttacccc tccctgctgg ctgcccctgt tttgatgcag    7140
cccagggtac tgttggcctt tcaggctccc agaccccttg ctgatttgtg tcaagctttt    7200
catccaccag aacccacgct tcctggttaa tacttctgcc ctcacttctg taagcttgtt    7260
tcaggagact tccattcttt aggacagact gtgttacacc tacctgccct attcttgcat    7320
atatacattt cagttcatgt ttcctgtaac aggacagaat atgtattcct ctaacaaaaa    7380
tacatgcaga attcctagtg ccatctcagt agggttttca tggcagtatt agcacatagt    7440
caatttgctg caagtaccct ccaagctgcg gcctcccata aatcctgtat ttgggatcag    7500
ttaccttttg gggtaagctt ttgtatctgc agagaccctg ggggttctga tgtgcttcag    7560
ctctgctctg ttctgactgc accattttct agatcaccca gttgttcctg tacaacttcc    7620
ttgtcctcca tccttccca gcttgtatct ttgacaaata caggcctatt tttgtgtttg    7680
cttcagcagc catttaattc ttcagtgtca tcttgttctg ttgatgccac tggaacagga    7740
ttttcagcag tcttgcaaag aacatctagc tgaaaacttt ctgccattca atattcttac    7800
cagttcttct tgtttgaggt gagccataaa ttactagaac ttcgtcactg acaagtttat    7860
gcattttatt acttctatta tgtacttact ttgacataac acagacacgc acatattttg    7920
ctgggatttc cacagtgtct ctgtgtcctt cacatggttt tactgtcata cttccgttat    7980
aaccttggca atctgcccag ctgcccatca caagaaaaga gattccttt ttattacttc    8040 tcttcagcca ataaacaaaa tgtgagaagc ccaaacaaga acttgtgggg caggctgcca    8100
tcaagggaga gacagctgaa gggttgtgta gctcaataga attaagaaat aataaagctg    8160
tgtcagacag ttttgcctga tttatacagg cacgccccaa gccagagagg ctgtctgcca    8220
aggccacctt gcagtccttg gtttgtaaga taagtcatag gtaacttttc tggtgaattg    8280
cgtggagaat catgatggca gttccttgctg tttactatgg taagatgcta aaataggaga    8340
cagcaaagta acacttgctg ctgtaggtgc tctgctatcc agacagcgat ggcactcgca    8400
caccaagatg agggatgctc ccagctgacg gatgctgggg cagtaacagt gggtcccatg    8460
ctgcctgctc attagcatca cctcagccct caccagccca tcagaaggat catcccaagc    8520
tgaggaaagt tgctcatctt cttcacatca tcaaacctt ggcctgactg atgcctcccg    8580
gatgcttaaa tgtggtcact gacatcttta tttttctatg atttcaagtc agaacctccg    8640
```

```
gatcaggagg gaacacatag tgggaatgta ccctcagctc caaggccaga tcttccttca   8700
atgatcatgc atgctactta ggaaggtgtg tgtgtgtgaa tgtagaattg cctttgttat   8760
tttttcttcc tgctgtcagg aacattttga ataccagaga aaaagaaaag tgctcttctt   8820
ggcatgggag gagttgtcac acttgcaaaa taaaggatgc agtcccaaat gttcataatc   8880
tcagggtctg aaggaggatc agaaactgtg tatacaattt caggcttctc tgaatgcagc   8940
ttttgaaagc tgttcctggc cgaggcagta ctagtcagaa ccctcggaaa caggaacaaa   9000
tgtcttcaag gtgcagcagg aggaaacacc ttgcccatca tgaaagtgaa taaccactgc   9060
cgctgaagga atccagctcc tgtttgagca ggtgctgcac actcccacac tgaaacaaca   9120
gttcattttt ataggacttc caggaaggat cttcttctta agcttcttaa ttatggtaca   9180
tctccagttg gcagatgact atgactactg acaggagaat gaggaactag ctgggaatat   9240
ttctgtttga ccaccatgga gtcacccatt tctttactgg tatttggaaa taataattct   9300
gaattgcaaa gcaggagtta gcgaagatct tcatttcttc catgttggtg acagcacagt   9360
tctggctatg aaagtctgct tacaaggaag aggataaaaa tcatagggat aataaatcta   9420
agtttgaaga caatgaggtt ttagctgcat ttgacatgaa gaaattgaga cctctactgg   9480
atagctatgg tatttacgtg tcttttttgct tagttactta ttgacccag ctgaggtcaa   9540 gtatgaactc aggtctctcg ggctactggc atggattgat tacatacaac tgtaatttta   9600
gcagtgattt agggtttatg agtacttttg cagtaaatca tagggttagt aatgttaatc   9660
tcagggaaaa aaaaaaaaag ccaaccctga cagacatccc agctcaggtg gaaatcaagg   9720
atcacagctc agtgcggtcc cagagaacac agggactctt ctcttaggac ctttatgtac   9780
agggcctcaa gataactgat gttagtcaga agactttcca ttctggccac agttcagctg   9840
aggcaatcct ggaattttct ctccgctgca cagttccagt catcccagtt tgtacagttc   9900
tggcactttt tgggtcaggc cgtgatccaa ggagcagaag ttccagctat ggtcagggag   9960
tgcctgaccg tcccaactca ctgcactcaa acaaggcga aaccacaaga gtggcttttg  10020
ttgaaattgc agtgtggccc agaggggctg caccagtact ggattgacca cgaggcaaca  10080
ttaatcctca gcaagtgcaa tttgcagcca ttaaattgaa ctaactgata ctacaatgca  10140
atcagtatca acaagtggtt tggcttggaa gatggagtct aggggctcta caggagtagc  10200
tactctctaa tggagttgca ttttgaagca ggacactgtg aaaagctggc ctcctaaaga  10260
ggctgctaaa cattagggtc aattttccag tgcactttct gaagtgtctg cagttcccca  10320
tgcaaagctg cccaaacata gcacttccaa ttgaatacaa ttatatgcag gcgtactgct  10380
tcttgccagc actgtccttc tcaaatgaac tcaacaaaca atttcaaagt ctagtagaaa  10440
gtaacaagct ttgaatgtca ttaaaaagta tatctgcttt cagtagttca gcttatttat  10500
gcccactaga aacatcttgt acaagctgaa cactggggct ccagattagt ggtaaaacct  10560
actttataca atcatagaat catagaatgg cctgggttgg aagggacccc aaggatcatg  10620
aagatccaac accccgcca caggcagggc caccaacctc cagatctggt actagaccag  10680
gcagcccagg gctccatcca acctggccat gaacacctcc agggatggag catccacaac  10740
ctctctgggc agcctgtgcc agcacctcac caccctctct gtgaagaact tttccctgac  10800
atccaatcta agccttccct ccttgaggtt agatccactc ccccttgtgc tatcactgtc  10860
tactcttgta aaaagttgat tctcctcctt tttggaaggt tgcaatgagg tctccttgca  10920
gccttcttct cttctgcagg atgaacaagc ccagctccct cagcctgtct ttataggaga  10980
```

-continued

```
ggtgctccag ccctctgatc atctttgtgg ccctcctctg gacccgctcc aagagctcca    11040
catctttcct gtactggggg ccccaggcct gaatgcagta ctccagatgg ggcctcaaaa    11100
gagcagagta aagagggaca atcaccttcc tcaccctgct ggccagccct cttctgatgg    11160
agccctggat acaactggct ttctgagctg caacttctcc ttatcagttc cactattaaa    11220
acaggaacaa tacaacaggt gctgatggcc agtgcagagt ttttcacact tcttcatttc    11280
ggtagatctt agatgaggaa cgttgaagtt gtgcttctgc gtgtgcttct tcctcctcaa    11340
atactcctgc ctgatacctc accccacctg ccactgaatg gctccatggc cccctgcagc    11400
cagggccctg atgaacccgg cactgcttca gatgctgttt aatagcacag tatgaccaag    11460
ttgcacctat gaatacacaa acaatgtgtt gcatccttca gcacttgaga agaagagcca    11520
aatttgcatt gtcaggaaat ggtttagtaa ttctgccaat taaaacttgt ttatctacca    11580
tggctgtttt tatggctgtt agtagtggta cactgatgat gaacaatggc tatgcagtaa    11640
aatcaagact gtagatattg caacagacta taaaattcct ctgtggctta gccaatgtgg    11700
tacttcccac attgtataag aaatttggca gtttagagc aatgtttgaa gtgttgggaa     11760
atttctgtat actcaagagg gcgttttga caactgtaga acagaggaat caaaaggggg     11820
tgggaggaag ttaaagaag aggcaggtgc aagagagctt gcagtcccgc tgtgtgtacg     11880
acactggcaa catgaggtct ttgctaatct tggtgctttg cttcctgccc ctggctgcct    11940
tagggtgcga tctgcctcag acccacagcc tgggcagcag gaggaccctg atgctgctgg    12000
ctcagatgag gagaatcagc ctgtttagct gcctgaagga taggcacgat tttggctttc    12060
ctcaagagga gtttggcaac cagtttcaga aggctgagac catccctgtg ctgcacgaga    12120
tgatccagca gatctttaac ctgtttagca ccaaggatag cagcgctgct tgggatgaga    12180
ccctgctgga taagttttac accgagctgt accagcagct gaacgatctg gaggcttgcg    12240
tgatccaggg cgtgggcgtg accgagaccc tctgatgaa ggaggatagc atcctggctg    12300
tgaggaagta cttcagagg atcaccctgt acctgaagga gaagaagtac agcccctgcg    12360
cttgggaagt cgtgagggct gagatcatga ggagctttag cctgagcacc aacctgcaag    12420
agagcttgag gtctaaggag taaaaagtct agagtcgggg cggcgcgtgg taggtggcgg    12480
ggggttccca ggagagcccc cagcgcggac ggcagcgccg tcactcaccg ctccgtctcc    12540
ctccgcccag ggtcgcctgg cgcaaccgct gcaagggcac cgacgtccag gcgtggatca    12600
gaggctgccg gctgtgagga gctgccgcgc ccggcccgcc cgctgcacag ccggccgctt    12660
tgcgagcgcg acgctacccg cttggcagtt ttaaacgcat ccctcattaa aacgactata    12720
cgcaaacgcc ttcccgtcgg tccgcgtctc tttccgccgc cagggcgaca ctcgcgggga    12780
gggcgggaag ggggccgggc gggagcccgc ggccaaccgt cgcccgtga cggcaccgcc     12840
ccgcccccgt gacgcggtgc gggcgccggg gccgtggggc tgagcgctgc ggcggggccg    12900
ggccgggccg gggcgggagc tgagcgcggc gcggctgcgg gcggcgcccc ctccggtgca    12960
atatgttcaa gagaatggct gagttcgggc ctgactccgg gggcagggtg aaggtgcggc    13020
gcgggcggag ggacggggcg ggcgcggggc cgccgcgcgg gtgccgggc ctctgccggc     13080
ccgcccggct cgggctgctg cggcgcttac gggcgcgctt ctcgccgctg ccgcttctct    13140
tctctcccgc gcaagggcgt caccatcgtg aagccggtag tgtacgggaa cgtgcgcggt    13200
tacttcggga agaagaggga ggaggacggg cacacgcatc agtggacggt ttacgtgaag    13260
ccctacagga acgaggtagg gcccgagcgc gtcggccgcc gttctcggag cgccggagcc    13320
gtcagcgccg cgcctggggtg cgctgtggga cacagcgagc ttctctcgta ggacatgtcc    13380
```

```
gcctacgtga aaaaaatcca gttcaagctg cacgagagct acgggaatcc tctccgaggt  13440
gggtgttgcg tcgggggtt tgctccgctc ggtcccgctg aggctcgtcg ccctcatctt  13500
tctttcgtgc cgcagtcgtt accaaaccgc cgtacgagat caccgaaacg ggctggggcg  13560
aatttgaaat catcatcaag atattttca ttgatccaaa cgagcgaccc gtaagtacgc  13620
tcagcttctc gtagtgcttc ccccgtcctg gcggcccggg gctgggctgc tgctgctgc  13680 cggtcacagt cccgccagcc gcggagctga ctgagctccc tttcccggga cgtgtgctct  13740
gtgttcggtc agcgaggcta tcgggagggc tttggctgca tttggcttct ctggcgctta  13800
gcgcaggagc acgttgtgct acgcctgaac tacagctgtg agaaggccgt ggaaaccgct  13860
ctcaaactga tttattggcg aaatggctct aaactaaatc gtctcctctc tttggaaatg  13920
ctttagagaa ggtctctgtg gtagttctta tgcatctatc ctaaagcact tggccagaca  13980
atttaaagac atcaagcagc atttatagca ggcacgttta ataacgaata ctgaatttaa  14040
gtaactctgc tcacgttgta tgacgtttat tttcgtattc ctgaaagcca ttaaaatcct  14100
gtgcagttgt ttagtaagaa cagctgccac tgttttgtat ctaggagata actggtgttt  14160
ccctacagtt ctcaagctga taaaactctg tctttgtatc taggtaaccc tgtatcactt  14220
gctgaagctt tttcagtctg acaccaatgc aatcctggga agaaaactg tagtttctga  14280 attctatgat gaaatggtat gaaaatttta atgtcaaccg agcctgactt tatttaaaaa  14340
aaattattga tggtgctgtg tattttggtc cttccttaga tatttcaaga tcctactgcc  14400
atgatgcagc aactgctaac gacgtcccgt cagctgacac ttggtgctta caagcatgaa  14460
acagagtgta agtgcaaaat gaggatacct tcgccgaccg tcattcacta ctaatgtttt  14520
ctgtgggatg tgatcgtaca gtgagtttgg ctgtgtgaaa tttgaatagc ttggtattgg  14580
cagtgatgac gtgatcgatg ccttgcttat catgtttgaa atgaagtaga ataaatgcag  14640
cctgctttat ttgagatagt ttggttcatt ttatggaatg caagcaaaga ttatacttcc  14700
tcactgaatt gcactgtcca aaggtgtgaa atgtgtgggg atctggagga ccgtgaccga  14760
gggacattgg atcgctatct cccatttctt ttgctgttac cagttcagat tttcttttca  14820
cctagtcttt aattcccagg gttttgtttt ttccttggtc atagttttttg tttttcactc  14880 tggcaaatga tgttgtgaat tacactgctt cagccacaaa actgatggac tgaatgaggt  14940
catcaaacaa acttttcttc ttccgtattt ccttttttt cccccactta tcatttttac  15000
tgctgttgtt gagtctgtaa ggctaaaagt aactgttttg tgcttttca ggacgtgtgc  15060 tttccaaatt actgccacat atataaagaa aggttggaat tttaaagata attcatgttt  15120
cttcttcttt tttgccacca cagttgcaga tcttgaagta aaaaccaggg aaaagctgga  15180
agctgccaaa aagaaaacca gttttgaaat tgctgagctt aaagaaaggt taaaagcaag  15240
tcgtgaaacc atcaactgct aaagagtga atcagaaaa ctcgaagagg atgatcagtc  15300
taaagatatg tgatgagtgt tgacttggca gggagcctat aatgagaatg aaaggacttc  15360
agtcgtggag ttgtatgcgt tctctccaat tctgtaacgg agactgtatg aatttcattt  15420
gcaaatcact gcagtgtgtg acaactgact ttttataaat ggcagaaaac aagaatgaat  15480
gtatcctcat tttatagtta aaatctatgg gtatgtactg gtttatttca aggagaatgg  15540
atcgtagaga cttggaggcc agattgctgc ttgtattgac tgcatttgag tggtgtagga  15600 acatttgtc tatggtcccg tgttagttta cagaatgcca ctgttcactg ttttgtttg  15660 tattttactt tttctactgc aacgtcaagg ttttaaaagt tgaaaataaa acatgcaggt  15720
```

```
tttttttaaa tatttttttg tctctatcca gtttgggctt caagtattat tgttaacagc    15780
aagtcctgat ttaagtcaga ggctgaagtg taatggtatt caagatgctt aagtctgttg    15840
tcagcaaaac aaaagagaaa acttcataaa atcaggaagt tggcatttct ataacttct     15900 ttatcaacag ataagagttt ctagccctgc atctactttc acttatgtag ttgatgcctt    15960
tatattttgt gtgtttggat gcaggaagtg attcctactc tgttatgtag atattctatt    16020
taacacttgt actctgctgt gcttagcctt tccccatgaa aattcagcgg ctgtaaatcc    16080
ccctcttctt ttgtagcctc atacagatgg cagaccctca ggcttataaa ggcttgggca    16140
tcttctttac tgctttgaga ttctgtgttg cagtaacctc tgccagagag gagaaaagcc    16200
ccacaaacct catccccttc ttctatagca atcagtatta ctaatgcttt gagaacagag    16260
cactggtttg aaacgtttga taattagcat ttaacatggc ttggtaaaga tgcagaactg    16320
aaacagctgt gacagtatga actcagtatg gagacttcat taagacaaac agctgttaaa    16380
atcaggcatg tttcattgag gaggacgggg caacttgcac cagtggtgcc cacacaaatc    16440
cttcctggcg ctgcagacca attttttctgg cattctgact gccgttgctg ctggtcacag    16500
agagcaacta ttttatcag ccacaggcaa tttgcttgta gtattttcca agtgttgtag     16560
gtaagtataa atgcatcggc tccagagcac tttgagtata cttattaaaa acataaatga    16620
aagacaaatt agctttgctt gggtgcacag aacatttta gttccagcct gcttttggt      16680 agaagccctc ttctgaggct agaactgact ttgacaagta gagaaactgg caacggagct    16740
attgctatcg aaggatcctt gttaacaaag ttaatcgtct tttaaggttt ggtttattca    16800
ttaaatttgc ttttaagctg tagctgaaaa agaacgtgct gtcttccatg caccaggtgg    16860
cagctctgtg caaagtgctc tctggtctca ccagccttt aattgccggg attctggcac     16920
gtctgagagg gctcagactg gcttcgtttg tttgaacagc gtgtactgct ttctgtagac    16980
atggccggtt tctctcctgc agcttatgaa actgttcaca ctgaacacac tggaacaggt    17040
tgcccaagga ggccgtggat gccccatccc tggaggcatt caaggccagg ctggatgtgg    17100
ctctgggcag cctggtctgg tggttggcga tcctgcacat agcagcgggg ttgaaactcg    17160
atgatcactg tggtcctttt caacccaggc tattctatga ttctatgatt caacagcaaa    17220
tcatatgtac tgagagagga aacaaacaca agtgctactg tttgcaagtt ttgttcatt     17280 ggtaaaagag tcaggtttta aaattcaaaa tctgtctggt tttggtgttt ttttttttt     17340 atttattatt tctttggggt tcttttgat gctttatctt tctctgccag gactgtgtga     17400
caatgggaac gaaaaagaac atgccaggca ctgtcctgga ttgcacacgc tggttgcact    17460
cagtagcagg ctcagaactg ccagtctttc cacagtatta cttctaaac ctaatttaa      17520 tagcgttagt agacttccat cactgggcag tgcttagtga atgctctgtg tgaacgtttt    17580
acttataagc atgttggaag ttttgatgtt cctggatgca gtagggaagg acagattagc    17640
tatgtgaaaa gtagattctg agtatcgggg ttacaaaaag tatagaaacg atgagaaatt    17700
cttgttgtaa ctaattggaa tttctttaag cgttcactta tgctacattc atagtatttc    17760
catttaaaag taggaaaagg taaacgtga aatcgtgtga ttttcggatg gaacaccgcc     17820
ttcctatgca cctgaccaac ttccagagga aaagcctatt gaaagccgag attaagccac    17880
caaaagaact catttgcatt ggaatatgta gtatttgccc tcttcctccc gggtaattac    17940
tatactttat agggtgctta tatgttaaat gagtggctgg cacttttat tctcacagct     18000 gtggggaatt ctgtcctcta ggacagaaac aattttaatc tgttccactg gtgactgctt    18060
tgtcagcact tccacctgaa gagatcaata cactcttcaa tgtctagttc tgcaacactt    18120
```

-continued

```
ggcaaacctc acatcttatt tcatactctc ttcatgccta tgcttattaa agcaataatc    18180
tgggtaattt ttgttttaat cactgtcctg accccagtga tgaccgtgtc ccacctaaag    18240
ctcaattcag gtcctgaatc tcttcaactc tctatagcta acatgaagaa tcttcaaaag    18300
ttaggtctga gggacttaag gctaactgta gatgttgttg cctggtttct gtgctgaagg    18360
ccgtgtagta gttagagcat tcaacctcta g                                   18391
```

<210> SEQ ID NO 11
<211> LENGTH: 586
<212> TYPE: DNA
<213> ORGANISM: Artificial sequence
<220> FEATURE:
<223> OTHER INFORMATION: MDOT artificial promoter

<400> SEQUENCE: 11

```
gtaccgggcc cccctcgag gtgaatatcc aagaatgcag aactgcatgg aaagcagagc       60
tgcaggcacg atggtgctga gccttagctg cttcctgctg ggagatgtgg atgcagagac     120
gaatgaagga cctgtccctt actcccctca gcattctgtg ctatttaggg ttctaccaga    180
gtccttaaga ggttttttttt tttttggtc caaaagtctg tttgtttggt tttgaccact    240
gagagcatgt gacacttgtc tcaagctatt aaccaagtgt ccagccaaaa tcgatgtcac    300
aacttgggaa ttttccattt gaagccccctt gcaaaaacaa agagcacctt gcctgctcca   360
gctcctggct gtgaagggtt ttggtgccaa agagtgaaag gcttcctaaa aatgggctga    420
gccggggaag gggggcaact tggggggctat tgagaaacaa ggaaggacaa acagcgttag   480
gtcattgctt ctgcaaacac agccagggct gctcctctat aaaaggggaa gaaagaggct    540
ccgcagccat cacagaccca gaggggacgg tctgtgaatc aagctt                  586
```

<210> SEQ ID NO 12
<211> LENGTH: 11
<212> TYPE: PRT
<213> ORGANISM: Artificial sequence
<220> FEATURE:
<223> OTHER INFORMATION: SV40 terminator

<400> SEQUENCE: 12

Cys Gly Gly Pro Lys Lys Lys Arg Lys Val Gly
1               5                   10

<210> SEQ ID NO 13
<211> LENGTH: 20
<212> TYPE: DNA
<213> ORGANISM: Artificial sequence
<220> FEATURE:
<223> OTHER INFORMATION: Lys051

<400> SEQUENCE: 13
tgcatccttc agcacttgag                                                  20

<210> SEQ ID NO 14
<211> LENGTH: 20
<212> TYPE: DNA
<213> ORGANISM: Artificial sequence
<220> FEATURE:
<223> OTHER INFORMATION: Primer IFN-3rev

<400> SEQUENCE: 14
aactcctctt gaggaaagcc                                                  20

```
<210> SEQ ID NO 15
<211> LENGTH: 34
<212> TYPE: DNA
<213> ORGANISM: Artificial sequence
<220> FEATURE:
<223> OTHER INFORMATION: Primer LYSBSU

<400> SEQUENCE: 15 cccccccta aggcagccag ggcaggaag caaa                              34

<210> SEQ ID NO 16
<211> LENGTH: 12
<212> TYPE: DNA
<213> ORGANISM: Artificial sequence
<220> FEATURE:
<223> OTHER INFORMATION: Primer SaltoNotI

<400> SEQUENCE: 16
tcgagcggcc gc                                                    12

<210> SEQ ID NO 17
<211> LENGTH: 83
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 17
atggctttga cctttgcctt actggtggct ctcctggtgc tgagctgcaa gagcagctgc    60
tctgtgggct gcgatctgcc tca                                            83

<210> SEQ ID NO 18
<211> LENGTH: 100
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 18
gacccacagc ctgggcagca ggaggaccct gatgctgctg gctcagatga ggagaatcag    60
cctgtttagc tgcctgaagg ataggcacga ttttggcttt                          100

<210> SEQ ID NO 19
<211> LENGTH: 62
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 19
ctcaagagga gtttggcaac cagtttcaga aggctgagac catccctgtg ctgcacgaga    60
tg                                                                   62

<210> SEQ ID NO 20
<211> LENGTH: 94
<212> TYPE: DNA
<213> ORGANISM: Artificial Sequence
<220> FEATURE:
<223> OTHER INFORMATION: primer used in the formation
      of the chicken codon optimized human interferon
```

-continued

```
    2b-encoding nucleic acid

<400> SEQUENCE: 20
tccagcagat ctttaacctg tttagcacca aggatagcag cgctgcttgg gatgagaccc    60
tgctggataa gttttacacc gagctgtacc agca                                94

<210> SEQ ID NO 21
<211> LENGTH: 77
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 21
ctgaacgatc tggaggcttg cgtgatccag ggcgtgggcg tgaccgagac ccctctgatg    60
aaggaggata gcatcct                                                   77

<210> SEQ ID NO 22
<211> LENGTH: 82
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 22
gctgtgagga agtactttca gaggatcacc ctgtacctga aggagaagaa gtacagccct    60
tgcgcttggg aagtcgtgag gg                                             82

<210> SEQ ID NO 23
<211> LENGTH: 65
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 23
ctgagatcat gaggagcttt agcctgagca ccaacctgca agagagcttg aggtctaagg    60
agtaa                                                                65

<210> SEQ ID NO 24
<211> LENGTH: 34
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 24
cccaagcttt caccatggct ttgacctttg cctt                                34

<210> SEQ ID NO 25
<211> LENGTH: 19
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid
```

<400> SEQUENCE: 25
atctgcctca gacccacag                                              19

<210> SEQ ID NO 26
<211> LENGTH: 26
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 26
gattttggct ttcctcaaga ggagtt                                      26

<210> SEQ ID NO 27
<211> LENGTH: 21
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 27
gcacgagatg atccagcaga t                                           21

<210> SEQ ID NO 28
<211> LENGTH: 20
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 28
atcgttcagc tgctggtaca                                             20

<210> SEQ ID NO 29
<211> LENGTH: 20
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 29
cctcacagcc aggatgctat                                             20

<210> SEQ ID NO 30
<211> LENGTH: 20
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 30
atgatctcag ccctcacgac                                             20

<210> SEQ ID NO 31
<211> LENGTH: 19
<212> TYPE: DNA

```
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 31
ctgtgggtct gaggcagat                                                  19

<210> SEQ ID NO 32
<211> LENGTH: 26
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 32
aactcctctt gaggaaagcc aaaatc                                          26

<210> SEQ ID NO 33
<211> LENGTH: 21
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 33
atctgctgga tcatctcgtg c                                               21

<210> SEQ ID NO 34
<211> LENGTH: 36
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 34
tgctctagac tttttactcc ttagacctca agctct                               36

<210> SEQ ID NO 35
<211> LENGTH: 19
<212> TYPE: DNA
<213> ORGANISM: Artificial Sequence
<220> FEATURE:
<223> OTHER INFORMATION: neo for-1 primer for detecting the interferon
      transgene

<400> SEQUENCE: 35
tggattgcac gcaggttct                                                  19

<210> SEQ ID NO 36
<211> LENGTH: 20
<212> TYPE: DNA
<213> ORGANISM: Artificial Sequence
<220> FEATURE:
<223> OTHER INFORMATION: neo rev-1 primer for detecting the interferon
      transgene

<400> SEQUENCE: 36
gtgcccagtc atagccgaat                                                 20
```

```
<210> SEQ ID NO 37
<211> LENGTH: 20
<212> TYPE: DNA
<213> ORGANISM: Artificial Sequence
<220> FEATURE:
<223> OTHER INFORMATION: FAM labeled NEO-PROBE1 for detecting the
      interferon transgene

<400> SEQUENCE: 37
cctctccacc caagcggccg                                                     20

<210> SEQ ID NO 38
<211> LENGTH: 25
<212> TYPE: DNA
<213> ORGANISM: Artificial Sequence
<220> FEATURE:
<223> OTHER INFORMATION: primer used in the synthesis of the MDOT
      promoter

<400> SEQUENCE: 38
tcactcgagg tgaatatcca agaat                                               25

<210> SEQ ID NO 39
<211> LENGTH: 25
<212> TYPE: DNA
<213> ORGANISM: Artificial Sequence
<220> FEATURE:
<223> OTHER INFORMATION: primer used in the synthesis of the MDOT
      promoter

<400> SEQUENCE: 39
gagatcgatt ttggctggac acttg                                               25

<210> SEQ ID NO 40
<211> LENGTH: 25
<212> TYPE: DNA
<213> ORGANISM: Artificial Sequence
<220> FEATURE:
<223> OTHER INFORMATION: primer used in the synthesis of the MDOT
      promoter

<400> SEQUENCE: 40
cacatcgatg tcacaacttg ggaat                                               25

<210> SEQ ID NO 41
<211> LENGTH: 25
<212> TYPE: DNA
<213> ORGANISM: Artificial Sequence
<220> FEATURE:
<223> OTHER INFORMATION: primer used in the synthesis of the MDOT
      promoter

<400> SEQUENCE: 41
tctaagcttc gtcacagacc gtccc                                               25

<210> SEQ ID NO 42
<211> LENGTH: 75815
<212> TYPE: DNA
<213> ORGANISM: artificial
<220> FEATURE:
<223> OTHER INFORMATION: description of artificial sequence: plasmid

<400> SEQUENCE: 42
agcttgcatg cctgcaggtc gactctagag gatccccggg taccgagctc gaattcgccc         60
tatagtgagt cgtattacaa ttcactggcc gtcgttttac aacgtcgtga ctgggaaaac        120
cctggcgtta cccaacttaa tcgccttgca gcacatcccc ctttcgccag ctggcgtaat        180
```

```
agcgaagagg cccgcaccga tcgcccttcc caacagttgc gcagcctgaa tggcgaatgg    240
cgcctgatgc ggtatttcct ccttacgcat ctgtgcggta tttcacaccg catatggtgc    300
actctcagta caatctgctc tgatgccgca tagttaagcc agccccgaca cccgccaaca    360
cccgctgacg cgaaccccctt gcggccgcat cgaatataac ttcgtataat gtatgctata    420
cgaagttatt agcgatgagc tcggacttcc attgttcatt ccacgacaa aaacagagaa     480 aggaaacgac agaggccaaa agctcgctt tcagcacctg tcgtttcctt tcttttcaga     540
gggtatttta aataaaaaca ttaagttatg cgaagaaga acggaaacgc cttaaaccgg     600
aaaattttca taaatagcga aaacccgcga ggtcgccgcc ccgtaacctg tcggatcacc    660
ggaaaggacc cgtaaagtga taatgattat catctacata tcacaacgtg cgtggaggcc    720
atcaaaccac gtcaaataat caattatgac gcaggtatcg tattaattga tctgcatcaa    780
cttaacgtaa aaacaacttc agacaataca aatcagcgac actgaatacg ggcaacctc    840 atgtccgagc tcgcgagctc gtcgacagcg acacacttgc atcggatgca gcccggttaa    900
cgtgccggca cggcctgggt aaccaggtat tttgtccaca taaccgtgcg caaaatgttg    960
tggataagca ggacacagca gcaatccaca gcaggcatac aaccgcacac cgaggttact    1020
ccgttctaca ggttacgacg acatgtcaat acttgcccctt gacaggcatt gatgaatcg    1080 tagtctcacg ctgatagtct gatcgacaat acaagtggga ccgtggtccc agaccgataa    1140
tcagaccgac aacacgagtg ggatcgtggt cccagactaa taatcagacc gacgatacga    1200
gtgggaccgt ggtcccagac taataatcag accgacgata cgagtgggac cgtggttcca    1260
gactaataat cagaccgacg atacgagtgg gaccgtggtc ccagactaat aatcagaccg    1320
acgatacgag tgggaccatg gtcccagact aataatcaga ccgacgatac gagtgggacc    1380
gtggtcccag tctgattatc agaccgacga tacgagtggg accgtggtcc cagactaata    1440
atcagaccga cgatacgagt gggaccgtgg tcccagacta ataatcagac cgacgatacg    1500
agtgggaccg tggtcccagt ctgattatca gaccgacgat acaagtggaa cagtgggccc    1560
agagagaata ttcaggccag ttatgctttc tggcctgtaa caaggacat taagtaaaga    1620 cagataaacg tagactaaaa cgtggtcgca tcagggtgct ggcttttcaa gttccttaag    1680
aatggcctca attttctcta tacactcagt tggaacacga gacctgtcca ggttaagcac    1740 catttatcg cccttataca atactgtcgc tccaggagca aactgatgtc gtgagcttaa     1800
actagttctt gatgcagatg acgttttaag cacagaagtt aaaagagtga taacttcttc    1860
agcttcaaat atcaccccag ctttttttctg ctcatgaagg ttagatgcct gctgcttaag   1920
taattcctct ttatctgtaa aggcttttg aagtgcatca cctgaccggg cagatagttc     1980
accggggtga gaaaaagag caacaactga tttaggcaat ttggcggtgt tgatacagcg    2040
ggtaataatc ttacgtgaaa tattttccgc atcagccagc gcagaaatat ttccagcaaa    2100
ttcattctgc aatcggcttg cataacgctg accacgttca taagcacttg ttgggcgata    2160
atcgttaccc aatctggata atgcagccat ctgctcatca tccagctcgc caaccagaac    2220
acgataatca ctttcggtaa gtgcagcagc tttacgacgg cgactcccat cggcaatttc    2280
tatgacacca gatactcttc gaccgaacgc cggtgtctgt tgaccagtca gtagaaaaga    2340
agggatgaga tcatccagtg cgtcctcagt aagcagctcc tggtcacgtt cattacctga    2400
ccatacccga gaggtcttct caacactatc accccggagc acttcaagag taaacttcac    2460
atcccgacca catacaggca aagtaatggc attaccgcga gccattactc ctacgcgcgc    2520
```

```
aattaacgaa tccaccatcg gggcagctgg tgtcgataac gaagtatctt caaccggttg   2580
agtattgagc gtatgttttg gaataacagg cgcacgcttc attatctaat ctcccagcgt   2640
ggtttaatca gacgatcgaa aatttcattg cagacaggtt cccaaataga aagagcattt   2700
ctccaggcac cagttgaaga gcgttgatca atggcctgtt caaaaacagt tctcatccgg   2760
atctgacctt taccaacttc atccgtttca cgtacaacat tttttagaac catgcttccc   2820
caggcatccc gaatttgctc ctccatccac ggggactgag agccattact attgctgtat   2880
ttggtaagca aaatacgtac atcaggctcg aacccttTaa gatcaacgtt cttgagcaga   2940
tcacgaagca tatcgaaaaa ctgcagtgcg gaggtgtagt caaacaactc agcaggcgtg   3000
ggaacaatca gcacatcagc agcacatacg acattaatcg tgccgatacc caggttaggc   3060
gcgctgtcaa taactatgac atcatagtca tgagcaacag tttcaatggc cagtcggagc   3120
atcaggtgtg gatcggtggg cagtttacct tcatcaaatt tgcccattaa ctcagtttca   3180
atacggtgca gagccagaca ggaaggaata atgtcaagcc ccggccagca agtgggcttt   3240
attgcataag tgacatcgtc cttttcccca agatagaaag gcaggagagt gtcttctgca   3300
tgaatatgaa gatctggtac ccatccgtga tacattgagg ctgttccctg ggggtcgtta   3360
ccttccacga gcaaaacacg tagccccttc agagccagat cctgagcaag atgaacagaa   3420
actgaggttt tgtaaacgcc acctttatgg gcagcaaccc cgatcaccgg tggaaatacg   3480
tcttcagcac gtcgcaatcg cgtaccaaac acatcacgca tatgattaat ttgttcaatt   3540
gtataaccaa cacgttgctc aacccgtcct cgaatttcca tatccgggtg cggtagtcgc   3600
cctgctttct cggcatctct gatagcctga gaagaaaccc caactaaatc cgctgcttca   3660
cctattctcc agcgccgggt tattttcctc gcttccgggc tgtcatcatt aaactgtgca   3720
atggcgatag ccttcgtcat ttcatgacca gcgtttatgc actggttaag tgtttccatg   3780
agtttcattc tgaacatcct ttaatcattg ctttgcgttt ttttattaaa tcttgcaatt   3840
tactgcaaag caacaacaaa atcgcaaagt catcaaaaaa ccgcaaagtt gtttaaaata   3900
agagcaacac tacaaaagga gataagaaga gcacatacct cagtcactta ttatcactag   3960
cgctcgccgc agccgtgtaa ccgagcatag cgagcgaact ggcgaggaag caaagaagaa   4020
ctgttctgtc agatagctct tacgctcagc gcaagaagaa atatccaccg tgggaaaaac   4080
tccaggtaga ggtacacacg cggatagcca attcagagta ataaactgtg ataatcaacc   4140
ctcatcaatg atgacgaact aaccccgat atcaggtcac atgacgaagg gaaagagaag   4200
gaaatcaact gtgacaaact gccctcaaat ttggcttcct taaaaattac agttcaaaaa   4260
gtatgagaaa atccatgcag gctgaaggaa acagcaaaac tgtgacaaat taccctcagt   4320
aggtcagaac aaatgtgacg aaccaccctc aaatctgtga cagataaccc tcagactatc   4380
ctgtcgtcat ggaagtgata tcgcggaagg aaaatacgat atgagtcgtc tggcggcctt   4440 tcttttttctc aatgtatgag aggcgcattg gagttctgct gttgatctca ttaacacaga   4500
cctgcaggaa gcggcggcgg aagtcaggca tacgctggta actttgaggc agctggtaac   4560
gctctatgat ccagtcgatt ttcagagaga cgatgcctga gccatccggc ttacgatact   4620
gacacaggga ttcgtataaa cgcatggcat acggattggt gatttctttt gtttcactaa   4680
gccgaaactg cgtaaaccgg ttctgtaacc cgataaagaa gggaatgaga tatgggttga   4740
tatgtacact gtaaagccct ctggatggac tgtgcgcacg tttgataaac caaggaaaag   4800
attcatagcc tttttcatcg ccggcatcct cttcagggcg ataaaaaacc acttccttcc   4860
ccgcgaaact cttcaatgcc tgccgtatat ccttactggc ttccgcagag gtcaatccga   4920
```

```
atatttcagc atatttagca acatggatct cgcagatacc gtcatgttcc tgtagggtgc      4980
catcagattt tctgatctgg tcaacgaaca gatacagcat acgttttga tcccgggaga       5040 gactatatgc cgcctcagtg aggtcgtttg actggacgtc tcgcgggcta tttttacgtt      5100
tcttgtgatt gataaccgct gtttccgcca tgacagatcc atgtgaagtg tgacaagttt      5160
ttagattgtc acactaaata aaaagagtc aataagcagg gataactttg tgaaaaaaca       5220
gcttcttctg agggcaattt gtcacagggt taagggcaat ttgtcacaga caggactgtc      5280
atttgagggt gatttgtcac actgaaaggg caatttgtca caacaccttc tctagaacca     5340
gcatggataa aggcctacaa ggcgctctaa aaagaagat ctaaaaacta taaaaaaaat      5400
aattataaaa atatcccgt ggataagtgg ataaccccaa gggaagtttt ttcaggcatc       5460
gtgtgtaagc agaatatata agtgctgttc cctggtgctt cctcgctcac tcgagggctt     5520
cgccctgtcg ctcgactgcg gcgagcacta ctggctgtaa aaggacagac cacatcatgg     5580
ttctgtgttc attaggttgt tctgtccatt gctgacataa tccgctccac ttcaacgtaa     5640
caccgcacga agatttctat tgttcctgaa ggcatattca aatcgttttc gttaccgctt     5700
gcaggcatca tgacagaaca ctacttccta taaacgctac acaggctcct gagattaata     5760
atgcggatct ctacgataat gggagatttt cccgactgtt tcgttcgctt ctcagtggat     5820
aacagccagc ttctctgttt aacagacaaa aacagcatat ccactcagtt ccacatttcc     5880
atataaaggc caaggcattt attctcagga taattgtttc agcatcgcaa ccgcatcaga     5940
ctccggcatc gcaaactgca cccggtgccg ggcagccaca tccagcgcaa aaaccttcgt     6000
gtagacttcc gttgaactga tggacttatg tcccatcagg ctttgcagaa ctttcagcgg     6060
tataccggca tacagcatgt gcatcgcata ggaatggcgg aacgtatgtg gtgtgaccgg     6120
aacagagaac gtcacaccgt cagcagcagc ggcggcaacc gcctcccaa tccaggtcct      6180 gaccgttctg tccgtcactt cccagatccg cgctttctct gtccttcctg tgcgacggtt     6240
acgccgctcc atgagcttat cgcgaataaa tacctgtgac ggaagatcac ttcgcagaat     6300
aaataaatcc tggtgtccct gttgataccg ggaagccctg ggccaacttt tggcgaaaat     6360
gagacgttga tcggcacgta agaggttcca actttcacca taatgaaata agatcactac     6420
cgggcgtatt ttttgagtta tcgagatttt caggagctaa ggaagctaaa atggagaaaa     6480
aaatcactgg atataccacc gttgatatat cccaatggca tcgtaaagaa cattttgagg     6540
catttcagtc agttgctcaa tgtacctata accagaccgt tcagctggat attacggcct     6600
ttttaaagac cgtaaagaaa aataagcaca gttttatcc ggcctttatt cacattcttg      6660
cccgcctgat gaatgctcat ccggaattta catctggaat tacgtatggc aatgaaagac     6720
ggtgagctgg tgatatggga tagtgttcac ccttgttaca ccgttttcca tgagcaaact     6780
gaaacgtttt catcgctctg gagtgaatac cacgacgatt tccggcagtt tctacacata     6840
tattcgcaag atgtggcgtg ttacggtgaa aacctggcct atttccctaa agggtttatt     6900
gagaatatgt ttttcgtctc agccaatccc tgggtgagtt tcaccagttt tgatttaaac     6960
gtggccaata tggacaactt cttcgccccc gttttcacca tgggcaaata ttatacgcaa     7020
ggcgacaagg tgctgatgcc gctggcgatt caggttcatc atgccgtttg tgatggcttc     7080
catgtcggca gaatgcttaa tgaattacaa cagtactgcg atgagtggca gggcggggcg     7140 taatttttt aaggcagtta ttggtgccct taaacgcctg gttgctacgc ctgaataagt      7200
gataataagc ggatgaatgg cagaaattcg atgataagct gtcaaacatg agaattggtc    7260
```

```
gacggcccgg gcggccgcaa ggggttcgcg ttggccgatt cattaatgca gctggcacga   7320
caggtttccc gactggaaag cgggcagtga gcgcaacgca attaatgtga gttagctcac   7380
tcattaggca ccccaggctt tacactttat gcttccggct cgtatgttgt gtggaattgt   7440
gagcggataa caatttcaca caggaaacag ctatgaccat gattacgcca agctatttag   7500
gtgacactat agaatactca agctttgtgc tttctgcctg aataaaagaa acctgaactc   7560
tgttcaccca gtccctgtca ggcaattact gacagagcac ctatggtctg tgtttggcca   7620
gaacataggc taaggaagat acctcctgtt tataaagcac gcctttggca tctggcaagt   7680
aattagtgat ggcgcatgag agctctgact agggcagggt gtgggacagg ctggctctaa   7740
ttgtgccctg tttatcttgt tgatgcacac ggctggtttc tttcacccac agctgtctct   7800
ctagacaaca tacctttatg gagaggaacg tgtcttttcc aatcttgggt tttcattcag   7860
aattggagtg aactggtctc catcagatag cattggctgc ggtgatttat tcttttacac   7920
ttcctagtta agcaggataa ctctctggct ctgctgtgtc taggcaattt aaatgattta   7980
taaagcatag ctgttttaag gaaatctttt tttaaacatt tgacttgcca atgtgtggtc   8040
ctaaaggcag aaggactgtt ccagagtgtc aggcagagac ctaccctgga tttcgttgtt   8100
cagctaccca ttcagtgtgg cttttggcaa ggaattctct ggacctgact tccctacctg   8160
cagagctggg ataagctatc aaaccatctc ctccacacac tgtgagggtg ggaaaaaaac   8220
ccaaacccct aaaagtgctg tataaaggcg ccttaaggct cagtatagca tgtgtgctgc   8280
tgatgcccca gacctgtttg cgggtcctga aggtcatagg agaactgctc agaagagaca   8340
gaaatgctta agaaggtttt actacaaaag tcttgtgatg ttaacacata atatcacatt   8400
gtgcagaagg tacaaatgcc ccctcctatc cctgcacacc tggaagctca aggtatggaa   8460
gggtttgttg tctgcagcct cttcgctgcc ctctgctttt taagatcctg ggtagtgtgc   8520
tcagtgtgtg ccctcagcag tttgggaaac ggacatcttc atgcaaaatt aagcaaggaa   8580
gtgttgcttt tatactcaga gtagaatcta agttcttcag gcaggctctt gtgtgccgcc   8640
tctattagaa ataaaactcc cccggatcag aagatgaatg tgctcagcta agaacacaga   8700
tttatttgct ttacaatgcg tgctatggtt taagaaaaac acatcaggca aacaatttat   8760
ggtttgccac tgagttgtgc ctgaaggaaa cacaactgtt agagatgtaa ttgattgggc   8820
ggtgacgctg tgtggattca tgggagatgc atcttggtca gcatgtctgt gtgaaaccac   8880
atttctggtg ctgctgcagg acgagtgccg ggagttccgg gatctgttca agaatgggaa   8940
gctttcctgc acgagggaga atgatcccgt ccgggattcc tcggggaagc agcacagcaa   9000
taagtgcatc atgtgtgcgg agaagttgtg agtagaggaa gccaatgttt gttatcgaga   9060
gtggcaatgg ggcgggtgg ggctcctaca gcaatgttct cctcactttc tcatccttct   9120
ctttcagcaa aagggagaat gagcagaagg cgacctcaac cagagggaaa caaaaggtga   9180
ggttaaagta ttgggttcat atacaagtct ataggattct tacccaatat taccacactt   9240
gatttctttg tcactctggg gatccatgtg gctttcctg cttgtatctc gttgatgctc   9300
tttcatgccc tgagagaata gtttgtctga acgctgcagt ctatcccact gaccgcagtg   9360
acatgggagc aaacccatc gcaataagaa gctgagcaga actgccctga catctggcac   9420
aagggcaaga aggcactgct gctgagagcg ctaatgaggt tgaaagaaa atctgggtga   9480 gaagctttaa atgtgagctc tgagatgctc aaaagttcat tatgtcgtgg gaggagagtt   9540
cagccctgtg ctgtccctgg ggtggctcgg tttcagctttt ccctgattgg aaacctcact   9600
ctcatgatgc agctgctgtg cccttgtgca ccgatacttc tctggtgaga gcaattcagc   9660
```

```
aaggggaagg aaaaagaagc actaagtaaa tcttgccatt tctgtcttgc gaggaactgg   9720
tacggtcccc ttaagcctca ttcttgggga taatcctgtt tcagtgcttt tcctaatgac   9780
agtggcacaa aaaaaatgga agcgttaatg aaacttgctg atggcaaagc tgggagggag   9840
gatcagcaga tcactcagga ctaattggat agcactgagg cctggagtaa tagaaacaag   9900
ataaaatgta ataacagaga gtgcaagatc acacaggcag tgattaacga gaattcctgc   9960
tcatcaatta gaaatgacaa aggataagaa agctctgcat ttattagtgg gtcacggatg  10020
cggcaggcct gagaaggagg caaatgcaca tctcagcaag gtctgtgcag cagaggtcgg  10080
gctggcagca aatctccaga aatactgctt tgaagagaga gggtttgaga gacgctgtta  10140
gggagaagca gctctgccac agcaggtctg gggttcacct gggtttggc tcattgcctc    10200
cctgtgtccc tcctccacgc tgccagtgct gcactgggaa ggtgtgggta agaagcaatg  10260
gctaagggat ctggttatac acctcctgta tctgctattt gggattggct actgcagggc  10320
ctcaggtccc tgacttaaaa gtggggactt cgaagcatgt ttgcattgtg ctgtcgtgcc  10380
ttagatgttg ctgctgggtc ctcaaagtcc tgttggttgt ggggtggggg ggacttcttg  10440
cttcctatgt gaagttttct gagctgcaac ttcagcaaca gctgtaagag tgcattaagg  10500
gcagtgggag aagtgggagg gaccccatta cctcatcggg tatcgctggc atgctttgga  10560
tagccccacg tggagcgtga caattagagc acggcagaga gctcccaaca cgtgccatgc  10620
aggcagaggc acccgccgct cttctgactc actctgtttg tagccatgag gctgtgccac  10680
gtgccctctt ctctctctca cacctgggct ctcctggggc gcgtttggga agcctctgga  10740
ggatcggagg gatgtggcag ggtgccctga ctgctgctcc ttccgcagga tgactgcagt  10800
gagtaccgct cccagtttga ggctggcgga cgcctgtcct gcacgcggga gaacgacccc  10860
gtcagggatt cctctggcaa gcagcacacc aacaagtgcc tcatgtgtgc cgagaagctg  10920
tgagtacagt tcctggcaac agcaaagagg gaaacctcac attgcgaaac tgcagcttct  10980
gcctgtgtgg ctgcgcctgg gggagtcccg agtcccagcg gccccccagg agctgctcct  11040
gctgtagggc tgtggctact gcccctcttc ccacctcccc cctaacccct cagggagcag  11100
aggagaagca gggttgatag agagcagccc tttccttggg gcagctccca aggaaagttt  11160
cccacgcgtg tactttgcct tccagatgct ctctctactc ccatagagca tatgcagaag  11220
cagccctgat atgaaagcag ccacctggag ccgggatgta gcatacagtg ggaatggtga  11280
ggagaaggga gaaggcttag gggtgggaat taggtgcagg gccaccaggg atggggaggc  11340
tggtgcctaa tgacatgatg ctggcttgca gggcagcccc aggtcctggc agcgttcgca  11400
ctgccatagt gctcctttct ttctcctctc cctttttttcc agcaaaaaag aagctcaaag  11460
aggaggtcag tctggtggaa ctgcccagcg caacaagcag tccactgcag agtgtgcaaa  11520
ccaggtgaga ctgagctcag agcctcacca ggcttgggaa aaggggttgg tggatctggg  11580
gaccccgatg gtcaagggct gcctgtggtc ctggtgtttg gggtgcagga gcctgctggt  11640
gatggcagag aggcaggttg cattgcaagc cctgctagtt catggatgg gtttgtgtat    11700
gagcgtgcat agtgggcagt tctggactcc tctatggggc acgcatcaga gctatttctt  11760
cagaaagagc cccatggttc ctagggtcca gggggatgag agggaaggac aggagctgct  11820
ttaatctcac tgctttactg cttggttgtc aaacacgatc ctgcccctttt tccagaagag  11880
ctgcagtggc tcagggttac agcggggtgt aaatgagaga cggccgttct ccacaaacag  11940
agggtgagta cagcagcact gggatcccag cctggcccca caagtcctgg ggtcttgaca  12000
```

```
ctgagaagaa acacataaaa tagggcatat acaacccttt ctcctttcca aagacattct   12060
tgcttcccct gcacacgaag cactggtgac tgctacactc aaaatccctc cccagccttg   12120 cccccctgaat cctgcctcct ggcaggcaca cacttgtcct gctgcctggt ccagcgcatc   12180
ctcatctgct gacctgaggc agtgctgtgt gtgcaccatg tgctgtctgg gcactgagcg   12240
actcctctgg gtttttaggg ctgccaggct ctggcagggt gcagatgctg tgttatctaa   12300
gccttgagga actctcttag tcttcctgtt tttgttggtg aggcccattc atctgccccc   12360
agtcagcact gccagcagac aaacagtgca cagctctcca tggcagcaat ggctgtagca   12420
tatgtagggg ccaggtttct gggatcatct ctgtgacgga catctcttgc tgaccgccca   12480
taaggactca aaagtcccgt tgcagggagt gcctccatcc catggcaagc caagtgccct   12540
gttgaaaaaa caaggtgcag aataatggca atggacctta tgcagttta attccaccct   12600 ggggtgatga tgtggctgag tgggtctgca tacccttggc tgtgccatga gctctgtgct   12660
ttctctccct gccagcccac aaggagactt ggctcaggac tgcagcccgg cacctggccg   12720
ccagggacag agcggaggca ccaacaccta ccagccggta tgcccagctc atgtgggtca   12780
ggcacagcct ttcccagcag ctgccccagt ttccattgtc aacctaaagc ctcacaatgg   12840
gacctgtatc cttggagggg tttaaatggg tggtagagtc cgtaccctga tgctgtcccc   12900
tggcctcaaa gaggagtgag gctgcacacg tccaaacggg agtcactgaa gccagtgctg   12960
ctgctggtgt tggctcactg tagaagtatg tcaggtatga gagagcatcc tccaggaggt   13020
gatggtggtg tcccttcctg catgctgaga tgttgggttg aagactgtgg ccagagcagg   13080
gtgctggggc tgagcggggg ataaggacaa ggctgataag aggaggggag agggagtagt   13140
gggggaggac acggtgagca atagataacg actgtttgtg gaatcatgtg ggagggagaa   13200
gagggtgtat gctctctcca tctccacaaa aagaaaattt gttattttca accaagctaa   13260
agcagaaatt atgaaactaa taggagaaaa taagttacta taaaaaggat gactaacctg   13320
tggatcttgc tgtcacgggg tgttgccaag agctacagtg attaaaaaaa atgacttgcc   13380
acttatagtc catacagcaa tttaggtaac attttggaag ggataggaaa tgcctttctg   13440
tggggctgga gggacctgag tgcagactgc cttaactctc tctgaagtct ctgtcactga   13500
ctgcccttag aaaaatgata ttagaataga aaaccaggg aggcggttca ggtatggcag   13560
ttttaatgca ttccagagga agcattaggc ataataatgc cagtctgctt cagggcttag   13620
tggtatttcc tggtagctcc ggtgaaggag tggatgctga tcagcctgac tgacgagggg   13680
tgattcagag agcagatctg tgtctctcct cgctgcaggg ccacccgtgg gctctgtccc   13740
agggagatgc tgtcctgaag gagaggtggc agtcactgtg aggactgtgg ggactgttg   13800 gtgtggcggc ggttgcacac gcgtgggtca caccgtgggc agtggtgtct ggtgtgtggg   13860
aaggcatctg gcagggaact gcaaaggtca gcgctgtctg tctttgtgtc atcgttaatt   13920
acccaggtga gggaggaagc agcacattaa tgaaattagc aagtgatgtt taaacagagg   13980
gtgttactgc agcaacctgt gccactgaac cccctgcatt gcccagctgg gaaacctttc   14040
ttctccatgg tgctttcaac cccatagtgc tgctgacccc agcaaagcaa tgagccattg   14100
cttagtgctg aatgggtttt ttttctcca gtgggacag gaggtgagat gtccttcctg   14160
cagctcttct ccaattgcac catttgcagt cattgcaaca ttttttatag gacctggaga   14220
aggggatggg aacagagaat tcactccttt tgtctctgca tctttttttt tttggccttt   14280
ggtgcagagg tgggcagtga ggctgaggaa gagaggggc tgtaggatct ctgacctctg   14340
ctgtctgaaa cttgccatga ttctgcaggc acctgtgcca gaatgctcat gggctgataa   14400
```

```
tctaatcatg aggagtcttg ttcctcctgc tccgagctct ttctagctgt gccacgtctg   14460
ctttgtagga aattcgatgc ctagatgctc ctgctgttat gctggagaat aaaacgagag   14520
ggcacgctta attagtcaga gcttttcata catgtttgca tctcttcatt ccgtgggtgt   14580
caagttgtgc tgtgtgtcgg gctgcccttg ggcagctgga ctcaattgtc aaggttttcc   14640
ctttgtttct gccaagtggc ttgcagaagc aacaggtgtg aaagctctga taaaggacaa   14700
aggacaggta gcagaagttt attgtattct cgtggatttg cagggagaag taaaagtgcc   14760
ctggactgag atgtcagggt ggatcagatg agtgtatcca tgcctggcaa tggggtcagg   14820
gcagctttgt ccccacatcg tggctggttg gcccaatagg aggcgttacc tctttgctga   14880
aggtgtgatg gagctcaggg caacgcctgg tttgtgagtg ctttgagcgg tgcgcaggag   14940
ggtcttgcaa gagaaccagc accaaatgtg atttctttct ctcttcagct ggactgtgat   15000
cgaattctgc acggggtaaa gggtggaagg attttctgca gcgaatcctc acaacccgtc   15060
tgtggcactg atgggaaaac atacagaaat gaatgtgact tgtgttcagc tgccatgtga   15120
gtaggcggag agatttcagt aatacagggc catccaccat tcccgagtgt cttttgcagc   15180
acagtgtttg ttttgatata ccatgactca ctatcaagtg tgtccttggt gcctcgctgt   15240
taagcaaaca tagatcaaat gtctgagatt aatatgatga cagctaatta agatacacaa   15300 cttttccagag tcccttattc cctttctgct caatcatagg attgtttggg gagtaataaa   15360
tgccatcaaa ttggaagtag catcaaaggt ttaaggagcc cacagaggac caccgtgacg   15420
atgtcaggga gctgtggcac tggaagtgaa taagcaatgt cttgttctcc ctttgcagga   15480
gagcatcagt ttacatcacg gtaaactacc gaggtgaatg ccgaaagact gtccctgaaa   15540
tggtaagtgc ctccctgctg tggcatccca tttcttgttc tgggtgtgtg ctggagaccc   15600
agcctggatc ccgtatctgt ggtgggatca tcagagccct gttagcaggg tgcttgtggt   15660
tcacatgcgt aaatacactt caggcttgga tttaaggcat tttgaggcat aatctccacg   15720
ttttttccag gctgtgtggt aggggagtga catgtctggg aaaacatgtg gctttcctcc   15780
tgggattttg gtgaggccaa gaaaagattg caatcgcaca aaccataagg gcctaatttc   15840
ccaaatgata tccaggcagt tggttgggaa ggaaatatat tccctaagtg gtatccttt   15900 gggaaaggtc ttgaatcttg tgtgattgcc ttgtagtaga tgagtcaaag atttgttagt   15960
ggtgctttgt cttcccgctc gtggcagctc agcggcattc agagctttgg tttggagcca   16020
gggtgtccca gtttgtgtgt cttgagtgta tgggactgac cttagtgttg gcatggactg   16080
ttggaaagct gagtattcat ttccccaggg aaacaccgac atctatcccc attccaaact   16140
tggaatgaat caaaatatca aatcagccaa atggagaagt tgtgcaagtt ttttttgcaa   16200
tgagagagat ggcttctgaa tatgaatttg ctgacagttt gtaggtaaaa cagtattgcc   16260
cgttgaaaag ctttagagca aaattaccat cataggggctt ttactctcct ctgcttattg   16320
acaggatgcc cacccatccc cacaacatta gaaatgaggc atccccattc ctcttcctct   16380
cttctgtgaa gtaccagagt gctctcaacg ctgtttaaag ctgaagaaaa aatgcagaga   16440
aagagttttg cttgtgatcg tgctggaggt ctttgtgtct cgcccttttgg tgcgatggag   16500 ccattgctgg tttgtgtatg ctgggagtgg aggcactatg catacctgct ggtggctgtg   16560
ctaatgatgc tggagacaga caaggttggg tgtaccacgg caactgaaaa ccagagagga   16620
ctccctcaga gttgtgcctg gctgggattc ctcaccattt tgtgttttac caagacgttt   16680
taccagctct ccagtctttg cagttagagg aatatgccat acactaaaag tcagacaatt   16740
```

```
tgtagctatt ccaaggagag ctggaagcaa ttaaagggaa agtgataagg ttttccact    16800 ggggaaaatc ccccacaaaa aacacccctc caaacaaaga cttattattt cgttctttat    16860
gtatattgtg tcacctgaag aatcagattg gaaatttatg gaagcccatt tccttagcaa    16920
accccttgtg tccatcaaag acttcccttt tttttctcag ttggaagctt atgaacaatg    16980
tactgaccag tgttatttta tgcctctgaa attcatgcta acattcagct taatgcatcc    17040
ttctgaaggc ccaggcactc gctgtgtgaa ggagatcaca gtgcctttgg cgtcagaaat    17100
gatttcaggc tgttgcaata cgcagcacga agatgcaaag gcccaaagac ttgagccttg    17160
gaaaaagata ggagattgct gcccgaaaat gtagtttgtc cttgagttgt gttttgaaat    17220
tagccacggt aatgctgtgt tgcctgccaa aatgtgtgtc caagctcaga gcctgcagcc    17280
attcctgcta gcaaagcccc tcctggattt ccagcagttt gtggcagtcc ttccctagca    17340
gtggctggat tgccatcagg gagggatggc tgtaggaagg gacaggagaa atgtggttgg    17400
agagagatct gacattaaag ggtgcatccg gacagcctgc actgatgtgg tggaaaacct    17460
tcctgcagag agagccctgg ggctggctgg cagctgggcc cctgctgcct gtgtgagctc    17520
tgtgccacaa ccagcctcct ctgatcctgt tctgctttac tgcagatgaa tgtagctgag    17580
tctagggttt agatttctat gtttatttt aacaaggcag ctggcctctg cgtcctccat    17640
gctgtgacat acagctgtat taatggtggg tcttttccaga atgtttcact ttcaatgctg    17700 tattttttt tattttgcag tttctctttt tgttcagatg cttttcaca catctcccat    17760 gtgacagata ccagtctgtc catgttagtt gacaggtcag gcaaaaaaaa aaaagggata    17820
tccagtttct ccttttaat ctgttttcta aagaacaaag aactcccagc tttctaatgg    17880
gcaaggccat tttcttacag tgctcttttt gtcataccct tcttaagaat gtagtagaag    17940
ggaaaagaaa caaacaaaaa acccaggacc ttttccagct tgatattggt tttggaaagc    18000
acacagatcc aggctgaaat ctgtttgttt tctgagtctg gcagtgaccc atccactgcc    18060
ccatcccacc tggttcctgt ggccactgag ctgcccaaag gggctgtcat gtagccccta    18120
atgctctgcc agcgtaacag cagtggatgt acttgtggat ccacttatat tttgctcttt    18180 cttccagaa ataatggagt tcagactgcc agcaaatacc agggatcagc tgtgaccaaa    18240
ggtacagtgg tgcggtgatt tgctccctct tggacaactt gtccgcattt cacaagggtt    18300
tgggtgtcag accttgcctg ggcaggctgc tgggtatgtc tggggcaaag ggctctgcaa    18360 cacaccttc cctattgcca cagcacaaga atgaggcgtg tgtcttttgc agaagtagca    18420
aggtgatggg aagcccctgc caaggggct gagccctttg gggtgtgcaa acttcatgag    18480
gacctcctca tctctcaggg gtgggccttg cccgttcctt ttccctcaga tatccctgca    18540
gagggggaag gatgctggca gagcagagta ctgcagtccc tcctcacaag gaggtggagg    18600
tggcccaaag caacctggct ttgagctttc cttgtggttc ttctgtgtcc cttgcctttt    18660
ggagccatag taataaaccc gtctgccccc tgtttctcta ggacaagtaa aggaagatct    18720
gatgtcaggc accagggaag ctgctgagtt ccccagtgct gttggatcca ccttcatctc    18780
cttctgcagc caacgggcct gtccttgctc aggtggaggg tgaagggctg tggggaccca    18840
gtggtggctt cccacgttgg ccccacgcat gttgttgtag tcgctgctcg gctcgggctc    18900
tgccgcctcg ctgtgtctta gcatgttcct acaataaaga taactccaca gcgtcctgtc    18960
gcttttcttc actgagcctc acgggaggga cgtgtgagtc cccgctccgg ctgctcgcca    19020
cgcgtccctt gagctctaaa gcaccaaacc caagcggaga tgtcagacgc agagaagaag    19080
aacgtggtct gggttctgtt agcagggacc agcagttggg ttctctgact cgctgtgtag    19140
```

```
ggctttgggt gtatctcttt gtctcccttc agccctttc tcttgcctgt aaaaacggac   19200
attaaaggat gcttacctac ctcagagggt tgtttggaga ttttaattgg tttacgttag   19260
agagcccacg ggtggaattc tgttcctatg tgccaatgct ggtgtgcagg aggtttaact   19320
gttgcagtca tggcctcttc cagccaacac ccgatgggcc gtatgtattt cctgttcttt   19380
cgtttatggc tgttacttaa agcaaatatg ttcttatttg tataaacttt attgcaggac   19440
atttccagaa gaccttgagt gaacgtacag tgtttgagtc cactttagct gtgacctgat   19500
ctgcaaatac actctgctgt agataaggct ggagtaactt tcagattttg cagggtttc    19560 gctcaatgcc aattaatttg ctccctcca cagatattga ttttttttt tcttttcaat    19620 taagttatcg agatcttttt ttcttaatgc agctaatgaa aatcgatttt tactctcata   19680
aagtacttcc gcatgtgtca cattgatctg tctatggctt gattatcggc aggctttgac   19740
atgaggttaa tattttgtgt gctggttttt tttcaccgtg tgcaaacact gtggtttaga   19800
aatatgttac cgctgcttat ttctacgtgg aaaatcccac ggcgtggtta tgcatggcag   19860
aagtcaccag tttgatccaa tttagctgtt tctagggatg caagattcct ctgcctttga   19920
gcgggtgaat cctcgggtgt tatttataca ttctgagaag gatgaacaga agacggtaaa   19980
aacgtttgct aatgatgtct gctggctgat tccggctaaa atcgtgtgca gggacctcga   20040
cgtgattttt ataaaggcag ctcacaattt gaggcttaaa gtaagttctt gcaaatgaaa   20100
atgggcgcac ttgagcgcgc tattataact tgtagtgatt tcaagcactt agattttgaa   20160
ataatcgccc ataaaaacct gcattaattg tgctccaaaa ccaatgagct gatgaggagg   20220
gtgccctggt agcctctttt gctggatttg agcaccttct gaatttctcc tgccaccagc   20280
agaaattagc cacagaaatc atagctgcta taagggttta ttaatcagat tacgaaactg   20340
ctaagaaggc acacaacagt gacttgctga agctgcctgt gctgctgtta gcgagcctcc   20400
cgtaggtagc aatgctaact ccttccttt agcagtttac ccactgcttc cttccatcac    20460
tccttccttt tgtagggcct acttttgcag tttgatccag tggcttgcag gcaatatctg   20520
tccccagcgg tgctctatgc agctgacctc caggtagggc tccatgtgag cgatgcaatg   20580
tgttatttcc atggggttcc taagaaggag gaagcaaaaa gctcaggagg tgctccaaat   20640
atattatcct gtcctctgtt ttgctctttg tggtgccctt taacactgta aagagaccat   20700
aggagtcctc tatgaacctg gaaaggtacc agcactatgg gaggtcttca gtttgctgta   20760
aattatgctt tattagaggt atttcttctg ccaagaccca ctgaccccat gcggctcaca   20820
gtgttttcta aggctttgca ggactggtgt tacgaattgg caccctccag gcctctcaca   20880 aatctccctgc ttctcacagc gtttcttcaa gttctcccaa gcacagctga gttttgagct   20940
caactgctcc ctgcaggggc cttgagcctc ctgcctttt gcataaaagg tgtcaggtac    21000
ttatgcaatc cttagaggca tgcaaatgct gctctggtta tatactgagg actgttgatt   21060
ctggcagaac cctttgcaga ccttgtactc ccttgctatt tcccaatccc tgcagcctag   21120
cagctctgcc taacaactgc catagccaac acagcagcag gctgtgcatg gtgcaaggtg   21180
atgtggaaag ggatgattgt atgaaagcgt gatgctgtgg tactgcctct gcaggagact   21240
cgcactattt gtgtaagagg accttatttg tctgctgcag agctgtttca aggctgtcca   21300
tacacccctg tgatgctgag cccctccaag caatgcactg ggaaaaggag gctgggggga   21360
gaccttattg ctctcctcca atatttgaaa ggtgcttaca gcgagagcag ggttggtctc   21420
ttctcactgg tgacaggatg agggaaatg gcctcaagtt gcaccagggt atgtttagat    21480
```

```
tggatatcag gaaacactta tttactaaaa ggttgttaag cactggaatc agctccccag   21540
ggaggtggtt gagtcaccat ccctggatgt gtttaaaaac tgtttggata tggtgctcag   21600
ggacatgatt tagcggaggg ttgttagtta gggtagtgtg gttaggttgt ggttcactcg   21660
atggtcttta aggtcttttc caacctgagc aattctatga tatggatccc tggggctttc   21720
agtcttatct ccctggatta tcacaggttc agctctatgg cccatttgat ttataccggg   21780
gtctgatgaa caggtttttc tcttggctct tcagggatcc tatttagcac ttttttggtac  21840 attcccctgc cctacaagtc tccctgatac acagagctct tatccaagac ttgggacctt   21900
ccctactcca gccctctgca ggaggtttct tgctaaccag tcctccaacc aggactgcag   21960
tacacgacaa agagctggaa gaggtctgca atacttcccc agcatgaagg tatgagcact   22020 cctttttgagt aggttactga aagtagtaag atgtcaatac aaccaactgc aagatacaaa  22080
accgcatgaa aattcagttt actttgatgc tgaagggctg aaaagaaatg ctgtggtgtt   22140
agcacagatg cactgctggc aaagtgaaaa tgagcaaaga ggatgagatg gatggacagc   22200
tgatggaaaa actcttccta attgctccac agagcagctt gctcgcctgc agggctgcag   22260 catgagctg cttgtgcata atgcagacac cccaagacca gtgctgtttg tcttagccaa    22320
gacacagttg cagctgcagc aattttttct agatgtcagt tccttcccta tgttgctgac   22380
aggtgtttgc tgttctgtcc ctttaatctg tatcctacag caaacattcc ttgaatttaa   22440
taacttagct ggaagacaat tgctgtgatc ttgatagaac atgctgagcc aatctatttt   22500
aactgcagat ttagtttgca atactgtct ccttgccgat aagattcagg tgtcatcttt    22560
gtggacattg gcaggaattt tcttgaccgt gacaggtttt acagagtctg gcaattaagc   22620
tgtcaagaca catttcctc tgccaggaag cattaattga tgatagtctt ggctgcaata    22680
ggcacagaga gatggatatt gtaatcagaa tgaatagagg tccttgtagt tgagagctac   22740
gttggtccaa agttttgtag tcgttgacgt ttggtgatac tgagataagg aacaaggcac   22800
gagatattag agctaaatat caggcacagc atgagaataa agacctctct agctggaact   22860
gttggtatct ggggagattt taactttctg gatgcatact gcaaagtact aatattagta   22920
gagctactgg atgcgagagc aaatagtttt ccattaagta atcccaaaaa tcatgttgtt   22980
gttggtttgc ttttcaagtg cgagggtgt tggagatgta tttccctcag aaaataaacc    23040
tgatatgatt caacctgagc tctctctgtt taaatcacac tgaaaataga tctgcaaatg   23100
gggattttga ttaccgagta cagaatatga aagattaaaa cttgggaaag ttagggttct   23160
gattgagaaa acttttgttt ttgtggccga cccttgcagc ttacaaaaat ctgcctaaat   23220
aaaggagaaa accacattta gaacccatcc aagctatgct acttcagtac tgggcaaaac   23280
ttcaggagac gtttgaagaa aactgaagac gtgaagtata aaggaatgat tgatgtgcac   23340
agtaaacttt cttggaaggt aatcacgcat gggctaatat caatctttac aaagttggct   23400
gacttcctag ataaaggaag tacagtagat ctagtctacc caggcagcaa aaatgtttga   23460
cctgttgccc tgtggggtgg tgtcacctgg gcttggggag gggggtcagg atgaggttac   23520
aggggatgtg gaagcatact gtggaggagc aggtggggca cccacaggag ttagcagtga   23580
gcagacagaa aggtggatct gaggaccgaa cttcgtattt tgttccttg cattaataca    23640 caaaaagcag acacacacac agagcagatt gctgctggtt tttgttttct tttttaaaca   23700
gcagaagagc aggatttttc ccacagagaa tggggtgacc ttctaggctg tgattgcctg   23760
ggctcaagct gagatgaaac gcagtgatga ggagcacaaa accgtgctct gaggttaaat   23820
aatgagggct tcggctatca gttcagagct cagtaaaaac tgcagaggag gaggaagacc   23880
```

```
taattgcatg tagccagcca cagggcaaat gagagctgca gcgtgctggg gcagatccgg   23940
gagcagaggg gccgtggcac gctccctgtt cactggctcc cctggagcca cacaaaaggc   24000
cccttcctgg caattgtgcc cacatcaatc attagctaga aacccagagc tgggtaaata   24060
cgttttggct tcccgtcttg atgacagatt gggtgttaca tcacaaggtg ggaccacttg   24120
atatgacaac acgctatata ttcccgctgc tacctctgcc cttcctcccc cactctgaga   24180
gcaagcgggc tgtgtgtgca ccgaggtgct ctgccatgag gactgccagg cagtttgtac   24240
aggtggctct ggccctctgc tgctttgcag gtgagtgttt cctgctatac cccgtaggtg   24300
actatagcta gaccagagac taggctatct gtgagagtat ctgggtattg taatgtgtta   24360
gagagccttg ttccatgaag gaatgctctt tctgacagtg tagcaaaaca ccagactgca   24420
agatccaggt ttcagcaaac ctcatacaga cgactgtttt cgtcgtggtt tataggagca   24480
aattgctgag ggagcagtgc tagtgcaggg caggagcttg cacgtgcaag cactgagtat   24540
aacggcaaag caaagctatg tgaaatggct cctgtgtcca tgtaagcaat acaaacactg   24600
catcttgtat catctataaa ttttctgtgc tgttcctggc agctgagaag tttgttgtgg   24660
gaagaacagt gctagtggtc aacagccacc tgaaacgtgc atgtctgagc tcctgcaagt   24720
caaatacaga gtcttgcaga agagtttaaa ctcagtgcag gcttgaaaat acctacattt   24780
cttccctggg gcatcttagg aactggctaa cacatgtggc ctcctactga aagtgcagtg   24840
aaacttcatt taataacctc tgattcattt tatggacgta catcactggc ataatgtaaa   24900
attgcatttt cctaaaccca ataagccaat caacaacggt atctaaatgt aactgtttca   24960
tcgaaagatt tgcatatgtc atctctgcat attaataata tgtatttatt ttctgtctct   25020
acttttcttt tagatattgc ctttggaatt gaggtgagtt acagattttt tttcccattt   25080
attcttttct attccaggct tctggtcaaa taagagcagt atataattac ctgatgagca   25140
agtggattaa tctaatgaaa gcctggttgc tcaaataata cttgccagtg catgattgaa   25200
tgatattgcc aagtcacgaa aaagtaaaac acccccgtt tatactattt tccattcatg   25260
caataaaatg aagaaggaa gaattgtacg atcctattat gttaactttt ggatataact   25320
gcgttagtcc aagtcaaggg gtggtagtta cctcctcgag aggaaagctg tcttaagatg   25380
ataagctcca aagcatcaaa gacagtgatt ctggtatctt tttctataca gtaagcacac   25440
cactacagtg ttcctgccta tacccatatc aaagcgagga aagcagcagg gtctgtgcag   25500
tgcatttgtc tgcaggttct tcccacgcag ttatgagatt cctgcaaatc accagagact   25560
gcagcgtgat tggaaacgat cagattttga gttgagcggc tgtggagcat ggccaggctc   25620
ccaattacca gctgccttcg ttaggcgctg tctcacccac agctctcctt cctccatgtc   25680
atgcttcccc cagtcccccg caggaaagcg tgatcagaag aagattccca cctcctgact   25740
gcctgagcag attccaaatg ataccctcagg tgtttgtccc ggctggagct gtgggtggca   25800
ggaggtttcc atactgtctt tgttgtgga aactgacccc agggctgatg ttgtgctgct   25860
tccataggtt aattgcagcc tgtatgccag cggcatcggc aaggatggga cgagttgggt   25920
agcctgcccg aggaacttga agcctgtctg tggcacagat ggctccacat acagcaatga   25980
gtgcgggatc tgcctctaca acaggtgagc ttatgtggaa gcccaggga gctgcagggc   26040
aggagactcg aggtgagggc ggcagctctg tcccccaaaat atggtctgtg tggaggagta   26100
tgtgagttag taccaggatg ctgacctcca gcctgggggt ggtggctgct ctctgccatc   26160
tctgacacag atctgcgttc ttccagggag cacggggcaa acgtgagaa ggaatatgat   26220
```

```
ggagagtgca ggccaaagca cgttacggta agtccaacag taagatgaag tcttgctctg   26280
ttggtgccca taaagactta tttttatttc atagaatcat tgaacagctt aggttggaag   26340
ggaccttaaa gatcattggg ctctaacccc cctggcctgg ccgggctgcc ttcaaccaaa   26400
tcagtttgcc cagtcaaatg ggccttgggc acctccaggg atgggcacc tgctctgctc    26460 agcctgttac ttatttactt gttttttcc cattcctgct atccttacag attgattgct    26520
ctccgtacct ccaagttgta agagatggta acaccatggt agcctgccca aggattctga   26580
aaccagtctg tggctcagat agcttcactt atgacaacga atgtgggatt tgcgcctaca   26640
acgcgtaagt cttttctgtg gagcatcctt ctgggtaatt agagatggct aagtcccttg   26700
gaaacgctta cataaaacac tttctaagcc tttcttaggg tagatgtttc tgtgggactc   26760
tttgaagctg gctacttgtg attctccagc cagctgcaga tttcttcccc atcctctgtc   26820
tgtgctcatg aagggaatca caaaaagac agaggacaac ccacagcaga ggcatgaata    26880
gatcaaagtg ttgctcagtg ctgtgtgata tggaaatacc atgcattttc tgctcacaag   26940
tggttgctac cacctgtggg ctgcatccag accactcagc agttccttac gtgaagggtg   27000
ggaccttgct ttcttgcccc agtatctaag gcttttcacg aggctctcta actaaaacag   27060
ctctttcttt cagagaacat cacaccaaca tttccaaact gcacgatgga gaatgcaagc   27120
tggagatcgg ctcggtaagt gtaacagaaa taaaaatcca tctcctaggg ctgttaacgg   27180
agagaatccc attgattttc ctaagaaaat gtatgaccgg gctgatcggg ggtcccggtc   27240
cacgctctgc ttcctgcctg gtgagggtgg cttctgaaac aaagcggtaa aggaagaggc   27300
cccagatttt ccttgcattg tgctgtgcag attggcaggt ttctctctgg aggcgacaag   27360
catttccacc ctttgtaaca agcattcaaa attctagtgc tggtagcttg gttagatata   27420
gtgagattca taagagcacc aagcatacat atttataggg tatagcttat tgtatattta   27480
tactggggta agagtccagt gcctcaggaa gaaaagctta tatatttcag cacaaaaatt   27540
ctgggatgca gggagtccgt tctccaacag acggattcct cctttatcac ttcaactccc   27600
gtgcttaact gcagggaatc tgaattatta agcaatcaca gcactgggga aggaaggaga   27660
aaaaccaaca caaaccaaaa caatgttaat cagatttcca gctgttggaa atatttccc    27720 acttaattca aggctgttgt gtcgatgaga agagggctga aaaggctgtt ttcagttcct   27780
ctgcctgaag gtttcattct ctaagagagg tcccttttct tgtctcctag agaatgaggg   27840
tagtgttctg aaagcctatt tctgatagac agtttagtta agtgtagcag ggctttgtcc   27900
tgtcacaaaa actaggaagc cgggaataca ggatgaaaag gtgttacatt gacttctccc   27960
gtgtagcaca ggctccggga gggcttattc tccttatttt ggcaggttga ctgcagtaag   28020
tacccatcca cagtctctaa ggatggcagg actttggtag cctgcccaag gatcctgagc   28080
ccggtttgcg gcaccgatgg tttcacctat gacaacgaat gcgggatctg cgcccacaat   28140
gcgtaagtgc tgctcatctc ccactcctcc aaagtagcca gcaatgcttt gccgtgctgg   28200
gagccttcct tctacgttgc tgcttatgcc tgtttcttca gcctcttag aaactgcatt    28260 ttttttgttg ttgttcttac tgagttttct tctgatgcct tctttgtgat cacgagggga   28320
aatctgcaag actcagaaca cagctccttg gattagtctg tgggctgggc agtgactgag   28380
cagagaaagg aatagttcag aatcttgctt taaataacac gagaagacgt gatgagcttg   28440
ttaacgagca gagtaatgta gctatatcaa tacaatcgtg cagagaggct gaagccctac   28500
tttgttaggt acctgcttta ggctacgtct ggttcattct gcatgcaagt gtttaaacca   28560
agagttaaag catctcctta ctcactttgt ctccctcttt cagagagcag aggacccatg   28620
```

```
tcagcaagaa gcatgatgga aaatgcaggc aggagattcc tgaagtgagt atacaacgta   28680
aggtgtattt ctccccttgc ctctgcccac tgagctattt gctgaggcca cgtctactct   28740
gaaagtgagc tggcttgaag cctggctctc tgcacgtgtc ctttgggatg tgccaacgtg   28800
tatccaacac acaaacagtg tggaagttgg gcaggggaa cttaggtctt ttaaggatga    28860
tcactaaatg cattgccagc aaagtccttt tgtgccagtg aagtcctatt atgtttgcct   28920
tcttttgttt cattctatag tgcagagaga aaaggagatg atatatcttt gttggttttt   28980
tttttgtttg tttgttttgc ttttctgcca tatctagcaa actgtttcag taggttgtga   29040
cccctttgga tcacaagtga agctcagtgg catttgggat tgactgagct gtctgccctg   29100
gtgatttggc atctcacaga ttacacagcg ccatgtagct cctcctgggc atgagagagt   29160
ttctgcagag ctgactcagg ctggctttga gagaactgaa gtgtagcacc agcgttgttt   29220
cagcatccca gcgtaaaaga catggattgc agcaggaggc aatgctaggg tttgtctttg   29280
agagcaaggg ctttttcagg gctgacgctc ctacttttg cagattgact gtgatcaata    29340
cccaacaaga aaaccactg gtggcaaact cctggtgcgc tgcccaagga ttctgctccc    29400
agtctgtggc acagacggat ttacttatga caacgagtgt ggcatttgtg cccataatgc   29460
gtaagtactg caaacaggac ttccttttgt agcgactagc cacgttagta ctgcagatgg   29520
cttccctcc acccttcatc ttcttcttc tttcttttt tttgatagca gtatgtctat      29580
atgtctcctg ttcttccttc aacctcctga agctctgtcg cctcggtttc ctttcctgat   29640
gtgctcctca gggagctgtg ggagagccag ctaacagctg agtgtcctat gagggctgtg   29700
gcatttgtgc agaggaaaaa gagaatgggt ctgctacaag tagacctgag aagcctgtaa   29760
cttcttagga tcatgatccc taatggcagc ctttcccttt cagacaacat gggactgagg   29820
ttaagaagag ccacgatgga agatgcaagg agcggagcac cccggtaagt ggggatggat   29880
gtcagatgag cgccagctcc tgtacgtgcc ttgtggctgc agaggttgct aaccagggtc   29940
tgtccattca ggcagcagag aaggggaatg ggccaggatt taggtaacaa aatgtcccaa   30000
tactgcaggt ctctggaggg aaacatcaga ggcagcccag aacagcacag cctgttttag   30060
cacagtagga gaggaagagc agaagctgtg ttagatgcct gtgtagtcat tcagtgctag   30120
gatttccatt gcagcagaca ggttaaaaaa tctctgtacc gtggtcagcc aagaaaaggc   30180
tgcttgcagg aatgcacgca gaaatagctc tataaacatg cacggtaaca atatgtgctg   30240
ataatatctc agcacattta ttctgcttat gcagagcagc tctaaaacac tgaaaataac   30300
tttgtgcatc tcaagggatt gctgtatctt ttctgtagta aagacacact gttatggtgc   30360
tgtctttgct ataatttgct cttggactgt gtggggaaat atgggtaata agagctacta   30420
cacaggggaa ggtatgcaaa acgattgtga agtgtcagaa gcttagccag tgtagactga   30480
cttccagtgc catcagtaga tacttgctta tttatcctca aatattggaa ctgttttaa    30540
gtactgtgag gatttctgca gcagcagctg atgagctgat ggaacagttt cttcttgccg   30600
ttttgaaaac gtggaaacaa aatctaaggc ttagctaagt caggcatgac ctaatgtcaa   30660
actggacata acatcaaact ccttatatca aattcctttg aataatgctt gttttgaaac   30720
ttggacatac gctgcataag gaagatgatc tttctggtct gctattcctt tgcgttccct   30780
ttgttagtga gcaatatcaa acccaaccac aattagttca tttataatgg gagactaaac   30840
tgaaatcaac cctgattttt cctatggctc gaggcagtct gtcccccagc tcccagcacc   30900
tgactcagca tccttactgt tttctcccca gcttgactgc acccaatacc tgagcaatac   30960
```

```
ccaaaacggt gaagccatta ccgcctgccc cttcatcctg caggaggtct gtggcactga    31020
cggcgtcacc tacagcaacg actgttctct gtgtgcccac aacatgtaag ccctgcaggt    31080
cacccactcg tgtgtcaccg cagctgcttg ttgagctttg tcaactctgt tttctctctc    31140
ttccagtgaa ttgggaacca gcgttgccaa aaagcacgat gggaggtgca gagaggaggt    31200
tcctgaggta agcgataaag aaaacaagag cttgaggtgg tgcttattgc ctaacaagta    31260
caacgctggc tggttttggt gatgctgggt catgccctcc tgctgccatc cttcctgcag    31320
gtaaacatca accctggcag cagggatgct gtgcattttc tgcatgtagt cagggaaaga    31380
aagagaagag gacgggtgag gaatgagtta tgatgcaggt agcataaatg atttaaggcg    31440
ttacgaagaa atctctttcc cacagcagtc tatcatacct gccgtgggag tgtagctgtc    31500
tgttctggca atatgggaaa gggacacaga gcacccgcag gtacctggtg ccttctggat    31560
acctgtgctg tgcaaaagga tgttgtgcaa agatcagaaa actacctgca ttttgaatgc    31620
ttttacctaa tgtaccagag gattcaaaca cctctctctt cctattgtaa atgcgatata    31680
atgtaatgta taccaacaat gaatcttgta aaataccag ataaactata tttggccagc    31740
tctaaactat ttacgctcac tggggaatag aaaaacaaag ccatctcatt atcttgtgtt    31800
tgaaagagtc aacgtcgtga gtcagatatt tcatttctat gcaaacagac tatgaaatgt    31860
cattgctttg tttcctgcgt atgctctgtg ctcagaccaa gtcagatgca taaatcagtg    31920
aggaagagct cacactggag aaactgggat agctgaaact caaggccagt tcttcaaatg    31980
gcataaatca ttttgaactg ctgttggtcc ttctgtccga ttgcaacaca cagaaccagc    32040
ccctcgcaac aaaaggcatg tcagcacatc tcctcagttc ttgtgggccg tgacacactc    32100
cttggccaca ctgagcttct cttgcaggaa ttgcataaat cacgccagtt tgatttgcag    32160
attatttatg agctgcgttt tgcagcgtcc cagcaagtgg ttcagcaagc tctaagggca    32220
tcgtgataaa tgcagggctg aatgagtgat acgcgcctcc aagctttgat tcagtcttct    32280
ccagtataag gctgtgacag aaaattgata gttttcaatg aagaatgagt caatgcataa    32340
ccataatcca tcctgtggca gatcttgaaa ggcagaggcg taaggaaggg ggttgtgtct    32400 gagcacccctt acacagagca tttgctgcct ttgtttccta gcttgactgc agcaagtaca    32460
aaacctccac gctgaaggat ggcagacagg tggtggcctg caccatgatc tacgatcccg    32520
tctgtgctac caatggtgtc acctatgcca gcgaatgcac gctgtgcgct cacaacctgt    32580
aagtactcat tcatctccag ggggacccac cgtggctgtg actggacaca tctttgagtg    32640
ctgaataaca tgcaagggct ctgtctaaaa tctcgtgctg catgggtcct gtctgcctat    32700
ccccgtttcc ctggttgcca tggttggtgt ttgagatggg catttagcaa ggcccactgc    32760
ccccagtgac ccagaaaaag ggttcactgc ctgggaaagc attattccaa aagacacatc    32820
cctagtcctt aagggcatgt tcttgctaat gcttctcagg caatgcttag ctaatttatc    32880
tgaaattgtc ctgtgtacca catgggaacg aggttgtgct cttgtactac ggttgtaaat    32940
gggaagggtt tctgctaata tccatctctc cttcctccag ggagcagcgg accaatcttg    33000
gcaagagaaa gaatgaaga tgtgaagagg atataacaaa ggtgagtgtg aaaggatggg    33060
cacaaagagt tacagtcgta ggggaccgtc ctctgctcca catcaaaaac tggggagcg    33120 gtgtgcagcc ctggcgaggt cgcttggaa tgtcatactg gttatagaat agctgccatc    33180
catcccatgg gaatggacat ggcagtgaac aggaacagtg tgaggtcaca tccctcacca    33240
ggaggaactg agctgattac tgccgtaatt ttccagtttc actctttgtg ctgggggaat    33300
actgtttgct cccaggcaga gactcacatc ttccttgtgt gtgcaggaac attgccgtga    33360
```

```
gttccagaaa gtctctccca tctgcaccat ggaatacgta ccccactgtg gctctgatgg   33420
cgtaacatac agcaacagat gtttcttctg caacgcatat gtgtaagtat aggagtgaaa   33480
cccttcctgt aactgctaca aacgcagagt tgattttata aggagttctt tactaacact   33540
ttatgggtgt gtgctagaca tttcggatgc accgtgacgt gcaaggaggt gcttttttgc   33600 ttttaagaa aaaatgcaaa gcacccacat ctgcccatgt gtatgtggct tcctgtttta   33660
tttagtttca aagacatttt gctaattttc accagcatag tttgtcccac aagctcatca   33720
gggtatgggg aaagtacttc accaaaactac ctggagcgtt tcaagtgtgt gaaacctgtc   33780
atctttcctt taattttcat aatgaaagga agtggttggc cttctgagac tgttctttat   33840
cttctgccaa cattatcaac atttgggctg taaggagag gaacaaggct gcagcacaaa   33900
ttctattgtg tttaatcctt tcttctcttt tcattaggca gagcaatagg actctcaacc   33960
tcgtgagtat ggcagcgtgt taactctgca ctggagtcca tcgtgggaaa caatctgcct   34020
tgcacatgag tcttcgtggg ccaatattcc ccaacggttt tccttcagct tgtcttgtct   34080
cccaagctct caaaacacct ttttggtgaa taaactcact tggcaacgtt tatctgtctt   34140
accttagtgt cacgtttcat ccctattccc ctttctcctc ctccgtgtgg tacacagtgg   34200
tgcacactgg ttcttctgtt gatgttctgc tctgacagcc aatgtgggta aagttcttcc   34260
tgccatgtgt ctgtgttgtt ttcacttcaa aaagggccct gggctcccct tggagctctc   34320
aggcatttcc ttaatcatca cagtcacgct ggcaggatta gtctctccta aaccttagaa   34380
tgacctgaac gtgtgctccc tctttgtagt cagtgcaggg agacgtttgc ctcaagatca   34440
gggtccatct cacccacagg gcaattccca agatgaggtg gatggtttac tctcacaaaa   34500
agttttctta cgttttgcta gaaaggagag ctcactgcct acctgtgaat tcccctagtc   34560
ctggttctgc tgccaccgct gcctgtgcag cctgtcccat ggagggggca gcaactgctg   34620
tcacaaaggt gatcccaccc tgtctccact gaaatgacct cagtgccacg tgttgtatag   34680
gatataaagt acgggagggg aatgcccggc tcccttcagg gttgcagggc agaagtgtct   34740
gtgtatagag tgtgtgtctt aatctattaa tgcaacagaa caacttcagt cctggtgttt   34800
tgtgggctgg aattgcccat gtggtaggga caggcctgct aaatcactgc aatcgcctat   34860
gttctgaagg tatttgggaa agaaagggat ttggggggatt gcctgtgatt ggctttaatt   34920
gaatggcaaa tcacaggaaa gcagttctgc tcaacagttg gttgtttcag ccaattcttg   34980
cagccaaaga gccgggtgcc cagcgatata atagttgtca cttgtgtctg tatggatgac   35040
agggaggtag ggtgacctga ggaccaccct ccagcttctg ccagcgtagg tacagtcacc   35100
acctccagct ccacacgagt cccatcgtgg tttaccaaag aaacacaatt atttggacca   35160
gtttggaaag tcacccggtg tattgtgagg ctagattaat aggctgaagg caaatgttcc   35220
caacttggag atactgttgg tattgtatca gggaacaggg ccatagcacc tccatgctat   35280
tagattccgg ctggcatgta cttttcaaga tgatttgtaa ctaacaatgg cttattgtgc   35340
ttgtcttaag tctgtgtcct aatgtaaatg ttcctttggt ttatataacc ttcttgccgt   35400
ttgctcttca ggtgttcttg cagaacactg gctgctttaa tctagtttaa ctgttgcttg   35460
attattctta gggataagat ctgaataaac tttttgtggc tttggcagac tttagcttgg   35520
gcttagctcc cacattagct tttgcagcct tttctgtgaa gctatcaaga tcctactcag   35580
tgacattagc tgggtgcagg tgtaccaaat cctgctctgt ggaacacatt gtctgatgat   35640
accgaaggca aacgtgaact caaagaggca cagagttaag aagaagtctg tgcaattcag   35700
```

```
aggaaaagcc aaagtggcca ttagacacac tttccatgca gtatttgcca gtaggtttca   35760
tataaaacta caaaatggaa taaaccacta caaatgggaa aaacctgata ctggaattta   35820
aatattcacc caggctcaag gggtgtttca tggagtaaca tcactctata aaagtagggc   35880
agccaattat tcacagacaa agcttttttt tttttctgtg ctgcagtgct gttttcggc    35940 tgatccaggg ttacttattg tgggtctgag agctgaatga tttctccttg tgtcatgttg   36000
gtgaaggaga tatggccagg gggagatgag catgttcgag aggaaacgtt gcattttggt   36060
ggcttgggag aaaggtagaa cgatatcagg tctacagtgt cactaaggga tctgaaggat   36120
ggttttacag aacagttgac ttggctgggt gcaggcttgg ctgtaaatgg atggaaggat   36180
ggacagatgg gtggacagag atttctgtgc aggagatcat ctcctgagct cggtgcttga   36240
cagactgcag atccatccca taaccttctc cagcatgaga gcgcggggag ctttggtact   36300
gttcagtctg ctgcttgttg cttcctgggt gcacagtggt gattttctta ctcacacagg   36360
gcaaaaacct gagcagcttc aaagtgaaca ggttgctctc ataggccatt cagttgtcaa   36420
gatgaggttt ttggtttctt gttttgtaag gtgggaagaa gcactgaagg atcggttgcg   36480
agggcagggg tttagcactg ttcagagaag tcttatttta actcctctca tgaacaaaaa   36540
gagatgcagg tgcagattct ggcaaggatg cagtgaagga gaaagccctg aatttctgat   36600
atatgtgcaa tgttgggcac ctaacattcc ctgctgaagc acagcagctc cagctccatg   36660
cagtactcac agctggtgca gccctcggct ccagggtctg agcagtgctg ggactcatga   36720
ggttccatgt ctttcacact gataatggtc caatttctgg aatgggtgcc catccttgga   36780
ggtccccaag gccaggctgg ctgcgtctcc gagcagcccg atctggtggt gagtagccag   36840
cccatggcag gagttagagc ctgatggtct ttaaggtccc ttccaaccta agccatccta   36900
cgattctagg aatcatgact tgtgagtgtg tattgcagag gcaatatttt aaagttataa   36960 atgtttctc cccttccttg tttgtcaaag ttatcttgat cgccttatca atgcttttgg    37020
agtctccagt catttttctt acaacaaaaa gaggaggaag aatgaagaga atcatttaat   37080
ttcttgattg aatagtagga ttcagaaagc tgtacgtaat gccgtctctt tgtatcgagc   37140
tgtaaggttt ctcatcattt atcagcgtgg tacatatcag cacttttcca tctgatgtgg   37200
aaaaaaaaat ccttatcatc tacagtctct gtacctaaac atcgctcaga ctctttacca   37260
aaaaagctat aggttttaaa actacatctg ctgataattt gccttgtttt agctcttctt   37320
ccatatgctg cgtttgtgag aggtgcgtgg atgggcctaa actctcagtt gctgagcttg   37380
atgggtgctt aagaatgaag cactcactgc tgaaactgtt ttcatttcac aggaatgttt   37440
tagtggcatt gttttatca ctacatattc ctcagataaa tgaaatccag aaataattat   37500
gcaaactcac tgcatccgtt gcacaggtct ttatctgcta gcaaaggaaa taatttgggg   37560
atggcaaaaa cattccttca gacatctata tttaaaggaa tataatcctg gtacccaccc   37620
acttcatccc tcattatgtt cacactcaga gatactcatt ctcttgttgt tatcatttga   37680
tagcgttttc tttggttctt tgccacgctc tgggctatgg ctgcacgctc tgcactgatc   37740
agcaagtaga tgcgagggaa gcagcagtga gagggctgc cctcagctgg cacccagccg    37800
ctcagcctag gaggggacct tgcctttcca ccagctgagg tgcagcccta caagcttaca   37860
cgtgctgcga gcaggtgagc aaagggagtc tcatggtgt gtttcttgct gcccggaagc    37920
aaaactttac tttcattcat tcccttgaa gaatgaggaa tgtttggaaa cggactgctt    37980
tacgttcaat ttctctcttc cctttaaggc tcagccaggg gccattgctg aggacggcat   38040
cggggccccc tggaccaaat ctgtggcaca gatggtttca cttacatcag tggatgtggg   38100
```

-continued

```
atctgcgcct gtaatgtgtc cttctgaagg aaggaacgtg ccttccaagt gccagcccca    38160
cagcccccag cccctccctg tgctgctcca attcatctcc tcttcctcct tctcccttttg   38220 ctgtttgtgc tcgggtagaa atcatgaaga tttagaagag aaaacaaaat aactggagtg    38280
gaaacccagg tgatgcagtt cattcagctg tcataggttt gtcattgcta taggtctgta    38340
tcagagatgc taacaccact ttgctgtcgg tgcttaactc gggtgaactc tccttcactc    38400
gcatcatttg cgggccttat ttacatcccc agcatccatc accctctggg aaaatgggca    38460
cactggatct ctaatggaag actttccctc tttcagagcc tgtgggatgt gcagtgacaa    38520
gaaacgtgga ggggctgagc agcagcactg cccccaggga gcaggagcgg atgccatcgg    38580
tggcagcatc ccaaatgatg tcagcggatg ctgagcaggc agcggacgaa cagacagaag    38640
cgatgcgtac accttctgtt gacatggcat ttggcagcga tttaacactc gcttcctagt    38700
cctgctattc tccacaggct gcattcaaat gaacgaaggg aagggaggca aaagatgca     38760 aaatccgaga caagcagcag aaatatttct tcgctacgga agcgtgcgca aacaaccttc    38820
tccaacagca ccagaagagc acagcgtaac cttttttcaag accagaaaag gaaattcaca   38880
aagcctctgt ggataccagc gcgttcagct ctcctgatag cagatttctt gtcaggttgc    38940
aaatggggta tggtgccagg aggtgcaggg accatatgat catatacagc acagcagtca    39000
ttgtgcatgt attaatatat attgagtagc agtgttactt tgccaaagca atagttcaga    39060
gatgagtcct gctgcatacc tctatcttaa aactaactta taaatagtaa aaccttctca    39120
gttcagccac gtgctcctct ctgtcagcac caatggtgct tcgcctgcac ccagctgcaa    39180
ggaatcagcc cgtgatctca ttaacactca gctctgcagg ataaattaga ttgttccact    39240
ctcttttgtt gttaattacg acggaacaat tgttcagtgc tgatggtcct aattgtcagc    39300
tacagaaaac gtctccatgc agttccttct gctccagcaa actgtccagg ctatagcacc    39360
gtgatgcatg ctacctctca ctccatcctt cttctctttc ccaccaggga gagctgtgtg    39420
ttttcactct cagccgctct gaacaatacc aaactgctac gcactgcctc cctcggaaag    39480
agaatcccct tgttgctttt ttatttacag gatccttctt aaaaagcaga ccatcattca    39540
ctgcaaaccc agagcttcct gcctctcctt ccacaaccga aaacagccgg cttcatttgt    39600 ctttttttaaa tgctgttttc caggtgaatt ttggccagcg tgttggctga atccaggag    39660 cacgtgtcag ctttctgctc tcattgctcc tgttctgcat tgcctctttc tggggcttcc    39720 aagaggggg gagactttgc acggggatga gataatgccc cttttcttag ggtggctgct    39780
gggcagcaga gtggctctgg gtcactgtgg caccaatggg aggcaccagt gggggtgtgt    39840
tttgtgcagg gaggaagcat tcacagaatg gggctgatcc tgaagcttgc agtccaaggc    39900
tttgtctgtg tacccagtga aatccttcct ctgttacata aagcccagat aggactcaga    39960
aatgtagtca ttccagcccc cctcttcctc agatctggag cagcacttgt ttgcagccag    40020
tcctccccaa aatgcacaga cctcgccgag tggagggaga tgtaaacagc gaaggttaat    40080
tacctccttg tcaaaaacac tttgtggtcc atagatgttt ctgtcaatct tacaaaacag    40140
aaccgagggc agcgagcact gaaggcgtgt tcccatgctg agttaatgag acttggcagc    40200
tcgctgtgca gagatgatcc ctgtgcttca tgggaggctg taacctgtct ccccatcgcc    40260
ttcacaccgc agtgctgtcc tggacacctc accctccata agctgtagga tgcagctgcc    40320
cagggatcaa gagactttc ctaaggctct taggactcat cttttgccgct cagtagcgtg    40380 cagcaattac tcatcccaac tatactgaat gggtttctgc cagctctgct tgtttgtcaa    40440
```

-continued

```
taagcatttt ttcattttgc ctctaagttt ctctcagcag caccgctttg ggtgacttca   40500
gtggccgcct ggaacccgag gggcacagcc accacctccc tgttgctgct gctccgggga   40560
ctcacgtgct gctggatggg gggaagcatg aagttcctca cccagacacc tgggttgcaa   40620
tggttgcagt gtgctcttct tggtatgcag attgtttcta gccattactt gtagaaatgt   40680
gctgtgaag ccctttgtat ctctttctgt ggcccttcag caaaagctgt gggaaagctc     40740
tgaggctgct ttcttgggtc gtggaggaat tgtatgttcc ttcttaaca aaaattatcc     40800
ttaggagaga gcactgtgca agcattgtgc acataaaaca attcaggttg aaagggctct    40860
ctggaggttt ccagcctgac tactgctcga agcaaggcca ggttcaaaga tggctcagga    40920
tgctgtgtgc cttcctgatt atctgtgcca ccaatggagg agattcacag ccactctgct    40980
tcccgtgcca ctcatggaga ggaatattcc cttatattca gatagaatgt catccttag     41040
ctcagccttc cctataaccc catgagggag ctgcagatcc ccatactctc ctcttctctg    41100
gggtgaaggc cgtgtcctcc agccccctt cccaccctgt gccctgagca gcccgctggc     41160
ctctgctgga tgtgtgccca tatgtcaatg cctgtccttg cagtccagcc tggaacattt    41220
aattcatcac cagggtaatg tggaactgtg tcatcttccc ctgcagggta caagttctg     41280
cacggggtcc tttcggttca ggaaaacctt cgctggtgct acctgaatca agctctattt    41340
aataagttca taagcacatg gatgtgtttt cctagagata cgttttaatg gtatcagtga    41400
ttttatttg ctttgttgct tacttcaaac agtgcctttg ggcaggaggt gagggacggg     41460
tctgccgttg gctctgcagt gatttctcca ggcgtgtggc tcaggtcaga tagtggtcac    41520
tctgtggcca gaagaaggac aaagatggaa attgcagatt gagtcatgtt aagcaggcat    41580
cttggagtga tttgaggcag tttcatgaaa gagctacgac cacttattgt tgttttcccc    41640
ttttacaaca gaagttttca tcaaaataac gtggcaaagc ccaggaatgt ttgggaaaag    41700
tgtagttaaa tgttttgtaa ttcatttgtc ggagtgttac cagctaagaa aaagtcctta   41760
cctttggtat ggtagtcctg cagagaatac gacatcaata ttagtttgga aaaaaacacc    41820
accaccacca gaaactgtaa tggaaaatgt aaaccaagaa attccttggg taagagagaa    41880
aggatgtcgt atactggcca agtcctgccc agctgtcagc ctgctgaccc tctgcagctc    41940
aggaccatga aacgtggcac tgtaagacgt gtccctgcct ttgcttgctc acagatctct    42000
gccctcgtgc tgactcctgc acacaagagc atttccctgt agccaaacag cgattagcca    42060
taagctgcac ctgactttga ggattaagag tttgcaatta agtggattgc agcaggagat    42120
cagtggcagg gttgcagatg aaatcctttc taggggtagc taagggctga gcaacctgtc    42180
ctacagcaca agccaaacca gccaagggtt ttcctgtgct gttcacagag gcagggccag    42240
ctggagctgg aggaggttgt gctgggactc ttctccctgt gctgagaatg gagtgatttc    42300
tgggtgctgt tcctgtggct tgcactgagc agctcaaggg agatcggtgc tcctcatgca    42360
gtgccaaaac tcgtgtttga tgcagaaaga tggatgtgca cctccctcct gctaatgcag    42420
ccgtgagctt atgaaggcaa tgagccctca gtgcagcagg agctgtagtg cactcctgta    42480
ggtgctaggg aaaatctctg gttcccaggg atgcattcat aaggacaata tatcttgagg    42540
ctgtgccaaa tctttctgaa atattcatgc atgttccctt aatttataga aacaaacaca    42600
gcagaataat tattccaatg cctcccctcg aaggaaaccc atatttccat gtagaaatgt    42660
aacctatata cacacagcca tgctgcatcc ttcagaacat gccagtgctc atctcccatg    42720
gcaaaatact acaggtattc tcactatgtt ggacctgtga aaggaaccat ggtaagaaac    42780
tcaggttaaa ggtatggctg caaaactact cataccaaaa cagcagagct ccagacctcc    42840
```

```
tcttaggaaa gagccacttg gagagggatg gtgtgaaggc tggaggtgag agacagagcc   42900
tgtcccagtt ttcctgtctc tattttctga aatgtctgca ggaggaaagg acaactgtac   42960
tttcaggcat agctggtgcc ctcacgtaaa taagttcccc gaacttctgt gtcatttgtt   43020
cttaagatgc tttggcagaa cactttgagt caattcgctt aactgtgact aggtctgtaa   43080
ataagtgctc cctgctgata aggttcaagt gacatttta gtggtatttg acagcattta    43140
ccttgctttc aagtcttcta ccaagctctt ctatacttaa gcagtgaaac cgccaagaaa   43200
cccttccttt tatcaagcta gtgctaaata ccattaactt cataggttag atacggtgct   43260
gccagcttca cctggcagtg gttggtcagt tctgctggtg acaaagcctc cctggcctgt   43320
gcttttacct agaggtgaat atccaagaat gcagaactgc atggaaagca gagctgcagg   43380
cacgatggtg ctgagcctta gctgcttcct gctgggagat gtggatgcag agacgaatga   43440
aggacctgtc ccttactccc ctcagcgttc tgtgctattt agggttctac cagagtcctt   43500
aagaggtttt ttttttttt tggtccaaaa gtctgtttgt ttggttttga ccactgagag    43560
catgtgacac ttgtctcaag ctattaacca agtgtccagc caaaatcaat tgcctggaga   43620
acgcagacca ttacctggag gtcaggacct caataaatat taccagcctc attgtgccgc   43680
tgacagattc agctggctgc tctgtgttcc agtccaacag ttcggacgcc acgtttgtat   43740
atatttgcag gcagcctcgg ggggaccatc tcaggagcag agcaccggca gccgcctgca   43800
gagccgggca gtacctcacc atggccatgg caggcgtctt cgtgctgttc tctttcgtgc   43860
tttgtggctt cctcccaggt gagtaactcc cagagtgctg cagaagcttt gtgcctgcca   43920
gtcctggctc tccttagcag aacatggtgg tgaccatcag agagagactc ccctacaaag   43980
tgcctgcaaa ggctgcctca gtacatcagt attaaacgga ttactgttgt gctgggtgtc   44040
tgttgggttc tgtgctccca acacatttct tacgctctca gctctgttac actgcttgca   44100
tttgctgcac agttgcatag aatggataaa tgcttgaaac aaggccataa cgaggtggtc   44160
agacctccag gaactagtta gggaaatatt gtcatggccc aagcaagctc tgtgcaggaa   44220
cctggcagct ttcctgcaat gcttttgctg ctaatggaga aacaagagat gcaaacaagc   44280
caggatctga tgttctcctt ctgtatttac atctcatgaa attacaaagt caaagacaag   44340
cgtggtttat ttcttacact cagcttcttt aaaatgtata tccctgacaa cagatgctgt   44400
gtatgtttgc ttatcctgta tgtgactatt tgcatttgca tttatctcta ttgactcagg   44460
tttctttttca gatatgtgat agatgttttc tagggacaaa acggatgtgt gaatagataa   44520
ggaaggaaaa gatattcatt tttcaattaa taaatctacc tatctcttaa cttttttttt   44580
tttttaagaa cagagctatt caagaactcg tttcatcagc cagcaataag aagctaaatt   44640
atgtttatca gcattaaaca aaaatcatat atagtttgct tagttcaaga atcgaatcgg   44700
tggaaatcac tcagtttggt tctctgtgct ggagttttgc acacacattt cagctagctg   44760
tggtctcact gatcagactg cctttgtttc ccattttgt cccctttttt tccccagatg    44820
ctgcctttgg ggctgaggtg agtaagagag ttcttcttgt ccacttttct cttttctctt   44880
ttctctctct ctctttttt ccccccgtct taattagtat cactataatc agatcccaga    44940
gtgtaaaatg ttaaattatg cagttctgag ctctacatct atgctgcatg taagtaatgt   45000
agcagtgata taaaactgtt agatgaatta atttctgacc aactctgaac tggtctaagc   45060
tttaagttga tcatatgttc tactaaataa tacagtggtt tgggttggaa gggtcccttta  45120
agatcatcta cttccaaccc ctctgctata ggcagggaca actcccacta gacaagattg   45180
```

```
ctcaaagctc catccatatg atcagctgta gactgatggc tgtagactat agcattaaaa  45240
actaccccaa agcagcctac tgaaagaaga aagtactgtg aggtgctaca gcttccaaat  45300
cccatgttgt tagacctgtt cttttgaata acgtgtttg tacgttgaga atgaatgagt  45360
aacaatggca gaacactgga ggggccaact ctcaggcttt gcaaaatggt gcctgggggg  45420
catgatagat ccctgctggt ttatcacatg gggagctgca tggctataac cccattgccc  45480
agttctctcc cactgcatgg agagaaggct ggatctggtc gctgccctgc tgaaaatggc  45540
agatgtaact acaaaatgtc actttgtcct gttactgtgt gtttctttgt caggtggact  45600
gcagtaggtt tcccaacgct acagacaagg aaggcaaaga tgtattggtt tgcaacaagg  45660
acctccgccc catctgtggt accgatggag tcacttacac caacgattgc ttgctgtgtg  45720
cctacagcat gtgtgtactg cagagagagc tcatactgca agcaagcagc tgtgcttagg  45780
gctcctgaca gcacccctt ccaacaaaca gtgatctgtc acatgtcact tatgtcaact  45840
cttccaggga aagcttgagt atcactgcgt gacactcggt tgcctagaca tcactttggt  45900
tactgtgtct tttttgttga tgtaatttat tcaggttttt ctcctccatc tcggggatga  45960
ggcagatgac agcccctagg gcatatttca tcccagcaaa aaaggagcaa aaggatggag  46020
aggtgctcca gtctgaatgg tccaaaacag tcctaaagat ttcagagtct ttagatccct  46080
gccagccact cagtatggca ctaccctctc aatacaaat atatatatat acaaagatga  46140
cttagccaga ctcagcctca ttgcattagg tacatattcc caataacgag aagctgagct  46200
tcctaatacc tgttttccct cttcagagaa tttggaacca atatcagcaa agagcacgat  46260
ggagaatgca aggaaactgt tcctgtaagt gaaaccaagt tcatcctttg tgcagccaaa  46320
actgcttatt gacttgccca ataaataatg taaatgctga ctaagaggcc atgtgagatg  46380
tcagaatctt gtattgatca tcttcaggtg aagtttcatc acaataacac aaaaaaagac  46440
tttatttcct gctgaggtgg cattttagga gacccaacgc acgcgctccg ctggtctacg  46500
tggtccctgt aagccctcac cagcgctttg ctgtgtgctc cttccacaga tgaactgcag  46560
tagttatgcc aacacgacaa gcgaggacgg aaaagtgatg gtcctctgca cagggcctt  46620 caaccccgtc tgtggtactg atggagtcac ctacgacaat gagtgtctgc tgtgtgccca  46680
caaagtgtaa gtaccgagct gtgctccctt ggcaggaatg ggtcctgcgc tcctggcagc  46740
cactctttga gcactgggat ttccaatgag gcttttctg tatggctctt ggactccgtc  46800
cctcctctcc ctgataacct catgctgttt tcctttgtga ttagaaagag aactgtggct  46860
ttgatcttga gagagaagca gagagctggg tggggactta agagaagcac tctgttctgt  46920
gttaactaag ttaaagggt ctgtgtggca cacactgcct tgcagaggac agcagtgaac  46980
ctctgctgca cctatattgt aaaacaacct agctcctagg ccatgacagc ctgtcacctc  47040
tcctcctttg catcatgcaa tactgcaaca ctgtggcaca tagtaccacc tcccataagg  47100
actgatatgt tgaaccagtg tgtcagagac cagtagcatc tctgtcttca ggatcatcag  47160
gtagcattct atatacaggg tgttgcccag gactccgagt cccatgaagt atggcagggg  47220
ttttggaact ggatgacctt cgaggtcact tccaacccaa gccattctat tattctgtga  47280
aagccaggga ggtgggggtg cttgcagggc tggtatcttg agcagtgtgg gcacaaacta  47340
ggctgggcat ctgcagccca tcagcactgc ggggatgtgg agttcagcac agcaggatgc  47400
aggcacagct ccctaacatg gatttttttc ctttcagaga gcaggggcc agcgttgaca  47460 agaggcatga tggtggatgt aggaaggaac ttgctgctgt gagtgtgagt agcacaatga  47520
aggagcaggt tctggtccca ctgatgtcaa gggaaacatg gccagcatct ttagtagcct  47580
```

```
caggagcatc agttgtgctt cagcacagag aagattttac tttctacaca cgtaatacac   47640
attatccaca gtaatgtcag gaagggaaga ggatgactgc acaggcaggg atcagtaaaa   47700
gaccataagc agaaataacc catgagggca gaactgagaa taagaactga gactagatcc   47760 aggggggtcag accaatgggc catcaaaccc atgatggttt gatgcagagt ccactctttc   47820
agcattcata agaattgagt aggggggagt aagggtgggg tgagtacgta cggatcttcc   47880
caaacaccct tccaacctac agctatgcac ctcagccagg tgtgatttct gtgtagttca   47940
caagcctcag tggatttctc tcccatggga ttctccagcc tctttctgga cctgtataca   48000
cggtagttgg gttggttttt tttttctgtc tctcttttt tccccccact acaatgtccc    48060
tcagcaaaca tagtcctcat ctctcaaaca aacaaatctc attctctaag tacccagata   48120
agagctgatt tttgctttaa gcctgtgggg gagatgctgg actattataa aggtatcagt   48180
gctgcctctt ctccagacac caatgttttt tccatttaat ttcctgaaca ggtcaggaac   48240
acggtgcaac atgattgtaa gcacagcacg ttcatggagc gagctgctgc tgcagctcag   48300
aaatgcagca gtcagattgt gatatgcatc tcttacacag gaaattatgc tctatttta    48360 tattattaaa tctagcatac gagaaaggac atccagttta tatcagatcg tgcaaggaag   48420
ttaattattt ttagtttgat cattatcatc ggcactgcag ctgtagctag ggaggggttg   48480
aagctcttca gctatcgact ccttcatatc ctccacgtta caattgtgtt tttgcaggtt   48540
gactgcagcg agtaccctaa gcctgactgc acggcagaag acagacctct ctgtggctcc   48600
gacaacaaaa catatggcaa caagtgcaac ttctgcaatg cagtcgtgta cgtacagccc   48660
tgattgcatt cacgttgtcg gctgcctcct acaggcacca gcttgcacag ttcctgcttt   48720
cgttgctgat tgctgaccag gatctggggg cagaaaagaa caccgggcat cacgccagcc   48780
attcatttga tttttcacca gagcttgtct ggtttgttag gatggatgtt ttgaacgcca   48840
ttaaccttaa gggaagtttt ccttgctgcg aagaaaatca gatttggtgt ttcattatag   48900
ttttcagaag gggttaaacg atttcactca tctcctaata atcaggtagc tgaggagatg   48960
ctgagtctgc cagttcttgg gctctgggca ggatcccatc tcctgccttc tctaggacag   49020
agctcagcag gcagggctct gtggctctgt gtctaaccca cttcttcctc tcctcgcttt   49080
cagggaaagc aacgggactc tcactttaag ccatttggga aaatgctgaa tatcagagct   49140
gagagaattc accacaggat ccccactggc gaatcccagc gagaggtctc acctcggttc   49200
atctcgcact ctggggagct cagctcactc ccgatttctc ttctcaataa actaaatcag   49260
caacactcct ttgtcttgtt taatgctctg cctcatgcaa tgttttcttc tgatttgttg   49320
gacggtgata ccagactcaa tatgttccat gctcgtggct ctggggtata acaagaacaa   49380
catcttgctc ccatccctgt cataaaaggc agaaaattaa atacagatgc ataaacctcg   49440
gctgtgtgac tttgcgcata aatgacagtc agcctccatt agtgttcaga ccctttaga    49500 cagctgaaat actgctacga actgctgatg ctggctgagc tccccatggt acgtgtggtg   49560
cactttccct gcgcagcatt agcagtgaaa gcagctcagg gtgcggtggt ggccaaaccc   49620
agggccgatc ccacggcctc ctgtacctgg tcatacccac gggcacagct gctagtgagg   49680
tgcgtgcttt tcagacacgt catataagtg tgccctgcct acatgtctgg gtcctccaaa   49740
tgacgttgca aggtttatct catcttggaa ttgtcccta ctgaccacca agtgttttga    49800
gatgaatgcc ctcctaggtc tggttctgct cttgcctgct ggtctttct catagtagtc     49860 cttgccagcc caagtatctg agcagtgttt tgcaatccaa ggacaaagta cccctctgcc   49920
```

```
tttgagagtg tgacctctgt cattggcaca ttgtccgtga aatatatttt gcttttgtcc   49980
tttgttggtg tattgaactg atgttttctt gatccacatg agagaaactt taataaaaat   50040
tataaaaaat aatgcctccc ttaagcattt cttttccctg atggaatgag gccattcaaa   50100
agaaggatgc tttggcggta aaacagagga tttatgttga gatgggcaga tgaatcaagc   50160
agtgatttcc agtttggatt gaacttttct gggatccagg ctgtgggcct catgtcattc   50220
tgtcatcatc aggctatcag tctgctgctg caaatcctcc ccacaacgct aatggctttt   50280
agggaaaatc gcaattgtta gttctttgct aatgcccata aaacttcttc catcacttgt   50340
ccagctccag gactcccttc agccccaggt ttccctcttg ctctctctcc cagttcagtt   50400
tttctggatt tgctatgatt tgatgatgca ttattgacag acaaggggaa aatggtttca   50460
aaccagagga gaggagattt agactggaca taagcaagac attttttaca atggtggtga   50520
ggcactgaca gaggttgccc agagaggtgg tggtgcccca tccatggaga cagccaaggt   50580
caggaggggc tctgagcact gatggagctg tgggtgcccc tgttcattgc aggggggttgg   50640 accagatggc ctttaaagat cccttccaac tcaaatgctt caatgattct gtgattctat   50700
tgggttgaag catgccaact aagactttcc actctggaaa acattcaatt cagttcaaca   50760
acattttcca gcaacagtga gaaagcactg catataggta agcactgata acatgcacat   50820
ggaggaaatc ctgcagcatt ctctcttcag gtttgtacag ttgccctttt gcccacagga   50880
attttccatg gtccttcagc aggcacctgt cacacacttc actggaaata atgaagccga   50940
gggcgtactt cacatattta aacctgcaat tgctgttgat aaagaagcat tctttgtggc   51000
tcacttgtgt aagtgccatc aagatttaca accctgacac cagagctgga acgctggtta   51060
tttcaaagta gggggtggct aaaccaaacg tgaatgcaca cagccacgca cacacagatc   51120
aggtggccat ccaagggcag aagggccgca ttccatgagc acgatgcact tctgcccttt   51180
gctgctgccc aggtgagtgg ctgtgctcct gctccgtgct tcgtcgagtg ctggctgtaa   51240
aaacacaaca aacatcctca gactggaaag agctgtgttc tacaaggact tatttactcc   51300
tagagggatg gtgttgaaaa gacttgacat caaagactat cacttatggg gtaatatttt   51360
agcaacagaa ctgagtgggt aagaacaact gtgggaacag ctccgcgctc ggtgctagtt   51420
tatgcataat gaaagcagtg acacgtacgt ggtaccacga catccaccat tgaacctccg   51480
aaacgctgca gaatcacaaa ttcttttact gaatggaagc gagcgtttcc cgcagtcatc   51540
ctgaactgag atgcaattgg aggggctgag cggctgcagc agcgttaggg gagtttcacc   51600
tcgctgagcc ctcccgttat ttcagtgctg ttgtggagct gcacgcagga gctgccgcca   51660
gtccgtgcca gctctgcggc cctgcttccc cggcaccttg cttatctctg agcacctgtc   51720
cttgctcatc ctgtgaatca cggagaattg cttttctcttc ctcccttttca tttcgcgcgt   51780 ccttctccac ccgggctgta accctcctga gaaaaaacgt agtacggaat cgatgttgta   51840
aacactcagc gtggcacaac gttttgcctg aaatcccttt tgtctgagag tcacacactg   51900
aattgcaagt tgtttattca ggacatgcac tcacggattt taacactaac gaaggagatg   51960
aattgcattt gtgtcacact tcctattccc ttcttactc cagaccccac tgcactgaag   52020
gtaagggaca gatctttcag gttttttttt tttttctcc atcatttctt tcctcaaagc   52080
agtttccgta taaatcatta ctaatcgcat tgtgatcgag cgtttgaaag ccctgagtca   52140
tcccacagcc tgagcaatat ttgctacaga tattaccgag tgaaatggcc atttcatct   52200 gatggtttca aaaaaaaaaa aaagataata ataataataa taataataaa taatagcgc   52260 agcattcagt tggtgtccaa gttattgtca cggttactgc agcagcactg aggatgttta   52320
```

```
catgggattt acatcactgg aggctgaaag ggcactgcag gcgtgtaccg cgctattcgc   52380
tgccccatcc ttaagctctt ctttgacatc tgctgatggt cggtgctggg ggaagcccgg   52440
ggctgtgggg gtctcctggc atctgccctg ctgatagctg tgctgctgag gtatttctg    52500 tgagcacaag gctgcatcga tccacagggc gactgcagtg cctgcgccgt accccgcaat   52560
ttctgctctc gggagcgcat cccacactgc gggtctgatg gcgtaacata tgccagcgag   52620
tgtttattcc gcaatgcatt tctgggtgta tgaaaataaa tctcttcgct cactgagtgg   52680
tgaacttcaa ctgtcttatc aacctcaggg actgcctgga gatggaaggt ggttgtgttt   52740
ggcgctctcc tcttctcttg ctagcaaggg cagcactttt ttttttaaac tgggaggatt   52800
taccagggac tccttctt caggtaaaaa gaagtcacat ttagcagaga tcttcatctc     52860
cacgttgggt aatttgctga agagctcgct tccagcaaat acagtctatt tcctacagcc   52920
tatttgttct tctttaaat taagtcttta tcgtgccttt gaatgttagt aataagagga    52980
agtagctgga atagctttcc gaatgttctg ttttggttaa gttcctctgt gatgtatcct   53040
taagcagagg gagggatgca cagcagaagc gcagaggttc aatctctgag gccctgagct   53100 cttctctcc agaactcatt gagttctcac cttgctgtgc cctgcgcagc gctcacatca    53160
cagcccaccg ggctccagct cagacaggag gaccctctct ggctgtgttc cttacagggg   53220
atgctgccca aagcctcgtc ctgaactttg agtgctcctg ataaagcctg aagctatgct   53280
caataaaaaa aaaaaaccctt cagcattttg gtcttgcttt catactacgt atcatgctgt   53340 tgttttttt tcttaagatg ctgtgtgatt gcatcactgc aacagtcctg gggtgtgggt    53400
cttaatggga aaattacagg gagaaagaac gggttgtctg atttatgaag aaatcaaccc   53460
ctccaaaagg ccatgagctt ctgctttctt ccagatttcc aaaagaaagc cactgctggg   53520
gatgagatcc agtgcagtgt tcagggcatc ctgtgcagac attgactcct taggagctga   53580
aaataaagta gtggtgggta cccgtaggtg tgggaagcct ttctgcagcc acctggtctg   53640
cctcccaaag cagaggatgg gatgttttcc cctccgggca gcaccaacag aggggtggca   53700
gcagggtgag gaagatgatt ggcccctctg ctctgctctt gtggggacca catgcagtat   53760
tgcatccagg cctggggccc cagcatgaga aagacgtgga actgttggag tgggtccata   53820
ggaggccatg aagacaatca cagggctgga gcacctctct tatgaagaaa ggctgaggga   53880
gctgggcttg ttcagcatca agaagggaaa gctgagagga cacctcattg gagtcttcca   53940
gtacttgaag ggagcttgca agcaggaagg ggaacaaact tctacatggt ctgacagaga   54000
tagaacaagg gggagtggct ttaagctaaa agagggaaga tttgggtgag atgttgggaa   54060
gaaatacttt actcagaggt tggtgtgaca ctggcactgc tgcccagagc tgtgggtgcc   54120
ccatccctgt acatgagctg aaggccagat tggatggggc tctgtgcagc ctgatctggt   54180 gggggggcagc cagcccatgg cagggggtgg ggtagatggg ttgtatggcc cttttcaacc   54240
caaaccattc aatgattcta tgattctcag ataagcctgc ctgcccacat ctgagctcac   54300
ggtgctcgct gggggtgggg tatggtacac taaatgatgc tcagaggact gcacgcagga   54360
cctgccgcag acgtttatca cctcacccac cacttagctg ctgcttgtag ttaattacgt   54420
cagctgtcac ttgtagagaa tccttttgaga tccttgggcc tccggaaatc ttggctgatg   54480
aaaggaaggg ctcagagtca tagcgttaat ttattattca ttaacaccaa agtgtcggct   54540
gtacgggcag tgggctcaca gtcaaatagt taatgatctt aagtgacaat gtgtcacttt   54600
gcagacagca gagagaacag ctctcctaag ggagacagca tctttccaat tctgcagcca   54660
```

```
ttcagtgcca agctcctctt tgggacgaaa gtgaagatga ggaaggcaat gaggatgagg    54720
agggccctca aggaacctgg ctggcttgga gacaagtgat gatcccagct gctctcaggg    54780
tcccagcggt cttcaaaggg catcttgcag gggctgtgtc ctctgaacag caaaacccag    54840
gtcatagagg ggaaagtgtg agcagagatg ggacaaatct cccatcctgc cacggagctg    54900
cactgctaag ggggtgatgg ggagcagcat gggaccccag cgttcccccc atccctgcac    54960
caggcccagc tctgcgggat ggcgaggagg acaaggctct gtcacaagca tcgctggcaa    55020
ttattatttt gttgttgctg ctcaataaaa tcctgacaca gtacaacaca atatcctctc    55080
atcattacta atctaactct ccctccagga aatttcaggc aggaaacgtt gtctgcctgc    55140
cgaggtgctt tatggcactg ttctttagtg gtacctcagc acttcgtgtc attatctggt    55200
gtcagtgaat ttaggaaatg ccattcaatt accccgcaaa ctgattaacg cattgcgtgc    55260
agttattttg ttctgctcta ttttatatca gttcctctgt tttatgtatt tctctacttg    55320
ttgctggcca gaacacacct cgggccagtc tagaccttgc tgttgatgca gcttttcccc    55380
agggcttcat cagcacaaat ggtttgtcaa cgtggggaaa aataaaatta tgctttaaaa    55440
taaaaccacc tggagatgct gttctggggt ctggctgtgt cacagctatt gcagcgatgg    55500
agctgaggga ttgggatgtg ctgggccgga tcctcagcgc tttgctataa gccaaataat    55560
tccagacacc cttcttccct cagatatcat ctgtgcttaa gcagcaggag atatgcaggc    55620
agcgatcaga tagctgagct gcaaggagaa atatcacaag agcgcggctt agagcagggg    55680
ctttgctcgc tctaaattga attcccatcc tcataggaga tccagtcctg cccccgtgtg    55740
catcgctccg gtaacagcaa tgtgttttgc tccatcttgc agagggtcca gaagctgggg    55800
aaaggaaatg tgtcgtgcgt tcgtccctgc agcagctcgg cccataaaat taatgaaaat    55860
cttttttagg tcatggtaga ttacagattt ctttgagata gagaatctca agagcagagg    55920
agaagattct cagaaaatag cagtgatatg agatggcata acgctgagtt ggaaactggg    55980
gaggatttcc agggttactg gaaatttact taagcacgag agaatgcatc gtgtgactgc    56040
cagtgcttcc ccactcacat ggctataacc ttcttgcata caattaccat cttggaactt    56100
gaaatagctg aaagagtttt atttgatctt ttcaatggat cttacatctg cagaaaaaaa    56160 aaaaaaggc tagaaataat cctgcactca aactcacttt actgaaccac catcatgaaa    56220
ctccagcaac acacagggat ttgggcaggc gtgttcatct tcctcttccc atttgcaaca    56280
tgtgtatggc atttcctgaa gctcactcct ccaaatgcat tgagacagtt gtttttcatt    56340
cttcctaatg cctgcatcca cccatctgct gatcggcaat tatttctatc ccattccctt    56400
ctgtttctta ttaatcaagc tctttatgca atcccacgta acactttgcc cagctgccct    56460
gccctaacca ctaccaatta tctcatcctg ttttatagac cctgtagcaa gactctggcc    56520
ttgctcctct tcctctccct gatagagctt ttggtgcagg gctggctggc tcctcaggtg    56580
ttcagaggat cagaggtctc ccagaaggat cttgttaatc aaggacaggt gctggctata    56640
tgggaggatg gcaccgtatc ctaaagctct acaagaagga gacggagctc agcctgggag    56700
gacagagaga agcagcagca caggtttcag gatccaggga tggcagacct gggtgtgggc    56760
tcataggatt gaagaaggga taggctgtgc tcctgtagcc tcactgcaga agcagcactg    56820
ctatctcccc agcgaagctg tgtgtgcccc atccctggag gtgctcagga ccaggtggga    56880
tggggccctg ggcagtctga gccggaggga gcagccggcc cacagcaggg gttggaatgg    56940
ggtgggtttt aagttcccct ccaaccaaag ccatttcttg atctctgttg gtggctggtg    57000
caagttctga ggaaacctca ttttcagctc aggcgttctt gtccctgggg aaaaatcaat    57060
```

```
attaatgctt cagtgattac tgctcgcctt ccaaatgtgc ttctgatcag ttcaagaaat    57120
ctgacagtca cgtcgctcag gatgctaaga atacaacaga aacagctttg aaaggaaccc    57180
ttcaactctt gatatttgtg aatgagctcc aaagaacatt actcatttat ttttcaggaa    57240
aatgatttca ttgacatgaa caggccaaag cctacaagct ctgttttgtg actgcagctc    57300
cttcactttt cagctgcatt ttcatgattt atgtgcccat gatgagactt gaacacctcc    57360
caggataatg ggaaaagcag ttctgatttc ccatttaaaa cgtaggctgc ctttaagcca    57420
tgtgtgtggc tcaggctcct tctgaagcac aaaggtgttc caccccctcgc tccttttttca   57480 ttacaacttt caatcaaaaa tgtgttttat gagatatttg ttttgccatg tatctgtgac    57540
ggagttgaac cccttagtga aacctctgtt cttcacttag ctgagaggta tttcttaggg    57600
aatgtgatgc cctaaattta ttgtggtgta atagaagggg ggatgtgtgg actcaccttc    57660
tgtttgttgt ggctgcagtg gttttatgca ctacctgagt attaagcaag ccctttttcat   57720 ctgcacggaa cacctcctgc ttgccagtgg gatgaaacaa caacaacaaa gatttaaggt    57780
ttgctattct caatgtttct taatcgggtt cacattgatt gccaacagat gaataattcc    57840
tccttctcca tggatgtacc tcttaaactt gtgaagtctt aggtaacgct tttctgctgt    57900
gatgactgtt tcagtcccct cagtgagaaa tcaggcgcac cagtaagaca caaaggagac    57960
cgtggagatg ttcattgtgc cctcagcatc tccaaaaggc actgctgcct gccgagcccc    58020
agacttcgct cctgtaaaag caaagcatgt ccaattctgc tgtgccataa gagtcctgtg    58080
gagcccagac acggcgtagc gtgtgtaaca tagcgtgcac gagctcaaac gctttcaaca    58140
aatcagcttt tttgctttgc caacttccat atgtaatttc acaacatcta gtattgagac    58200
agtgctgttg tttgggcagc ataaatcact cattgtacag cagggcgcct ctcttaacaa    58260
gttgggtgta gttcatgttt ttgtctaatt cctctgcgca tctctctaac aaacaactat    58320
tctttagggc tcgactcaat aatcaataca ttttttttcag tttacagagc aaataattac    58380
ttgacctgat gacttcacaa ggttagggag atgggtgtat aaagtctgca gtgtgaaggc    58440
agagcaacat ctctgcagac cttgagagca acaggtctgc aagtaacagg ctgcacagcc    58500
acctctgcca tggaggcaat gagagctgct gccctccttg gattggtgct tctcagctcc    58560
tttcctggta agttgttttt gttacattct ctgcttatat ctctactcct actgaactaa    58620
atgtggttca ggatgccttt agaatcctaa aagagagctc agcctgccgg agaagtgatg    58680
gtttggtaaa acatgagctc tcttctaatg atctttatcc ttgtgcaaat atttacgtaa    58740
ctctagcagg atgcctctgt ctgacataaa ctcattatcc tcagtaagtc tcatagcact    58800
cgagagagaa aatgtatacc ctatttcttc cttagtgagt caaagtttat attttcaccc    58860
aaaatggcta tttttttttaa tcataggata tagcttgctt ataggaactg gataaaatat    58920
ttaggaaaca agtaattctc agtgataaaa agaagtatg tgatgactct gtagggaaat    58980
tgataattcc agaggaattg taaccaagga cgccgtaaca ttctgtattt tataacctct    59040
gttttttcca gatattgttt ctggtcatca acgggtgagt agcagatctg catcatttag    59100
ttgtggtttc tatgaataga tgaataattc atactcacac catatcctac gggagcctag    59160
agggagaaaa aaaaaaaga aagaaaata acaaggaag gagaaaaagg gcccccagga     59220
attatgtgac attttttcccc cagcaaataa gaaaacatct ttgtcagaga aagataacgt    59280
accacgttgg tgataagagt tggcaattaa taatgcagag tgggagccgg cgtggcacag    59340
cgtgccagca gaaaatctgc acagcttttc cctaactgcc tccatatctc ccctgcctga    59400
```

```
ttccctgagg acccatcagt cagtcgtgtg tctgccatgc caaaagcctc agtagtgaca    59460
ctgtgctcag gcatactgta aggaacgctg taatttgctc ccacttcttc accgtggagg    59520
agtgacagag aataaaatga ccgcctgcag cacggctatg cgtggaaaac acaagcagac    59580
ccttccgtgc cctgcagagc tgtcccactt gtgctcttcc caggcctcct gcggtgagta    59640
ccggctgtta ggcagcagga acctcgcctt ttccaggatc ttccagcccg tctgtggcac    59700
caataacatc acctacccca atgagtgctc gctctgcaga gaaatcctgt gagtagcgat    59760
cgcccgatta cccatcgtga tggctcaggt ggcagacaga agccttttga attgtgacta    59820
atcacgggtg gattcgattt ttttccccc tgtttctgtc ttcccagagt gcaggctgtg    59880
tttcttcctt gtcaaaactc ctgagtctaa ttaattagtg gggctgggcg tggagaggct    59940
tgatgagtga ggtgactgca tggcaccacc aggttaaccc ttcccctcct tctctcctag    60000
ccggagtggg acggttgaca agaagcacga tgggaggtgt gtgaaggtat ggttccagct    60060
cagccactgt gtggagcgat ggcagaatcc cttcccagca ctgattgtac atttagaatg    60120
gacagctcca aacccattgg aaatgtaaca gaaaggaaga atttcaggtc ttttatatat    60180
atatatatat atatatatat gtatgtatta atttcatttt gaacagtgca aatctgtttc    60240
aacggtgagt tttgagatgt tatcttgtgt agcacagctg acttaaaaac agaatcctct    60300
catttcaata atcctttggt gttgttgaaa tagttcccct tagacttaga cagaagtctg    60360
ttgaaattaa gaagttcccc aaggaagtct ggattttgac taaatcataa ttttgtaaca    60420
gggaaaaaga aaaaaaaaaa ggattccatc agaacatcta ccctgaggtt tgtttatcaa    60480
tacacggagc tgccacgaag tggagaagtg tctctatttt tagattagag ataatgta     60540
aagaaacact ccggctgtgc aattgaacat aatgctacaa ttttcacttc agtacactca    60600
gagtaatggc aggaacaccg aggtgagcat cagctccatt ttcaagtgga gcagacattt    60660
cacagcagca gttgctgcca tgtagggcat gttaggcaca gatcctatgt ggtggcattt    60720
ggggtggaaa gccctaagat gacaccaaca aaacccattc tgtgaaccca tttcctccag    60780
gattctgctg ggctcatgtc ctcaaaggca ggacttcacc tgcctgtgct cccttgcccg    60840
cactgtgctg ggttggaagc tcacatctcc atacagcccc actcaccgtg agtctggggg    60900
tgggagacac ctctcacacc atgcaccatt acacagggct gacggaagtg ttgttctgtg    60960
gctgtttcag gttgattgca ctggctacat gagaacaact gatgggcttg aacagcctg    61020
catccagcag tacagcccgc tctatgccac caacgggctc gtctacagca acaagtgcac    61080
cttctgctcg gcagtggcgt gagtggtggg tcacaccctg ggtgctgggg tctgggtggt    61140
ggtgtttgca gcatattgag gcttctggag tggctgtgct gtgctcattc attctcaact    61200
tgctttcttc cccaaggaat ggagaggaca tagatctgct cgctgttgga aaagagcccg    61260
aggtaaagct cgaaagtctg cgctatgaac tgttgttata atatattata cagcacaaat    61320
tcagtgagtc agaactacgc aatagcaatg tcttcactgt gctggtgtat ttgtcctgga    61380
aaagggtttt gaggaaaatg actcaagtat gccagggtca gaggacgatg aacaaaactc    61440
ctggctcctg tgtcagtatc acctgcacag cccctgacag gggttgatgc tcagagcatt    61500
gttcagatgg tggctgtgcc agaggtgctc accgctcctg gtgagcgtgg ggctcatgca    61560
gcaccagctg tcattacttg ggtggtggac ttcatagtg tgctgttgga gacacactgc    61620
ttcctggcag cccctctctg ctggctgctg aaccagagca gagcaggtag cgggccgcca    61680
gccggggagc actgctttgg ctgtgtcgct gcttctgagg gtatttagta gattttccc    61740
tctgacttct ccttttgtgc tctgctgggc aagagcatta gaatttgcag agttgctaga    61800
```

```
acaacaggag cctgcatctg aaaaaatgtt tttttttgctt tgccatgaca taaatgtaaa   61860
gcgcccatgt aggaaaatac accaaacaaa ggcttctcaa tacgttcttg ctccattacc   61920
tacagattga ctgcagtgaa ttcaagagca ctgatgccta ctgcactgaa gagtacatgc   61980 cccttttgcgg ctctgacggc gtaacgtatg ggaacaaatg ccacttctgc attgcagttt   62040
tgtaagtaca gtgctcccca tgcagccatg aaaccactgc tgtgccggag tatgaaggca   62100
gaagctgcca ggaagccttt gtgctcccgt tatccccttg gtaaatccgt ccccatcccc   62160
aacctgatcc cagctctacc tctgctgtgc cttccccaag cactgcagat cttgaacaca   62220
ggtgagtctt ctccctccct caccattaaa ttcagattct catttgcggg ctcatagcgc   62280
tcctgatcca tccctgcgag agtaatttga gtggtaactg tagaaggagt atccaaaatt   62340
acagggtttg tcccagatct ctctaacatg acaaaacgtg taacctgggg aatcaggaga   62400
cgggtgaagg tgcaactggg acagcatgga gcattggctt gcccatgcaa agtcagcagt   62460
ggcaccatca gggctataaa accaccttcc atgtcagtga ttttggcctc ctcctttctc   62520
tgcaggaaga gtcatggatc tctgtctctg cagcaccgtg gagaatgctg aatgctggat   62580
cgtaaccttt accctcatcc atctttcact tccaaagcct gcaattccaa cacgctcttc   62640
cccgctccct gctgtacatt gctttctgcc ttgacccgcc agtaaatcac agacagcaac   62700
tctcttcgcc atgggctggt gtgttattta tttatttatt tatttattgt tgttattatt   62760
ttttccaggg cagaggtaaa agtcttcagg cttttcaggca cttatctgtc aggcaggaga   62820
agttttgaaa taaccacaa taaaggccaa agtgcaacac ccatcacaca aaagccataa   62880
gccctcacga aagtgcgtca ccccattcca aaccatcaga agaggaaatg ttgctataaa   62940
acacatgctg ctctccccag ttctgtgtct tacagcacat aaatggattt gctttaagag   63000
tcaggatgtg gctttgtaga agcacggagc cctggaggaa gcagtccttt tgggagcctt   63060
ggtatggagg aaagatggct ttgatacacc tgagcaaggg gcaagtctgg cggcacgtta   63120
caaggaggct tatggcaaag ggaggagact atctcacagg gaagaaaatt aggaactgtt   63180
gcttccttga agggtgtgtc ccttgagagt gtggtgatca gcagaaaatt gcagccagct   63240
gggcaaggct gtaatgagcc taatgaggac cagaggagaa accagattgg gctcaggctt   63300
cttggaaaag agatctgaaa agctgcactg ggagcgtttg aggcagagga aagagaaagg   63360
actcttcagg aaaaggtttg ggagtcttca tgcctagaaa agaaaggaca gaaggagtgc   63420
ttggtagctc caaggtcgtt tctgtctgca gtgaaaggtg atgtgtggat gatgcgtgtg   63480
agcgttcaca gtgatgtgcc atctctttgg gcgagtcaag gaatgagtat gcaaacaaca   63540
ggtgaaaagt cccaagtgcc tccactcatg ccaccttccc cttcctttct ccacctccca   63600
tcctctcatt acgtaggaag acattcagct gttcaggctg atattgagga caaaatctgt   63660
gacttccaag cttttctctg ctttatttc ctgaaatagg ctgtatcttg acctagaaat   63720
cttatgggtg cttcctgcca gaagatggga agctgtcctt taatagcgtg tcagggcagt   63780
gctccgtcct aggaagacag atggaacttt gaaatgttta ttctattagc acaggcagta   63840
taaagcacag tgtgcctctg tgcctgctgg tgagaaaagg caagctgcag agccgtgagg   63900
gtgctccctg ctaatctgcc tagaagggaa aagagtagac aagaaatagc atatgctact   63960
actgaatgtg agcagaagac ctttagtgaa ggacacagct cagctgtaat gtcctgttgg   64020
ccaggaggtt tgttgagtta tcgcagagcg gtagagttct ggtcagagca ggaaggtgcc   64080
ttcaacagca agatcccatg gtaggcctct tctgcagtgt gctggcacaa gcctggtacc   64140
```

```
tgctcaggag caaaaaaagg ctttggaaaa gctcaaagaa gggctgatgt cttacaggga   64200
aagggagggc aaaaggcaag tgcagagcat atggctgtac agacaaaaac ccttcagaaa   64260
atggaaaagg tttttatcaa gtaagcccag aagttggccc agtgcaggta aacacttggc   64320
taggtaacag tgaggctctg cccagccata cccattcctc tgtaaggcaa atcccaggtg   64380
cctttgtctt gtctggtcct gttctgttcc tattttctg agaaatcaga cagaacttcc   64440
ccacctacag catcaagcag ctactttata ggtgaagaag tgcaaagaga agcaataagg   64500
ataatcacca cttggctaat ttagtctctt cctctcagcc cacaaaggac tggtccctgt   64560
ggtacatttt ctaaggcttt tcccagtcag ctgtgctgta gcaaatgaaa tgtttggcta   64620
gataaagagc tgaggtatta gtgctggggc ggcgagcagt gtctggagca agaaaaggca   64680
aacgagggat tctgcgagtg gcagaactaa gcctgatttt gaatggcgtt gtggctggcg   64740
gacttgtaaa ttatatgaga ggctgtgctg tgagctcacc ctaatagaca tctgagaact   64800
cacctgtcaa tcgcggttcc tctgctgtgt gggttttatg tgtctagtg agctgcaagc   64860 tctaatgctt tcccaggtgc agggcagttg tggcattgct ctcctacaga aactctcact   64920
tgctggctga ggatgtttag gaagtccttg gttgctagaa aaatatatt gaagtgcttt   64980 ttttgtttgt ttgttttcca ttcttgtgtg aaattttgtt ggaatcacag aatcatagag   65040
gttgaaagag aaactctgga aattatcaag ttcaaccct tgctaaagca ggcttcatac   65100
agtaggttgc agttacaaca tttgctgggg aaatgaatat gaagatctgt ctataaagag   65160
tgttcccata gcacttgttt ctttaggaaa gcatgctgaa attctaaagg ctgtgcctat   65220
ctgaagagat actttgcaag tggtgcaact aaatgctgct cttggtggag agatggctgg   65280
agatggatcg atggttgggt gatcttcgtg gtcttttcca actttaatga ttctatgatt   65340
ctatactctt tacacagaat cagctgggaa tagagtgaga gtctcctgat tccccaccaa   65400
attcctttga ttgatgcttg gtgtggaagc agagctctgg gacacgttgg tgagtgtgaa   65460
aactggaaaa cattgacagc tatagtttaa atagttcagg gaggagaggc agccatccta   65520
tgtgggactc tgcacacggc tatgagagca tcagtgcgct tctccacccc aacccaacaa   65580
atttagagcc atcctccaaa atagccaggg aacaacgcat aattggtttc acagacaaca   65640
cattctcatg ctgtgattta tttcgtaatg tctggtgagt gtcatcacgc cgtgctcaaa   65700
gcctggagct ggcattcagc gaggacccag agaatgaaaa ttaccagctt ccccgatgaa   65760
tcaccacttt gaaaattcac ccttgtgaga atcctgtgac tattcagaaa aaaaaaaaa   65820 aaagaagaag aagaagaaga agatattaca ggcccaagtc tatcagtcat gtaattagcc   65880
ctttctaggt ttgatgtgga cagggcggca ttcctaaagc accataaaca cggccgggac   65940
caataatggc tctagaatcg aagcggagaa gttctcacaa ttaaggtgag gatgaggcc   66000 agcagcggat aggtacataa atacacggag gcagggccgt gagcacgctg tgggcttgtg   66060
gctgagacaa cacctcccaa accggtcgct tgccggggac taaaagagca gcatgaaggc   66120
aacaggcacc tcggtgctcc tcagcctgct gctgctgctg tcgttcttct cgggtaagtt   66180
atatttctgt agcctagaaa gaaactttat gacgagagca acttcagaga gccttgatca   66240
acggatgaca ggcttgaaga gaaagctgag caagtagaaa atatctgcgg gactcgcttg   66300
cttgtgtcac atctttccat tcctcgtgtg cctccgcagt gaataacact gtggaggtgt   66360
cactgggaga cagaatgagc aaattgtaag cagctcgttc agcagaggca ccaaagcaga   66420
gcgtaattat gagttttggt ggaaatgttt gctggagagc tttgctgaac cagttagaga   66480
agaaactcat acctcagggt catcagctcc tgttctgatg ctaagcactt gggggttggt   66540
```

```
gttctcctca gagatgtggc agcgtaatta gatgaaagtt tcagcttcca aatacgttgc   66600
agaggagggc tcgaaaatta aattcagatg tcctcgagga acccgaacaa agagggcaaa   66660
ttgaaagggt ccagcgttta tttatcttga ggtttacacg tctctctgtt ggtctgggga   66720
ggctggctga tggtttgggg gtgtgtaggg cacaccgggg tgctcaaatg ctcgcgtgcg   66780
gccgatgcga atgtggaagc gttgcggtgg ccattactga agactgcaga ccaaggatta   66840
tttatacttg tttttctgtg aataatttga ataaagaatt cgcttgagaa aatcgcaggc   66900
tgtgcatgga gagaagaggt gaattacttt gtacacatca ttaattatga aatattcatc   66960
tgtctttaat tgagtcttaa ttggggctgg gttccgtcag agtgctaaag cttctttcca   67020
aggccaggca gaatagcagc aaactctgtg atctcaaata agataaacag atgccaagag   67080
acgttctcac aaagtcttgt gtagctgcat gtaatattta taaaaattat ctaatgagct   67140
gttttgtaaa taatatgcag atagccctaa cggcggcttc cctgtccagc ctagctgagg   67200
atgtgacaga tacagcagtg gcaaggatca aacactgaaa ggcatcgcag caggcagaag   67260
ctgggtgggg tgatggatgg tcccgctgag cgtgatgctg caatgctccc agcctgcacc   67320
ctaaccaaag ggatgcccca ttgcaatgcg ccccagcccc tgcagcgctg tgtgcagccc   67380
actccctgtc cccgacacca caggatccat cccgtggctg tgacctggcc ccatgcaaag   67440
tttgcaggca ggaaatagca aagaggatgg actgattgtc tccaggccca gagcctgtgc   67500
ctgcagcagg tattttttgct ctgctgctgt ctggcactgc ctgttctgcc ccagatcacg   67560
ccaggctatc cctttgtatc tcatccggat gaggctgttc tgggagcctc ggctgtgctg   67620
tactgcagac ggctctgatg ctgactgcgg ggtctcctcc atctcccctg tgtgcttttg   67680
ttaccgtact ggcagttttt gtaattcaga ggtgcaagag cctaaaagcc ataagactca   67740
atgaagcttt aaaatctctg ctgagagagg ctcagctctt acatagctcc ccgcttcccc   67800
ggcggtggct gcctgccagg gagatgggtt tatgtgtctg tggtgcagtt agcagctgaa   67860
tgactgatta catggtattt tagtaacatt tttcaaatag caaaatactg aaaagcaatt   67920
ccgataatgt atttcctacc cctcctccac cacacagaac ggcagaggag ggaaaacctg   67980
gtgtgtgctg tgctgcagtt tgcaaaggga tttgtgactt cggttcagtc ctctcagaaa   68040
ataatgctaa tgtggataaa atctttttt ttgttgcaat tctaggtgta gcagctcaag   68100
acattgaaga ggttagtgca gctctttctg ctttctgaat ctgcattttc tcctggctct   68160
ggaagaatgc ttttctaaca gatccttgtg cattggtgca tgctgaactg ctttgggttt   68220
tgctgggatc aggtgggtcc tgccaaggtg ccccaatgct tcggagtgct cacacagtac   68280
agggtgtta gctatggcca cagtagcaaa caagttgggg atgatttagc tggtttagca   68340
catgctcccc atggtctgat ccagcacagg gctgtctgca gtatcgcttc tgtctgcttt   68400
gctcctccac gaaacaaatg tgatatcagg agtgatatac tcctttaaac catatccata   68460
actgggcctt gtccaaaagc ctgttcactt catagaatca ttaaggttgg aaagaccact   68520
atggtcatcg agtgcaacca ctccatgccc agatccctgt gtatggcagc cccaggccac   68580
gtggtggtgt gagctgcatg gtaccgggca ctgatatggg gctgcatcag tgctgatgct   68640
ctcctgttga acccactcat gttccttgaa caccagagct gctccctggt ggtgacagct   68700
tccctcctct gccacagggc agaaattccc ccatttcagc cagttctgac aggcctttgt   68760
ttttcaagta gcaggccgt gcctcgttgc tgcttttggc ctctgggtgg gaagaagatc   68820
acattagaga tcttctttcc tgtttggaaa gcgaaacccg acggtttatt gctgttatta   68880
```

```
tttttgattt cttttgcaga tctgcaaaga gttcttaaac aggagcgtgt tctgcaccag  68940
ggagtccaac cctcactgcg gcacggatgg cgtgacgtac ggcaacaagt gtgccttctg  69000
caaggccgtg ctgtaagtgg gggcggtggg atacggaccc acacagggat ggtccacttc  69060
caaccccgcg ctgctgctcc cctcacacag agcaatccct ggccatagaa tcatagaact  69120
agagaatggt taaggttgga aaagaccaat aagtgcatct agttcaaatg gcagctcctc  69180
accgccacgc ttgggaatat ttcagcttaa tgttgattca tttctaggct tagtgtgatg  69240
ctcatagccg tacagagatg gcacagagcc tgggaggcca ttgtacctgc ctgtaccttc  69300
tgcgtgggct aaattgatgc acattttcct ctgtgtgcca caggctgaag ctctccctgt  69360
ccacacctct ggatgctgaa gtgtgtggag gaacgcaggc ttatgcatgc caaattatta  69420
gaggaaagtc atagactcgt agaatcatag attcgtttga gtcgaatggg acctttgaag  69480
gtcatctggt ccagcatccc tgcaacgagc agggaaagtg ctgaaatgaa agtctgaatg  69540
gacttagtgg aaaagtacac aaaatctcag aggaagggct gcagtttctc ctctcctgtc  69600
tcctctaaag gagctgtaat aggagccaac acctctggac tgaaggcctg caaaaattga  69660
tttatcctta tcaatcctgc actctggagg ctgccttatc ctaagggaaa ttagagaaga  69720
gggaaagatg gcttgatgct ccctgtgagg caccagagtg aggcaaatga tcgtgctcgg  69780
agggacaagc tccctgtccc agccgctgtg tctgtgctgg atgccataca ctgctttgtt  69840
tccataccgc tccttttaca ggaggagtgg agggaagata cgattgaagc acatgggaa  69900
gtgctgagcc tgagcaccaa gcactgatct tcgtcggtca caggtgcagg agcctgggca  69960
cggcagcagc tgtcctcatc tctgccatat ctgctcaata aagtaaagct cagcacacct  70020
ccttgactgg attccttttt ccataacacc cggataagcc ttccatgcag ccgtgctagc  70080
agctaaaatg tttgccgcac tgtgctgtta catcttagaa tcacagaatc aggcaccatg  70140
ctgcctgagc aggagcaatg attcccacag ctcttccatg ccatgccatg ccatgccatg  70200
ccatgccatg ccatgccatg ccatgccatg ccatgccatg ccatgccatg ccatgccatc  70260
ccatcccatc ccatcccatc ccatcccact gacaaatgga cacatggcca cccagcttga  70320
ctgtcccatg ggtgggtgac agcatgcaac gttgcctctc agcagcctcc ccatatgtgt  70380
ccctctcgct gaggtgtgag catgaaggtg gcagagagct atgagtggtg tggctgtgga  70440
tgcctcatct gcttgggaag ccagaagcaa acaggctgag gctgaggagt gttgctgcat  70500
gtaagcctgc accgggaagg tggcagggga agctggcttt aggcagaaac acaaaggctt  70560
tgctttcctt gtgtgtccta agagaggact ttgcctcaaa gactgtcaac tcgccagcat  70620
caggttgcag ttgcacacaa acttgatttc tttctttagt tttcacactg ctgctctctc  70680
tctccttgat gctggctgga aaatccttct ttgcgccagc gagggaaaat aaagcctata  70740
gtctctcccc attcgctgta caaaatatac acagggaaat gcttgtggca tccccctcgtt  70800
aaaacgttgg cagcacatca atgggactct actcacttaa tgttgaacac ttaagtttca  70860
aagggagctt tagattttat cgtgaggtca gccaactcat tttgcaaaca cctctatgct  70920
gagcatctca gctcctggat ggtgtttgga cagctgagt gtttgcctg tggtgccacg  70980
ctgcaggctt tgaagtgaat tgggacatta tattttgtag ccaaggagag ttgcagtttg  71040
cttttgttcca attcagatgt ttcttttagta aacacaacag ctagacctcc agaacatgga  71100
taagcttgag gggaggaaaa agcacctcct gcacgaggac agctgatcac aaaggacccc  71160
agtgggcagt gggagaacct tcatcatcct ctctaccgcc tggatcagga tgagccctgc  71220
atacccttc caactggagt taccctgtga gccaacttgt ggctctggag tagtgctgta  71280
```

```
tctcaataca gtttctcaga tgggaagagg catttcaatg agagggggga tatgggacat    71340
ttctatgcct gagatggctc tcggagactc caaaagcctc acggcgtatc cccatgccta    71400
atccttttta atctggaggc tgaaataaca aggacagatc acaagagaac agaagcggcg    71460
agacttctct gctttataat cagcctgcat tttgctcttt cagtgcaaac agcaaataga    71520
accgcctctg taccccctcca gacccaacca ccatccccag caacactgtg gcaggctgga    71580
gaagggtggc tctgcccctc cttgcctcaa ctggttgtgt cagcacgacc ataaccagag    71640
ctctccttgg ccccagctgg gcttatccat gtaaacctct cagtgcccca ggagctggct    71700
ggtggtcctg tccatttcac tttcctccag caggtgttcc ctttaacaag catccaagtg    71760
cctggagcag gagcaggcac tgcagaagat gagctcaggc aaggacatgg catgtgggga    71820
tccatgctgt tgtgcaatgc agatgacgtt agatacgtgc aaagcagatc tcagcaatca    71880
cccaacgact cataactgca atcatggaac gcaattgcat ctggaagtat aaaagcacag    71940
tgataccagg aagctcttgt taatggcaca gccattttgg agcaatttgc ccaggtgggg    72000
agagccctca cagcgccttc agtcacaggg agtggtgtga gtgccccccat ggctgctccc    72060
agccccagc cctgggtgat gggggtcact tggctgtaac cctctgaaca cagggacagt    72120
gagacagccc tctggcctgg ctgagctctt ggctacgtcc agctgcagtc ctgggcacat    72180
actgaaccag aaagcaagca ttcagctggt attttttcctt taatttcctt cctccacatt    72240
ttaagttgtg ggatttttttt tttttttttt tgacagcttt gagagatgag tgagtcacga    72300
agcactcgag atctctatta gataacagag catctctgca gctcttcctg ggagggagt     72360
tccttggacc aagggccaag gctgggtgag aattgtccca gcatcacagt ggctgctcca    72420
tcacctgaca cagcccctct gcagtgaaac aagggaagca ttacatcttt gcacggctgc    72480
tttcactgaa caaaaagcgc tgcttcacag ctgagcacca tgatgaaggg gaaggagcat    72540
ctccatgatg aaggggaagg agcatctcca catctccatc acgagctctg ctctgctggt    72600
gatgcggctg acaccatggt gtgccctgac tcctggccca tttaactgct gtgcaccagt    72660
gcctcctccc cagcatagcc ctgtgtccct gccacaactc attgcaatcc tttgtcctac    72720
ttcttccctt gacattcaca gctcttgata aggcttttg agccactcct ggctgatgtg    72780
ggctggtggt tcctgctgca gggttcccac cacccagctg ggcagcattc ggttgttgtt    72840
ccagttccca ggggattggg acagattgga agggtctttg gactgtggga agagtatctc    72900
ctgaagtcag gcagactgc tcagcgctttt gtcccatcca gacttgaaaa catccaaggg    72960
tggagaacac acagactccc tgggctgcca gtcccagagt ttgactgtca tcacgttgaa    73020
gactttttgc cttgtctcca tttgcaacct cttttccttttc agctgcccca tctctcagcc    73080
atgcaccact ggggagccca gctctgtctg gtcaggaaca gagcccttac agagccacag    73140
catcctcctg aagtgtccat ctcaccactc agcctcagca agtgctccag ccctcaactc    73200
ccatttttcca ttatctttct atcactggat atgggaggga aggcagagct gtgggccaa    73260
gagaaacgat tgctcaggag gcagttggga gaactttatt gcaaagcact gaagagatat    73320
aaagtgacat ttgcaggaaa aagtagaagg gtatctgtgt gtgttggttc ctttaaggat    73380
tagagagcag ctgagctttg ggatgagagg gctcccagat gctgtgaatc agctaacaga    73440
tccctccacc ccgtcattgg tggtgaagtt aaatagggggc ccaggggaaa catcagggtt    73500
gttttttcttt ttacggactc cagagcaagg agaaggtgag ggggttgtgc tttgaatgg    73560
gagtgaaaga gtttgttggt gttttcctct ccccagaata agtagtgtgg tgtaggagcg    73620
```

```
tctcatagga gtagctgcgt taattgtggc tggtgttagc atcctataat gttgctccag    73680
aaatgctgga gcaggcttat aatgatgtgt atgtattacc ataatacatg aagggagaat    73740
gggggggggg gggtagatt taagatgtat gcccttagaa aggcgggtgt cacttaaaga     73800
agtacttgct ttatagctcc agtgatagaa ttcattgaga tactctgaac ctatgggca     73860 tgaagtgacc agatcttcag tttggtcagc tctgggggtt tctgggggga gcgggatag    73920 agcctcaatc caggtctgaa agacaaggct gagatgtgct gggcctgggg tgctgccctg    73980
agcaacgtgg ggctggccct agagagcagc attagtgcct gcagcagggc tggcccttgt    74040
gcccagtgtg tggggtaagg tggggaacgt aggtgctgca taatgtggtg cttctgatct    74100
aaaactgctc tgttaattgg gagtgaccag agatggccct atggctttct tcccaaagag    74160
ctctgtgtcc ttctctgcag gtaatctgt gataaaaaca tcgcctatgc tctgccctgc     74220
agatgcaggg gttttgtca tcctccttct cgagacatac tctaatcctt acgcaagcag     74280
ggagctccaa gcttttggtg ataacctctc aaggaggagc tggaagggca gctctgccga    74340
gcagtgactg cgctgcacgg ggcgcatcct gcaggaggcg gtggtgtaag cgggactccg    74400
ctcgttcccg gctatggggc tcccctgct gaccgccggg cggtggccag gagacctcgg     74460
ggccgctgct gcccctcggt ggtgcttttc gggacagctt tcaggatggg gcagcccagc    74520
tgctctcgcg gggaattaag cggctcggtc cagggcggca cggcgctgag ctgccccagc    74580
aaagcgccgc tcgtcccgcg gcaccttcgg tagatgctct ctgcttggca gctccttggt    74640
cgttctcttg gccggtggcc accccagcat cgctcgggc tcggtgccat ccccccagg      74700 gcctgcggag gtgccggtgc ccgtcccggg ggtggcggac gggcggtgca gtaccgatgc    74760
tgggcgctgg gtgctgccgc agaccgagcg gcgctgcgcg gctccggggc gctcctggag    74820
tgcgagctga gcaacctggt agaaaaataa gtgttgtccc gtgataaacg tcatcgtgct    74880
gagctctcag actctgccag aggcctgaat gaagctgcgt caggggagaa tcaggttggg    74940
gctaaggaaa ggtcctgccc cagagggcgg tgggtataga aggggtgccc agggcagtgg    75000
gtgcagtgct gggctcccag agctggagga gcgtctggac agtgctcagg tttggatgtt    75060
gggtggtttt ctgaagggac ggattctggg ctcgtttatc ctgagggtcc cttccaactt    75120
gggttgttct attcaatgaa tattgtttat gttcattcta ttctatgatc ttgttcaggc    75180
tctcactgct gcctccaagg gttcagctcc cccagagctg gcagggcttc agccacttgc    75240
ttacagtgct catttcatgc ctggcccatg gcttctgcct gagccttgtg ggagatcagc    75300
tgctgccaga aacccagccc tcagcactcc acttgcccag cttgctgcct tagtagtcta    75360
acttggcagt ggtctgacat gacttgaggt tgtttttat ttccaaggtg ccactgactt     75420
ttttccttcc atagtttctg gaagcatttc cttcctactt gactgagtcg tgctctgtgg    75480
atctgtaatt atccaccttg gctatgtgtc ctttacggga tttatatgt taacctccca     75540 agatcatttt gctgctctca tcttagtggc tgctgtgagc tccaccagca ccacactgga    75600
tgagctgcag gctgaggccg ggcacctctc ctgactctgc tcttctctga cccagagct     75660 gtgcagttgg gatcctaaca ccatgcagat gctccaggac ctgcaccgag ccccagcact    75720
ggcactcatc tcttctttcc accctctga gagcaacaag tggctctgca atggcaatgt     75780
aagtgaaacc gggcgggtat cttagagcac ctgga                               75815
```

<210> SEQ ID NO 43
<211> LENGTH: 26
<212> TYPE: DNA
<213> ORGANISM: artificial

```
<220> FEATURE:
<223> OTHER INFORMATION: description of artificial sequence: primer

<400> SEQUENCE: 43
cgggcagtac ctcaccatgg acatgt                                          26

<210> SEQ ID NO 44
<211> LENGTH: 21
<212> TYPE: DNA
<213> ORGANISM: artificial
<220> FEATURE:
<223> OTHER INFORMATION: description of artificial sequence: primer

<400> SEQUENCE: 44
attcgcttaa ctgtgactag g                                               21

<210> SEQ ID NO 45
<211> LENGTH: 20
<212> TYPE: DNA
<213> ORGANISM: artificial
<220> FEATURE:
<223> OTHER INFORMATION: description of artificial sequence: primer

<400> SEQUENCE: 45
cgaggaactt gaagcctgtc                                                 20

<210> SEQ ID NO 46
<211> LENGTH: 20
<212> TYPE: DNA
<213> ORGANISM: artificial
<220> FEATURE:
<223> OTHER INFORMATION: description of artificial sequence: primer

<400> SEQUENCE: 46
ggcctgcact ctccatcata                                                 20

<210> SEQ ID NO 47
<211> LENGTH: 1148
<212> TYPE: DNA
<213> ORGANISM: artificial
<220> FEATURE:
<223> OTHER INFORMATION: description of artificial sequence: DNA
      expression cassette
<220> FEATURE:
<221> NAME/KEY: misc_feature
<222> LOCATION: (652)..(1116)
<223> OTHER INFORMATION: n is a, c, g, or t

<400> SEQUENCE: 47
gaattccgcc cctctccctc cccccccct aacgttactg gccgaagccg cttggaataa      60
ggccggtgtg cgtttgtcta tatgttattt tccaccatat tgccgtcttt tggcaatgtg     120
agggcccgga aacctggccc tgtcttcttg acgagcattc ctaggggtct ttcccctctc     180
gccaaaggaa tgcaaggtct gttgaatgtc gtgaaggaag cagttcctct ggaagcttct     240
tgaagacaaa caacgtctgt agcgaccctt gcaggcagc ggaaccccc acctggcgac       300 aggtgcctct gcggccaaaa gccacgtgta agatacac ctgcaaaggc ggcacaaccc       360
cagtgccacg ttgtgagttg atagttgtg gaaagagtca atggctctc ctcaagcgta       420 ttcaacaagg ggctgaagga tgcccagaag gtaccccatt gtatgggatc tgatctgggg     480
cctcggtgca catgctttac gtgtgtttag tcgaggttaa aaaacgtcta ggccccccga     540
accacgggga cgtggttttc ctttgaaaaa cacgatgata agcttgccac aaccatggga     600
tggagctgta tcatcctctt cttggtggcc acagctaccg gtgtgcactc cnnnnnnnn      660
```

```
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnnnnnnn nnnnnnnnnn nnnnnnnnnn nnnnnnnnnn nnnnnnnnnn nnnnnnnnnn   1080
nnnnnnnnnn nnnnnnnnnn nnnnnnnnnn nnnnnntagg gatccactag tccagtgtgg   1140
tggaattc                                                            1148

<210> SEQ ID NO 48
<211> LENGTH: 2039
<212> TYPE: DNA
<213> ORGANISM: artificial
<220> FEATURE:
<223> OTHER INFORMATION: description of artificial sequence: DNA
      expression cassette
<220> FEATURE:
<221> NAME/KEY: misc_feature
<222> LOCATION: (652)..(1995)
<223> OTHER INFORMATION: n is a, c, g, or t

<400> SEQUENCE: 48
gaattccgcc cctctccctc cccccccct aacgttactg gccgaagccg cttggaataa     60
ggccggtgtg cgtttgtcta tatgttattt tccaccatat tgccgtcttt tggcaatgtg    120
agggcccgga aacctggccc tgtcttcttg acgagcattc ctaggggtct ttcccctctc    180
gccaaaggaa tgcaaggtct gttgaatgtc gtgaaggaag cagttcctct ggaagcttct    240
tgaagacaaa caacgtctgt agcgaccctt gcaggcagc ggaaccccc acctggcgac     300 aggtgcctct gcggccaaaa gccacgtgta agatacac ctgcaaaggc ggcacaaccc     360
cagtgccacg ttgtgagttg gatagttgtg gaaagagtca atggctctc ctcaagcgta    420 ttcaacaagg ggctgaagga tgcccagaag gtaccccatt gtatgggatc tgatctgggg    480
cctcggtgca catgctttac gtgtgtttag tcgaggttaa aaaacgtcta ggccccccga    540
accacgggga cgtggttttc cttttgaaaaa cacgatgata agcttgccac aaccatggga    600
tggagctgta tcatcctctt cttggtggcc acagcaaccg tgtccatag tnnnnnnnn    660 nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnnnnnnn nnnnnnnnnn nnnnnnnnnn nnnnnnnnnn nnnnnnnnnn nnnnnnnnnn   1080
nnnnnnnnnn nnnnnnnnnn nnnnnnnnnn nnnnnnnnnn nnnnnnnnnn nnnnnnnnnn   1140
nnnnnnnnnn nnnnnnnnnn nnnnnnnnnn nnnnnnnnnn nnnnnnnnnn nnnnnnnnnn   1200
nnnnnnnnnn nnnnnnnnnn nnnnnnnnnn nnnnnnnnnn nnnnnnnnnn nnnnnnnnnn   1260
nnnnnnnnnn nnnnnnnnnn nnnnnnnnnn nnnnnnnnnn nnnnnnnnnn nnnnnnnnnn   1320
nnnnnnnnnn nnnnnnnnnn nnnnnnnnnn nnnnnnnnnn nnnnnnnnnn nnnnnnnnnn   1380
```

```
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnnnnnnnnn nnnnnnnnnn    1560
nnnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740
nnnnnnnnnn nnnnnnnnnn nnnnnnnnnn nnnnnnnnnn nnnnnnnnnn nnnnnnnnnn    1800
nnnnnnnnnn nnnnnnnnnn nnnnnnnnnn nnnnnnnnnn nnnnnnnnnn nnnnnnnnnn    1860
nnnnnnnnnn nnnnnnnnnn nnnnnnnnnn nnnnnnnnnn nnnnnnnnnn nnnnnnnnnn    1920
nnnnnnnnnn nnnnnnnnnn nnnnnnnnnn nnnnnnnnnn nnnnnnnnnn nnnnnnnnnn    1980
nnnnnnnnnn nnnnntgagt gcgacggccg gcaagggatc ccccgggctg caggaattc     2039
```